(12) United States Patent
Furet et al.

(10) Patent No.: US 8,815,926 B2
(45) Date of Patent: Aug. 26, 2014

(54) SUBSTITUTED PYRROLO[3,4-D]IMIDAZOLES FOR THE TREATMENT OF MDM2/4 MEDIATED DISEASES

(71) Applicant: Novartis AG, Basel (CH)

(72) Inventors: Pascal Furet, Thann (FR); Vito Guagnano, Basel (CH); Philipp Holzer, Sissach (CH); Joerg Kallen, Basel (CH); Lv Liao, Shanghai (CN); Robert Mah, Muttenz (CH); Liang Mao, Shanghai (CN); Keiichi Masuya, Basel (CH); Achim Schlapbach, Lorrach (DE); Stefan Stutz, Basel (CH); Andrea Vaupel, Riehen (CH)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 13/748,790

(22) Filed: Jan. 24, 2013

(65) Prior Publication Data

US 2014/0011798 A1 Jan. 9, 2014

Related U.S. Application Data

(63) Continuation of application No. PCT/CN2012/086703, filed on Dec. 14, 2012.

(60) Provisional application No. 61/669,902, filed on Jul. 10, 2012, provisional application No. 61/591,001, filed on Jan. 26, 2012.

(51) Int. Cl.
| | |
|---|---|
| *A61K 31/4188* | (2006.01) |
| *C07D 235/02* | (2006.01) |
| *C07D 487/04* | (2006.01) |
| *A61K 45/06* | (2006.01) |
| *A61K 31/541* | (2006.01) |
| *A61K 31/4439* | (2006.01) |
| *A61K 31/506* | (2006.01) |
| *A61K 31/5377* | (2006.01) |
| *A61K 31/501* | (2006.01) |

(52) U.S. Cl.
CPC .............. *C07D 487/04* (2013.01); *A61K 45/06* (2013.01); *A61K 31/4188* (2013.01); *A61K 31/541* (2013.01); *A61K 31/4439* (2013.01); *A61K 31/506* (2013.01); *A61K 31/5377* (2013.01); *A61K 31/501* (2013.01)
USPC ............. 514/393; 544/61; 544/111; 544/224; 544/333; 546/199; 546/268.1; 548/303.1; 548/335.1; 548/373.1; 548/950

(58) Field of Classification Search
CPC ........................ A61K 31/4188; C07D 235/02
USPC ................... 514/393; 544/61, 111, 224, 333; 546/199, 268.1; 548/303.1, 335.1, 548/373.1, 950
See application file for complete search history.

(56) References Cited

U.S. PATENT DOCUMENTS

| | | | |
|---|---|---|---|
| 6,734,302 | B2 | 5/2004 | Kong et al. |
| 7,541,354 | B2 | 6/2009 | Fancelli et al. |
| 8,101,644 | B2 | 1/2012 | Kai et al. |
| 2003/0153580 | A1 | 8/2003 | Kong et al. |
| 2006/0069085 | A1 | 3/2006 | Zhao et al. |
| 2009/0163545 | A1 | 6/2009 | Goldfarb |
| 2011/0183939 | A1 | 7/2011 | Kai et al. |
| 2011/0230457 | A1 | 9/2011 | Berghausen et al. |
| 2012/0065210 | A1 | 3/2012 | Chu et al. |
| 2013/0317024 | A1 | 11/2013 | Cotesta et al. |

FOREIGN PATENT DOCUMENTS

| | | | |
|---|---|---|---|
| EP | 2 143 713 | A1 | 1/2010 |
| WO | 95/19362 | A1 | 7/1995 |
| WO | 02/12242 | A2 | 2/2002 |
| WO | 03051359 | | 6/2003 |
| WO | 03095625 | | 11/2003 |
| WO | 2005110996 | | 11/2005 |
| WO | 2006074262 | | 7/2006 |
| WO | 2007068637 | | 6/2007 |
| WO | 2007096334 | | 8/2007 |
| WO | 2008034039 | | 3/2008 |
| WO | 2008/120725 | A1 | 10/2008 |
| WO | 2010141738 | | 12/2010 |
| WO | 2011/076786 | A1 | 6/2011 |
| WO | 2012046030 | | 4/2012 |
| WO | WO 2013/111105 | * | 8/2013 |

OTHER PUBLICATIONS

Jordan, V. C. Nature Reviews: Drug Discovery, Feb. 2003, 205.*
Hackam, et al. JAMA, 296(14), 2006, 1731-1732.*
Richter, et al., "An Optimised Small-Molecule Stabiliser of the 14-3-3-PMA2 Protein-Protein Interaction", Chem. Eur. J., 2012, pp. 6520-6527, vol. 18, No. 21, Wiley-VCH Verlag GmbH & Co.

(Continued)

*Primary Examiner* — Douglas M Willis
(74) *Attorney, Agent, or Firm* — Scott W. Reid

(57) ABSTRACT

The invention relates to compounds of formula (I):

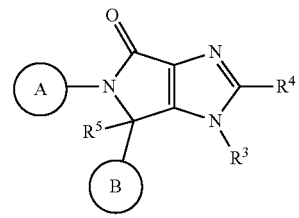

as described herein, pharmaceutical preparations comprising such compounds, uses and methods of use for such compounds in the treatment of a disorder or a disease mediated by the activity of MDM2 and/or MDM4, and combinations comprising such compounds.

25 Claims, 7 Drawing Sheets

(56) References Cited

OTHER PUBLICATIONS

Miyazaki, et al., "Lead optimization of novel p53-MDM2 interaction inhibitors possessing dihydroimidazothiazole scaffold", Bioorganic and Medicinal Chemistry Letters, 2013, pp. 728-732, vol. 23, Elsevier Ltd.

Wang, et al., "Benzimidazole-2-one: a novel anchoring principle for antagonizing p53-Mdm2", Bioorganic & Medicinal Chemistry, 2013, pp. 3982-3995, vol. 21, Elsevier Ltd.

Lee, et al., "Novel Pyrrolopyrimidine-Based alpha-Helix Mimetics: Cell Permeable Inhibitors of Protein-Protein Interactions", Journal of the American Chemical Society, 2010, pp. 676-679, vol. 133, American Chemical Society.

Vanotti, et al., "Cdc7 Kinase Inhibitors: Pyrrolopyrimidinones as Potential Antitumor Agents. 1. Synthesis and Structure-Activity Relationships", Journal of Medicinal Chemistry, 2008, pp. 487-501, vol. 51, American Chemical Society.

Andreichikov, Yu.S. et al., "Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine", Journal of Organic Chemistry vol. XXII, Issue 8, 1986.

Dohrn, M. et al., Berichte der Deutschen Chemischen Gesellschaft [Abteilung] B: Abhandlungen (1931), 64B.

Gein, V. L. et al., "5-Membered 2,3-Dioxoheterocyclic Compounds", Journal of General Chemistry, vol. 63, Issue 10, pp. 2324-2328, 1993.

Gein, V. L. et al., "Reactions of 4-Acyl-1-alkoxyaryl-5-aryl-3-hydroxy-2,5-dihydro-1H-pyrrol-2-ones with Nucleophilic Reagents", Russian Journal of Organic Chemistry, 2011, vol. 47, No. 1, pp. 95-99, Pleiades Publishing, Ltd., 2011.

Westphal, Gunter, "The formation of pyrrolo[3,4-c]pyrazoles", Journal for Practical Chemistry, vol. 311, pp. 379-384, 1969.

* cited by examiner

SUBSTITUTED PYRROLO[3,4-D]IMIDAZOLES FOR THE TREATMENT OF MDM2/4 MEDIATED DISEASES

BACKGROUND OF THE INVENTION

The present invention relates to novel imidazopyrrolidinone compounds, capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor supressor. "MDM2" (originally from the oncogene "murine double minute 2") refers both to the name of the gene as well as the protein encoded by that gene. MDM2 protein functions both as an E3 ubiquitin ligase that recognizes the N-terminal transactivation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to cancers such as tumors, leukemias or other proliferative diseases.

There is a need for new drugs that are capable of interfering with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

It has now been found that a novel class of imidazopyrrolidinone compounds shows inhibition of the MDM2/p53 and/or MDM4/p53 interaction (this term including in particular Hdm2/p53 and Hdm4/p53 interaction), and in particular potent inhibition of the MDM2/p53 interaction. In particular, the compounds of the invention herein act as inhibitors of MDM2 interaction with p53 by binding to MDM2, and/or act as inhibitors of MDM4 interaction with p53 by binding to MDM4.

The corresponding compounds thus represent a novel type of compound that are useful in the treatment of a number of disorders, such as proliferative diseases, especially cancer. The invention relates therefore to these compounds as drugs as well as to the other inventive embodiments indicated herein.

Particularly interesting compounds of the invention herein are highly potent in the p53-Hdm2 inhibition (TR-FRET) Assay described herein. Compounds of particular interest possess favourable pharmacokinetic properties. They should be non-toxic and demonstrate few side-effects. Furthermore, the ideal drug candidate will exist in a physical form that is stable, non-hygroscopic and easily formulated.

BRIEF SUMMARY OF THE INVENTION

According to a first aspect of the invention, there is provided a compound of formula (I) or a salt thereof,

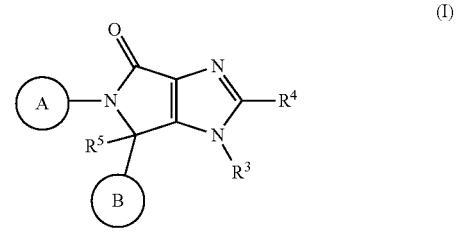

(I)

wherein

A is selected from:

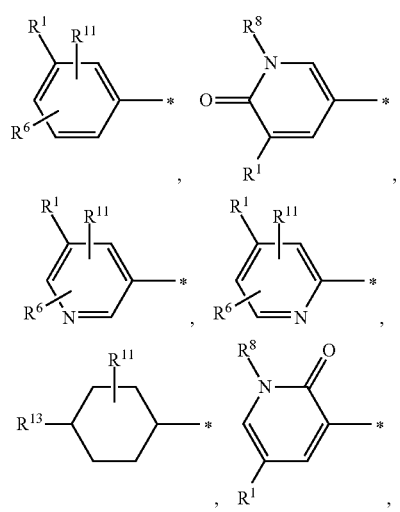

-continued

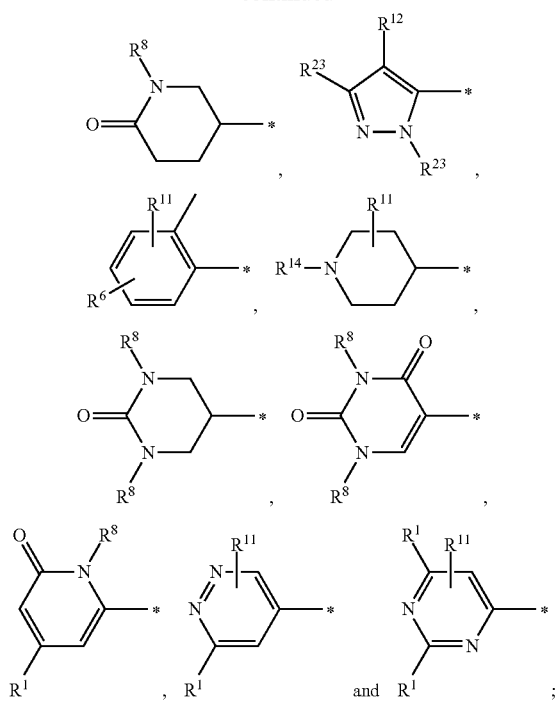

B is selected from:

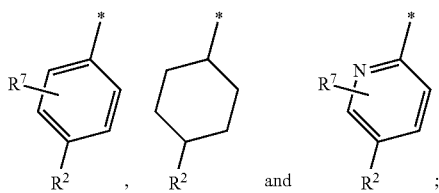

each $R^1$ is independently selected from halo and methyl;
$R^2$ is selected from chloro, fluoro, trifluoromethyl, methyl and cyano;
$R^3$ is selected from isopropyl, cyclopropyl, isobutyl, cyclobutyl and cyclopentyl, or $R^3$ is:

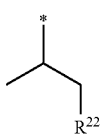

wherein $R^{22}$ is selected from OH, $OCH_3$, $NH_2$, NHMe, $NMe_2$, NHCOMe and NHCOH;
$R^4$ is selected from:

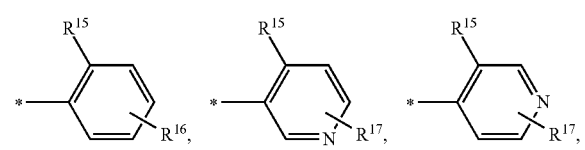

-continued

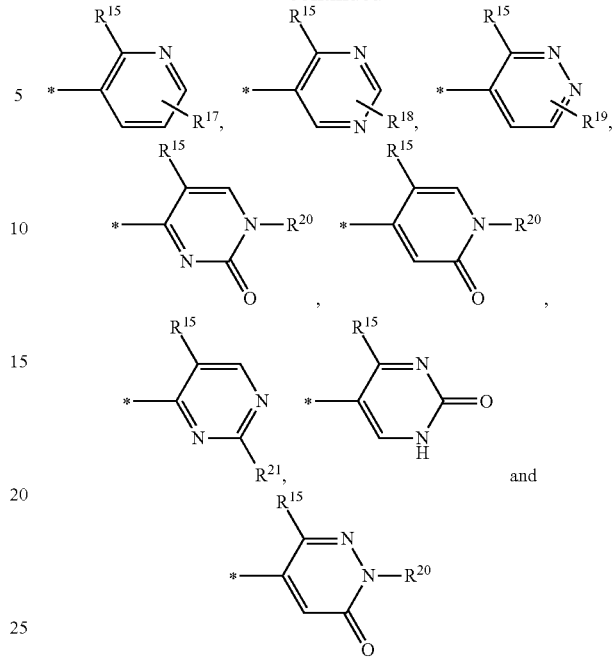

wherein
$R^{15}$ is independently selected from $OCH_3$, $CH_2CH_3$, OH, $OCF_3$ and H;
$R^{16}$ is selected from H, $—O—(C_1-C_4)$alkyl, halo, $OCF_3$, CN, $—C(O)NR^9R^{10}$, —C(O)-morpholinyl-4-yl, hydroxy-azetidin-1-yl-carbonyl, $—CH_2NR^9R^{10}$, $—CH_2NR^9—C(O)$ $R^{10}$, $CH_2CN$, methyl-imidazolyl-, $—CH_2C(O)NR^9R^{10}$, $—CH_2C(O)OH$, $—C(O)OH$, $—CH_2C(O)O—(C_1-C_4)$ alkyl, $—N(R^9)—C(O)—(C_1-C_4)$alkyl, $—NR^9R^{10}$ and $(C_1-C_4)$alkyl optionally substituted by 1 or 2 OH;
$R^{17}$ is selected from H, $O(C_1-C_4)$alkyl, $—CH_2C(O)NR^9R^{10}$, $—CH_2C(O)O—(C_1-C_4)$alkyl, $—CH_2C(O)OH$, $—NR^9R^{10}$, $—C(O)NR^9R^{10}$, $—CH_2NR^9R^{10}$, $—C(O)$ $OCH_3$ and $—CH_2CN$;
$R^{18}$ is selected from H, $O(C_1-C_4)$alkyl, OH, $CH_2NR^9R^{10}$, $—NR^9R^{10}$ and azetidin-1-yl, said azetidin-1-yl being substituted with OH or both $CH_3$ and OH,
$R^{19}$ is selected from H, $O(C_1-C_4)$alkyl, $(C_1-C_4)$alkyl, $—NR^9R^{10}$, $—N(R^9)—C(O)—(C_1-C_4)$alkyl and $—C(O)$ $NR^9R^{10}$;
$R^{20}$ is selected from H, $CH_3$ and $—CH_2CH_3$;
$R^{21}$ is selected from $—NR^9R^{10}$, $—CH_2NR^9R^{10}$, $C(O)$ $NR^9R^{10}$ and CN;
$R^5$ is selected from:
H,
heterocyclyl$^1$-C(O)—(CH$_2$)$_n$—,
$(C_1-C_4)$alkyl-, said $(C_1-C_4)$alkyl- being optionally substituted with 1 or 2 substituents independently selected from OH, =O,
heterocyclyl$^1$-$(C_1-C_4)$alkyl-, wherein said alkyl of heterocyclyl$^1$-$(C_1-C_4)$alkyl- is optionally substituted by 1 or 2 OH, and said heterocyclyl$^1$ can be optionally substituted by methyl or ethyl,
$(C_1-C_4)$alkyl-O—C(O)—(CH$_2$)$_m$—, and
cyano;
$R^6$ is selected from:
H,
$(C_1-C_4)$alkyl-, optionally substituted with $(C_1-C_4)$alkoxy,
$(C_1-C_4)$alkoxy, optionally substituted with $(C_1-C_4)$alkoxy, (C$_1$-C$_4$)alkoxy(C$_1$-C$_4$)alkoxy(C$_1$-C$_4$)alkyl-,
halo,
R$^9$(R$^{10}$)N—C(O)—(CH$_2$)$_m$—,
cyano,
R$^9$(R$^{10}$)N—(CH$_2$)$_m$—,
R$^9$(R$^{10}$)N—(CH$_2$)$_n$—O—(CH$_2$)$_m$—,
(C$_1$-C$_4$)alkyl-C(O)—(R$^{10}$)N—(CH$_2$)$_m$—,
—O—(CH$_2$)$_p$-heteroaryl$^2$;

R$^7$ is selected from:
  H,
  halo, and
  (C$_1$-C$_4$)alkyl-, optionally substituted with (C$_1$-C$_4$)alkoxy;
each R$^8$ is independently selected from H, methyl, ethyl, hydroxyethyl and methoxyethyl-, wherein said methyl or ethyl is optionally substituted with 1, 2 or 3 fluoro substituents;
each R$^9$ is independently selected from H, methyl or ethyl;
each R$^{10}$ is independently selected from H and (C$_1$-C$_4$) alkyl wherein said (C$_1$-C$_4$) alkyl is optionally substituted by 1 or 2 substituents independently selected from methoxy, ethoxy, hydroxy and halo;
or R$^9$ and R$^{10}$, together with the N atom to which they are attached, can join to form a saturated 5 or 6 membered heterocyclic ring further comprising ring carbon atoms and optionally one ring heteroatom independently selected from N, O and S, and wherein when the ring contains a S atom, said S is optionally substituted with one or two oxo substituents;
R$^{11}$ is H, (C$_1$-C$_4$)alkyl, (C$_1$-C$_4$) alkoxy or halo;
R$^{12}$ is H or halo;
R$^{13}$ is selected from NH$_2$, —C(O)OH, —NH(C(O)—CH$_3$) and —C(O)—NH(CH$_3$);
R$^{14}$ is selected from —C(O)—NR$^9$(R$^{10}$), (C$_1$-C$_4$)alkyl, —C(O)(C$_1$-C$_4$)alkyl, —C(O)O(C$_1$-C$_4$)alkyl;
each R$^{23}$ is independently selected from H, halo, cyclopropyl and (C$_1$-C$_4$)alkyl;
n is 1, 2 or 3;
p is 0, 1, 2 or 3;
heterocyclyl$^1$ is a 3, 4, 5 or 6 membered fully saturated or partially unsaturated monocyclic group comprising ring carbon atoms and 1 or 2 ring heteroatoms independently selected from N, O and S;
heteroaryl$^2$ is 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1; and
m is 0, 1 or 2.
* indicates the point of attachment to the remainder of the molecule.

DETAILED DESCRIPTION OF THE INVENTION

Unless specified otherwise, the terms "compounds of the present invention" or a "compound of formula (I)" refer to compounds of formula (I) and subformulae thereof, salts thereof, hydrates or solvates of the compounds or salts, as well as all stereoisomers (including diastereoisomers and enantiomers), tautomers and isotopically labeled compounds (including deuterium substitutions), as well as inherently formed moieties (e.g., polymorphs, solvates and/or hydrates).

For example, a "compound of the present invention" or a "compound of formula (I)" can exist in tautomeric forms when R$^8$ is H. Where an embodiment is directed to one tautomer, the embodiment includes all possible tautomeric forms.

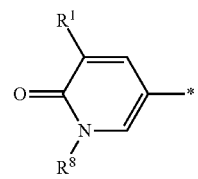

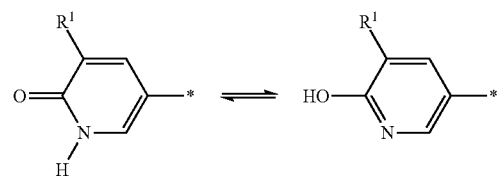

Various embodiments of the invention are described herein. It will be recognized that features specified in each embodiment may be combined with other specified features to provide further embodiments. For purposes of interpreting this specification, terms used in the singular will also include the plural and vice versa.

In another embodiment of the invention there is provided a compound of formula (I) or salt thereof, wherein A is selected from

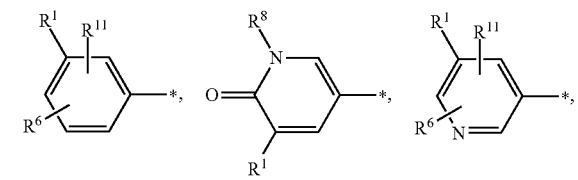

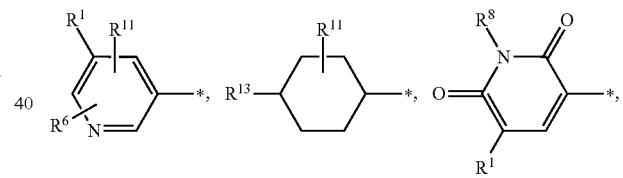

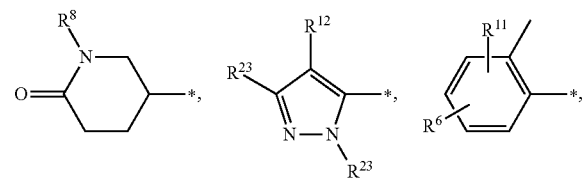

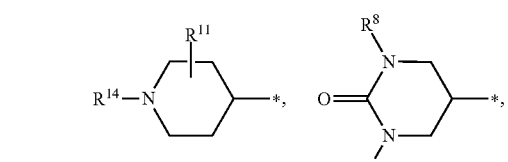

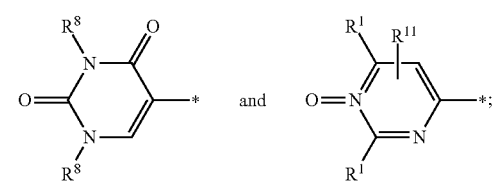

B is selected from

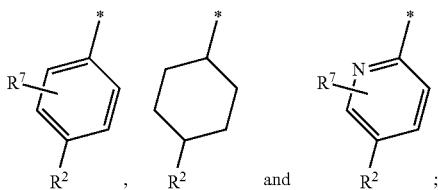

each $R^1$ is independently selected from halo and methyl;

$R^2$ is selected from chloro, fluoro, trifluoromethyl, methyl and cyano;

$R^3$ is selected from isopropyl, cyclopropyl, isobutyl, cyclobutyl and cyclopentyl, or $R^3$ is:

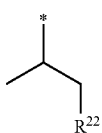

wherein $R^{22}$ is selected from OH, $OCH_3$, $NH_2$, NHMe, $NMe_2$, NHCOMe and NHCOH;

$R^4$ is selected from:

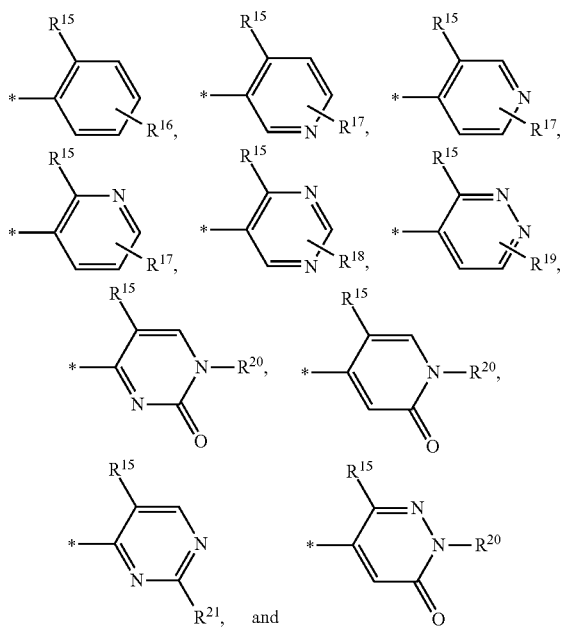

wherein $R^{15}$ is independently selected from $OCH_3$, $CH_2CH_3$, OH, $OCF_3$ and H;

$R^{16}$ is selected from H, —O—$(C_1$-$C_4)$alkyl, halo, $OCF_3$, CN, —C(O)$NR^9R^{10}$, —C(O)-morpholinyl-4-yl, hydroxy-azetidin-1-yl-carbonyl, —$CH_2NR^9R^{10}$, —$CH_2NR^9$—C(O)$R^{10}$, $CH_2CN$, methyl-imidazolyl-, —$CH_2C(O)NR^9R^{10}$, —$CH_2C(O)OH$, —C(O)OH, —$CH_2C(O)O$—$(C_1$-$C_4)$ alkyl, —N($R^9$)—C(O)—$(C_1$-$C_4)$alkyl, —$NR^9R^{10}$ and $(C_1$-$C_4)$alkyl optionally substituted by 1 or 2 OH;

$R^{17}$ is selected from H, $O(C_1$-$C_4)$alkyl, —$CH_2C(O)NR^9R^{10}$, —$CH_2C(O)O$—$(C_1$-$C_4)$alkyl, —$CH_2C(O)OH$, —$NR^9R^{10}$, —C(O)$NR^9R^{10}$, —$CH_2NR^9R^{10}$, —C(O)$OCH_3$ and —$CH_2CN$;

$R^{18}$ is selected from H, $O(C_1$-$C_4)$alkyl, $CH_2NR^9R^{10}$, —$NR^9R^{10}$ and azetidin-1-yl, said azetidin-1-yl being substituted with OH or both $CH_3$ and OH;

$R^{19}$ is selected from H, $O(C_1$-$C_4)$alkyl, $(C_1$-$C_4)$alkyl, —$NR^9R^{10}$, —N($R^9$)—C(O)—$(C_1$-$C_4)$alkyl and —C(O)$NR^9R^{10}$;

$R^{20}$ is selected from H, $CH_3$ and —$CH_2CH_3$;

$R^{21}$ is selected from —$NR^9R^{10}$, —$CH_2NR^9R^{10}$, C(O)$NR^9R^{10}$ and CN;

$R^5$ is selected from:
H,
heterocyclyl$^1$-C(O)—$(CH_2)_n$—,
$(C_1$-$C_4)$alkyl-, said $(C_1$-$C_4)$alkyl- being optionally substituted with 1 or 2 substituents independently selected from OH, =O,
heterocyclyl$^1$-$(C_1$-$C_4)$alkyl-, wherein said alkyl of heterocyclyl$^1$-$(C_1$-$C_4)$alkyl- is optionally substituted by 1 or 2 OH, and said heterocyclyl$^1$ can be optionally substituted by methyl or ethyl,
$(C_1$-$C_4)$alkyl-O—C(O)—$(CH_2)_m$—, and
cyano;

$R^6$ is selected from:
H,
$(C_1$-$C_4)$alkyl-, optionally substituted with $(C_1$-$C_4)$alkoxy,
$(C_1$-$C_4)$alkoxy, optionally substituted with $(C_1$-$C_4)$alkoxy,
$(C_1$-$C_4)$alkoxy$(C_1$-$C_4)$alkoxy$(C_1$-$C_4)$alkyl-,
halo,
$R^9(R^{10})$N—C(O)—$(CH_2)_m$—,
cyano,
$R^9(R^{10})$N—$(CH_2)_m$—,
$R^9(R^{10})$N—$(CH_2)_n$—O—$(CH_2)_m$—,
$(C_1$-$C_4)$alkyl-C(O)—$(R^{10})$N—$(CH_2)_m$—,
—O—$(CH_2)_p$-heteroaryl$^2$;

$R^7$ is selected from:
H,
halo, and
$(C_1$-$C_4)$alkyl-, optionally substituted with $(C_1$-$C_4)$alkoxy;

each $R^8$ is independently selected from H, methyl, ethyl, hydroxyethyl and methoxyethyl-;

each $R^9$ is independently selected from H, methyl or ethyl;

each $R^{10}$ is independently selected from H and $(C_1$-$C_4)$ alkyl wherein said $(C_1$-$C_4)$alkyl is optionally substituted by 1 or 2 substituents independently selected from methoxy, ethoxy, hydroxy and halo;

or $R^9$ and $R^{10}$, together with the N atom to which they are attached, can join to form a saturated 5 or 6 membered heterocyclic ring further comprising ring carbon atoms and optionally one ring heteroatom independently selected from N, O and S;

$R^{11}$ is H, $(C_1$-$C_4)$alkyl, $(C_1$-$C_4)$alkoxy or halo;

$R^{12}$ is H or halo;

$R^{13}$ is selected from $NH_2$, —C(O)OH, —NH(C(O)—$CH_3$) and —C(O)—NH($CH_3$);

$R^{14}$ is selected from —C(O)—$NR^9(R^{10})$, $(C_1$-$C_4)$alkyl, —C(O)$(C_1$-$C_4)$alkyl, —C(O)O$(C_1$-$C_4)$alkyl;

each $R^{23}$ is independently selected from H, halo and $(C_1$-$C_4)$ alkyl;

n is 1, 2 or 3;

p is 0, 1, 2 or 3;

heterocyclyl$^1$ is a 3, 4, 5 or 6 membered fully saturated or partially unsaturated monocyclic group comprising ring carbon atoms and 1 or 2 ring heteroatoms independently selected from N, O and S;

heteroaryl² is 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1, m is 0, 1 or 2; and

* indicates the point of attachment to the remainder of the molecule.

In another embodiment, A is selected from:

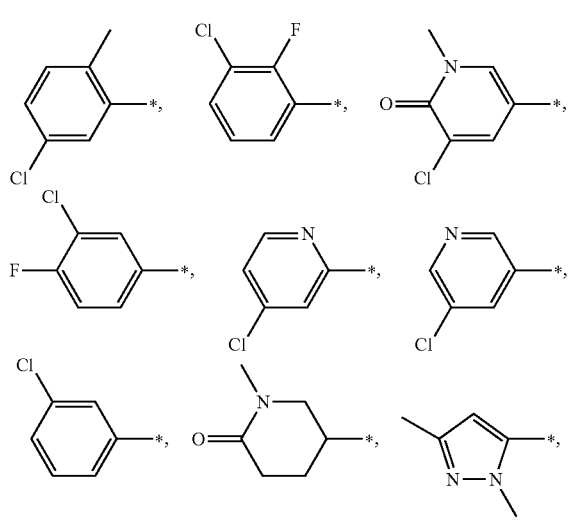

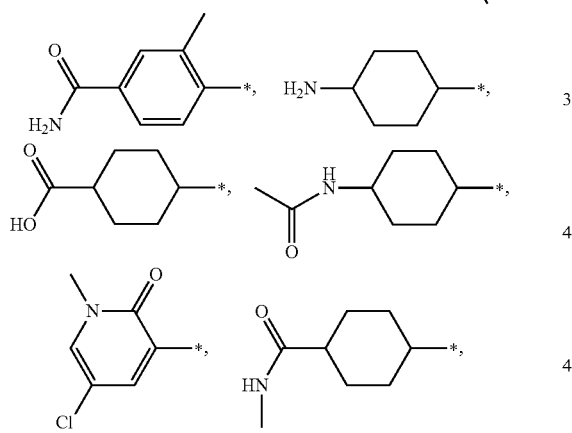

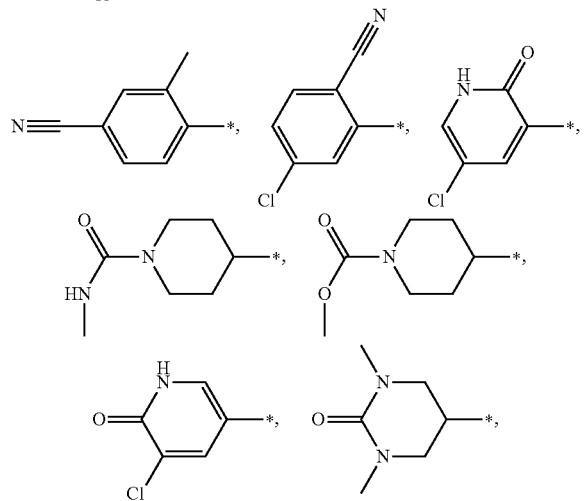

-continued

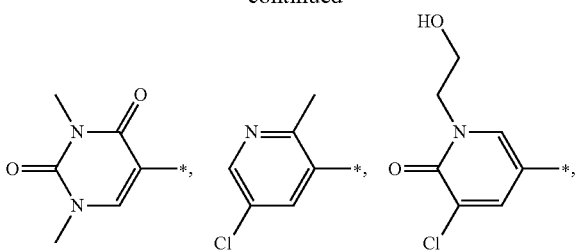

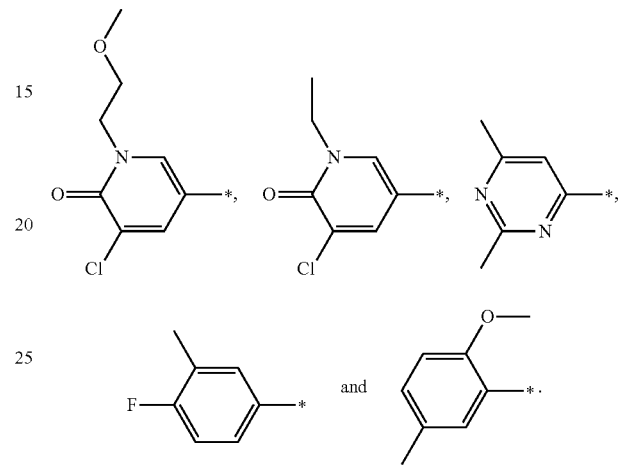

In a further embodiment, A is selected from:

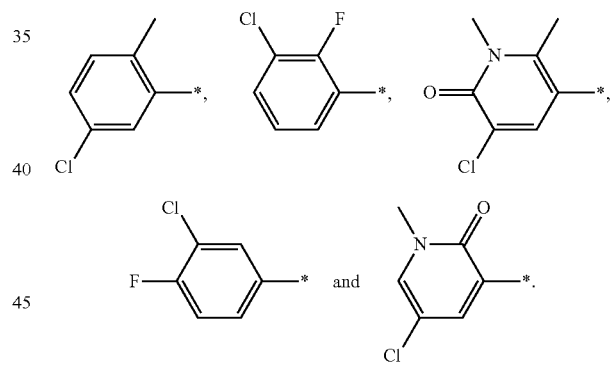

In a still further embodiment, A is selected from:

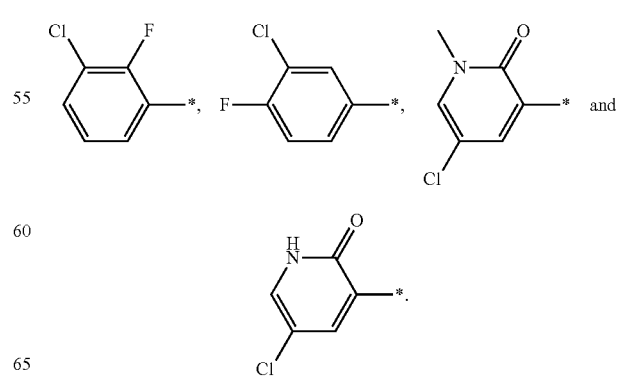

In another embodiment, when A is

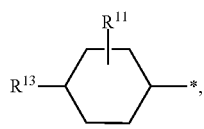

the stereochemistry is:

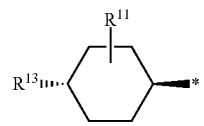

In another embodiment, B is selected from

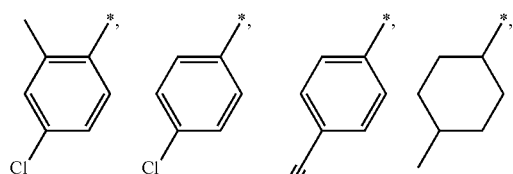

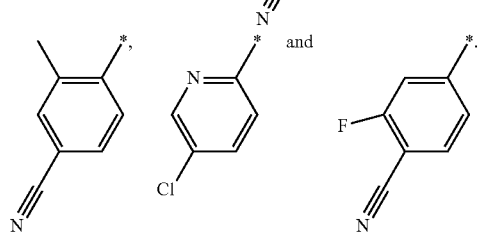

In a further embodiment, B is selected from:

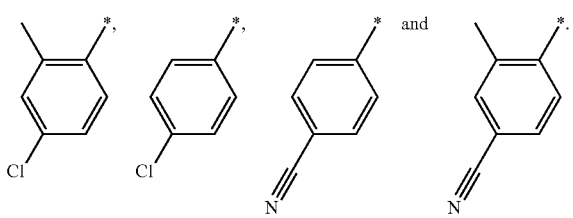

In a still further embodiment, B is selected from:

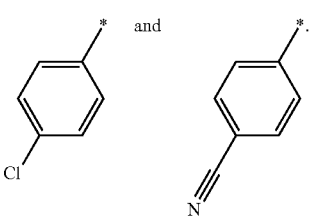

In another embodiment, each $R^1$ is independently selected from chloro, fluoro and methyl.

In another embodiment, $R^2$ is selected from chloro and cyano.

In another embodiment, $R^3$ is selected from isopropyl, cyclobutyl, cyclopropyl, 2-methoxy-1-methyl-ethyl and 2-hydroxy-1-methyl-ethyl.

In another embodiment $R^3$ is selected from isopropyl and

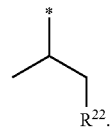

In a particular embodiment, when $R^3$ is

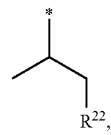

the stereochemistry is

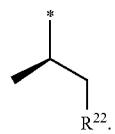

In another particular embodiment, when $R^3$ is

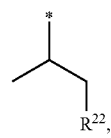

the stereochemistry is

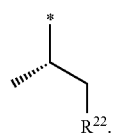

In a still further embodiment, $R^3$ is isopropyl or 1-methoxypropan-2-yl, in particular isopropyl.

In another embodiment $R^4$ is selected from

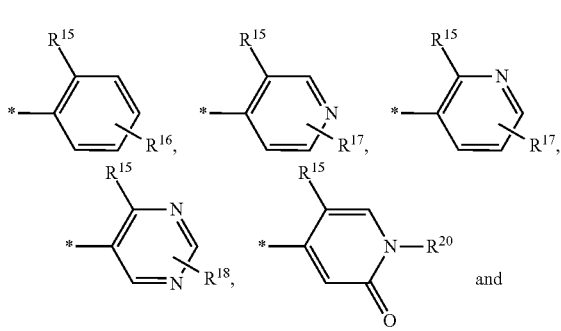

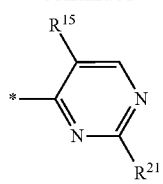

In a further embodiment, $R^4$ is selected from

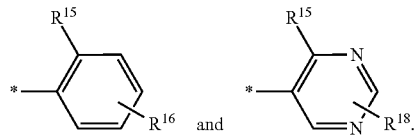

In a further embodiment, $R^4$ is selected from:

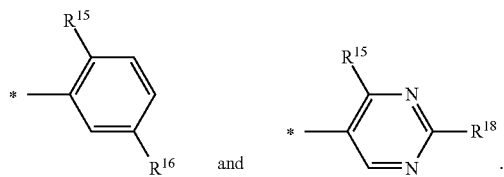

In a still further embodiment, $R^4$ is selected from

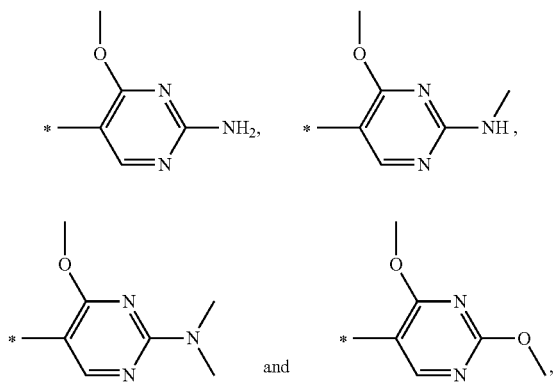

in particular

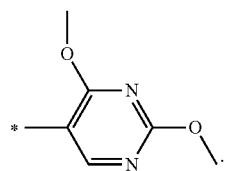

As discussed herein, the terms "compounds of the present invention" or a "compound of formula (I)" include isotopically labeled compounds, such as deuterium substitutions. As such the invention includes a compound of formula (I) wherein $R^4$ is:

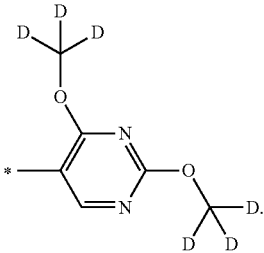

In another embodiment, when $R^4$ is selected from a group which is or includes:

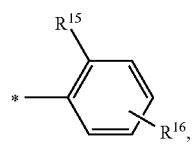

$R^{16}$ is substituted at the following positions:

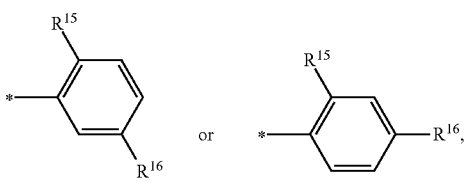

in particular

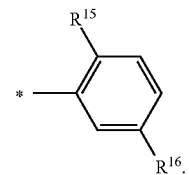

In another embodiment, when $R^4$ is selected from a group which is or includes:

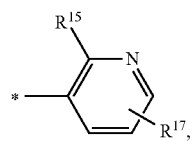

$R^{17}$ is substituted at the following positions:

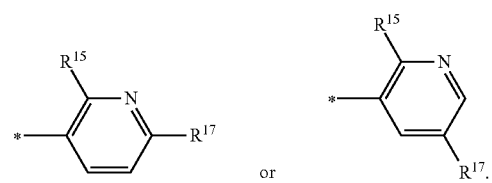

In another embodiment, when $R^4$ is selected from a group which is or includes:

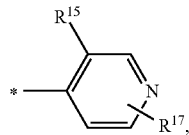

$R^{17}$ is substituted at the following position:

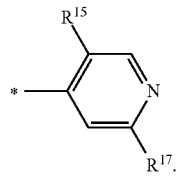

In another embodiment, when $R^4$ is selected from a group which is or includes:

$R^{18}$ is substituted at the following position:

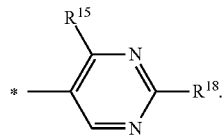

In another embodiment, $R^5$ is selected from:
H,
$(C_1-C_4)$alkyl-, said $(C_1-C_4)$alkyl- being optionally substituted with 1 or 2 substituents independently selected from OH, =O,
$(C_1-C_4)$alkyl-O—C(O)—$(CH_2)_m$—, and
cyano.
In another embodiment $R^5$ is selected from:
H,
$(C_1-C_4)$alkyl-, said $(C_1-C_4)$alkyl- being optionally substituted with 1 or 2 substituents independently selected from OH and =O, and
$(C_1-C_4)$alkyl-O—C(O)—$(CH_2)_m$—.
In a further embodiment $R^5$ is selected from H, methyl and $(C_1-C_2)$alkyl-O—C(O)—.
In a still further embodiment $R^5$ is selected from H, —C(O)—O-ethyl and methyl.
In a particular embodiment, $R^5$ is H.
In another embodiment $R^6$ is selected from:
H,
$(C_1-C_4)$alkyl-, optionally substituted with $(C_1-C_4)$alkoxy,
$(C_1-C_4)$alkoxy, optionally substituted with $(C_1-C_4)$alkoxy,
$(C_1-C_4)$alkoxy$(C_1-C_4)$alkoxy$(C_1-C_4)$alkyl-,
halo,
$R^9(R^{10})N$—C(O)—$(CH_2)_m$—,
cyano,
$R^9(R^{10})N$—$(CH_2)_m$—, and
$(C_1-C_4)$alkyl-C(O)—$(R^{10})N$—$(CH_2)_m$—.
In another embodiment $R^6$ is selected from:
H,
methyl,
methoxy,
halo,
$R^9(R^{10})N$—C(O)— and
cyano.
In a further embodiment $R^6$ is selected from:
H,
methyl,
methoxy
fluoro
chloro
cyano and
—C(O)NH$_2$.
In another embodiment $R^7$ is selected from H and $(C_1-C_4)$alkyl-, in particular H and methyl.
In another embodiment each $R^9$ is independently selected from H, methyl or ethyl;
In another embodiment each $R^{19}$ is independently selected from H and $(C_1-C_4)$alkyl wherein said $(C_1-C_4)$alkyl is optionally substituted by 1 or 2 substituents independently selected from methoxy, ethoxy, hydroxy and halo;
In another embodiment $R^{11}$ is H.
In another embodiment $R^{12}$ is H or fluoro.
In another embodiment $R^{14}$ is selected from —C(O)—NH(CH$_3$) and —C(O)OCH$_3$.
In another embodiment $R^{16}$ is selected from H, O(C$_1$-C$_4$)alkyl, halo, OCF$_3$, CN, —C(O)N(CH$_3$)$_2$, —C(O)NH(CH$_3$), —C(O)NH(CH$_2$CH$_2$OH), —C(O)NH[CH(CH$_3$)$_2$], —C(O)-morpholinyl-4-yl, hydroxy-azetidin-1-yl-carbonyl-, —CH$_2$NH$_2$, —CH$_2$NH—C(O)CH$_3$, CH$_2$OH, CH$_2$CN, methyl-imidazolyl-, —CH$_2$C(O)NH(CH$_3$), —CH$_2$C(O)N(CH$_3$)$_2$, —CH$_2$C(O)OH, —C(O)OH, —CH$_2$C(O)OCH$_3$, —C(O)NH$_2$, —CH$_2$NH—C(O)CH$_2$OH, —CH(OH)CH(CH$_3$)$_2$, —CH(OH)CH$_3$, —N(CH$_3$)—C(O)CH$_3$, —NH—C(O)CH$_3$, —CH$_2$N(CH$_3$)—C(O)CH$_3$ and NH$_2$.
In another embodiment $R^{16}$ is selected from H, OCH$_3$, halo, OCF$_3$, CN, —C(O)N(CH$_3$)$_2$, —C(O)NH(CH$_3$), —C(O)NH(CH$_2$CH$_2$OH), —C(O)NH[CH(CH$_3$)$_2$], —C(O)-morpholinyl-4-yl, hydroxy-azetidin-1-yl-carbonyl-, —CH$_2$NH$_2$, —CH$_2$NH—C(O)CH$_3$, CH$_2$OH, CH$_2$CN, methyl-imidazolyl-, —CH$_2$C(O)NH(CH$_3$), —CH$_2$C(O)N(CH$_3$)$_2$, CH$_2$C(O)OH, —C(O)OH, —CH$_2$C(O)OCH$_3$, —C(O)NH$_2$, —CH$_2$NH—C(O)CH$_2$OH, —CH(OH)CH(CH$_3$)$_2$ and —CH(OH)CH$_3$.
In another embodiment $R^{17}$ is selected from H, O(C$_1$-C$_4$)alkyl, CH$_2$CN, —CH$_2$C(O)NH(CH$_3$), —CH$_2$C(O)OCH$_2$CH$_3$, —CH$_2$C(O)OH, NH$_2$, C(O)NH$_2$, —C(O)N(CH$_3$)$_2$, C(O)NH(CH$_3$), —C(O)OCH$_3$, and —CH$_2$CN.
In a further embodiment $R^{17}$ is selected from H, OCH$_3$, CH$_2$CN, —CH$_2$C(O)NH(CH$_3$), —CH$_2$C(O)OCH$_2$CH$_3$, —CH$_2$C(O)OH, NH$_2$ and —CH$_2$CN.
In another embodiment $R^{18}$ is selected from H, O(C$_1$-C$_4$)alkyl, —CH$_2$NH$_2$, —NH(CH$_3$), —N(CH$_3$)$_2$, NH$_2$, —NCH$_3$(CH$_2$CH$_2$OH), —NH(CH$_2$CH$_2$OH), azetidin-1-yl, said azetidin-1-yl being substituted with OH or both CH$_3$ and OH.
In a further embodiment $R^{18}$ is selected from H, OCH$_3$, —CH$_2$NH$_2$, —NH(CH$_3$), —N(CH$_3$)$_2$, NH$_2$, —NCH$_3$(CH$_2$CH$_2$OH), —NH(CH$_2$CH$_2$OH), azetidin-1-yl, said azetidin-1-yl being substituted with OH or both CH$_3$ and OH.
In another embodiment $R^{19}$ is selected from H, OCH$_3$ and —C(O)N(CH$_3$)$_2$.

In another embodiment $R^{21}$ is selected from —NCH$_3$(CH$_2$CH$_2$OH), C(O)NH$_2$, CN, N(CH$_3$)$_2$ and —C(O)N(CH$_3$)$_2$.

In another embodiment, each $R^{23}$ is independently selected from H, fluoro, methyl and ethyl.

In another embodiment, when A is:

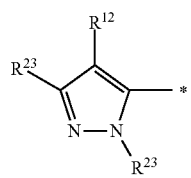

$R^{23}$ is in particular $R^{23A}$ and $R^{23B}$ as shown:

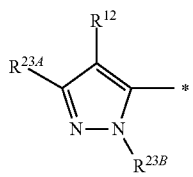

wherein $R^{23A}$ is selected from H, halo and (C$_1$-C$_4$)alkyl, and $R^{23B}$ is selected from H and (C$_1$-C$_4$)alkyl;

In another embodiment, the compound of formula (I) has the stereochemistry shown in formula (IA):

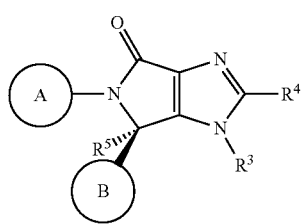

(IA)

In another embodiment, the compound of formula (I) has the stereochemistry shown in formula (IB):

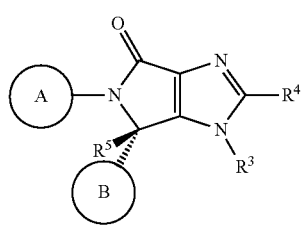

(IB)

In another embodiment heterocyclyl$^1$ is a 5 or 6 membered fully saturated monocyclic group comprising ring carbon atoms and 1 or 2 ring heteroatoms independently selected from N, O and S.

In particular heterocyclyl$^1$ is pyrrolidinyl or morpholinyl.

In another embodiment heteroaryl$^2$ is a 5 or 6 membered fully unsaturated monocyclic group comprising ring carbon atoms and 1, 2, 3 or 4 ring N heteroatoms. In particular, heteroaryl$^2$ is tetrazole or imidazole.

Described below are a number of embodiments (E) of the first aspect of the invention, where for convenience E1 is identical thereto.

E1 A compound of formula (I) as defined above, or a salt thereof.

E2 A compound of formula (I) a salt thereof according to E1, wherein A is selected from

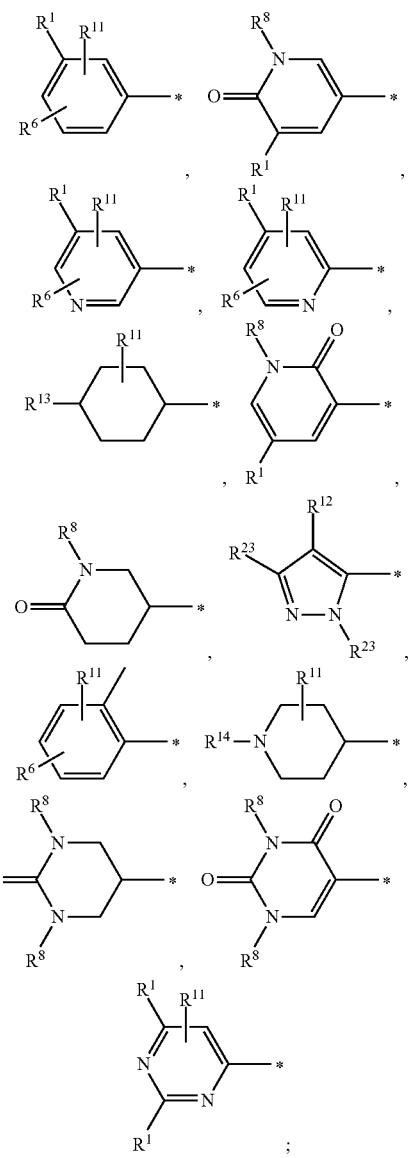

B is selected from

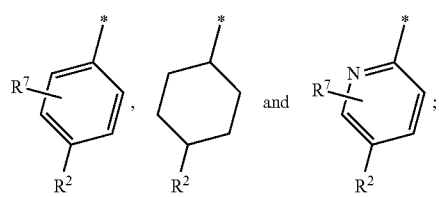

each $R^1$ is independently selected from halo and methyl;

$R^2$ is selected from chloro, fluoro, trifluoromethyl, methyl and cyano;

$R^3$ is selected from isopropyl, cyclopropyl, isobutyl, cyclobutyl and cyclopentyl, or $R^3$ is:

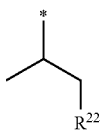

wherein $R^{22}$ is selected from OH, $OCH_3$, $NH_2$, NHMe, $NMe_2$, NHCOMe and NHCOH;

$R^4$ is selected from:

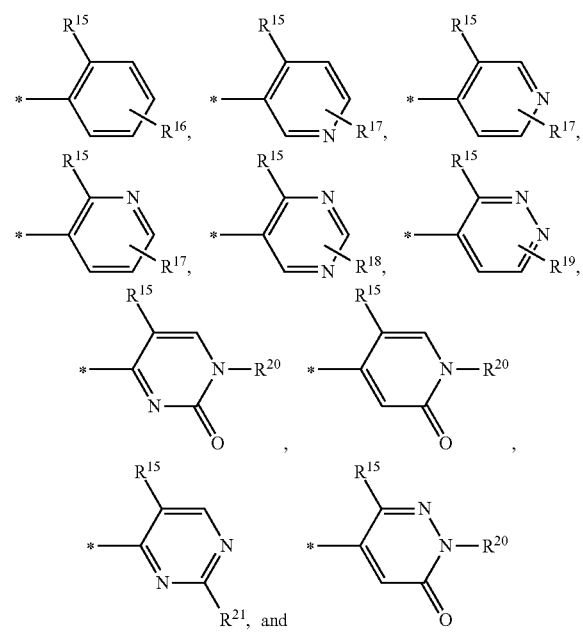

wherein $R^{15}$ is independently selected from $OCH_3$, $CH_2CH_3$, OH, $OCF_3$ and H;

$R^{16}$ is selected from H, —O—$(C_1-C_4)$alkyl, halo, $OCF_3$, CN, —C(O)$NR^9R^{10}$, —C(O)-morpholinyl-4-yl, hydroxy-azetidin-1-yl-carbonyl, —$CH_2NR^9R^{10}$, —$CH_2NR^9$—C(O)$R^{10}$, $CH_2CN$, methyl-imidazolyl-, —$CH_2C(O)NR^9R^{10}$, —$CH_2C(O)OH$, —C(O)OH, —$CH_2C(O)O$—$(C_1-C_4)$alkyl, —$N(R^9)$—C(O)—$(C_1-C_4)$alkyl, —$NR^9R^{10}$ and $(C_1-C_4)$alkyl optionally substituted by 1 or 2 OH;

$R^{17}$ is selected from H, $O(C_1-C_4)$alkyl, —$CH_2C(O)NR^9R^{10}$, —$CH_2C(O)O$—$(C_1-C_4)$alkyl, —$CH_2C(O)OH$, —$NR^9R^{16}$, —C(O)$NR^9R^{10}$, —$CH_2NR^9R^{10}$, —C(O)$OCH_3$ and —$CH_2CN$;

$R^{18}$ is selected from H, $O(C_1-C_4)$alkyl, $CH_2NR^9R^{10}$, —$NR^9R^{10}$ and azetidin-1-yl, said azetidin-1-yl being substituted with OH or both $CH_3$ and OH;

$R^{19}$ is selected from H, $O(C_1-C_4)$alkyl, $(C_1-C_4)$alkyl, —$NR^9R^{10}$, —$N(R^9)$—C(O)—$(C_1-C_4)$alkyl and —C(O)$NR^9R^{10}$;

$R^{20}$ is selected from H, $CH_3$ and —$CH_2CH_3$;

$R^{21}$ is selected from —$NR^9R^{10}$, —$CH_2NR^9R^{10}$, C(O)$NR^9R^{10}$ and CN;

$R^5$ is selected from:
H,
heterocyclyl$^1$-C(O)—$(CH_2)_n$—,
$(C_1-C_4)$alkyl-, said $(C_1-C_4)$alkyl- being optionally substituted with 1 or 2 substituents independently selected from OH, =O,
heterocyclyl$^1$-$(C_1-C_4)$alkyl-, wherein said alkyl of heterocyclyl$^1$-$(C_1-C_4)$alkyl- is optionally substituted by 1 or 2 OH, and said heterocyclyl$^1$ can be optionally substituted by methyl or ethyl,
$(C_1-C_4)$alkyl-O—C(O)—$(CH_2)_m$—, and
cyano;

$R^6$ is selected from:
H,
$(C_1-C_4)$alkyl-, optionally substituted with $(C_1-C_4)$alkoxy,
$(C_1-C_4)$alkoxy, optionally substituted with $(C_1-C_4)$alkoxy,
$(C_1-C_4)$alkoxy$(C_1-C_4)$alkoxy$(C_1-C_4)$alkyl-,
halo,
$R^9(R^{10})N$—C(O)—$(CH_2)_m$—,
cyano,
$R^9(R^{10})N$—$(CH_2)_m$—,
$R^9(R^{10})N$—$(CH_2)_n$—O—$(CH_2)_m$—,
$(C_1-C_4)$alkyl-C(O)—$(R^{10})N$—$(CH_2)_m$—,
—O—$(CH_2)_p$-heteroaryl$^2$;

$R^7$ is selected from:
H,
halo, and
$(C_1-C_4)$alkyl-, optionally substituted with $(C_1-C_4)$alkoxy;

each $R^8$ is independently selected from H, methyl, ethyl, hydroxyethyl and methoxyethyl-;

each $R^9$ is independently selected from H, methyl or ethyl;

each $R^{10}$ is independently selected from H and $(C_1-C_4)$alkyl wherein said $(C_1-C_4)$alkyl is optionally substituted by 1 or 2 substituents independently selected from methoxy, ethoxy, hydroxy and halo;

or $R^9$ and $R^{10}$, together with the N atom to which they are attached, can join to form a saturated 5 or 6 membered heterocyclic ring further comprising ring carbon atoms and optionally one ring heteroatom independently selected from N, O and S;

$R^{11}$ is H, $(C_1-C_4)$alkyl, $(C_1-C_4)$alkoxy or halo;

$R^{12}$ is H or halo;

$R^{13}$ is selected from $NH_2$, —C(O)OH, —NH(C(O)—$CH_3$) and —C(O)—NH($CH_3$);

$R^{14}$ is selected from —C(O)—$NR^9(R^{10})$, $(C_1-C_4)$alkyl, —C(O)$(C_1-C_4)$alkyl, —C(O)O$(C_1-C_4)$alkyl;

each $R^{23}$ is independently selected from H, halo and $(C_1-C_4)$alkyl;

n is 1, 2 or 3;

p is 0, 1, 2 or 3;

heterocyclyl$^1$ is a 3, 4, 5 or 6 membered fully saturated or partially unsaturated monocyclic group comprising ring carbon atoms and 1 or 2 ring heteroatoms independently selected from N, O and S;

heteroaryl$^2$ is 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;

m is 0, 1 or 2; and

* indicates the point of attachment to the remainder of the molecule.

E3 A compound or salt thereof according to E1 or E2 wherein A is selected from:

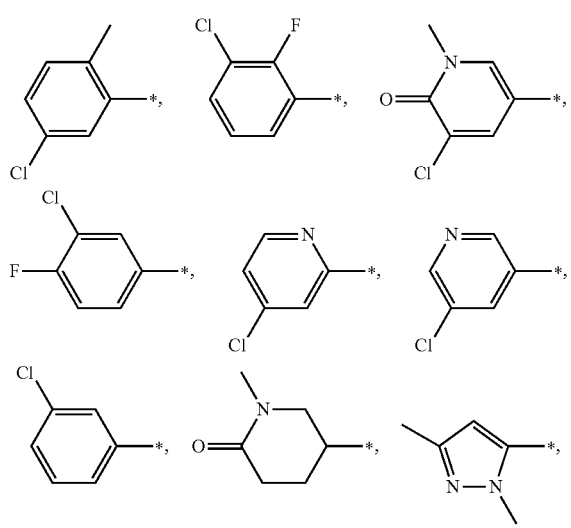
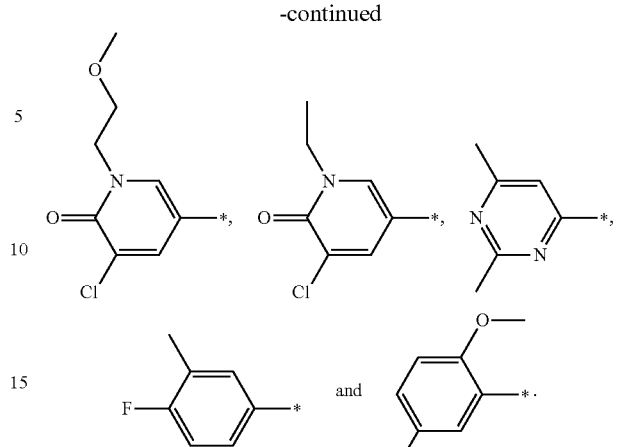
E4 A compound or salt thereof according to any of E1 to E3, wherein A is selected from:
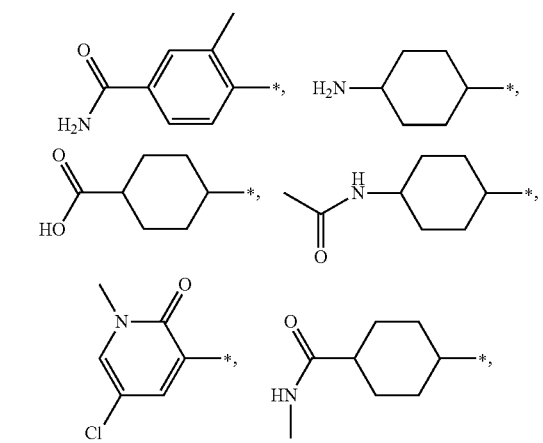
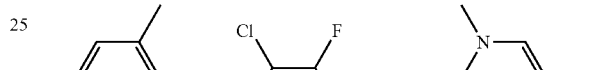
E5 A compound or salt thereof according to any of E1 to E3, wherein A is selected from:
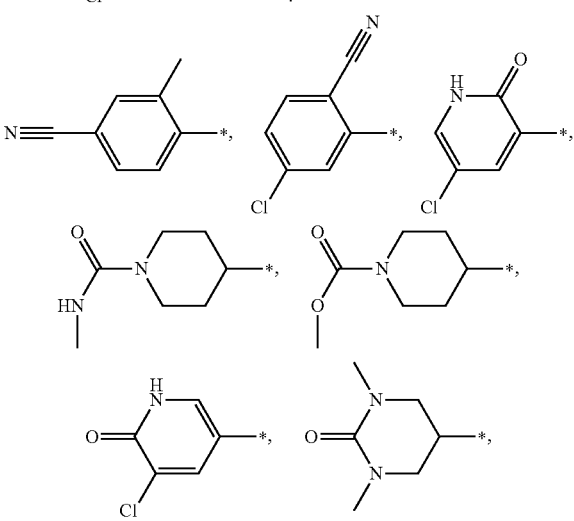
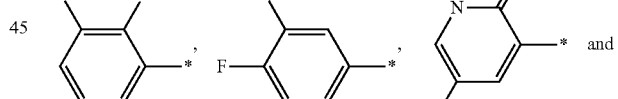
E6 A compound or salt thereof according to any of E1 to E3, wherein when A is
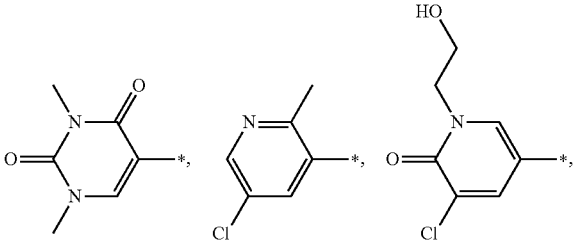
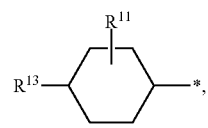

the stereochemistry is:

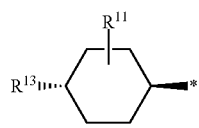

E7 A compound or salt thereof according to any of E1 to E6, wherein B is selected from

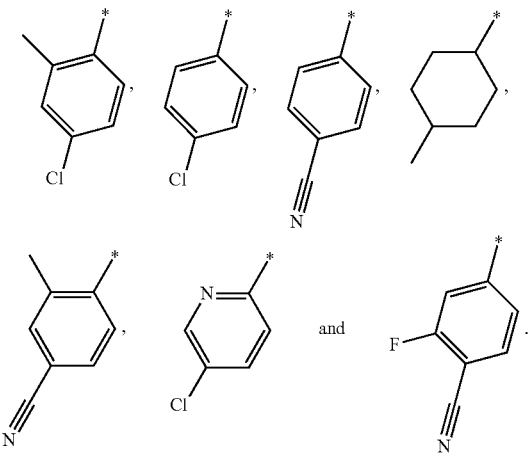

E8 A compound or salt thereof according to any of E1 to E7, wherein B is selected from:

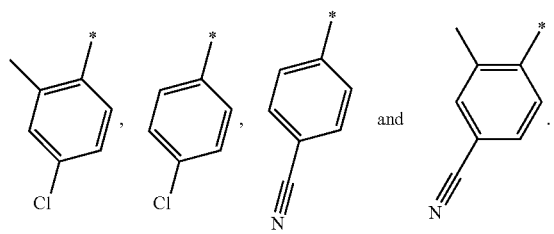

E9 A compound or salt thereof according to any of E1 to E8, wherein B is selected from:

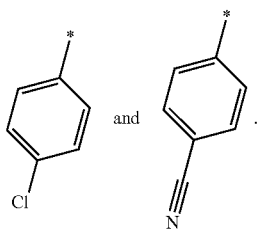 [SMILES: *c1ccc(Cl)cc1 ; *c1ccc(C#N)cc1]

E10 A compound or salt thereof according to any of E1, E2 and E7 to E9, wherein each $R^1$ is independently selected from chloro, fluoro and methyl.

E11 A compound or salt thereof according to any of E1 to E6 and E10, wherein $R^2$ is selected from chloro and cyano.

E12 A compound or salt thereof according to any of E1 to E11, wherein $R^3$ is selected from isopropyl, cyclobutyl, cyclopropyl, 2-methoxy-1-methyl-ethyl and 2-hydroxy-1-methyl-ethyl.

E13 A compound or salt thereof according to any of E1 to E12, wherein $R^3$ is selected from isopropyl and

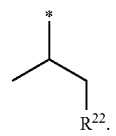

E14 A compound or salt thereof according to any of E1 to E13, wherein $R^3$ is isopropyl or 1-methoxypropan-2-yl, in particular isopropyl.

E15 A compound or salt thereof according to any of E1 to E14, wherein when $R^3$ is

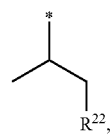

the stereochemistry is

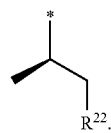

E16 A compound or salt thereof according to any of E1 to E14, wherein when $R^3$ is

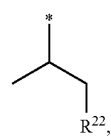

the stereochemistry is

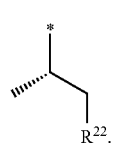

E17 A compound or salt thereof according to any of E1 to E14, wherein $R^3$ is isopropyl.

E18 A compound or salt thereof according to any of E1 to E17, wherein $R^4$ is selected from

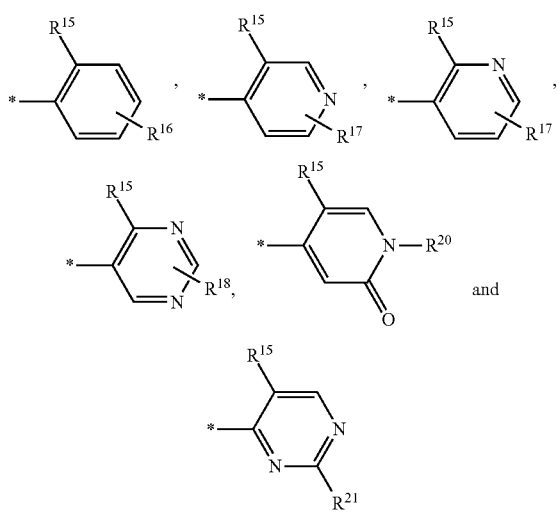

E19 A compound or salt thereof according to any of E1 to E18, wherein $R^4$ is selected from

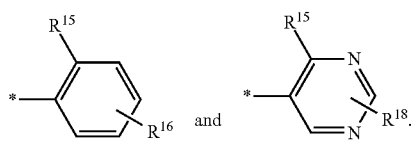

E20 A compound or salt thereof according to any of E1 to E19, wherein $R^4$ is selected from:

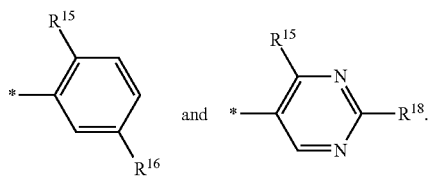

E21 A compound or salt thereof according to any of E1 to E20, wherein $R^4$ is selected from

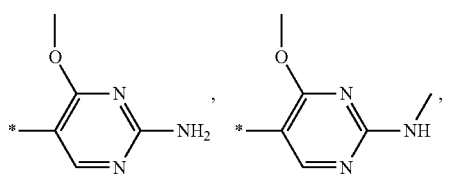

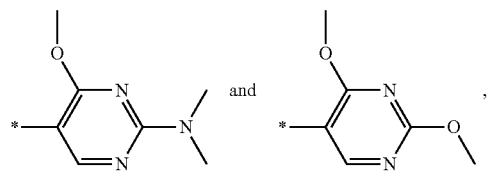

in particular

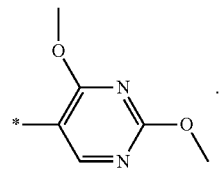 [SMILES: *c1cnc(OC)nc1OC]

E22 A compound or salt thereof according to any of E1 to E19, wherein when $R^4$ is selected from a group which is or includes:

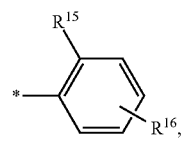

$R^{16}$ is substituted at the following positions:

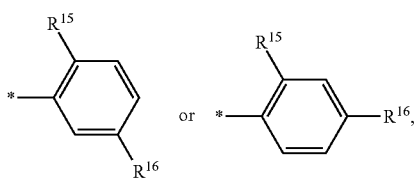

in particular

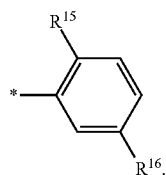

E23 A compound or salt thereof according to any of E1 to E18, wherein when $R^4$ is selected from a group which is or includes:


$R^{17}$ is substituted at the following positions:

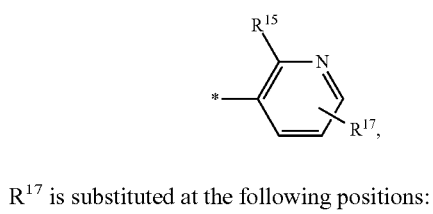

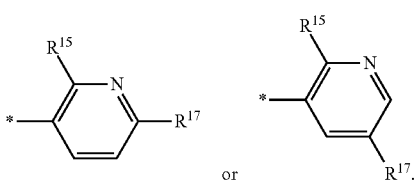

E24 A compound or salt thereof according to any of E1 to E18, wherein when $R^4$ is selected from a group which is or includes:

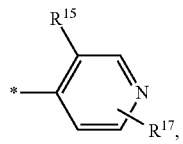

$R^{17}$ is substituted at the following position:

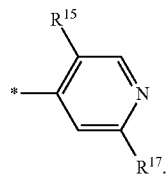

E25 A compound or salt thereof according to any of E1 to E19, wherein when $R^4$ is selected from a group which is or includes:

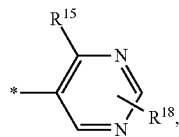

$R^{18}$ is substituted at the following position:

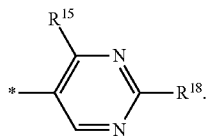

E26 A compound or salt thereof according to any of E1 to E25, wherein $R^5$ is selected from:
H,
$(C_1-C_4)$alkyl-, said $(C_1-C_4)$alkyl- being optionally substituted with 1 or 2 substituents independently selected from OH, =O,
$(C_1-C_4)$alkyl-O—C(O)—$(CH_2)_m$—, and
cyano.

E27 A compound or salt thereof according to any of E1 to E26, wherein $R^5$ is selected from:
H,
$(C_1-C_4)$alkyl-, said $(C_1-C_4)$alkyl- being optionally substituted with 1 or 2 substituents independently selected from OH and =O, and
$(C_1-C_4)$alkyl-O—C(O)—$(CH_2)_m$—.

E28 A compound or salt thereof according to any of E1 to E27, wherein $R^5$ is selected from H, methyl and $(C_1-C_2)$alkyl-O—C(O)—.

E29 A compound or salt thereof according to any of E1 to E28, wherein $R^5$ is selected from H, —C(O)—O-ethyl and methyl.

E30 A compound or salt thereof according to any of E1 to E29, wherein $R^5$ is H.

E31 A compound or salt thereof according to any of E1, E2 and E7 to E30, wherein $R^6$ is selected from:
H,
$(C_1-C_4)$alkyl-, optionally substituted with $(C_1-C_4)$alkoxy,
$(C_1-C_4)$alkoxy, optionally substituted with $(C_1-C_4)$alkoxy,
$(C_1-C_4)$alkoxy$(C_1-C_4)$alkoxy$(C_1-C_4)$alkyl-,
halo,
$R^9(R^{10})$N—C(O)—$(CH_2)_m$—,
cyano,
$R^9(R^{10})$N—$(CH_2)_m$—, and
$(C_1-C_4)$alkyl-C(O)—$(R^{10})$N—$(CH_2)_m$—.

E32: A compound or salt thereof according to any of E1, E2, and E7 to E31, wherein $R^6$ is selected from:
H,
methyl,
methoxy,
halo,
$R^9(R^{10})$N—C(O)— and
cyano.

E33 A compound or salt thereof according to any of E1, E2, and E7 to E32, wherein $R^6$ is selected from:
H,
methyl,
methoxy
fluoro
chloro
cyano and
—C(O)$NH_2$.

E34 A compound or salt thereof according to any of E1 to E6 and E10 to E33 wherein $R^7$ is selected from H and $(C_1-C_4)$alkyl-, in particular H and methyl.

E35 A compound or salt thereof according to any of E1 to E34, wherein each $R^9$ is independently selected from H, methyl and ethyl;

E36 A compound or salt thereof according to any of E1 to E34, wherein each $R^{19}$ is independently selected from H and $(C_1-C_4)$alkyl, wherein said $(C_1-C_4)$alkyl is optionally substituted by 1 or 2 substituents independently selected from methoxy, ethoxy, hydroxy and halo.

E37 A compound or salt thereof according to any of E1, E2, and E6 to E36, wherein $R^{11}$ is H.

E38 A compound or salt thereof according to any of E1, E2, and E6 to E36, wherein $R^{12}$ is H or fluoro.

E39 A compound or salt thereof according to any of E1, E2, E7 to E9, E11 to E30 and E34 to 37, wherein $R^{14}$ is selected from —C(O)—$NH(CH_3)$ and —C(O)$OCH_3$.

E40 A compound or salt thereof according to any of E1 to E20, E22 and E26 to E39, wherein $R^{16}$ is selected from H, $O(C_1-C_4)$alkyl, halo, $OCF_3$, CN, —C(O)$N(CH_3)_2$, —C(O)$NH(CH_3)$, —C(O)$NH(CH_2CH_2OH)$, —C(O)$NH[CH(CH_3)_2]$, —C(O)-morpholinyl-4-yl, hydroxy-azetidin-1-yl-carbonyl-, —$CH_2NH_2$, —$CH_2NH$—C(O)$CH_3$, $CH_2OH$, $CH_2CN$, methyl-imidazolyl-, —$CH_2C(O)NH(CH_3)$, —$CH_2C(O)N(CH_3)_2$, —$CH_2C(O)OH$, —C(O)OH, —$CH_2C(O)OCH_3$, —C(O)$NH_2$, —$CH_2NH$—C(O)$CH_2OH$, —CH(OH)CH$(CH_3)_2$, —CH(OH)$CH_3$, —N(CH_3)—C(O)$CH_3$, —NH—C(O)$CH_3$, —$CH_2N(CH_3)$—C(O)$CH_3$ and $NH_2$.

E41 A compound or salt thereof according any of E1 to E20, E22 and E26 to E40, wherein $R^{16}$ is selected from H, $OCH_3$, halo, $OCF_3$, CN, —C(O)$N(CH_3)_2$, —C(O)$NH(CH_3)$, —C(O)$NH(CH_2CH_2OH)$, —C(O)$NH[CH(CH_3)_2]$, —C(O)-morpholinyl-4-yl, hydroxy-azetidin-1-yl-carbonyl-, —$CH_2NH_2$, —$CH_2NH$—C(O)$CH_3$, $CH_2OH$, $CH_2CN$, methyl-imidazolyl-, —$CH_2C(O)NH(CH_3)$, —$CH_2C(O)N(CH_3)_2$, $CH_2C(O)OH$, —C(O)OH, —$CH_2C(O)OCH_3$, —C(O)$NH_2$, —$CH_2NH$—C(O)$CH_2OH$, —CH(OH)CH$(CH_3)_2$ and —CH(OH)$CH_3$.

E42 A compound or salt thereof according to any of E1 to E18, E23, E24 and E26 to E39, wherein $R^{17}$ is selected from H, O($C_1$-$C_4$)alkyl, $CH_2CN$, —$CH_2C(O)NH(CH_3)$, —$CH_2C(O)OCH_2CH_3$, —$CH_2C(O)OH$, $NH_2$, $C(O)NH_2$, —$C(O)N(CH_3)_2$, $C(O)NH(CH_3)$, —$C(O)OCH_3$, and —$CH_2CN$.

E43 A compound or salt thereof according to any of E1 to E18, E23, E24, E26 to E39 and E42, wherein $R^{17}$ is selected from H, $OCH_3$, $CH_2CN$, —$CH_2C(O)NH(CH_3)$, —$CH_2C(O)OCH_2CH_3$, —$CH_2C(O)OH$, $NH_2$ and —$CH_2CN$.

E44 A compound or salt thereof according to any of E1 to E20, and E25 to E39, wherein $R^{18}$ is selected from H, O($C_1$-$C_4$)alkyl, —$CH_2NH_2$, —$NH(CH_3)$, —$N(CH_3)_2$, $NH_2$, —$NCH_3(CH_2CH_2OH)$, —$NH(CH_2CH_2OH)$, azetidin-1-yl, said azetidin-1-yl being substituted with OH or both $CH_3$ and OH.

E45 A compound or salt thereof according to any of E1 to E20, E25 to E39 and E44, wherein $R^{18}$ is selected from H, $OCH_3$, —$CH_2NH_2$, —$NH(CH_3)$, —$N(CH_3)_2$, $NH_2$, —$NCH_3(CH_2CH_2OH)$, —$NH(CH_2CH_2OH)$, azetidin-1-yl, said azetidin-1-yl being substituted with OH or both $CH_3$ and OH.

E46 A compound or salt thereof according to any of E1 to E17 and E26 to E39, wherein $R^{19}$ is selected from H, $OCH_3$ and —$C(O)N(CH_3)_2$.

E47 A compound or salt thereof according to any of E1 to E18 and E26 to E39, wherein $R^{21}$ is selected from —$NCH_3(CH_2CH_2OH)$, $C(O)NH_2$, CN, $N(CH_3)_2$ and —$C(O)N(CH_3)_2$.

E48 A compound or salt thereof according to any of E1, E2, E7 to E9, E11 to E30, E34 to E36, E38 and E40 to E47 wherein each $R^{23}$ is independently selected from H, fluoro, methyl and ethyl.

E49 A compound or salt thereof according to any of E1, E2, E7 to E9, E11 to E30, E34 to E36, E38 and E40 to E48, wherein when A is:

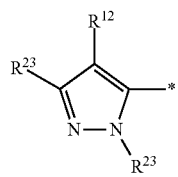

$R^{23}$ is in particular $R^{23A}$ and $R^{23B}$ as shown:

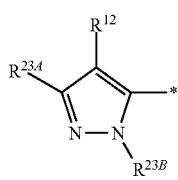

wherein $R^{23A}$ is selected from H, halo and ($C_1$-$C_4$)alkyl, and $R^{23B}$ is selected from H and ($C_1$-$C_4$)alkyl.

E50 A compound or salt thereof according to any of E1 to E49, wherein the compound of formula (I) has the stereochemistry shown in formula (IA):

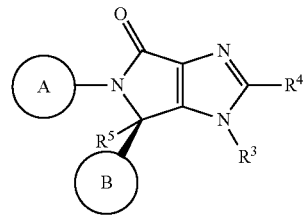

(IA)

E51 A compound or salt thereof according to any of E1 to E49, wherein the compound of formula (I) has the stereochemistry shown in formula (IB):

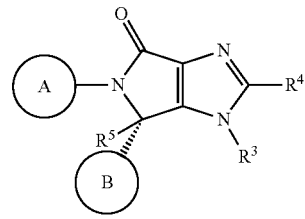

(IB)

E52 A compound of formula (I) or a salt thereof,

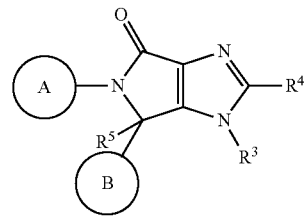

(I)

wherein
A is selected from:

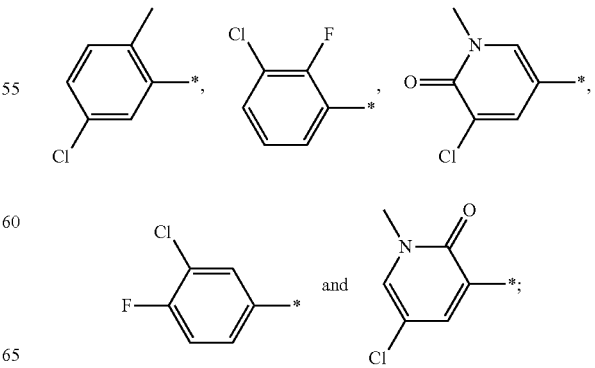

B is selected from:

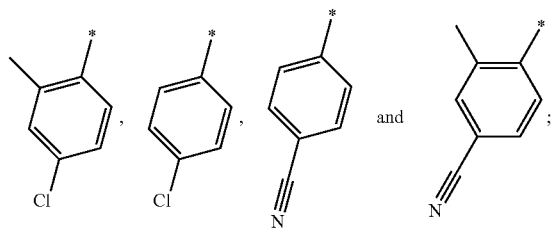

$R^3$ is isopropyl;
$R^4$ is selected from

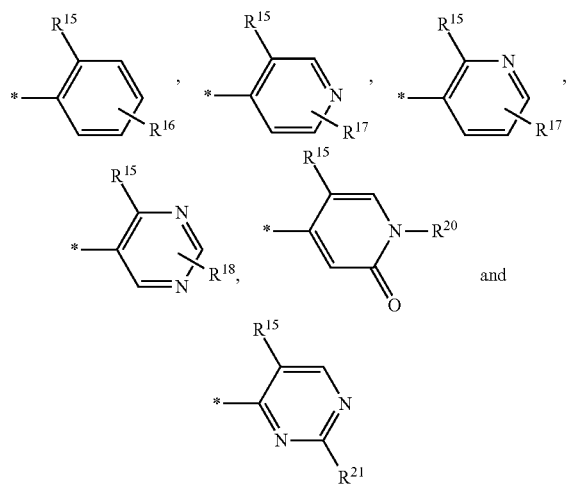

$R^5$ is H;
and $R^{15}$, $R^{16}$, $R^{17}$, $R^{18}$, $R^{20}$ and $R^{21}$ are as described in any of E1, E2, E40 to E45 and E47.

E53 A compound of formula (I) or a salt thereof according to E52, wherein $R^4$ is selected from

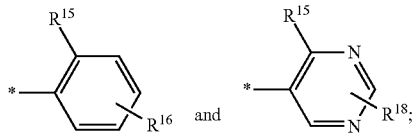

E54 A compound of formula (I) or a salt thereof according to E52 or E53, wherein $R^4$ is selected from:

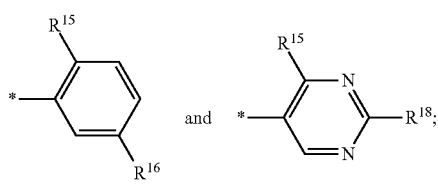

E55 A compound of formula (I) or a salt thereof according to any of E52 to E54, wherein $R^4$ is selected from

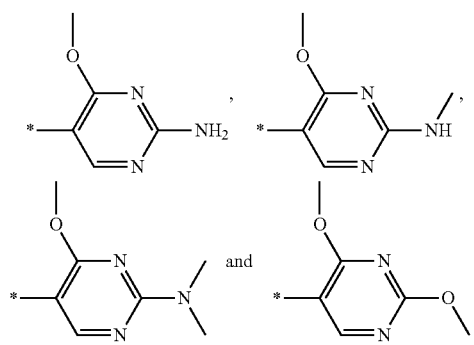

E56 A compound of formula (I) or a salt thereof according to any of E1 to E25 and E31 to E51, wherein heterocyclyl$^1$ is a 5 or 6 membered fully saturated monocyclic group comprising ring carbon atoms and 1 or 2 ring heteroatoms independently selected from N, O and S.

E57 A compound of formula (I) or a salt thereof according to any of to any of E1 to E25 and E31 to E51, E56, wherein heterocyclyl$^1$ is pyrrolidinyl or morpholinyl.

E58 A compound of formula (I) or a salt thereof according to any of to any of E1, E2, E7 to E30, E34 to E37, E40 to E47, E50 and E51, wherein heteroaryl$^2$ is a 5 or 6 membered fully unsaturated monocyclic group comprising ring carbon atoms and 1, 2, 3 or 4 ring N heteroatoms.

E59 A compound of formula (I) or a salt thereof according to any of to any of E1, E2, E7 to E30, E34 to E37, E40 to E47, E50, E51 and E58, wherein heteroaryl$^2$ is tetrazole or imidazole.

E60 A compound of formula (I) or a salt thereof, wherein A is selected from:

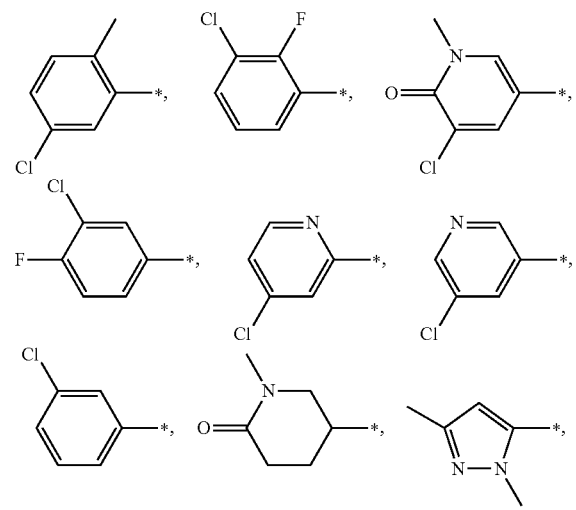

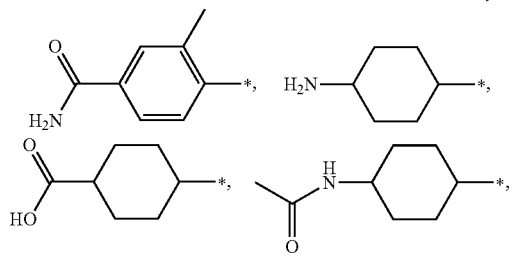

-continued

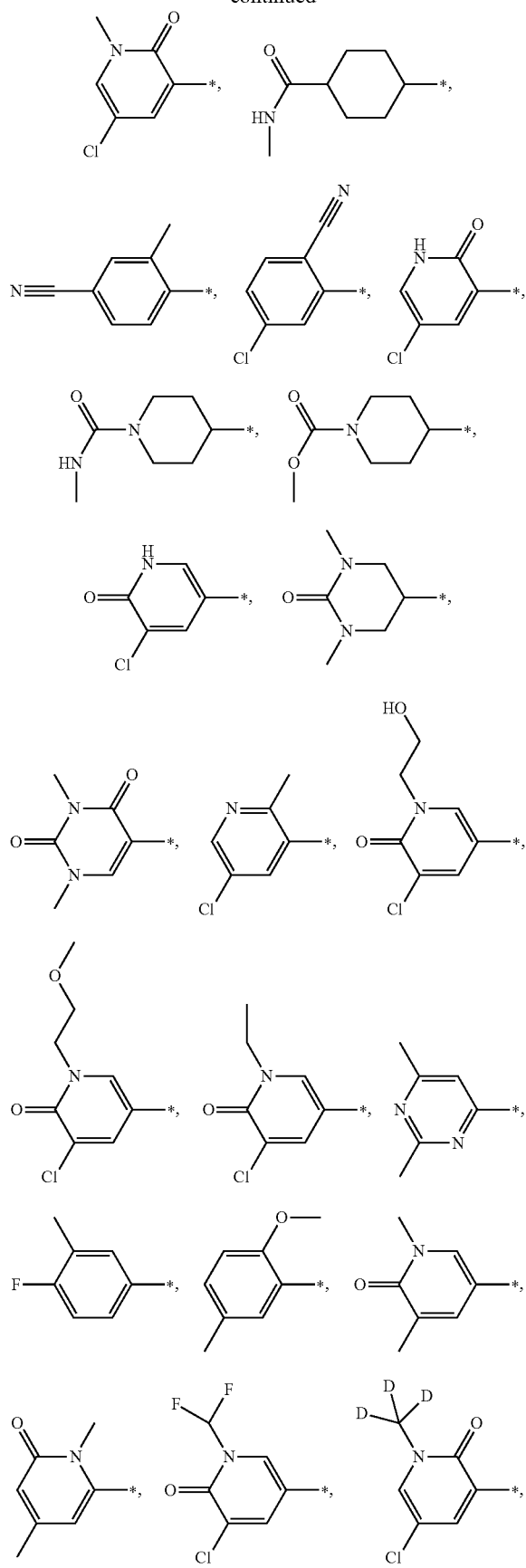

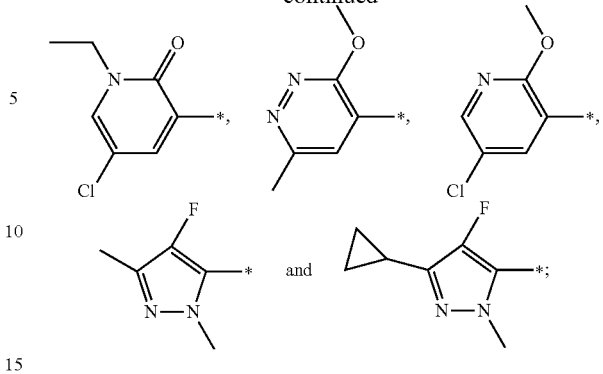

B is selected from:

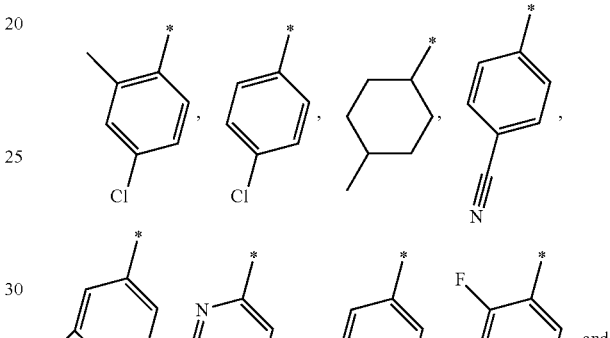

R³ is selected from isopropyl, cyclobutyl, cyclopropyl, 2-methoxy-1-methyl-ethyl, 2-hydroxy-1-methyl-ethyl,
R⁴ is selected from:

a.

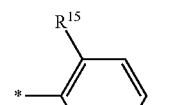

wherein $R^{15}$ is methoxy, trifluoromethoxy, ethyl, hydroxy or H, and $R^{16}$ is fluoro, H, CN, dimethylaminocarbonyl, methylaminocarbonyl, aminocarbonyl, hydroxyethylaminocarbonyl, isopropylaminocarbonyl, morpholin-4-ylcarbonyl, 3-hydroxy-azetidin-1-yl-carbonyl, aminomethyl, methylcarbonylaminomethyl, hydroxymethyl, cyanomethyl, 2-methylimidazol-4-yl, methylaminocarbonylmethyl-, dimethylaminocarbonylmethyl-, methoxycarbonylmethyl-, hydroxycarbonylmethyl-, hydroxycarbonyl-, hydroxymethylcarbonylaminomethyl-, 1-hydroxy-2-methyl-propyl- or 1-hydroxyethyl-;

b.

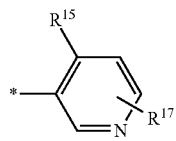

wherein $R^{15}$ is methoxy and $R^{17}$ is H;

c.

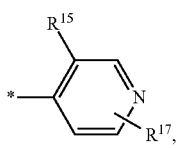

wherein $R^{15}$ is methoxy, and $R^{17}$ is H, cyanomethyl or methylaminocarbonylmethyl-;

d.

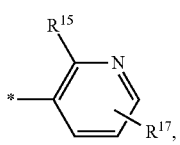

wherein $R^{15}$ is methoxy or ethyl, and $R^{17}$ is H, methoxy, cyanomethyl or ethoxycarbonylmethyl-, hydroxycarbonylmethyl- or methylaminocarbonylmethyl-;

e.

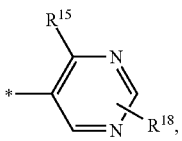

wherein $R^{15}$ is methoxy, H or OH, and $R^{18}$ is methoxy, H, methylamino-, dimethylamino-, amino; hydroxyethyl(methyl)amino-, hydroxyethylamino-, 3-hydroxy-3-methyl-azetidin-1-yl-, 3-hydroxy-azetidin-1-yl-, OH, 1,1-dioxo-1-thiomorpholin-4-yl or 3-hydroxy-piperidin-1-yl;

f.

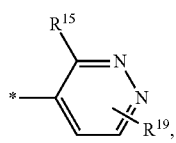

wherein $R^{15}$ is methoxy, and $R^{19}$ is methoxy or dimethylaminocarbonyl;

g.

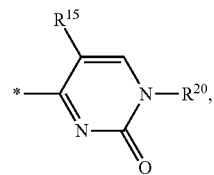

wherein $R^{15}$ is methoxy and $R^{20}$ is H;

h.

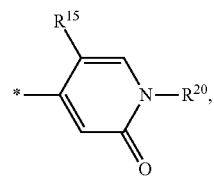

wherein $R^{15}$ is methoxy, and $R^{20}$ is methyl or ethyl;

j.

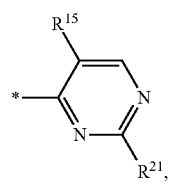

wherein $R^{15}$ is methoxy, and $R^{21}$ is methoxy, hydroxyethyl(methyl)amino, aminocarbonyl or cyano; dimethylamino, dimethylaminocarbonyl, k.

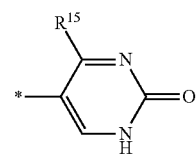

wherein $R^{15}$ is methoxy;
and l.

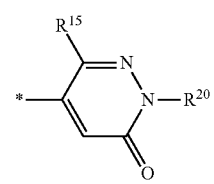

wherein $R^{15}$ is methoxy, and $R^{20}$ is methyl;
and wherein
$R^5$ is selected from H, ethoxycarbonyl and methyl.
E61 A compound of formula (I) or a salt thereof, selected from:

1: 5-(5-Chloro-2-methyl-phenyl)-6-(4-chloro-2-methyl-phenyl)-2-(5-fluoro-2-methoxy-phenyl)-1-isopropyl-4-oxo-5,6,-dihydro-1H-pyrrolo[3,4-d]imidazol-4-one 2: 5-(5-Chloro-2-methyl-phenyl)-6-(4-chloro-2-methyl-phenyl)-2-(6-fluoro-2-methoxy-phenyl)-1-isopropyl-4-oxo-5,6,-dihydro-1H-pyrrolo[3,4-d]imidazol-4-one 3: 5-(5-Chloro-2-methyl-phenyl)-6-(4-chloro-2-methyl-phenyl)-1-isopropyl-2-(2-trifluoromethoxy-phenyl)-5,6,-dihydro-1H-pyrrolo[3,4-d]imidazol-4-one 4: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidaol-2-yl]-4-methoxy-benzonitrile 5: 5-(5-Chloro-2-methyl-phenyl)-6-(4-chloro-2-methyl-phenyl)-1-isopropyl-2-(2-methoxy-phenyl)-5,6,-dihydro-1H-pyrrolo[3,4-d]imidazol-4-one 6: 5-(5-Chloro-2-methyl-phenyl)-6-(4-chloro-2-methyl-phenyl)-2-(4-methoxy-pyridin-3-yl)-1-isopropyl-5,6,-dihydro-1H-pyrrolo[3,4-d]imidazol-4-one 7: 5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one 8: 5-(5-Chloro-2-methyl-phenyl)-6-(4-chloro-2-methyl-phenyl)-2-(2-methoxy-pyridin-3-yl)-1-isopropyl-5,6,-dihydro-1H-pyrrolo[3,4-d]imidazol-4-one 9: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N,N-dimethyl benzamide 10: 5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N-methyl benzamide 11: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-N-(2-hydroxyethyl)-4-methoxy-benzamide 12: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-N-isopropyl-4-methoxy-benzamide 13: 5-(5-Chloro-2-methyl-phenyl)-6-(4-chloro-2-methyl-phenyl)-1-isopropyl-2-[2-methoxy-5-(morpholine-4-carbonyl)-phenyl]-5,6-dihydro-1H-pyrrolo[3,4-d]imidazol-4-one 14: 5-(5-Chloro-2-methyl-phenyl)-6-(4-chloro-2-methyl-phenyl)-2-[5-(3-hydroxy-azetidine-1-carbonyl)-2-methoxy-phenyl]1-isopropyl-5,6-dihydro-1H-pyrrolo[3,4-d]imidazol-4-one 15: 5-(5-Chloro-2-methyl-phenyl)-6-(4-chloro-2-methyl-phenyl)-1-isopropyl-2-(3-methoxy-pyridin-4-yl)-5,6,-dihydro-1H-pyrrolo[3,4-d]imidazol-4-one 16: 2-(5-Amino methyl-2-methoxy-phenyl-5-(5-chloro-2-methyl-phenyl)-6-(4-chloro-2-methyl-phenyl)-1-isopropyl-5,6-dihydro-1H-pyrrolo[3,4-d]imidazole-4-one 17: N-{3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-benzyl}-acetamide 18: 5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one 19: 5-(5-Chloro-2-methyl-phenyl)-6-(4-chloro-phenyl)-2-(5-hydroxymethyl-2-methoxy-phenyl)-1-isopropyl-5,6-dihydro-1H-pyrrolo[3,4-d]imidazole-4-one 20: 5-(3-Chloro-2-fluoro-phenyl)-6-(4-chloro-phenyl)-2-(5-hydroxymethyl-2-methoxy-phenyl)-1-isopropyl-5,6-dihydro-1H-pyrrolo[3,4-d]imidazole-4-one 21: 5-(5-Chloro-2-methyl-phenyl)-6-(4-chloro-phenyl)-2-(4-hydroxymethyl-2-methoxy-phenyl)-1-isopropyl-5,6-dihydro-1H-pyrrolo[3,4-d]imidazole-4-one 22: 5-(5-Chloro-2-methyl-phenyl)-6-(4-chloro-2-methyl-phenyl)-2-(4-hydroxymethyl-2-methoxy-phenyl)-1-isopropyl-5,6-dihydro-1H-pyrrolo[3,4-d]imidazole-4-one 23: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl benzamide 24: 3-[5-(5-Chloro-2-methyl-phenyl)-6-(4-chloro-phenyl)-1-isopropyl-4-oxo-1,4,5,6-tetrahydro-pyrrolo[3,4-d]imidaol-2-yl]-4-methoxy-benzonitrile 25: 5-(5-Chloro-2-methyl-phenyl)-6-(4-chloro-phenyl)-1-isopropyl-2-[2-methoxy-5-(morpholine-4-carbonyl)-phenyl]-5,6-dihydro-1H-pyrrolo[3,4-d]imidazol-4-one 26: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzonitrile 27: 5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazole-4-one 28: 5-(5-Chloro-2-methyl-phenyl)-6-(4-chloro-phenyl)-2-(3,6-pyridazin-4-yl)-1-isopropyl-5,6-dihydro-1H-pyrrolo[3,4-d]imidazole-4-one 29: 5-(5-Chloro-2-methyl-phenyl)-6-(4-chloro-2-methyl-phenyl)-2-(2,6-dimethoxy-pyridin-3-yl)-1-isopropyl-5,6-dihydro-1H-pyrrolo[3,4-d]imidazol-4-one 30: 5-(5-Chloro-2-methyl-phenyl)-6-(4-chloro-2-methyl-phenyl)-1-isopropyl-2-(4-methoxy-pyrimidin-5-yl)-5,6-dihydro-1H-pyrrolo[3,4-d]imidazol-4-one 31: 5-(5-Chloro-2-methyl-phenyl)-6-(4-chloro-phenyl)-1-isopropyl-2-(4-methoxy-2-methylamino-pyrimidin-5-yl)-5,6-dihydro-1H-pyrrolo[3,4-d]imidazol-4-one 32: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one 33: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one 34: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-ethyl-benzonitrile 35: 5-(5-Chloro-2-methyl-phenyl)-6-(4-chloro-2-methyl-phenyl)-2-(2-dimethylamino-4-methoxy-pyrimidin-5-yl)-1-isopropyl-5,6-dihydro-1H-pyrrolo[3,4-d]imidazol-4-one 36: 5-(5-Chloro-2-methyl-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 37: 2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one 38: 5-(5-Chloro-2-methyl-phenyl)-6-(4-chloro-phenyl)-2-{2-[(2-hydroxy-ethyl)-methyl-amino]-4-methoxy-pyrimidin-5-yl}-1-isopropyl-5,6-dihydro-1H-pyrrolo[3,4-d]imidazol-4-one 39: 5-(5-Chloro-2-methyl-phenyl)-6-(4-chloro-phenyl)-2-[2-(2-hydroxy-ethyl amino)-4-methoxy-pyrimidin-5-yl]-1-isopropyl-5,6-dihydro-1H-pyrrolo[3,4-d]imidazol-4-one 40: 4-[2-(2-Amino-4-methoxy-pyrimidin-5-yl)-5-(5-chloro-2-methyl-phenyl)-3-isopropyl-6-oxo-3,4,5,6-tetrahydro-pyrrolo[3,4-d]imidazol-4-yl]-benzonitrile 41: 4-[5-(5-Chloro-2-methyl-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile 42: 4-[5-(5-Chloro-2-methyl-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 43: 4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 44: 4-[5-(5-Chloro-1-methyl-6-oxo-1,6-dihydro-pyridin-3-yl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile 45: 4-[2-(2-Amino-4-methoxy-pyrimidin-5-yl)-5-(5-chloro-1-methyl-6-oxo-1,6-dihydro-pyridin-3-yl)-3-isopropyl-6-oxo-3,4,5,6-tetrahydro-pyrrolo[3,4-d]imidazol-4-yl]-benzonitrile 46: 5-(5-Chloro-2-methyl-phenyl)-6-(4-chloro-2-methyl-phenyl)-1-isopropyl-2-(4-methoxy-2-methylamino-pyrimidin-5-yl)-5,6-dihydro-1H-pyrrolo[3,4-d]imidazol-4-one 47: 5-(5-Chloro-2-methyl-phenyl)-6-(4-chloro-2-methyl-phenyl)-2-(2-ethyl-6-methoxy-pyridin-3-yl)-1-isopropyl-5,6-dihydro-1H-pyrrolo[3,4-d]imidazol-4-one 48: 2-(2-Amino-4-methoxy-pyrimidin-5-yl)-5-(5-chloro-2-methyl-phenyl)-6-(4-chloro-2-methyl-phenyl)-1-isopropyl-5,6-dihydro-1H-pyrrolo[3,4-d]imidazol-4-one 49: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-ethyl-benzonitrile 50: 5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-d]imidazol-4-one 51: 5-(5-Chloro-2-methyl-phenyl)-6-(4-chloro-2-methyl-phenyl)-2-{2-[(2-hydroxy-ethyl)-methyl-amino]-4-methoxy-pyrimidin-5-yl}-1-isopropyl-5,6-dihydro-1H-pyrrolo[3,4-d]imidazol-4-one 52: 5-(5-Chloro-2-methyl-phenyl)-6-(4-chloro-2-methyl-phenyl)-2-[2-(2-hydroxy-ethyl amino)-4-methoxy-pyrimidin-5-yl]-1-isopropyl-5,6-dihydro-1H-pyrrolo[3,4-d]imidazol-4-one 53: 4-[2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile 54: 4-[5-(3-Chloro-2-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile 55: 4-[5-(3-Chloro-2-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 56: 4-[2-(2-Amino-4-methoxy-pyrimidin-5-yl)-5-(3-chloro-4-fluoro-phenyl)-3-isopropyl-6-oxo-3,4,5,6-tetrahydro-pyrrolo[3,4-d]imidazol-4-yl]-benzonitrile 57: 4-[5-(3-Chloro-4-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile 58: 4-[5-(3-Chloro-4-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 59: 5-(5-Chloro-2-methyl-phenyl)-6-(4-chloro-phenyl)-2-[2-(3-hydroxy-3-methyl-azetidin-1-yl)-4-methoxy-pyrimidin-5-yl]-1-isopropyl-5,6-dihydro-1H-pyrrolo[3,4-d]imidazol-4-one 60: 5-(5-Chloro-2-methyl-phenyl)-6-(4-chloro-2-methyl-phenyl)-2-[2-(3-hydroxy-3-methyl-azetidin-1-yl)-4-methoxy-pyrimidin-5-yl]-1-isopropyl-5,6-dihydro-1H-pyrrolo[3,4-d]imidazol-4-one 61: 5-(5-Chloro-2-methyl-phenyl)-6-(4-chloro-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one 62: 5-(5-Chloro-2-methyl-phenyl)-6-(4-chloro-2-methyl-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one 63: 2-(4-Amino methyl-2-methoxy-phenyl-5-(5-chloro-2-methyl-phenyl)-6-(4-chloro-phenyl)-1-isopropyl-5,6-dihydro-1H-pyrrolo[3,4-d]imidazole-4-one 64: 5-(3-Chloro-2-fluoro-phenyl)-6-(4-chloro-2-methyl-phenyl)-1-isopropyl-2-(2-methoxy-phenyl)-5,6-dihydro-1H-pyrrolo[3,4-d]imidazole-4-one 65: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 66: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 67: 2-(2-Amino-4-methoxy-pyrimidin-5-yl)-5-(5-chloro-1-methyl-6-oxo-1,6-dihydro-pyridin-3-yl)-6-(4-chloro-phenyl)-1-isopropyl-5,6-dihydro-1H-pyrrolo[3,4-d]imidazol-4-one 68: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide 69: 5-(3-Chloro-2-fluoro-phenyl)-6-(4-chloro-phenyl)-1-isopropyl-2-[2-methoxy-5-(morpholine-4-carbonyl)phenyl]-5,6-dihydro-1H-pyrrolo[3,4-d]imidazole-4-one 70: 3-[5-(3-Chloro-2-fluoro-phenyl)-6-(4-chloro-phenyl)-1-isopropyl-4-oxo-1,4,5,6-tetrahydropyrrolo[3,4-d]imidazol-2-yl]-4-methoxy-N,N-dimethyl benzamide 71: 6-(4-Chloro-2-methyl-phenyl)-5-(4-chloro-pyrimidin-2-yl)-1-isopropyl-2-(2-methoxy-phenyl)-5,6,-dihydro-1H-pyrrolo[3,4-d]imidazol-4-one 72: 6-(4-Chloro-phenyl)-5-(5-chloro-pyridin-3-yl)-2-(2,4-dimethoxy-pyrimidin-5-yl)-1-isopropyl-5,6-dihydro-1H-pyrrolo[3,4-d]imidazole-4-one 73: 3-[5-(3-Chloro-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl benzamide 74: 4-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N,N-dimethyl benzamide 75: (S)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one 76: (R)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one 77: 4-[5-(5-Chloro-2-methyl-phenyl)-3-isopropyl-2-(2-methoxy-phenyl)-6-oxo-3,4,5,6-tetrahydro-pyrrolo[3,4-d]imidazol-4-yl]-benzonitrile 78: 4-[5-(5-Chloro-2-methyl-phenyl)-2-(2-hydroxy-phenyl)-3-isopropyl-6-oxo-3,4,5,6-tetrahydro-pyrrolo[3,4-d]imidazol-4-yl]-benzonitrile 79: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 80: 4-[5-(3-Chloro-4-fluoro-phenyl)-3-isopropyl-2-(2-methoxy-phenyl)-6-oxo-3,4,5,6-tetrahydro-pyrrolo[3,4-d]imidazol-4-yl]-benzonitrile 81: 3-[5-(3-Chloro-4-fluoro-phenyl)-6-(4-cyano-phenyl)-1-isopropyl-4-oxo-1,4,5,6-tetrahydro-pyrrolo[3,4-d]imidazol-2-yl]-4-methoxy-N,N-dimethyl-benzamide 82: 4-[5-(3-Chloro-4-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 83: 6-(4-Chloro-phenyl)-1-isopropyl-2-(2-methoxy-phenyl)-5-(1-methyl-6-oxo-piperidin-3-yl)-5,6-dihydro-1H-pyrrolo[3,4-d]imidazol-4-one 84: 6-(4-Chloro-phenyl)-2-(2,4-dimethoxy-pyrimidin-5-yl)-1-isopropyl-5-(1-methyl-6-oxo-piperidin-3-yl)-5,6-dihydro-1H-pyrrolo[3,4-d]imidazol-4-one 85: 5-(3-Chloro-4-fluoro-phenyl)-6-(4-chloro-phenyl)-1-cyclobutyl-2-(2,4-dimethoxy-pyrimidin-5-yl)-5,6-dihydro-1H-pyrrolo[3,4-d]imidazol-4-one 86: 5-(5-Chloro-2-methyl-phenyl)-6-(4-chloro-phenyl)-1-cyclobutyl-2-(2,4-dimethoxy-pyrimidin-5-yl)-5,6-dihydro-1H-pyrrolo[3,4-d]imidazol-4-one 87: 4-[5-(3-Chloro-4-fluoro-phenyl)-3-cyclobutyl-2-(2,4-dimethoxy-pyrimidin-5-yl)-6-oxo-3,4,5,6-tetrahydro-pyrrolo[3,4-d]imidazol-4-yl]-benzonitrile 88: 5-(3-Chloro-4-fluoro-phenyl)-6-(4-chloro-phenyl)-1-cyclopropyl-2-(2,4-dimethoxy pyrimidin-5-yl)-5,6-dihydro-1H-pyrrolo[3,4-d]imidazol-4-one 89: (S)-5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one 90: (R)-5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one 91: 6-(4-Chloro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-d]imidazol-4-one 92: 6-(4-Chloro-phenyl)-2-(2,4-dimethoxy-pyrimidin-5-yl)-5-(2,5-dimethyl-2H-pyrazol-3-yl)-1-isopropyl-5,6-dihydro-1H-pyrrolo[3,4-d]imidazol-4-one 93: {4-[5-(3-Chloro-2-fluoro-phenyl)-6-(4-chloro-2-methyl-phenyl)-1-isopropyl-4-oxo-1,4,5,6-tetrahydro-pyrrolo[3,4-d]imidazol-2-yl]-5-methoxy-pyridin-2-yl}-acetonitrile 94: 4-[6-(4-Chloro-phenyl)-2-(2-dimethylamino-4-methoxy-pyrimidin-5-yl)-1-isopropyl-4-oxo-4,6-dihydro-1H-pyrrolo[3,4-d]imidazol-5-yl]-3-methyl-benzamide 95: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-3-methyl-benzamide 96: 5-(3-Chloro-2-fluoro-phenyl)-6-(4-chloro-phenyl)-1-isopropyl-2-(5-methoxy-2-oxo-1,2-dihydro-pyrimidin-4-yl)-5,6-dihydro-1H-pyrrolo[3,4-d]imidazol-4-one 97: 5-(4-Amino-cyclohexyl)-6-(4-chloro-phenyl)-2-(2,4-dimethoxy-pyrimidin-5-yl)-1-isopropyl-5,6-dihydro-1H-pyrrolo[3,4-d]imidazol-4-one 98: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid 99: N-{4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexyl}-acetamide 100: 4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 101: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 102: (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 103: (R)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 104: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid methylamide 105: 5-(3-Chloro-4-fluoro-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one 106: {4-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-5-methoxy-pyridin-2-yl}-acetonitrile 107: {4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile 108: {4-[5-(5-Chloro-1-methyl-2-oxo-1,2-dihydro-pyridin-3-yl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile 109: 5-(3-Chloro-2-fluoro-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one 110: 5-(5-Chloro-2-methyl-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one 111: 5-(5-Chloro-2-methyl-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one 112: 5-(3-Chloro-4-fluoro-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one 113: 5-(5-Chloro-2-methyl-phenyl)-6-(4-chloro-phenyl)-2-(2-dimethylamino-4-methoxy-pyrimidin-5-yl)-1-((R)-2-hydroxy-1-methyl-ethyl)-5,6-dihydro-1H-pyrrolo[3,4-d]imidazol-4-one 114: 5-(3-Chloro-2-fluoro-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one 115: 5-(5-Chloro-2-methyl-phenyl)-2-(2,4-dimethoxy-pyrimidin-5-yl)-1-isopropyl-6-(4-methyl-cyclohexyl)-5,6-dihydro-1H-pyrrolo[3,4-d]imidazol-4-one 116: 4-(4-Chloro-2-methyl-phenyl)-5-(5-chloro-2-methyl-phenyl)-2-(2,4-dimethoxy-pyrimidin-5-yl)-3-isopropyl-6-oxo-3,4,5,6-tetrahydro-pyrrolo[3,4-d]imidazole-4-carboxylic acid ethyl ester 117: 5-(5-Chloro-2-methyl-phenyl)-6-(4-chloro-phenyl)-2-(2,4-dimethoxy-pyrimidin-5-yl)-1-((R)-2-hydroxy-1-methyl-ethyl)-5,6-dihydro-1H-pyrrolo[3,4-d]imidazol-4-one 118: 4-[2-(2-Amino-4-methoxy-pyrimidin-5-yl)-6-(4-chloro-phenyl)-1-isopropyl-4-oxo-4,6-dihydro-1H-pyrrolo[3,4-d]imidazol-5-yl]-3-methyl-benzonitrile 119: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-3-methyl-benzonitrile 120: 4-Chloro-2-[6-(4-chloro-phenyl)-2-(2,4-dimethoxy-pyrimidin-5-yl)-1-isopropyl-4-oxo-4,6-dihydro-1H-pyrrolo[3,4-d]imidazol-5-yl]-benzonitrile 121: 5-(5-Chloro-2-methyl-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one 122: 5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 123: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid methylamide 124: 4-[5-(5-Chloro-1-methyl-2-oxo-1,2-dihydro-pyridin-3-yl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 125: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid methyl ester 126: 2-{4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-N-methyl-acetamide 127: 5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 128: 2-(2-Amino-4-methoxy-pyrimidin-5-yl)-6-(4-chloro-phenyl)-5-(1,3-dimethyl-2-oxo-hexahydro-pyrimidin-5-yl)-1-isopropyl-5,6-dihydro-1H-pyrrolo[3,4-d]imidazol-4-one 129: 6-(4-Chloro-phenyl)-2-(2-dimethylamino-4-methoxy-pyrimidin-5-yl)-5-(1,3-dimethyl-2-oxo-hexahydro-pyrimidin-5-yl)-1-isopropyl-5,6-dihydro-1H-pyrrolo[3,4-d]imidazol-4-one 130: 4-[5-(3-Chloro-2-fluoro-phenyl)-2-(5-cyanomethyl-2-methoxy-phenyl)-3-isopropyl-6-oxo-3,4,5,6-tetrahydro-pyrrolo[3,4-d]imidazol-4-yl]-benzonitrile 131: 4-[5-(5-Chloro-2-methyl-phenyl)-2-(5-cyanomethyl-2-methoxy-pyridin-3-yl)-3-isopropyl-6-oxo-3,4,5,6-tetrahydro-pyrrolo[3,4-d]imidazol-4-yl]-benzonitrile 132: 4-[5-(3-Chloro-2-fluoro-phenyl)-2-(5-cyanomethyl-2-methoxy-pyridin-3-yl)-3-isopropyl-6-oxo-3,4,5,6-tetrahydro-pyrrolo[3,4-d]imidazol-4-yl]-benzonitrile 133: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetonitrile 134: 4-[5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile 135: 4-[5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile 136: {4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile 137: {5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester 138: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid 139: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carboxylic acid amide 140: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid 141: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid 142: 4-[(S)-2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile 143: 4-[(R)-2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile 144: 5-(5-Chloro-2-methyl-phenyl)-6-(4-chloro-phenyl)-1-isopropyl-2-[3-(2-methyl-3H-imidazol-4-yl)-phenyl]-5,6-dihydro-1H-pyrrolo[3,4-d]imidazol-4-one 145: 6-(4-Chloro-phenyl)-2-(2,4-dimethoxy-pyrimidin-5-yl)-5-(1,3-dimethyl-2-oxo-hexahydro-pyrimidin-5-yl)-1-isopropyl-5,6-dihydro-1H-pyrrolo[3,4-d]imidazol-4-one 146: {5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid 147: 2-{5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-N-methyl-acetamide 148: 2-{5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-N-methyl-acetamide 149: 5-(5-Chloro-2-methyl-phenyl)-6-(4-chloro-phenyl)-2-(2,4-dimethoxy-pyrimidin-5-yl)-1-((S)-2-hydroxy-1-methyl-ethyl)-5,6-dihydro-1H-pyrrolo[3,4-d]imidazol-4-one 150: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester 151: 2-{5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-N-methyl-acetamide 152: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid ethyl ester 153: 6-(4-Chloro-2-methyl-phenyl)-5-(5-chloro-2-methyl-phenyl)-2-(2,4-dimethoxy-pyrimidin-5-yl)-1-isopropyl-6-methyl-5,6-dihydro-1H-pyrrolo[3,4-d]imidazol-4-one 154: 2-{3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-phenyl}-N-methyl-acetamide 155: 2-{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-N,N-dimethyl-acetamide 156: 5-(5-Chloro-2-methyl-phenyl)-6-(4-chloro-phenyl)-2-(2,4-dimethoxy-pyrimidin-5-yl)-1-((S)-2-methoxy-1-methyl-ethyl)-5,6-dihydro-1H-pyrrolo[3,4-d]imidazol-4-one 157: 2-{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-N-methyl-acetamide 158: 5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 159: 2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one 160: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 161: 4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 162: {3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid 163: (R)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 164: (S)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 165: {3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid methyl ester 166: 4-[(R)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 167: 4-[5-(3-Chloro-4-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile 168: (R)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one 169: (S)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one 170: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carbonitrile 171: 5-(3-Chloro-2-fluoro-phenyl)-6-(4-chloro-phenyl)-2-(2-dimethylamino-5-methoxy-pyrimidin-4-yl)-1-isopropyl-5,6-dihydro-1H-pyrrolo[3,4-d]imidazol-4-one 172: 5-(5-Chloro-2-methyl-phenyl)-6-(4-chloro-phenyl)-2-(2-dimethylamino-5-methoxy-pyrimidin-4-yl)-1-isopropyl-5,6-dihydro-1H-pyrrolo[3,4-d]imidazol-4-one 173: 3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide 174: 3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide 175: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-benzamide 176: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-benzamide 177: 5-(5-Chloro-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-d]imidazol-4-one 178: 5-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-1,3-dimethyl-1H-pyrimidine-2,4-dione 179: 5-[6-(4-Chloro-phenyl)-2-(2-dimethylamino-4-methoxy-pyrimidin-5-yl)-1-isopropyl-4-oxo-4,6-dihydro-1H-pyrrolo[3,4-d]imidazol-5-yl]-1,3-dimethyl-1H-pyrimidine-2,4-dione 180: 5-[2-(2-Amino-4-methoxy-pyrimidin-5-yl)-6-(4-chloro-phenyl)-1-isopropyl-4-oxo-4,6-dihydro-1H-pyrrolo[3,4-d]imidazol-5-yl]-1,3-dimethyl-1H-pyrimidine-2,4-dione 181: 5-(5-Chloro-2-methyl-phenyl)-6-(4-chloro-phenyl)-1-cyclopropyl-2-(2,4-dimethoxy-pyrimidin-5-yl)-5,6-dihydro-1H-pyrrolo[3,4-d]imidazol-4-one 182: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-3-methyl-benzonitrile 183: 4-[5-(3-Chloro-2-fluoro-phenyl)-3-isopropyl-2-(2-methoxy-phenyl)-6-oxo-3,4,5,6-tetrahydro-pyrrolo[3,4-d]imidazol-4-yl]-3-methyl-benzonitrile 184: 5-(3-Chloro-2-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 185: 5-(3-Chloro-4-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 186: 3-[5-(5-Chloro-2-methyl-phenyl)-6-(4-cyano-2-methyl-phenyl)-1-isopropyl-4-oxo-1,4,5,6-tetrahydro-pyrrolo[3,4-d]imidazol-2-yl]-4-methoxy-N,N-dimethyl-benzamide 187: 4-[5-(5-Chloro-2-methyl-phenyl)-2-(1-ethyl-5-methoxy-2-oxo-1,2-dihydro-pyridin-4-yl)-3-isopropyl-6-oxo-3,4,5,6-tetrahydro-pyrrolo[3,4-d]imidazol-4-yl]-benzonitrile 188: 4-[5-(5-Chloro-2-methyl-phenyl)-2-(2,4-dimethoxy-pyrimidin-5-yl)-3-isopropyl-6-oxo-3,4,5,6-tetrahydro-pyrrolo[3,4-d]imidazol-4-yl]-3-methyl-benzonitrile 189: 3-[(R)-5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide 190: 3-[(S)-5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide 191: 4-[5-(5-Chloro-2-methyl-phenyl)-3-isopropyl-2-(2-methoxy-phenyl)-6-oxo-3,4,5,6-tetrahydro-pyrrolo[3,4-d]imidazol-4-yl]-3-methyl-benzonitrile 192: 2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one 193: 2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one 194: 3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide 195: 5-(3-Chloro-4-fluoro-phenyl)-6-(4-chloro-phenyl)-1-isopropyl-2-[2-methoxy-5-(morpholine-4-carbonyl)-phenyl]-5,6-dihydro-1H-pyrrolo[3,4-d]imidazol-4-one 196: 5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 197: 3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide 198: 5-(3-Chloro-4-fluoro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one 199: 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 200: 3-[5-(5-Chloro-1-methyl-2-oxo-1,2-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide 201: 5-(5-Chloro-1-methyl-2-oxo-1,2-dihydro-pyridin-3-yl)-6-(4-chloro-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one 202: 5-(5-Chloro-1-methyl-2-oxo-1,2-dihydro-pyridin-3-yl)-6-(4-chloro-phenyl)-2-(4-methoxy-2-methylamino-pyrimidin-5-yl)-5,6-dihydro-1H-pyrrolo[3,4-d]imidazol-4-one 203: (S)-2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one
204: (R)-2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one
205: (S)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one
206: (R)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one
207: 3-[6-(4-Chloro-phenyl)-5-(5-chloro-pyridin-3-yl)-1-isopropyl-4-oxo-1,4,5,6-tetrahydro-pyrrolo[3,4-d]imidazol-2-yl]-4-methoxy-N,N-dimethyl-benzamide
208: 5-(3-Chloro-2-fluoro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one
209: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-N-isopropyl-4-methoxy-benzamide
210: 5-(3-Chloro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one
211: 3-[5-(3-Chloro-phenyl)-6-(4-chloro-phenyl)-1-isopropyl-4-oxo-1,4,5,6-tetrahydro-pyrrolo[3,4-d]imidazol-2-yl]-4-methoxy-benzonitrile
212: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzoic acid
213: 6-(4-Chloro-2-methyl-phenyl)-5-(3-chloro-phenyl)-1-isopropyl-2-[2-methoxy-5-(morpholine-4-carbonyl)-phenyl]-5,6-dihydro-1H-pyrrolo[3,4-d]imidazol-4-one
214: 6-(4-Chloro-2-methyl-phenyl)-5-(3-chloro-phenyl)-2-(2,4-dimethoxy-pyrimidin-5-yl)-1-isopropyl-5,6-dihydro-1H-pyrrolo[3,4-d]imidazol-4-one
215: 3-[6-(4-Chloro-2-methyl-phenyl)-5-(3-chloro-phenyl)-1-isopropyl-4-oxo-1,4,5,6-tetrahydro-pyrrolo[3,4-d]imidazol-2-yl]-4-methoxy-benzonitrile
216: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzonitrile
217: 3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-4-methoxy-benzamide
218: 3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-4-methoxy-benzamide
219: 4-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-3-methoxy-benzamide
220: 4-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-3-methoxy-benzamide
221: 5-(5-Chloro-2-methyl-phenyl)-6-(4-chloro-2-methyl-phenyl)-2-(2-ethyl-phenyl)-1-isopropyl-5,6-dihydro-1H-pyrrolo[3,4-d]imidazol-4-one
222: 3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-N,N-dimethyl-benzamide
223: 3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-N,N-dimethyl-benzamide
224: 6-(4-Chloro-2-methyl-phenyl)-5-(4-chloro-pyridin-2-yl)-2-(5-hydroxymethyl-2-methoxy-phenyl)-1-isopropyl-5,6-dihydro-1H-pyrrolo[3,4-d]imidazol-4-one
225: 3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-4-methoxy-benzamide
226: 3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-4-methoxy-benzamide
227: 6-(4-Chloro-2-methyl-phenyl)-5-(5-chloro-2-methyl-pyridin-3-yl)-1-isopropyl-2-(2-methoxy-phenyl)-5,6-dihydro-1H-pyrrolo[3,4-d]imidazol-4-one
228: N-{3-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-benzyl}-2-hydroxy-acetamide
229: 5-[5-Chloro-1-(2-hydroxy-ethyl)-6-oxo-1,6-dihydro-pyridin-3-yl]-6-(4-chloro-2-methyl-phenyl)-1-isopropyl-2-(2-methoxy-phenyl)-5,6-dihydro-1H-pyrrolo[3,4-d]imidazol-4-one
230: 5-[5-Chloro-1-(2-methoxy-ethyl)-6-oxo-1,6-dihydro-pyridin-3-yl]-6-(4-chloro-2-methyl-phenyl)-1-isopropyl-2-(2-methoxy-phenyl)-5,6-dihydro-1H-pyrrolo[3,4-d]imidazol-4-one
231: 5-(5-Chloro-1-methyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-d]imidazol-4-one
232: 5-(5-Chloro-1-ethyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-d]imidazol-4-one
233: 2-(2-Amino-pyridin-4-yl)-5-(3-chloro-2-fluoro-phenyl)-6-(4-chloro-phenyl)-1-isopropyl-5,6-dihydro-1H-pyrrolo[3,4-d]imidazol-4-one
234: 5-(3-Chloro-2-fluoro-phenyl)-6-(4-chloro-phenyl)-2-[5-(1-hydroxy-2-methyl-propyl)-2-methoxy-phenyl]-1-isopropyl-5,6-dihydro-1H-pyrrolo[3,4-d]imidazol-4-one
235: 5-(3-Chloro-2-fluoro-phenyl)-6-(4-chloro-phenyl)-2-[5-(1-hydroxy-ethyl)-2-methoxy-phenyl]-1-isopropyl-5,6-dihydro-1H-pyrrolo[3,4-d]imidazol-4-one
236: 5-(3-Chloro-2-fluoro-phenyl)-6-(4-chloro-phenyl)-1-isopropyl-2-(4-methoxy-pyridin-3-yl)-5,6-dihydro-1H-pyrrolo[3,4-d]imidazol-4-one
237: 5-(5-(3-chloro-2-fluorophenyl)-6-(4-chlorophenyl)-1-isopropyl-4-oxo-1,4,5,6-tetrahydropyrrolo[3,4-d]imidazol-2-yl)-6-methoxy-N,N-dimethylpyridazine-3-carboxamide
238: 2-(4-(5-(5-chloro-1-methyl-2-oxo-1,2-dihydropyridin-3-yl)-6-(4-chloro-2-methylphenyl)-1-isopropyl-4-oxo-1,4,5,6-tetrahydropyrrolo[3,4-d]imidazol-2-yl)-5-methoxypyridin-2-yl)acetonitrile
239: 4-(5-(3-chloro-2-fluorophenyl)-2-(2-(cyanomethyl)-5-methoxypyridin-4-yl)-3-isopropyl-6-oxo-3,4,5,6-tetrahydropyrrolo[3,4-d]imidazol-4-yl)-3-methylbenzonitrile
240: 4-(5-(3-chloro-4-fluorophenyl)-2-(2-(cyanomethyl)-5-methoxypyridin-4-yl)-3-isopropyl-6-oxo-3,4,5,6-tetrahydropyrrolo[3,4-d]imidazol-4-yl)benzonitrile
241: {4-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile 242: 4-[5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-3-methyl-benzonitrile 243: 6-(4-Chloro-phenyl)-5-(2,6-dimethyl-pyrimidin-4-yl)-1-isopropyl-2-(5-methoxy-1-methyl-2-oxo-1,2-dihydro-pyridin-4-yl)-5,6-dihydro-1H-pyrrolo[3,4-d]imidazol-4-one 244: 5-(3-Chloro-2-fluoro-phenyl)-6-(4-chloro-phenyl)-1-isopropyl-2-(3-methoxy-1-methyl-6-oxo-1,6-dihydro-pyridazin-4-yl)-5,6-dihydro-1H-pyrrolo[3,4-d]imidazol-4-one 245: 5-(5-Chloro-2-methyl-phenyl)-6-(5-chloro-pyridin-2-yl)-2-(2-dimethylamino-4-methoxy-pyrimidin-5-yl)-1-isopropyl-5,6-dihydro-1H-pyrrolo[3,4-d]imidazol-4-one 246: 4-[5-(3-Chloro-2-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-2-fluoro-benzonitrile 247: 4-[5-(3-Chloro-2-fluoro-phenyl)-2-(dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile 248: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile 249: 4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carboxylic acid dimethylamide 250: {4-[(S)-5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile 251: {4-[(R)-5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile 252: 4-[(S)-5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile 253: 4-[(R)-5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile 254: 4-[(S)-5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile 255: 4-[(R)-5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile 256: 4-[5-(3-Chloro-2-fluoro-phenyl)-2-(2,4-dimethoxy-pyrimidin-5-yl)-3-((R)-2-methoxy-1-methyl-ethyl)-6-oxo-3,4,5,6-tetrahydro-pyrrolo[3,4-d]imidazol-4-yl]-benzonitrile 257: 4-[5-(5-chloro-2-methyl-phenyl)-2-(2,4-dimethoxy-pyrimidin-5-yl)-3-((R)-2-methoxy-1-methyl-ethyl)-6-oxo-3,4,5,6-tetrahydro-pyrrolo[3,4-d]imidazol-4-yl]-benzonitrile 258: 5-(3-Chloro-2-fluoro-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one 259: 5-(3-Chloro-4-fluoro-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one 260: 6-(4-Chloro-phenyl)-2-(2,4-dimethoxy-pyrimidin-5-yl)-5-(4-fluoro-3-methyl-phenyl)-1-isopropyl-5,6-dihydro-1H-pyrrolo[3,4-d]imidazol-4-one 261: 6-(4-Chloro-phenyl)-2-(2,4-dimethoxy-pyrimidin-5-yl)-1-isopropyl-5-(2-methoxy-5-methyl-phenyl)-5,6-dihydro-1H-pyrrolo[3,4-d]imidazol-4-one 262: 6-(4-Chloro-phenyl)-2-(2,4-dimethoxy-pyrimidin-5-yl)-5-(2,6-dimethyl-pyrimidin-4-yl)-1-isopropyl-5,6-dihydro-1H-pyrrolo[3,4-d]imidazol-4-one 263: (S)-2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one 264: (R)-2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one 265: (S)-2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one 266: (R)-2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one 267: 6-(4-Chloro-phenyl)-5-(4-fluoro-3-methyl-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one, and 268: 6-(4-Chloro-phenyl)-1-isopropyl-2-(5-methoxy-1-methyl-2-oxo-1,2-dihydro-pyridin-4-yl)-5-(2-methoxy-5-methyl-phenyl)-5,6-dihydro-1H-pyrrolo[3,4-d]imidazol-4-one.

269: 5-(5-Chloro-1-methyl-6-oxo-1,6-dihydro-pyridin-3-yl)-6-(4-chloro-phenyl)-1-isopropyl-2-(2-methoxy-pyrimidin-5-yl)-5,6-dihydro-1H-pyrrolo[3,4-d]imidazol-4-one 270: 5-(5-Chloro-1-methyl-6-oxo-1,6-dihydro-pyridin-3-yl)-6-(4-chloro-2-methyl-phenyl)-1-isopropyl-2-(2-methoxy-pyridine-3-yl)-5,6-dihydro-1H-pyrrolo[3,4-d]imidazol-4-one 271: 6-(4-Chloro-2-phenyl)-5-(1,5-dimethyl-6-oxo-1,6-dihydro-pyridin-3-yl)-1-isopropyl-2-(2-methoxy-pyrimidin-5-yl)-5,6-dihydro-1H-pyrrolo[3,4-d]imidazol-4-one 272: 6-(4-Chloro-phenyl)-5-(1,5-dimethyl-6-oxo-1,6-dihydro-pyridin-3-yl)-1-isopropyl-2-(2-methoxy-pyridin-3-yl)-5,6-dihydro-1H-pyrrolo[3,4-d]imidazol-4-one 273: 6-(4-Chloro-2-phenyl)-2-(2,4-dimethoxy-pyrimidin-5-yl)-5-(1,5-dimethyl-6-oxo-1,6-dihydro-pyridin-3-yl)-1-isopropyl-5,6-dihydro-1H-pyrrolo[3,4-d]imidazol-4-one 274: 6-(4-Chloro-2-phenyl)-1-cyclobutyl-2-(2,4-dimethoxy-pyrimidin-5-yl)-5-(1,5-dimethyl-6-oxo-1,6-dihydro-pyridin-3-yl)-5,6-dihydro-1H-pyrrolo[3,4-d]imidazol-4-one 275: 5-(5-Chloro-2-methyl-phenyl)-6-(5-chloro-pyridin-2-yl)-2-(2-dimethylamino-4-methoxy-pyrimidin-5-yl)-1-isopropyl-5,6-dihydro-1H-pyrrolo[3,4-d]imidazol-4-one 276: 5-(5-Chloro-2-methyl-phenyl)-6-(5-chloro-pyridin-2-yl)-2-(2,4-dimethoxy-pyrimidin-5-yl)-1-isopropyl-5,6-dihydro-1H-pyrrolo[3,4-d]imidazol-4-one 277: 4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluorobenzonitrile 278: 4-[5-(5-Chloro-1-methyl-2-oxo-1,2-dihydro-pyridin-3-yl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile 279: (S)-5-(5-Chloro-1-methyl-2-oxo-1,2-dihydro-pyridin-3-yl)-6-(4-chloro-phenyl)-2-(2,4-dihydroxy-pyrimidin-5-yl)-1-isopropyl-5,6-dihydro-1H-pyrrolo[3,4-d]imidazol-4-one 280: (R)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 281: (S)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 282: (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 283: (R)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 284: 6-(4-Chloro-3-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one 285: 6-(4-Chloro-3-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one 286: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-d]imidazol-4-one 287: 6-(4-Chloro-3-fluoro-phenyl)-5-(5-chloro-1-methyl-6-oxo-1,6-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one 288: 4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile 289: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile 290: 6-(4-Chloro-3-fluoro-phenyl)-5-(5-chloro-1-methyl-6-oxo-1,6-dihydro-pyridin-3-yl)-2-(2,4-dimethoxy-pyrimidin-5-yl)-1-isopropyl-5,6-dihydro-1H-pyrrolo[3,4-d]imidazol-4-one 291: 6-(4-Chloro-phenyl)-2-(2,4-dimethoxy-pyrimidin-5-yl)-5-(1,4-dimethyl-6-oxo-1,6-dihydro-pyridin-2-yl)-1-isopropyl-5,6-dihydro-1H-pyrrolo[3,4-d]imidazol-4-one 292: 6-(4-Chloro-phenyl)-2-(2,4-dimethoxy-pyrimidin-5-yl)-5-(1,5-dimethyl-2-oxo-1,2-dihydro-pyridin-3-yl)-1-isopropyl-5,6-dihydro-1H-pyrrolo[3,4-d]imidazol-4-one 293: 6-(4-Chloro-phenyl)-2-(2-dimethylamino-4-methoxy-pyrimidin-5-yl)-5-(1,5-dimethyl-2-oxo-1,2-dihydro-pyridin-3-yl)-1-isopropyl-5,6-dihydro-1H-pyrrolo[3,4-d]imidazol-4-one 294: 5-(5-Chloro-1-difluoromethyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 295: 5-(5-Chloro-1-methyl-d3-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 296: 5-(5-Chloro-1-ethyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 297: 5-(5-Chloro-1-methyl-2-oxo-1,2-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-d]imidazol-4-one 298: 5-(5-Chloro-1-methyl-2-oxo-1,2-dihydro-pyridin-3-yl)-6-(4-chloro-phenyl)-1-isopropyl-2-(4-methoxy-2-oxo-1,2-dihydro-pyrimidin-5-yl)-5,6-dihydro-1H-pyrrolo[3,4-d]imidazol-4-one 299: 6-(4-Chloro-phenyl)-5-(2,6-dimethyl-pyrimidin-4-yl)-1-isopropyl-2-(5-methoxy-1-methyl-2-oxo-1,2-dihydro-pyridin-4-yl)-5,6-dihydro-1H-pyrrolo[3,4-d]imidazol-4-one 300: 6-(4-Chloro-phenyl)-2-(2,4-dimethoxy-pyrimidin-5-yl)-1-isopropyl-5-(3-methoxy-6-methyl-pyridazin-4-yl)-5,6-dihydro-1H-pyrrolo[3,4-d]imidazol-4-one 301: 5-(5-Chloro-2-methoxy-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 302: 6-(4-Chloro-phenyl)-2-(2-dimethylamino-4-methoxy-pyrimidin-5-yl)-1-isopropyl-5-(3-methoxy-6-methyl-pyridazin-4-yl)-5,6-dihydro-1H-pyrrolo[3,4-d]imidazol-4-one 303: 6-(4-Chloro-2-fluoro-phenyl)-5-(3-chloro-2-fluoro-phenyl)-2-(2-dimethylamino-4-methoxy-pyrimidin-5-yl)-1-isopropyl-5,6-dihydro-1H-pyrrolo[3,4-d]imidazol-4-one 304: 6-(4-Chloro-2-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one 305: 6-(4-Chloro-2-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one 306: 6-(4-Chloro-phenyl)-2-(2-dimethylamino-4-methoxy-pyrimidin-5-yl)-5-(4-fluoro-2,5-dimethyl-2H-pyrazol-3-yl)-1-isopropyl-5,6-dihydro-1H-pyrrolo[3,4-d]imidazol-4-one 307: (S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 308: (R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 309: 6-(4-Chloro-phenyl)-5-(5-cyclopropyl-4-fluoro-2-methyl-2H-pyrazol-3-yl)-2-(2,4-dimethoxy-pyrimidin-5-yl)-1-isopropyl-5,6-dihydro-1H-pyrrolo[3,4-d]imidazol-4-one 310: 6-(4-Chloro-phenyl)-5-(5-cyclopropyl-4-fluoro-2-methyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-d]imidazol-4-one 311: 4-{5-(3-Chloro-2-fluoro-phenyl)-2-[2-(1,1-dioxo-1-thiomorpholin-4-yl)-4-methoxy-pyrimidin-5-yl]-3-isopropyl-6-oxo-3,4,5,6-tetrahydro-pyrrolo[3,4-d]imidazol-4-yl}-benzonitrile 312: 4-{5-(3-Chloro-2-fluoro-phenyl)-2-[2-((S)-3-hydroxy-piperidin-1-yl)-4-methoxy-pyrimidin-5-yl]-3-isopropyl-6-oxo-3,4,5,6-tetrahydro-pyrrolo[3,4-d]imidazol-4-yl}-benzonitrile 313: 2-(2-amino-4-methoxypyrimidin-5-yl)-5-(3-chloro-4-fluorophenyl)-6-(4-chlorophenyl)-1-((R)-1-methoxypropan-2-yl)-5,6-dihydropyrrolo[3,4-d]imidazol-4(1H)-one 314: 2-(2-amino-4-methoxypyrimidin-5-yl)-5-(5-chloro-2-methylphenyl)-6-(4-chlorophenyl)-1-((R)-1-methoxypropan-2-yl)-5,6-dihydropyrrolo[3,4-d]imidazol-4(1H)-one 315: (R)-5-(3-chloro-2-fluorophenyl)-6-(4-chlorophenyl)-2-(2,4-dimethoxypyrimidin-5-yl)-1-((R)-1-hydroxypropan-2-yl)-5,6-dihydropyrrolo[3,4-d]imidazol-4(1H)-one 316: (S)-5-(3-chloro-2-fluorophenyl)-6-(4-chlorophenyl)-2-(2,4-dimethoxypyrimidin-5-yl)-1-((R)-1-hydroxypropan-2-yl)-5,6-dihydropyrrolo[3,4-d]imidazol-4(1H)-one 317: (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one 318: (R)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one 319: 5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one 320: 5-(5-chloro-1-methyl-2-oxo-1,2-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one 321: 5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one 322: (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one 323: (S)-5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one 324: (R)-5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one 325: (S)-5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one and 326: (R)-5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one.

E62: A compound of formula (I) or a salt thereof, selected from:

66: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 75: (S)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one 79: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 101: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 102: (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 122: 5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 160: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile 164: (S)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 199: 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile 205: (S)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one 281: (S)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one 282: (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 286: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-d]imidazol-4-one 289: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile 295: 5-(5-Chloro-1-methyl-d3-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 296: 5-(5-Chloro-1-ethyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 297: 5-(5-Chloro-1-methyl-2-oxo-1,2-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-d]imidazol-4-one 304: 6-(4-Chloro-2-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one 317: (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one and 322: (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one.

E63: A compound of formula (I) or a salt thereof, selected from:

102: (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 199: 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]benzonitrile 282: (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one 317: (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one and 322: (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one.

In the above definitions, halo means fluoro, chloro or bromo, particularly fluoro or chloro.

Alkyl, and alkoxy groups, containing the requisite number of carbon atoms, can be unbranched or branched. Examples of alkyl include, but are not limited to, methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

'=O' means an oxo substituent.

Specific preferred compounds according to the invention are those listed in the Examples section below.

Where there is more than one R group of the same type in the compound of formula (I), each may be selected independently of the other; they need not be the same group or atom.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non- superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}F$, $^{32}F$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Reseach Park, Madison Wis., USA, which uses the algorithm of Smith and Waterman (Adv. Appl. Math. 2: 482-489 (1981)., especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by MDM2 and/or MDM4, or (ii) associated with MDM2 and/or MDM4 activity, or (iii) characterized by activity (normal or abnormal) of MDM2 and/or MDM4, or (2) reducing or inhibiting the activity of MDM2 and/or MDM4, or (3) reducing or inhibiting the expression of MDM2 and/or MDM4. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of MDM2 and/or MDM4; or at least partially reducing or inhibiting the expression of MDM2 and/or MDM4.

In a further embodiment, the compounds of formula (I) are particularly useful for the treatment of disorders of diseases associated with the activity of MDM2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration.

In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs. Solvates or hydrates may be useful in producing crystalline forms of a compound of formula (I).

In another aspect, the present invention provides a pharmaceutical composition comprising compound of formula (I) or salt thereof as defined herein, and one or more pharmaceutically acceptable carriers. In another aspect, the present invention provides a pharmaceutical composition comprising a therapeutically effective amount of a compound of formula (I) or salt thereof as defined herein, and one or more pharmaceutically acceptable carriers.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compounds of formula I in free form or in salt form exhibit valuable pharmacological properties, e.g. MDM2 and/or MDM4 modulating properties, e.g. as indicated in tests as provided in the next sections, and are therefore indicated for therapy.

Having regard to their inhibitory effect on p53/MDM2 and/or p53/MDM4 interaction, compounds of the formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative and/or inflammatory conditions, e.g. by activation of the P53/MDM2 interaction, and/or that are responsive (meaning especially in a therapeutically beneficial way) to inhibition of the p53/MDM2 interaction, most especially a disease or disorder as mentioned herein below.

Compounds of the invention are believed to be useful in the treatment of a disease based on dysregulation of cell cycle, such as a proliferative disorder or disease, for example cancer or tumour diseases. In particular, such diseases or disorders include benign or malignant tumors, a soft tissue sarcoma or a sarcoma such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, meningioma, glioma, mesothelioma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma, such as of B- or T-cell origin, and metastases in other organs), viral infections (e.g. herpes, papilloma, HIV, Kaposi's, viral hepatitis). Particular uses are for the treatment of benign or malignant tumors, a soft tissue sarcoma or a sarcoma such as liposarcoma, rhabdomyosarcoma or bone cancer, e.g. osteosarcomas, a carcinoma, such as of the kidney, liver, adrenal gland, bladder, breast, gastric, ovary, colon, rectum, prostate, pancreas, lung, vagina or thyroid, mesothelioma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma, such as of B- or T-cell origin, and metastases in other organs.

Compounds of the invention are also believed to be useful in the treatment of or a disorder or disease involving the immune system, in particular autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin or hyperproliferative disorders, (e.g. Li-Fraumeni syndrome).

In another embodiment there is provided a compound of the formula (I) or salt thereof as defined herein, for use as a pharmaceutical.

A further embodiment provides a compound of the formula (I) or salt thereof as defined herein, for use in the treatment of a disorder or a disease mediated by the activity of MDM2 and/or MDM4.

A still further embodiment provides the use of a compound of formula (I) or salt thereof as defined herein, for the manufacture of a medicament for the treatment of a disorder or a disease in a subject mediated by the activity of MDM2 and/or MDM4.

As a further embodiment, the present invention provides the use of a compound of formula (I) in therapy. In a further embodiment, the therapy is selected from a disease which may be treated by inhibition of the MDM2/p53 and/or MDM4/p53 interaction, in particular the diseases or disorders listed herein. In one embodiment, the disease or disorder is a proliferative disease, in particular cancer. More particularly, the cancer is one of the cancer types disclosed herein.

In another embodiment, the invention provides a method of treating a disease or disorder which is treated by inhibition of the MDM2/p53 and/or MDM4/p53 interaction, comprising administration of a therapeutically acceptable amount of a compound of formula (I) or salt thereof, in particular a method of treating the diseases or disorders listed herein.

In another embodiment, the invention provides a method for the treatment of a disorder or a disease mediated by the activity of MDM2 and/or MDM4, comprising the step of administering to a subject a therapeutically acceptable amount of a compound of formula (I) or salt thereof as defined herein, in particular a method of treating the diseases or disorders listed herein.

A further embodiment provides a method of modulating MDM2 and/or MDM4 activity in a subject, comprising the step of administering to a subject a therapeutically effective amount of a compound of formula (I) or salt thereof as defined herein.

The compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side. Disruption of the formation of the p53-MDM2 or p53-MDM4 complex is due to an inhibitor molecule binding to the p53 binding site of MDM2 or MDM4.

The invention also relates to the use of a compound of the formula (I) (or a pharmaceutical formulation comprising a compound of the formula (I)) in the treatment of one or more of the diseases mentioned above and below where the disease(s) respond or responds (in a beneficial way, e.g. by partial or complete removal of one or more of its symptoms up to complete cure or remission) to an inhibition of the MDM2/p53 and/or MDM4/p53 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

A compound of the formula (I) may also be used to advantage in combination with other anti-proliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibittors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825);

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™) Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d] pyrimidine derivatives which are disclosed in WO 03/013541, also; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235 or BKM120;

n) compounds targeting, decreasing or inhibiting the activity of the cyclin dependent kinase family, such as PD 0332991.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, $\alpha$- $\gamma$- or $\delta$-tocopherol or $\alpha$- $\gamma$- or $\delta$-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon $\gamma$.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TK1258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™), rituximab (Rituxan™) PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]amino]-methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2

IgG1 antibody, Angiozyme (RPI 4610) and Bevacizumab (Avastin™), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)-2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®).

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The above-mentioned compounds, which can be used in combination with a compound of the formula (I), can be prepared and administered as described in the art, such as in the documents cited above.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

In another embodiment, the invention provides a compound of the formula (I) or salt thereof as defined herein, in combination with one or more therapeutically active agents. In particular, the other therapeutic agent is selected from one or more of the combination partners disclosed herein.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by inhibition of the MDM2/p53 and/or MDM4/p53 interaction. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by inhibition of the MDM2/p53 and/or MDM4/p53 interaction, wherein the medicament is prepared for administration with another therapeutic agent. The invention also provides the use of another therapeutic agent for treating a disease or condition mediated by inhibition of the MDM2/p53 and/or MDM4/p53 interaction, wherein the medicament is administered with a compound of formula (I).

The invention also provides a compound of formula (I) for use in a method of treating a disease or condition mediated by inhibition of the MDM2/p53 and/or MDM4/p53 interaction, wherein the compound of formula (I) is prepared for administration with another therapeutic agent. The invention also provides another therapeutic agent for use in a method of treating a disease or condition mediated by inhibition of the MDM2/p53 and/or MDM4/p53 interaction, wherein the other therapeutic agent is prepared for administration with a compound of formula (I). The invention also provides a compound of formula (I) for use in a method of treating a disease or condition mediated by inhibition of the MDM2/p53 and/or MDM4/p53 interaction, wherein the compound of formula (I) is administered with another therapeutic agent. The invention also provides another therapeutic agent for use in a method of treating a disease or condition mediated by inhibition of the MDM2/p53 and/or MDM4/p53 interaction, wherein the other therapeutic agent is administered with a compound of formula (I). In particular the disease or condition mediated by inhibition of the MDM2/p53 and/or MDM4/p53 interaction is a proliferative disease, preferably cancer, more preferably one of the cancer types described herein.

The invention also provides the use of a compound of formula (I) for treating a disease or condition mediated by inhibition of the MDM2/p53 and/or MDM4/p53 interaction, wherein the patient has previously (e.g. within 24 hours) been treated with another therapeutic agent. The invention also provides the use of another therapeutic agent for treating a disease or condition mediated by inhibition of the MDM2/p53 and/or MDM4/p53 interaction, wherein the patient has previously (e.g. within 24 hours) been treated with a compound of formula (I).

SYNTHETIC METHODS

Typically, the compounds of formula (I) can be prepared according to the Schemes, intermediate processes and examples provided infra. The skilled person is aware that such methods can be modified using methods known in the art. For example, chiral separation can take place earlier or later in a route. Reagents, or quantities of them, can be exchanged or optimized, and reactions can be modified to enable one-pot reactions.

| Abbreviations | |
|---|---|
| Ac | acetyl |
| AcOH | acetic acid |
| $AlCl_3$ | aluminium trichloride |
| aq. | aqueous |
| API | atmospheric pressure ionization |
| Boc | tert-butoxycarbonyl |
| brine | saturated (at rt) sodium chloride solution |
| bs | broad singulet |
| $^n$BuOH | n-butanol |
| $^t$Bu | tert-butyl |
| CDI | carbonyl diimidazole |
| Celite | trademark of Celite Corp. (World Minerals Inc.), Santa Barbara, CA, USA, for filtering aid based on kieselguhr |
| $CH_3CN$ | acetonitrile |
| conc. | concentrated |
| d | doublett |
| DCM | dichloromethane |
| DEA | diethylamine |
| DIEIA | N,N-diethyl-isopropylamine |
| DMAP | 4-dimethylaminopyridine |
| DMF | N,N-dimethylformamide |
| DMSO | dimethylsulfoxide |
| ES-MS | electrospray mass spectrometry |
| Et | ethyl |
| $Et_3N$ | triethylamine |
| $Et_2O$ | diethyl ether |
| EtOAc | ethyl acetate |
| EtOH | ethanol |
| equiv | equivalents |
| h | hour(s) |
| HATU | O-(7-azabenzotriazol-1-yl)-N,N,N',N'-tetramethyluronium-hexafluorophosphat |
| HBr | hydrogen bromide |
| HCl | hydrogen chloride |
| HOAt | 1-hydroxy-7-azabenzotriazole |

| Abbreviations | |
|---|---|
| HPLC | high-performance liquid chromatography |
| IPAm | isopropylamine |
| iPr | isopropyl |
| $K_2CO_3$ | potassium carbonate |
| KHMDS | potassium hexamethyldisilazide |
| KO$^t$Bu | potassium-tert-butoxylate |
| KOH | potassium hydroxide |
| $K_3PO_4$ | potassium phosphate |
| LAH | lithium aluminium hydride |
| LC | liquid chromatography |
| LDA | lithium diisopropylamide |
| LiOH | lithium hydroxide |
| Me | methyl |
| MeI | methyl iodide |
| MeOH | methanol |
| $MgSO_4$ | magnesium sulfate |
| M | multiplett |
| min | minute(s) |
| mL | milliliter(s) |
| MS | Mass Spectrometry |
| MsCl | methanesulfonyl chloride |
| $Ms_2O$ | methanesulfonic acid anhydride |
| NaH | sodium hydride |
| $NaHCO_3$ | sodium bicarbonate |
| $Na_2CO_3$ | sodium carbonate |
| NaOH | sodium hydroxide |
| NaOMe | sodium methoxide |
| NaOEt | sodium ethoxide |
| NaO$^t$Bu | sodium tert-butoxide |
| $Na_2SO_4$ | sodium sulfate |
| NBS | N-bromosuccinimide |
| NCS | N-chlorosuccinimide |
| n.d. | not determined |
| $NH_4Cl$ | ammonium chloride |
| $NH_4OH$ | ammonium hydroxide |
| NIS | N-iodosuccinimide |
| NMM | 4-N-methylmorpholine |
| NMR | nuclear magnetic resonance |
| Ph | phenyl |
| $POCl_3$ | phosphorus (III) oxychloride |
| rt (or RT) | room temperature |
| $R_f$ | TLC retention factor |
| s | singulet |
| $scCO_2$ | super critical $CO_2$ |
| sep | septet |
| t | triplet |
| TBAF | tetrabutylammonium fluoride |
| TBAHS | tetrabutylammonium hydrogen sulfate |
| TBME | tert-butylmethylether |
| TBTU | O-(benzotriazol-1-yl)-N,N,N',N'-tetramethylammonium tetrafluoroborate |
| TEA | triethylamine |
| TFA | trifluoroacetic acid |
| TFAA | trifluoroacetic anhydride |
| THF | tetrahydrofurane |
| TLC | thin layer chromatography |
| TMS | trimethylsilyl |
| TMSCl | trimethylsilyl chloride |
| $t_R$ | time of retention |
| TsCl | p-toluenesulfonyl chloride |
| TsOH | p-toluenesulfonic acid |
| UV | ultraviolet |

1H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer using or not trimethylsilane as an internal standard. Chemical shifts (d-values) are reported in ppm downfield from tetramethylsilane, coupling constants (J) are given in Hz, spectra splitting pattern are designated as singulet (s), doublet (d), doublet doublet (dd), triplet (t), quadruplet (q), multiplet or more overlapping signals (m), broad signal (br). Solvents are given in parentheses.

TLC were performed with precoated silica gel 60 $F_{254}$ glass plates (Merck, Darmstadt, Germany) using the respective named solvent systems. Visualization was generally done by UV light (254 nm).

HPLC Conditions:

LC-MS 1:

Column: Ascentis Express C18 2.1×30 mm, 2.7 µm. Flow: 1.2 mL/min. Column temperature: 50° C. Gradient: 2% to 98% B in 1.4 min, 98% B for 0.75 min, 98% to 2% B in 0.04 min, 98% B for 0.01 min; A=water+0.05% formic acid+ 0.05% ammonium acetate, B=acetonitrile+0.04% formic acid Detection full scan: 215-350 nM

LC-MS 2:

Column: Acquity HSS T3 2.1×50 mm, 1.8 µm. Flow: 1.2 mL/min. Column temperature: 50° C.

Gradient: 2% to 98% B in 1.4 min, 98% B for 0.75 min, 98% to 2% B in 0.04 min, 2% B for 0.01 min; A=water+ 0.05% formic acid+3.75 mM ammonium acetate, B=acetonitrile+0.04% formic acid Detection full scan: 215-350 nM

LC-MS 3:

Column: Acquity HSS T3 2.1×50 mm, 1.8 µm. Flow: 1.2 mL/min. Column temperature: 50° C.

Gradient: 2% to 98% B in 1.4 min, 98% B for 0.75 min, 98% to 2% B in 0.04 min, 2% B for 0.01 min; A=water+ 0.05% formic acid+0.05% ammonium acetate, B=acetonitrile+0.04% formic acid Detection full scan: 215-350 nM

LC-MS 4:

Column: Acquity HSS T3 2.1×50 mm, 1.8 µm. Flow: 1.0 mL/min. Column temperature: 60° C.

Gradient: 5% to 98% B in 1.4 min, 98% B for 0.75 min, 98% to 2% B in 0.04 min, 2% B for 0.01 min; A=water+ 0.05% formic acid+3.75 mM ammonium acetate, B=acetonitrile+0.04% formic acid Detection full scan: 215-350 nM HPLC Methods:

HPLC 1:

Column: Waters Chromolith Performance RP-18e 100-4, 6. Flow: 2 mL/min. Column temperature: Rt. Gradient: 2% B for 1 min, 2% to 100% B in 8 min, 100% B for 2 min, A=0.1% HCOOH in water, B=acetonitrile 0.1% HCOOH

HPLC 2:

Column: Nucleosil 100-3 C18 HD, 4.0×70 mm. Flow: 1 mL/min. Column temperature: 30° C.

Gradient: 2% to 100% B in 5 min, 100% B for 1.5 min, 100% to 2% B in 0.5 min; A=0.01% TFA in water, B=0.01% TFA in acetonitrile MS Methods:

MS 1:

Electrospray ionization mass spectra. Positive and negative alternating.

DAD-UV 210-400 nm.

Scan range 100-1600 Da in 0.4 seconds

Reaction Scheme 1:

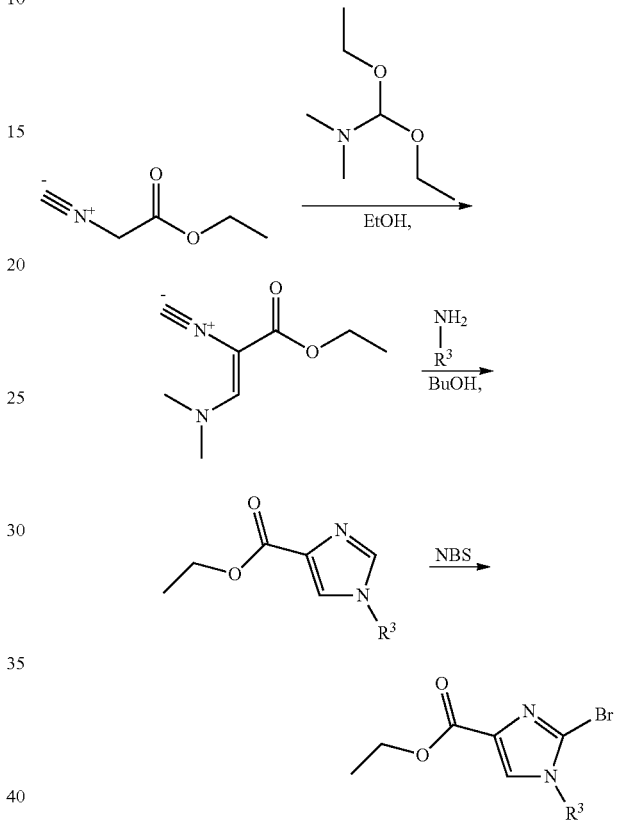

Scheme 1 illustrates one representative method of preparing 2-bromo-N-alkyl-1H-imidazole-4-carboxylic acid ester intermediates (e.g. intermediate A). The illustrated method follows the known literature procedure (Org. Lett. 2002, 4(23), 4133) for the preparation of (Z)-3-dimethylamino-2-isocyano-acrylic acid ethyl ester [CAS 72130-97-3] and the subsequent cyclization reaction with primary amines to build up the imidazole scaffold typically conducted in refluxing n-butanol. The following bromination step is typically performed at room temperature using N-bromosuccinimide in THF, acetonitrile, acetic acid or mixtures thereof as solvent systems.

Reaction Scheme 2:

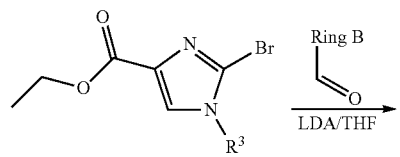

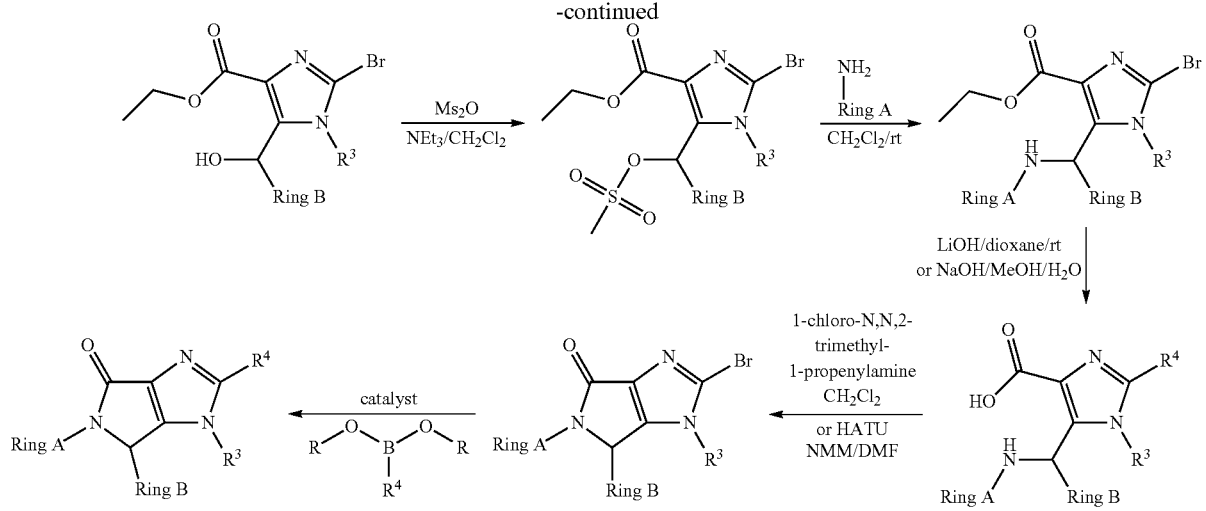

Scheme 2 illustrates one method of preparing compounds of the invention (e.g. example 1). 2-Bromo imidazole 4-carboxylic acid ester is metallated at low temperature (typically LDA at −70° C. to −80° C.; THF) and quenched by addition of a representative benzaldeyde. The resulting alcohol products are converted to corresponding mesylate derivatives by treatment with mesyl anhydride in the presence of a base such as triethylamine in a solvent such as dichloromethane in a temperature range from 0° C. to 10° C. Mesylates are subjected in situ to nucleophilic substitution by addition of appropriate primary amines or anilines; where typically the reaction is allowed to come to completion at ambient temperature. Hydrolysis of the carboxylic ester is achieved by treatment with alkali base such as lithium or sodium hydroxide in solvent mixture of THF/methanol/water at ambient or slightly elevated temperature. Ring closure to build the bicyclic core is effected by intramolecular amide coupling using reagents such as HATU or TBTU in the presence of organic base (e.g. NMM; Hünig's base) typically using DMF as solvent, or using 1-chloro-N,N,2-trimethyl-1-propenylamine in $CH_2Cl_2$, or $POCl_3$ or $POBr_3$ to form the acid chloride or bromide respectively, which can undergo cyclisation. Final cross coupling reactions of the resulting 2-bromo imidazo pyrrolidinone intermediates with aryl- or heteroarylboronic esters or -acids are conducted under Suzuki-type conditions; utilizing catalysts such as $Pd(PPh_3)_4$ or $Pd(dppf)Cl_2$—$CH_2Cl_2$ complex in the presence of excess of an inorganic base (e.g. $K_3PO_4$ or KF) in solvent systems such as dioxane/water in a temperature range from 80° C. to 100° C.

Reaction Scheme 3:

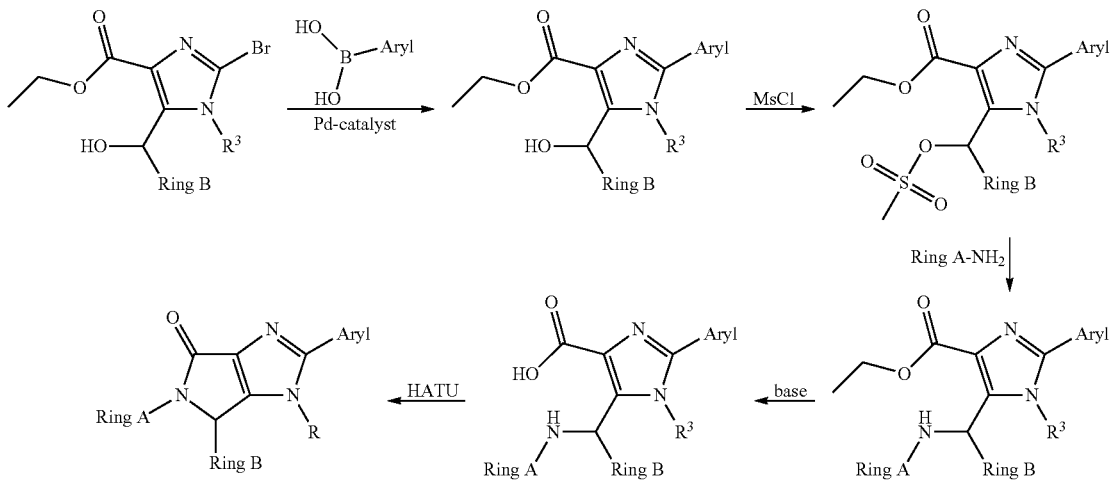

Scheme 3 illustrates an alternative method of preparing compounds of the invention (e.g. example 64) by reversal order of steps. Alcohol intermediates obtained by the same methods as described above are subjected to palladium catalyzed cross coupling reactions with aryl boronates or boronic acids. The alcohol functionality of resulting products is then mesylated and submitted to nucleophilic substitution reactions with appropriate amines using similar or identical conditions (MsCl or $Ms_2O$) as described above. Finally the bicyclic imidazo-pyrrolidinone scaffold is built up by ester hydrolysis and again intramolecular amide coupling using HATU as coupling reagent in a solvent such as DMF at slightly elevated temperature (60-80° C.).

Reaction Scheme 4:

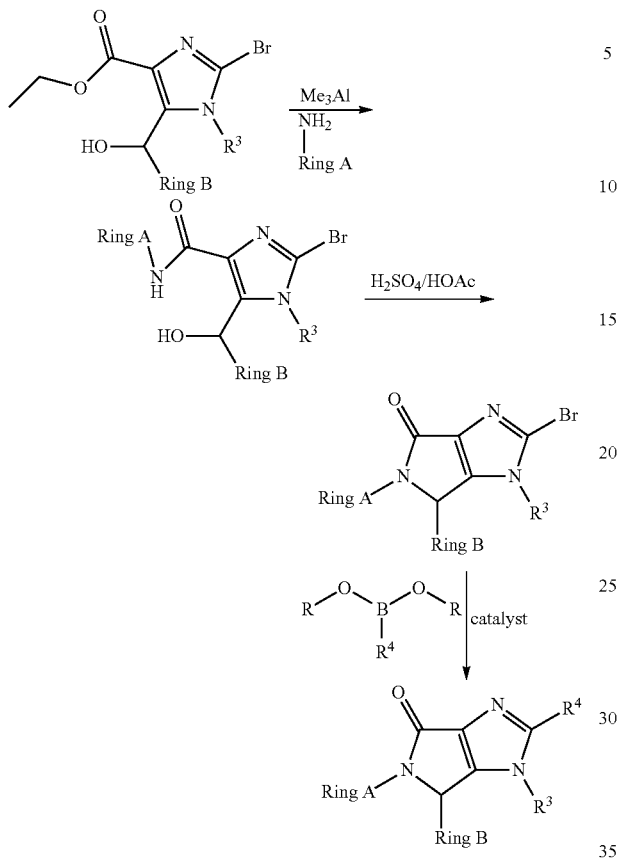

Scheme 4 illustrates another alternative route for the preparation of compounds of this invention (e.g. examples 85/86). Herewith direct amidation of imidazo ester intermediates is effected by trimethyl aluminium followed by construction of the 5/5 bicycle through intramolecular substitution of the benzylic alcohol under acidic conditions (e.g. H₂SO₄). Final coupling steps with aryl boronic acid or esters are performed according to the protocols as described above.

Unless otherwise stated all reactions are performed under an inert atmosphere (argon).

Intermediate A

2-Bromo-1-isopropyl-1H-imidazole-4-carboxylic acid ethyl ester

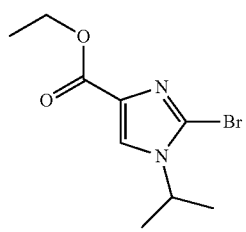

NBS (38.9 g, 218 mmol) was added to a solution of 1-isopropyl-1H-imidazole-4-carboxylic acid ethyl ester (step A1; 30.6 g, 168 mmol) in THF (500 ml) and stirred for 18 h at rt. The reaction mixture was diluted with EtOAc, washed twice with 30% aq. Na₂S₂O₃ and water and re-extracted with EtOAc. Combined organic layers were dried and evaporated. The remaining crude product was purified by flash chromatography (silica gel, heptanes/EtOAc, 100:0→25:75). $t_R$: 0.81 min (LC-MS 2); ESI-MS: 261.3/263.3 [M+H]⁺ (LC-MS 2); ¹H-NMR (DMSO-d₆, 600 MHz) δ (ppm) 8.20 (s, 1H), 4.46 (sep, 1H), 4.23 (q, 2H), 1.42 (d, 6H), 1.26 (t, 3H).

Step A1: 1-Isopropyl-1H-imidazole-4-carboxylic acid ethyl ester

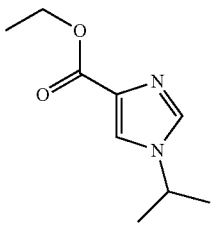

Propane-2-amine (161 ml, 189 mmol) was added to a solution of ((Z)-2-N,N-dimethylamino-1-ethoxycarbonyl-vinyl)-methylidyne-ammonium (step A2; 32g, 189 mmol) in n-BuOH (250 ml) and stirred for 15 h at 130° C. The solvent was evaporated under reduced pressure and the remaining crude material purified by flash chromatography (heptanes/EtOAc, 100:0→20:80). ¹H-NMR (DMSO-d₆, 400 MHz) δ (ppm) 7.96 (s, 1H), 7.81 (s, 1H), 4.44 (sep, 1H), 4.19 (q, 2H), 1.40 (d, 6H), 1.23 (t, 3H).

Step A2: (Z)-3-Dimethylamino-2-isocyano-acrylic acid ethyl ester

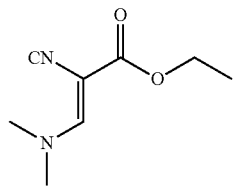

To a solution of ethyl-2-isocyanate (575 g, 5083 mmol) in EtOH (6.5 L) at 0° C. was added dropwise 1,1-diethoxy-N,N-dimethanamine (1.2 L, 6608 mmol). The mixture was stirred at rt for 30 h. The reaction mixture was diluted with TBME (1.5 L), fixed on silica gel and filtered. The mother liquor was concentrated. The residue was purified by MPLC (Column 880×150 mm, 7 kg silica gel, Flow 1000 mL/min, heptane/EtOAc, 85:15→0:100). $t_R$: 0.74 min (LC-MS 2); ESI-MS: 169.1 [M+H]⁺ (LC-MS 2); ¹H-NMR (CDCl₃, 400 MHz) δ (ppm) 7.15 (s, 2H), 4.18 (q, 2H), 3.20 (bs, 6H), 1.26 (t, 3H).

Intermediate B

2-Bromo-5-[(4-chlorophenyl)-hydroxy-methyl]-1-isopropyl-1H-imidazole-4-carboxylic acid ethyl ester

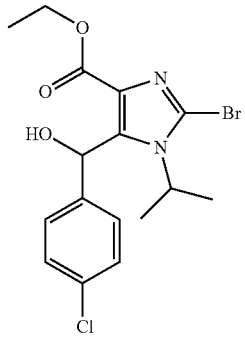 [SMILES: CCOC(=O)c1nc(Br)n(C(C)C)c1C(O)c1ccc(Cl)cc1]

LDA (63 mL, 2M solution in THF, 126 mmol) was slowly (over 30 min) added to a solution of 2-bromo-1-isopropyl-1H-imidazole-4-carboxylic acid ethyl ester (intermediate A; 11.0 g, 42.1 mmol) in THF (200 mL) at −78° C. After 2 h at −78° C., a solution of 4-chlorobenzaldehyde (8.9 g, 63.2 mmol) in THF (10 mL) was slowly added and the reaction mixture was allowed to warm to −20° C. over 30 min. The reaction mixture was quenched at −20° C. with 6 ml of acetic acid, concentrated and taken up in EtOAc/water, extracted twice with EtOAc. The combined organic extracts were washed with water and brine, dried ($Na_2SO_4$) and concentrated. The crude material was purified by chromatography (hexane/EtOAc, 60:40) to afford an orange foam. This was treated with 100 ml of 10% $Et_2O$/hexane overnight and the resulting solid was filtered and rinsed with hexane to give the title compound as a white solid. ESI-MS: 403.1 [M+H]$^+$ (LC-MS 2); $^1$H-NMR (DMSO-$d_6$, 400 MHz) δ ppm 0.90 (d, J=7.04 Hz, 3 H) 1.26 (t, J=7.04 Hz, 3 H) 1.45 (d, J=7.04 Hz, 3 H) 4.25 (qd, J=7.04, 3.13 Hz, 2 H) 4.69 (quin, J=7.04 Hz, 1 H) 6.73 (d, J=4.30 Hz, 1 H) 6.83 (d, J=4.30 Hz, 1 H) 7.27 (m, J=8.60 Hz, 2 H) 7.41 (m, J=8.60 Hz, 2 H); $R_f$=0.15 (hexane/EtOAc, 60:40)

Intermediate C

2-Bromo-5-[(4-chloro-2-methyl-phenyl)-hydroxy-methyl]-1-isopropyl-1H-imidazole-4-carboxylic acid ethyl ester

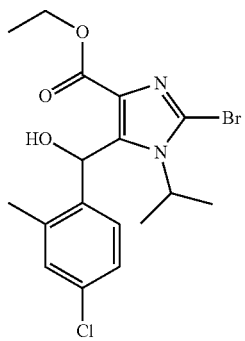 [SMILES: CCOC(=O)c1nc(Br)n(C(C)C)c1C(O)c1ccc(Cl)cc1C]

The title compound was obtained in analogy to the procedure described for intermediate B using 4-chloro-2-methyl benzaldehyde. ESI-MS: 417.2 [M+H]$^+$ (LC-MS 1); $^1$H-NMR (DMSO-$d_6$, 400 MHz) δ ppm 7.46 (d, 1H), 7.31 (d, 1H), 7.25 (s, 1H), 6.83 (s, 1H), 6.57 (s, 1H), 4.77 (sep, 1H), 4.25 (q, 2H), 2.09 (s, 3H), 1.47 (d, 3H), 1.26 (t, 3H), 1.02 (d, 3H).

Intermediate D

5-[(4-Chloro-2-methyl-phenyl)hydroxymethyl]-1-isopropyl-2-(2-methoxy-phenyl)-1H-imidazole-4-carboxylic acid ethyl ester

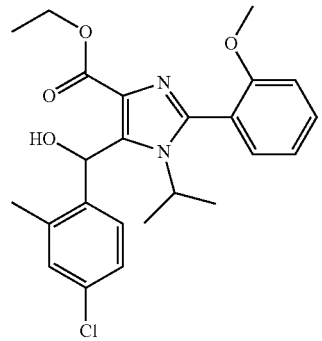 [SMILES: CCOC(=O)c1nc(-c2ccccc2OC)n(C(C)C)c1C(O)c1ccc(Cl)cc1C]

To a solution of 2-bromo-5-[(4-chloro-2-methyl-phenyl)-hydroxy-methyl]-1-isopropyl-1H-imidazole-4-carboxylic acid ethyl ester (intermediate C, 3.5 g, 8.4 mmol) in dioxane (80 ml)/$H_2O$ (20 ml) were added 2-methoxy-phenyl boronic acid (2.0 g, 13.2 mmol), $K_2CO_3$ (3 g, 21.7 mmol). The mixture was degassed for 5 min and then Pd(PPh$_3$)$_4$ (1.7 g, 1.5 mmol) was added. The mixture was stirred at 100° C. for 2 h to give a complete conversion. Dioxane was removed under reduced pressure. The residual material was dissolved in EtOAc and extracted with brine. The aqueous layer was washed with EtOAc. The combined organic layers were dried ($Na_2SO_4$), filtered and concentrated under reduced pressure. The product was fixed on silica gel and purified by flash chromatography (silica gel, solvent: $CH_2Cl_2$/EtOAc, 100:0→80:20) to give the title compound as a yellow foam. $t_R$: 1.27 min (LC-MS 2); ESI-MS 433.3 [M+H]$^+$ (LC-MS 2). $^1$H-NMR (DMSO-$d_6$, 400 MHz) δ ppm 7.56-7.48 (m, 2H), 7.29-7.05 (m, 3H), 7.34-7.29 (m, 1H), 7.10-7.96 (m, 1H), 6.94-6.91 (m, 1H), 6.52 (d, 1H), 4.58-4.52 (m, 1H), 4.24 (q, 2H), 3.73/3.68 (s, 3H), 2.16 (s, 3H), 1.27 (t, 3H), 1.05 (d, 3H), 0.58 (d, 3H).

Intermediate E

2-Bromo-5-[(5-chloro-2-methyl-phenyl)-6-(4-chloro-phenyl)-1-isopropyl-5,6-dihydro-1H-pyrrolo[3,4-d]imidazol-4-one

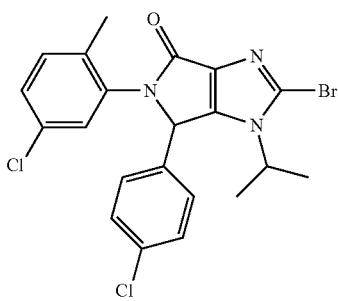

2-Bromo-5-[(4-chloro-phenyl)-5-chloro-2-methyl-phenylamino]-1-isopropyl-1H-imidazole-4-carboxylic acid (step E1; 4.7 g, 9.4 mmol), TBTU (3.6 g, 11.3 mmol), DIEA (3.6 g, 28.2 mmol) were dissolved in DMF (50 mL) and stirred at 80°

C. for 7 h. The reaction mixture was diluted in EtOAc/water, extracted twice with EtOAc and the combined organic extracts were washed with water and brine, dried (Na$_2$SO$_4$) and concentrated. The crude material was purified by flash chromatography (silica gel, hexanes/EtOAc, 100:0→40:60) to afford the title compound as a white solid; ESI-MS: 479.2 [M+H]$^+$ (LC-MS 2); $^1$H-NMR (DMSO-d$_6$, 400 MHz) δ ppm 0.74 (d, J=6.65 Hz, 3 H) 1.25 (d, J=6.65 Hz, 1 H) 1.30-1.46 (m, 3 H) 1.84 (br. s., 2 H) 4.52 (dt, J=13.39, 6.79 Hz, 1 H) 6.55 (br. s., 1 H) 7.03-7.30 (m, 4 H) 7.36 (d, J=7.82 Hz, 2 H) 7.72 (d, J=1.56 Hz, 1 H).

Step E1: 2-Bromo-5-[(4-chloro-phenyl)-5-chloro-2-methyl-phenylamino]-1-isopropyl-1H-imidazole-4-carboxylic acid

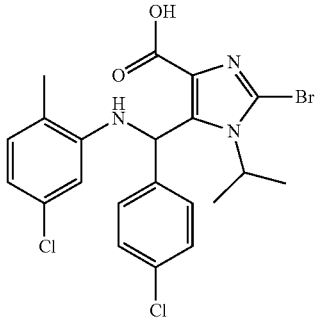 [SMILES: Cc1ccc(Cl)cc1NC(c1ccc(Cl)cc1)c1c(C(=O)O)nc(Br)n1C(C)C]

NaOH (100 mL, 2 M aqueous solution, 200 mmol) was added to a solution of 2-bromo-5-[(4-chloro-phenyl)-5-chloro-2-methyl-phenylamino]-1-isopropyl-1H-imidazole-4-carboxylic acid ethyl ester (step E2; 5.0 g, 9.6 mmol) in THF (100 mL) and MeOH (100 mL) at rt and reactants were stirred at rt for 2 h. THF and MeOH were evaporated, then the mixture was diluted in EtOAc/H$_2$O and the pH was adjusted to 5 with diluted HCl. The aqueous layer was extracted once with EtOAc. The organic extract was dried (Na$_2$SO$_4$) and concentrated to afford an off-white foam; ESI-MS: 598.2 [M+H]$^+$ (LC-MS 2); $^1$H-NMR (DMSO-d$_6$, 400 MHz) δ ppm 1.20 (d, J=18.38 Hz, 3 H) 1.44 (d, J=6.65 Hz, 3 H) 2.16 (s, 3 H) 4.97 (d, J=7.04 Hz, 1 H) 6.62 (dd, J=7.82, 1.95 Hz, 2 H) 6.78 (d, J=2.35 Hz, 1 H) 7.03 (d, J=7.82 Hz, 1 H) 7.27 (m, 2 H) 7.42 (m, J=8.60 Hz, 2 H).

Step E2: 2-Bromo-5-[(4-chloro-phenyl)-5-chloro-2-methyl-phenylamino]-1-isopropyl-1H-imidazole-4-carboxylic acid ethyl ester

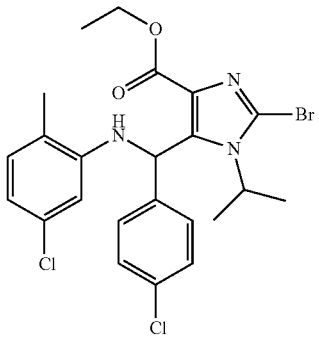 [SMILES: CCOC(=O)c1nc(Br)n(C(C)C)c1C(Nc1cc(Cl)ccc1C)c1ccc(Cl)cc1]

Ms$_2$O (3.6 g, 20.9 mmol) was added to a stirred solution of 2-bromo-5-[(4-chlorophenyl)-hydroxy-methyl]-1-isopropyl-1H-imidazole-4-carboxylic acid ethyl ester (intermediate B; 4.2 g, 20.9 mmol) and TEA (5.3 g, 52.0 mmol) in DCM (80 mL) at 5° C. and the reaction mixture was stirred at 5° C. for 15 min. 5-Chloro-2-methyl aniline (2.2 g, 15.7 mmol) was then added. The reaction mixture was allowed to reach rt in 45 min and stirred at rt for 2 h. The reaction mixture was diluted in DCM/water, extracted twice with DCM and the combined organic extracts were washed with brine, dried (Na$_2$SO$_4$) and concentrated. The crude material was purified by flash chromatography (silica gel, EtOAc/hexanes 2:8) to afford the title compound as a white foam; ESI-MS: 526.2 [M+H]$^+$ (LC-MS 2); $^1$H-NMR (DMSO-d$_6$, 400 MHz) δ ppm 1.15 (dd, J=9.97, 4.11 Hz, 2 H) 1.15 (s, 1 H) 1.24 (t, J=7.23 Hz, 3 H) 1.45 (d, J=7.04 Hz, 3 H) 2.17 (s, 3 H) 4.24 (quin, J=6.74 Hz, 2 H) 4.83-5.04 (m, 1 H) 5.92 (d, J=5.47 Hz, 1 H) 6.47 (bs, 1 H) 6.63 (dd, J=7.82, 1.95 Hz, 1H) 6.79 (bs, 1H) 7.04 (d, J=8.21 Hz, 1 H) 7.26 (m, J=8.60 Hz, 2 H) 7.43 (m, J=8.60 Hz, 2 H).

Intermediate F

2-Bromo-5-(5-chloro-2-methyl-phenyl)-6-(4-chloro-2-methyl-phenyl)-1-isopropyl-5,6-dihydro-1H-pyrrolo[3,4-d]imidazole-4-one

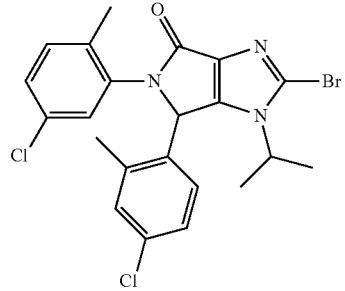 [SMILES: Cc1cc(Cl)ccc1C1c2c(nc(Br)n2C(C)C)C(=O)N1c1cc(Cl)ccc1C]

The product from step F1 (4.6 g, 7.1 mmol) was dissolved in DMF (100 mL) and NMM (2.2 g, 2.3 mL, 21.3 mmol) and HATU (2.8 g, 7.5 mmol) were added and the reaction mixture stirred at rt for 18 h. After completion the temperature was raised to 80° C. and stirring continued for 3 h. DMF was removed under reduced pressure and the residual material dissolved in EtOAc. The organic solution was washed with aqueous citric acid solution, saturated aqueous NaHCO$_3$ solution and brine, dried (Na$_2$SO$_4$) and concentrated. The crude material was crystallized in hexanes/EtOAc to give the title compound as white solid. t$_R$: 1.27 min (LC-MS 1); ESI-MS: 491.1 [M+H]$^+$ (LC-MS 1).

Step F1: 2-Bromo-5-[(4-chloro-2-methyl-phenyl)-5-chloro-2-methyl-phenylamino]-1-isopropyl-1H-imidazole-4-carboxylic acid

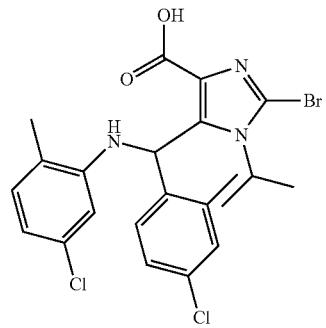 [SMILES: Cc1ccc(Cl)cc1NC(c1ccc(Cl)cc1C)c1c(C(=O)O)nc(Br)n1C(C)C]

The title compound was prepared in analogy to the procedure described for step E1 with the product from step F2 as starting material; ESI-MS: 512.1 [M+H]$^+$ (LC-MS 1);

¹H-NMR (DMSO-d₆, 400 MHz) δ ppm 7.28 (s, 1H), 7.18 (d, 1H), 6.95-6.88 (m, 2H), 6.69 (s, 1H), 6.50 (s, 1H), 4.84-4.79 (m, 1H), 2.33 (s, 3H), 2.03 (3H), 1.50 (bs, 3H), 1.29 (bs, 3H).

Step F2: 2-Bromo-5-[(4-chloro-2-methyl-phenyl)-5-chloro-2-methyl-phenylamino]-1-isopropyl-1H-imidazole-4-carboxylic acid ethyl ester

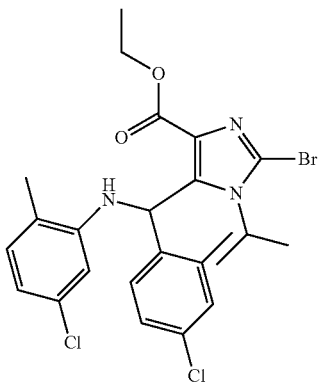 [SMILES: CCOC(=O)c1nc(Br)n(C(C)C)c1C(Nc1cc(Cl)ccc1C)c1ccc(Cl)cc1C]

The title compound was prepared in analogy to the procedure described for step E2 using 2-bromo-5-[(4-chloro-2-methyl-phenyl)-hydroxy-methyl]-1-isopropyl-1H-imidazole-4-carboxylic acid ethyl ester (intermediate C) and 2-methyl-5-chloroaniline as starting materials. t_r: 1.46 min (LC-MS 1); ESI-MS: 540.2 [M+H]⁺ (LC-MS 1); ¹H-NMR (DMSO-d₆, 400 MHz) δ ppm 7.36 (s, 1H), 7.23 (d, 1H), 6.97 (dd, 2H), 6.73 (bs, 1H), 6.58 (d, 1H), 6.35 (s, 1H), 5.91 (d, 1H), 5.02 (sep, 1H), 4.21 (q, 2H), 2.19 (s, 3H), 2.09 (s, 3H), 1.38 (d, 3H), 1.31 (d, 3H), 1.22 (t, 3H).

Intermediate G

2-Bromo-5-(3-chloro-2-fluoro-phenyl)-6-(4-chloro-phenyl)-1-isopropyl-5,6-dihydro-1H-pyrrolo[3,4-d]imidazol-4-one

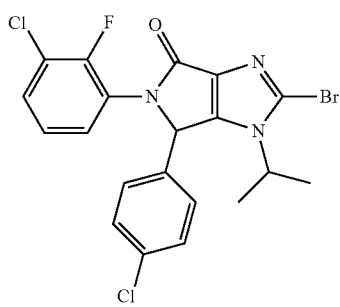 [SMILES: CC(C)n1c(Br)nc2c1C(c1ccc(Cl)cc1)N(c1cccc(Cl)c1F)C2=O]

The title compound was prepared in analogy to the procedure described for intermediate F using the product from step G1 as starting material. t_R: 1.19 min (LC-MS 1); ESI-MS: 484.0 [M+H]⁺ (LC-MS 1).

Step G1: 2-Bromo-5-[(3-chloro-2-fluoro-phenyl)-4-chloro-phenylamino]-1-isopropyl-1H-imidazole-4-carboxylic acid

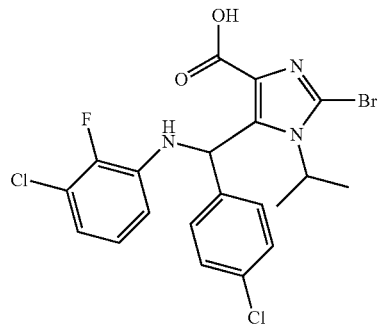 [SMILES: CC(C)n1c(Br)nc(C(=O)O)c1C(Nc1cccc(Cl)c1F)c1ccc(Cl)cc1]

The title compound was prepared in analogy to the procedure described for step E1 with the product from step G2 as starting material; ESI-MS: 502.2 [M+H]⁺ (LC-MS 1); ¹H-NMR (DMSO-d₆, 400 MHz) δ ppm 7.46 (d, 2H), 7.29 (d, 2H), 6.99 (dd, 1H), 6.82 (d, 1H), 6.73-6.69 (m, 2H), 4.82 (sep, 1H), 1.45 (d, 3H), 1.18 (d, 3H).

Step G2: 2-Bromo-5-[(3-chloro-2-fluoro-phenyl)-4-chloro-phenylamino]-1-isopropyl-1H-imidazole-4-carboxylic acid ethyl ester

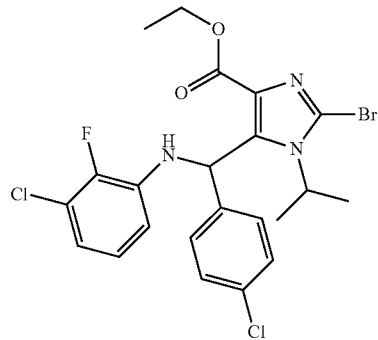 [SMILES: CCOC(=O)c1nc(Br)n(C(C)C)c1C(Nc1cccc(Cl)c1F)c1ccc(Cl)cc1]

The title compound was prepared in analogy to the procedure described for step E2 using 2-bromo-5-[(4-chlorophenyl)-hydroxy-methyl]-1-isopropyl-1H-imidazole-4-carboxylic acid ethyl ester (intermediate B) and 2-fluoro-3-chloro-aniline as starting materials; ¹H-NMR (DMSO-d₆, 400 MHz) δ ppm 7.46 (d, 2H), 7.30 (d, 2H), 6.98 (dd, 1H), 6.82 (d, 1H), 6.73-6.69 (m, 2H), 4.82 (sep 1H), 4.26 (q, 2H), 1.45 (d, 3H), 1.24 (t, 3H), 1.17 (d, 3H).

Intermediate H

4-[2-Bromo-5-(5-chloro-2-methyl-phenyl)-3-isopropyl-6-oxo-3,4,5,6-tetrahydro-pyrrolo[3,4-d]imidazol-4-yl]-benzonitrile

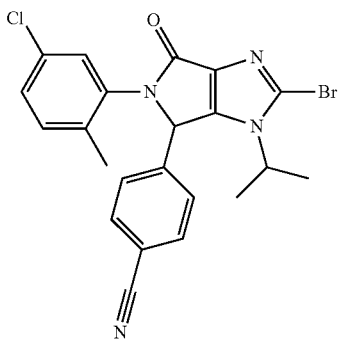 [SMILES: Cc1ccc(Cl)cc1N1C(=O)c2nc(Br)n(C(C)C)c2C1c1ccc(C#N)cc1]

The title compound was prepared in analogy to the procedure described for intermediate E using the product from step H1 as starting material. $t_R$: 1.09 min (LC-MS 2); ESI-MS: 469.3 [M+H]$^+$ (LC-MS 2).

Step H1: 2-Bromo-5-[(5-chloro-2-methyl-phenylamino)-(4-cyano-phenyl)-methyl]-1-isopropyl-1H-imidazole-4-carboxylic acid

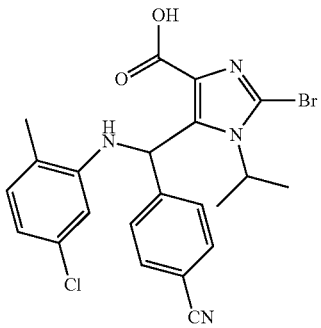 [SMILES: Cc1ccc(Cl)cc1NC(c1ccc(C#N)cc1)c1c(C(=O)O)nc(Br)n1C(C)C]

The title compound was prepared in analogy to the procedure described for step E1 with the product from step H2 as starting material. $t_r$: 1.13 min (LC-MS 2); ESI-MS: 486.9 [M–H]$^+$ (LC-MS 2).

Step H2: 2-Bromo-5-[(5-chloro-2-methyl-phenylamino)-(4-cyano-phenyl)-methyl]-1-isopropyl-1H-imidazole-4-carboxylic acid ethyl ester

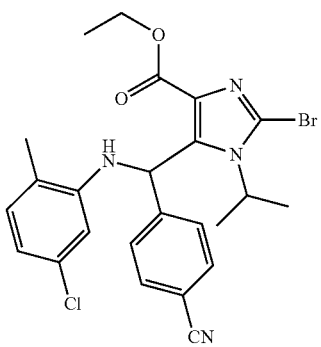 [SMILES: CCOC(=O)c1nc(Br)n(C(C)C)c1C(Nc1cc(Cl)ccc1C)c1ccc(C#N)cc1]

The title compound was prepared in analogy to the procedure described for step E2 using 2-bromo-5-[(4-cyano-phenyl)-hydroxy-methyl]-1-isopropyl-1H-imidazole-4-carboxylic acid ethyl ester (step H3) and 5-chloro-2-methylaniline as starting materials. $t_R$: 1.35 min (LC-MS 2); ESI-MS: 515.2 [M–H]$^+$ (LC-MS 2); $R_f$=0.16 (hexane/ EtOAc, 3:1).

Step H3: 2-Bromo-5-[(4-cyano-phenyl)-hydroxy-methyl]-1-isopropyl-1H-imidazole-4-carboxylic acid ethyl ester

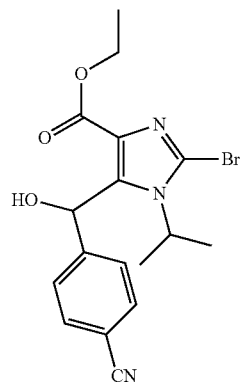 [SMILES: CCOC(=O)c1nc(Br)n(C(C)C)c1C(O)c1ccc(C#N)cc1]

LDA (2 M in THF, 53.6 mL, 107 mmol) was added slowly (over 30 min) to a cold (–78° C.) solution of intermediate A (20 g, 77 mmol) in THF (400 mL) (during the addition, the temperature raised to –70° C.). The mixture was stirred for 1 h at –78° C. A solution of 4-cyanobenzaldehyde (14 g, 107 mmol) in THF (100 mL) was added slowly. The reaction mixture was stirred for 30 min at –78° C., allowed to warm to –20° C. over 1 h, quenched by addition of acetic acid (10 mL), diluted with EtOAc/water, and extracted with EtOAc. The organic extracts were washed with water and brine, dried (Na$_2$SO$_4$), filtered, and concentrated. The residue was purified by flash chromatography (hexane/EtOAc, 1:1), followed by trituration in EtOAc, to provide 20.1 g of the title compound. $t_R$: 0.99 min (LC-MS 2); ESI-MS: 392.2/394.1 [M+H]$^+$ (LC-MS 2); $R_f$=0.29 (hexane/EtOAc, 1:1).

Intermediate I

2-Bromo-6-(4-chloro-2-methyl-phenyl)-5-(4-chloropyridinyl)-1-isopropyl-5,6-dihydro-1H-pyrrolo[3,4-d]imidazole-4-one

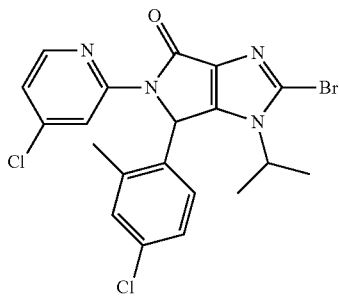 [SMILES: Cc1cc(Cl)ccc1C1c2c(nc(Br)n2C(C)C)C(=O)N1c1cc(Cl)ccn1]

The title compound was prepared in analogy to the procedure described for intermediate F with the product from step I1 as starting material. $t_R$: 1.38 min (LC-MS 1); ESI-MS: 481.0 [M+H]$^+$ (LC-MS 1); $^1$H-NMR (DMSO-d$_6$, 400 MHz) δ ppm 8.27 (d, 1H), 8.23 (s, 1H), 7.36 (s, 1H), 7.19 (d, 1H), 7.12 (d, 1H), 6.87 (s, 1H), 6.75 (d, 1H), 4.49 (sep, 1H), 2.80 (s, 3H); 1.36 (d, 3H), 0.69 (d, 3H).

Step I1: 2-Bromo-5-[(4-chloro-2-methyl-phenyl)-(4-chloro-pyridin-2-ylamino)-methyl]-1-isopropyl-1H-imidazole-4-carboxylic acid

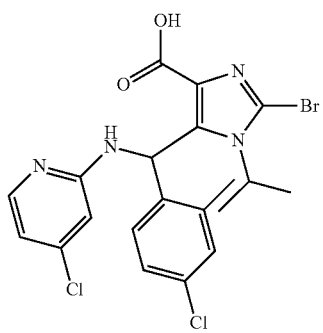 [SMILES: Cc1cc(Cl)ccc1C(Nc1cc(Cl)ccn1)c1c(C(=O)O)nc(Br)n1C(C)C]

The title compound was prepared in analogy to the procedure described for step E1 using the product from step I2 as starting material. $t_R$: 1.24 min (LC-MS 1); ESI-MS: 499.2 [M+H]$^+$ (LC-MS 1); $^1$H-NMR (DMSO-d$_6$, 400 MHz) δ ppm 7.91 (d, 1H), 7.57 (bs, 1H), 7.33 (s, 1H), 7.21 (d, 1H), 7.11 (bs, 1H), 7.00 (d, 1H), 6.65 (s, 1H), 6.63 (d, 1H), 4.72 (sep, 1H), 2.16 (s, 3H), 1.43 (d, 3H), 0.99 (d, 3H).

Step I2: 2-Bromo-5-[(4-chloro-2-methyl-phenyl)-(4-chloro-pyridin-2-ylamino)-methyl]-1-isopropyl-1H-imidazole-4-carboxylic acid ethyl ester

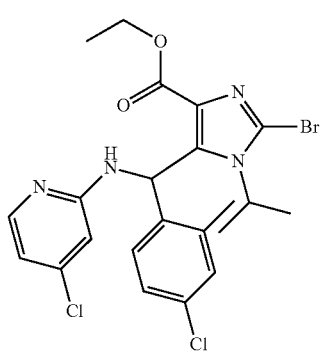 [SMILES: CCOC(=O)c1nc(Br)n(C(C)C)c1C(Nc1cc(Cl)ccn1)c1ccc(Cl)cc1C]

The title compound was prepared in analogy to the procedure described for step E2 using 2-bromo-5-[(4-chloro-2-methyl-phenyl)-hydroxy-methyl]-1-isopropyl-1H-imidazole-4-carboxylic acid ethyl ester (intermediate C) and 2-amino-4-chloro-pyridine as starting materials. $t_R$: 1.42 min (LC-MS 1); ESI-MS: 527.2 [M+H]$^+$ (LC-MS 1).

Intermediate J

2-Bromo-5-(5-chloro-1-methyl-6-oxo-1,6-dihydro-pyridin-3-yl)-6-(4-chloro-phenyl)-1-isopropyl-5,6-dihydro-1H-pyrrolo[3,4-d]imidazol-4-one

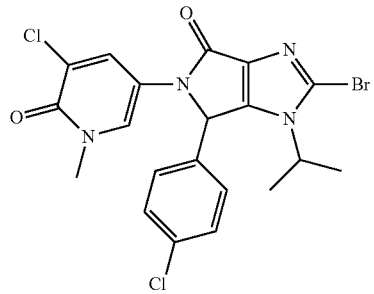 [SMILES: CC(C)n1c(Br)nc2c1C(c1ccc(Cl)cc1)N(c1cc(Cl)c(=O)n(C)c1)C2=O]

The title compound was prepared in analogy to the procedure described for intermediate F using the product from step J1 as starting material. $t_R$: 0.97 min (LC-MS 2); ESI-MS: 497.1 [M+H]$^+$ (LC-MS 2); $^1$H-NMR (DMSO-d$_6$, 400 MHz) δ ppm 7.88 (s, 2H), 7.46 (d, 2H), 7.24 (d, 2H), 6.43 (s, 1H), 4.55 (sep, 1H), 3.45 (s, 3H), 1.42 (d, 3H), 0.68 (d, 3H).

Step J1: 2-Bromo-5-[(5-chloro-1-methyl-6-oxo-1,6-dihydro-pyridin-3-ylamino)-4-chloro-phenyl)-methyl]-1-isopropyl-1H-imidazole-4-carboxylic acid

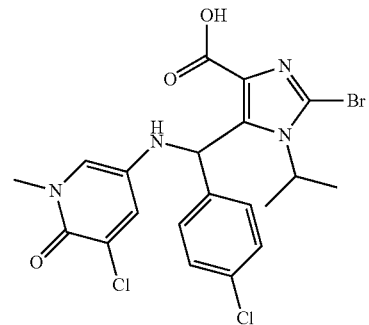 [SMILES: CC(C)n1c(Br)nc(C(=O)O)c1C(Nc1cc(Cl)c(=O)n(C)c1)c1ccc(Cl)cc1]

The title compound was prepared in analogy to the procedure described for step E1 using the product from step J2. $t_R$: 0.94 min (LC-MS 2); ESI-MS: 515.1 [M+H]$^+$ (LC-MS 2). $^1$H-NMR (DMSO-d$_6$, 400 MHz) δ ppm 7.64 (s, 1H), 7.46 (d, 2H), 7.35 (s, 1H), 7.33 (d, 2H), 6.47 (bs, 1H), 4.61 (sep, 1H), 3.47 (s, 3H), 1.34 (d, 3H), 1.27 (d, 3H).

Step J2: 2-Bromo-5-[(5-chloro-1-methyl-6-oxo-1,6-dihydro-pyridin-3-ylamino)-4-chloro-phenyl)-methyl]-1-isopropyl-1H-imidazole-4-carboxylic acid ethyl ester

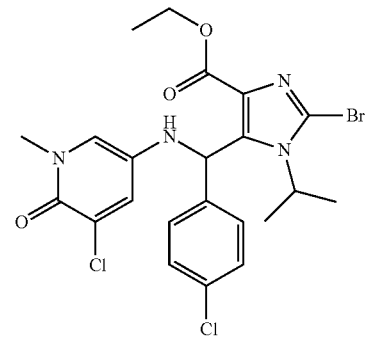 [SMILES: CCOC(=O)c1nc(Br)n(C(C)C)c1C(Nc1cc(Cl)c(=O)n(C)c1)c1ccc(Cl)cc1]

The title compound was prepared in analogy to the procedure described for step E2 using 2-bromo-5-[(4-chlorophenyl)-hydroxy-methyl]-1-isopropyl-1H-imidazole-4-carboxylic acid ethyl ester (intermediate B) and the product from step J3 as starting materials. $t_R$: 1.09 min (LC-MS 2).; ESI-MS: 543.2 [M+H]$^+$ (LC-MS 2).

Step J3:
5-Amino-3-chloro-1-methyl-1H-pyridin-2-one

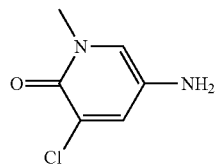

A mixture of the compound prepared in step J4 (3.4 g, 18.1 mmol), iron powder (3 g, 54.3 mmol), EtOH (68 mL) and an aqueous saturated NH$_4$Cl solution (17 mL) was stirred for 1 h at reflux. The reaction mixture was allowed to cool to rt, filtered through a pad of celite and concentrated. The residue was purified by flash chromatography (CH$_2$Cl$_2$/MeOH, 97:3) to provide 2.7 g of the title compound; ESI-MS: 159 [M+H]$^+$ (LC-MS 2); R$_f$=0.06 (CH$_2$Cl$_2$/MeOH, 95:5). $^1$H-NMR (DMSO-d$_6$, 400 MHz) δ ppm 7.36 (s, 1H), 6.88 (s, 1H), 4.42 (bs, 2H), 3.36 (s, 3H).

Step J4:
3-Chloro-1-methyl-5-nitro-1H-pyridin-2-one

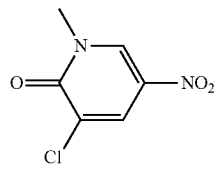

Methyl iodide (0.12 mL, 1.73 mmol) was added to a cold (0° C.) mixture of 3-chloro-2-hydroxy-5-nitropyridine (0.2 g, 1.15 mmol) and K$_2$CO$_3$ (0.32 g, 2.23 mmol) in DMF (5 mL). The reaction mixture was allowed to warm to rt, stirred for 2 h, quenched by addition of water, and extracted with EtOAc. The organic phase was washed with brine, dried (Na$_2$SO$_4$), filtered and concentrated. The crude material was purified by flash chromatography (hexane/EtOAc, 9:1) to afford 0.136 g of the title compound. $t_R$: 0.64 min (LC-MS 2); ESI-MS: 189 [M+H]$^+$ (LC-MS 2); R$_f$=0.50 (hexane/EtOAc, 1:1).

Intermediate K

5-N-Methyl-carboxamido-2-methoxy-phenyl boronic acid

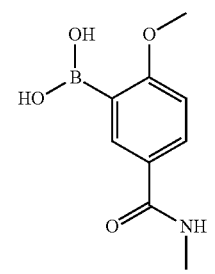

5-Carboxy-2-methoxyphenyl boronic acid (200 mg, 1.0 mmol) was dissolved in DMF (6 mL) and methylamine (2 M solution in THF, 2.0 mmol) was added followed by HATU (430 mg, 1.1 mmol) and NMM (450 µL, 4.0 mmol). The reaction mixture was allowed to stir at rt for 2 days and concentrated. The residue diluted in EtOAc and the organic phase washed with brine, dried and concentrated to give the crude product which was recrystallized in DCM to give the title compound as a white solid; ESI-MS: 210.1 [M+H]$^+$ (LC-MS 2); $^1$H-NMR (DMSO-d$_6$, 400 MHz) δ ppm 8.23 (bs, 1H), 8.00 (s, 1H), 7.84 (d, 1H), 6.99 (d, 1H), 3.81 (s, 3H), 2.73 (s, 3H).

Intermediate L

5-N-(2-Hydroxyethyl)-carboxamido-2-methoxy-phenyl boronic acid

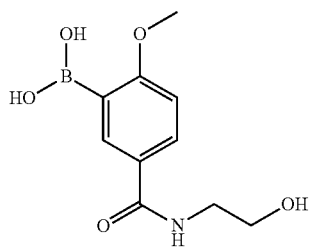 [SMILES: COc1ccc(C(=O)NCCO)cc1B(O)O]

The title compound was prepared in analogy to the procedure described for Intermediate K using 5-carboxy-2-methoxyphenyl boronic acid and ethanolamine; ESI-MS: 240.2 [M+H]$^+$ LC-MS 2); $^1$H-NMR (DMSO-d$_6$, 400 MHz) δ ppm 8.60 (bs, 1H), 8.30 (s, 1H), 7.96 (d, 1H), 7.08 (d, 1H), 3.85 (s, 3H), 3.55-3.48 (m, 2H), 3.35-3.30 (m, 2H).

Intermediate M

5-N,N-Dimethyl-carboxamido-2-methoxy-phenyl boronic acid

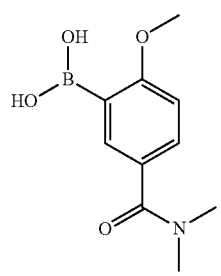 [SMILES: COc1ccc(C(=O)N(C)C)cc1B(O)O]

The title compound was prepared in analogy to the procedure described for intermediate K using 5-carboxy-2-methoxyphenyl boronic acid and dimethylamine (2M solution in THF); ESI-MS: 223.2 [M+H]$^+$ (LC-MS 2); $^1$H-NMR (DMSO-d$_6$, 400 MHz) δ 7.83 (s, 1H), 7.58 (s, 1H), 7.46 (d, 1H), 7.02 (d, 1H), 3.83 (s, 3H), 2.51 (s, 6H).

Intermediate N

5-N-Isopropyl-carboxamido-2-methoxy-phenyl boronic acid

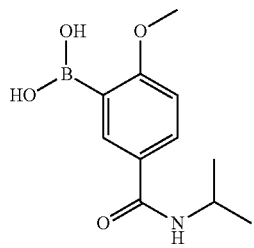 [SMILES: COc1ccc(C(=O)NC(C)C)cc1B(O)O]

The title compound was prepared in analogy to the procedure described for intermediate K using 5-carboxy-2-methoxyphenyl boronic acid and isopropylamine; ESI-MS: 238.2 [M+H]$^+$ (LC-MS 2); $^1$H-NMR (DMSO-d$_6$, 400 MHz) δ 8.08 (d, 1H), 8.03 (s, 1H), 7.90 (d, 1H), 7.00 (d, 1H), 4.21 (sept, 1H), 3.84 (s, 3H), 1.15 (d, 6H).

Intermediate O

5-Morpholine-carbonyl-2-methoxy-phenyl boronic acid

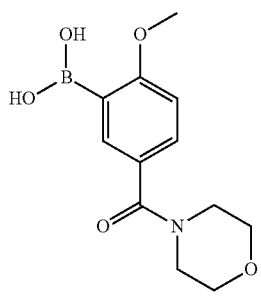 [SMILES: COc1ccc(C(=O)N2CCOCC2)cc1B(O)O]

The title compound was prepared in analogy to the procedure described for intermediate K using 5-carboxy-2-methoxyphenyl boronic acid and morpholine; ESI-MS: 266.5 [M+H]$^+$ (LC-MS 2); $^1$H-NMR (DMSO-d$_6$, 400 MHz) δ 7.84 (s, 1H), 7.57 (d, 1H), 7.46 (d, 1H), 7.03 (d, 1H), 3.83 (s, 3H), 3.62-3.60 (m, 4H), 3.49-3.42 (m, 4H).

Intermediate P

5-(3-Hydroxy-azetidine)-carbonyl-2-methoxy-phenyl boronic acid

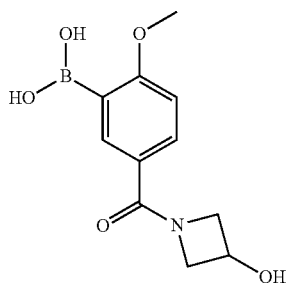 [SMILES: COc1ccc(C(=O)N2CC(O)C2)cc1B(O)O]

The title compound was prepared in analogy to the procedure described for intermediate K using 5-carboxy-2-methoxyphenyl boronic acid and 2-hydroxy-azetidine. t$_R$: 0.45 min (LC-MS 2); ESI-MS: 254.4 [M+H]$^+$ (LC-MS 2).

Intermediate Q

2-Bromo-5-(3-chloro-4-fluoro-phenyl)-6-(4-chloro-phenyl)-1-isopropyl-5,6-dihydro-1H-pyrrolo[3,4-d]imidazol-4-one

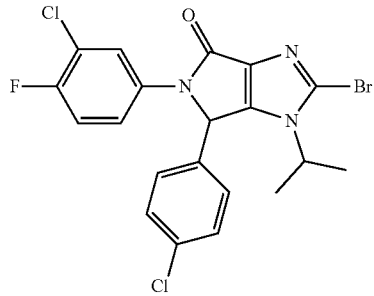

The title compound was prepared in analogy to the procedure described for intermediate F with the product from step Q1. t$_R$: 1.21 min (LC-MS 2); ESI-MS: 484.1 [M+H]$^+$ (LC-MS 2).

Step Q1: 2-Bromo-5-[(3-chloro-4-fluoro-phenyl)-4-chloro-phenylamino]-1-isopropyl-1H-imidazole-4-carboxylic acid

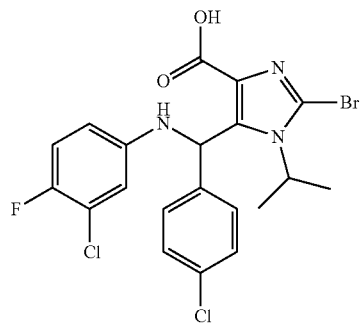

The title compound was prepared in analogy to the procedure described for step E1. t$_R$: 1.20 min (LC-MS 2); ESI-MS: 502.0 [M+H]$^+$ (LC-MS 2); $^1$H-NMR (DMSO-d$_6$, 400 MHz) δ ppm 7.46 (d, 2H), 7.32 (d, 2H), 7.09 (dd, 1H), 6.89 (d, 1H), 6.71 (d, 1H), 4.57 (bs, 1H), 4.01 (sep, 1H), 1.36 (d, 3H), 1.17 (d, 3H).

Step Q2: 2-Bromo-5-[(3-chloro-4-fluoro-phenyl)-4-chloro-phenylamino]-1-isopropyl-1H-imidazole-4-carboxylic acid ethyl ester

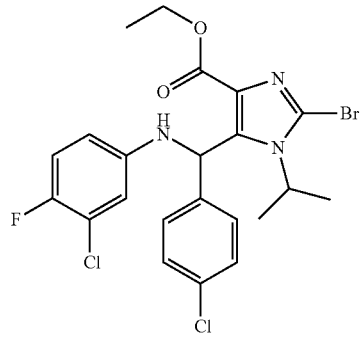 [SMILES: CCOC(=O)c1nc(Br)n(C(C)C)c1C(Nc1ccc(F)c(Cl)c1)c1ccc(Cl)cc1]

The title compound was prepared in analogy to the procedure described for step E2 using 2-bromo-5-[(4-chlorophenyl)-hydroxy-methyl]-1-isopropyl-1H-imidazole-4-carboxylic acid ethyl ester (intermediate B) and 3-chloro-4-fluoro-aniline as starting materials. $t_R$ 1.38 min (LC-MS 2); ESI-MS: 530.1 [M+H]$^+$ (LC-MS 2).

Intermediate R 4-(Hydroxymethyl)-2-methoxy-phenyl boronic acid

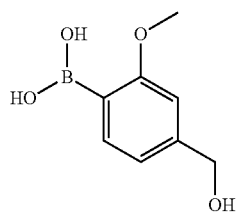

4-Carboxy-2-methoxyphenylboronic acid (500 mg, 2.5 mmol) was dissolved in THF (25 mL) and cooled to 0° C. At this temperature LAH (2 M solution in THF; 3.3 mL, 6.6 mmol) was added drop wise and the reaction mixture allowed to stir for 1 h at 0° C. and then allowed to warm to rt and stirred for 16 h. The reaction mixture was recooled to 0° C. and quenched by addition of MeOH. Celite and Na$_2$SO$_4$ were added, stirred for 15 min and then filtered. The filtrate was concentrated and the residue was dried under high vacuum to give the title compound which was used without further purification. $t_R$: 0.46 min (LC-MS 2).

Intermediate S

3-Methoxy-4-(4,4,5,5-tetramethyl-[1,3,2]dioxaborolan-2-ylbenzonitrile

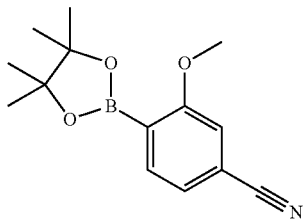 [SMILES: COc1cc(C#N)ccc1B1OC(C)(C)C(C)(C)O1]

4-Bromo-3-methoxy-benzonitrile (300 mg, 1.4 mmol) was dissolved in dioxane (2.5 mL) and the solution was flushed with argon. Bis-pinacolatodiboron (719 mg, 2.8 mmol), Pd(dppf)Cl$_2$ (58 mg, 0.07 mmol) and KOAc (417 mg, 4.2 mmol) were added and the reaction mixture was heated to 100° C. and stirred at this temperature for 19 h. It was then allowed to cool to rt and diluted with EtOAc. The organic phase was washed with brine, dried (Na$_2$SO$_4$) and concentrated. The residual crude product was purified by flash chromatography (25 g silica gel cartridge, hexanes/EtOAc, 100:0→60:40) to give the title compound as a white solid;

$^1$H-NMR (DMSO-d$_6$, 400 MHz) δ ppm 7.68 (d, 1H), 7.42 (s, 1H), 7.39 (d, 1H), 3.82 (s, 3H), 1.32 (s, 12H).

Intermediate T

4-Methoxy-5-(4,4,5,5-tetramethyl-[1,3,2]dioxaborolan-2-yl)-pyrimidine

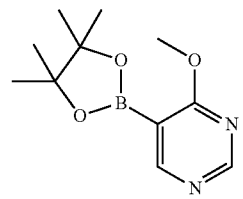 [SMILES: COc1ncncc1B1OC(C)(C)C(C)(C)O1]

A mixture of the compound prepared in step T1 (3 g, 15.9 mmol), bis(pinacolato)diboron (4.43 g, 17.5 mmol), PdCl$_2$(dppf)-CH$_2$Cl$_2$ complex (0.648 g, 0.794 mmol) and KOAc (4.67 g, 47.6 mmol) in DMSO (2 mL) was heated to 100° C. under argon and stirred for 2 h, allowed to cool to rt, diluted with EtOAc/water, and extracted with EtOAc. The organic layer was washed with water and brine, dried (Na$_2$SO$_4$), filtered, and concentrated. The residue was boiled in Et$_2$O and filtered. The filtrate was concentrated, triturated in hexane, and filtered to afford 1.19 g of the title compound. For the corresponding boronic acid. $t_R$: 0.36 min (LC-MS 2); ESI-MS: 155.1 [M+H]$^+$ (LC-MS 2).

Step T1: 5-Bromo-4-methoxy-pyrimidine

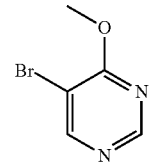

A mixture of the compound prepared in step T2 (3.13 g, 17.9 mmol) and POCl$_3$ (16.7 mL, 179 mmol) was stirred for 1 h at 80° C. and concentrated. The residue was dissolved in CH$_2$Cl$_2$ (30 mL) and cooled to 5° C. MeOH (20 mL) was added. The mixture was stirred for 1 h at rt and concentrated. The residue was triturated in CH$_2$Cl$_2$ to afford 3.2 g of the title compound; API-MS: 189.0 [M+H]$^+$.

Step T2: 5-Bromo-3H-pyrimidin-4-one

A mixture of 3H-pyrimidin-4-one (11 g, 114 mmol), bromine (6.5 mL, 126 mmol), and KOAc (33.7 g, 343 mmol) in AcOH (100 mL) was stirred for 30 min at rt. The resulting precipitate was collected by filtration to provide 30 g of a white solid. This solid was dissolved in CH$_2$Cl$_2$/water, extracted with CH$_2$Cl$_2$/MeOH (9:1). The organic layer was dried (Na$_2$SO$_4$), filtered, and concentrated to afford 3.1 g of the title compound (compound was soluble in water and stayed in the aqueous layer despite repeated extractions). $t_R$: 0.35 min (LC-MS 2); ESI-MS: 175.0 [M+H]$^+$ (LC-MS 2).

Intermediate U

4-Methoxy-5-(4,4,5,5-tetramethyl-[1,3,2]dioxaborolan-2-yl)-pyrimidin-2-ylamine

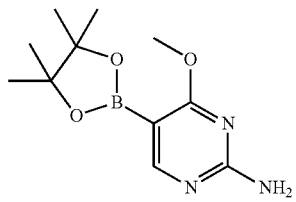 [SMILES: COc1nc(N)ncc1B1OC(C)(C)C(C)(C)O1]

A mixture of 5-bromo-4-methoxypyrimidin-2-amine (2.27 g, 11.1 mmol), bis(pinacolato)diboron (3.1 g, 12.2 mmol), PdCl$_2$(dppf)-CH$_2$Cl$_2$ complex (0.453 g, 0.555 mmol) and KOAc (3.27 g, 33.3 mmol) in dioxane (60 mL) was stirred at 115° C. for 20 h under argon, allowed to cool to rt, diluted with toluene (60 mL), sonicated, and filtered through a pad of celite. The filter cake was rinsed with hot toluene. The filtrate was concentrated to afford 3.9 g (30% purity) of the title compound which was used without purification. For the corresponding boronic acid. $t_R$: 0.22 min (LC-MS 2); ESI-MS: 170.1 [M+H]$^+$ (LC-MS 2).

Intermediate V

4-Ethyl-3-(4,4,5,5-tetramethyl-[1,3,2]dioxaborolan-2-yl)-benzonitrile

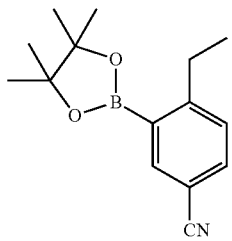 [SMILES: CCc1ccc(C#N)cc1B1OC(C)(C)C(C)(C)O1]

The title compound was prepared in analogy to the procedure described for intermediate T but using 2 equivalents of 3-bromo-4-ethylbenzonitrile (Wagner, P. J.; Wang, L. *Organic Letters*, 2006, 8, 645-647), and stirring the reaction mixture for 4 h at 100° C. The reaction mixture was quenched by addition of a saturated aqueous solution of NaHCO$_3$, and filtered through a pad of celite. The filtrate was extracted with EtOAc. The organic layer was washed with a saturated aqueous solution of NaHCO$_3$, dried (Na$_2$SO$_4$), filtered, and concentrated. The residue was purified by flash chromatography (hexane/EtOAc, 1:0→92:8) to afford the title compound (75% purity). $t_R$: 1.39 min (LC-MS 2); ESI-MS: 275.4 [M+18]$^+$ (LC-MS 2).

Intermediate W

[4-Methoxy-5-(4,4,5,5-tetramethyl-[1,3,2]dioxaborolan-2-yl)-pyrimidin-2-yl]-dimethyl-amine

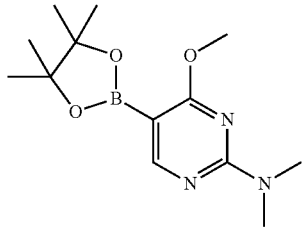

The title compound was prepared in analogy to the procedure described for intermediate U but using the compound prepared in step W1, 0.1 equivalents of PdCl$_2$(dppf)-CH$_2$Cl$_2$ complex, and stirring the reaction mixture for 10 h at 105° C. The reaction mixture was allowed to cool to rt, diluted with toluene, sonicated, and filtered. The filter cake was rinsed with hot toluene. The filtrate was concentrated to afford the title compound (50% purity) which was used without purification. For the corresponding boronic acid. $t_R$: 0.40 min (LC-MS 2); ESI-MS: 198.1 [M+H]$^+$ (LC-MS 2).

Step W1:
(5-Bromo-4-methoxy-pyrimidin-2-yl)-dimethyl-amine

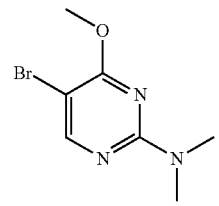

A mixture of 5-bromo-2-chloro-4-methoxypyrimidine (3 g, 13.4 mmol) and dimethylamine (2 M in THF, 33.6 mL, 67.1 mmol) in THF (20 mL) was stirred for 18 h at rt and concentrated. The residue was purified by flash chromatography (hexane/EtOAc, 9:1) to afford 2.95 g of the title compound. $t_R$: 1.04 min (LC-MS 2); ESI-MS: 232.0/234.0 [M+H]$^+$ (LC-MS 2); R$_f$: 0.34 (hexane/EtOAc 9:1).

Intermediate X

2-{[4-Methoxy-5-(4,4,5,5-tetramethyl-[1,3,2]dioxaborolan-2-yl)-pyrimidin-2-yl]-methyl-amino}-ethanol

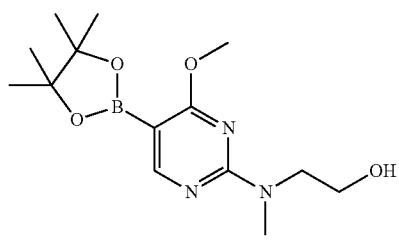 [SMILES: COc1nc(N(C)CCO)ncc1B1OC(C)(C)C(C)(C)O1]

The title compound was prepared in analogy to the procedure described for intermediate U but using the compound prepared in step X1, 0.15 equivalents of PdCl$_2$(dppf)-CH$_2$Cl$_2$ complex, and stirring the reaction mixture for 8 h at 110° C. The reaction mixture was allowed to cool to rt, diluted with toluene, sonicated, and filtered. The filter cake was rinsed with hot toluene. The filtrate was concentrated to give the title compound (50% purity) which was used without purification. For the corresponding boronic acid. $t_R$: 0.38 min (LC-MS 2); ESI-MS: 228.2 [M+H]$^+$ (LC-MS 2).

Step X1: 2-[(5-Bromo-4-methoxy-pyrimidin-2-yl)-methyl-amino]-ethanol

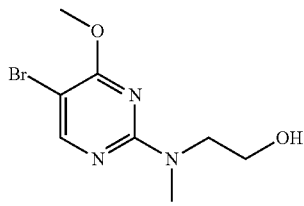

A mixture of 5-bromo-2-chloro-4-methoxypyrimidine (5 g, 22.4 mmol) and 2-(methylamino)ethanol (2.19 g, 29.1 mmol) in THF (40 mL) was stirred for 18 h at rt and concentrated. The residue was purified by flash chromatography (hexane/EtOAc, 3:2) to afford 5.38 g of the title compound. $t_R$: 0.84 min (LC-MS 2); ESI-MS: 262.1/264.1 [M+H]$^+$ (LC-MS 2); $R_f$: 0.15 (hexane/EtOAc 3:2).

Intermediate Y

2-[4-Methoxy-5-(4,4,5,5-tetramethyl-[1,3,2]dioxaborolan-2-yl)-pyrimidin-2-ylamino]-ethanol

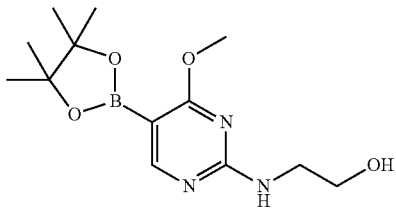 [SMILES: COc1nc(NCCO)ncc1B1OC(C)(C)C(C)(C)O1]

The title compound was prepared in analogy to the procedure described for intermediate U but using the compound prepared in step Y1, 0.15 equivalents of PdCl$_2$(dppf)-CH$_2$Cl$_2$ complex, and stirring the reaction mixture for 4 h at 110° C. The reaction mixture was allowed to cool to rt, diluted with toluene, sonicated, and filtered. The filter cake was rinsed with hot toluene. The filtrate was concentrated to give the title compound (30% purity) which was used without purification. $t_R$: 0.38 min (LC-MS 2); API-MS: 296.1 [M+H]$^+$ (LC-MS 2).

Step Y1:
2-(5-Bromo-4-methoxy-pyrimidin-2-ylamino)-ethanol

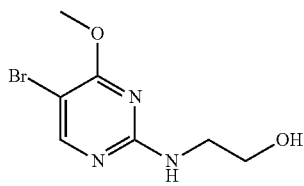

A mixture of 5-bromo-2-chloro-4-methoxypyrimidine (5 g, 22.4 mmol) and 2-amino ethanol (1.76 mL, 29.1 mmol) in THF (50 mL) was stirred for 18 h at rt. 2-Amino ethanol (2 mL) was added. The reaction mixture was stirred for 18 h at rt and concentrated. The residue was purified by flash chromatography (hexane/EtOAc, 3:2) to afford 4.08 g of the title compound. $t_R$: 0.70 min (LC-MS 2); ESI-MS: 248.2 [M+H]$^+$ (LC-MS 2); $R_f$: 0.06 (hexane/EtOAc 3:2).

Intermediate Z

[4-Methoxy-5(4,4,5,5-tetramethyl-[1,3,2]dioxaborolan-2-yl)-pyrimidin-2-yl]-methyl-amine

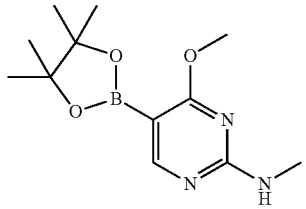

The title compound was prepared in analogy to the procedure described for intermediate U but using the compound prepared in step Z1, 0.1 equivalents of PdCl$_2$(dppf)-CH$_2$Cl$_2$ complex, and stirring the reaction mixture for 16 h at 105° C. The reaction mixture was allowed to cool to rt, diluted with toluene, sonicated for 30 min, and filtered. The filter cake was rinsed with hot toluene. The filtrate was concentrated. The residue was diluted in hexane, sonicated for 30 min, filtered, and concentrated to give the title compound (50% purity) which was used without purification. For the corresponding boronic acid. $t_R$: 0.35 min (LC-MS 2); ESI-MS: 184.2 [M+H]$^+$ (LC-MS 2).

Step Z1:
(5-Bromo-4-methoxy-pyrimidin-2-yl)-methyl-amine

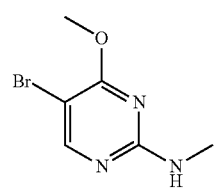

A mixture of 5-bromo-2-chloro-4-methoxypyrimidine (3 g, 13.4 mmol) and methylamine (2 M in THF, 50 mL, 100 mmol) in THF (20 mL) was stirred for 40 h at rt and concentrated. The residue was purified by flash chromatography (hexane/EtOAc, 1:1) to afford 2.5 g of the title compound. $t_R$: 0.81 min (LC-MS 2); ESI-MS: 218/220.1 [M+H]$^+$ (LC-MS 2); $R_f$: 0.39 (hexane/EtOAc 1:1).

Intermediate AA

4-[2-Bromo-5-(5-chloro-1-methyl-6-oxo-1,6-dihydro-pyridin-3-yl)-3-isopropyl-6-oxo-5,6-dihydro-pyrrolo[3,4-d]imidazol-4-yl]-benzonitrile

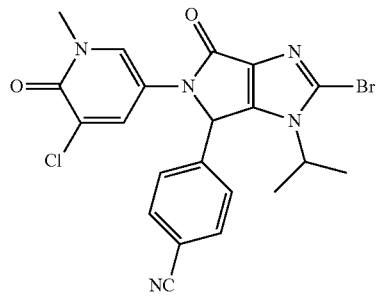 [SMILES: CC(C)n1c(Br)nc2c1C(c1ccc(C#N)cc1)N(c1cc(Cl)c(=O)n(C)c1)C2=O]

A mixture of the compound prepared in step AA1 (541 mg, 1.1 mmol), TBTU (482 mg, 1.5 mmol), DIEA (0.562 mL, 3.2 mmol) in DMF (6 mL) was stirred at 80° C. for 1 h. The reaction mixture was diluted in EtOAc/water, extracted twice with EtOAc and the combined organic extracts were washed with water and brine, dried (Na$_2$SO$_4$) and concentrated. The residue was purified by trituration in EtOAc to afford 385 mg of the title compound. t$_R$: 0.83 min (LC-MS 2); ESI-MS: 486.1/488.2 [M+H]$^+$ (LC-MS 2).

Step AA1: 2-Bromo-5-[(5-chloro-1-methyl-6-oxo-1,6-dihydro-pyridin-3-ylamino)-(4-cyano-phenyl)-methyl]-1-isopropyl-1H-imidazole-4-carboxylic acid

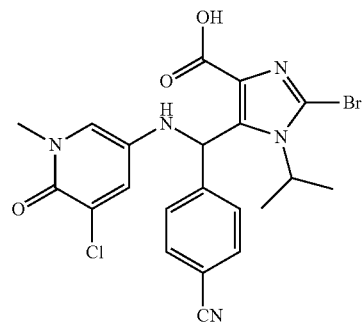 [SMILES: CC(C)n1c(Br)nc(C(=O)O)c1C(Nc1cc(Cl)c(=O)n(C)c1)c1ccc(C#N)cc1]

A mixture of the compound prepared in step AA2 (675 mg, 1.27 mmol) and NaOH (2 M in water, 5 mL, 10 mmol) in THF (5 mL) and MeOH (5 mL) was stirred for 30 min at rt. THF and MeOH were evaporated. The resulting mixture was diluted in EtOAc/water, and pH was adjusted to 5 with diluted HCl. The aqueous layer was separated and extracted with EtOAc. The combined organic layers were dried (Na$_2$SO$_4$) and concentrated to provide 545 mg of the title compound. t$_R$: 0.81 min (LC-MS 2); ESI-MS: 504.2/506.2 [M+H]$^+$ (LC-MS 2).

Step AA2: 2-Bromo-5-[(5-chloro-1-methyl-6-oxo-1,6-dihydro-pyridin-3-ylamino)-(4-cyano-phenyl)-methyl]-1-isopropyl-1H-imidazole-4-carboxylic acid ethyl ester

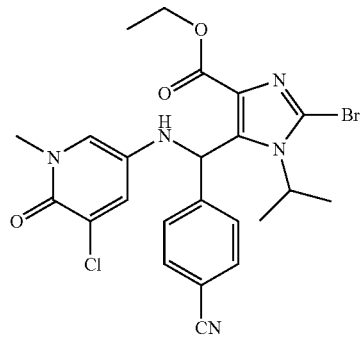 [SMILES: CCOC(=O)c1nc(Br)n(C(C)C)c1C(Nc1cc(Cl)c(=O)n(C)c1)c1ccc(C#N)cc1]

Ms$_2$O (1.05 g, 6.05 mmol) was added to a cold (5° C.) solution of the compound prepared in step H3 (1.19 g, 3.02 mmol) and Et$_3$N (2.1 mL, 15.1 mmol) in CH$_2$Cl$_2$ (25 mL) under argon. The mixture was stirred for 15 min at 5° C. The compound prepared in Step J3 (719 mg, 4.54 mmol) was added. The reaction mixture was allowed to warm to rt, stirred for 48 h, diluted with CH$_2$Cl$_2$/water and extracted with CH$_2$Cl$_2$. The organic extracts were washed with brine, dried (Na$_2$SO$_4$), filtered, and concentrated. The residue was purified by flash chromatography (CH$_2$Cl$_2$/EtOAc, 1:1), followed by trituration in Et$_2$O to provide 681 mg of the title compound. t$_R$: 0.96 min (LC-MS 2); ESI-MS: 532.2/534.1 [M+H]$^+$ (LC-MS 2); R$_f$: 0.14 (CH$_2$Cl$_2$/EtOAc 1:1).

Intermediate AB

4-[2-Bromo-5(3-chloro-2-fluoro-phenyl)-3-isopropyl-6-oxo-5,6-dihydro-pyrrolo[3,4-d]imidazol-4-yl]-benzonitrile

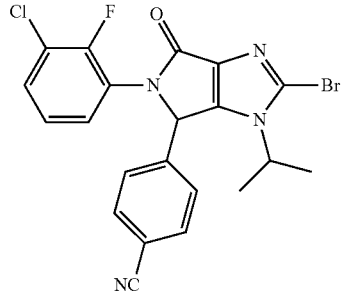 [SMILES: CC(C)n1c(Br)nc2c1C(c1ccc(C#N)cc1)N(c1cccc(Cl)c1F)C2=O]

A mixture of the compound prepared in step AB1 (2 g, 4.07 mmol), TBTU (1.83 g, 5.69 mmol), DIEA (2.1 mL, 12.2 mmol) in DMF (20 mL) was stirred at 80° C. for 10 h. The reaction mixture was diluted in EtOAc/water, extracted twice with EtOAc and the combined organic extracts were washed with water and brine, dried (Na$_2$SO$_4$), filtered and concentrated. The crude was purified twice by flash chromatography (CH$_2$Cl$_2$/EtOAc 85:15→30:70) to afford 350 mg of the title compound. t$_R$: 1.07 min (LC-MS 2); ESI-MS: 473.2/475.2 [M+H]$^+$ (LC-MS 2); R$_f$=0.23 (CH$_2$Cl$_2$/EtOAc, 85:15).

Step AB1: 2-Bromo-5-[(3-chloro-2-fluoro-phenylamino)-(4-cyano-phenyl)-methyl]-1-isopropyl-1H-imidazole-4-carboxylic acid

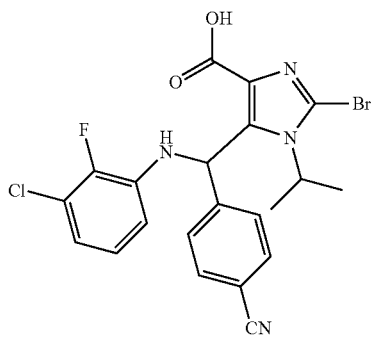 [SMILES: CC(C)n1c(Br)nc(C(=O)O)c1C(Nc1cccc(Cl)c1F)c1ccc(C#N)cc1]

A mixture of the compound prepared in step AB2 (4.92 g, 9.47 mmol) and NaOH (2 M in water, 30 mL, 60 mmol) in THF (30 mL) and MeOH (30 mL) was stirred for 30 h at rt. THF and MeOH were evaporated. The resulting mixture was diluted in EtOAc/water, and pH was adjusted to 5 with diluted HCl. The aqueous layer was separated and extracted with EtOAc. The combined organic layers were dried (Na$_2$SO$_4$), filtered and concentrated. The residue was triturated in Et$_2$O to provide 4.02 g of the title compound. $t_R$: 1.10 min (LC-MS 2); ESI-MS: 491.2/493.1 [M+H]$^+$ (LC-MS 2).

Step AB2: 2-Bromo-5-[(3-chloro-2-fluoro-phenylamino)-(4-cyano-phenyl)-methyl]-1-isopropyl-1H-imidazole-4-carboxylic acid ethyl ester

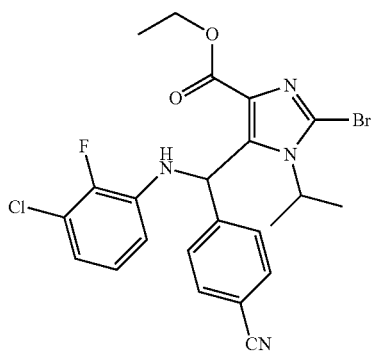 [SMILES: CCOC(=O)c1nc(Br)n(C(C)C)c1C(Nc1cccc(Cl)c1F)c1ccc(C#N)cc1]

Ms$_2$O (3.55 g, 20.4 mmol) was added to a cold (5° C.) solution of the compound prepared in step H3 (4 g, 10.2 mmol) and Et$_3$N (7.1 mL, 51 mmol) in CH$_2$Cl$_2$ (80 mL) under argon. The mixture was stirred for 30 min at 5° C. 3-Chloro-2-fluoroaniline (2.23 g, 15.3 mmol) was added. The reaction mixture was allowed to warm to rt, stirred for 40 h, diluted with CH$_2$Cl$_2$/water and extracted with CH$_2$Cl$_2$. The organic extracts were washed with brine, dried (Na$_2$SO$_4$), filtered and concentrated. The residue was purified by flash chromatography (hexane/EtOAc, 7:3), followed by trituration in Et$_2$O, to provide 4.93 g of the title compound. $t_R$: 1.28 min (LC-MS 2); ESI-MS: 519.2/521.0 [M+H]$^+$ (LC-MS 2); R$_f$: 0.20 (hexane/EtOAc 7:3).

Intermediate AC

4-[2-Bromo-5-(3-chloro-4-fluoro-phenyl)-3-isopropyl-6-oxo-5,6-dihydro-pyrrolo[3,4-d]imidazol-4-yl]-benzonitrile

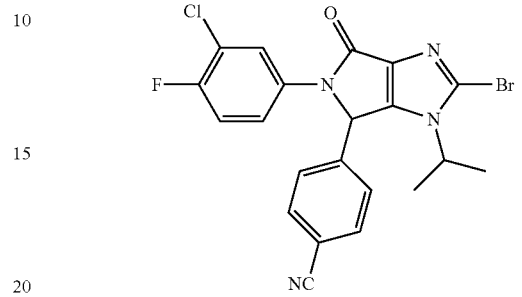

A mixture of the compound prepared in step AC1 (3.3 g, 6.71 mmol), TBTU (3.02 g, 9.40 mmol), DIEA (3.5 mL, 20.1 mmol) in DMF (33 mL) was stirred at 80° C. for 5 h. The reaction mixture was diluted in EtOAc/water, extracted twice with EtOAc and the combined organic extracts were washed with water and brine, dried (Na$_2$SO$_4$), filtered, and concentrated. The crude was purified twice by flash chromatography (CH$_2$Cl$_2$/EtOAc 30:70), followed by trituration in EtOAc, to afford 1.46 g of the title compound. $t_R$: 1.09 min (LC-MS 2); ESI-MS: 473.1/475.1 [M+H]$^+$ (LC-MS 2); Rf=0.22 (CH$_2$Cl$_2$/EtOAc 30:70).

Step AC1: 2-Bromo-5-[(3-chloro-4-fluoro-phenylamino)-(4-cyano-phenyl)-methyl]-1-isopropyl-1H-imidazole-4-carboxylic acid

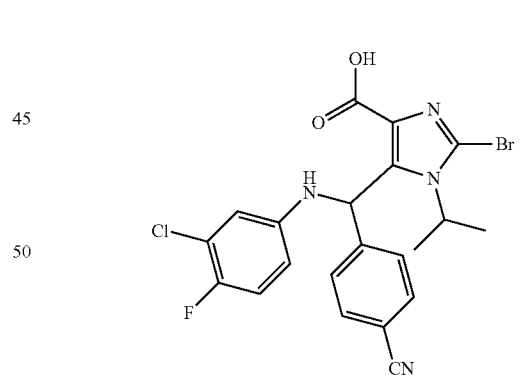

A mixture of the compound prepared in step AC2 (4.54 g, 8.73 mmol) and NaOH (2 M in water, 30 mL, 60 mmol) in THF (30 mL) and MeOH (30 mL) was stirred for 30 min at rt. THF and MeOH were evaporated. The resulting mixture was diluted in EtOAc/water, and pH was adjusted to 5 with diluted HCl. The aqueous layer was separated and extracted with EtOAc. The combined organic layers were dried (Na$_2$SO$_4$), filtered, and concentrated. The residue was triturated in Et$_2$O to provide 3.3 g of the title compound. $t_R$: 1.11 min (LC-MS 2); ESI-MS: 491.2/493.2 [M+H]$^+$ (LC-MS 2).

Step AC2: 2-Bromo-5-[(3-chloro-4-fluoro-phenylamino)-(4-cyano-phenyl)-methyl]-1-isopropyl-1H-imidazole-4-carboxylic acid ethyl ester

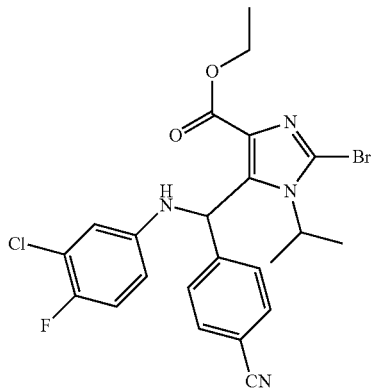 [SMILES: CCOC(=O)c1nc(Br)n(C(C)C)c1C(Nc1ccc(F)c(Cl)c1)c1ccc(C#N)cc1]

Ms$_2$O (3.55 g, 20.4 mmol) was added to a solution of the compound prepared in step H3 (4 g, 10.2 mmol) and Et$_3$N (7.1 mL, 51 mmol) in CH$_2$Cl$_2$ (80 mL) at rt, under argon. The mixture was stirred for 30 min at rt. 3-Chloro-4-fluoroaniline (2.23 g, 15.3 mmol) was added. The reaction mixture was stirred for 40 h at rt, diluted with CH$_2$Cl$_2$/water, and extracted with CH$_2$Cl$_2$. The organic extracts were washed with brine, dried (Na$_2$SO$_4$), filtered, and concentrated. The residue was purified by flash chromatography (hexane/EtOAc 7:3) to provide 4.60 g of the title compound. $t_R$: 1.25 min (LC-MS 2); ESI-MS: 519.2/521.2 [M+H]$^+$ (LC-MS 2); R$_f$: 0.16 (hexane/EtOAc, 7:3).

Intermediate AD

1-[4-Methoxy-5-(4,4,5,5-tetramethyl-[1,3,2]dioxaborolan-2-yl)-pyrimidin-2-yl]-3-methyl-azetidin-3-ol

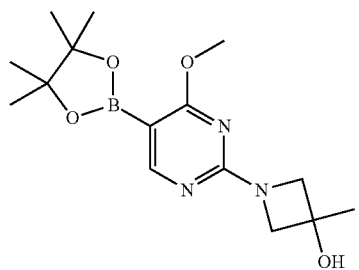

The title compound was prepared in analogy to the procedure described for intermediate U but using the compound prepared in step AD1, 0.15 equivalents of PdCl$_2$(dppf)-CH$_2$Cl$_2$ complex, and stirring the reaction mixture for 4 h at 110° C. The reaction mixture was allowed to cool to rt, diluted with toluene, sonicated, and filtered. The filter cake was rinsed with hot toluene. The filtrate was concentrated to give the title compound (30% purity) which was used without purification. For the boronic acid. $t_R$: 0.40 min (LC-MS 2); ESI-MS: 240.2 [M+H]$^+$ (LC-MS 2).

Step AD1: 1-(5-Bromo-4-methoxy-pyrimidin-2-yl)-3-methyl-azetidin-3-ol

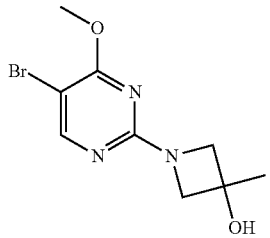

A mixture of 5-bromo-2-chloro-4-methoxypyrimidine (3.5 g, 15.7 mmol), 3-methylazetidin-3-ol hydrochloride (2.90 g, 23.5 mmol), and Et$_3$N (4.4 mL, 31.3 mmol) in THF (50 mL) was stirred for 18 h at rt. 3-Methylazetidin-3-ol hydrochloride (1 g) was added. The reaction mixture was stirred for 72 h at rt and concentrated. The residue was purified by flash chromatography (hexane/EtOAc 1:1) to afford 2.5 g of the title compound. $t_R$: 0.81 min (LC-MS 2); ESI-MS: 274.2 [M+H]$^+$ (LC-MS 2); Rf: 0.25 (hexane/EtOAc 1:1).

Intermediate AE

1-[4-Methoxy-5-(4,4,5,5-tetramethyl-[1,3,2]dioxaborolan-2-yl)-pyrimidin-2-yl]-azetidin-3-ol

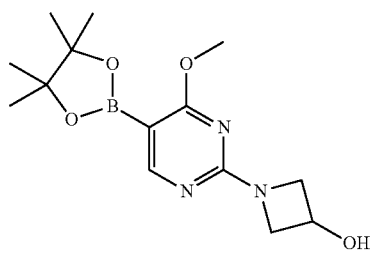 [SMILES: COc1nc(N2CC(O)C2)ncc1B1OC(C)(C)C(C)(C)O1]

The title compound was prepared in analogy to the procedure described for intermediate U but using the compound prepared in step AE1, 0.15 equivalents of PdCl$_2$(dppf)-CH$_2$Cl$_2$ complex, and stirring the reaction mixture for 4 h at 110° C. The reaction mixture was allowed to cool to rt, diluted with toluene, sonicated, and filtered. The filter cake was rinsed with hot toluene. The filtrate was concentrated to give the title compound (30% purity) which was used without purification. For the boronic acid. $t_R$: 0.36 min (LC-MS 2); ESI-MS: 226.2 [M+H]$^+$ (LC-MS 2).

Step AE1: 1-(5-Bromo-4-methoxy-pyrimidin-2-yl)-azetidin-3-ol

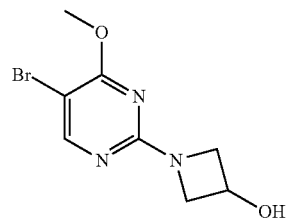

A mixture of 5-bromo-2-chloro-4-methoxypyrimidine (3.3 g, 14.8 mmol), 3-hydroxyazetidine hydrochloride (3.2 g, 29.5 mmol), and Et$_3$N (4.3 mL, 31.0 mmol) in THF (50 mL) was stirred for 18 h at rt. 3-Hydroxyazetidine hydrochloride (1 g) was added. The reaction mixture was stirred for 24 h at rt and concentrated. The residue was diluted in CH$_2$Cl$_2$/water and extracted with CH$_2$Cl$_2$. The combined organic extracts were washed with brine, dried (Na$_2$SO$_4$), filtered, and concentrated. The crude material was purified by flash chromatography (hexane/EtOAc, 1:1) to afford 3 g of the title compound. $t_R$: 0.73 min (LC-MS 2); ESI-MS: 260.1/262.1 [M+H]$^+$ (LC-MS 2); R$_f$=0.18 (hexane/EtOAc 1:1).

Intermediate AF

2-Bromo-6-(4-chloro-phenyl)-5-(5-chloro-pyridin-3-yl)-1-isopropyl-5,6-dihydro-1H-pyrrolo[3,4-d]imidazole-4-one

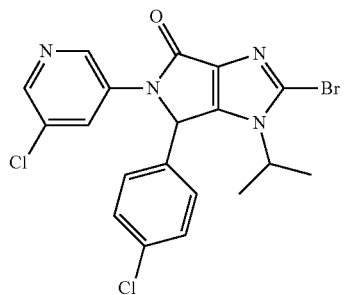 [SMILES: CC(C)n1c(Br)nc2c1C(c1ccc(Cl)cc1)N(c1cncc(Cl)c1)C2=O]

The title compound was prepared in analogy to the procedure described for intermediate F with the product from step AF1 as starting material. $t_R$: 1.14 min (LC-MS2); ESI-MS: 465.1/467.1 [M+H]$^+$ (LC-MS 2); $^1$H-NMR (DMSO-d$_6$, 400 MHz) δ ppm 8.76 (s, 1H), 8.33 (s, 1H), 8.23 (s, 1H), 7.49-7.44 (m, 4H), 6.87 (s, 1H), 4.56 (sep, 1H), 1.47 (d, 3H), 0.66 (d, 3H).

Step AF1: 2-Bromo-5-[(4-chloro-2-methyl-phenyl)-(5-chloro-pyridin-3-ylamino)-methyl]-1-isopropyl-1H-imidazole-4-carboxylic acid

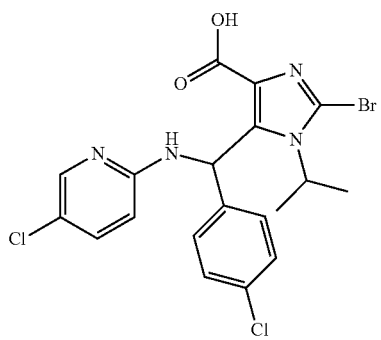 [SMILES: CC(C)n1c(Br)nc(C(=O)O)c1C(Nc1ccc(Cl)cn1)c1ccc(Cl)cc1]

The title compound was prepared in analogy to the procedure described for step AA1 using the product from step AF2 as starting material. $t_R$: 1.03 min (LC-MS 2); ESI-MS: 483.0/485.0 [M+H]$^+$ (LC-MS 2); $^1$H-NMR (DMSO-d$_6$, 400 MHz) δ ppm 8.19 (s, 1H), 7.89 (s, 1H), 7.59 (bs, 1H), 7.48 (d, 2H), 7.26 (d, 2H), 7.23 (s, 2H), 6.95 (bs, 1H), 4.47 (sep, 1H), 1.37 (d, 3H), 1.17 (d, 3H).

Step AF2: 2-Bromo-5-[(4-chloro-phenyl)-(5-chloro-pyridin-3-ylamino)-methyl]-1-isopropyl-1H-imidazole-4-carboxylic acid ethyl ester

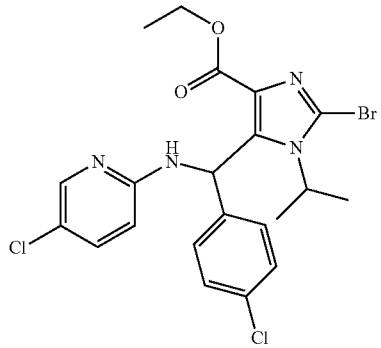 [SMILES: CCOC(=O)c1nc(Br)n(C(C)C)c1C(Nc1ccc(Cl)cn1)c1ccc(Cl)cc1]

The title compound was prepared in analogy to the procedure described for step E2 using 2-bromo-5-[(4-chloro-phenyl)-hydroxy-methyl]-1-isopropyl-1H-imidazole-4-carboxylic acid ethyl ester (intermediate B) and 3-amino-5-chloro-pyridine as starting materials. $t_R$: 1.31 min (LC-MS 2); ESI-MS: 511.1/513.1 [M+H]$^+$ (LC-MS 2).

Intermediate AG

2-Bromo-5-(3-chloro-phenyl)-6-(4-chloro-phenyl)-1-isopropyl-5,6-dihydro-1H-pyrrolo[3,4-d]imidazol-4-one

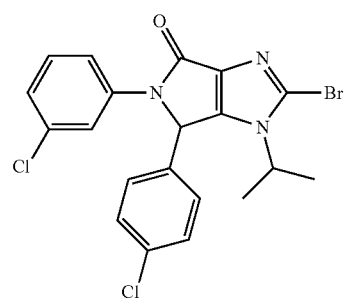 [SMILES: CC(C)n1c(Br)nc2c1C(c1ccc(Cl)cc1)N(c1cccc(Cl)c1)C2=O]

The title compound was prepared in analogy to the procedure described for intermediate F with the product from step AG1 as starting material. $t_R$: 1.27 min (LC-MS2); ESI-MS: 464.0/466.1 [M+H]$^+$ (LC-MS 2).

Step AG1: 2-Bromo-5-[(4-chloro-phenyl)-(3-chloro-2-phenylamino)-methyl-1-isopropyl-1H-imidazole-4-carboxylic acid

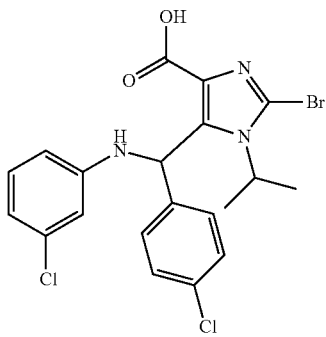 [SMILES: CC(C)n1c(Br)nc(C(=O)O)c1C(Nc1cccc(Cl)c1)c1ccc(Cl)cc1]

The title compound was prepared in analogy to the procedure described for step AA1 using the product from step AG2 as starting material. $t_R$: 1.19 min (LC-MS 2); ESI-MS: 481.8/484.0 [M+H]$^+$ (LC-MS 2).

Step AG2: 2-Bromo-5-[(4-chloro-phenyl)-(3-chloro-phenylamino)-methyl]-1-isopropyl-1H-imidazole-4-carboxylic acid ethyl ester

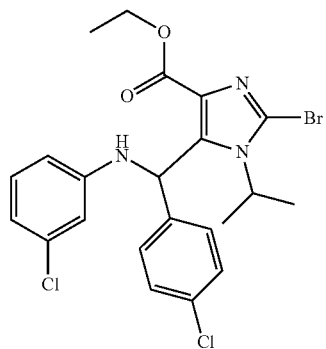 [SMILES: CCOC(=O)c1nc(Br)n(C(C)C)c1C(Nc1cccc(Cl)c1)c1ccc(Cl)cc1]

The title compound was prepared in analogy to the procedure described for step E2 using 2-bromo-5-[(4-chloro-phenyl)-hydroxy-methyl]-1-isopropyl-1H-imidazole-4-carboxylic acid ethyl ester (intermediate B) and 3-chloro-aniline as starting materials. $t_R$: 1.45 min (LC-MS 2); ESI-MS: 510.1/512.1 [M+H]$^+$ (LC-MS 2).

Intermediate AH

4-N,N-Dimethyl-carboxamido-2-methoxy-phenyl boronic acid

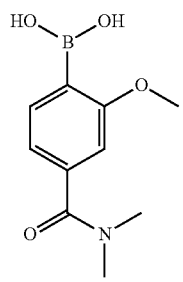

The title compound was prepared in analogy to the procedure described for intermediate K using 4-carboxy-2-methoxyphenyl boronic acid and dimethylamine (2M solution in THF). $t_R$: 0.53 min (LC-MS 2); ESI-MS: 223.2 [M+H]$^+$ (LC-MS 2).

Intermediate AI

2-Bromo-6-(4-chloro-phenyl)-1-isopropyl-5-(1-methyl-6-oxo-piperidin-3-yl)-5,6-dihydro-1H-pyrrolo[3,4-d]imidazol-4-one

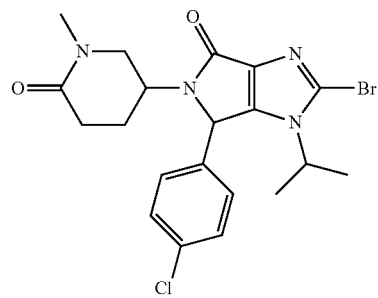 [SMILES: CC(C)n1c(Br)nc2c1C(c1ccc(Cl)cc1)N(C1CCC(=O)N(C)C1)C2=O]

The title compound was prepared in analogy to the procedure described for intermediate E using the product from step AI1 as starting material. $t_r$: 0.88 min (LC-MS 2); ESI-MS: 467.0 [M+H]$^+$ (LC-MS 2).

Step AI1: 2-Bromo-5-[(4-chloro-phenyl)-(1-methyl-6-oxo-piperidin-3-ylamino)-methyl]-1-isopropyl-1H-imidazole-4-carboxylic acid

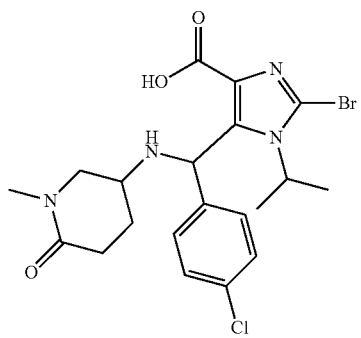 [SMILES: CC(C)n1c(Br)nc(C(=O)O)c1C(NC1CCC(=O)N(C)C1)c1ccc(Cl)cc1]

The title compound was prepared in analogy to the procedure described for step E1 with the product from step AI2 as starting material. $t_r$: 0.73 min (LC-MS 2); ESI-MS: 483.1 [M−H]$^+$ (LC-MS 2).

Step AI2: 2-Bromo-5-[(4-chloro-phenyl)-(1-methyl-6-oxo-piperidin-3-ylamino)-methyl]-1-isopropyl-1H-imidazole-4-carboxylic acid ethyl ester

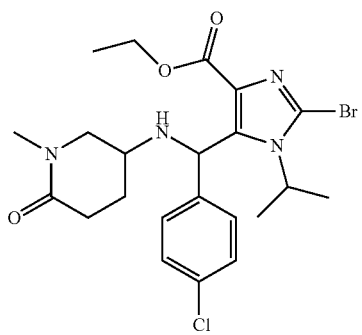 [SMILES: CCOC(=O)c1nc(Br)n(C(C)C)c1C(NC1CCC(=O)N(C)C1)c1ccc(Cl)cc1]

The title compound was prepared in analogy to the procedure described for step E2 using 2-bromo-5-[(4-chlorophenyl)-hydroxy-methyl]-1-isopropyl-1H-imidazole-4-carboxylic acid ethyl ester (intermediate B) and 5-amino-1-methylpiperidin-2-one (ChemBridge, free base was made from the purchased HCl salt) as starting materials. The crude reaction mixture was diluted with EtOAc and washed with aqueous NaHCO$_3$ solution and brine. $t_r$: 1.07 min (LC-MS 2); ESI-MS: 511.1 [M+H]$^+$ (LC-MS 2); $^1$H-NMR (DMSO-d$_6$, 400 MHz) δ ppm 7.42 (m, 2H), 7.30 (m, 2H), 6.28 (NH, br, 1H), 4.85-5.00 (m, 1 H), 4.25 (quin, 2 H), 3.15-3.05 (m, 2H), 2.84-2.75 (m, 1H), 2.72 (d, 3H), 2.38-1.85 (m, 4H), 1.75-1.58 (m, 1), 1.45 (d, 3 H), 1.24 (t, 3 H), 0.83 (t, 3H).

Intermediate AK

2-Bromo-5-(3-chloro-4-fluoro-phenyl)-6-(4-chloro-phenyl)-1-cyclobutyl-5,6-dihydro-1H-pyrrolo[3,4-d]imidazol-4-one

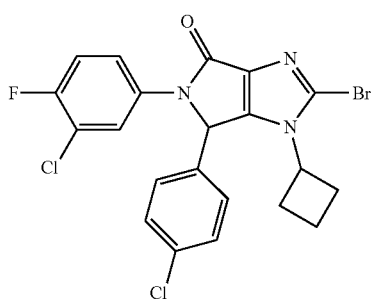 [SMILES: O=C1c2nc(Br)n(C3CCC3)c2C(c2ccc(Cl)cc2)N1c1ccc(F)c(Cl)c1]

To a stirred solution of 2-bromo-5-[(4-chloro-phenyl)-hydroxy-methyl]-1-cyclobutyl-1H-imidazole-4-carboxylic acid (3-chloro-4-fluoro-phenyl)-amide (step AK1; 0.470 g, 0.907 mmol) and AcOH (4.53 ml) was added H$_2$SO$_4$ 98% (0.592 ml, 10.88 mmol). The solution was stirred for 7 h at 110° C. The reaction mixture was concentrated in vacuo. The residue was neutralized with 1M NaHCO$_3$ and extracted with EtOAc (2×). The organic phases were washed with brine and dried (Na$_2$SO$_4$), filtered and concentrated. The residue was purified by flash chromatography (hexane/EtOAc, 1:1), then triturated in diisopropyl ether/hexane to afford the title compound. $t_R$: 1.29 min (LC-MS 2); ESI-MS: 496.0 [M+H]$^+$ (LC-MS 2); $^1$H-NMR (DMSO-d$_6$, 400 MHz) δ ppm 7.79 (m, 1H), 7.49 (m, 1H), 7.38 (s, 4H), 7.35 (m, 1H), 6.89 (s, 1H), 4.73 (m, 1H), 2.45 (m, 2H), 1.86 (m, 1H), 1.63 (m, 1H), 1.42 (m, 2H).

Step AK1: 2-Bromo-5-[(4-chloro-phenyl)-hydroxy-methyl]-1-cyclobutyl-1H-imidazole-4-carboxylic acid (3-chloro-4-fluoro-phenyl)-amide

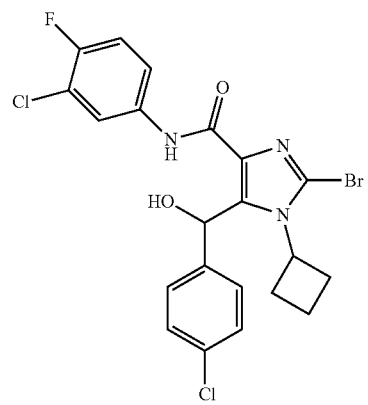 [SMILES: O=C(Nc1ccc(F)c(Cl)c1)c1nc(Br)n(C2CCC2)c1C(O)c1ccc(Cl)cc1]

To the stirred solution of trimethylaluminium (2M in toluene) (0.87 ml, 1.74 mmol) was added drop wise the solution of 3-chloro-4-fluoroaniline (0.267 g, 1.80 mmol) and toluene (2.0 ml) at 0° C. and then the temperature was raised to rt. The mixture was concentrated. 2-bromo-5[(4-chloro-phenyl)-hydroxyl-methyl]-1-cyclobutyl-1H-imidazole-4-carboxylic acid ethyl ester (step AK2; 0.502 g, 1.20 mol) in toluene (6.0 ml) was added and the mixture was stirred for 3 h at 80° C., then cooled to rt. The reaction mixture was taken up in Teac (40 ml), poured onto "Rochelle Salt-Solution" (1M in water) and stirred for 15 min at rt. The organic phase was washed with brine and dried (Na$_2$SO$_4$), filtered and concentrated. The residue was purified by flash chromatography (EtOAc/hexane, 1:4), then triturated in hexane to afford the title compound. $t_R$: 1.46 min (LC-MS 2); ESI-MS: 514.1 [M+H]$^+$ (LC-MS 2).

Step AK2: 2-Bromo-5-[(4-chloro-phenyl)-hydroxy-methyl]-1-cyclobutyl-1H-imidazole-4-carboxylic acid ethyl ester

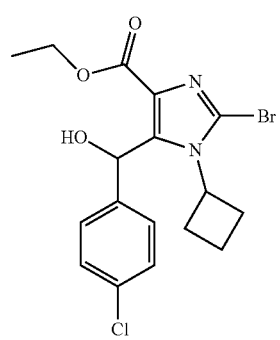 [SMILES: CCOC(=O)c1nc(Br)n(C2CCC2)c1C(O)c1ccc(Cl)cc1]

The title compound was obtained in analogy to the procedure described for intermediate B using 2-bromo-1-cyclobutyl-1H-imidazole-4-carboxylic acid ethyl ester (step AK3)

and 4-chlorobenzaldehyde. $t_R$: 1.21 min (LC-MS 2); ESI-MS: 415.1 [M+H]$^+$ (LC-MS 2).

Step AK3: 2-Bromo-1-cyclobutyl-1H-imidazole-4-carboxylic acid ethyl ester

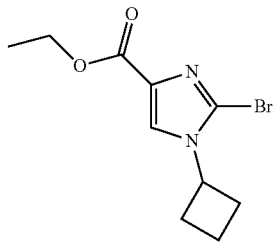

The title compound was obtained in analogy to the procedure described for intermediate A using 1-cyclobutyl-1H-imidazole-4-carboxylic acid ethyl ester (step AK4). $t_R$: 0.89 min (LC-MS 2); ESI-MS: 273.1/ 275.2 [M+H]$^+$ (LC-MS 2); TLC (EtOAc/n-heptane 1:5) $R_f$=0.49; $^1$H-NMR (DMSO-d$_6$, 400 MHz) δ ppm 8.25 (s, 1H), 4.68 (m, 1H), 4.20 (q, 2H), 2.40 (m, 4H), 1.77 (m, 2H), 1.25 (t, 3H).

Step AK4: 1-Cyclobutyl-1H-imidazole-4-carboxylic acid ethyl ester

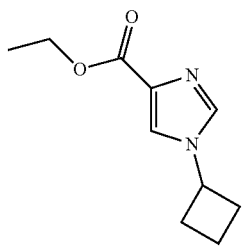

The stirred mixture of (Z)-3-dimethylamino-2-isocyano-acrylic acid ethyl ester (17.0 g, 100 mmol) and cyclobutaneamine (21.79 g, 300 mmol) was heated for 2.5 h at 70° C. The reaction mixture was cooled to rt and concentrated. The residue was purified by flash chromatography (EtOAc/hexane, 5:1) to afford the title compound as an orange oil. $t_R$: 0.70 min (LC-MS 2); ESI-MS: 195.2 [M+H]$^+$ (LC-MS 2); $^1$H-NMR (DMSO-d$_6$, 400 MHz) δ ppm 8.03 (s, 1H), 7.83 (s, 1H), 4.73 (m, 1H), 4.18 (q, 2H), 2.36 (m, 4H), 1.74 (m, 2H), 1.24 (t, 3H).

Intermediate AL

2-Bromo-5-(3-chloro-4-fluoro-phenyl)-6-(4-chloro-phenyl)-1-cyclobutyl-5,6-dihydro-1H-pyrrolo[3,4-d]imidazol-4-one

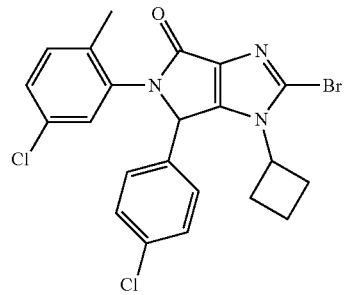 [SMILES: Cc1ccc(Cl)cc1N1C(=O)c2nc(Br)n(C3CCC3)c2C1c1ccc(Cl)cc1]

The title compound was obtained in analogy to the procedure described for intermediate AK and step AK1 using 2-bromo-5-[(4-chloro-phenyl)-hydroxy-methyl]-1-cyclobutyl-1H-imidazole-4-carboxylic acid ethyl ester (step AK2) and 3-chloro-4-fluoroaniline. $t_R$: 1.28 min (LC-MS 2); ESI-MS: 492.0 [M+H]$^+$ (LC-MS 2).

Intermediate AM

4-[2-Bromo-5-(3-chloro-4-fluoro-phenyl)-3-cyclobutyl-6-oxo-3,4,5,6-tetrahydro-pyrrolo[3,4-d]imidazol-4-yl]-benzonitrile

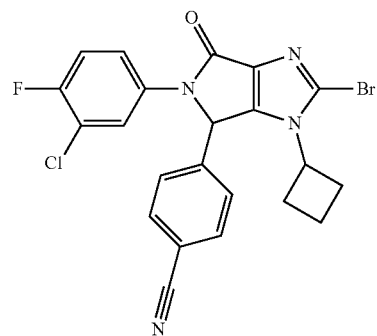 [SMILES: N#Cc1ccc(C2c3c(nc(Br)n3C3CCC3)C(=O)N2c2ccc(F)c(Cl)c2)cc1]

The title compound was obtained in analogy to the procedure described for intermediate F using 2-bromo-5-[(3-chloro-4-fluoro-phenylamino)-(4-cyano-phenyl)-methyl]-1-cyclobutyl-1H-imidazole-4-carboxylic acid (step AM1). $t_R$: 1.12 min (LC-MS 2); ESI-MS: 487.0 [M+H]$^+$ (LC-MS 2).

Step AM1: 2-Bromo-5-[(3-chloro-4-fluoro-phenylamino)-(4-cyano-phenyl)-methyl]-1-cyclobutyl-1H-imidazole-4-carboxylic acid

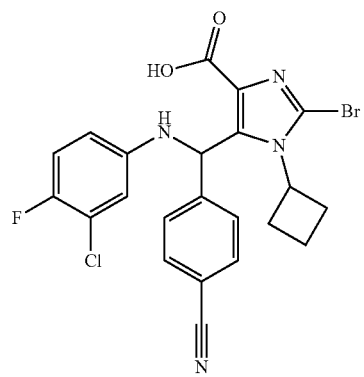 [SMILES: N#Cc1ccc(C(Nc2ccc(F)c(Cl)c2)c2c(C(=O)O)nc(Br)n2C2CCC2)cc1]

The title compound was obtained in analogy to the procedure described for step AB1 using 2-bromo-5-[(3-chloro-4-fluoro-phenylamino)-(4-cyano-phenyl)-methyl]-1-cyclobutyl-1H-imidazole-4-carboxylic acid ethyl ester (step AM2). $t_R$: 1.15 min (LC-MS 2); ESI-MS: 503.1 [M+H]$^+$ (LC-MS 2).

Step AM2: 2-Bromo-5-[(3-chloro-4-fluoro-phenylamino)-(4-cyano-phenyl)-methyl]-1-cyclobutyl-1H-imidazole-4-carboxylic acid ethyl ester

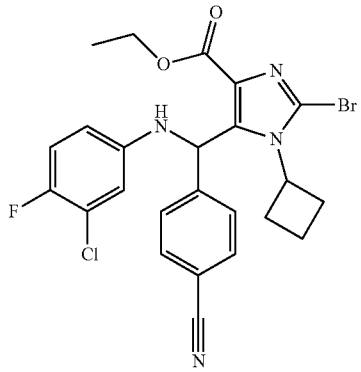 [SMILES: CCOC(=O)c1nc(Br)n(C2CCC2)c1C(Nc1ccc(F)c(Cl)c1)c1ccc(C#N)cc1]

The title compound was obtained in analogy to the procedure described for step AB2 using 2-bromo-5-[(4-chloro-phenyl)-hydroxy-methyl]-1-cyclobutyl-1H-imidazole-4-carboxylic acid ethyl ester (step AK2). $t_R$: 1.33 min (LC-MS 2); ESI-MS: 533.1 [M+H]$^+$ (LC-MS 2).

Intermediate AN

2-Bromo-5-(3-chloro-4-fluoro-phenyl)-6-(4-chloro-phenyl)-1-cyclopropyl-5,6-dihydro-1H-pyrrolo[3,4-d]imidazol-4-one

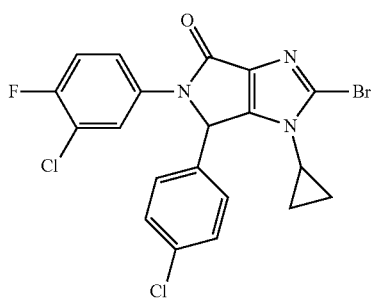 [SMILES: O=C1c2nc(Br)n(C3CC3)c2C(c2ccc(Cl)cc2)N1c1ccc(F)c(Cl)c1]

The title compound was obtained in analogy to the procedure described for intermediate AK using 2-bromo-5-[(4-chloro-phenyl)hydroxy-methyl]-1-cyclopropyl-1H-imidazole-4-carboxylic acid (3-chloro-4-fluoro-phenyl)-amide (step AN1). $t_R$: 1.24 min (LC-MS 2); ESI-MS: 482.0 [M+H]$^+$ (LC-MS 2).

Step AN1: 2-bromo-5-[(4-chloro-phenyl)-hydroxy-methyl]-1-cyclopropyl-1H-imidazole-4-carboxylic acid (3-chloro-4-fluoro-phenyl)-amide

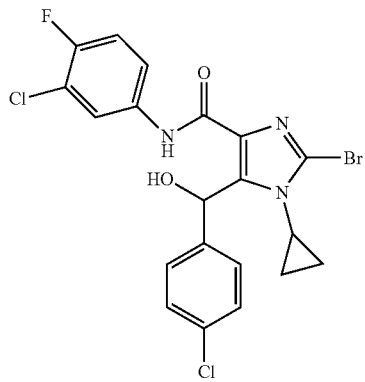 [SMILES: O=C(Nc1ccc(F)c(Cl)c1)c1nc(Br)n(C2CC2)c1C(O)c1ccc(Cl)cc1]

The title compound was obtained in analogy to the procedure described for step AK1 using 2-bromo-5-[(4-chloro-phenyl)-hydroxy-methyl]-1-cyclopropyl-1H-imidazole-4-carboxylic acid ethyl ester (step AN2) and 3-chloro-4-fluoro-phenylamine. $t_R$: 1.40 min (LC-MS 2); ESI-MS: 500.0 [M+H]$^+$ (LC-MS 2).

Step AN2: 2-Bromo-5-[(4-chloro-phenyl)-hydroxy-methyl]-1-cyclopropyl-1H-imidazole-4-carboxylic acid (3-chloro-4-fluoro-phenyl)-amide

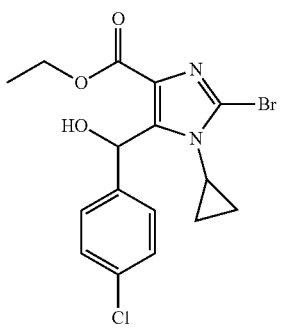 [SMILES: CCOC(=O)c1nc(Br)n(C2CC2)c1C(O)c1ccc(Cl)cc1]

The title compound was obtained in analogy to the procedure described for intermediate B using 2-bromo-1-cyclopropyl-1H-imidazole-4-carboxylic acid ethyl ester (step AN3) and 4-chlorobenzaldehyde. $t_R$: 1.09 min (LC-MS 2); ESI-MS: 401.1 [M+H]$^+$ (LC-MS 2).

Step AN3: 2-Bromo-1-cyclopropyl-1H-imidazole-4-carboxylic acid ethyl ester

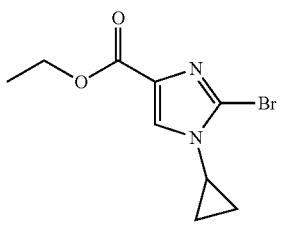

The title compound was obtained in analogy to the procedure described for intermediate A using 1-cyclopropyl-1H-imidazole-4-carboxylic acid ethyl ester (step AN4). $t_R$: 0.79 min (LC-MS 2); ESI-MS: 259.1/261.2 [M+H]$^+$ (LC-MS 2;

TLC (EtOAc/ n-heptane 1:5) $R_f$=0.49; $^1$H-NMR (DMSO-$d_6$, 400 MHz) δ ppm 7.95 (s, 1H), 4.19 (q, 2H), 3.37 (m, 1H), 1.23 (t, 3H), 1.03 (d, 4H).

Step AN4:
1-Cyclopropyl-1H-imidazole-4-carboxylic acid ethyl ester

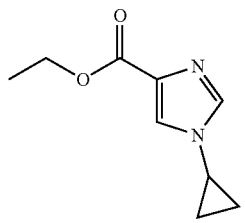

The stirred mixture of (Z)-3-dimethylamino-2-isocyano-acrylic acid ethyl ester (17.0 g, 100 mmol) and cyclopropylamine (17.21 g, 300 mmol) was heated for 5 h at 75° C. The reaction mixture was cooled to rt and concentrated. Purification of the residue by flash chromatography (EtOAc/hexane, 5:1) gave the title compound as an orange oil. $t_R$: 0.61 min (LC-MS 2); ESI-MS: 181.2 [M+H]$^+$ (LC-MS 2); $^1$H-NMR (DMSO-$d_6$, 400 MHz) δ ppm 7.85 (s, 1H), 7.79 (s, 1H), 4.18 (q, 2H), 3.55 (m, 1H), 1.23 (t, 3H), 0.91-1.02 (m, 4H).

Another embodiment of the invention provides a novel intermediate compound as named, or described by structure, herein. Such compounds are disclosed as "intermediate" or "step" compounds.

Example 1

5-(5-Chloro-2-methyl-phenyl)-6-(4-chloro-2-methyl-phenyl)-2-(5-fluoro-2-methoxy-phenyl)-1-isopropyl-4-oxo-5,6,-dihydro-1H-pyrrolo[3,4-d]imidazol-4-one

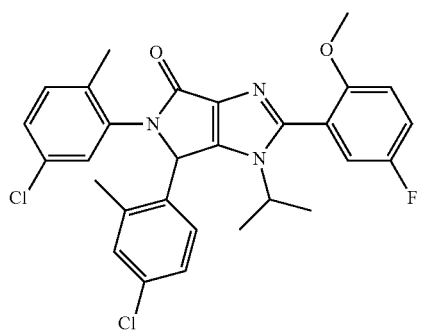 [SMILES: COc1ccc(F)cc1-c1nc2c(n1C(C)C)C(c1ccc(Cl)cc1C)N(c1cc(Cl)ccc1C)C2=O]

To a solution of intermediate F (60 mg, 0.12 mmol) in dioxane (2 ml)/H$_2$O (1 ml) were added 5-fluoro-2-methoxyphenylboronic acid (41 mg, 0.24 mmol) and K$_3$PO$_4$ (103 mg, 0.48 mmol). The mixture was degassed for 5 min and then Pd(PPh$_3$)$_4$ (28 mg, 0.02 mmol) was added. The mixture was stirred at 100° C. for 1.5 h until complete conversion. Dioxane was removed under reduced pressure. The residual suspension was diluted with EtOAc and extracted with brine. The aqueous layer was repeatedly back-extracted with EtOAc. The combined organic extracts were dried (Na$_2$SO$_4$), filtered and concentrated. The remaining crude material was purified by preparative HPLC (Waters Sun Fire C18, 30×100 mm, 5 μm; 0.1% TFA-water/acetonitrile; gradient acetonitrile 50-70% in 16 min) to give the title compound as a foam. $t_R$: 1.33 min (LC-MS 2); ESI-MS: 538.2/540.3 [M+H]$^+$ (LC-MS 2).

Example 2

5-(5-Chloro-2-methyl-phenyl)-6-(4-chloro-2-methyl-phenyl)-2-(6-fluoro-2-methoxy-phenyl)-1-isopropyl-4-oxo-5,6,-dihydro-1H-pyrrolo[3,4-d]imidazol-4-one

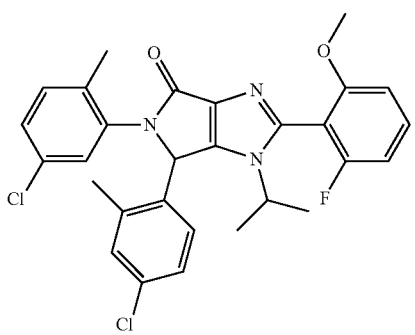 [SMILES: COc1cccc(F)c1-c1nc2c(n1C(C)C)C(c1ccc(Cl)cc1C)N(c1cc(Cl)ccc1C)C2=O]

The title compound was prepared in analogy to the procedure described for example 1 using intermediate F and 6-fluoro-2-methoxy-phenylboronic acid. $t_R$: 1.32 min (LC-MS 2); ESI-MS: 538.3/540.2 [M+H]$^+$ (LC-MS 2).

Example 3

5-(5-Chloro-2-methyl-phenyl)-6-(4-chloro-2-methyl-phenyl)-1-isopropyl-2-(2-trifluoromethoxy-phenyl)-5,6,-dihydro-1H-pyrrolo[3,4-d]imidazol-4-one

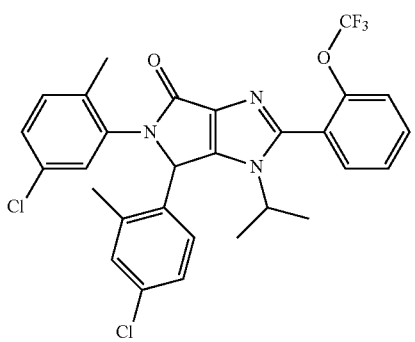 [SMILES: Cc1cc(Cl)ccc1C1c2c(nc(-c3ccccc3OC(F)(F)F)n2C(C)C)C(=O)N1c1cc(Cl)ccc1C]

The title compound was prepared in analogy to the procedure described for example 1 using intermediate F and 2-trifluoro-methoxy-phenylboronic acid. $t_R$: 1.38 min (LC-MS 2); ESI-MS: 574.3/576.3 [M+H]$^+$ (LC-MS 2).

Example 4

3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidaol-2-yl]-4-methoxy-benzonitrile

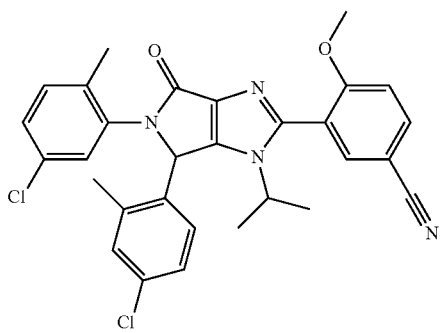 [SMILES: COc1ccc(C#N)cc1-c1nc2c(n1C(C)C)C(c1ccc(Cl)cc1C)N(c1cc(Cl)ccc1C)C2=O]

The title compound was prepared in analogy to the procedure described for example 1 using intermediate F and 2-methoxy-5-cyano-phenylboronic acid. $t_R$: 1.27 min (LC-MS 2); ESI-MS: 545.3/547.3 [M+H]$^+$ (LC-MS 2).

Example 5

5-(5-Chloro-2-methyl-phenyl)-6-(4-chloro-2-methyl-phenyl)-1-isopropyl-2-(2-methoxy-phenyl)-5,6,-dihydro-1H-pyrrolo[3,4-d]imidazol-4-one

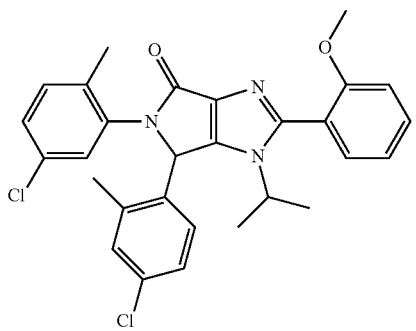

The title compound was prepared in analogy to the procedure described for example 1 using intermediate F and 2-methoxy-phenylboronic acid. $t_R$: 1.29/1.32 min (LC-MS 2); ESI-MS: 520.2/522.3 [M+H]$^+$ (LC-MS 2).

Example 6

5-(5-Chloro-2-methyl-phenyl)-6-(4-chloro-2-methyl-phenyl)-2-(4-methoxy-pyridin-3-yl)-1-isopropyl-5,6,-dihydro-1H-pyrrolo[3,4-d]imidazol-4-one

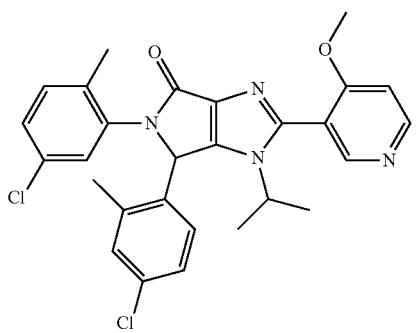 [SMILES: COc1ccncc1-c1nc2c(n1C(C)C)C(c1ccc(Cl)cc1C)N(c1cc(Cl)ccc1C)C2=O]

The title compound was prepared in analogy to the procedure described for example 1 using intermediate F and 2-methoxy-pyridin-4-yl boronic acid. $t_R$: 1.25/1.28 min (LC-MS2); ESI-MS: 521.2/523.2 [M+H]$^+$ (LC-MS 2).

Example 7

5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one

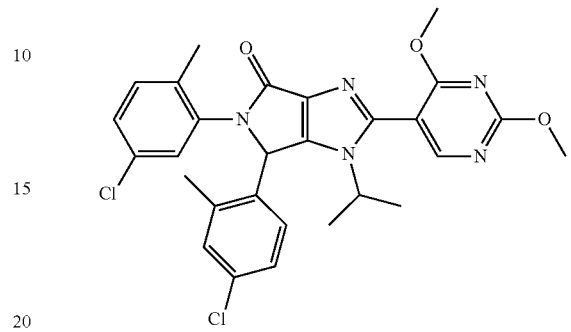

The title compound was prepared in analogy to the procedure described for example 1 using intermediate F and 2,4-dimethoxy-pyrimidin-5-yl boronic acid. $t_R$: 1.23/1.26 min (LC-MS 2); ESI-MS: 552.3/554.3 [M+H]$^+$ (LC-MS 2).

Example 8

5-(5-Chloro-2-methyl-phenyl)-6-(4-chloro-2-methyl-phenyl)-2-(2-methoxy-pyridin-3-yl)-1-isopropyl-5,6,-dihydro-1H-pyrrolo[3,4-d]imidazol-4-one

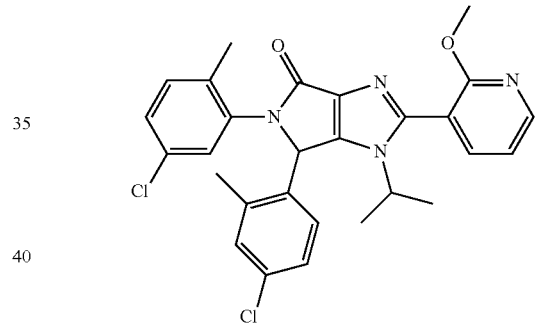

The title compound was prepared in analogy to the procedure described for Example 1 using intermediate F and 2-methoxy-pyridin-3-yl boronic acid. $t_R$: 1.28 min (LC-MS 2); ESI-MS: 521.4/523.1 [M+H]$^+$ (LC-MS 2).

Example 9

3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N,N-dimethyl benzamide

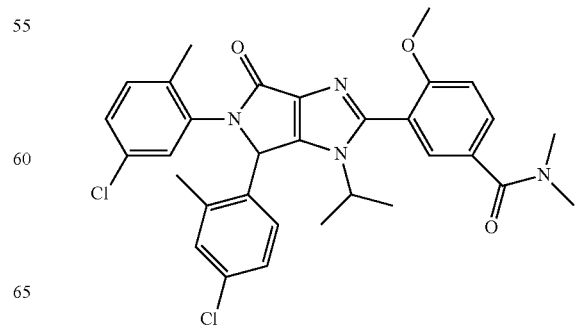

The title compound was prepared in analogy to the procedure described for example 1 using intermediate F and intermediate M. $t_R$: 1.20 min (LC-MS 2); ESI-MS: 591.3/593.3 [M+H]$^+$ (LC-MS 2).

Example 10

5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N-methyl benzamide

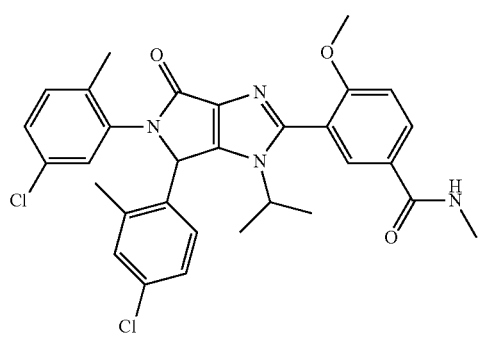 [SMILES: CNC(=O)c1ccc(OC)c(-c2nc3c(n2C(C)C)C(c2ccc(Cl)cc2C)N(c2cc(Cl)ccc2C)C3=O)c1]

The title compound was prepared in analogy to the procedure described for example 1 using intermediate F and intermediate K. $t_R$: 1.18 min (LC-MS 2); ESI-MS: 577.3/579.3 [M+H]$^+$ (LC-MS 2).

Example 11

3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-N-(2-hydroxyethyl)-4-methoxy-benzamide

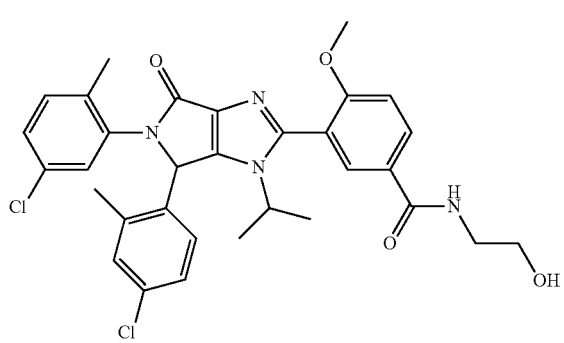 [SMILES: COc1ccc(C(=O)NCCO)cc1-c1nc2c(n1C(C)C)C(c1ccc(Cl)cc1C)N(c1cc(Cl)ccc1C)C2=O]

The title compound was prepared in analogy to the procedure described for example 1 using intermediate F and intermediate L. $t_R$: 1.10/1.13 min (LC-MS 2); ESI-MS: 607.3/609.3 [M+H]$^+$ (LC-MS 2).

Example 12

3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-N-isopropyl-4-methoxy-benzamide

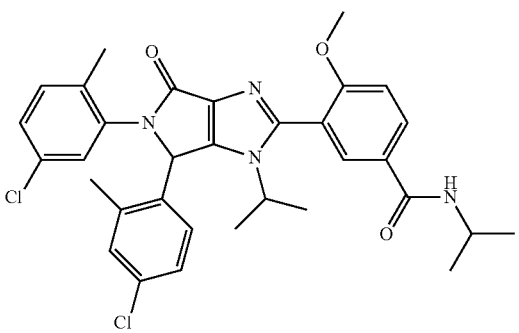 [SMILES: COc1ccc(C(=O)NC(C)C)cc1-c1nc2c(n1C(C)C)C(c1ccc(Cl)cc1C)N(c1cc(Cl)ccc1C)C2=O]

The title compound was prepared in analogy to the procedure described for example 1 using intermediate F and intermediate N. $t_R$: 1.23/1.26 min (LC-MS); (LC-MS 2); ESI-MS: 605.3/607.3 [M+H]$^+$ (LC-MS 2).

Example 13

5-(5-Chloro-2-methyl-phenyl)-6-(4-chloro-2-methyl-phenyl)-1-isopropyl-2-[2-methoxy-5-(morpholine-4-carbonyl)-phenyl]-5,6-dihydro-1H-pyrrolo[3,4-d]imidazol-4-one

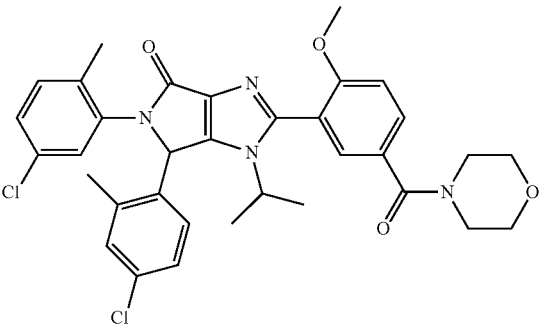 [SMILES: COc1ccc(C(=O)N2CCOCC2)cc1-c1nc2c(n1C(C)C)C(c1ccc(Cl)cc1C)N(c1cc(Cl)ccc1C)C2=O]

The title compound was prepared in analogy to the procedure described for example 1 using intermediate F and intermediate O. $t_R$: 1.16/1.19 min (LC-MS 2); ESI-MS: 633.3/635.3 [M+H]$^+$ (LC-MS 2).

Example 14

5-(5-Chloro-2-methyl-phenyl)-6-(4-chloro-2-methyl-phenyl)-2-[5-(3-hydroxy-azetidine-1-carbonyl)-2-methoxy-phenyl]1-isopropyl-5,6-dihydro-1H-pyrrolo[3,4-d]imidazol-4-one

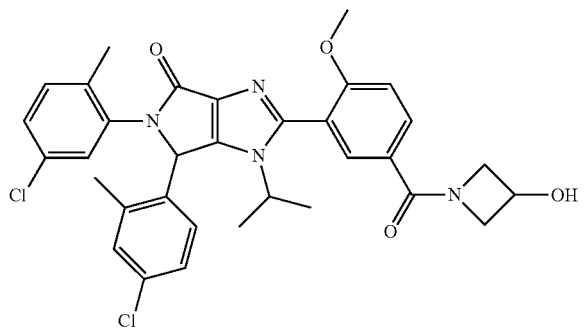 [SMILES: COc1ccc(C(=O)N2CC(O)C2)cc1-c1nc2c(n1C(C)C)C(c1ccc(Cl)cc1C)N(c1cc(Cl)ccc1C)C2=O]

The title compound was prepared in analogy to the procedure described for example 1 using intermediate F and intermediate P. $t_R$: 1.09/1.11 min (LC-MS 2); ESI-MS: 619.3/621.2 [M+H]$^+$ (LC-MS 2).

Example 15

5-(5-Chloro-2-methyl-phenyl)-6-(4-chloro-2-methyl-phenyl)-1-isopropyl-2-(3-methoxy-pyridin-4-yl)-5,6,-dihydro-1H-pyrrolo[3,4-d]imidazol-4-one

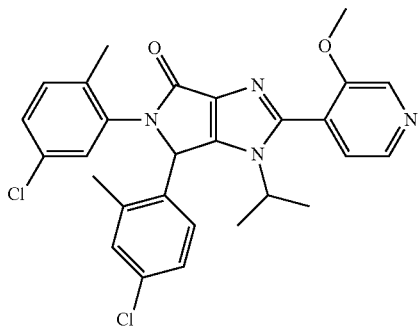 [SMILES: COc1cnccc1-c1nc2c(n1C(C)C)C(c1ccc(Cl)cc1C)N(c1cc(Cl)ccc1C)C2=O]

The title compound was prepared in analogy to the procedure described for example 1 using intermediate F and 2-methoxy-pyridin-4-yl boronic acid. $t_R$: 1.16/1.19 min (LC-MS); ESI-MS: 521.3/523.3 [M+H]$^+$ (LC-MS 2).

Example 16

2-(5-Amino methyl-2-methoxy-phenyl-5-(5-chloro-2-methyl-phenyl)-6-(4-chloro-2-methyl-phenyl)-1-isopropyl-5,6-dihydro-1H-pyrrolo[3,4-d]imidazole-4-one

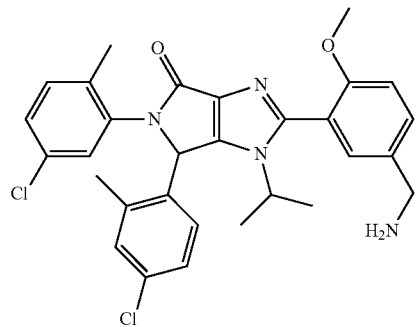 [SMILES: COc1ccc(CN)cc1-c1nc2c(n1C(C)C)C(c1ccc(Cl)cc1C)N(c1cc(Cl)ccc1C)C2=O]

The product from example 4 (135 mg, 0.25 mmol) was dissolved in THF (3.5 mL) and Raney Nickel (27 mg, 0.31 mmol) and aqueous NH$_4$OH solution (30% wt; 0.81 mL) were added. The reaction mixture was allowed to stir under an atmosphere of hydrogen at rt for 20 h. It was then filtered over a pad of celite and concentrated under reduced pressure. The remaining crude product was purified by preparative HPLC (Waters SunFire C18, 30×100 mm; 0.1% TFA/acetonitrile, gradient acetonitrile 40-60%). $t_R$: 1.00/1.02 min (LC-MS 2); ESI-MS: 549.3/551.3 [M+H]$^+$ (LC-MS 2).

Example 17

N-{3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-benzyl}-acetamide

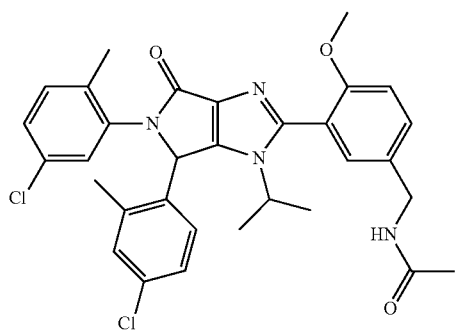 [SMILES: COc1ccc(CNC(C)=O)cc1-c1nc2c(n1C(C)C)C(c1ccc(Cl)cc1C)N(c1cc(Cl)ccc1C)C2=O]

The product from example 16 (30 mg, 0.05 mmol) was dissolved in THF (0.7 mL) and TEA (10 mL, 0.07 mmol) was added. The reaction was cooled in an ice bath and acetyl chloride (5 mL, 0.06 mmol) was added. The cooling bath was removed and the reaction mixture allowed to stir at rt for 0.5 h. It was then diluted with EtOAc and brine and the aqueous phase extracted with EtOAc. The combined extracts were dried (Na$_2$SO$_4$) and concentrated. The remaining crude product was triturated with acetonitrile to give the title compound as a white solid, which was isolated by filtration and dried under reduced pressure. $t_R$: 1.18/1.21 min (LC-MS 2); ESI-MS: 591.2/593.2 [M+H]$^+$ (LC-MS 2).

Example 18

5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one

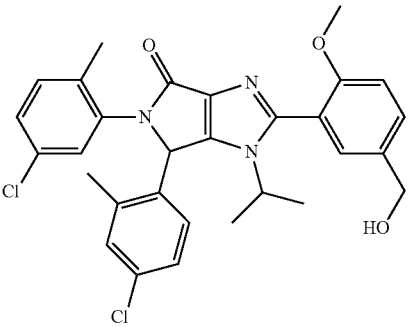

The product from step 18.1 (100 mg, 0.18 mmol) was dissolved in MeOH (3 mL) at rt and NaBH$_4$ (11 mg, 0.27 mmol) was added. The reaction mixture was allowed to stir at rt for 0.5 h and then diluted with EtOAc and washed with brine. The aqueous layer was extracted with EtOAc, combined organic layers dried over Na$_2$SO$_4$ and concentrated. The residual crude material was purified by preparative HPLC (Waters SunFire C18, 30×100 mm, 5 μm; 0.1% TFA-water/acetonitrile, gradient acetonitrile 50-70%, 16 min). $t_R$: 1.18/1.20 min (LC-MS2); ESI-MS: 550.3/552.3 [M+H]$^+$ (LC-MS 2).

Step 18.1: 3-[5-(5-Chloro-2-methyl-phenyl)-6-(4-chloro-2-methyl-phenyl)-1-isopropyl-4-oxo-5,6,-dihydro-1H-pyrrolo[3,4-d]imidazol-2-yl]-4-methoxybenzaldehyde

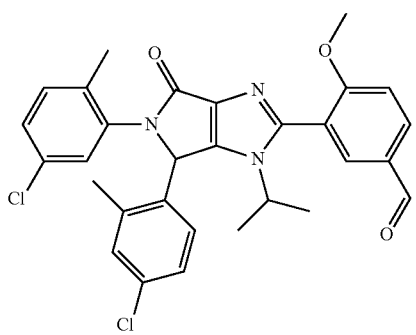 [SMILES: COc1ccc(C=O)cc1-c1nc2c(n1C(C)C)C(c1ccc(Cl)cc1C)N(c1cc(Cl)ccc1C)C2=O]

The title compound was prepared in analogy to the procedure described for example 1 using intermediate F and 5-formyl-2-methoxy-phenylboronic acid. $t_R$: 1.22/1.25 min (LC-MS2); ESI-MS: 548.3/550.3 [M+H]$^+$ (LC-MS 2).

Example 19

5-(5-Chloro-2-methyl-phenyl)-6-(4-chloro-phenyl)-2-(5-hydroxymethyl-2-methoxy-phenyl)-1-isopropyl-5,6-dihydro-1H-pyrrolo[3,4-d]imidazole-4-one

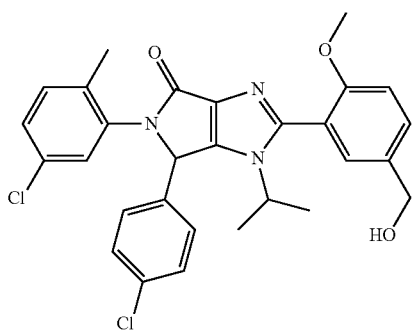 [SMILES: COc1ccc(CO)cc1-c1nc2c(n1C(C)C)C(c1ccc(Cl)cc1)N(c1cc(Cl)ccc1C)C2=O]

The title compound was prepared in 2 steps in analogy to the procedure described for example 18 using intermediate E and 5-formyl-2-methoxy-phenylboronic acid. $t_R$: 1.15 min (LC-MS2); ESI-MS: 536.2/538.2 [M+H]$^+$ (LC-MS 2).

Example 20

5-(3-Chloro-2-fluoro-phenyl)-6-(4-chloro-phenyl)-2-(5-hydroxymethyl-2-methoxy-phenyl)-1-isopropyl-5,6-dihydro-1H-pyrrolo[3,4-d]imidazole-4-one

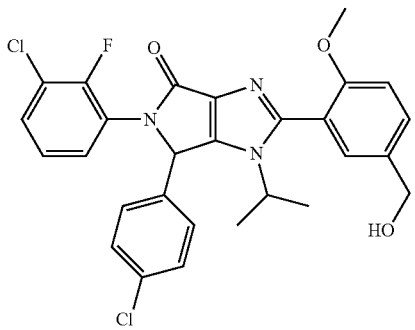 [SMILES: COc1ccc(CO)cc1-c1nc2c(n1C(C)C)C(c1ccc(Cl)cc1)N(c1cccc(Cl)c1F)C2=O]

The title compound was prepared in analogy to the 2 steps procedure described for example 18 using intermediate G and 5-formyl-2-methoxy-phenylboronic acid. $t_R$: 1.12 min (LC-MS2); ESI-MS: 540.3/542.3 [M+H]$^+$ (LC-MS 2).

Example 21

5-(5-Chloro-2-methyl-phenyl)-6-(4-chloro-phenyl)-2-(4-hydroxymethyl-2-methoxy-phenyl)-1-isopropyl-5,6-dihydro-1H-pyrrolo[3,4-d]imidazole-4-one

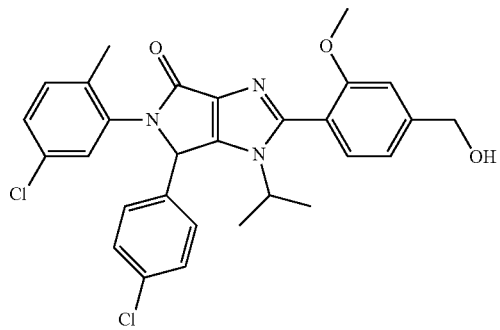 [SMILES: COc1cc(CO)ccc1-c1nc2c(n1C(C)C)C(c1ccc(Cl)cc1)N(c1cc(Cl)ccc1C)C2=O]

The title compound was prepared in analogy to the procedure described for example 1 using intermediate E and intermediate R. $t_R$: 1.14 min (LC-MS2); ESI-MS: 536.2/538.2 [M+H]$^+$ (LC-MS 2).

Example 22

5-(5-Chloro-2-methyl-phenyl)-6-(4-chloro-2-methyl-phenyl)-2-(4-hydroxymethyl-2-methoxy-phenyl)-1-isopropyl-5,6-dihydro-1H-pyrrolo[3,4-d]imidazole-4-one

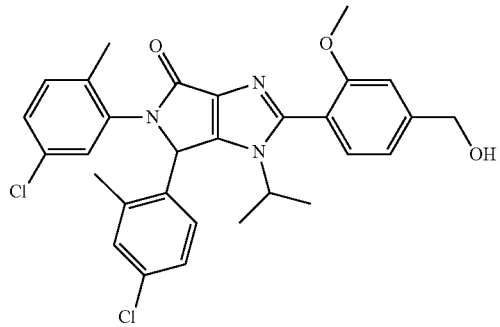 [SMILES: COc1cc(CO)ccc1-c1nc2c(n1C(C)C)C(c1ccc(Cl)cc1C)N(c1cc(Cl)ccc1C)C2=O]

The title compound was prepared in analogy to the 2 steps procedure described for example 18 using intermediate F and intermediate R. $t_R$: 1.17/1.20 min (LC-MS); ESI-MS: 550.2/552.2 [M+H]$^+$ (LC-MS 2).

Example 23

3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl benzamide

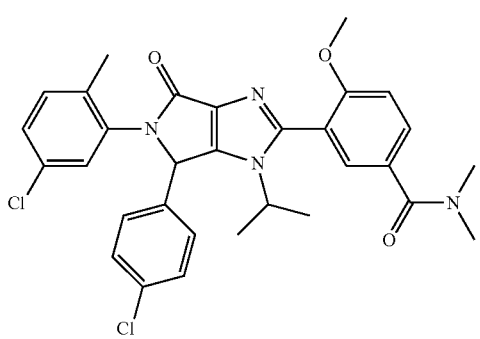 [SMILES: COc1ccc(C(=O)N(C)C)cc1-c1nc2c(n1C(C)C)C(c1ccc(Cl)cc1)N(c1cc(Cl)ccc1C)C2=O]

The title compound was prepared in analogy to the procedure described for example 1 starting using intermediate E and intermediate M. $t_R$: 1.14 min (LC-MS); ESI-MS: 577.2/579.2 [M+H]$^+$ (LC-MS 2). $^1$H-NMR (DMSO-d$_6$, 400 MHz) δ 7.79 (s, 1H), 7.63 (d, 1H), 7.48 (s, 1H), 7.39 (d, 2H), 7.31 (d, 2H), 7.25 (d, 1H), 7.18 (d, 1H), 7.12 (d, 1H), 6.62 (s, 1H), 4.04 (sep, 1H), 3.83 (s, 3H), 2.97 (s, 6H), 1.94 (s, 3H), 1.31 (d, 3H), 0.52 (bs, 3H).

Example 24

3-[5-(5-Chloro-2-methyl-phenyl)-6-(4-chloro-phenyl)-1-isopropyl-4-oxo-1,4,5,6-tetrahydro-pyrrolo[3,4-d]imidaol-2-yl]-4-methoxy-benzonitrile

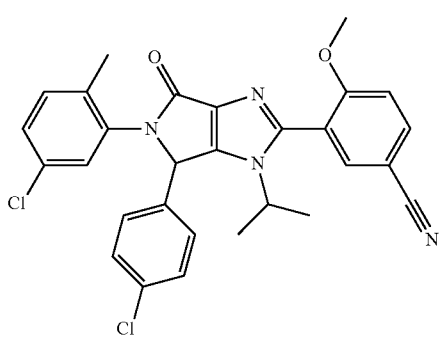

The title compound was prepared in analogy to the procedure described for example 1 starting using intermediate E and 5-cyano-2-methoxy-phenyl- boronic acid. $t_R$: 1.22 min (LC-MS2); ESI-MS: 531.2/533.2 [M+H]$^+$ (LC-MS 2). $^1$H-NMR (DMSO-d$_6$, 400 MHz) δ 8.06 (d, 1H), 7.94 (s, 1H), 7.79 (s, 1H), 7.42-7.38 (m, 3H), 7.32-7.28 (m, 2H), 7.19 (d, 1H), 7.14 (d, 1H), 6.64 (s, 1H), 4.01 (sep, 1H), 3.88 (s, 3H), 1.95 (s, 3H), 1.31 (d, 3H), 0.53 (bs, 3H).

Example 25

5-(5-Chloro-2-methyl-phenyl)-6-(4-chloro-phenyl)-1-isopropyl-2-[2-methoxy-5-(morpholine-4-carbonyl)-phenyl]-5,6-dihydro-1H-pyrrolo[3,4-d]imidazol-4-one

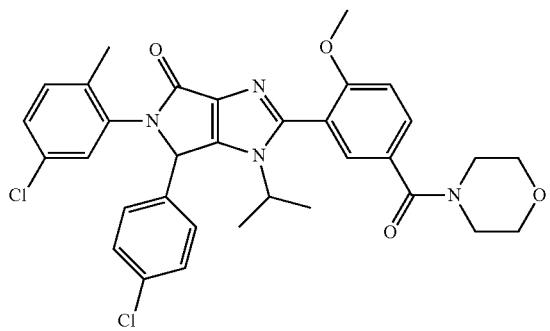 [SMILES: COc1ccc(C(=O)N2CCOCC2)cc1-c1nc2c(n1C(C)C)C(c1ccc(Cl)cc1)N(c1cc(Cl)ccc1C)C2=O]

The title compound was prepared in analogy to the procedure described for example 1 starting using intermediate E and intermediate O. $t_R$: 1.13 min (LC-MS 2); ESI-MS: 619.2/621.2 [M+H]$^+$ (LC-MS 2); $^1$H-NMR (DMSO-d$_6$, 400 MHz) δ 8.06 (d, 1H), 7.94 (s, 1H), 7.79 (s, 1H), 7.42-7.38 (m, 3H), 7.32-7.28 (m, 2H), 7.19 (d, 1H), 7.14 (d, 1H), 6.64 (s, 1H), 4.01 (sep, 1H), 3.88 (s, 3H), 1.95 (s, 3H), 1.31 (d, 3H), 0.53 (bs, 3H).

Example 26

4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzonitrile

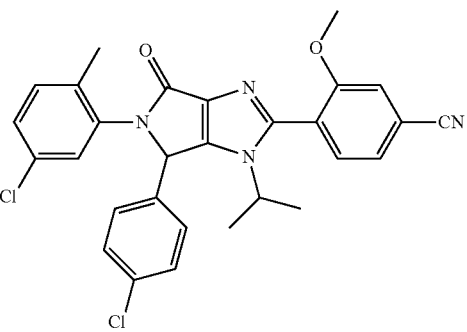 [SMILES: COc1cc(C#N)ccc1-c1nc2c(n1C(C)C)C(c1ccc(Cl)cc1)N(c1cc(Cl)ccc1C)C2=O]

The title compound was prepared in analogy to the procedure described for example 1 starting using intermediate E and intermediate S. $t_R$: 1.23 min (LC-MS 2); ESI-MS: 531.1/533.2 [M+H]$^+$ (LC-MS 2).

Example 27

5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazole-4-one

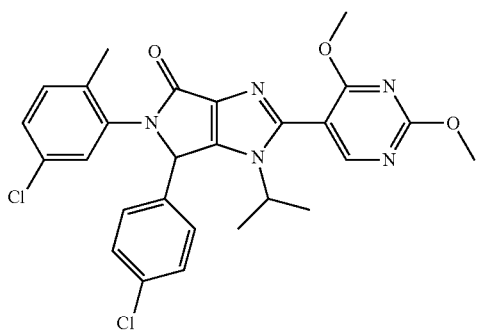 [SMILES: COc1ncc(-c2nc3c(n2C(C)C)C(c2ccc(Cl)cc2)N(c2cc(Cl)ccc2C)C3=O)c(OC)n1]

The title compound was prepared in analogy to the procedure described for example 1 starting using intermediate E and 2,4-dimethoxy-pyrimidin-5-yl boronic acid. $t_R$: 1.20 min (LC-MS 2); ESI-MS: 538.2/540.2 [M+H]$^+$ (LC-MS 2); $^1$H-NMR (DMSO-d$_6$, 400 MHz) δ 8.51 (s, 1H), 7.79 (s, 1H), 7.41-7.29 (m, 4H), 7.19-7.09 (m, 2H), 6.62 (s, 1H), 4.15 (sep, 1H), 3.99 (s, 3H), 3.90 (s, 3H), 1.92 (s, 3H), 1.42 (d, 3H), 0.49 (d, 3H).

Example 28

5-(5-Chloro-2-methyl-phenyl)-6-(4-chloro-phenyl)-2-(3,6-pyridazin-4-yl)-1-isopropyl-5,6-dihydro-1H-pyrrolo[3,4-d]imidazole-4-one

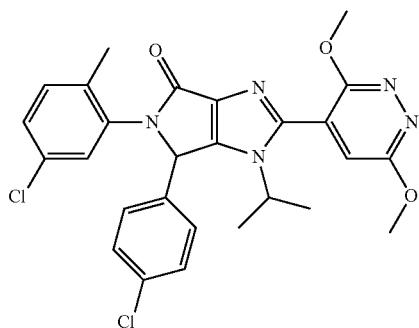 [SMILES: COc1cc(-c2nc3c(n2C(C)C)C(c2ccc(Cl)cc2)N(c2cc(Cl)ccc2C)C3=O)c(OC)nn1]

The title compound was prepared in analogy to the procedure described for example 1 using intermediate E and 3,6-dimethoxy-pyridazin-4-yl boronic acid. $t_R$: 1.20 min (LC-MS 2); ESI-MS: 538.2/540.2 [M+H]$^+$ (LC-MS 2).

Example 29

5-(5-Chloro-2-methyl-phenyl)-6-(4-chloro-2-methyl-phenyl)-2-(2,6-dimethoxy-pyridin-3-yl)-1-isopropyl-5,6-dihydro-1H-pyrrolo[3,4-d]imidazol-4-one

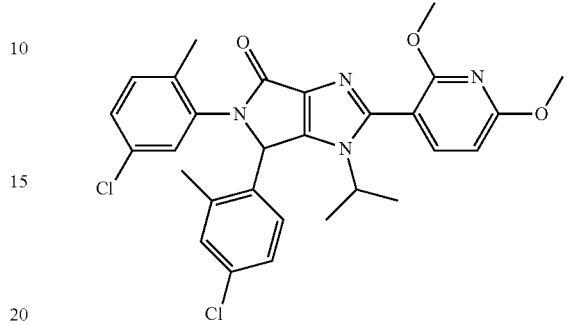

PdCl$_2$(dppf)-CH$_2$Cl$_2$ complex (33.1 mg, 0.041 mmol) was added to a heated (80° C.) mixture of intermediate F (200 mg, 0.405 mmol) and K$_3$PO$_4$ (344 mg, 1.62 mmol) in dioxane (3 mL) and water (1 mL), under argon. The temperature was increased to 100° C. and 2,6-dimethoxypyridin-3-yl boronic acid (89 mg, 0.487 mmol) was added. The reaction mixture was stirred for 15 min at 100° C., allowed to cool to rt, diluted with EtOAc/water, and extracted with EtOAc. The organic layer was washed with water and brine, dried (Na$_2$SO$_4$), filtered, and concentrated. The residue was purified by flash chromatography (hexane/EtOAc, 3:1), followed by trituration in Et$_2$O/hexane (4:1), to afford 85 mg of the title compound. $t_R$: 1.40 min (LC-MS 2); ESI-MS: 551.3/553.3 [M+H]$^+$ (LC-MS 2); Rf: 0.31 (hexane/EtOAc, 3:1).

Example 30

5-(5-Chloro-2-methyl-phenyl)-6-(4-chloro-2-methyl-phenyl)-1-isopropyl-2-(4-methoxy-pyrimidin-5-yl)-5,6-dihydro-1H-pyrrolo[3,4-d]imidazol-4-one

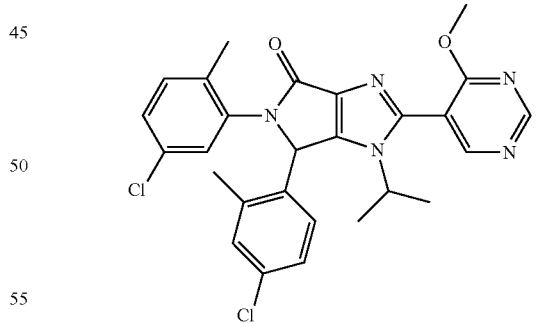

The title compound was prepared in analogy to the procedure described for example 29 but using intermediate T (2.3 equiv) and stirring the reaction mixture for 7 h at 100° C. After flash chromatography (CH$_2$Cl$_2$/MeOH, 95:5) of the crude product and subsequent trituration in Et$_2$O, the resulting material was further purified by preparative HPLC (Column: Sunfire C18, 30×100 mm, 5 pm. Flow: 30 mL/min. Gradient 30-70% B in 30 min; A=0.1% TFA in water, B=CH$_3$CN). $t_R$: 1.20 min (LC-MS 2); ESI-MS: 522.2/524.3 [M+H]$^+$ (LC-MS 2); R$_f$: 0.12 (CH$_2$Cl$_2$/MeOH, 95:5).

Example 31

5-(5-Chloro-2-methyl-phenyl)-6-(4-chloro-phenyl)-1-isopropyl-2-(4-methoxy-2-methylamino-pyrimidin-5-yl)-5,6-dihydro-1H-pyrrolo[3,4-d]imidazol-4-one

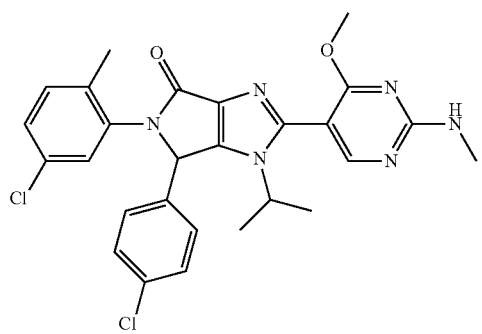

The title compound was prepared in analogy to the procedure described for example 29 but using intermediate E, intermediate Z (2 equiv), 0.15 equivalents of PdCl$_2$(dppf)-CH$_2$Cl$_2$ complex, and stirring the reaction mixture for 30 min at 100° C. After flash chromatography (CH$_2$Cl$_2$/MeOH, 95:5) of the crude product and subsequent trituration in Et$_2$O, the resulting material was further purified by preparative HPLC (Column: Sunfire C18, 30×100 mm, 5 µm. Flow: 30 mL/min. Gradient 30-60% B in 30 min; A=0.1% TFA in water, B=CH$_3$CN). $t_R$: 1.22 min (LC-MS 2); ESI-MS: 537.2/539.2 [M+H]$^+$ (LC-MS 2); R$_f$: 0.24 (CH$_2$Cl$_2$/MeOH, 95:5).

Example 32

5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one

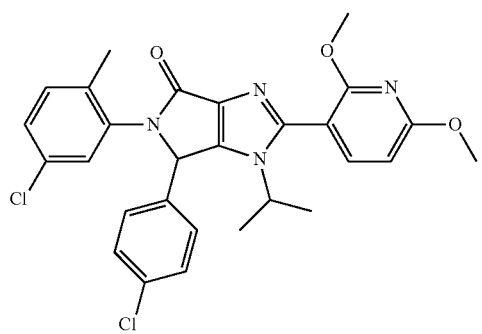 [SMILES: COc1ccc(-c2nc3c(n2C(C)C)C(c2ccc(Cl)cc2)N(c2cc(Cl)ccc2C)C3=O)c(OC)n1]

The title compound was prepared in analogy to the procedure described for example 29 but using intermediate E, 1.5 equivalents of 2,6-dimethoxypyridin-3-yl boronic acid, 0.15 equivalents of PdCl$_2$(dppf)-CH$_2$Cl$_2$ complex, and stirring the reaction mixture for 30 min at 100° C. The crude product was purified by flash chromatography (hexane/EtOAc, 1:3) and subsequent trituration in Et$_2$O. $t_R$: 1.35 min (LC-MS 2); ESI-MS: 537.2/539.2 [M+H]$^+$ (LC-MS 2); R$_f$: 0.32 (hexane/EtOAc, 1:3).

Example 33

5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one

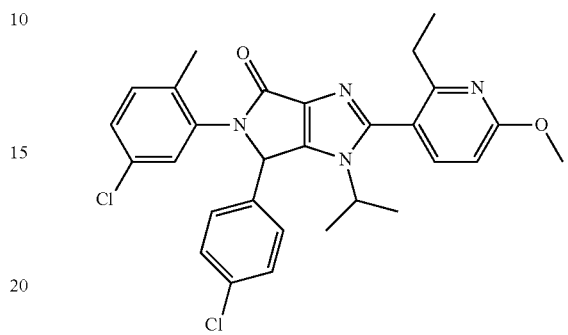

The title compound was prepared in analogy to the procedure described for example 29 but using intermediate E, 1.5 equivalents of 2-ethyl-6-methoxypyridin-3-ylboronic acid, 0.15 equivalents of PdCl$_2$(dppf)-CH$_2$Cl$_2$ complex, and stirring the reaction mixture for 30 min at 100° C. The crude product was purified by flash chromatography (hexane/EtOAc, 1:3) and subsequent trituration in Et$_2$O/hexane (1:4). $t_R$: 1.38 min (LC-MS 2); ESI-MS: 535.3/537.2 [M+H]$^+$ (LC-MS 2); R$_f$: 0.44 (hexane/EtOAc, 1:3).

Example 34

3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-ethyl-benzonitrile

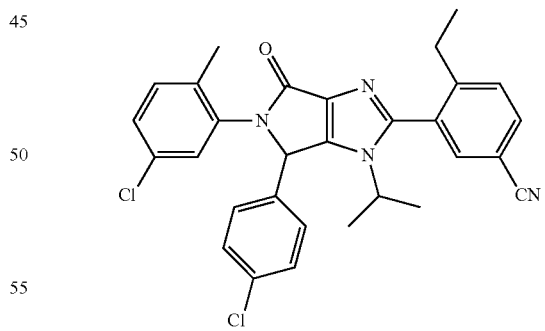

The title compound was prepared in analogy to the procedure described for example 29 but using intermediate E, 1.8 equivalents of intermediate V, 0.15 equivalents of PdCl$_2$(dppf)-CH$_2$Cl$_2$ complex, and stirring the reaction mixture for 30 min at 100° C. The crude product was purified by flash chromatography (hexane/EtOAc, 1:1) and subsequent trituration in Et$_2$O. $t_R$: 1.34 min (LC-MS 2); ESI-MS: 529.2/531.2 [M+H]$^+$ (LC-MS 2); R$_f$: 0.14 (hexane/EtOAc, 1:1).

Example 35

5-(5-Chloro-2-methyl-phenyl)-6-(4-chloro-2-methyl-phenyl)-2-(2-dimethylamino-4-methoxy-pyrimidin-5-yl)-1-isopropyl-5,6-dihydro-1H-pyrrolo[3,4-d]imidazol-4-one

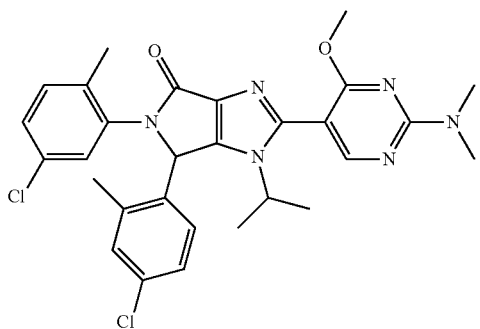 [SMILES: COc1nc(N(C)C)ncc1-c1nc2c(n1C(C)C)C(c1ccc(Cl)cc1C)N(c1cc(Cl)ccc1C)C2=O]

The title compound was prepared in analogy to the procedure described for example 29 but using 2 equivalents of intermediate W, 0.15 equivalents of PdCl$_2$(dppf)-CH$_2$Cl$_2$ complex, and stirring the reaction mixture for 1 h at 100° C. After flash chromatography (CH$_2$Cl$_2$/MeOH, 95:5) of the crude product and subsequent trituration in Et$_2$O, the resulting material was further purified by preparative HPLC (Column: Sunfire C18, 30×100 mm, 5 µm. Flow: 30 mL/min. Gradient 30-60% B in 30 min; A=0.1% TFA in water, B=CH$_3$CN). t$_R$: 1.35/1.38 min (LC-MS 2); ESI-MS: 565.2/567.1 [M+H]$^+$ (LC-MS 2); R$_f$: 0.25 (CH$_2$Cl$_2$/MeOH, 95:5).

Example 36

5-(5-Chloro-2-methyl-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

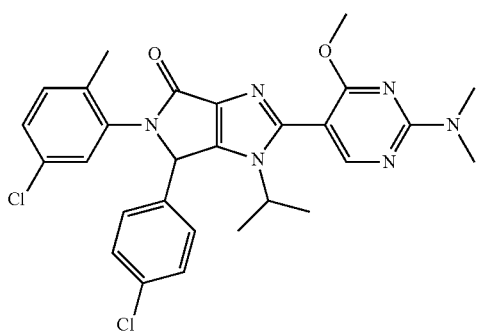

The title compound was prepared in analogy to the procedure described for example 29 but using intermediate E, 2 equivalents of intermediate W, 0.15 equivalents of PdCl$_2$ (dppf)-CH$_2$Cl$_2$ complex, and stirring the reaction mixture for 1 h at 100° C. After flash chromatography (CH$_2$Cl$_2$/MeOH, 95:5) and subsequent trituration in Et$_2$O, the resulting material was further purified by preparative HPLC (Column: Sunfire C18, 30×100 mm, 5 µm. Flow: 30 mL/min. Gradient 30-60% B in 30 min; A=0.1% TFA in water, B=CH$_3$CN). t$_R$: 1.33 min (LC-MS 2); ESI-MS: 551.2/553.2 [M+H]$^+$ (LC-MS 2); R$_f$: 0.28 (CH$_2$Cl$_2$/MeOH, 95:5); $^1$H NMR (DMSO-d$_6$, 400 MHz) δ ppm 0.54 (d, J=6.3 Hz, 3 H), 1.30 (d, J=7.0 Hz, 3 H), [1.94 (br. s) and 2.24 (br. s), 3 H, rotamers], 3.17 (s, 6 H), 3.88 (s, 3 H), 4.00-4.18 (m, 1 H), [6.11 (br. s) and 6.58 (br. s), 1 H, rotamers], 7.10-7.40 (m, 6 H), 7.75 (br. s, 1 H), 8.21 (s, 1 H).

Example 37

2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one

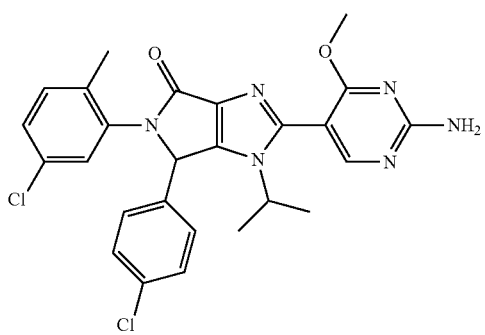 [SMILES: COc1nc(N)ncc1-c1nc2c(n1C(C)C)C(c1ccc(Cl)cc1)N(c1cc(Cl)ccc1C)C2=O]

The title compound was prepared in analogy to the procedure described for example 29 but using intermediate E, 2 equivalents of intermediate U, 0.15 equivalents of PdCl$_2$ (dppf)-CH$_2$Cl$_2$ complex, and stirring the reaction mixture for 1 h at 100° C. The crude product was purified by flash chromatography (CH$_2$Cl$_2$/MeOH, 95:5) and subsequent trituration in Et$_2$O. t$_R$: 1.13 min (LC-MS 2); ESI-MS: 523.2/525.2 [M+H]$^+$ (LC-MS 2); R$_f$: 0.13 (CH$_2$Cl$_2$/MeOH, 95:5); $^1$H NMR (DMSO-d$_6$, 400 MHz) δ ppm 0.55 (d, J=6.26 Hz, 3 H), 1.30 (d, J=6.65 Hz, 3 H), [1.94 (br. s) and 2.24 (br. s), 3 H, rotamers], 3.83 (s, 3 H), 4.10 (qd, J=6.71, 6.5 Hz, 1 H), [6.10 (br. s) and 6.58 (br. s), 1 H, rotamers], 7.00-7.45 (m, 8 H), 7.76 (br. s, 1 H), 8.10 (s, 1 H).

Example 38

5-(5-Chloro-2-methyl-phenyl)-6-(4-chloro-phenyl)-2-{2-[(2-hydroxy-ethyl)-methyl-amino]-4-methoxy-pyrimidin-5-yl}-1-isopropyl-5,6-dihydro-1H-pyrrolo[3,4-d]imidazol-4-one

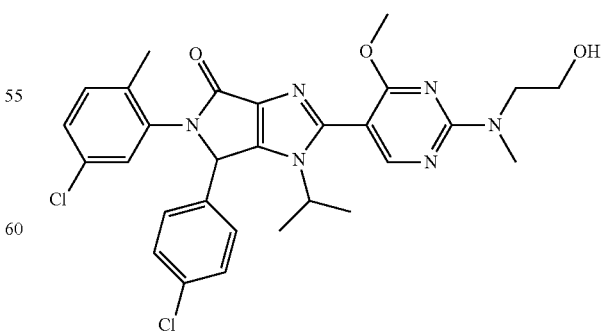

The title compound was prepared in analogy to the procedure described for example 29 but using intermediate E, 1.5 equivalents of intermediate X, 0.15 equivalents of PdCl$_2$(dppf)-CH$_2$Cl$_2$ complex, and stirring the reaction mixture for 2 h at 110° C. The crude product was loaded onto a VARIAN column PL-Thiol MP-Resin (to remove metal traces) and eluted with MeOH. The filtrate was concentrated and purified twice by flash chromatography (CH$_2$Cl$_2$/MeOH, 95:5). Trituration of the resulting material in Et$_2$O/hexane (1:1) provided the title compound. t$_R$: 1.19 min (LC-MS 2); ESI-MS: 581.3/583.3 [M+H]$^+$ (LC-MS 2); R$_f$: 0.12 (CH$_2$Cl$_2$/MeOH, 95:5).

Example 39

5-(5-Chloro-2-methyl-phenyl)-6-(4-chloro-phenyl)-2-[2-(2-hydroxy-ethyl amino)-4-methoxy-pyrimidin-5-yl]-1-isopropyl-5,6-dihydro-1H-pyrrolo[3,4-d]imidazol-4-one

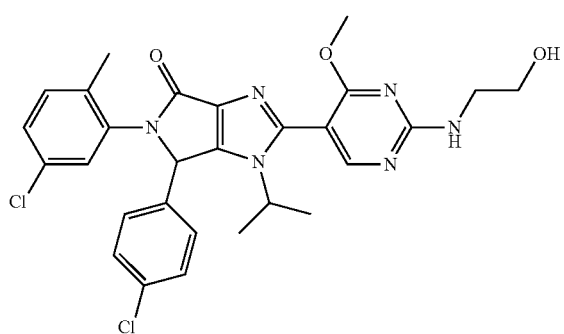 [SMILES: COc1nc(NCCO)ncc1-c1nc2c(n1C(C)C)C(c1ccc(Cl)cc1)N(c1cc(Cl)ccc1C)C2=O]

The title compound was prepared in analogy to the procedure described for example 29 but using intermediate E, 1.5 equivalents of intermediate Y, 0.15 equivalents of PdCl$_2$(dppf)-CH$_2$Cl$_2$ complex, and stirring the reaction mixture for 1.5 h at 110° C. The crude product was purified by flash chromatography (CH$_2$Cl$_2$/MeOH, 92.5:7.5), followed by preparative HPLC (Column: Sunfire C18, 30×100 mm, 5 µm. Flow: 30 mL/min. Gradient 30-60% B in 30 min; A=0.1% TFA in water, B=CH$_3$CN). t$_R$: 1.12 min (LC-MS 2); ESI-MS: 567.2/569.2 [M+H]$^+$ (LC-MS 2); R$_f$: 0.14 (CH$_2$Cl$_2$/MeOH, 92.5:7.5).

Example 40

4-[2-(2-Amino-4-methoxy-pyrimidin-5-yl)-5-(5-chloro-2-methyl-phenyl)-3-isopropyl-6-oxo-3,4,5,6-tetrahydro-pyrrolo[3,4-d]imidazol-4-yl]-benzonitrile

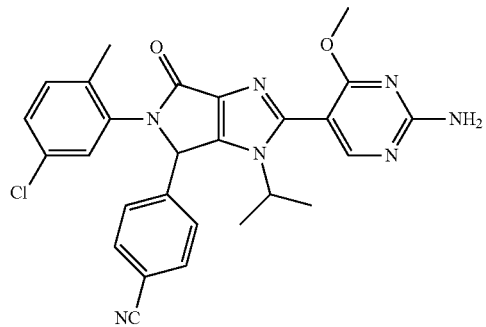 [SMILES: COc1nc(N)ncc1-c1nc2c(n1C(C)C)C(c1ccc(C#N)cc1)N(c1cc(Cl)ccc1C)C2=O]

The title compound was prepared in analogy to the procedure described for example 29 but using intermediate H, 2 equivalents of intermediate U, 0.15 equivalents of PdCl$_2$(dppf)-CH$_2$Cl$_2$ complex, and stirring the reaction mixture for 2 h at 110° C. The crude product was purified by flash chromatography (CH$_2$Cl$_2$/MeOH, 92.5:7.5), followed by preparative HPLC (Column: Sunfire C18, 30×100 mm, 5 µm. Flow: 30 mL/min. Gradient 30-60% B in 20 min; A=0.1% TFA in water, B=CH$_3$CN) and trituration in Et$_2$O. t$_R$: 0.98 min (LC-MS 2); ESI-MS: 514.3/516.2 [M+H]$^+$ (LC-MS 2); R$_f$: 0.29 (CH$_2$Cl$_2$/MeOH, 92.5:7.5).

Example 41

4-[5-(5-Chloro-2-methyl-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile

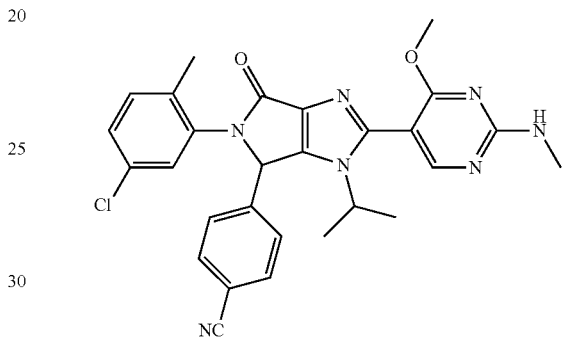

The title compound was prepared in analogy to the procedure described for example 29 but using intermediate H, 2 equivalents of intermediate Z, 0.15 equivalents of PdCl$_2$(dppf)-CH$_2$Cl$_2$ complex, and stirring the reaction mixture for 30 min at 110° C. The crude product was purified by flash chromatography (CH$_2$Cl$_2$/MeOH, 92.5:7.5), followed by preparative HPLC (Column: Sunfire C18, 30×100 mm, 5 µm. Flow: 30 mL/min. Gradient 30-60% B in 20 min; A=0.1% TFA in water, B=CH$_3$CN) and trituration in Et$_2$O. t$_R$: 1.06 min (LC-MS 2); ESI-MS: 528.3/530.3 [M+H]$^+$ (LC-MS 2); R$_f$: 0.33 (CH$_2$Cl$_2$/MeOH, 92.5:7.5).

Example 42

4-[5-(5-Chloro-2-methyl-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

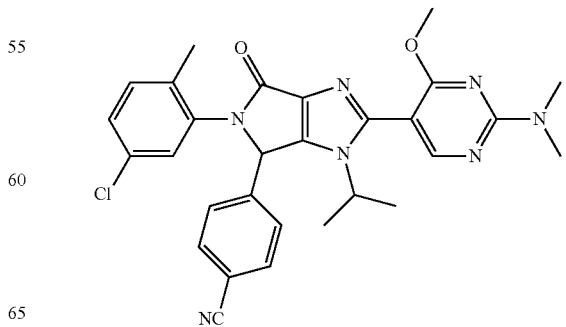

The title compound was prepared in analogy to the procedure described for example 29 but using intermediate H, 2 equivalents of intermediate W, 0.15 equivalents of PdCl$_2$(dppf)-CH$_2$Cl$_2$ complex, and stirring the reaction mixture for 30 min at 110° C. The crude product was purified by flash chromatography (CH$_2$Cl$_2$/MeOH, 95:5), followed by preparative HPLC (Column: Sunfire C18, 30×100 mm, 5 μm. Flow: 30 mL/min. Gradient 30-60% B in 20 min; A=0.1% TFA in water, B=CH$_3$CN) and trituration in Et$_2$O/hexane (1:1). t$_R$: 1.16 min (LC-MS 2); ESI-MS: 542.3/544.3 [M+H]$^+$ (LC-MS 2); R$_f$: 0.25 (CH$_2$Cl$_2$/MeOH, 95:5).

Example 43

4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

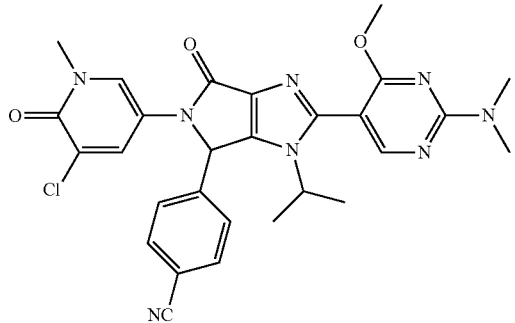 [SMILES: COc1nc(N(C)C)ncc1-c1nc2c(n1C(C)C)C(c1ccc(C#N)cc1)N(c1cc(Cl)c(=O)n(C)c1)C2=O]

The title compound was prepared in analogy to the procedure described for example 29 but using intermediate AA, 2 equivalents of intermediate W, 0.15 equivalents of PdCl$_2$(dppf)-CH$_2$Cl$_2$ complex, and stirring the reaction mixture for 30 min at 110° C. The crude product was purified by flash chromatography (CH$_2$Cl$_2$/MeOH, 92.5:7.5), followed by preparative HPLC (Column: Sunfire C18, 30×100 mm, 5 μm. Flow: 30 mL/min. Gradient 30-60% B in 20 min; A=0.1% TFA in water, B=CH$_3$CN). t$_R$: 0.94 min (LC-MS 2); ESI-MS: 559.3/561.3 [M+H]$^+$ (LC-MS 2); R$_f$: 0.24 (CH$_2$Cl$_2$/MeOH, 92.5:7.5).

Example 44

4-[5-(5-Chloro-1-methyl-6-oxo-1,6-dihydro-pyridin-3-yl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile

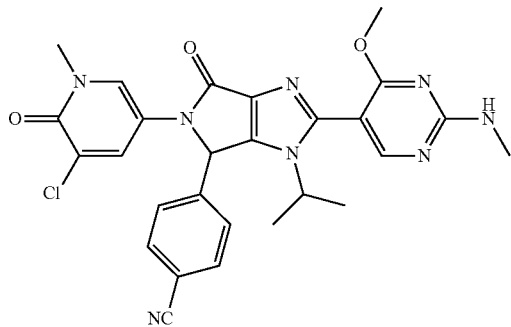 [SMILES: CNc1ncc(-c2nc3c(n2C(C)C)C(c2ccc(C#N)cc2)N(c2cc(Cl)c(=O)n(C)c2)C3=O)c(OC)n1]

The title compound was prepared in analogy to the procedure described for example 29 but using intermediate AA, 2 equivalents of intermediate Z, 0.15 equivalents of PdCl$_2$(dppf)-CH$_2$Cl$_2$ complex, and stirring the reaction mixture for 15 min at 110° C. The crude product was purified by flash chromatography (CH$_2$Cl$_2$/MeOH, 92.5:7.5), followed by preparative HPLC (Column: Sunfire C18, 30×100 mm, 5 μm. Flow: 30 mL/min. Gradient 5-50% B in 18 min; A=0.1% TFA in water, B=CH$_3$CN) and trituration in Et$_2$O. t$_R$: 0.82 min (LC-MS 2); ESI-MS: 545.3/547.3 [M+H]$^+$ (LC-MS 2); R$_f$: 0.13 (CH$_2$Cl$_2$/MeOH, 92.5:7.5).

Example 45

4-[2-(2-Amino-4-methoxy-pyrimidin-5-yl)-5-(5-chloro-1-methyl-6-oxo-1,6-dihydro-pyridin-3-yl)-3-isopropyl-6-oxo-3,4,5,6-tetrahydro-pyrrolo[3,4-d]imidazol-4-yl]-benzonitrile

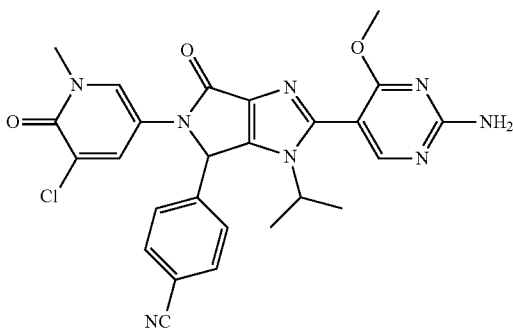 [SMILES: COc1nc(N)ncc1-c1nc2c(n1C(C)C)C(c1ccc(C#N)cc1)N(c1cc(Cl)c(=O)n(C)c1)C2=O]

The title compound was prepared in analogy to the procedure described for example 29 but using intermediate AA, 2 equivalents of intermediate U, 0.15 equivalents of PdCl$_2$(dppf)-CH$_2$Cl$_2$ complex, and stirring the reaction mixture for 15 min at 110° C. The crude product was purified by flash chromatography (CH$_2$Cl$_2$/MeOH, 92.5:7.5), followed by preparative HPLC (Column: Sunfire C18, 30×100 mm, 5 μm. Flow: 30 mL/min. Gradient 5-50% B in 18 min; A=0.1% TFA in water, B=CH$_3$CN) and trituration in Et$_2$O. t$_R$: 0.73 min (LC-MS 2); ESI-MS: 531.3/533.3 [M+H]$^+$ (LC-MS 2); R$_f$: 0.09 (CH$_2$Cl$_2$/MeOH, 92.5:7.5).

Example 46

5-(5-Chloro-2-methyl-phenyl)-6-(4-chloro-2-methyl-phenyl)-1-isopropyl-2-(4-methoxy-2-methylamino-pyrimidin-5-yl)-5,6-dihydro-1H-pyrrolo[3,4-d]imidazol-4-one

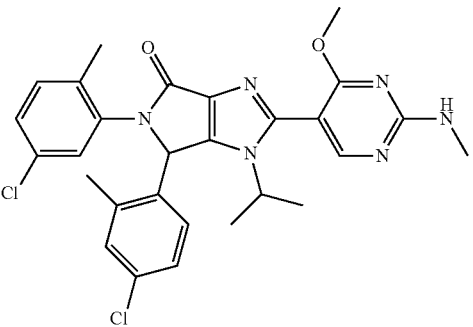 [SMILES: CNc1ncc(-c2nc3c(n2C(C)C)C(c2ccc(Cl)cc2C)N(c2cc(Cl)ccc2C)C3=O)c(OC)n1]

The title compound was prepared in analogy to the procedure described for example 29 but using 2 equivalents of intermediate U, 0.15 equivalents of PdCl₂(dppf)-CH₂Cl₂ complex, and stirring the reaction mixture for 30 min at 100° C. The crude product was purified by flash chromatography (CH₂Cl₂/MeOH, 95:5), followed by preparative HPLC (Column: Sunfire C18, 30×100 mm, 5 μm. Flow: 30 mL/min. Gradient 30-60% B in 30 min; A=0.1% TFA in water, B=CH₃CN) and trituration in Et₂O. t$_R$: 1.25/1.27 min (LC-MS 2); ESI-MS: 551.2/553.2 [M+H]⁺ (LC-MS 2); R$_f$: 0.24 (CH₂Cl₂/MeOH, 95:5).

Example 47

5-(5-Chloro-2-methyl-phenyl)-6-(4-chloro-2-methyl-phenyl)-2-(2-ethyl-6-methoxy-pyridin-3-yl)-1-isopropyl-5,6-dihydro-1H-pyrrolo[3,4-d]imidazol-4-one

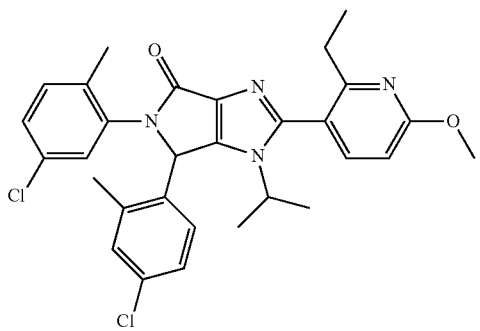 [SMILES: CCc1nc(OC)ccc1-c1nc2c(n1C(C)C)C(c1ccc(Cl)cc1C)N(c1cc(Cl)ccc1C)C2=O]

The title compound was prepared in analogy to the procedure described for example 29 but using 2-ethyl-6-methoxy-pyridin-3-ylboronic acid, and stirring the reaction mixture for 1 h at 100° C. The crude product was purified by flash chromatography (hexane/EtOAc, 1:3) and subsequent trituration in Et₂O/hexane (1:4). t$_R$: 1.43 min (LC-MS 2); ESI-MS: 549.3/551.3 [M+H]⁺ (LC-MS 2); R$_f$: 0.40 (hexane/EtOAc, 1:3).

Example 48

2-(2-Amino-4-methoxy-pyrimidin-5-yl)-5-(5-chloro-2-methyl-phenyl)-6-(4-chloro-2-methyl-phenyl)-1-isopropyl-5,6-dihydro-1H-pyrrolo[3,4-d]imidazol-4-one

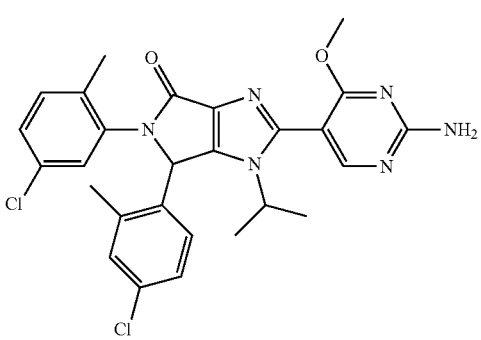 [SMILES: COc1nc(N)ncc1-c1nc2c(n1C(C)C)C(c1ccc(Cl)cc1C)N(c1cc(Cl)ccc1C)C2=O]

The title compound was prepared in analogy to the procedure described for example 29 but using 2 equivalents of intermediate U, 0.15 equivalents of PdCl₂(dppf)-CH₂Cl₂ complex, and stirring the reaction mixture for 30 min at 100° C. The crude product was purified by flash chromatography (CH₂Cl₂/MeOH, 95:5) and subsequent trituration in Et₂O. t$_R$: 1.15 min (LC-MS 2); ESI-MS: 537.3/539.3 [M+H]⁺ (LC-MS 2); R$_f$: 0.12 (CH₂Cl₂/MeOH, 95:5).

Example 49

3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-ethyl-benzonitrile

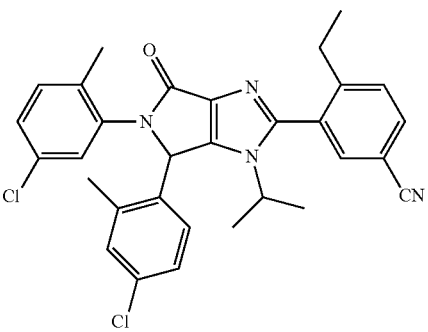 [SMILES: CCc1ccc(C#N)cc1-c1nc2c(n1C(C)C)C(c1ccc(Cl)cc1C)N(c1cc(Cl)ccc1C)C2=O]

The title compound was prepared in analogy to the procedure described for example 29 but using 1.8 equivalents of intermediate V, and 0.15 equivalents of PdCl₂(dppf)-CH₂Cl₂ complex. The crude product was purified by flash chromatography (hexane/EtOAc, 1:1) and subsequent trituration in Et₂O. t$_R$: 1.30/1.33 min (LC-MS 2); ESI-MS: 543.3/545.2 [M+H]⁺ (LC-MS 2); R$_f$: 0.13 (hexane/EtOAc, 1:1).

Example 50

5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-d]imidazol-4-one

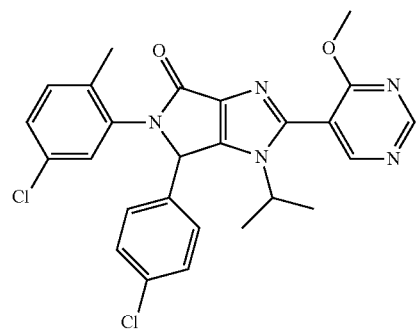 [SMILES: COc1ncncc1-c1nc2c(n1C(C)C)C(c1ccc(Cl)cc1)N(c1cc(Cl)ccc1C)C2=O]

The title compound was prepared in analogy to the procedure described for example 29 but using intermediate E, 2 equivalents of intermediate T, 0.15 equivalents of PdCl₂(dppf)-CH₂Cl₂ complex, and stirring the reaction mixture for 3 h at 100° C. After flash chromatography (CH₂Cl₂/MeOH, 95:5) of the crude product and subsequent trituration in Et₂O, the resulting material was further purified by preparative HPLC (Column: Sunfire C18, 30×100 mm, 5 μm. Flow: 30 mL/min. Gradient 30-60% B in 30 min; A=0.1% TFA in water, B=CH₃CN) and trituration in Et₂O. $t_R$: 1.19 min (LC-MS 2); ESI-MS: 508.2/510.2 [M+H]⁺ (LC-MS 2); $R_f$: 0.26 (CH₂Cl₂/MeOH, 95:5).

Example 51

5-(5-Chloro-2-methyl-phenyl)-6-(4-chloro-2-methyl-phenyl)-2-{2-[(2-hydroxy-ethyl)-methyl-amino]-4-methoxy-pyrimidin-5-yl}-1-isopropyl-5,6-dihydro-1H-pyrrolo[3,4-d]imidazol-4-one

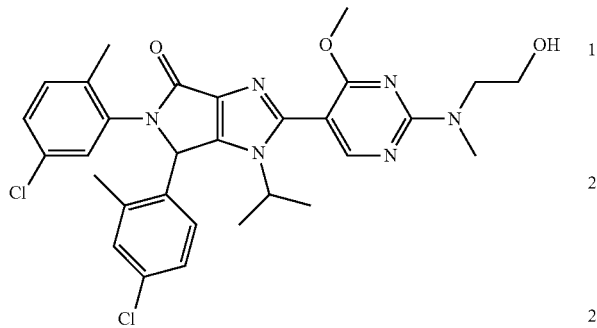

The title compound was prepared in analogy to the procedure described for example 29 but using 1.5 equivalents of intermediate X, 0.15 equivalents of PdCl₂(dppf)-CH₂Cl₂ complex, and stirring the reaction mixture for 2 h at 110° C. The crude product was purified by flash chromatography (CH₂Cl₂/MeOH, 95:5), followed by preparative HPLC (Column: Sunfire C18, 30×100 mm, 5 μm. Flow: 30 mL/min. Gradient 30-60% B in 20 min; A=0.1% TFA in water, B=CH₃CN) and trituration of the resulting material in Et₂O/hexane (1:1). $t_R$: 1.22/1.25 min (LC-MS 2); ESI-MS: 595.3/597.3 [M+H]⁺ (LC-MS 2); $R_f$: 0.14 (CH₂Cl₂/MeOH, 95:5).

Example 52

5-(5-Chloro-2-methyl-phenyl)-6-(4-chloro-2-methyl-phenyl)-2-[2-(2-hydroxy-ethyl amino)-4-methoxy-pyrimidin-5-yl]-1-isopropyl-5,6-dihydro-1H-pyrrolo[3,4-d]imidazol-4-one

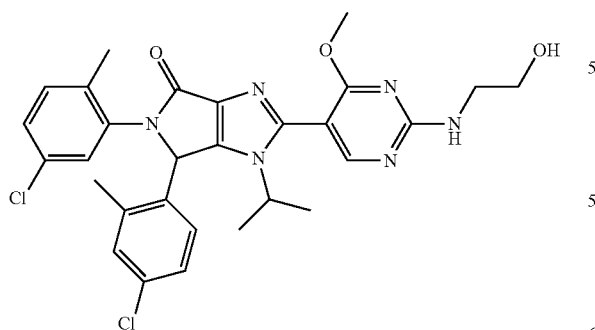

The title compound was prepared in analogy to the procedure described for example 29 but using 1.5 equivalents of intermediate Y, 0.15 equivalents of PdCl₂(dppf)-CH₂Cl₂ complex, and stirring the reaction mixture for 1 h at 110° C. The crude product was purified by flash chromatography (CH₂Cl₂/MeOH, 92.5:7.5), followed by preparative HPLC (Column: Sunfire C18, 30×100 mm, 5 pm. Flow: 30 mL/min. Gradient 30-60% B in 30 min; A=0.1% TFA in water, B=CH₃CN) and trituration of the resulting material in Et₂O/hexane (1:1). $t_R$: 1.15/1.18 min (LC-MS 2); ESI-MS: 581.3/583.2 [M+H]⁺ (LC-MS 2); $R_f$: 0.15 (CH₂Cl₂/MeOH, 92.5:7.5).

Example 53

4-[2-(2-Amino-4-methoxy-pyrimidin-5-yl)-5(3-chloro-2-fluoro-phenyl)-3-isopropyl-6-oxo-3,4,5,6-tetrahydro-pyrrolo[3,4-d]imidazol-4-yl]-benzonitrile

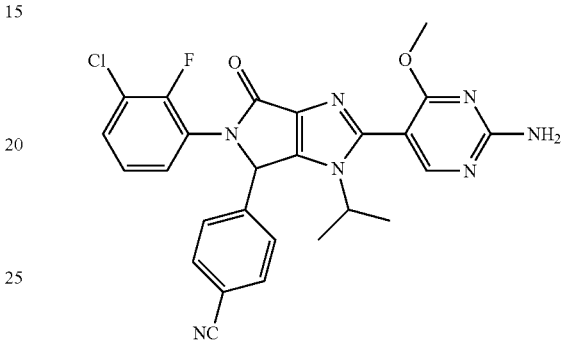

The title compound was prepared in analogy to the procedure described for example 29 but using intermediate AB, 2 equivalents of intermediate U, 0.15 equivalents of PdCl₂(dppf)-CH₂Cl₂ complex, and stirring the reaction mixture for 30 min at 110° C. The crude product was purified by flash chromatography (CH₂Cl₂/MeOH, 92.5:7.5), followed by preparative HPLC (Column: Sunfire C18, 30×100 mm, 5 μm. Flow: 30 mL/min. Gradient 30-60% B in 20 min; A=0.1% TFA in water, B=CH₃CN) and trituration in Et₂O. $t_R$: 0.96 min (LC-MS 2); ESI-MS: 518.2/520.2 [M+H]⁺ (LC-MS 2); $R_f$: 0.28 (CH₂Cl₂/MeOH, 92.5:7.5).

Example 54

4-[5-(3-Chloro-2-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile

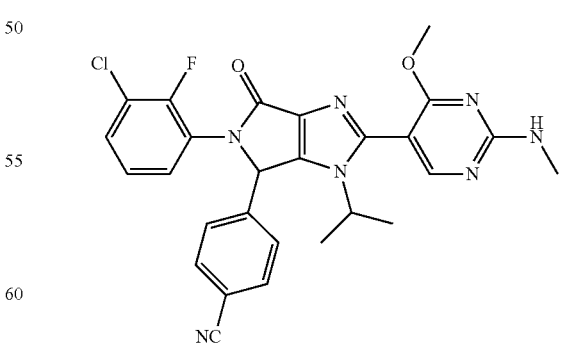

The title compound was prepared in analogy to the procedure described for example 29 but using intermediate AB, 2 equivalents of intermediate Z, 0.15 equivalents of PdCl₂(dppf)-CH₂Cl₂ complex, and stirring the reaction mixture for 30 min at 110° C. The crude product was purified by flash chromatography (CH$_2$Cl$_2$/MeOH, 95:5) followed by preparative HPLC (Column: Sunfire C18, 30×100 mm, 5 μm. Flow: 20 mL/min. Gradient 30-60% B in 20 min; A=0.1% TFA in water, B=CH$_3$CN) and trituration in Et$_2$O. t$_R$: 1.03 min (LC-MS 2); ESI-MS: 532.3/534.3 [M+H]$^+$ (LC-MS 2); R$_f$: 0.23 (CH$_2$Cl$_2$/MeOH, 95:5).

Example 55

4-[5-(3-Chloro-2-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

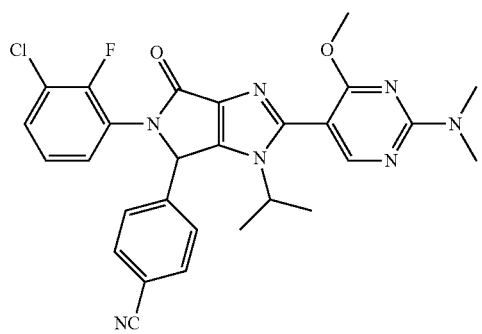 [SMILES: COc1nc(N(C)C)ncc1-c1nc2c(n1C(C)C)C(c1ccc(C#N)cc1)N(c1cccc(Cl)c1F)C2=O]

The title compound was prepared in analogy to the procedure described for example 29 but using intermediate AB, 2 equivalents of intermediate W, 0.15 equivalents of PdCl$_2$ (dppf)-CH$_2$Cl$_2$ complex, and stirring the reaction mixture for 30 min at 110° C. The crude product was purified by flash chromatography (CH$_2$Cl$_2$/MeOH, 95:5), followed by preparative HPLC (Column: Sunfire C18, 30×100 mm, 5 μm. Flow: 30 mL/min. Gradient 30-60% B in 20 min; A=0.1% TFA in water, B=CH$_3$CN) and trituration in Et$_2$O. t$_R$: 1.14 min (LC-MS 2); ESI-MS: 546.3/548.3 [M+H]$^+$ (LC-MS 2); R$_f$: 0.39 (CH$_2$Cl$_2$/MeOH, 95:5).

Example 56

4-[2-(2-Amino-4-methoxy-pyrimidin-5-yl)-5-(3-chloro-4-fluoro-phenyl)-3-isopropyl-6-oxo-3,4,5,6-tetrahydro-pyrrolo[3,4-d]imidazol-4-yl]-benzonitrile

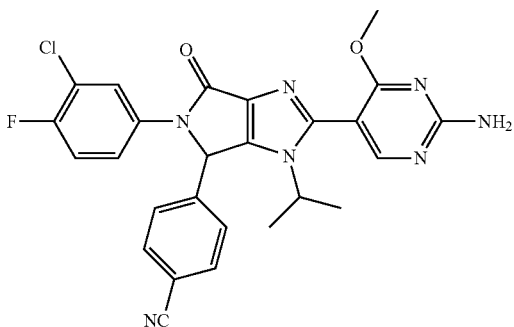 [SMILES: COc1nc(N)ncc1-c1nc2c(n1C(C)C)C(c1ccc(C#N)cc1)N(c1ccc(F)c(Cl)c1)C2=O]

The title compound was prepared in analogy to the procedure described for example 29 but using intermediate AC, 2 equivalents of intermediate U, 0.15 equivalents of PdCl$_2$ (dppf)-CH$_2$Cl$_2$ complex, and stirring the reaction mixture for 30 min at 110° C. The crude product was purified by flash chromatography (CH$_2$Cl$_2$/MeOH, 92.5:7.5), followed by preparative HPLC (Column: Sunfire C18, 30×100 mm, 5 μm. Flow: 30 mL/min. Gradient 30-60% B in 20 min; A=0.1% TFA in water, B=CH$_3$CN). t$_R$: 0.99 min (LC-MS 2); ESI-MS: 518.3/520.3 [M+H]$^+$ (LC-MS 2); R$_f$: 0.24 (CH$_2$Cl$_2$/MeOH, 92.5:7.5).

Example 57

4-[5-(3-Chloro-4-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile

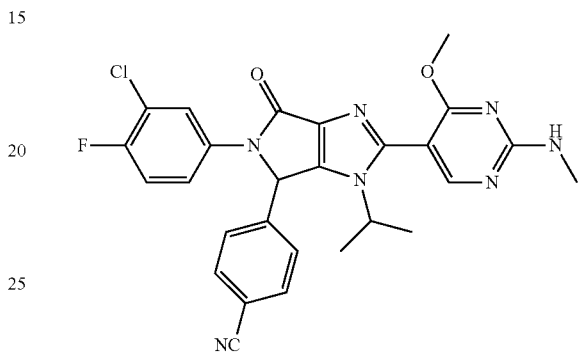

The title compound was prepared in analogy to the procedure described for example 29 but using intermediate AC, 2 equivalents of intermediate Z, 0.15 equivalents of PdCl$_2$ (dppf)-CH$_2$Cl$_2$ complex, and stirring the reaction mixture for 30 min at 110° C. The crude product was purified by flash chromatography (CH$_2$Cl$_2$/MeOH, 92.5:7.5), followed by preparative HPLC (Column: Sunfire C18, 30×100 mm, 5 μm. Flow: 20 mL/min. Gradient 30-60% B in 20 min; A=0.1% TFA in water, B=CH$_3$CN) and trituration in Et$_2$O. t$_R$: 1.06 min (LC-MS 2); ESI-MS: 532.3/534.3 [M+H]$^+$ (LC-MS 2); R$_f$: 0.31 (CH$_2$Cl$_2$/MeOH, 92.5:7.5).

Example 58

4-[5-(3-Chloro-4-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

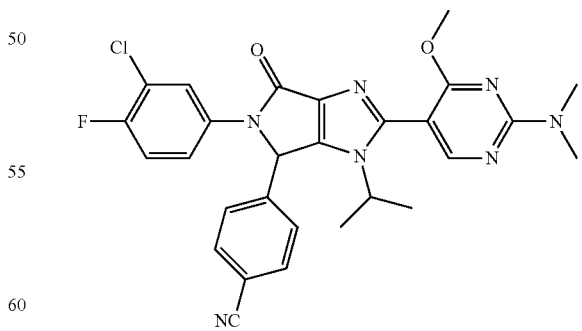

The title compound was prepared in analogy to the procedure described for example 29 but using intermediate AC, 2 equivalents of intermediate W, 0.15 equivalents of PdCl$_2$ (dppf)-CH$_2$Cl$_2$ complex, and stirring the reaction mixture for 30 min at 110° C. The crude product was purified by flash chromatography (CH₂Cl₂/MeOH, 95:5), followed by preparative HPLC (Column: Sunfire C18, 30×100 mm, 5 μm. Flow: 30 mL/min. Gradient 30-70% B in 20 min; A=0.1% TFA in water, B=CH₃CN) and trituration in Et₂O. $t_R$: 1.16 min (LC-MS 2); ESI-MS: 546.3/548.3 [M+H]⁺ (LC-MS 2); $R_f$: 0.30 (CH₂Cl₂/MeOH, 95:5).

Example 59

5-(5-Chloro-2-methyl-phenyl)-6-(4-chloro-phenyl)-2-[2-(3-hydroxy-3-methyl-azetidin-1-yl)-4-methoxy-pyrimidin-5-yl]-1-isopropyl-5,6-dihydro-1H-pyrrolo[3,4-d]imidazol-4-one

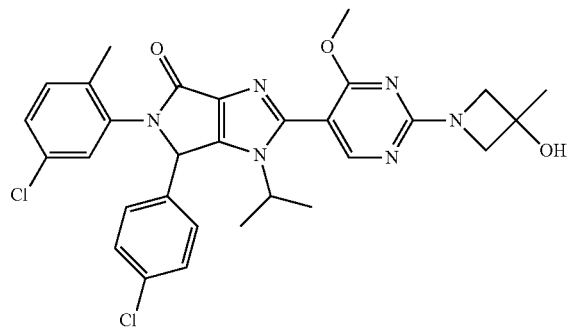 [SMILES: COc1nc(N2CC(C)(O)C2)ncc1-c1nc2c(n1C(C)C)C(c1ccc(Cl)cc1)N(c1cc(Cl)ccc1C)C2=O]

The title compound was prepared in analogy to the procedure described for example 29 but using intermediate E, 1.5 equivalents of intermediate AD, 0.15 equivalents of PdCl₂(dppf)-CH₂Cl₂ complex, and stirring the reaction mixture for 30 min at 110° C. The crude product was purified by flash chromatography (CH₂Cl₂/MeOH, 95:5), followed by preparative HPLC (Column: Sunfire C18, 30×100 mm, 5 μm. Flow: 30 mL/min. Gradient 30-60% B in 20 min; A=0.1% TFA in water, B=CH₃CN) and trituration in Et₂O. $t_R$: 1.15 min (LC-MS 2); ESI-MS: 593.3/595.3 [M+H]⁺ (LC-MS 2); $R_f$: 0.11 (CH₂Cl₂/MeOH, 95:5).

Example 60

5-(5-Chloro-2-methyl-phenyl)-6-(4-chloro-2-methyl-phenyl)-2-[2-(3-hydroxy-3-methyl-azetidin-1-yl)-4-methoxy-pyrimidin-5-yl]-1-isopropyl-5,6-dihydro-1H-pyrrolo[3,4-d]imidazol-4-one

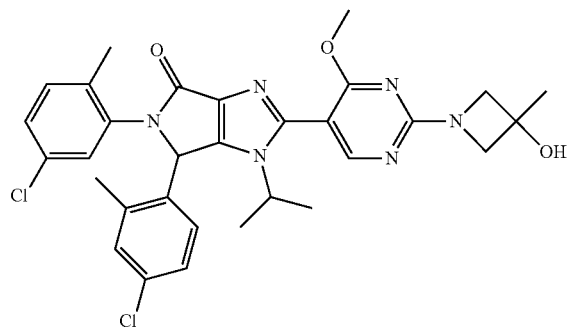 [SMILES: COc1nc(N2CC(C)(O)C2)ncc1-c1nc2c(n1C(C)C)C(c1ccc(Cl)cc1C)N(c1cc(Cl)ccc1C)C2=O]

The title compound was prepared in analogy to the procedure described for example 29 but using 1.5 equivalents of intermediate AD, 0.15 equivalents of PdCl₂(dppf)-CH₂Cl₂ complex, and stirring the reaction mixture for 30 min at 110° C. The crude product was purified by flash chromatography (CH₂Cl₂/MeOH, 95:5), followed by preparative HPLC (Column: Sunfire C18, 30×100 mm, 5 μm. Flow: 30 mL/min. Gradient 30-60% B in 20 min; A=0.1% TFA in water, B=CH₃CN). $t_R$: 1.17/1.19 min (LC-MS 2); ESI-MS: 607.3/609.3 [M+H]⁺ (LC-MS 2); $R_f$: 0.09 (CH₂Cl₂/MeOH, 95:5).

Example 61

5-(5-Chloro-2-methyl-phenyl)-6-(4-chloro-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one

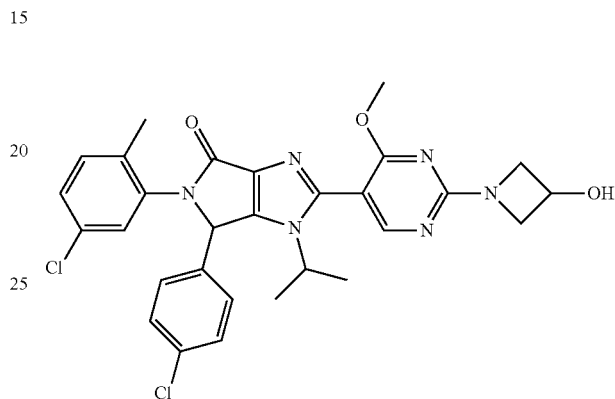

The title compound was prepared in analogy to the procedure described for example 29 but using intermediate E, 1.5 equivalents of intermediate AE, 0.15 equivalents of PdCl₂(dppf)-CH₂Cl₂ complex, and stirring the reaction mixture for 30 min at 110° C. The crude product was purified by flash chromatography (CH₂Cl₂/MeOH, 92.5:7.5), followed by preparative HPLC (Column: Sunfire C18, 30×100 mm, 5 μm. Flow: 30 mL/min. Gradient 30-60% B in 20 min; A=0.1% TFA in water, B=CH₃CN) and trituration in Et₂O. $t_R$: 1.10 min (LC-MS 2); ESI-MS: 579.2/581.2 [M+H]⁺ (LC-MS 2); $R_f$: 0.14 (CH₂Cl₂/MeOH, 92.5:7.5).

Example 62

5-(5-Chloro-2-methyl-phenyl)-6-(4-chloro-2-methyl-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one

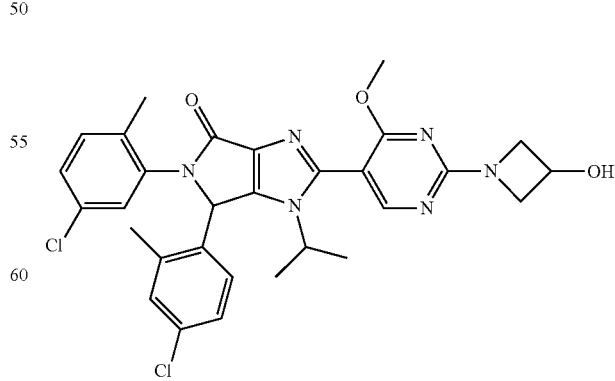

The title compound was prepared in analogy to the procedure described for example 29 but using 1.5 equivalents of intermediate AE, 0.15 equivalents of PdCl₂(dppf)-CH₂Cl₂ complex, and stirring the reaction mixture for 30 min at 110° C. The crude product was purified by flash chromatography (CH₂Cl₂/MeOH, 92.5:7.5), followed by preparative HPLC (Column: Sunfire C18, 30×100 mm, 5 µm. Flow: 30 mL/min. Gradient 20-60% B in 20 min; A=0.1% TFA in water, B=CH₃CN). t$_R$: 1.14-1.16 min (LC-MS 2); ESI-MS: 593.3/595.3 [M+H]⁺ (LC-MS 2); R$_f$ 0.17 (CH₂Cl₂/MeOH, 92.5:7:5).

Example 63

2-(4-Amino methyl-2-methoxy-phenyl-5-(5-chloro-2-methyl-phenyl)-6-(4-chloro-phenyl)-1-isopropyl-5,6-dihydro-1H-pyrrolo[3,4-d]imidazole-4-one

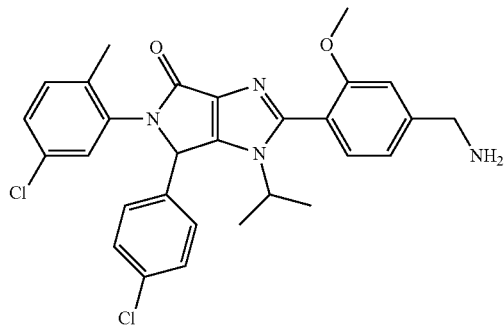 [SMILES: COc1cc(CN)ccc1-c1nc2c(n1C(C)C)C(c1ccc(Cl)cc1)N(c1cc(Cl)ccc1C)C2=O]

The title compound was obtained in analogy to the procedure described for the preparation of example 16 using the product from example 26 as starting material. t$_R$: 0.97 min (LC-MS 2); ESI-MS: 535.2/537.2 [M+H]⁺ (LC-MS 2).

Example 64

5-(3-Chloro-2-fluoro-phenyl)-6-(4-chloro-2-methyl-phenyl)-1-isopropyl-2-(2-methoxy-phenyl)-5,6-dihydro-1H-pyrrolo[3,4-d]imidazole-4-one

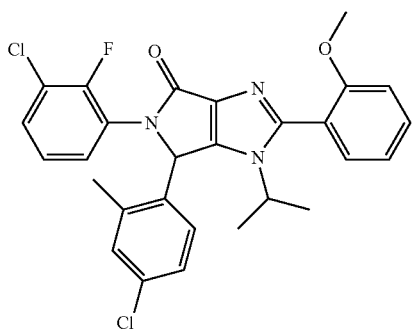 [SMILES: COc1ccccc1-c1nc2c(n1C(C)C)C(c1ccc(Cl)cc1C)N(c1cccc(Cl)c1F)C2=O]

The product from step 64.1 (160 mg, 0.23 mmol) was dissolved in DMF (5 mL) and HATU (98 mg, 0.26 mmol) and NMM (77 µL, 0.70 mmol) were added. The reaction mixture was stirred for 12 h at rt and then heated to 80° C. for 2 h. It was allowed to cool and concentrated. The residual crude material was purified by preparative HPLC (column xBridge 30×100 mm; 0.08% TFA-water/acetonitrile; gradient acetonitrile 5-100%). t$_R$: 1.29 min (LC-MS 2); ESI-MS: 524.2/526.2 [M+H]⁺ (LC-MS 2).

Step 64.1: 5-[(3-Chloro-2-fluoro-phenylamino)-(4-chloro-2-methyl-phenyl)-1-isopropyl-2-(2-methoxy-phenyl)-1H-imidazole-4-carboxylic acid

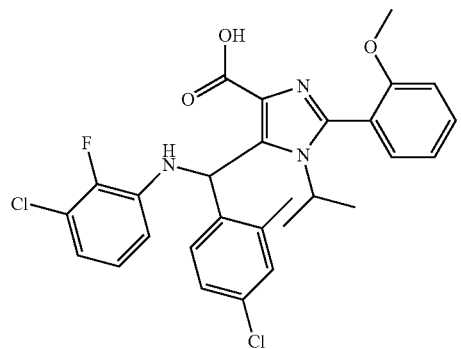 [SMILES: COc1ccccc1-c1nc(C(=O)O)c(C(Nc2cccc(Cl)c2F)c2ccc(Cl)cc2C)n1C(C)C]

The product from step 64.2 (280 mg, 0.50 mmol) was dissolved in dioxane (4 mL) and H₂O (1 mL). LiOH monohydrate (32 mg, 0.75 mml) was added and the reaction mixture stirred at 60° C. for 3 h. All volatiles were removed in vacuum and the residual crude material directly submitted to the next step.

Step 64.2: 5-[(3-Chloro-2-fluoro-phenylamino)-(4-chloro-2-methyl-phenyl)-1-isopropyl-2-(2-methoxy-phenyl)-1H-imidazole-4-carboxylic acid methyl ester

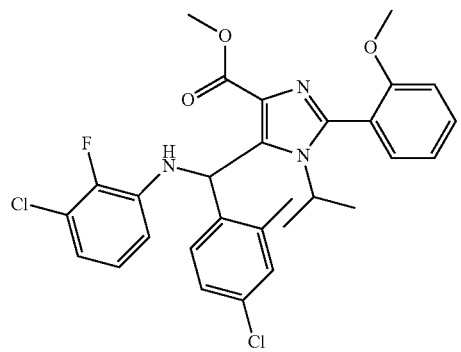 [SMILES: COC(=O)c1nc(-c2ccccc2OC)n(C(C)C)c1C(Nc1cccc(Cl)c1F)c1ccc(Cl)cc1C]

Intermediate D (620 mg, 1.45 mmol) was dissolved in DCM (15 mL). TEA (366 mg, 0.5 mL, 3.61 mmol) and MsCl (331 mg, 2.90 mmol) were added and the reaction mixture was stirred at rt for 6 h. All volatiles were removed under reduced pressure and the residual crude mesylate re-dissolved in DCM (10 mL). 3-Chloro-2-fluoro aniline (310 mg, 2.13 mmol) was added and stirring continued at rt for 16 h. The solvent was evaporated under reduced pressure. EtOAc (10 mL) and TEA (0.5 mL) were added and the mixture stirred for 5 min at rt. The white precipitate was filtered off and the filtrate concentrated to give the crude product which was purified by flash chromatography (heptanes/EtOAc, 100:0→1:1) to give the title compound. t$_R$: 1.42 min (LC-MS 2); ESI-MS: 556.3/558.3 [M+H]⁺ (LC-MS 2).

Example 65

5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one

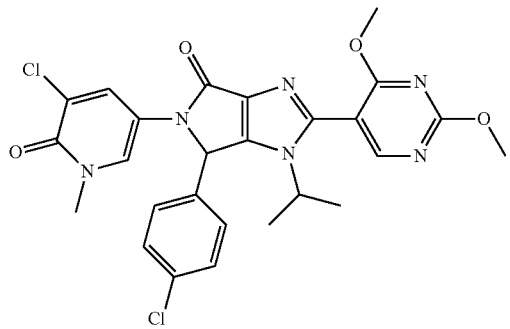 [SMILES: COc1ncc(-c2nc3c(n2C(C)C)C(c2ccc(Cl)cc2)N(c2cc(Cl)c(=O)n(C)c2)C3=O)c(OC)n1]

The title compound was prepared in analogy to the procedure described for example 29 using intermediate J and 2,4-dimethoxypyrimidin-5-yl boronic acid. $t_R$: 0.95 min (LC-MS 2); ESI-MS: 555.4/557.3 [M+H]$^+$ (LC-MS 2).

Example 66

5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

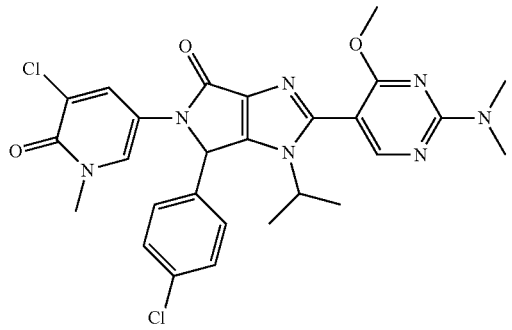 [SMILES: COc1nc(N(C)C)ncc1-c1nc2c(n1C(C)C)C(c1ccc(Cl)cc1)N(c1cc(Cl)c(=O)n(C)c1)C2=O]

The title compound was prepared in analogy to the procedure described for example 29 using intermediate J and intermediate W. $t_R$: 1.05 min (LC-MS 2); ESI-MS: 568.3/570.4 [M+H]$^+$ (LC-MS 2).

Example 67

2-(2-Amino-4-methoxy-pyrimidin-5-yl)-5-(5-chloro-1-methyl-6-oxo-1,6-dihydro-pyridin-3-yl)-6-(4-chloro-phenyl)-1-isopropyl-5,6-dihydro-1H-pyrrolo[3,4-d]imidazol-4-one

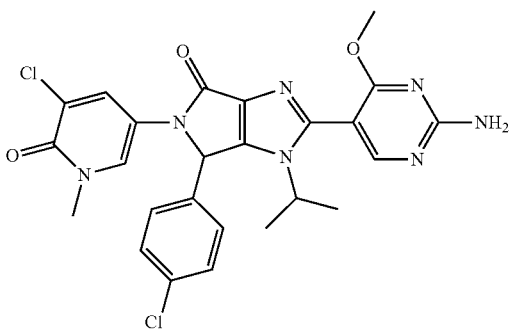 [SMILES: COc1nc(N)ncc1-c1nc2c(n1C(C)C)C(c1ccc(Cl)cc1)N(c1cc(Cl)c(=O)n(C)c1)C2=O]

The title compound was prepared in analogy to the procedure described for example 29 using intermediate J and intermediate U. $t_R$: 0.84 min (LC-MS 2); ESI-MS: 540.3/542.3 [M+H]$^+$ (LC-MS 2).

Example 68

3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide

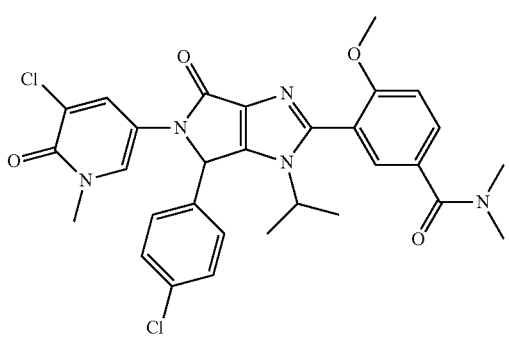 [SMILES: COc1ccc(C(=O)N(C)C)cc1-c1nc2c(n1C(C)C)C(c1ccc(Cl)cc1)N(c1cc(Cl)c(=O)n(C)c1)C2=O]

The title compound was prepared in analogy to the procedure described for example 29 using intermediate J and intermediate M. $t_R$: 0.92 min (LC-MS 2); ESI-MS: 594.2/596.4 [M+H]$^+$ (LC-MS 2).

Example 69

5-(3-Chloro-2-fluoro-phenyl)-6-(4-chloro-phenyl)-1-isopropyl-2-[2-methoxy-5-(morpholine-4-carbonyl)phenyl]-5,6-dihydro-1H-pyrrolo[3,4-d]imidazole-4-one

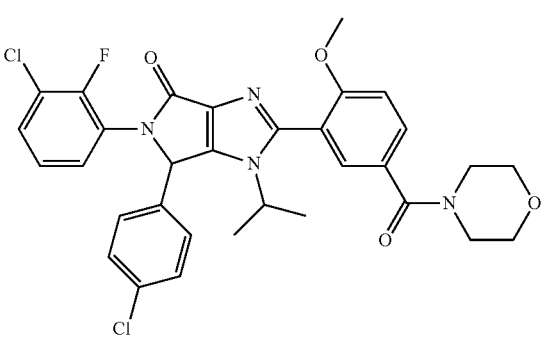 [SMILES: COc1ccc(C(=O)N2CCOCC2)cc1-c1nc2c(n1C(C)C)C(c1ccc(Cl)cc1)N(c1cccc(Cl)c1F)C2=O]

The title compound was prepared in analogy to the procedure described for example 1 using intermediate G and intermediate O. $t_R$: 1.11 min (LC-MS 2); ESI-MS: 623.2/625.2 [M+H]$^+$ (LC-MS 2).

Example 70

3-[5-(3-Chloro-2-fluoro-phenyl)-6-(4-chloro-phenyl)-1-isopropyl-4-oxo-1,4,5,6-tetrahydropyrrolo[3,4-d]imidazol-2-yl]-4-methoxy-N,N-dimethyl benzamide

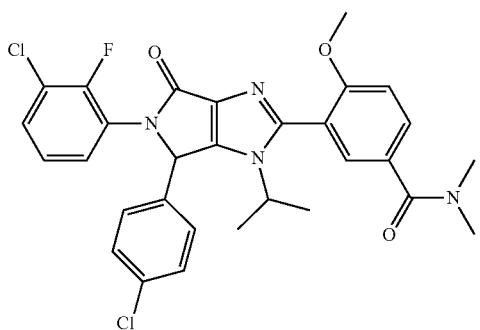 [SMILES: COc1ccc(C(=O)N(C)C)cc1-c1nc2c(n1C(C)C)C(c1ccc(Cl)cc1)N(c1cccc(Cl)c1F)C2=O]

The title compound was prepared in analogy to the procedure described for example 1 using intermediate G and intermediate M. $t_R$: 1.12 min (LC-MS 2); ESI-MS: 581.2/583.2 [M+H]$^+$ (LC-MS 2).

Example 71

6-(4-Chloro-2-methyl-phenyl)-5-(4-chloro-pyrimidin-2-yl)-1-isopropyl-2-(2-methoxy-phenyl)-5,6,-dihydro-1H-pyrrolo[3,4-d]imidazol-4-one

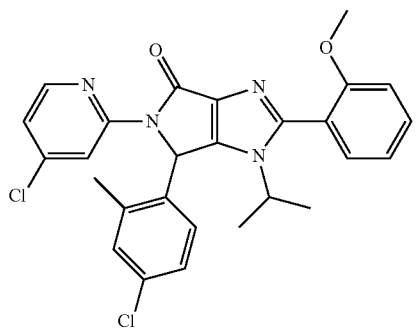 [SMILES: COc1ccccc1-c1nc2c(n1C(C)C)C(c1ccc(Cl)cc1C)N(c1cc(Cl)ccn1)C2=O]

The title compound was prepared in analogy to the procedure described for example 1 using intermediate 1 and 2-methoxy-phenylboronic acid. $t_R$: 1.37/1.40 min (LC-MS 2); ESI-MS: 507.2/509.3 [M+H]$^+$ (LC-MS 2).

Example 72

6-(4-Chloro-phenyl)-5-(5-chloro-pyridin-3-yl)-2-(2,4-dimethoxy-pyrimidin-5-yl)-1-isopropyl-5,6-dihydro-1H-pyrrolo[3,4-d]imidazole-4-one

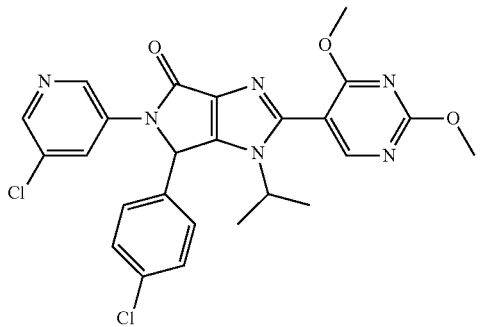 [SMILES: COc1ncc(-c2nc3c(n2C(C)C)C(c2ccc(Cl)cc2)N(c2cncc(Cl)c2)C3=O)c(OC)n1]

The title compound was prepared in analogy to the procedure described for example 1 using intermediate AF and 2,4-dimethoxy-pyrimidin-5-yl boronic acid. $t_R$: 1.11 min (LC-MS 2); ESI-MS: 525.2/527.3 [M+H]$^+$ (LC-MS 2).

Example 73

3-[5-(3-Chloro-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl benzamide

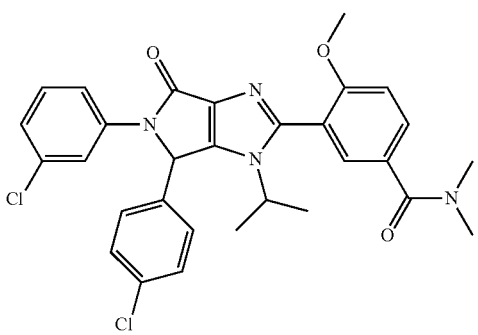 [SMILES: COc1ccc(C(=O)N(C)C)cc1-c1nc2c(n1C(C)C)C(c1ccc(Cl)cc1)N(c1cccc(Cl)c1)C2=O]

The title compound was prepared in analogy to the procedure described for example 29 using intermediate AG and intermediate M, except using Pd(PPh$_3$)$_2$Cl$_2$ (0.1 equiv) and Na$_2$CO$_3$ (3.0 equiv) instead of K$_3$PO$_4$. $t_R$: 1.16 min (LC-MS 2); ESI-MS: 563.2/565.2 [M+H]$^+$ (LC-MS 2).

Example 74

4-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N,N-dimethyl benzamide

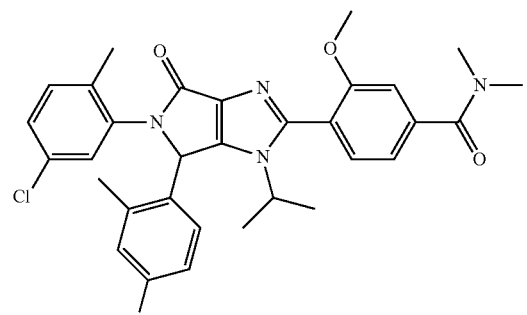

The title compound was prepared in analogy to the procedure described for example 1 using intermediate F and intermediate AH. $t_R$: 1.17/1.19 min (LC-MS 2); ESI-MS: 591.3/593.3 [M+H]$^+$ (LC-MS 2).

Example 75

(S)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one

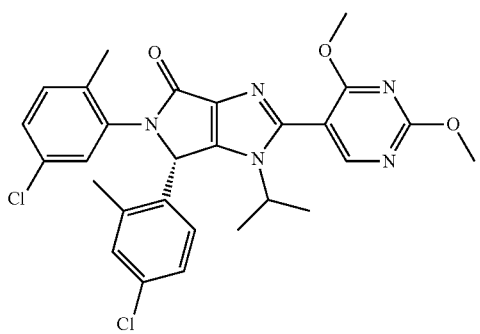 [SMILES: COc1ncc(-c2nc3c(n2C(C)C)[C@H](c2ccc(Cl)cc2C)N(c2cc(Cl)ccc2C)C3=O)c(OC)n1]

The title compound was obtained after preparative chiral HPLC separation of the racemic product of example 7 (column: Chiralcel OD 20 μM, 5×50 cm, flow 80 mL/min, heptanes/EtOH 65:35). $t_R$: 5.80 min; >99% ee (Column: Chiralcel OD H 5 μM 4.6×250 mm (DIACEL). Flow 1.0 mL/min. heptanes/EtOH 65:35. Detection: UV 210 nm). $t_R$: 1.22/1.26 min (LC-MS 2); ESI-MS: 552.3/554.3 [M+H]$^+$ (LC-MS 2); $^1$H NMR (DMSO-d$_6$, 400 MHz) δ ppm 8.54/8.52 (s, 1H; rotamers), 7.95/7.88 (d, 1H; rotamers), 7.26-7.23 (m, 3H), 7.16 (d, 1H), 7.03 (d, 1H), 6.87/6.67 (s, 1H; rotamers), 4.16 (sep, 1H), 4.00 (s, 3H), 3.96 (s, 3H), 2.34/2.30 (s, 3H; rotamers); 1.92/1.90 (s, 3H; rotamers), 1.30-12.6 (m, 3H; rotamers), 0.68/0.59 (d, 3H; rotamers).

Example 76

(R)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one

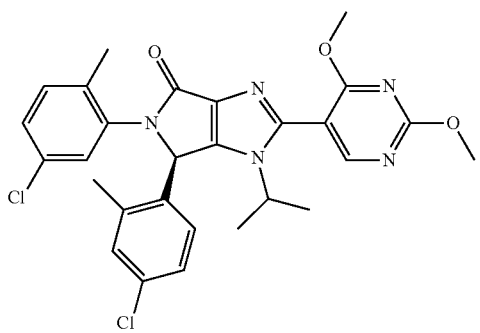 [SMILES: COc1ncc(-c2nc3c(n2C(C)C)[C@@H](c2ccc(Cl)cc2C)N(c2cc(Cl)ccc2C)C3=O)c(OC)n1]

The title compound was obtained after preparative chiral HPLC separation of the racemic product of example 7 (column: Chiralcel OD 20 δ M, 5×50 cm, flow 80 mL/min, heptanes/EtOH 65:35). $t_R$: 12.46 min (Column: Chiralcel OD H 5 δ M 4.6×250 mm (DIACEL). Flow 1.0 mL/min. heptanes/EtOH 65:35. Detection: UV 210 nM); >99% ee (Column: Chiralcel OD H 5 δ M 4.6×250 mm (DIACEL). Flow 1.0 mL/min. heptanes/EtOH 65:35. Detection: UV 210 nm). $t_R$: 1.22/1.26 min (LC-MS 2); ESI-MS: 552.3/554.3 [M+H]$^+$ (LC-MS2); $^1$H NMR (DMSO-d$_6$, 400 MHz) δ ppm 8.54/8.52 (s, 1H; rotamers), 7.95/7.88 (d, 1H; rotamers), 7.26-7.23 (m, 3H), 7.16 (d, 1H), 7.03 (d, 1H), 6.87/6.67 (s, 1H; rotamers), 4.16 (sep, 1H), 4.00 (s, 3H), 3.96 (s, 3H), 2.34/2.30 (s, 3H; rotamers); 1.92/1.90 (s, 3H; rotamers), 1.30-12.6 (m, 3H; rotamers), 0.68/0.59 (d, 3H; rotamers).

Example 77

4-[5-(5-Chloro-2-methyl-phenyl)-3-isopropyl-2-(2-methoxy-phenyl)-6-oxo-3,4,5,6-tetrahydro-pyrrolo[3,4-d]imidazol-4-yl]-benzonitrile

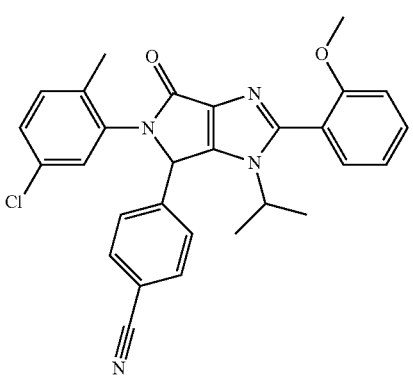 [SMILES: COc1ccccc1-c1nc2c(n1C(C)C)C(c1ccc(C#N)cc1)N(c1cc(Cl)ccc1C)C2=O]

The title compound was prepared in analogy to the procedure described for example 1 using intermediate H and 2-methoxy-phenylboronic acid. $t_R$: 1.12 min (LC-MS 2); ESI-MS: 497.3/499.3 [M+H]$^+$ (LC-MS 2).

Example 78

4-[5-(5-Chloro-2-methyl-phenyl)-2-(2-hydroxy-phenyl)-3-isopropyl-6-oxo-3,4,5,6-tetrahydro-pyrrolo[3,4-d]imidazol-4-yl]-benzonitrile

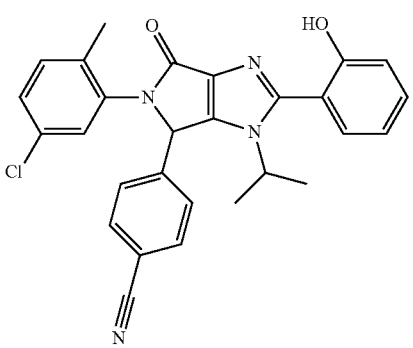 [SMILES: Cc1ccc(Cl)cc1N1C(=O)c2nc(-c3ccccc3O)n(C(C)C)c2C1c1ccc(C#N)cc1]

The title compound was prepared in analogy to the procedure described for example 1 using intermediate H and 2-hydroxyphenyl boronic acid pinacol ester. $t_R$: 1.06 min (LC-MS 2); ESI-MS: 483.3/485.3 [M+H]$^+$ (LC-MS 2); $^1$H-NMR (DMSO-d$_6$, 400 MHz) δ ppm 10.05 (s, 1H), 7.79 (m, 2H), 7.50 (m, 2H), 7.33 (m, 3H), 7.16 (m, 2H), 6.96 (m, 2H), 6.68 (s, 1H), 4.16 (m, 1H), 1.92 (s, 3H), 3.77 (m, 3H), 0.51 (m, 3H).

Example 79

4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile

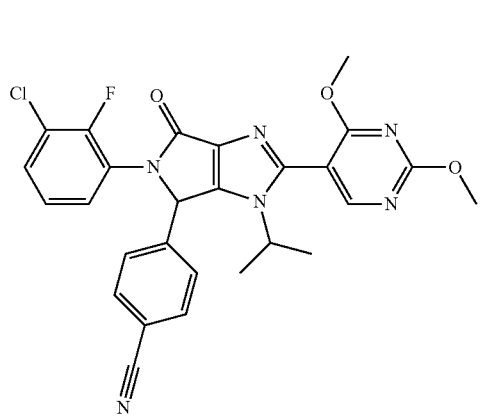 [SMILES: COc1ncc(-c2nc3c(n2C(C)C)C(c2ccc(C#N)cc2)N(c2cccc(Cl)c2F)C3=O)c(OC)n1]

The title compound was prepared in analogy to the procedure described for example 1 using intermediate AB and 2,4-dimethoxy-pyrimidin-5-yl boronic acid. $t_R$: 1.03 min (LC-MS 2); ESI-MS: 533.2 [M+H]$^+$ (LC-MS 2).

Example 80

4-[5-(3-Chloro-4-fluoro-phenyl)-3-isopropyl-2-(2-methoxy-phenyl)-6-oxo-3,4,5,6-tetrahydro-pyrrolo[3,4-d]imidazol-4-yl]-benzonitrile

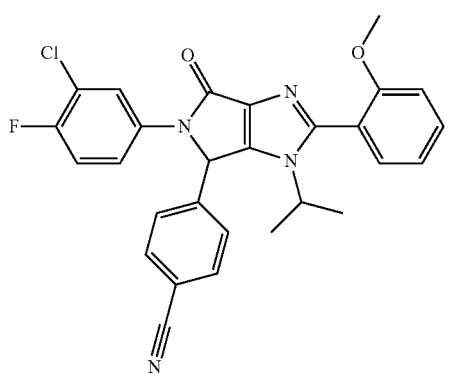 [SMILES: COc1ccccc1-c1nc2c(n1C(C)C)C(c1ccc(C#N)cc1)N(c1ccc(F)c(Cl)c1)C2=O]

The title compound was prepared in analogy to the procedure described for example 1 using intermediate AC and 2-methoxy-phenylboronic acid. $t_R$: 1.11 min (LC-MS 2); ESI-MS: 501.3/503.5 [M+H]$^+$ (LC-MS 2).

Example 81

3-[5-(3-Chloro-4-fluoro-phenyl)-6-(4-cyano-phenyl)-1-isopropyl-4-oxo-1,4,5,6-tetrahydro-pyrrolo[3,4-d]imidazol-2-yl]-4-methoxy-N,N-dimethyl-benzamide

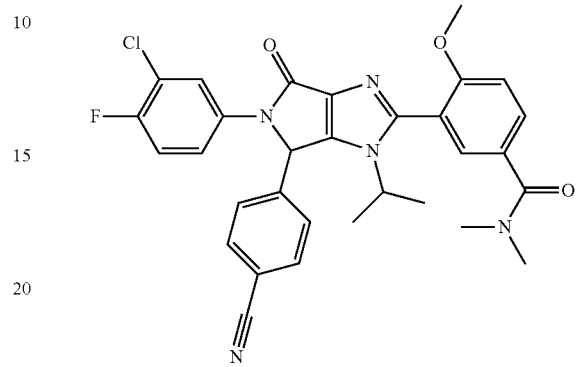

The title compound was prepared in analogy to the procedure described for example 1 using intermediate AC and intermediate M. $t_R$: 1.00 min (LC-MS 2); ESI-MS: 572.3/574.3 [M+H]$^+$ (LC-MS 2); $^1$H-NMR (DMSO-d$_6$, 400 MHz) δ ppm 7.83 (m, 3H), 7.62 (m, 3H), 7.53 (m, 1H), 7.45 (m, 1H), 7.34 (m, 1H), 7.23 (m, 1H), 6.86 (s, 1H), 4.04 (m, 1H), 3.60 (s, 3H), 2.95 (s, 6H), 1.37 (m, 3H), 0.42 (m, 3H).

Example 82

4-[5-(3-Chloro-4-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile

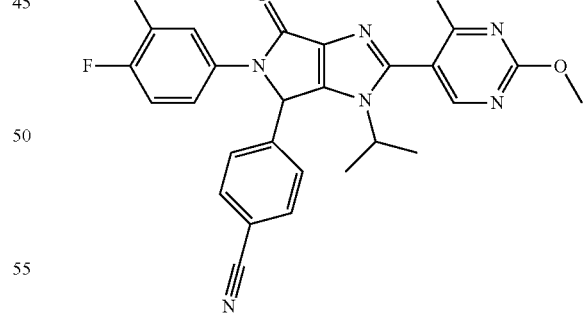

The title compound was prepared in analogy to the procedure described for example 1 using intermediate AC and 2,4-dimethoxy-pyrimidin-5-yl boronic acid. $t_R$: 1.04 min (LC-MS 2); ESI-MS: 533.3/535.3 [M+H]$^+$ (LC-MS 2); $^1$H-NMR (DMSO-d$_6$, 400 MHz) δ ppm 8.46 (s, 1H), 7.83 (m, 3H), 7.63 (m, 2H), 7.52 (m, 1H), 7.34 (m, 1H), 6.86 (s, 1H), 4.10 (s, 1H), 3.96 (s, 3H), 3.91 (s, 3H), 1.36 (m, 3H), 0.45 (m, 3H).

Example 83

6-(4-Chloro-phenyl)-1-isopropyl-2-(2-methoxy-phenyl)-5-(1-methyl-6-oxo-piperidin-3-yl)-5,6-dihydro-1H-pyrrolo[3,4-d]imidazol-4-one

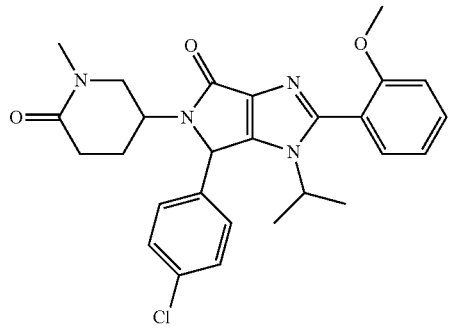 [SMILES: COc1ccccc1-c1nc2c(n1C(C)C)C(c1ccc(Cl)cc1)N(C1CCC(=O)N(C)C1)C2=O]

The title compound was prepared in analogy to the procedure described for example 1 using intermediate AI and 2-methoxy-phenylboronic acid. $t_R$: 0.98 min (LC-MS 2); ESI-MS: 493.3 [M+H]+ (LC-MS 2).

Example 84

6-(4-Chloro-phenyl)-2-(2,4-dimethoxy-pyrimidin-5-yl)-1-isopropyl-5-(1-methyl-6-oxo-piperidin-3-yl)-5,6-dihydro-1H-pyrrolo[3,4-d]imidazol-4-one

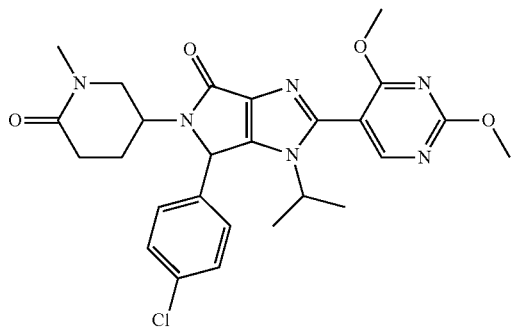 [SMILES: COc1ncc(-c2nc3c(n2C(C)C)C(c2ccc(Cl)cc2)N(C2CCC(=O)N(C)C2)C3=O)c(OC)n1]

The title compound was prepared in analogy to the procedure described for example 1 using intermediate AI and 2,4-dimethoxy-pyrimidin-5-yl boronic acid. $t_R$: 0.89 min (LC-MS 2); ESI-MS: 525.4/527.2 [M+H]+ (LC-MS 2).

Example 85

5-(3-Chloro-4-fluoro-phenyl)-6-(4-chloro-phenyl)-1-cyclobutyl-2-(2,4-dimethoxy-pyrimidin-5-yl)-5,6-dihydro-1H-pyrrolo[3,4-d]imidazol-4-one

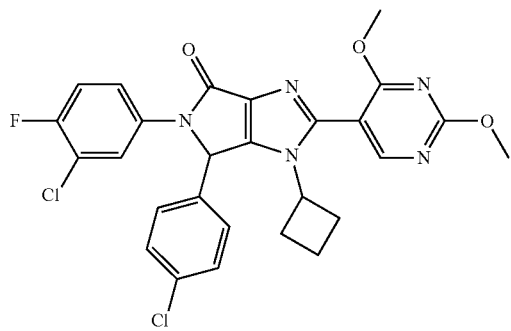 [SMILES: COc1ncc(-c2nc3c(n2C2CCC2)C(c2ccc(Cl)cc2)N(c2ccc(F)c(Cl)c2)C3=O)c(OC)n1]

The title compound was prepared in analogy to the procedure described for example 29 using intermediate AK and 2,4-dimethoxy-pyrimidin-5-yl boronic acid. $t_R$: 1.24 min (LC-MS 2); ESI-MS: 554.2/556.2 [M+H]+ (LC-MS 2).

Example 86

5-(5-Chloro-2-methyl-phenyl)-6-(4-chloro-phenyl)-1-cyclobutyl-2-(2,4-dimethoxy-pyrimidin-5-yl)-5,6-dihydro-1H-pyrrolo[3,4-d]imidazol-4-one

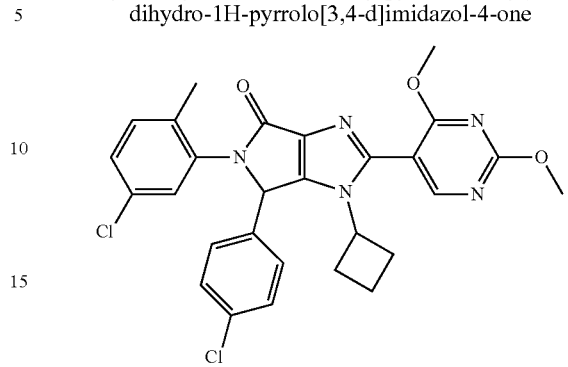

The title compound was prepared in analogy to the procedure described for example 29 using intermediate AL and 2,4-dimethoxy-pyrimidin-5-yl boronic acid. $t_R$: 1.27 min (LC-MS 2); ESI-MS: 550.0/552.0/552.7 [M+H]+ (LC-MS 2).

Example 87

4-[5-(3-Chloro-4-fluoro-phenyl)-3-cyclobutyl-2-(2,4-dimethoxy-pyrimidin-5-yl)-6-oxo-3,4,5,6-tetrahydro-pyrrolo[3,4-d]imidazol-4-yl]-benzonitrile

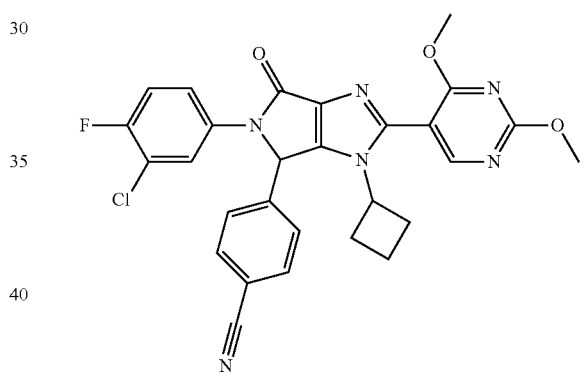

The title compound was prepared in analogy to the procedure described for example 29 using intermediate AM and 2,4-dimethoxy-pyrimidin-5-yl boronic acid. $t_R$: 1.07 min (LC-MS 2); ESI-MS: 545.3/547.4 [M+H]+ (LC-MS 2).

Example 88

5-(3-Chloro-4-fluoro-phenyl)-6-(4-chloro-phenyl)-1-cyclopropyl-2-(2,4-dimethoxy pyrimidin-5-yl)-5,6-dihydro-1H-pyrrolo[3,4-d]imidazol-4-one

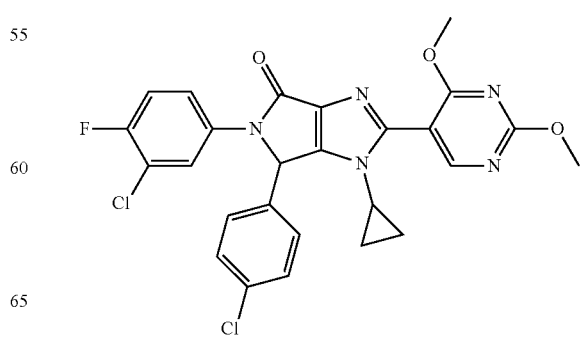

The title compound was prepared in analogy to the procedure described for example 29 using intermediate AN and 2,4-dimethoxy-pyrimidin-5-yl boronic acid. $t_R$: 1.21 min (LC-MS 2); ESI-MS: 540.2/542.2 [M+H]$^+$ (LC-MS 2).

Example 89

(S)-5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one

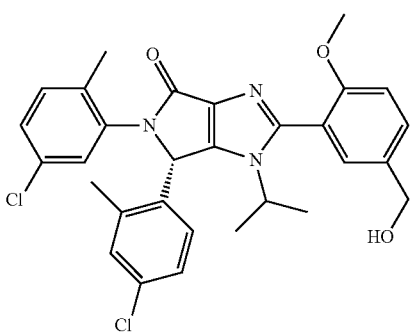 [SMILES: COc1ccc(CO)cc1-c1nc2c(n1C(C)C)[C@H](c1ccc(Cl)cc1C)N(c1cc(Cl)ccc1C)C2=O]

The title compound was obtained after preparative chiral HPLC separation of the racemic product of example 18 (column: Chiralpak IA 250 mm×30 mm×5 µM, flow 80 mL/min, isochratic 100% EtOH). $t_R$: 1.75 min (Column: Chiralpak IC 4.6×250 mm×20 µM. Flow: 1 mL/min. Mobile phase: EtOH/MeOH: 50:50).

Example 90

(R)-5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one

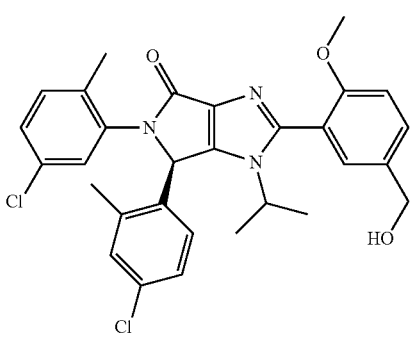 [SMILES: COc1ccc(CO)cc1-c1nc2c(n1C(C)C)[C@@H](c1ccc(Cl)cc1C)N(c1cc(Cl)ccc1C)C2=O]

The title compound was obtained after preparative chiral HPLC separation of the racemic product of example 18 (column: Chiralpak IA 250 mm×30 mm×5 µM, flow 80 mL/min, isochratic 100% EtOH). $t_R$: 2.65 min (Column: Chiralpak IC 4.6×250 mm×20 µM. Flow: 1 mL/min. Mobile phase: EtOH/MeOH: 50:50).

Example 91

6-(4-Chloro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-d]imidazol-4-one

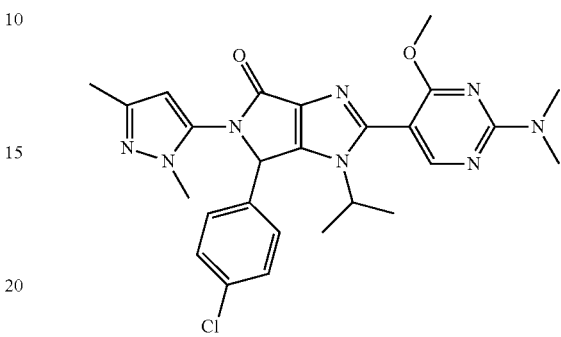

The title compound was prepared in analogy to the procedure described for example 1 but using the product from step 91.1 and intermediate W. After completion, the water phase was removed with a pipette. The reaction mixture was diluted in MeOH then filtered through a StratoSphere SPE cartridge (PL-Thiol MP SPE) and washed with MeOH. The residue was purified by flash chromatography (CH$_2$Cl$_2$/MeOH, 100:0→90:10). The residue was then purified by preparative HPLC (Column: Sunfire C18, 30×100 mm, 5 µm. Flow: 30 mL/min. Gradient 5-100% B in 20 min; A=0.1% TFA in water, B=CH$_3$CN). $t_R$: 1.07 min (LC-MS 2); ESI-MS: 521.2/523.2 [M+H]$^+$ (LC-MS 2); $^1$H-NMR (DMSO-d$_6$, 400 MHz) δ ppm 8.20 (s, 1H), 7.44 (m, 2H), 7.36 (m, 2H), 6.27 (s, 1H), 5.86 (s, 1H), 4.09 (m, 1H), 3.88 (s, 3H), 3.42 (s, 3H), 3.16 (s, 6H), 2.03 (s, 3H), 1.29 (m, 3H), 0.51 (m, 3H).

Step 91.1: 2-Bromo-6-(4-chloro-phenyl)-5-(2,5-dimethyl-2H-pyrazol-3-yl)-1-isopropyl-5,6-dihydro-1H-pyrrolo[3,4-d]imidazol-4-one

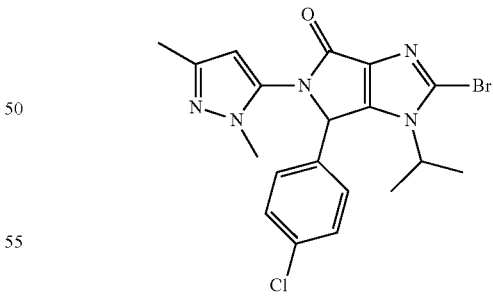

To a solution of the product from step 91.2 (315 mg, 0.675 mmol) in CH$_2$Cl$_2$ (3.3 mL) was added 1-chloro-N,N,2-trimethyl-1-propenylamine (107 µl, 0.810 mmol) at 0° C. and the mixture was stirred overnight at rt. The reaction mixture was extracted with EtOAc. The organic layers were washed with water then brine, dried (Na$_2$SO$_4$), filtered and concentrated. The product was used without further purification. $t_R$: 0.97 min (LC-MS 2); ESI-MS: 448.1/450.1/452.0 [M+H]$^+$ (LC-MS 2).

Step 91.2: 2-Bromo-5-[(4-chloro-phenyl)-(2,5-dimethyl-2H-pyrazol-3-ylamino)-methyl]-1-isopropyl-1H-imidazole-4-carboxylic acid

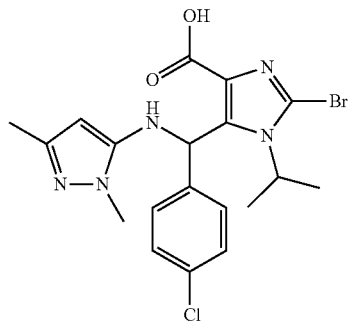 [SMILES: Cc1cc(NC(c2ccc(Cl)cc2)c2c(C(=O)O)nc(Br)n2C(C)C)n(C)n1]

The title compound was prepared in analogy to the procedure described for step E1 but using the product from step 91.3. $t_R$: 0.90 min (LC-MS 3); ESI-MS: 466.1/468.1/470.2 [M+H]$^+$ (LC-MS 3).

Step 91.3: 2-Bromo-5-[(4-chloro-phenyl)-(2,5-dimethyl-2H-pyrazol-3-ylamino)-methyl]-1-isopropyl-1H-imidazole-4-carboxylic acid ethyl ester

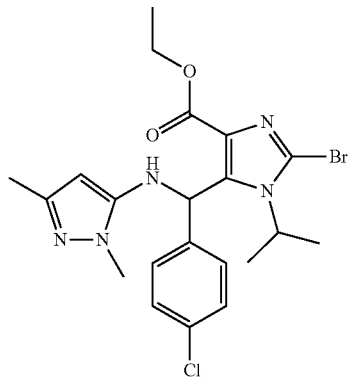 [SMILES: CCOC(=O)c1nc(Br)n(C(C)C)c1C(Nc1cc(C)nn1C)c1ccc(Cl)cc1]

The title compound was prepared in analogy to the procedure described for step E2 but using 5-amino-1,3-dimethylpyrazole. The crude product was purified by flash chromatography (CH$_2$Cl$_2$/EtOAc, 100:0→80:20). $t_R$: 1.10 min (LC-MS 2); ESI-MS: 494.1/496.1/498.1 [M+H]$^+$ (LC-MS 2); R$_f$=0.17 (CH$_2$Cl$_2$/EtOAc, 3:2).

Example 92

6-(4-Chloro-phenyl)-2-(2,4-dimethoxy-pyrimidin-5-yl)-5-(2,5-dimethyl-2H-pyrazol-3-yl)-1-isopropyl-5,6-dihydro-1H-pyrrolo[3,4-d]imidazol-4-one

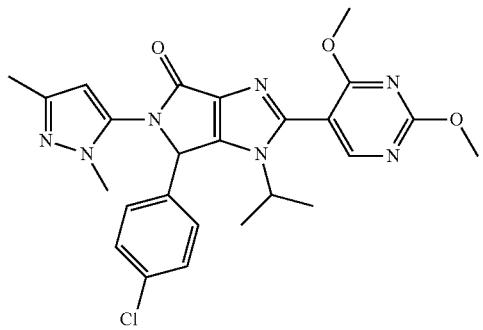

The title compound was prepared in analogy to the procedure described for example 91 but using 2,4-dimethylpyrimidine-5-boronic acid. $t_R$: 0.97 min (LC-MS 2); ESI-MS: 508.2/510.3 [M+H]$^+$ (LC-MS 2); $^1$H-NMR (DMSO-d$_6$, 400 MHz) δ ppm 8.48 (s, 1H), 7.45 (m, 2H), 7.38 (m, 1H), 6.30 (s, 1H), 5.87 (s, 1H), 5.75 (s, 1H), 4.13 (m, 1H), 3.96 (s, 3H), 3.93 (s, 3H), 3.43 (s, 3H), 2.03 (s, 3H), 1.30 (m, 3H), 0.52 (m, 3H).

Example 93

{4-[5-(3-Chloro-2-fluoro-phenyl)-6-(4-chloro-2-methyl-phenyl)-1-isopropyl-4-oxo-1,4,5,6-tetrahydro-pyrrolo[3,4-d]imidazol-2-yl]-5-methoxy-pyridin-2-yl}-acetonitrile

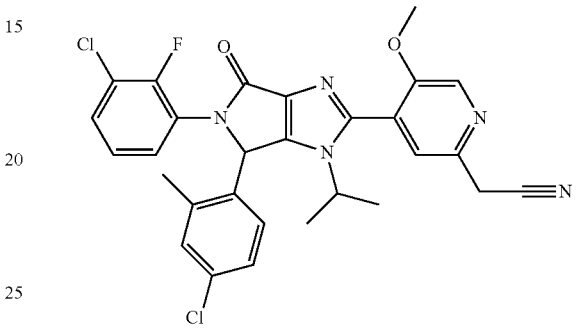

The title compound was prepared in analogy to the procedure described for step 91.1 but using the products from steps 93.1 and 93.4. The reaction was stirred at 80° C. for 1.5 h. The reaction mixture was poured into a saturated aqueous NaHCO$_3$ solution and extracted with EtOAc. The organic layers were washed with brine, dried (Na$_2$SO$_4$), filtered and concentrated. The crude product was purified by flash chromatography (heptane/CH$_2$Cl$_2$/EtOAc, 90:9:1→0:95:5) to give the title compound as a beige foam. $t_R$: 1.16 min (LC-MS 2); ESI-MS: 564.1/566.1 [M+H]$^+$ (LC-MS 2).

Step 93.1: 2-Bromo-5-(3-chloro-2-fluoro-phenyl)-6-(4-chloro-2-methyl-phenyl)-1-isopropyl-5,6-dihydro-1H-pyrrolo[3,4-d]imidazol-4-one

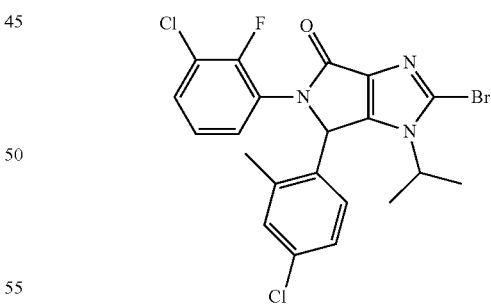

The title compound was prepared in analogy to the procedure described for step 91.1 but using the product from step 93.2. The reaction was performed in 30 min. The reaction mixture was poured into a saturated aqueous NaHCO$_3$ solution and extracted with EtOAc. The organic layers were washed with a saturated aqueous NaHCO$_3$ solution and brine, dried (Na$_2$SO$_4$), filtered and concentrated. The residue was triturated in Diisopropylether to give the title compound as a white solid. $t_R$: 1.23 min (LC-MS 2); ESI-MS: 496.0/498.0/500.0 [M+H]$^+$ (LC-MS 2).

Step 93.2: 2-Bromo-5-[(3-chloro-2-fluoro-phenylamino)-(4-chloro-2-methyl-phenyl)-methyl]-1-isopropyl-1H-imidazole-4-carboxylic acid

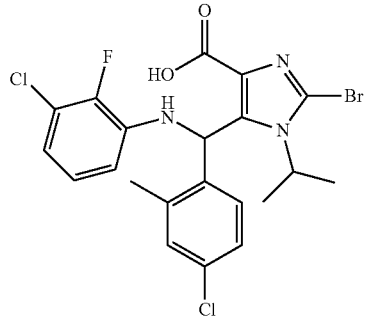 [SMILES: Cc1cc(Cl)ccc1C(Nc1cccc(Cl)c1F)c1c(C(=O)O)nc(Br)n1C(C)C]

The title compound was prepared in analogy to the procedure described for step E1 but using the product was step 93.3. The mixture was stirred at rt for 30 min. An aqueous citric acic (1M) solution was added until pH=4 and the mixture was extracted with $CH_2Cl_2$. The organic layers were dried ($Na_2SO_4$), filtered and concentrated. The product was purified by flash chromatography ($CH_2Cl_2$/MeOH, 95:5) to give the title compound as white solid. $t_R$: 1.26 min (LC-MS 2); ESI-MS: 514.0/516.0/518.0 $[M+H]^+$ (LC-MS 2).

Step 93.3: 2-Bromo-5-[(3-chloro-2-fluoro-phenylamino)-(4-chloro-2-methyl-phenyl)-methyl]-1-isopropyl-1H-imidazole-4-carboxylic acid ethyl ester

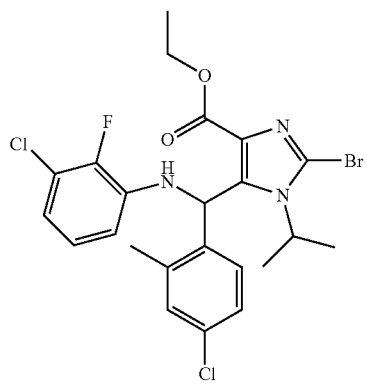 [SMILES: CCOC(=O)c1nc(Br)n(C(C)C)c1C(Nc1cccc(Cl)c1F)c1ccc(Cl)cc1C]

The title compound was prepared in analogy to the procedure described for step E2 but using intermediate C and 3-chloro-2-fluoroaniline. The reaction was stirred at rt for 1.5 h. The reaction mixture was diluted with $H_2O$ and extracted. The organic layers were washed with a saturated aqueous $NaHCO_3$ solution, dried ($Na_2SO_4$), filtered and concentrated. The product was purified by flash chromatography (hexane/EtOAc, 90:1→65:35). The residue was then triturated in $CH_2Cl_2$ to give the title compound as white foam. $t_R$: 1.45 min (LC-MS 2); ESI-MS: 542.0/544.0/546.0 $[M+H]^+$ (LC-MS 2).

Step 93.4: [5-Methoxy-4-(4,4,5,5-tetramethyl-[1,3,2]dioxaborolan-2-yl)-pyridin-2-yl]-acetonitrile

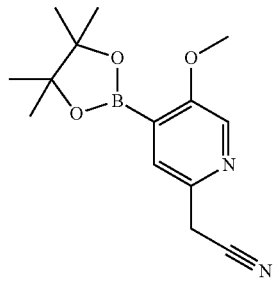 [SMILES: COc1cnc(CC#N)cc1B1OC(C)(C)C(C)(C)O1]

The title compound was prepared in analogy to the procedure described for intermediate S but using the product from step 93.5. The reaction mixture was dissolved in toluene, filtered over Hyflo and the mother liquor was concentrated to give the title compound (60% purity). $^1$H-NMR (DMSO-$d_6$, 400 MHz) δ ppm: 8.33 (s, 1H), 7.92 (s, 1H), 4.10 (s, 2H), 3.84 (s, 3H), 1.27 (s, 6H), 1.14 (s, 6H).

Step 93.5: (4-Bromo-5-methoxy-pyridin-2-yl)-acetonitrile

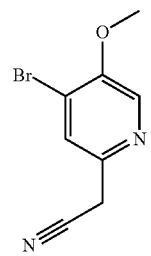

A suspension of the product from step 93.6 (1.2 g, 4.3 mmol), KCN (417 mg, 6.4 mmol) and aliquat 336 (35 mg, 0.085 mmol) in $H_2O$ was stirred at 50° C. for 2 h. The reaction mixture was dissolved in $CH_2Cl_2$, extracted with a saturated aqueous $NaHCO_3$ solution, washed with brine, dried ($Na_2SO_4$), filtered and concentrated. The crude product was purified by flash chromatography (hexane/EtOAc, 100:0→1:1). $t_R$: 3.83 min (HPLC 1).

Step 93.6: 4-Bromo-2-bromomethyl-5-methoxy-pyridine

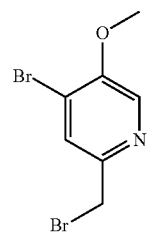

A solution of the product from step 93.7 (1.9 g, 9.4 mmol), NBS (1.8 g, 9.9 mmol), AIBN (15 mg, 0.094 mmol) and benzoyl peroxide (23 mg, 0.094 mmol) in CCl₄ (2 mL) was stirred at rt for 18 h. The reaction mixture was dissolved in EtOAc and extracted with a saturated aqueous NaHCO₃ solution, washed with brine, dried (Na₂SO₄), filtered and concentrated. The crude product was purified by flash chromatography (hexane/EtOAc, 100:0→70:30). t$_R$: 0.90 min (LC-MS 2); ESI-MS: 279.9/281.9/283.9 [M+H]⁺ (LC-MS 2).

Step 93.7: 4-Bromo-5-methoxy-2-methyl-pyridine

To a solution of the product from step 93.8 (150 mg, 0.7 mmol) in CHCl₃ (2 mL) at 10° C. was added dropwise PBr₃ (78 µL, 0.826 mmol). The mixture was stirred at rt for 4 h, then at 50° C. for 1 h. The reaction mixture was dissolved in CH₂Cl₂ and extracted with a saturated aqueous NaHCO₃ solution, washed with brine, dried (Na₂SO₄), filtered and concentrated. The product was crystallised (CH₂Cl₂/TBME). t$_R$: 0.69 min (LC-MS 2); ESI-MS: 202.0/204.0 [M+H]⁺ (LC-MS 2).

Step 93.8: 4-Bromo-5-methoxy-2-methyl-pyridine 1-oxide

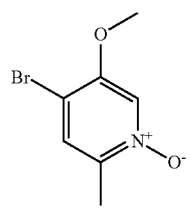

The product from step 93.9 (1.9 g, 10.3 mmol) and acetyl bromide (22.9 mL, 310 mmol) was added to AcOH (40 mL) and the reaction was stirred at 80° C. for 1 h. The mixture was concentrated (1/3) and a solution of NaOH was added. The resulting mixture was extracted with EtOAc, washed with brine, dried (Na₂SO₄), filtered and concentrated. The product was crystallised (EtOAc/TBME). t$_R$: 0.54 min (LC-MS 2); ESI-MS: 218.1/220.1 [M+H]⁺ (LC-MS 2).

Step 93.9: 5-Methoxy-2-methyl-4-nitro-pyridine-1-oxide

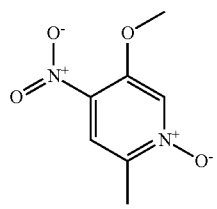

5-methoxy-2-methylpyridine-1-oxide (6 g, 43.1 mmol) and nitric acid (18.4 mL, 431 mmol, 1.48 g/mL) was added to AcOH (50 mL) and the reaction was stirred at 90° C. for 6 h. The mixture was concentrated (1/4) and neutralized at 0° C. was addition of ammonium hydroxide. The mixture was extracted with EtOAc, washed with brine and water, dried (Na₂SO₄), filtered and concentrated. The product crystallised during concentration. t$_R$: 0.50 min (LC-MS 2); ESI-MS: 185.1 [M+H]⁺ (LC-MS 2).

Example 94

4-[6-(4-Chloro-phenyl)-2-(2-dimethylamino-4-methoxy-pyrimidin-5-yl)-1-isopropyl-4-oxo-4,6-dihydro-1H-pyrrolo[3,4-d]imidazol-5-yl]-3-methyl-benzamide

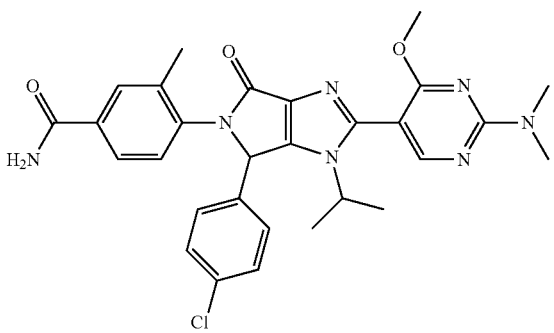 [SMILES: COc1nc(N(C)C)ncc1-c1nc2c(n1C(C)C)C(c1ccc(Cl)cc1)N(c1ccc(C(N)=O)cc1C)C2=O]

The title compound was prepared in analogy to the procedure described for example 1 but using the product from step 94.1 and intermediate W. The residue was purified by preparative HPLC (Waters Sun Fire C18, 30×100 mm, 5 µm; 0.1% TFA-water/acetonitrile; gradient acetonitrile 20-40% in 16 min) to give the title compound. t$_R$: 1.01 min (LC-MS 2); ESI-MS: 560.2 [M+H]⁺ (LC-MS 2).

Step 94.1: 4-[2-Bromo-6-(4-chloro-phenyl)-1-isopropyl-4-oxo-4,6-dihydro-1H-pyrrolo[3,4-d]imidazol-5-yl]-3-methyl-benzamide

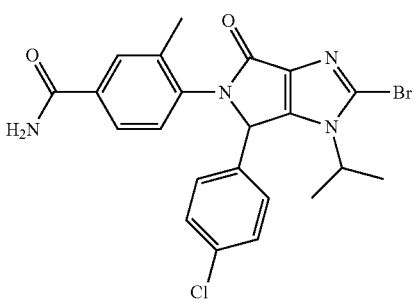 [SMILES: Cc1cc(C(N)=O)ccc1N1C(=O)c2nc(Br)n(C(C)C)c2C1c1ccc(Cl)cc1]

A solution of the product from step 94.2 (1.4 g, 3.0 mmol) in concentrated H₂SO₄ (31.8 mL, 596 mmol) was stirred at rt for 20 h. The reaction mixture was dissolved in EtOAc and H₂O, neutralized with a saturated aqueous NaHCO₃ solution and the phases were separated. The aqueous phase was washed with EtOAc. The organic layers were dried (Na₂SO₄), filtered and concentrated. t$_R$: 0.93 min (LC-MS 2); ESI-MS: 487.0/489.1 [M+H]⁺ (LC-MS 2).

Step 94.2: 4-[2-Bromo-6-(4-chloro-phenyl)-1-isopropyl-4-oxo-4,6-dihydro-1H-pyrrolo[3,4-d]imidazol-5-yl]-3-methyl-benzonitrile

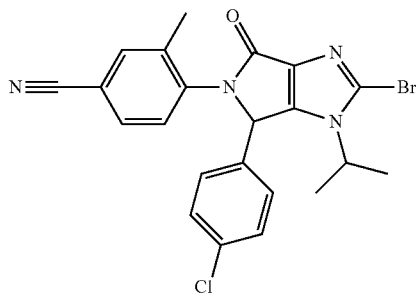 [SMILES: Cc1cc(C#N)ccc1N1C(=O)c2nc(Br)n(C(C)C)c2C1c1ccc(Cl)cc1]

The title compound was prepared in analogy to the procedure described for step 91.1 but using the product from step 94.3. The product was triturated in EtOAc and the resulting suspension was filtered to give the title compound. $t_R$: 1.12 min (LC-MS 2); ESI-MS: 469.2/471.2 [M+H]$^+$ (LC-MS 2).

Step 94.3: 2-Bromo-5-[(4-chloro-phenyl)-(4-cyano-2-methyl-phenylamino)-methyl]-1-isopropyl-1H-imidazole-4-carboxylic acid

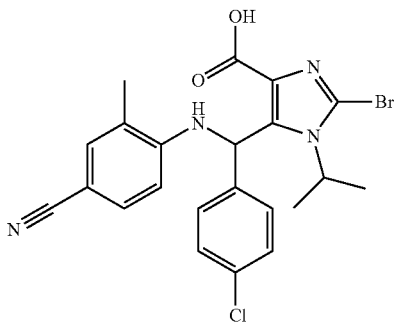 [SMILES: Cc1cc(C#N)ccc1NC(c1ccc(Cl)cc1)c1c(C(=O)O)nc(Br)n1C(C)C]

The title compound was prepared in analogy to the procedure described for step E1 but using the product from step 94.4. $t_R$: 1.13 min (LC-MS 2); ESI-MS: 487.2/489.2 [M+H]$^+$ (LC-MS 2).

Step 94.4: 2-Bromo-5-[(4-chloro-phenyl)-(4-cyano-2-methyl-phenylamino)-methyl]-1-isopropyl-1H-imidazole-4-carboxylic acid

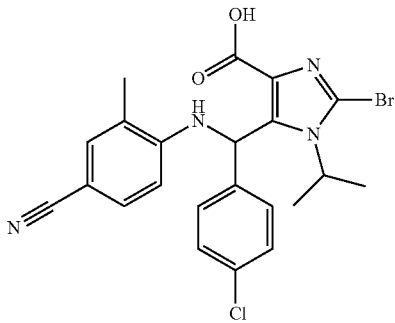 [SMILES: Cc1cc(C#N)ccc1NC(c1ccc(Cl)cc1)c1c(C(=O)O)nc(Br)n1C(C)C]

The title compound was prepared in analogy to the procedure described for step E2 but using intermediate B and 4-amino-3-methylbenzonitrile. The reaction mixture was stirred at rt for 20 h. The mixture was extracted with HCl 1M and with a saturated aqueous NaHCO$_3$ solution. The organic layers were dried (Na$_2$SO$_4$), filtered and concentrated. The product was triturated in Et$_2$O, the suspension was filtered and the solid was dried in HV. $t_R$: 1.30 min (LC-MS 2); ESI-MS: 515.2/517.1 [M+H]$^+$ (LC-MS 2).

Example 95

4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-3-methyl-benzamide

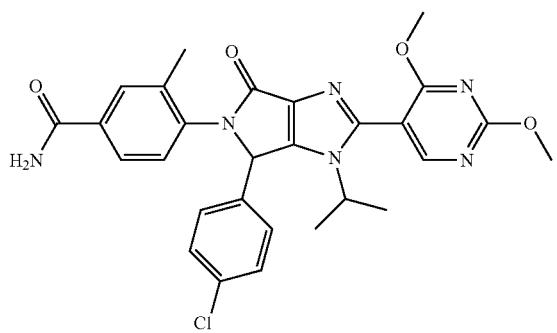 [SMILES: COc1ncc(-c2nc3c(n2C(C)C)C(c2ccc(Cl)cc2)N(c2ccc(C(N)=O)cc2C)C3=O)c(OC)n1]

The title compound was prepared in analogy to the procedure described for example 1 but using the product from step 94.1 and 2,4-dimethylpyrimidine-5-boronic acid. The residue was purified by SFC chromatography (Column 2-EP, 250×30 mm, 5 µm, flow 100 mL/min, grad 25-30% over 6 min) to give the title compound. $t_R$: 0.92 min (LC-MS 2); ESI-MS: 547.2/549.3 [M+H]$^+$ (LC-MS 2).

Example 96

5-(3-Chloro-2-fluoro-phenyl)-6-(4-chloro-phenyl)-1-isopropyl-2-(5-methoxy-2-oxo-1,2-dihydro-pyrimidin-4-yl)-5,6-dihydro-1H-pyrrolo[3,4-d]imidazol-4-one

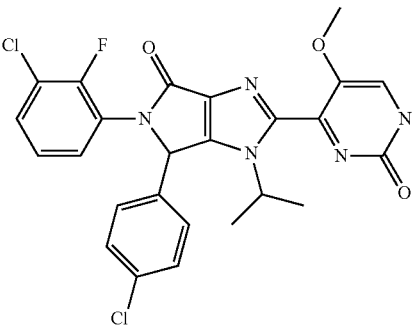 [SMILES: COc1c[nH]c(=O)nc1-c1nc2c(n1C(C)C)C(c1ccc(Cl)cc1)N(c1cccc(Cl)c1F)C2=O]

To a solution of the product from step 96.1 (20 mg, 0.04 mmol) in dioxane/H$_2$O (800 µl, 1:1) was added K$_2$CO$_3$ (9.1 mg, 0.07 mmol) and DABCO (2.0 mg, 0.02 mmol) and the mixture was stirred at 70° C. for 16 h. EtOAc and H$_2$O were added and the phases were separated. The organic layers were dried (Na$_2$SO$_4$), filtered and concentrated. The residue was purified by SFC chromatography (Column 2-EP, 250×30 mm, 5 µm, flow 100 mL/min, grad 18-23% over 6 min) to give the title compound. $t_R$: 0.98 min (LC-MS 2); ESI-MS: 528.2/530.2 [M+H]$^+$ (LC-MS 2).

Step 96.1: 5-(3-Chloro-2-fluoro-phenyl)-2-(2-chloro-5-methoxy-pyrimidin-4-yl)-6-(4-chloro-phenyl)-1-isopropyl-5,6-dihydro-1H-pyrrolo[3,4-d]imidazol-4-one

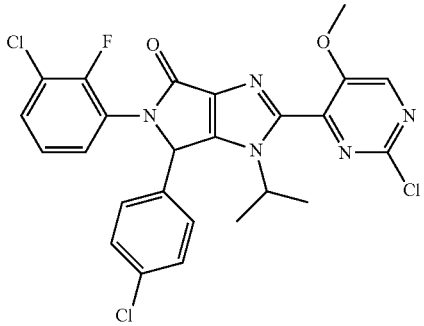 [SMILES: COc1cnc(Cl)nc1-c1nc2c(n1C(C)C)C(c1ccc(Cl)cc1)N(c1cccc(Cl)c1F)C2=O]

To a solution of intermediate G (300 mg, 0.6 mmol) in dioxane (6.4 mL) was added Pd(PPh$_3$)4 (144 mg, 0.1 mmol), then the product from step 96.2 (487 mg, 1.9 mmol) and the reaction mixture was stirred at 70° C. for 1 h and at 80° C. for 1 h more. The mixture was diluted with EtOAc and extracted with H$_2$O. The organic layers were dried (Na$_2$SO$_4$), filtered and concentrated. The residue was purified by preparative HPLC (Waters Sun Fire C18, 30×100 mm, 5 μm; 0.1% TFA-water/acetonitrile; gradient acetonitrile 50-70% in 16 min) to give the title compound. $t_R$: 1.22 min (LC-MS 2); ESI-MS: 546.1 [M+H]$^+$ (LC-MS 2).

Step 96.2: (2-Chloro-5-methoxypyrimidin-4-yl)zinc

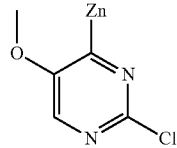

A solution of dry ZnCl (400 mg, 2.9 mmol) and 2,2,6,6-tetramethylpiperidinylmagnesiumchloride lithium chloride complex, 1M in THF (5.5 mL, 5.53 mmol) was stirred at RT for 16 h. Then 2-chloro-5-methoxypyrimidine (800 mg, 5.53 mmol) was added dropwise and the mixture was stirred at rt for 1 h. The product was used as a stock solution for the next step.

Example 97

5-(4-Amino-cyclohexyl)-6-(4-chloro-phenyl)-2-(2,4-dimethoxy-pyrimidin-5-yl)-1-isopropyl-5,6-dihydro-1H-pyrrolo[3,4-d]imidazol-4-one

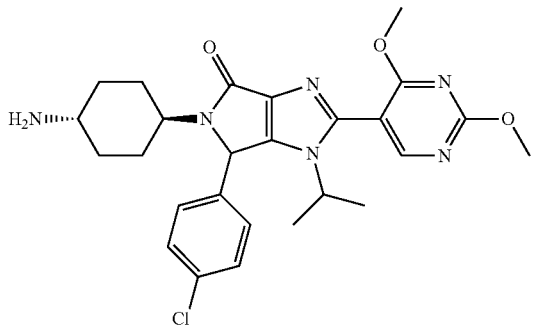 [SMILES: COc1ncc(-c2nc3c(n2C(C)C)C(c2ccc(Cl)cc2)N([C@H]2CC[C@H](N)CC2)C3=O)c(OC)n1]

A solution of the product from step 97.1 (158 mg, 0.2 mmol) and TFA (359 μl, 4.65 mmol) was stirred at rt for 1 h. At 0° C., the pH was adjusted to 8 with a saturated aqueous NaHCO$_3$ solution. The mixture was extracted with EtOAc. The organic layers were washed with brine, dried (MgSO$_4$), filtered and concentrated. The product was purified by preparative HPLC (Column Atlantis, Flow: 23 mL/min. Gradient 5-100% B in 7 min; A=0.1% TFA in water, B=acetonitrile) to provide the title compound. $t_R$: 0.76 min (LC-MS 2); ESI-MS: 511.3/513.2 [M+H]$^+$ (LC-MS 2).

Step 97.1: {4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexyl}-carbamic acid ethyl ester

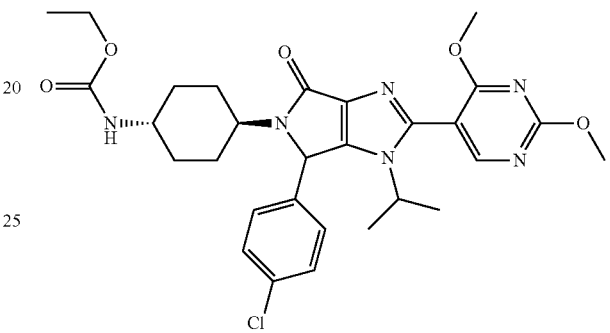

The title compound was prepared in analogy to the procedure described for example 29 but using the product from step 97.2 and 2,4-dimethoxypyrimidin-5-ylboronic acid. The reaction mixture was diluted with a saturated aqueous NaHCO$_3$ solution, and was extracted with EtOAc. The organic layer was washed with brine, dried (MgSO$_4$), filtered, and concentrated. The residue was purified by flash chromatography (hexane/EtOAc, 75:25→0:100). $t_R$: 1.17 min (LC-MS 2); ESI-MS: 611.5/613.5 [M+H]$^+$ (LC-MS 2).

Step 97.2: {4-[2-Bromo-6-(4-chloro-phenyl)-1-isopropyl-4-oxo-4,6-dihydro-1H-pyrrolo[3,4-d]imidazol-5-yl]-cyclohexyl}-carbamic acid tert-butyl ester

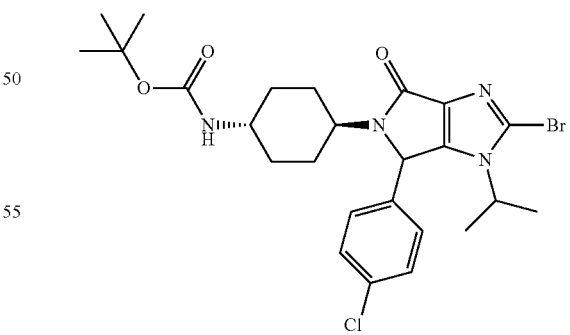

The title compound was prepared in analogy to the procedure described for step 93.1 but using the product was step 97.3. The crude was purified by flash chromatography (hexane/EtOAc, 70:30→0:100) to afford the title compound. $t_R$: 1.19 min (LC-MS 2); ESI-MS: 551.2/553.3 [M+H]$^+$ (LC-MS 2).

Step 97.3: 2-Bromo-5-[(4-tert-butoxycarbonylamino-cyclohexylamino)-(4-chloro-phenyl)-methyl]-1-isopropyl-1H-imidazole-4-carboxylic acid

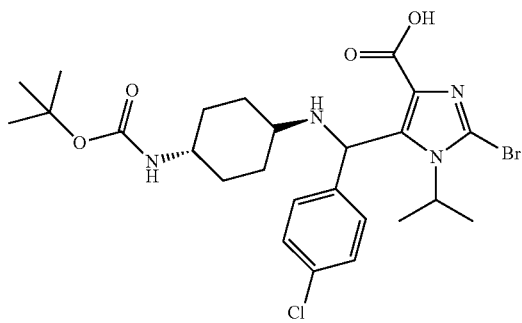

The title compound was prepared in analogy to the procedure described for step E1 but using the product from step 97.4. $t_R$: 0.91 min (LC-MS 2); ESI-MS: 569.3/571.3 [M+H]$^+$ (LC-MS 2).

Step 97.4: 2-Bromo-5-[(4-tert-butoxycarbonylamino-cyclohexylamino)-(4-chloro-phenyl)-methyl]-1-isopropyl-1H-imidazole-4-carboxylic acid ethyl ester

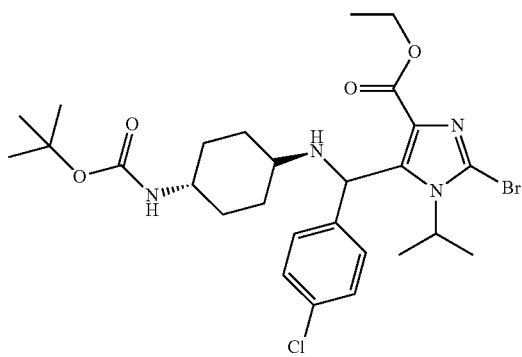

The title compound was prepared in analogy to the procedure described for step E2 but using intermediate B and trans-1-Boc-amino-1,4-cyclohexanediamine. The reaction mixture was stirred at 50° C. for 19 h. The reaction mixture was diluted in EtOAc/water and the phases were separated. The organic extracts were dried (Na$_2$SO$_4$) and concentrated. The crude was purified by flash chromatography (hexane/EtOAc, 80:20→0:100) to afford the title compound. $t_R$: 1.33 min (LC-MS 2); ESI-MS: 597.3/599.5 [M+H]$^+$ (LC-MS 2).

Example 98

4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid

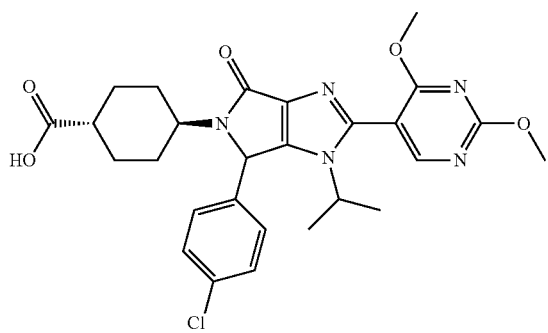

The title compound was prepared in analogy to the procedure described for step 97.1 but using the product from step 98.1. The residue was purified by flash chromatography (CH$_2$Cl$_2$/MeOH, 97:3→8:2). $t_R$: 0.96 min (LC-MS 2); ESI-MS: 540.3/542.3 [M+H]$^+$ (LC-MS 2).

Step 98.1: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid tert-butyl ester

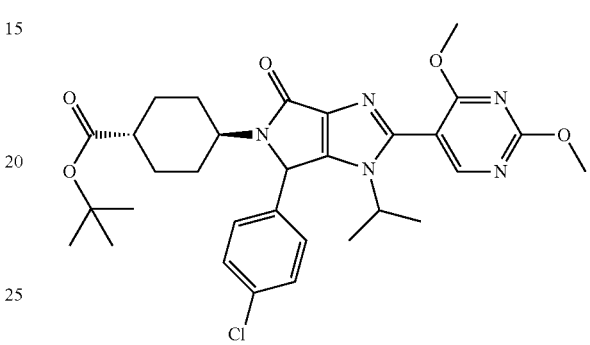

The title compound was prepared in analogy to the procedure described for example 29 but using the product from step 98.2 and 2,4-dimethoxypyrimidin-5-ylboronic acid. The reaction mixture was diluted with a saturated aqueous NaHCO$_3$ solution, and was extracted with EtOAc. The organic layer was washed with brine, dried (MgSO$_4$), filtered, and concentrated. The residue was purified by flash chromatography (hexane/EtOAc, 80:20→0:100). $t_R$: 1.28 min (LC-MS 2); ESI-MS: 596.4 [M+H]$^+$ (LC-MS 2).

Step 98.2: 4-[2-Bromo-6-(4-chloro-phenyl)-1-isopropyl-4-oxo-4,6-dihydro-1H-pyrrolo[3,4-d]imidazol-5-yl]-cyclohexanecarboxylic acid tert-butyl ester

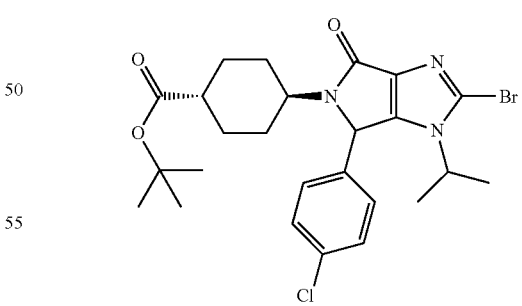

The title compound was prepared in analogy to the procedure described for step 93.1 but using the product was step 98.3. The crude was purified by flash chromatography (hexane/EtOAc, 70:30→0:100) to afford the title compound. $t_R$: 1.30 min (LC-MS 2); ESI-MS: 536.3/538.3 [M+H]$^+$ (LC-MS 2).

Step 98.3: 2-Bromo-5-[(4-tert-butoxycarbonyl-cyclohexylamino)-(4-chloro-phenyl)-methyl]-1-isopropyl-1H-imidazole-4-carboxylic acid

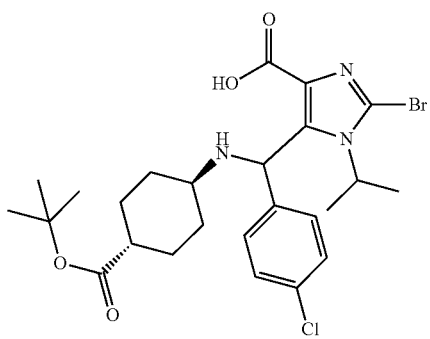 [SMILES: CC(C)n1c(Br)nc(C(=O)O)c1C(N[C@H]1CC[C@H](C(=O)OC(C)(C)C)CC1)c1ccc(Cl)cc1]

The title compound was prepared in analogy to the procedure described for step E1 but using the product was step 98.4. The mixture was stirred at rt for 3 h. $t_R$: 0.98 min (LC-MS 2); ESI-MS: 554.3/556.3 [M+H]$^+$ (LC-MS 2).

Step 98.4: 2-Bromo-5-[(4-tert-butoxycarbonyl-cyclohexylamino)-(4-chloro-phenyl)-methyl]-1-isopropyl-1H-imidazole-4-carboxylic acid ethyl ester

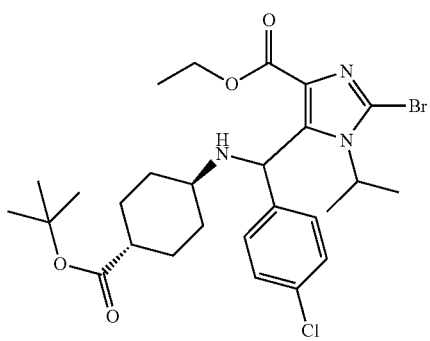 [SMILES: CCOC(=O)c1nc(Br)n(C(C)C)c1C(N[C@H]1CC[C@H](C(=O)OC(C)(C)C)CC1)c1ccc(Cl)cc1]

The title compound was prepared in analogy to the procedure described for step E2 but using the product from step 98.5. The reaction was performed at 45° C. The resulting mixture was diluted in H$_2$O and a saturated aqueous NaHCO$_3$ solution and extracted with CH$_2$Cl$_2$. The organic layers were washed with brine, dried (MgSO$_4$), filtered and concentrated. The crude product was purified by flash chromatography (heptane/EtOAc, 80:20→0:100). $t_R$: 1.48 min (LC-MS 2); ESI-MS: 584.3/584.3 [M+H]$^+$ (LC-MS 2).

Step 98.5: 4-Amino-cyclohexanecarboxylic acid tert-butyl ester

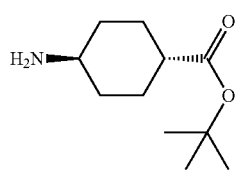

A mixture of the compound prepared in step 98.6 (1.3 g, 3.4 mmol) and Pd/C 10% (113 mg) in MeOH (25 mL) was stirred for 1 h at rt, under a hydrogen atmosphere. The reaction mixture was filtered through a pad of celite, washed with THF and MeOH and concentrated. $t_R$: 0.14 min (LC-MS 2); ESI-MS: 200.2 [M+H]$^+$ (LC-MS 2).

Step 98.6: 4-Benzyloxycarbonylamino-cyclohexanecarboxylic acid tert-butyl ester

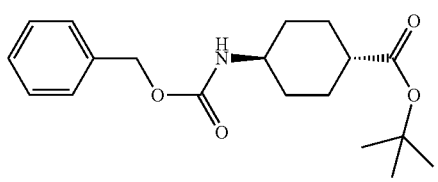 [SMILES: CC(C)(C)OC(=O)[C@H]1CC[C@H](NC(=O)OCc2ccccc2)CC1]

To a suspension of (1R,4R)-4-benzoylcarbonylamino-cyclohexanecarboxylic acid (1 g, 3.6 mmol) in toluene (20 mL) at 40° C. was added di-tert-butoxymethyl-dimethylamine (8.0 mL, 33.5 mmol) and the mixture was stirred at 95° C. for 10 h. The reaction mixture was extracted with a mixture of saturated aqueous NaHCO$_3$ solution and H$_2$O (1:1). The organic layer was washed with a saturated aqueous NaHCO$_3$ solution and brien, dried (MgSO$_4$), filtered and concentrated. The aqueous layer was washed with EtOAc. The resulting organic layer was washed with brine, dried (MgSO$_4$), filtered and concentrated. The product was used without further purification for the next step. $t_R$: 5.46 min (HPLC 2); ESI-MS: 332.1 [M−H]$^-$ (MS 1).

Example 99

N-{4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexyl}-acetamide

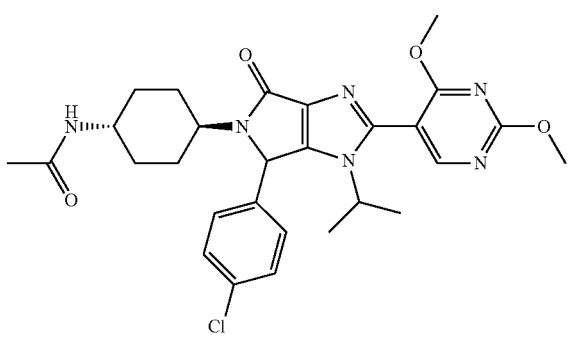 [SMILES: COc1ncc(-c2nc3c(n2C(C)C)C(c2ccc(Cl)cc2)N([C@H]2CC[C@H](NC(C)=O)CC2)C3=O)c(OC)n1]

To a solution of the product from example 97 (60 mg, 0.2 mmol) and TEA (33 µL, 0.2 mmol) was added acetic anhydride (13 µL, 0.1 mmol) and the mixture was stirred at rt for 30 in. The mixture was diluted in H$_2$O and EtOAc. The phases were separated and the organic layers were dried (MgSO$_4$), filtered and concentrated. The product was purified by flash chromatography (CH$_2$Cl$_2$/MeOH, 97:3→80:20) to provide the title compound. $t_R$: 0.91 min (LC-MS 2); ESI-MS: 553.3 [M+H]$^+$ (LC-MS 2).

Example 100

4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

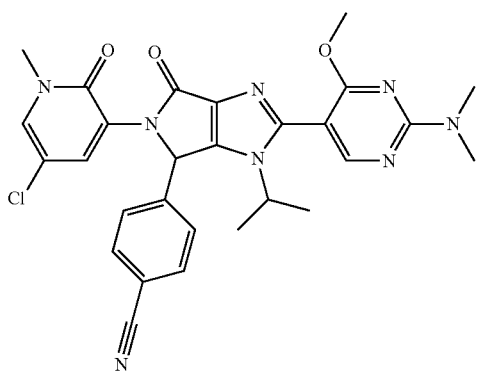 [SMILES: COc1nc(N(C)C)ncc1-c1nc2c(n1C(C)C)C(c1ccc(C#N)cc1)N(c1cc(Cl)cn(C)c1=O)C2=O]

The title compound was prepared in analogy to the procedure described for example 29 but using the product from step 100.1 and intermediate W. The reaction was performed at 110° C. The product was purified by flash chromatography (CH$_2$Cl$_2$/MeOH, 95:5), then the residue was triturated in Et$_2$O to provide the title compound. t$_R$: 0.97 min (LC-MS 2); ESI-MS: 559.4/561.4 [M+H]$^+$ (LC-MS 2); $^1$H-NMR (DMSO-d$_6$, 400 MHz) δ ppm 8.19 (s, 1H), 7.90 (d, 1H), 7.86-7.78 (m, 2H), 7.58-7.47 (m, 3H), 6.76 (s, 1H), 4.18-4.00 (m, 1H), 3.86 (s, 3H), 3.45-3.36 (m, 3H), 3.16 (s, 6H), 1.31 (d, 3H), 0.46 (d, 3H).

Step 100.1: 4-[2-Bromo-5-(5-chloro-1-methyl-2-oxo-1,2-dihydro-pyridin-3-yl)-3-isopropyl-6-oxo-3,4,5,6-tetrahydro-pyrrolo[3,4-d]imidazol-4-yl]-benzonitrile

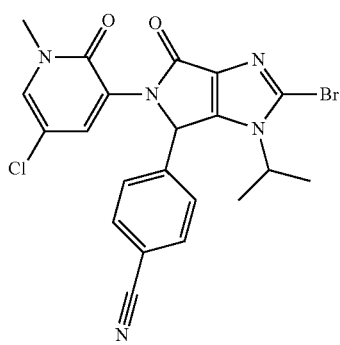 [SMILES: CC(C)n1c(Br)nc2c1C(c1ccc(C#N)cc1)N(c1cc(Cl)cn(C)c1=O)C2=O]

The title compound was prepared in analogy to the procedure described for intermediate E but using the product from step 100.2. t$_R$: 0.87 min (LC-MS 2); ESI-MS: 486.1/488.1 [M+H]$^+$ (LC-MS 2).

Step 100.2: 2-Bromo-5-[(5-chloro-1-methyl-2-oxo-1,2-dihydro-pyridin-3-ylamino)-(4-cyano-phenyl)-methyl]-1-isopropyl-1H-imidazole-4-carboxylic acid

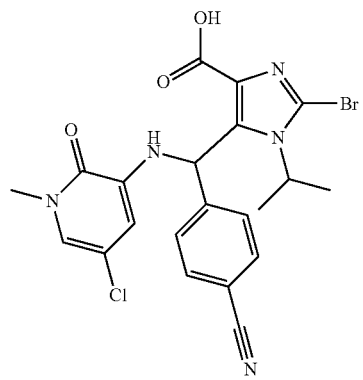 [SMILES: CC(C)n1c(Br)nc(C(=O)O)c1C(Nc1cc(Cl)cn(C)c1=O)c1ccc(C#N)cc1]

The title compound was prepared in analogy to the procedure described for step E1 but using the product from step 100.3. After extraction, the residue was triturated in EtOAc to afford the title compound. t$_R$: 0.89 min (LC-MS 2); ESI-MS: 504.2/506.2 [M+H]$^+$ (LC-MS 2).

Step 100.3: 2-Bromo-5-[(5-chloro-1-methyl-2-oxo-1,2-dihydro-pyridin-3-ylamino)-(4-cyano-phenyl)-methyl]-1-isopropyl-1H-imidazole-4-carboxylic acid ethyl ester

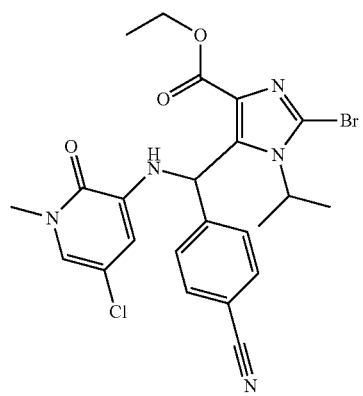 [SMILES: CCOC(=O)c1nc(Br)n(C(C)C)c1C(Nc1cc(Cl)cn(C)c1=O)c1ccc(C#N)cc1]

The title compound was prepared in analogy to the procedure described for step E2 but using intermediate H3 and the product from step 100.4. The reaction mixture was stirred at rt for 72 h. After the flash chromatography, the product was triturated in Et$_2$O to afford the title compound. t$_R$: 1.09 min (LC-MS 2); ESI-MS: 532.3/534.3 [M+H]$^+$ (LC-MS 2).

Step 100.4: 3-Amino-5-chloro-1-methyl-1H-pyridin-2-one

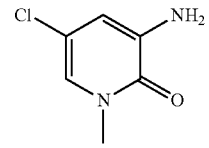

A mixture of the compound prepared in step 100.5 (1.7 g, 9 mmol) and Raney nickel (300 Mg) in MeOH (100 mL) and THF (30 mL) was stirred for 16.5 h at rt, under a hydrogen atmosphere. The reaction mixture was filtered through a pad of celite, and concentrated. The residue was purified by flash chromatography (hexane/EtOAc, 30:70) to afford the title compound. $t_R$: 0.52 min (LC-MS 2); ESI-MS: 159.1/161.1 [M+H]$^+$ (LC-MS 2), $R_f$=0.22 (hexane/EtOAc, 3:7).

Step 100.5:
5-Chloro-1-methyl-3-nitro-1H-pyridin-2-one

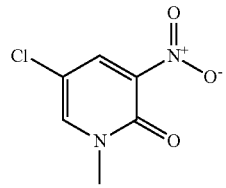

A mixture of NaH (577 mg, 14.4 mmol) and 5-chloro-2-hydroxy-3-nitropyridine (2.1 g, 12.0 mmol) in DMF (21 mL) was stirred for 1 h at 5° C. Methyl iodide (1.1 mL, 18.0 mmol) was added. The resulting mixture was allowed to warm to rt, stirred overnight, cooled to 0° C., quenched by addition of water, and extracted with EtOAc. The organic layer was dried (Na$_2$SO$_4$), filtered, and concentrated. The residue was used without further purification. $t_R$: 0.61 min (LC-MS 2); ESI-MS: 189.1/191.1 [M+H]$^+$ (LC-MS 2).

Example 101

5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one

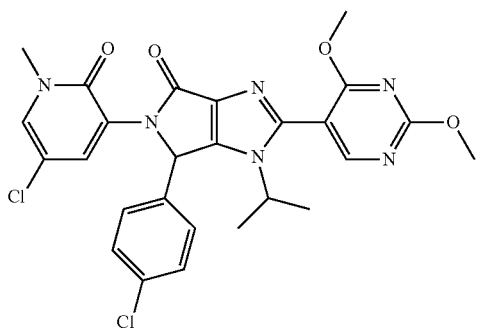 [SMILES: COc1ncc(-c2nc3c(n2C(C)C)C(c2ccc(Cl)cc2)N(c2cc(Cl)cn(C)c2=O)C3=O)c(OC)n1]

The title compound was prepared in analogy to the procedure described for example 29 but using the product from step 101.1 and 2,4-dimethoxypyrimidin.5.ylboronic acid. The reaction was performed at 110° C. The residue was purified by flash chromatography (CH$_2$Cl$_2$/MeOH, 95:5) then was purified by preparative HPLC (Column: Sunfire C18, 30×100 mm, 5 μm. Flow: 30 mL/min. Gradient 30-80% B in 20 min; A=0.1% TFA in water, B=CH$_3$CN) to afford the title compound. $t_R$: 1.05 min (LC-MS 2); ESI-MS: 555.3/557.2 [M+H]$^+$ (LC-MS 2); $R_f$=0.19 (CH$_2$Cl$_2$/MeOH, 95:5).

Step 101.1: 2-Bromo-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one

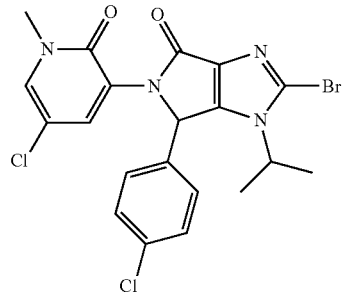 [SMILES: CC(C)n1c(Br)nc2c1C(c1ccc(Cl)cc1)N(c1cc(Cl)cn(C)c1=O)C2=O]

The title compound was prepared in analogy to the procedure described for intermediate E but using the product from step 101.2. After extraction, the residue was triturated in EtOAc to afford the title compound. $t_R$: 1.07 min (LC-MS 2); ESI-MS: 495.0/497.1/499.0 [M+H]$^+$ (LC-MS 2).

Step 101.2: 2-Bromo-5-[(5-chloro-1-methyl-2-oxo-1,2-dihydro-pyridin-3-ylamino)-(4-chloro-phenyl)-methyl]-1-isopropyl-1H-imidazole-4-carboxylic acid

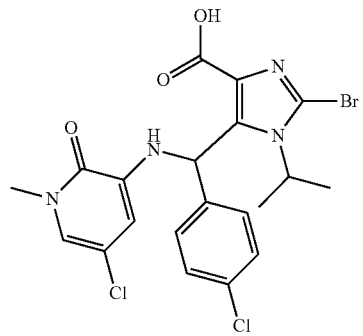 [SMILES: CC(C)n1c(Br)nc(C(=O)O)c1C(Nc1cc(Cl)cn(C)c1=O)c1ccc(Cl)cc1]

The title compound was prepared in analogy to the procedure described for step E1 but using the product from step 101.3. The residue was triturated in Et$_2$O to afford the title compound. $t_R$: 1.05 min (LC-MS 2); ESI-MS: 513.2/515.1/517.1 [M+H]$^+$ (LC-MS 2).

Step 101.3: 2-Bromo-5-[(5-chloro-1-methyl-2-oxo-1,2-dihydro-pyridin-3-ylamino)-(4-chloro-phenyl)-methyl]-1-isopropyl-1H-imidazole-4-carboxylic acid ethyl ester

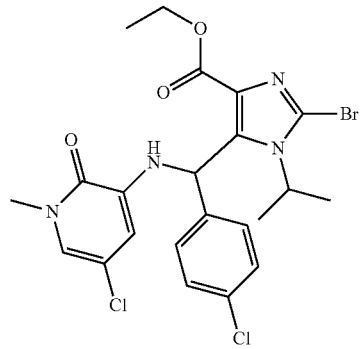 [SMILES: CCOC(=O)c1nc(Br)n(C(C)C)c1C(Nc1cc(Cl)cn(C)c1=O)c1ccc(Cl)cc1]

The title compound was prepared in analogy to the procedure described for step E2 but using the product from step 100.4. After extraction, the residue was triturated in EtOAc to afford the title compound. $t_R$: 1.27 min (LC-MS 2); ESI-MS: 541.1/543.1/545.1 [M+H]$^+$ (LC-MS 2).

Example 102

(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one

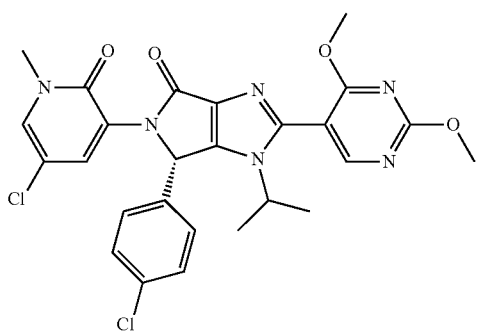 [SMILES: COc1ncc(-c2nc3c(n2C(C)C)[C@H](c2ccc(Cl)cc2)N(c2cc(Cl)cn(C)c2=O)C3=O)c(OC)n1]

The title compound was obtained after preparative chiral HPLC separation of the racemic product of example 101. (Column: Chiralpak AD, 76.5×390 mm. Flow 120 mL/min. hexane/EtOH/MeOH 50:25:25). $t_R$: 5.5 min (Column: Chiralpak AD, 4.6×250 mm. Flow 1 mL/min. hexane/EtOH/MeOH 50:25:25); $^1$H-NMR (DMSO-d$_6$, 400 MHz) δ ppm 8.49 (s, 1H), 7.92 (d, 1H), 7.51 (d, 1H), 7.41 (m, 2H), 7.33 (m, 2H), 6.71 (s, 1H), 4.10 (m, 1H), 3.97 (s, 3H), 3.93 (s, 3H), 3.43 (s, 3H), 1.33 (d, 3H), 0.51 (d, 3H).

Example 103

(R)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one

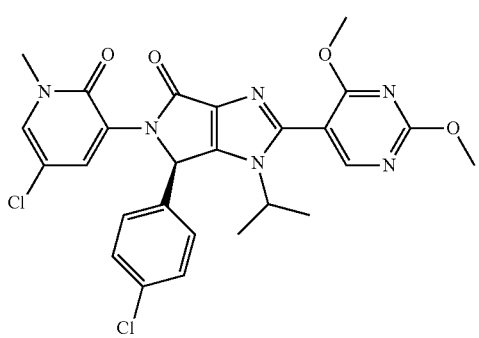 [SMILES: COc1ncc(-c2nc3c(n2C(C)C)[C@@H](c2ccc(Cl)cc2)N(c2cc(Cl)cn(C)c2=O)C3=O)c(OC)n1]

The title compound was obtained after preparative chiral HPLC separation of the racemic product of example 101. (Column: Chiralpak AD, 76.5×390 mm. Flow 120 mL/min. hexane/EtOH/MeOH 50:25:25). $t_R$: 10.9 min (Column: Chiralpak AD, 4.6×250 mm. Flow 1 mL/min. hexane/EtOH/MeOH 50:25:25). $^1$H-NMR (DMSO-d$_6$, 400 MHz) δ ppm 8.49 (s, 1H), 7.93 (d, 1H), 7.50 (d, 1H), 7.43 (m, 2H), 7.31 (m, 2H), 6.71 (s, 1H), 4.11 (m, 1H), 3.97 (s, 3H), 3.93 (s, 3H), 3.43 (s, 3H), 1.33 (d, 3H), 0.51 (d, 3H).

Example 104

4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid methylamide

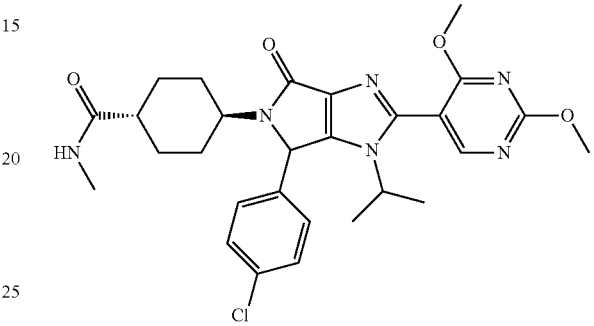

The title compound was prepared in analogy to the procedure described for intermediate K but using the product from example 98 and N-methylamine hydrochloride. The reaction was performed at 50° C. After extraction, the residue was purified by flash chromatography (CH$_2$Cl$_2$/MeOH, 97:3→80:20). The residue was triturated in isopropyl ether to afford the title compound. $t_R$: 0.92 min (LC-MS 2); ESI-MS: 553.4/555.4 [M+H]$^+$ (LC-MS 2), $^1$H-NMR (DMSO-d$_6$, 400 MHz) δ ppm 8.42 (s, 1H), 7.62 (m, 2H), 7.49 (m, 2H), 5.90 (s, 1H), 4.02 (m, 1H), 3.93 (s, 3H), 3.90 (s, 3H), 1.98 (s, 3H), 1.29 (m, 3H), 1.07-2.47 (m, 10H), 0.40 (m, 3H).

Example 105

5-(3-Chloro-4-fluoro-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one

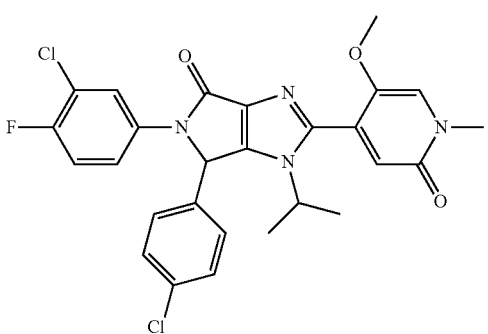 [SMILES: COc1cn(C)c(=O)cc1-c1nc2c(n1C(C)C)C(c1ccc(Cl)cc1)N(c1ccc(F)c(Cl)c1)C2=O]

The title compound was prepared in analogy to the procedure described for example 1 but using the product from step 105.1 and intermediate Q. $t_R$: 1.06 min (LC-MS 2); ESI-MS: 541.2/543.3 [M+H]$^+$ (LC-MS 2).

Step 105.1: 5-Methoxy-1-methyl-4-(4,4,5,5-tetramethyl-[1,3,2]dioxaborolan-2-yl)-1H-pyridin-2-one

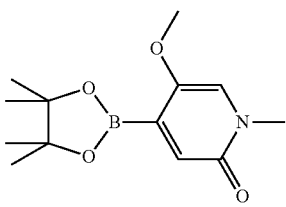

The title compound was prepared in analogy to the procedure described for example 29 but using the product from step 105.2. The reaction was performed at 110° C. After the reaction was completed, the reaction mixture was suspended in toluene, filtered. The resulting solid was dried to afford the title compound.

Step 105.2: 4-Bromo-5-methoxy-1-methyl-1H-pyridin-2-one

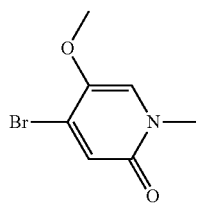

A solution of 4-bromo-2-chloro-5-methoxypyridine (1 g, 4.5 mmol) in dimethyl sulfate (1.9 mL, 19.5 mmol) was stirred at 120° C. for 16 h in a sealed tube. After cooling, acetonitrile and a saturated aqueous NaHCO$_3$ solution were added and the mixture was stirred at rt over week-end. DCM was added and extracted. The organic layer was dried (Na$_2$SO$_4$), filtered and concentrated to give the title compound. t$_R$: 0.57 min (LC-MS 2); ESI-MS: 218.0/220.0 [M+H]$^+$ (LC-MS 2).

Example 106

{4-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-5-methoxy-pyridin-2-yl}-acetonitrile

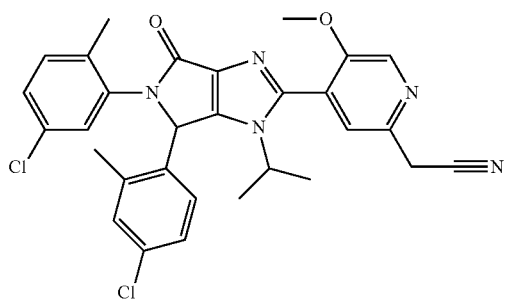 [SMILES: COc1cnc(CC#N)cc1-c1nc2c(n1C(C)C)C(c1ccc(Cl)cc1C)N(c1cc(Cl)ccc1C)C2=O]

The title compound was prepared in analogy to the procedure described for example 29 but using the product from step 93.4 and intermediate F. The residue was purified by flash chromatography (CH$_2$Cl$_2$/MeOH, 99.5:0.5→95:5). t$_R$: 1.17-1.20 min (LC-MS 2); ESI-MS: 560.2/562.2 [M+H]$^+$ (LC-MS 2).

Example 107

{4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile

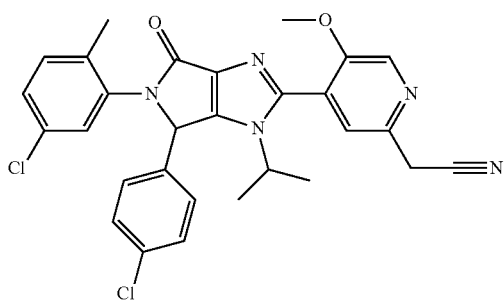 [SMILES: COc1cnc(CC#N)cc1-c1nc2c(n1C(C)C)C(c1ccc(Cl)cc1)N(c1cc(Cl)ccc1C)C2=O]

The title compound was prepared in analogy to the procedure described for example 29 but using the product from step 93.4 and intermediate E. The residue was purified by flash chromatography (CH$_2$Cl$_2$/MeOH, 99.5:0.5→95:5). t$_R$: 1.15 min (LC-MS 2); ESI-MS: 546.2/548.1 [M+H]$^+$ (LC-MS 2).

Example 108

{4-[5-(5-Chloro-1-methyl-2-oxo-1,2-dihydro-pyridin-3-yl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile

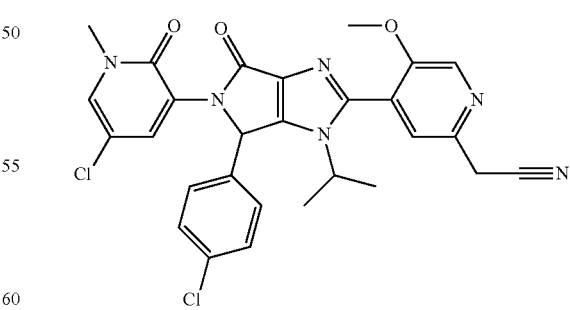

The title compound was prepared in analogy to the procedure described for example 29 but using the products from steps 93.4 and 101.1. The residue was purified by flash chromatography (CH$_2$Cl$_2$/MeOH, 99.5:0.5→90:10). t$_R$: 0.97 min (LC-MS 2); ESI-MS: 563.2/565.1 [M+H]$^+$ (LC-MS 2).

Example 109

5-(3-Chloro-2-fluoro-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one

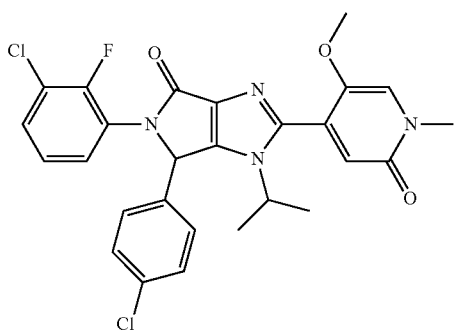 [SMILES: COc1cn(C)c(=O)cc1-c1nc2c(n1C(C)C)C(c1ccc(Cl)cc1)N(c1cccc(Cl)c1F)C2=O]

The title compound was prepared in analogy to the procedure described for example 1 but using the product from step 105.1 and intermediate G. $t_R$: 1.04 min (LC-MS 2); ESI-MS: 541.3/543.2 [M+H]$^+$ (LC-MS 2).

Example 110

5-(5-Chloro-2-methyl-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one

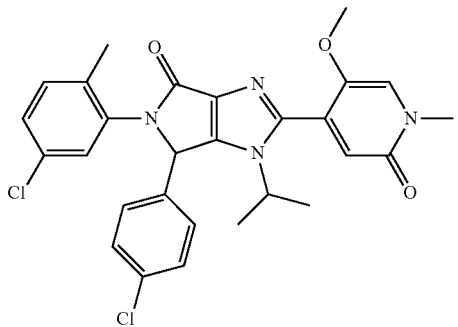 [SMILES: COc1cn(C)c(=O)cc1-c1nc2c(n1C(C)C)C(c1ccc(Cl)cc1)N(c1cc(Cl)ccc1C)C2=O]

The title compound was prepared in analogy to the procedure described for example 1 but using the product from step 105.1 and intermediate E. After the first purification on preparative HPLC, the product was purified by SFC chromatography (Column DEAP, 250×30 mm, 5 µm, flow 100 mL/min, grad 15-20% over 6 min) to give the title compound. $t_R$: 1.07 min (LC-MS 2); ESI-MS: 537.3/539.3 [M+H]$^+$ (LC-MS 2).

Example 111

5-(5-Chloro-2-methyl-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one

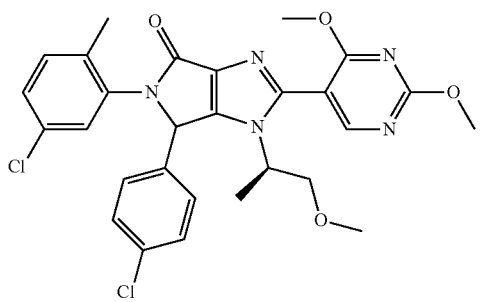 [SMILES: COC[C@@H](C)n1c(-c2cnc(OC)nc2OC)nc2c1C(c1ccc(Cl)cc1)N(c1cc(Cl)ccc1C)C2=O]

The title compound was prepared in analogy to the procedure described for example 97.1 but using the product from step 111.1. The residue was purified by flash chromatography (hexane/EtOAc, 100:0→0:100). $t_R$: 1.17 min (LC-MS 2); ESI-MS: 568.2/570.2 [M+H]$^+$ (LC-MS 2); $R_f$=0.33 (heptane/EtOAc, 1:4); $^1$H-NMR (DMSO-d$_6$, 400 MHz) δ ppm 8.45-8.42 (m, 1H), 7.75 (m, 1H), 7.42-7.13 (m, 6H), 6.63-6.50 (m, 1H), 4.16 (m, 1H), 3.98-3.93 (m, 6H), 3.54-3.50 (m, 2H), 3.20 (s, 3H), 1.98-1.90 (m, 3H), 0.56 (m, 3H).

Step 111.1: 2-Bromo-5-(5-chloro-2-methyl-phenyl)-6-(4-chloro-phenyl)-1-((R)-2-methoxy-1-methyl-ethyl)-5,6-dihydro-1H-pyrrolo[3,4-d]imidazol-4-one

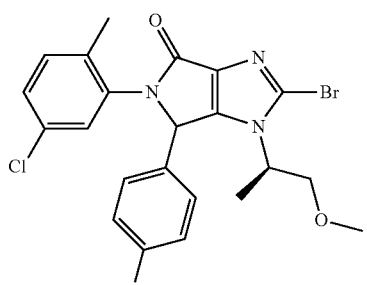

To a solution of the product from step 111.2 (122 mg, 0.2 mmol) in DME (2.4 mL) was added silver oxide (141 mg, 0.6 mmol) and methyl iodide (305 µl, 4.9 mmol) and the mixture was stirred at 40° C. for 40 h. MeOH was added and the reaction mixture was concentrated. The product was purified by flash chromatography (heptane/EtOAc, 100:0→0:100). $t_R$: 1.20 min (LC-MS 2); ESI-MS: 508.0/510.0/512.0 [M+H]$^+$ (LC-MS 2); $R_f$=0.33 (CH$_2$Cl$_2$/MeOH, 20:1).

Step 111.2: 2-Bromo-5-(5-chloro-2-methyl-phenyl)-6-(4-chloro-phenyl)-1-((R)-2-hydroxy-1-methyl-ethyl)-5,6-dihydro-1H-pyrrolo[3,4-d]imidazol-4-one

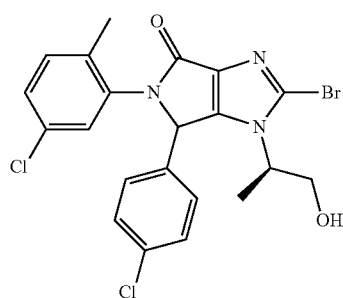 [SMILES: Cc1ccc(Cl)cc1N1C(=O)c2nc(Br)n([C@H](C)CO)c2C1c1ccc(Cl)cc1]

To a solution of the product from step 111.3 (417 mg, 0.6 mmol) in THF (6 mL) at 0° C. was added TBAF (1.2 mL, 1.2 mmol) and the mixture was stirred at 0° C. for 15 min. The reaction mixture was diluted in EtOAc and extracted with a 1M NaHCO$_3$ solution. The organic layer was washed with brine, dried (Na$_2$SO$_4$), filtered and concentrated. The product was purified by flash chromatography (heptane/EtOAc, 40:60→0:100). $t_R$: 1.05 min (LC-MS 2); ESI-MS: 494.0/496.1/498.1 [M+H]$^+$ (LC-MS 2).

Step 111.3: 2-Bromo-5-(5-chloro-2-methyl-phenyl)-6-(4-chloro-phenyl)-1-((R)-1-methyl-2-triisopropyl-silanyloxy-ethyl)-5,6-dihydro-1H-pyrrolo[3,4-d]imidazol-4-one

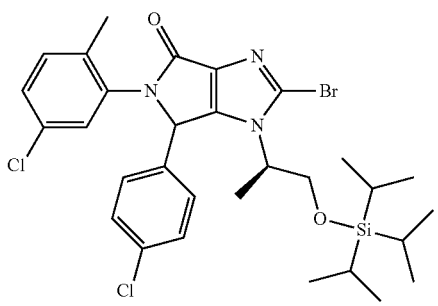 [SMILES: Cc1ccc(Cl)cc1N1C(=O)c2nc(Br)n([C@H](C)CO[Si](C(C)C)(C(C)C)C(C)C)c2C1c1ccc(Cl)cc1]

The title compound was prepared in analogy to the procedure described for step 93.2 but using the product from step 111.4. The product was purified by flash chromatography (heptane/EtOAc, 100:0→1:1). The residue was then triturated in diisopropylether, filtered and concentrated. $t_R$: 1.63 min (LC-MS 2); ESI-MS: 650.3/652.3/654.3 [M+H]$^+$ (LC-MS 2).

Step 111.4: 2-Bromo-5-[(5-chloro-2-methyl-phenylamino)-(4-chloro-phenyl)-methyl]-1-((R)-1-methyl-2-triisopropylsilanyloxy-ethyl)-1H-imidazole-4-carboxylic acid

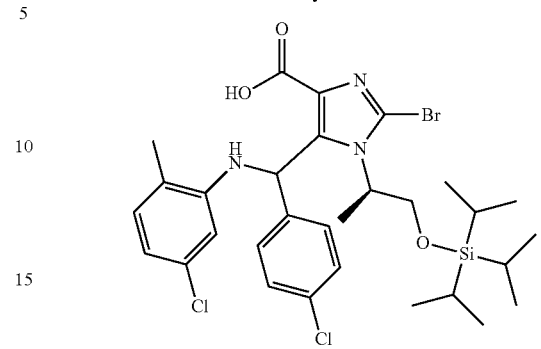

The title compound was prepared in analogy to the procedure described for step 93.2 but using the product from step 111.5. The product was purified by flash chromatography (CH$_2$Cl$_2$/MeOH, 20:1). $t_R$: 1.67 min (LC-MS 2); ESI-MS: 668.4/670.4/672.4 [M+H]$^+$ (LC-MS 2).

Step 111.5: 2-Bromo-5-[(5-chloro-2-methyl-phenylamino)-(4-chloro-phenyl)-methyl]-1-((R)-1-methyl-2-thisopropylsilanyloxy-ethyl)-1H-imidazole-4-carboxylic acid ethyl ester

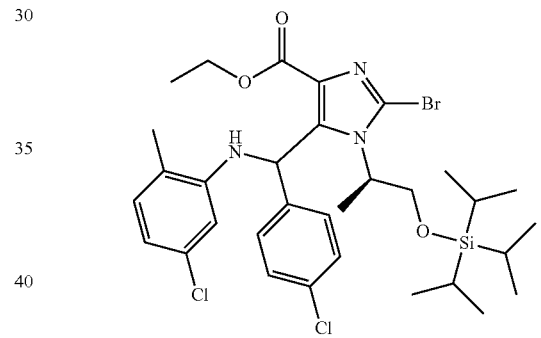

The title compound was prepared in analogy to the procedure described for step 93.3 but using the product from step 111.6 and 5-chloro-2-methylaniline. $t_R$: 1.80 min (LC-MS 2); ESI-MS: 696.4/698.4/700.4 [M+H]$^+$ (LC-MS 2); R$_f$=0.33 (heptane/EtOAc, 4:1).

Step 111.6: 2-Bromo-5-[(4-chloro-phenyl)-hydroxy-methyl]-14(R)-1-methyl-2-triisopropylsilanyloxy-ethyl)-1H-imidazole-4-carboxylic acid ethyl ester

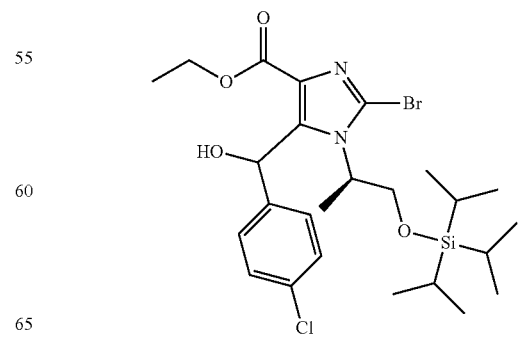

The title compound was prepared in analogy to the procedure described for intermediate B but using the product from step 111.7. The reaction was quenched with a 1M aqueous NH₄Cl solution and extracted with EtOAc. The organic layer was dried (Na₂SO₄), filtered and concentrated. The product was purified by flash chromatography (heptane/EtOAc, 100:0→60:40). $t_R$: 1.63 min (LC-MS 2); ESI-MS: 573.3/575.3 [M+H]⁺ (LC-MS 2); $R_f$=0.18 (heptane/EtOAc, 3:1).

Step 111.7: 2-Bromo-1-((R)-1-methyl-2-triisopropylsilanyloxy-ethyl)-1H-imidazole-4-carboxylic acid ethyl ester

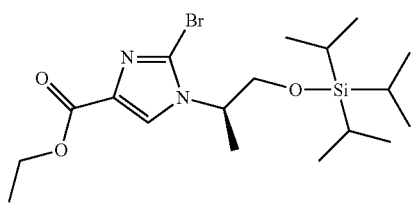 [SMILES: CCOC(=O)c1cn([C@H](C)CO[Si](C(C)C)(C(C)C)C(C)C)c(Br)n1]

To a solution of the product from step 111.8 (1.5 g, 5.5 mmol) in CH₂Cl₂ was added TIPS-Cl (1.8 mL, 8.3 mmol) and imidazole (622 mg, 9.1 mmol) and the reaction mixture was stirred at rt for 2 h. The mixture was poured into a 1M citric acid solution and extraction with CH₂Cl₂. The organic layer was washed with brine, dried (Na₂SO₄), filtered and concentrated. The product was purified by flash chromatography (heptane/EtOAc, 4:1). $t_R$: 1.50 min (LC-MS 2); ESI-MS: 433.4/435.3 [M+H]⁺ (LC-MS 2); $R_f$=0.17 (heptane/MeOH, 3:1).

Step 111.8: 2-Bromo-1-((R)-2-hydroxy-1-methyl-ethyl)-1H-imidazole-4-carboxylic acid ethyl ester

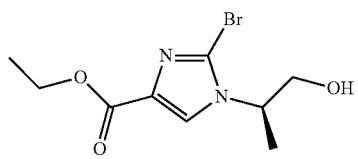

The title compound was prepared in analogy to the procedure described for intermediate A but using the product from step 111.9. The reaction was performed at rt for 70 h. The product was purified by flash chromatography (CH₂Cl₂/MeOH, 95:5). $t_R$: 0.61 min (LC-MS 2); ESI-MS: 277.0/279.1 [M+H]⁺ (LC-MS 2); $R_f$=0.27 (CH₂Cl₂/MeOH, 95:5).

Step 111.9: 1-((R)-2-Hydroxy-1-methyl-ethyl)-1H-imidazole-4-carboxylic acid ethyl ester

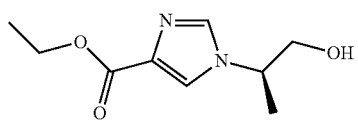

A solution of the product from step A2 (18.1 g, 100 mmol) and D-alaminol (17.3 g, 230 mmol) was stirred at 70° C. for 6 h in a sealed tube. The reaction mixture was concentrated and purified by flash chromatography (CH₂Cl₂/MeOH, 95:5). $t_R$: 0.49 min (LC-MS 2); ESI-MS: 199.1 [M+H]⁺ (LC-MS 2); $R_f$=0.11 (CH₂Cl₂/MeOH, 95:5).

Example 112

5-(3-Chloro-4-fluoro-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one

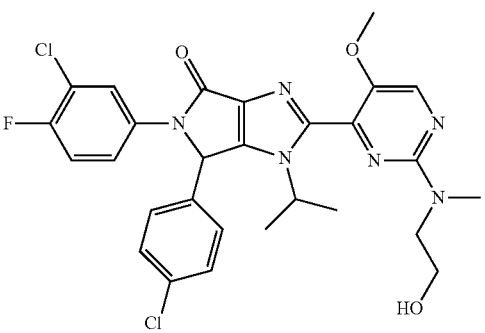 [SMILES: COc1cnc(N(C)CCO)nc1-c1nc2c(n1C(C)C)C(c1ccc(Cl)cc1)N(c1ccc(F)c(Cl)c1)C2=O]

To a solution of the product from step 112.1 (50 mg, 0.05 mmol) in NMP (0.6 mL) was added N-methyl ethanolamine (0.5 mL, 0.05 mmol) and the mixture was stirred at 90° C. for 4 h in a sealed tube. The reaction mixture as dissolved in toluene and H₂O and the phases were separated. The organic layer was dried (Na₂SO₄), filtered and concentrated. The product was purified by SFC chromatography (Column Diol, 250×30 mm, 5 µm, flow 100 mL/min, grad 18-23% over 6 min) to give the title compound. $t_R$: 1.14 min (LC-MS 2); ESI-MS: 585.3/587.3 [M+H]⁺ (LC-MS 2).

Step 112.1: 5-(3-Chloro-4-fluoro-phenyl)-2-(2-chloro-5-methoxy-pyrimidin-4-yl)-6-(4-chloro-phenyl)-1-isopropyl-5,6-dihydro-1H-pyrrolo[3,4-d]imidazol-4-one

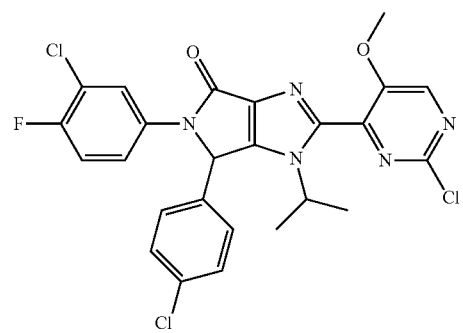 [SMILES: COc1cnc(Cl)nc1-c1nc2c(n1C(C)C)C(c1ccc(Cl)cc1)N(c1ccc(F)c(Cl)c1)C2=O]

The title compound was prepared in analogy to the procedure described for step 96.1 but using intermediate Q. The reaction was performed at 85° C. for 1 h. The product was purified by flash chromatography (CH₂Cl₂/MeOH, 100:0→90:10). $t_R$: 1.24 min (LC-MS 2); ESI-MS: 546.4/548.4 [M+H]⁺ (LC-MS 2).

Example 113

5-(5-Chloro-2-methyl-phenyl)-6-(4-chloro-phenyl)-2-(2-dimethylamino-4-methoxy-pyrimidin-5-yl)-1-((R)-2-hydroxy-1-methyl-ethyl)-5,6-dihydro-1H-pyrrolo[3,4-d]imidazol-4-one

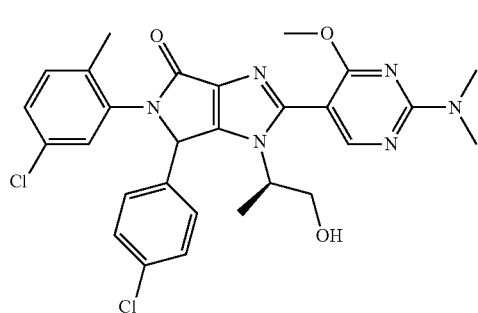 [SMILES: COc1nc(N(C)C)ncc1-c1nc2c(n1[C@H](C)CO)C(c1ccc(Cl)cc1)N(c1cc(Cl)ccc1C)C2=O]

The title compound was prepared in analogy to the procedure described for step 111.2 but using the product from step 113.1. The product was purified by flash chromatography (CH$_2$Cl$_2$/MeOH, 99:1→80:20). t$_R$: 1.13 min (LC-MS 2); ESI-MS: 567.1/569.2 [M+H]$^+$ (LC-MS 2); R$_f$=0.12 (CH$_2$Cl$_2$/MeOH, 20:1).

Step 113.1: 5-(5-Chloro-2-methyl-phenyl)-6-(4-chloro-phenyl)-2-(2-dimethylamino-4-methoxy-pyrimidin-5-yl)-1-((R)-1-methyl-2-triisopropylsilanyloxy-ethyl)-5,6-dihydro-1H-pyrrolo[3,4-d]imidazol-4-one

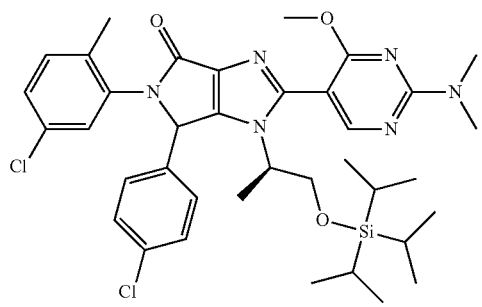 [SMILES: COc1nc(N(C)C)ncc1-c1nc2c(n1[C@H](C)CO[Si](C(C)C)(C(C)C)C(C)C)C(c1ccc(Cl)cc1)N(c1cc(Cl)ccc1C)C2=O]

The title compound was prepared in analogy to the procedure described for example 29 but using the product from step 111.3 and intermediate W. The product was purified by flash chromatography (heptane/EtOAc, 100:0→0:100). t$_R$: 1.65 min (LC-MS 2); ESI-MS: 725.3 [M+H]$^+$ (LC-MS 2); R$_f$=0.12 (heptane/EtOAc, 1:2).

Example 114

5-(3-Chloro-2-fluoro-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one

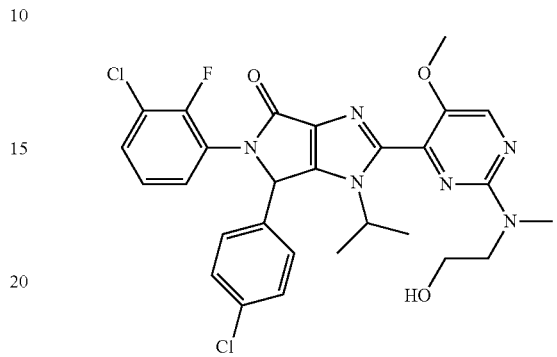

The title compound was prepared in analogy to the procedure described for example 112 but using the product from step 96.1. The product was purified by SFC chromatography (Column Diol, 250×30 mm, 5 µm, flow 100 mL/min, grad 17-22% over 6 min) to give the title compound. t$_R$: 1.12 min (LC-MS 2); ESI-MS: 585.3/587.3 [M+H]$^+$ (LC-MS 2).

Example 115

5-(5-Chloro-2-methyl-phenyl)-2-(2,4-dimethoxy-pyrimidin-5-yl)-1-isopropyl-6-(4-methyl-cyclohexyl)-5,6-dihydro-1H-pyrrolo[3,4-d]imidazol-4-one

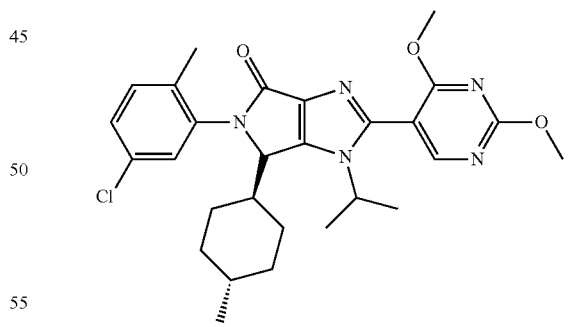

The title compound was prepared in analogy to the procedure described for example 29 but using the product from step 115.1 and 2,4-dimethoxypyrimidin-5-ylboronic acid. The residue was purified by preparative HPLC (Column: Sunfire C18, 30×100 mm, 5 µm. Flow: 30 mL/min. Gradient 5-100% B in 20 min; A=0.1% TFA in water, B=CH$_3$CN). t$_R$: 1.31 min (LC-MS 2); ESI-MS: 524.4/526.4 [M+H]$^+$ (LC-MS 2).

Step 115.1: 2-Bromo-5-(5-chloro-2-methyl-phenyl)-1-isopropyl-6-(4-methyl-cyclohexyl)-5,6-dihydro-1H-pyrrolo[3,4-d]imidazol-4-one

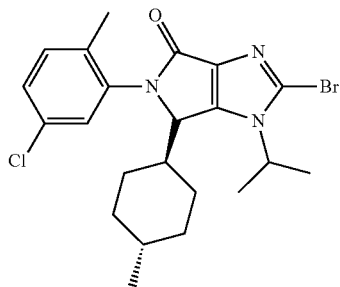 [SMILES: Cc1ccc(Cl)cc1N1C(=O)c2nc(Br)n(C(C)C)c2C1[C@H]1CC[C@H](C)CC1]

The title compound was prepared in analogy to the procedure described for step 91.1 but using the product from step 115.2. The reaction mixture was poured into a saturated aqueous NaHCO$_3$ solution and extracted with EtOAc. The organic layers were washed with a saturated aqueous NaHCO$_3$ solution and brine, dried (Na$_2$SO$_4$), filtered and concentrated. The residue was lyophilized to give the title compound as a white solid. $t_R$: 1.35 min (LC-MS 2); ESI-MS: 464.3/466.2 [M+H]$^+$ (LC-MS 2).

Step 115.2: 2-Bromo-5-[(5-chloro-2-methyl-phenylamino)-(4-methyl-cyclohexyl-1)-methyl]-1-isopropyl-1H-imidazole-4-carboxylic acid

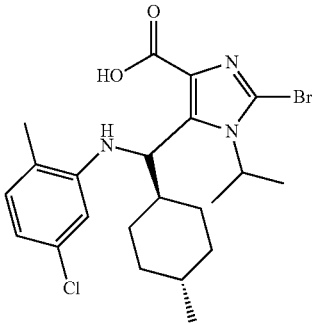 [SMILES: Cc1ccc(Cl)cc1NC(c1c(C(=O)O)nc(Br)n1C(C)C)[C@H]1CC[C@H](C)CC1]

The title compound was prepared in analogy to the procedure described for step E1 but using the product from step 115.3. The product was purified by flash chromatography (heptane/EtOAc, 100:0→70:30) to give the title compound. $t_R$: 1.34 min (LC-MS 2); ESI-MS: 482.2/484.2 [M+H]$^+$ (LC-MS 2).

Step 115.3: 2-Bromo-5-[(5-chloro-2-methyl-phenylamino)-(4-methyl-cyclohexyl)-methyl]-1-isopropyl-1H-imidazole-4-carboxylic acid ethyl ester

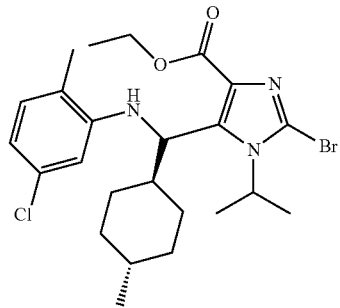 [SMILES: CCOC(=O)c1nc(Br)n(C(C)C)c1C(Nc1cc(Cl)ccc1C)[C@H]1CC[C@H](C)CC1]

The title compound was prepared in analogy to the procedure described for step 93.3 but using the product from step 115.4 and 5-chloro-2-methylaniline. The product was purified by flash chromatography (heptane/EtOAc, 100:0→70:30) to give the title compound. $t_R$: 1.55 min (LC-MS 2); ESI-MS: 510.3/512.3 [M+H]$^+$ (LC-MS 2).

Step 115.4: 2-Bromo-5-[hydroxy-(4-methyl-cyclohexyl)-methyl]-1-isopropyl-1H-imidazole-4-carboxylic acid ethyl ester

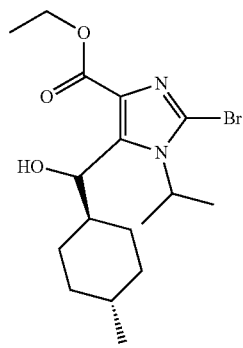 [SMILES: CCOC(=O)c1nc(Br)n(C(C)C)c1C(O)[C@H]1CC[C@H](C)CC1]

The title compound was prepared in analogy to the procedure described for intermediate B but using the product from step 115.5. The product was purified by flash chromatography (heptane/EtOAc, 100:0→70:30) to give the title compound. $t_R$: 1.22 min (LC-MS 2); ESI-MS: 387.2/389.2 [M+H]$^+$ (LC-MS 2).

Step 115.5: 4-Methyl-cyclohexanecarbaldehyde

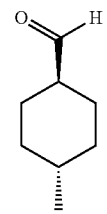

A mixture of the compound prepared in step 115.6 (8.8 g, 54.7 mmol) and Pd/C 10% (5.8 g, 54.7 mmol) in THF (150 mL) and 2,6-lutidine (11.7 g, 109 mmol) was stirred for 15.5 h at rt, under a hydrogen atmosphere. The reaction mixture was filtered through a pad of celite. The crude was dissolved in CH$_2$Cl$_2$ and extracted with 1N HCl then with a saturated aqueous NaHCO$_3$ solution. The organic layer was dried (Na$_2$SO$_4$), filtered and concentrated.

Step 115.6: 4-Methyl-cyclohexanecarbonyl chloride

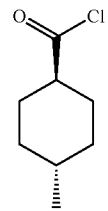

To a solution of trans-4-methyl-1-cyclohexane carboxylic acid (8.2 g, 56.5 mmol) in CH$_2$Cl$_2$ (350 mL) at 0° C. was added DMF (44 µl, 0.6 mmol) and oxalyl chloride (11.5 g, 90.0 mmol) dropwise. The reaction mixture was stirred at rt for 18 h. The reaction mixture was concentrated. The product was used without further purification.

Example 116

4-(4-Chloro-2-methyl-phenyl)-5-(5-chloro-2-methyl-phenyl)-2-(2,4-dimethoxy-pyrimidin-5-yl)-3-isopropyl-6-oxo-3,4,5,6-tetrahydro-pyrrolo[3,4-d]imidazole-4-carboxylic acid ethyl ester

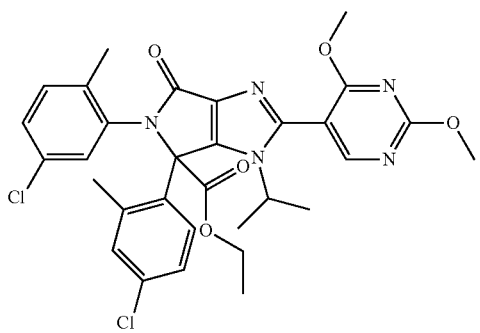 [SMILES: CCOC(=O)C1(c2ccc(Cl)cc2C)c2c(nc(-c3cnc(OC)nc3OC)n2C(C)C)C(=O)N1c1cc(Cl)ccc1C]

To a solution of the product from example 76 (100 mg, 0.2 mmol) in THF (3 mL) at −78° C. was added NaHMDS (181 µL, 0.2 mmol) and the mixture was stirred at −78° C. for 15 min. Ethyl carbonochloridate (86 µL, 0.9 mmol) was added at −78° C. and the mixture was allowed to warm up to rt and stirred for 1 h. The reaction mixture was quenched with a saturated aqueous NH$_4$Cl solution, then was diluted in EtOAc and extracted with brine. The organic layer was dried (Na$_2$SO$_4$), filtered and concentrated. The residue was purified by preparative HPLC (Column: Sunfire C18, 30×100 mm, 5 µm. Flow: 30 mL/min. Gradient 5-100% B in 20 min; A=0.1% TFA in water, B=CH$_3$CN). t$_R$: 1.39 min (LC-MS 2); ESI-MS: 624.4/626.4 [M+H]$^+$ (LC-MS 2).

Example 117

5-(5-Chloro-2-methyl-phenyl)-6-(4-chloro-phenyl)-2-(2,4-dimethoxy-pyrimidin-5-yl)-1-((R)-2-hydroxy-1-methyl-ethyl)-5,6-dihydro-1H-pyrrolo[3,4-d]imidazol-4-one

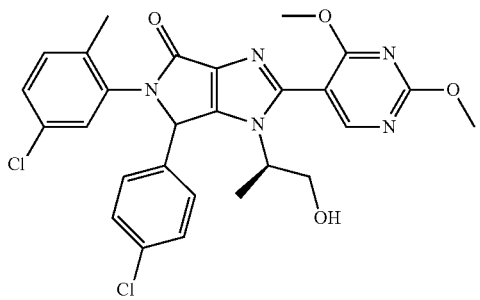 [SMILES: COc1ncc(-c2nc3c(n2[C@H](C)CO)C(c2ccc(Cl)cc2)N(c2cc(Cl)ccc2C)C3=O)c(OC)n1]

The title compound was prepared in analogy to the procedure described for step 111.2 but using the product from step 117.1. The product was purified by flash chromatography (heptane//MeOH, 80:19:1→8:88:4). t$_R$: 1.06 min (LC-MS 2); ESI-MS: 554.3/556.3 [M+H]$^+$ (LC-MS 2); R$_f$=0.05 (CH$_2$Cl$_2$/MeOH, 20:1).

Step 117.1: 5-(5-Chloro-2-methyl-phenyl)-6-(4-chloro-phenyl)-2-(2,4-dimethoxy-pyrimidin-5-yl)-1-((R)-1-methyl-2-triisopropylsilanyloxy-ethyl)-5,6-dihydro-1H-pyrrolo[3,4-d]imidazol-4-one

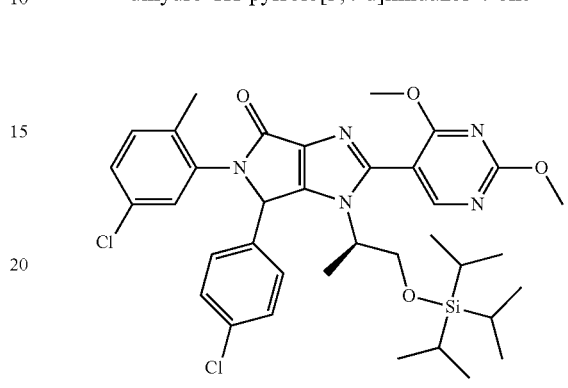

The title compound was prepared in analogy to the procedure described for example 29 but using the product from step 111.3 and 2,4-dimethoxypyrimidin-5-ylboronic acid. The product was purified by flash chromatography (heptane/EtOAc, 70:30→0:100). t$_R$: 1.58 min (LC-MS 2); ESI-MS: 710.5/712.5 [M+H]$^+$ (LC-MS 2); R$_f$=0.33 (heptane/EtOAc, 1:4).

Example 118

4-[2-(2-Amino-4-methoxy-pyrimidin-5-yl)-6-(4-chloro-phenyl)-1-isopropyl-4-oxo-4,6-dihydro-1H-pyrrolo[3,4-d]imidazol-5-yl]-3-methyl-benzonitrile

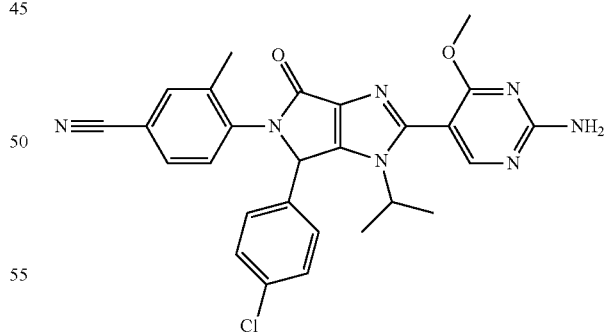

The title compound was prepared in analogy to the procedure described for example 1 but using the product from step 94.2 and intermediate U. The residue was purified by preparative HPLC (Waters Sun Fire C18, 30×100 mm, 5 µm; 0.1% TFA-water/acetonitrile; gradient acetonitrile 20-40% in 16 min) to give the title compound. t$_R$: 1.01 min (LC-MS 2); ESI-MS: 514.3/516.3 [M+H]$^+$ (LC-MS 2).

Example 119

4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-3-methyl-benzonitrile

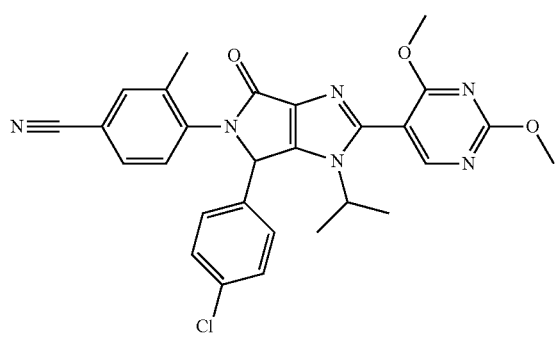 [SMILES: COc1ncc(-c2nc3c(n2C(C)C)C(c2ccc(Cl)cc2)N(c2ccc(C#N)cc2C)C3=O)c(OC)n1]

The title compound was prepared in analogy to the procedure described for example 1 but using the product from step 94.2 and 2,4-dimethoxypyrimidin-5-ylboronic acid. The residue was purified by preparative HPLC (Waters Sun Fire C18, 30×100 mm, 5 μm; 0.1% TFA-water/acetonitrile; gradient acetonitrile 40-60% in 16 min) to give the title compound. $t_R$: 1.12 min (LC-MS 3); ESI-MS: 529.2/531.3 [M+H]$^+$ (LC-MS 3).

Example 120

4-Chloro-2-[6-(4-chloro-phenyl)-2-(2,4-dimethoxy-pyrimidin-5-yl)-1-isopropyl-4-oxo-4,6-dihydro-1H-pyrrolo[3,4-d]imidazol-5-yl]-benzonitrile

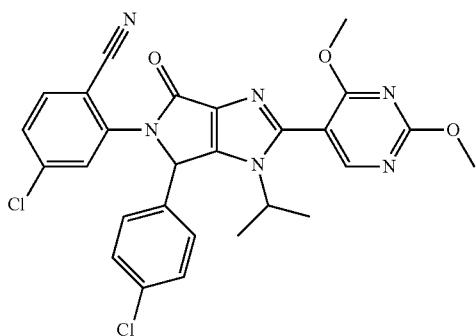 [SMILES: COc1ncc(-c2nc3c(n2C(C)C)C(c2ccc(Cl)cc2)N(c2cc(Cl)ccc2C#N)C3=O)c(OC)n1]

The title compound was prepared in analogy to the procedure described for example 1 but using the product from step 120.1 and 2,4-dimethoxypyrimidin-5-ylboronic acid. The residue was purified by SFC chromatography (Column Diol, 250×30 mm, 5 μm, flow 100 mL/min, grad 15-20% over 6 min) to give the title compound. $t_R$: 1.15 min (LC-MS 2); ESI-MS: 549.2/551.2 [M+H]$^+$ (LC-MS 2).

Step 120.1: 2-[2-Bromo-6-(4-chloro-phenyl)-1-isopropyl-4-oxo-4,6-dihydro-1H-pyrrolo[3,4-d]imidazol-5-yl]-4-chloro-benzonitrile

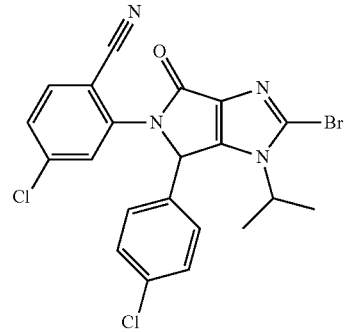 [SMILES: CC(C)n1c(Br)nc2c1C(c1ccc(Cl)cc1)N(c1cc(Cl)ccc1C#N)C2=O]

The title compound was prepared in analogy to the procedure described for step 91.1 but using the product from step 120.2. The product was triturated in Et$_2$O and the resulting suspension was filtered to give the title compound as a yellow solid. $t_R$: 1.17 min (LC-MS 2); ESI-MS: 489.1/491.2 [M+H]$^+$ (LC-MS 2).

Step 120.2: 2-Bromo-5-[(5-chloro-2-cyano-phenylamino)-(4-chloro-phenyl)-methyl]-1-isopropyl-1H-imidazole-4-carboxylic acid

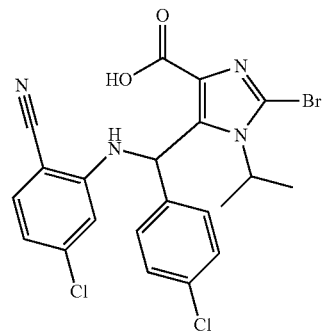 [SMILES: CC(C)n1c(Br)nc(C(=O)O)c1C(Nc1cc(Cl)ccc1C#N)c1ccc(Cl)cc1]

The title compound was prepared in analogy to the procedure described for step E1 but using the product from step 120.3. $t_R$: 1.17 min (LC-MS 2); ESI-MS: 507.2/509.1/511.1 [M+H]$^+$ (LC-MS 2).

Step 120.3: 2-Bromo-5-[(5-chloro-2-cyano-phenylamino)-(4-chloro-phenyl)-methyl]-1-isopropyl-1H-imidazole-4-carboxylic acid ethyl ester

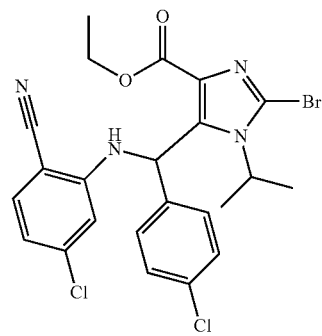 [SMILES: CCOC(=O)c1nc(Br)n(C(C)C)c1C(Nc1cc(Cl)ccc1C#N)c1ccc(Cl)cc1]

The title compound was prepared in analogy to the procedure described for step E2 but using intermediate B and 2-amino-4-chlorobenzonitrile. The reaction mixture was stirred at rt for 20 h. The mixture was extracted with HCl 1M and with a saturated aqueous NaHCO$_3$ solution. The organic layers were dried (Na$_2$SO$_4$), filtered and concentrated. The product was triturated in Et$_2$O, the suspension was filtered and the solid was dried in HV. $t_R$: 1.36 min (LC-MS 2); ESI-MS: 535.2/537.2/539.1 [M+H]$^+$ (LC-MS 2).

Example 121

5-(5-Chloro-2-methyl-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one

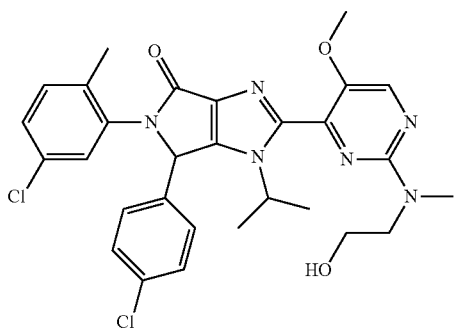 [SMILES: COc1cnc(N(C)CCO)nc1-c1nc2c(n1C(C)C)C(c1ccc(Cl)cc1)N(c1cc(Cl)ccc1C)C2=O]

The title compound was prepared in analogy to the procedure described for example 112 but using the product from step 121.1. The product was purified by SFC chromatography (Column 2-EP & 4-EP, 250×30 mm, 5 μm, flow 100 mL/min, grad 17-22% over 6 min) to give the title compound. $t_R$: 1.15 min (LC-MS 2); ESI-MS: 581.3/583.3 [M+H]$^+$ (LC-MS 2).

Step 121.1: 2-(2-Chloro-5-methoxy-pyrimidin-4-yl)-5-(5-chloro-2-methyl-phenyl)-6-(4-chloro-phenyl)-1-isopropyl-5,6-dihydro-1H-pyrrolo[3,4-d]imidazol-4-one

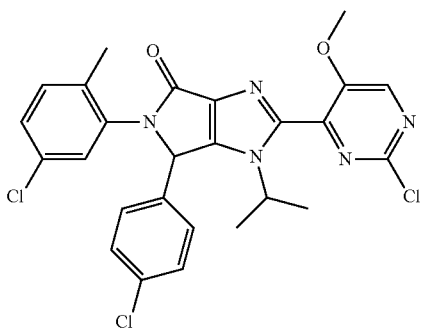 [SMILES: COc1cnc(Cl)nc1-c1nc2c(n1C(C)C)C(c1ccc(Cl)cc1)N(c1cc(Cl)ccc1C)C2=O]

The title compound was prepared in analogy to the procedure described for step 96.1 but using intermediate E. $t_R$: 1.25 min (LC-MS 2); ESI-MS: 542.2/544.2/546.3 [M+H]$^+$ (LC-MS 2).

Example 122

5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one

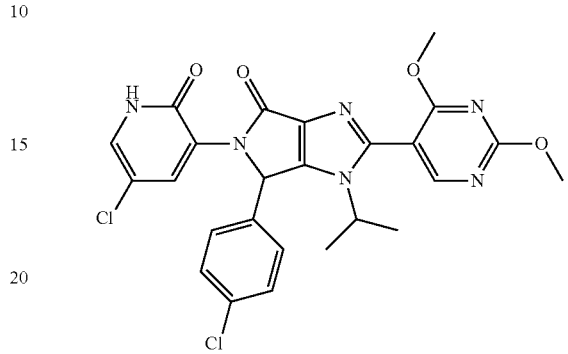

The title compound was prepared in analogy to the procedure described for example 97 but using the product from step 122.1. The mixture was extracted with CH$_2$Cl$_2$. The organic layer was washed with H$_2$O and brine, dried (Na$_2$SO$_4$), filtered and concentrated. The residue was purified by flash chromatography (CH$_2$Cl$_2$/MeOH, 95:5). The residue was triturated in Et$_2$O to give the title compound. $t_R$: 0.94 min (LC-MS 2); ESI-MS: 541.3/543.3 [M+H]$^+$ (LC-MS 2).

Step 122.1: 5-[5-Chloro-1-(4-methoxy-benzyl)-2-oxo-1,2-dihydro-pyridin-3-yl]-6-(4-chloro-phenyl)-2-(2,4-dimethoxy-pyrimidin-5-yl)-1-isopropyl-5,6-dihydro-1H-pyrrolo[3,4-d]imidazol-4-one

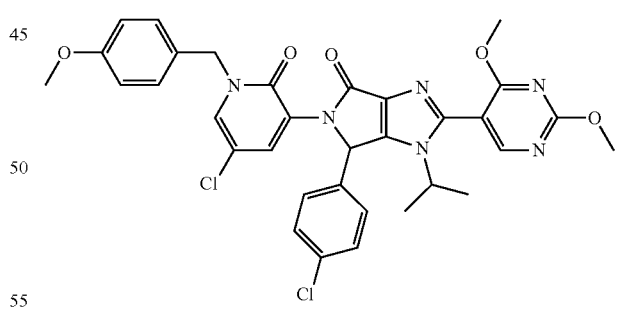

The title compound was prepared in analogy to the procedure described for example 29 but using the product from step 122.2 and 2,4-dimethoxypyrimidin-5-ylboronic acid. The reaction was performed at 110° C. for 30 min. The product was purified by flash chromatography (CH$_2$Cl$_2$/EtOAc, 1:1 and washed with CH$_2$Cl$_2$/MeOH, 95:5) The residue was purified by SFC chromatography (Column 2-ethyl pyridine, 250× 30 mm, 5 μm, flow 100 mL/min, grad 13-18%) to give the title compound. $t_R$: 1.16 min (LC-MS 2); ESI-MS: 661.4/663.3 [M+H]$^+$ (LC-MS 2).

Step 122.2: 2-Bromo-5-[5-chloro-1-(4-methoxy-benzyl)-2-oxo-1,2-dihydro-pyridin-3-yl]-6-(4-chloro-phenyl)-1-isopropyl-5,6-dihydro-1H-pyrrolo[3,4-d]imidazol-4-one

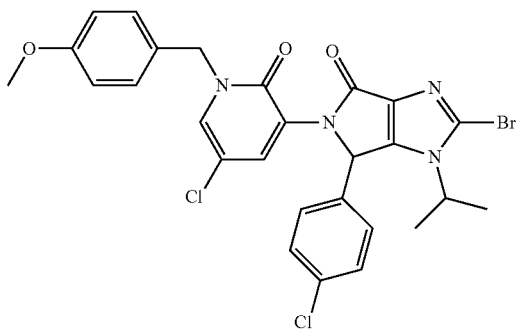 [SMILES: COc1ccc(Cn2cc(Cl)cc(N3C(=O)c4nc(Br)n(C(C)C)c4C3c3ccc(Cl)cc3)c2=O)cc1]

The title compound was prepared in analogy to the procedure described for step 91.1 but using the product from step 122.3. The residue was triturated in Et$_2$O to afford the title compound. $t_R$: 1.20 min (LC-MS 2); ESI-MS: 601.2/603.3/605.3 [M+H]$^+$ (LC-MS 2).

Step 122.3: 2-Bromo-5-[[5-chloro-1-(4-methoxy-benzyl)-2-oxo-1,2-dihydro-pyridin-3-ylamino]-(4-chloro-phenyl)-methyl]-1-isopropyl-1H-imidazole-4-carboxylic acid

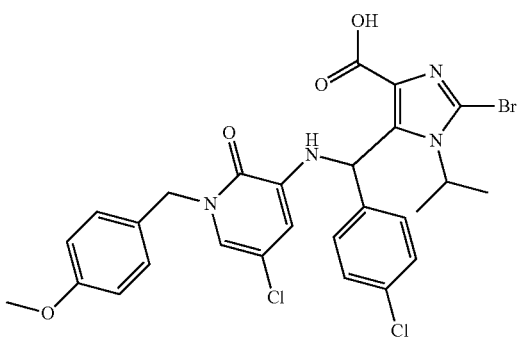 [SMILES: COc1ccc(Cn2cc(Cl)cc(NC(c3ccc(Cl)cc3)c3c(C(=O)O)nc(Br)n3C(C)C)c2=O)cc1]

The title compound was prepared in analogy to the procedure described for step E1 but using the product from step 122.4. The residue was triturated in Et$_2$O to afford the title compound. $t_R$: 1.20 min (LC-MS 2); ESI-MS: 619.3/621.3/623.3 [M+H]$^+$ (LC-MS 2).

Step 122.4: 2-Bromo-5-[[5-chloro-1-(4-methoxy-benzyl)-2-oxo-1,2-dihydro-pyridin-3-ylamino]-(4-chloro-phenyl)-methyl]-1-isopropyl-1H-imidazole-4-carboxylic acid ethyl ester

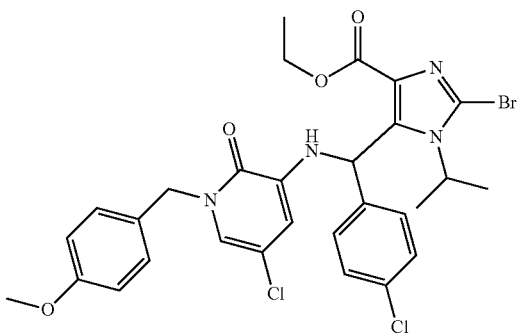 [SMILES: CCOC(=O)c1nc(Br)n(C(C)C)c1C(Nc1cc(Cl)cn(Cc2ccc(OC)cc2)c1=O)c1ccc(Cl)cc1]

The title compound was prepared in analogy to the procedure described for step E2 but using the product from step 122.5. After workup, the residue was triturated in EtOAc to afford the title compound. $t_R$: 1.39 min (LC-MS 2); ESI-MS: 647.2/649.3/651.2 [M+H]$^+$ (LC-MS 2).

Step 122.5: 3-Amino-5-chloro-1-(4-methoxy-benzyl)-1H-pyridin-2-one

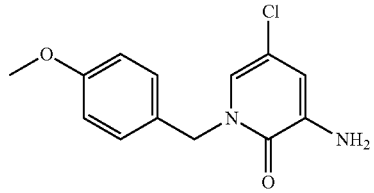

The title compound was prepared in analogy to the procedure described for step 100.4 but using the product from step 122.6. The residue was purified by flash chromatography (hexane/EtOAc, 1:1) to afford the title compound. $t_R$: 0.86 min (LC-MS 2); ESI-MS: 265.2 [M+H]$^+$ (LC-MS 2).

Step 122.6: 5-Chloro-1-(4-methoxy-benzyl)-3-nitro-1H-pyridin-2-one

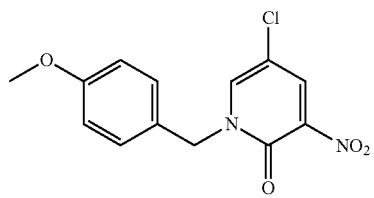 [SMILES: COc1ccc(Cn2cc(Cl)cc([N+](=O)[O-])c2=O)cc1]

The title compound was prepared in analogy to the procedure described for step 100.5 but using 4-methoxybenzyl chloride. The residue was triturated in Et$_2$O to give the title compound. $t_R$: 0.92 min (LC-MS 2); ESI-MS: 295.2 [M+H]$^+$ (LC-MS 2).

Example 123

4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid methylamide

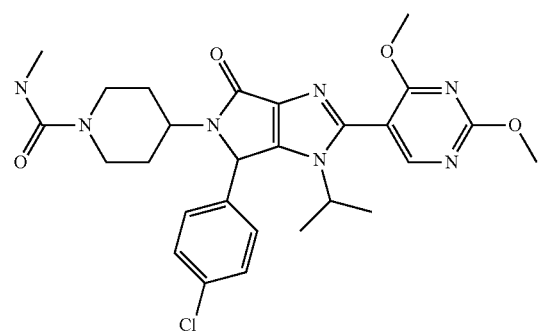 [SMILES: CNC(=O)N1CCC(N2C(=O)c3nc(-c4cnc(OC)nc4OC)n(C(C)C)c3C2c2ccc(Cl)cc2)CC1]

To a solution of the product from step 123.1 in CH$_2$Cl$_2$ (1.2 mL) in a microwave vial was added Et$_3$N (88 μL, 0.6 mmol) and methyl isocyanate (18 mg, 0.3 mmol) and the mixture was stirred at rt for 1.5 h. 4-nitrophenyl chloroformate (59 mg, 0.3 mmol) was added and the mixture was stirred at rt for 30 min. Methylamine 2M in THF (837 μL, 1.7 mmol) was added and the mixture was stirred at rt for 18 h and at 50° C. for 1.5 h. The reaction mixture was diluted with EtOAc and extracted with a saturated aqueous NaHCO₃ solution. The organic layer was dried (MgSO₄), filtered and concentrated. The product was purified by preparative HPLC (Waters Sun Fire C18, 30×100 mm, 5 μm; 0.1% TFA-water/acetonitrile; gradient acetonitrile 5-100% in 20 min). The residue was purified by flash chromatography (CH₂Cl₂/MeOH, 100:0→90:10) to give the title compound as a white solid. $t_R$: 0.90 min (LC-MS 2); ESI-MS: 554.6/556.3 [M+H]⁺ (LC-MS 2).

Step 123.1: 6-(4-Chloro-phenyl)-2-(2,4-dimethoxy-pyrimidin-5-yl)-1-isopropyl-5-piperidin-4-yl-5,6-dihydro-1H-pyrrolo[3,4-d]imidazol-4-one

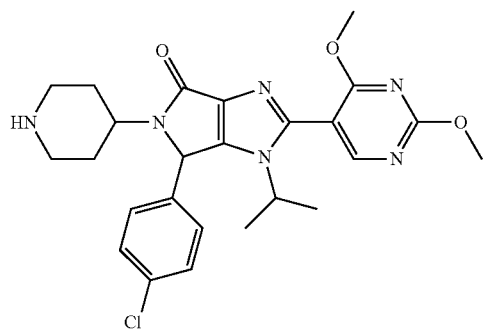 [SMILES: COc1ncc(-c2nc3c(n2C(C)C)C(c2ccc(Cl)cc2)N(C2CCNCC2)C3=O)c(OC)n1]

To a solution of the product from step 123.2 (500 mg, 0.8 mmol) was added a 4M HCl solution in dioxane (2 mL) and the mixture was stirred at rt for 4.5 h. At 0° C., the pH was adjusted to 7-8 with a saturated aqueous NaHCO₃ solution. The aqueous layer was saturated with NaCl and was extracted with THF/AcOEt 1:3. The organic layer was dried (MgSO₄), filtered and concentrated to afford the title compound. $t_R$: 0.76 min (LC-MS 2); ESI-MS: 497.3/499.4 [M+H]⁺ (LC-MS 2).

Step 123.2: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid tert-butyl ester

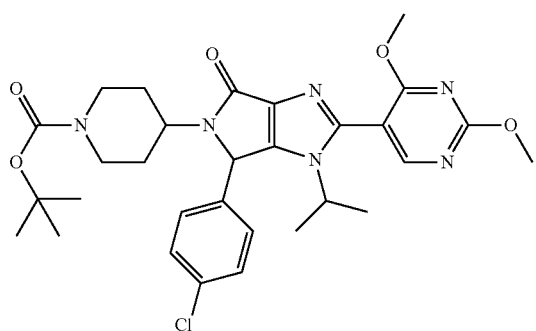 [SMILES: COc1ncc(-c2nc3c(n2C(C)C)C(c2ccc(Cl)cc2)N(C2CCN(C(=O)OC(C)(C)C)CC2)C3=O)c(OC)n1]

The title compound was prepared in analogy to the procedure described for step 97.1 but using the product from step 123.3. The residue was purified by flash chromatography (CH₂Cl₂/EtOAc, 80:20→0:100). A second flash chromatography was performed (CH₂Cl₂/MeOH, 100:0→90:10). The residue was purified by preparative chromatography (C18) to affort the title compound. $t_R$: 1.18 min (LC-MS 2); ESI-MS: 597.4/599.3 [M+H]⁺ (LC-MS 2).

Step 123.3: 4-[2-Bromo-6-(4-chloro-phenyl)-1-isopropyl-4-oxo-4,6-dihydro-1H-pyrrolo[3,4-d]imidazol-5-yl]-piperidine-1-carboxylic acid tert-butyl ester

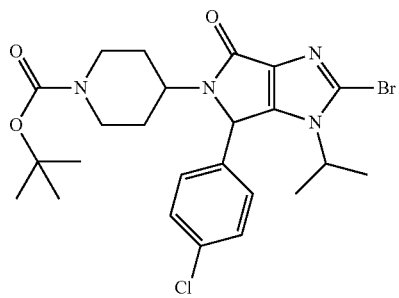 [SMILES: CC(C)n1c(Br)nc2c1C(c1ccc(Cl)cc1)N(C1CCN(C(=O)OC(C)(C)C)CC1)C2=O]

The title compound was prepared in analogy to the procedure described for step 93.1 but using the product was step 123.4. The crude was purified by flash chromatography (CH₂Cl₂/EtOAc, 80:20→0:100). $t_R$: 1.20 min (LC-MS 2); ESI-MS: 537.3/539.3 [M+H]⁺ (LC-MS 2).

Step 123.4: 4-{[(2-Bromo-5-carboxy-3-isopropyl-3H-imidazol-4-yl)-(4-chloro-phenyl)-methyl]-amino}-piperidine-1-carboxylic acid tert-butyl ester

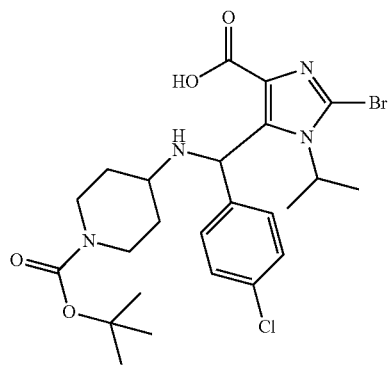 [SMILES: CC(C)n1c(Br)nc(C(=O)O)c1C(NC1CCN(C(=O)OC(C)(C)C)CC1)c1ccc(Cl)cc1]

The title compound was prepared in analogy to the procedure described for step E1 but using the product from step 123.5. $t_R$: 0.94 min (LC-MS 2); ESI-MS: 555.3/557.4 [M+H]⁺ (LC-MS 2).

Step 123.5: 4-{[(2-Bromo-5-ethoxycarbonyl-3-isopropyl-3H-imidazol-4-yl)-(4-chloro-phenyl)-methyl]-amino}-piperidine-1-carboxylic acid tert-butyl ester

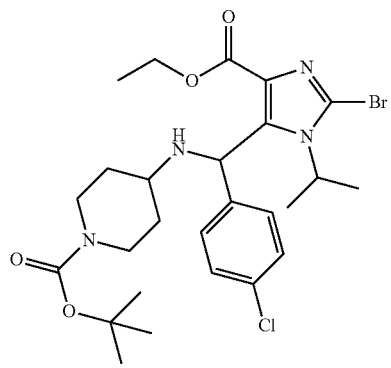 [SMILES: CCOC(=O)c1nc(Br)n(C(C)C)c1C(NC1CCN(C(=O)OC(C)(C)C)CC1)c1ccc(Cl)cc1]

The title compound was prepared in analogy to the procedure described for step 93.3 but using intermediate B and N-(4-aminocyclohexyl)pivalamide. The product was purified by flash chromatography (heptane/EtOAc, 80:20→0:100). $t_R$: 1.41 min (LC-MS 2); ESI-MS: 583.3/585.3 [M+H]$^+$ (LC-MS 2).

Example 124

4-[5-(5-Chloro-1-methyl-2-oxo-1,2-dihydro-pyridin-3-yl)-2-(2,4-dimethoxy-pyrimidin-5-yl)-3-isopropyl-6-oxo-3,4,5,6-tetrahydro-pyrrolo[3,4-d]imidazol-4-yl]-benzonitrile

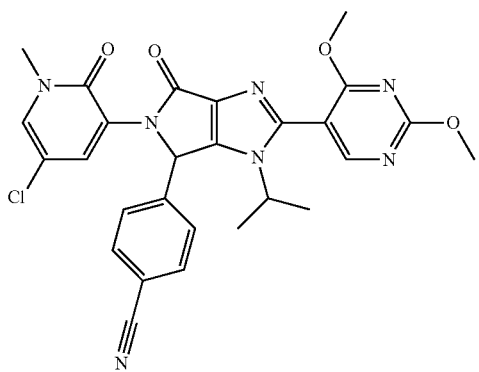 [SMILES: COc1ncc(-c2nc3c(n2C(C)C)C(c2ccc(C#N)cc2)N(c2cc(Cl)cn(C)c2=O)C3=O)c(OC)n1]

The title compound was prepared in analogy to the procedure described for example 29 but using the product from step 100.1 and 2,4-dimethoxypyrimidin-5-ylboronic acid. The product was purified by flash chromatography (CH$_2$Cl$_2$/MeOH, 95:5). The resulting foam was purified by preparative HPLC (Waters Sun Fire C18, 30×100 mm, 5 μm; 0.1% TFA-water/acetonitrile; gradient acetonitrile 20-60% in 20 min). The resulting solid was purified by SFC chromatography (Column Hilic silica, 100 mm, gradient 25-30%). The residue was triturated in Et$_2$O to afford the title compound. $t_R$: 0.86 min (LC-MS 2); ESI-MS: 546.3/548.3 [M+H]$^+$ (LC-MS 2).

Example 125

4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid methyl ester

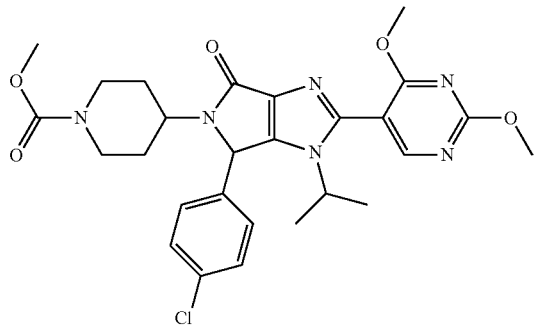 [SMILES: COC(=O)N1CCC(N2C(=O)c3nc(-c4cnc(OC)nc4OC)n(C(C)C)c3C2c2ccc(Cl)cc2)CC1]

To a solution of the product from step 123.1 (118 mg, 0.2 mmol) in CH$_2$Cl$_2$ was added Et3N (168 μL, 12 mmol), and methyl carbonochloridate (37 μL, 0.5 mmol) and the mixture was stirred at rt for 15 min. The mixture was quenched with H$_2$O and the layers were separated. The aqueous layer was washed with CH$_2$Cl$_2$. The organic layer was dried (MgSO$_4$), filtered and concentrated. The residue was purified by preparative HPLC (C18). $t_R$: 1.02 min (LC-MS 2); ESI-MS: 555.3/557.4 [M+H]$^+$ (LC-MS 2).

Example 126

2-{4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-N-methyl-acetamide

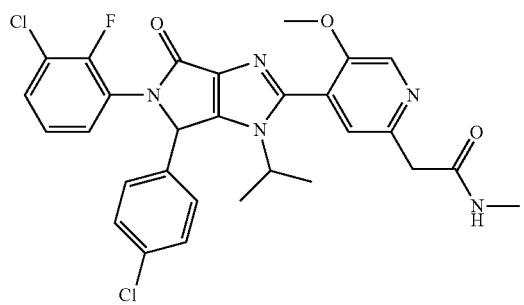 [SMILES: CNC(=O)Cc1cc(-c2nc3c(n2C(C)C)C(c2ccc(Cl)cc2)N(c2cccc(Cl)c2F)C3=O)c(OC)cn1]

The title compound was prepared in analogy to the procedure described for example 29 but using the product from step 126.1 and intermediate G. The reaction mixture was diluted with brine, and was extracted with EtOAc. The organic layer was washed with brine, dried (MgSO$_4$), filtered, and concentrated. The residue was purified by flash chromatography (CH$_2$Cl$_2$/MeOH/NH$_3$aq., 200:10:1). $t_R$: 1.02 min (LC-MS 2); ESI-MS: 582.4/584.3 [M+H]$^+$ (LC-MS 2).

Step 126.1: 2-[5-Methoxy-4-(4,4,5,5-tetramethyl-[1,3,2]dioxaborolan-2-yl)-pyridin-2-yl]-N-methyl-acetamide

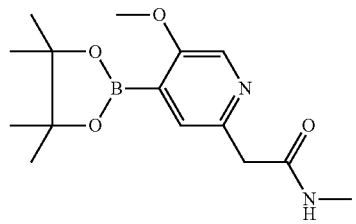

The title compound was prepared in analogy to the procedure described for intermediate F but using the product from step 126.2. The reaction was performed at 90° C. The product was used without further purification.

Step 126.2: 2-(4-Chloro-5-methoxy-pyridin-2-yl)-N-methyl-acetamide

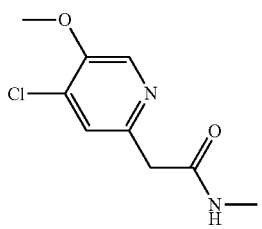

The title compound was prepared in analogy to the procedure described for intermediate F but using the product from step 126.3 and methanamine. The reaction was performed at rt. The reaction mixture was diluted with EtOAc and extracted with a saturated aqueous NaHCO$_3$ solution.

The organic layer was washed with a saturated aqueous NaHCO$_3$ solution, dried (MgSO$_4$), filtered and concentrated. The product was purified by flash chromatography (CH$_2$Cl$_2$/MeOH, 100:0→90:10). The residue was triturated in Et$_2$O and CH$_2$Cl$_2$ to afford the title compound. $t_R$: 0.58 min (LC-MS 2); ESI-MS: 215.1 [M+H]$^+$ (LC-MS 2).

Step 126.3: (4-Chloro-5-methoxy-pyridin-2-yl)-acetic acid

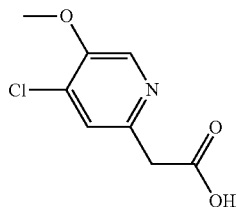

To a suspension of 2-(4-chloro-5-methoxypyridin-2-yl)acetonitrile (150 mg, 0.8 mmol) in EtOH (2 mL) was added a solution of KOH (184 mg, 3.3 mmol) in H$_2$O (2 mL) and the mixture was stirred at 80° C. for 1.5 h. at 0° C., the pH was adjusted to 3-4 with HCl 1 M. Sodium chloride, THF and EtOAc were added and the phases were separated. The organic layer was dried (MgSO$_4$), filtered and concentrated to afford the title compound. $t_R$: 0.59 min (LC-MS 2); ESI-MS: 202.1 [M+H]$^+$ (LC-MS 2).

Example 127

5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

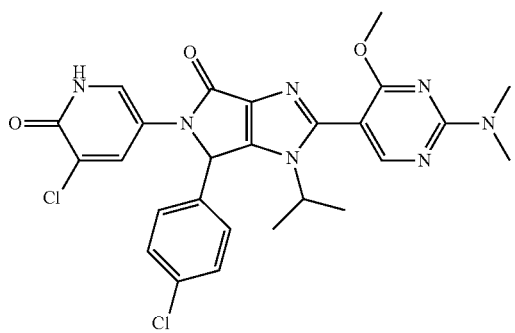 [SMILES: COc1nc(N(C)C)ncc1-c1nc2c(n1C(C)C)C(c1ccc(Cl)cc1)N(c1c[nH]c(=O)c(Cl)c1)C2=O]

The title compound was prepared in analogy to the procedure described for example 97 but using the product from step 127.1. The mixture was extracted with CH$_2$Cl$_2$ and a saturated aqueous NaHCO$_3$ solution. The organic layer was washed with H$_2$O and brine, dried (Na$_2$SO$_4$), filtered and concentrated. The residue was triturated in CH$_2$Cl$_2$ to give the title compound. $t_R$: 0.98 min (LC-MS 2); ESI-MS: 554.3/556.4 [M+H]$^+$ (LC-MS 2).

Step 127.1: 5-[5-Chloro-1-(4-methoxy-benzyl)-6-oxo-1,6-dihydro-pyridin-3-yl]-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

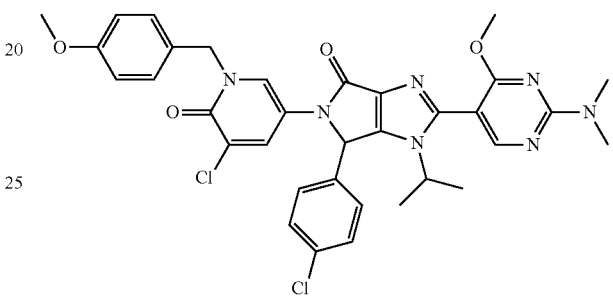

The title compound was prepared in analogy to the procedure described for example 29 but using the product from step 127.2 and intermediate W. The reaction was performed at 110° C. The product was purified by preparative HPLC (Column: Sunfire C18, 30×100 mm, 5 µm. Flow: 30 mL/min. Gradient 30-70% B in 20 min; A=0.1% TFA in water, B=CH$_3$CN) to afford the title compound. $t_R$: 1.17 min (LC-MS 2); ESI-MS: 674.4/676.4 [M+H]$^+$ (LC-MS 2).

Step 127.2: 2-Bromo-5-[5-chloro-1-(4-methoxy-benzyl)-6-oxo-1,6-dihydro-pyridin-3-yl]-6-(4-chloro-phenyl)-1-isopropyl-5,6-dihydro-1H-pyrrolo[3,4-d]imidazol-4-one

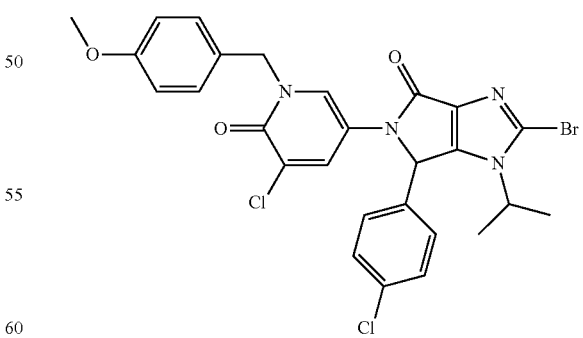

The title compound was prepared in analogy to the procedure described for intermediate E but using the product from step 127.3. After extraction, the residue was triturated in EtOAc to afford the title compound. $t_R$: 1.10 min (LC-MS 2); ESI-MS: 601.3/603.3/605.2 [M+H]$^+$ (LC-MS 2).

Step 127.3: 2-Bromo-5-[[5-chloro-1-(4-methoxy-benzyl)-6-oxo-1,6-dihydro-pyridin-3-ylamino]-(4-chloro-phenyl)-methyl]-1-isopropyl-1H-imidazole-4-carboxylic acid

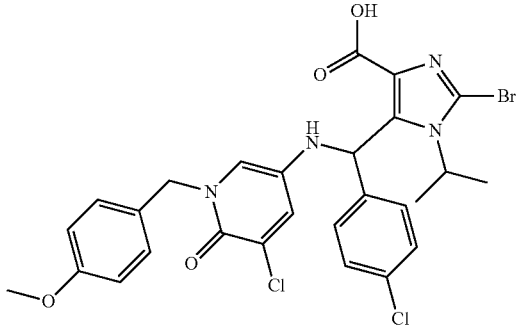 [SMILES: COc1ccc(Cn2cc(NC(c3ccc(Cl)cc3)c3c(C(=O)O)nc(Br)n3C(C)C)cc(Cl)c2=O)cc1]

The title compound was prepared in analogy to the procedure described for step E1 but using the product from step 127.4. After extraction, the residue was triturated in Et₂O to afford the title compound. $t_R$: 1.06 min (LC-MS 2); ESI-MS: 619.3/621.3/623.2 [M+H]⁺ (LC-MS 2).

Step 127.4: 2-Bromo-5-[[5-chloro-1-(4-methoxy-benzyl)-6-oxo-1,6-dihydro-pyridin-3-ylamino]-(4-chloro-phenyl)-methyl]-1-isopropyl-1H-imidazole-4-carboxylic acid ethyl ester

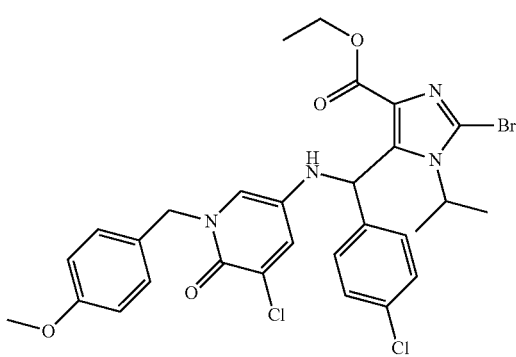 [SMILES: CCOC(=O)c1nc(Br)n(C(C)C)c1C(Nc1cc(Cl)c(=O)n(Cc2ccc(OC)cc2)c1)c1ccc(Cl)cc1]

The title compound was prepared in analogy to the procedure described for step E2 but using intermediate B and the product from step 127.5. The reaction mixture was stirred at rt for 16 h. The residue was purified by flash chromatography (CH₂Cl₂/EtOAc, 1:1). The product was then triturated in Et₂O to afford the title compound. $t_R$: 1.23 min (LC-MS 2); ESI-MS: 647.3/649.4/651.3 [M+H]⁺ (LC-MS 2).

Step 127.5: 5-Amino-3-chloro-1-(4-methoxy-benzyl)-1H-pyridin-2-one

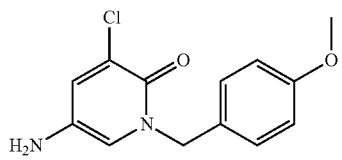

A saturated aqueous solution of NH₄Cl (99 mL) was added to a solution of the intermediate prepared in step 127.6 (6.8 g, 23.0 mmol) in EtOH (300 mL). After a 15 min stirring, iron powder (6.4 g, 115 mmol) was added and the resulting mixture was heated to reflux, stirred for 1 h, concentrated, diluted with EtOH, and filtered through a pad of celite. The filtrate was concentrated. The residue was purified by flash chromatography (CH₂Cl₂/MeOH, 100:0→96.5:3.5). $t_R$: 0.61 min (LC-MS 2); ESI-MS: 265.2 [M+H]⁺ (LC-MS 2); $R_f$=0.53 (CH₂Cl₂/MeOH, 9:1).

Step 127.6: 3-Chloro-1-(4-methoxy-benzyl)-5-nitro-1H-pyridin-2-one

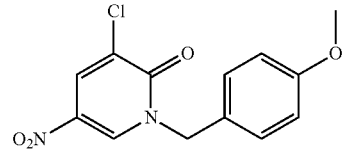 [SMILES: COc1ccc(Cn2cc([N+](=O)[O-])cc(Cl)c2=O)cc1]

4-methoxybenzyl bromide (5.0 mL, 34.4 mmol) was added to a cold (0° C.) mixture 3-chloro-2-hydroxy-5-nitropyridine (5 g, 28.6 mmol) and K₂CO₃ (7.9 g, 57.3 mmol) in DMF (25 mL). The reaction mixture was allowed to warm to rt, stirred for 2 h, quenched by addition of a saturated aqueous NaHCO₃ solution, and extracted with EtOAc. The organic layer was washed with brine, dried (Na₂SO₄), filtered, and concentrated. The residue was purified by trituration in EtOAc. $t_R$: 0.98 min (LC-MS 2); ESI-MS: 295.2 [M+H]⁺ (LC-MS 2).

Example 128

2-(2-Amino-4-methoxy-pyrimidin-5-yl)-6-(4-chloro-phenyl)-5-(1,3-dimethyl-2-oxo-hexahydro-pyrimidin-5-yl)-1-isopropyl-5,6-dihydro-1H-pyrrolo[3,4-d]imidazol-4-one

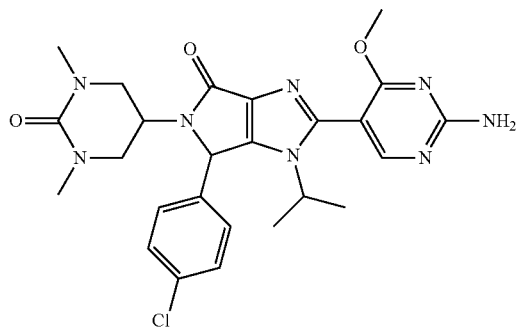 [SMILES: COc1nc(N)ncc1-c1nc2c(n1C(C)C)C(c1ccc(Cl)cc1)N(C1CN(C)C(=O)N(C)C1)C2=O]

The title compound was prepared in analogy to the procedure described for example 29 but using the product from step 128.1 and intermediate U. After extraction, the residue was purified by preparative HPLC to give the title compound. $t_R$: 0.80 min (LC-MS 2); ESI-MS: 525.4/527.3 [M+H]⁺ (LC-MS 2).

Step 128.1: 2-Bromo-6-(4-chloro-phenyl)-5-(1,3-dimethyl-2-oxo-hexahydro-pyrimidin-5-yl)-1-isopropyl-5,6-dihydro-1H-pyrrolo[3,4-d]imidazol-4-one

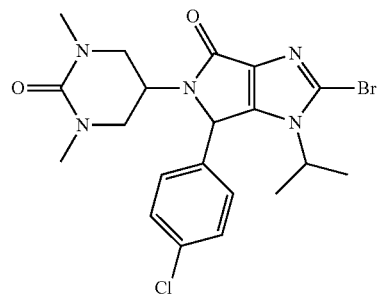 [SMILES: CC(C)n1c(Br)nc2c1C(c1ccc(Cl)cc1)N(C1CN(C)C(=O)N(C)C1)C2=O]

The title compound was prepared in analogy to the procedure described for intermediate E but using the product from step 128.2. The reaction mixture was diluted with toluene and extracted with H₂O and washed with brine. The organic layer was dried (Na₂SO₄), filtered and concentrated. The residue was triturated in dissopropylether/EtOAc 10:1 to give the title compound. $t_R$: 0.91 min (LC-MS 2); ESI-MS: 480.1/482.2 [M+H]⁺ (LC-MS 2).

Step 128.2: 2-Bromo-5-[(4-chloro-phenyl)-(1,3-dimethyl-2-oxo-hexahydro-pyrimidin-5-ylamino)-methyl]-1-isopropyl-1H-imidazole-4-carboxylic acid

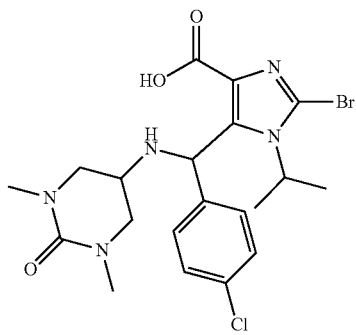 [SMILES: CC(C)n1c(Br)nc(C(=O)O)c1C(NC1CN(C)C(=O)N(C)C1)c1ccc(Cl)cc1]

The title compound was prepared in analogy to the procedure described for step E1 but using the product from step 128.3. $t_R$: 0.79 min (LC-MS 2); ESI-MS: 498.2/500.3/502.4 [M+H]⁺ (LC-MS 2).

Step 128.3: 2-Bromo-5-[(4-chloro-phenyl)-(1,3-dimethyl-2-oxo-hexahydro-pyrimidin-5-ylamino)-methyl]-1-isopropyl-1H-imidazole-4-carboxylic acid ethyl ester

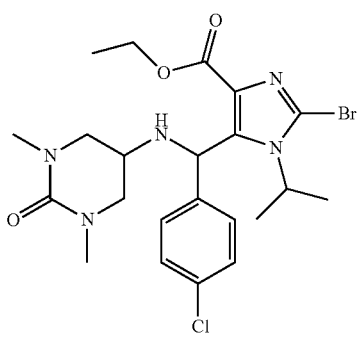 [SMILES: CCOC(=O)c1nc(Br)n(C(C)C)c1C(NC1CN(C)C(=O)N(C)C1)c1ccc(Cl)cc1]

The title compound was prepared in analogy to the procedure described for step E2 but using intermediate B and the product from step 128.4. The reaction mixture was extracted with a saturated aqueous NaHCO₃ solution. The organic layer was dried (Na₂SO₄), filtered and concentrated. The product was purified by flash chromatography (heptane/EtOAc/Et₃N, 100:0:1→0:100:1) to provide the title compound. $t_R$: 1.11 min (LC-MS 2); ESI-MS: 526.3/528.3/530.4 [M+H]⁺ (LC-MS 2).

Step 128.4:
5-Amino-1,3-dimethyl-tetrahydro-pyrimidin-2-one

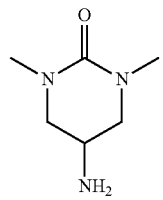

A mixture of the compound prepared in step 128.5 (2.5 g, 11.1 mmol) and Pd/C 10% (500 mg) in EtOH (70 mL) was stirred for 13.5 h at rt, under a hydrogen atmosphere. The reaction mixture was filtered through a pad of celite, washed with THF and MeOH and concentrated. The residue was dissolved in EtOAc and extracted with cold HCl 1N. The aqueous phase was basified with a saturated aqueous NaHCO₃ solution. The resulting aqueous phase was extracted with CH₂Cl₂/isopropanol 3:1. The organic layers were dried (Na₂SO₄), filtered and concentrated. ESI-MS: 144.1 [M+H]⁺ (MS 1).

Step 128.5:
5-Azido-1,3-dimethyl-tetrahydro-pyrimidin-2-one

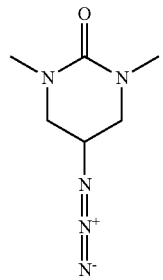

To a solution of the product from step 128.6 (3.2 g, 14.3 mmol) in DMF (75 mL) at rt was added sodium azide (1.9 g, 28.7 mmol) and the mixture was stirred at 70° C. for 13 h. The mixture was diluted with CH₂Cl₂/isopropanol 3:1 and extracted with a saturated aqueous NaHCO₃ solution. The organic phase was dried (Na₂SO₄), filtered and concentrated. ESI-MS: 170.1 [M+H]⁺ (MS 1).

Step 128.6: Methanesulfonic acid 1,3-dimethyl-2-oxo-hexahydro-pyrimidin-5-yl ester

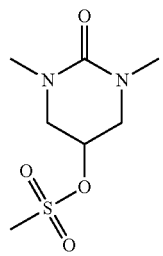

The title compound was prepared in analogy to the procedure described for step E2 but using the product from step 128.7. The reaction mixture was diluted with H₂O and a saturated aqueous NaHCO₃ solution and extracted with CH₂Cl₂/isopropanol 3:1. The organic layers were dried (Na₂SO₄), filtered and concentrated. ESI-MS: 223.1 [M+H]⁺ (MS 1).

Step 128.7:
5-Hydroxy-1,3-dimethyl-tetrahydro-pyrimidin-2-one

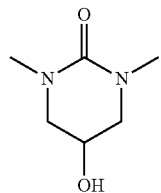

To a solution of the product from step 128.8 (9.1 g, 28 mmol) in EtOH (70 mL) was added a 1M HCl (140 mL, 140 mmol) and the mixture was stirred at rt for 3 h at 70° C. The mixture was concentrated, and the pH of the resulting aqueous phase was adjusted to 5 with a saturated aqueous NaHCO₃ solution. The aqueous layer was saturated with NaCl and was extracted with CH₂Cl₂/isopropanol 3:1. The organic layer was dried (Na₂SO₄), filtered and concentrated to afford the title compound. $t_R$: 0.33 min (LC-MS 2); ESI-MS: 145.1 [M+H]⁺ (LC-MS 2).

Step 128.8: 1,3-Dimethyl-5-triisopropylsilanyloxy-tetrahydro-pyrimidin-2-one

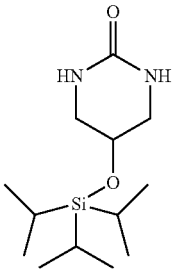 [SMILES: CC(C)[Si](OC1CNC(=O)NC1)(C(C)C)C(C)C]

The title compound was prepared in analogy to the procedure described for step 100.5 but using the product from step 128.9. The reaction mixture quenched by addition of water, and extracted with toluene. The aqueous layer was washed with EtOAc. The combined organic layers were washed with a saturated aqueous NaHCO₃ solution, dried (Na₂SO₄), filtered, and concentrated. The residue was used without further purification. $t_R$: 1.33 min (LC-MS 2); ESI-MS: 301.3 [M+H]⁺ (LC-MS 2).

Step 128.9: 5-Triisopropylsilanyloxy-tetrahydro-pyrimidin-2-one

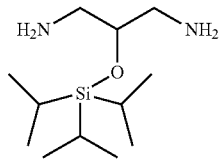 [SMILES: CC(C)[Si](OC(CN)CN)(C(C)C)C(C)C]

To a solution of the product prepared in step 128.10 (27.8 g, 113 mmol) in MeOH (450 mL) was added S,S-dimethyl carbonodithioate (17.7 mL, 169 mmol) and the mixture was stirred at 60° C. for 20 h. The reaction mixture was concentrated. The residue was purified by flash chromatography (CH₂Cl₂/MeOH, 100:0→5:1) to afford the title compound. ESI-MS: 273.3 [M+H]⁺ (LC-MS 2-flow injection).

Step 128.10:
2-Triisopropylsilanyloxy-propane-1,3-diamine

To a solution of 1,3-diaminopropan-2-ol (19.4 g, 215 mmol) in CH₂Cl₂ (250 mL) at 0° C. was added TIPS-Cl (50.2 mL, 237 mmol) and Et₃N (90 mL, 646 mmol) and the reaction mixture was stirred at rt for 20 h. The mixture was diluted with CH₂Cl₂. The organic layer was washed with a saturated aqueous NaHCO₃ solution, dried (Na₂SO₄), filtered and concentrated. The product was used without further purification. ESI-MS: 247.3 [M+H]⁺ (LC-MS 2-flow injection).

Example 129

6-(4-Chloro-phenyl)-2-(2-dimethylamino-4-methoxy-pyrimidin-5-yl)-5-(1,3-dimethyl-2-oxo-hexahydro-pyrimidin-5-yl)-1-isopropyl-5,6-dihydro-1H-pyrrolo[3,4-d]imidazol-4-one

Example 130

4-[5-(3-Chloro-2-fluoro-phenyl)-2-(5-cyanomethyl-2-methoxy-phenyl)-3-isopropyl-6-oxo-3,4,5,6-tetrahydro-pyrrolo[3,4-d]imidazol-4-yl]-benzonitrile

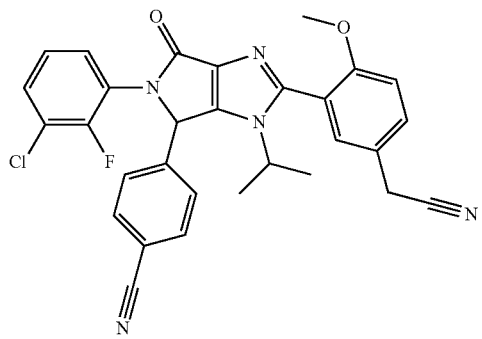 [SMILES: COc1ccc(CC#N)cc1-c1nc2c(n1C(C)C)C(c1ccc(C#N)cc1)N(c1cccc(Cl)c1F)C2=O]

The title compound was prepared in analogy to the procedure described for example 29 but using the product from step 130.1 and intermediate AB. The reaction was performed at 80° C. After extraction, the residue was purified by flash chromatography (CH$_2$Cl$_2$/EtOAc, 80:20→0:100) to afford the title compound. t$_R$: 1.07 min (LC-MS 2); ESI-MS: 540.4/542.2 [M+H]$^+$ (LC-MS 2).

Step 130.1: [4-Methoxy-3-(4,4,5,5-tetramethyl-[1,3,2]dioxaborolan-2-yl)-phenyl]-acetonitrile

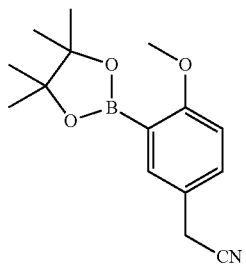 [SMILES: COc1ccc(CC#N)cc1B1OC(C)(C)C(C)(C)O1]

The title compound was prepared in analogy to the procedure described for intermediate S but using (3-bromo-4-methoxy-phenyl)-acetonitrile. The reaction mixture was diluted with EtOAc and extracted with brine, then washed with H$_2$O. The organic layer was dried (MgSO$_4$), filtered and concentrated. The residue was purified by flash chromatography (CH$_2$Cl$_2$/EtOAc, 95:5→0:100) to afford the title compound. t$_R$: 1.03 min (LC-MS 2).

The title compound was prepared in analogy to the procedure described for example 29 but using the product from step 128.1 and intermediate W. After extraction, the residue was purified by preparative HPLC. The residue was triturated in diisopropylether to give the title compound. t$_R$: 1.00 min (LC-MS 2); ESI-MS: 553.4/555.4 [M+H]$^+$ (LC-MS 2).

Example 131

4-[5-(5-Chloro-2-methyl-phenyl)-2-(5-cyanomethyl-2-methoxy-pyridin-3-yl)-3-isopropyl-6-oxo-3,4,5,6-tetrahydro-pyrrolo[3,4-d]imidazol-4-yl]-benzonitrile

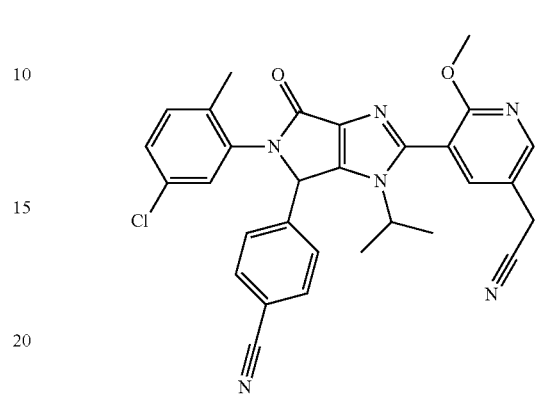

The title compound was prepared in analogy to the procedure described for example 29 but using intermediate H and the product from step 131.1. The reaction mixture was dissolved in EtOAc and extracted with a saturated aqueous NaHCO$_3$ solution. The organic layer was washed with brine, dried (Na$_2$SO$_4$), filtered and concentrated. The residue was purified by flash chromatography (hexane/EtOAc, 100:0→0:100). t$_R$: 1.04 min (LC-MS 2); ESI-MS: 537.4/539.4 [M+H]$^+$ (LC-MS 2).

Step 131.1: [6-Methoxy-5-(4,4,5,5-tetramethyl-[1,3,2]dioxaborolan-2-yl)-pyridin-3-yl]-acetonitrile

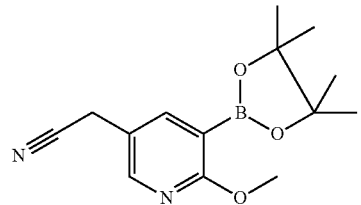 [SMILES: COc1ncc(CC#N)cc1B1OC(C)(C)C(C)(C)O1]

The title compound was prepared in analogy to the procedure described for intermediate S but using the product from step 131.2. The reaction mixture was diluted with EtOAc and extracted with brine, then washed with H$_2$O. The organic layer was dried (MgSO$_4$), filtered and concentrated. The residue was purified by flash chromatography (heptane/EtOAc, 70:30→0:100) to afford the title compound. t$_R$: 0.98 min (LC-MS 2); ESI-MS: 275.1 [M+H]$^+$ (LC-MS 2).

Step 131.2: (5-Bromo-6-methoxy-pyridin-3-yl)-acetonitrile

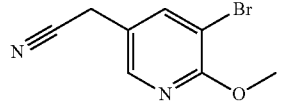

To a suspension of the product from step 131.3 (3.9 g, 14.0 mmol) in H₂O was added NaCN (750 mg, 15.3 mmol) and the mixture was stirred at 50° C. for 1.5 h. CH₂Cl₂ and a saturated aqueous NaHCO₃ solution were added and the phases were separated. The organic layer was washed with H₂O and brine, dried (MgSO₄), filtered and concentrated. The crude product was purified by flash chromatography (heptane/EtOAc, 80:20→0:100). $t_R$: 0.88 min (LC-MS 2).

Step 131.3:
3-Bromo-5-bromomethyl-2-methoxy-pyridine

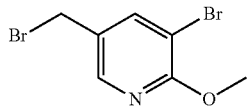

To a solution of the product from step 131.4 (3.0 g, 14.7 mmol), was added NBS (3.1 g, 17.6 mmol) and AIBN (121 mg, 0.7 mmol) and the mixture was stirred at 80° C. for 1 h. H₂O and CH₂Cl₂ were added and the phases were separated. The organic layer was dried (MgSO₄), filtered and concentrated. The crude product was purified by flash chromatography (heptane/EtOAc, 95:5→0:100). $t_R$: 1.10 min (LC-MS 2).

Step 131.4: 3-Bromo-2-methoxy-5-methyl-pyridine

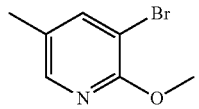

To a solution of 3-bromo-2-chloro-5-methylpyridine (5 g, 24.2 mmol) in MeOH (80 mL) was added a solution of sodium methoxide 5.4M in MeOH (25 mL, 135 mmol) and the mixture was stirred at 65° C. for 32 h. The resulting suspension was filtered and the mother liquor was concentrated. Et₂O and H₂O were added and the phases were separated. The organic layer was washed with H₂O and brine, dried (MgSO₄), filtered and concentrated. The residue was purified by flash chromatography (heptane/EtOAc: 90:10→0:100) to afford the title compound. $t_R$: 1.03 min (LC-MS 2).

Example 132

4-[5-(3-Chloro-2-fluoro-phenyl)-2-(5-cyanomethyl-2-methoxy-pyridin-3-yl)-3-isopropyl-6-oxo-3,4,5,6-tetrahydro-pyrrolo[3,4-d]imidazol-4-yl]-benzonitrile

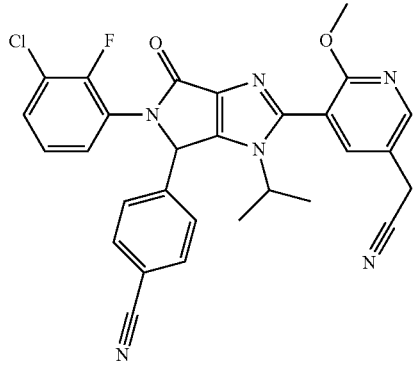 [SMILES: COc1ncc(CC#N)cc1-c1nc2c(n1C(C)C)C(c1ccc(C#N)cc1)N(c1cccc(Cl)c1F)C2=O]

The title compound was prepared in analogy to the procedure described for example 29 but using intermediate AB and the product from step 131.1. The reaction mixture was dissolved in EtOAc and extracted with a saturated aqueous NaHCO₃ solution. The organic layer was washed with brine, dried (Na₂SO₄), filtered and concentrated. The residue was purified by flash chromatography (hexane/EtOAc, 100:0→0:100). $t_R$: 1.03 min (LC-MS 2); ESI-MS: 541.3/543.3 [M+H]⁺ (LC-MS 2).

Example 133

{5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetonitrile

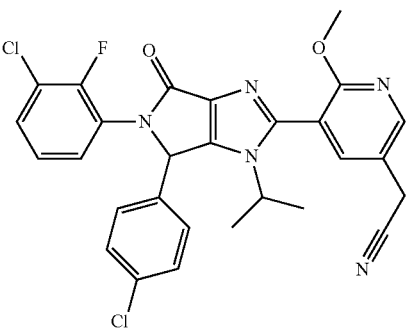 [SMILES: COc1ncc(CC#N)cc1-c1nc2c(n1C(C)C)C(c1ccc(Cl)cc1)N(c1cccc(Cl)c1F)C2=O]

The title compound was prepared in analogy to the procedure described for example 29 but using intermediate G and the product from step 131.1. The reaction mixture was dissolved in EtOAc and extracted with a saturated aqueous NaHCO₃ solution. The organic layer was washed with brine, dried (Na₂SO₄), filtered and concentrated. The residue was purified by flash chromatography (hexane/EtOAc, 100:0→0:100). $t_R$: 1.17 min (LC-MS 2); ESI-MS: 550.3/552.3 [M+H]⁺ (LC-MS 2).

Example 134

4-[5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile

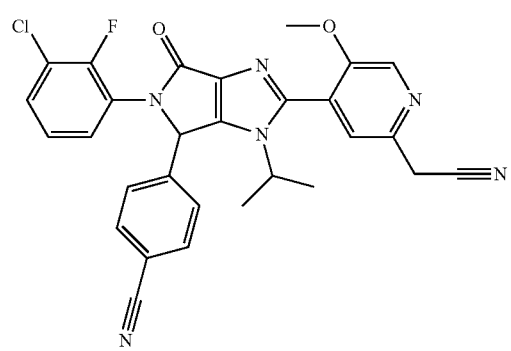 [SMILES: COc1cnc(CC#N)cc1-c1nc2c(n1C(C)C)C(c1ccc(C#N)cc1)N(c1cccc(Cl)c1F)C2=O]

The title compound was prepared in analogy to the procedure described for example 29 but using intermediate AB and the product from step 93.4. The reaction mixture was poured into brine and extracted with EtOAc. The organic layer was washed with brine, dried (Na₂SO₄), filtered and concentrated. The residue was purified by flash chromatography (heptane/

EtOAc/MeOH, 10:88:2→0:98:2). $t_R$: 0.98 min (LC-MS 2); ESI-MS: 541.4/543.4 [M+H]$^+$ (LC-MS 2).

Example 135

4-[5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile

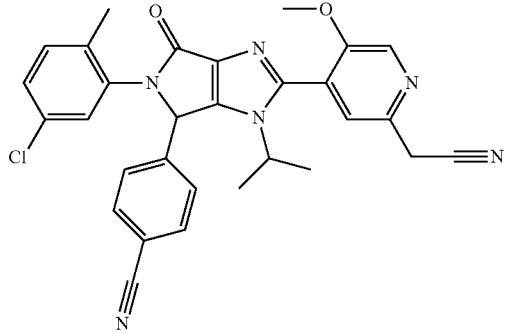 [SMILES: COc1cnc(CC#N)cc1-c1nc2c(n1C(C)C)C(c1ccc(C#N)cc1)N(c1cc(Cl)ccc1C)C2=O]

The title compound was prepared in analogy to the procedure described for example 29 but using intermediate H and the product from step 93.4. The reaction mixture was poured into brine and extracted with EtOAc. The organic layer was washed with brine, dried (Na$_2$SO$_4$), filtered and concentrated. The residue was purified by flash chromatography (heptane/EtOAc/MeOH, 10:88:2→0:98:2). $t_R$: 1.00 min (LC-MS 2); ESI-MS: 537.4/539.3 [M+H]$^+$ (LC-MS 2).

Example 136

{4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile

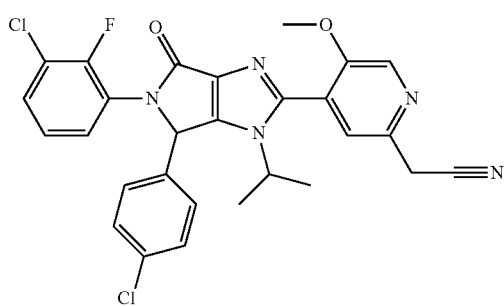 [SMILES: COc1cnc(CC#N)cc1-c1nc2c(n1C(C)C)C(c1ccc(Cl)cc1)N(c1cccc(Cl)c1F)C2=O]

The title compound was prepared in analogy to the procedure described for example 29 but using intermediate G and the product from step 93.4. The reaction mixture was poured into brine and extracted with EtOAc. The organic layer was washed with brine, dried (Na$_2$SO$_4$), filtered and concentrated. The residue was purified by flash chromatography (heptane/EtOAc/MeOH, 10:88:2→0:98:2). $t_R$: 1.12 min (LC-MS 2); ESI-MS: 550.2/552.2 [M+H]$^+$ (LC-MS 2).

Example 137

{5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester

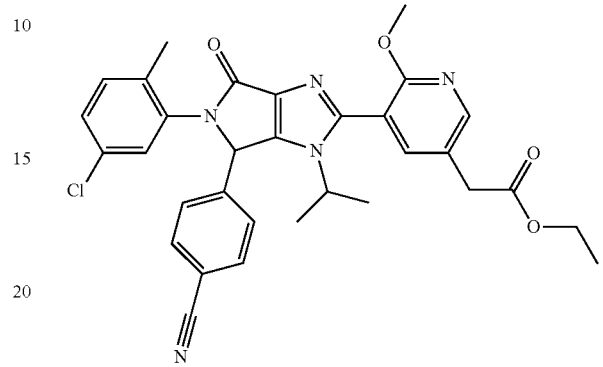

The title compound was prepared in analogy to the procedure described for example 29 but using intermediate H and the product from step 137.1. The reaction was performed at 80° C. The reaction mixture was poured into a saturated aqueous NaHCO$_3$ solution and extracted with EtOAc. The organic layer was washed with brine, dried (Na$_2$SO$_4$), filtered and concentrated. The residue was purified by flash chromatography (heptane/EtOAc, 1:4). $t_R$: 1.13 min (LC-MS 2); ESI-MS: 584.3/586.4 [M+H]$^+$ (LC-MS 2).

Step 137.1: [6-Methoxy-5-(4,4,5,5-tetramethyl-[1,3,2]dioxaborolan-2-yl)-pyridin-3-yl]-acetic acid ethyl ester

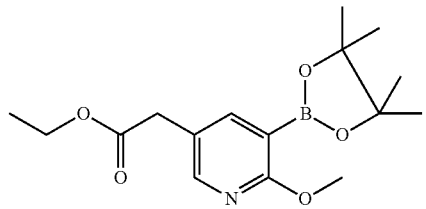 [SMILES: CCOC(=O)Cc1cnc(OC)c(B2OC(C)(C)C(C)(C)O2)c1]

The title compound was prepared in analogy to the procedure described for intermediate S but using the product from step 137.2 and PdCl$_2$(PPh$_2$)ferrocene.CH$_2$Cl$_2$. The reaction was performed at 90° C. After extraction, the residue was purified by flash chromatography (heptane/EtOAc, 80:20→0:100) to afford the title compound. $t_R$: 1.11 min (LC-MS 2); ESI-MS: 322.3 [M+H]$^+$ (LC-MS 2).

Step 137.2: (5-Bromo-6-methoxy-pyridin-3-yl)-acetic acid ethyl ester

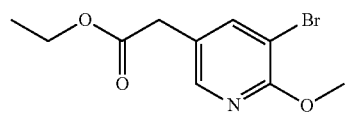

To a solution of the product from step 137.3 (400 mg, 1.6 mmol) in CH$_2$Cl$_2$ (0.8 mL) was added EtOH (285 L, 4.8 mmol) DCC (18 mg, 0.09 mmol) and DMAP (one spatula) and the mixture was stirred at rt 15 h. H$_2$O and EtOAc were added and the phases were separated. The organic layer was washed with brine, dried (MgSO$_4$), filtered and concentrated. The residue was purified by flash chromatography (heptane/EtOAc, 85:15→0:100). t$_R$: 1.05 min (LC-MS 2); ESI-MS: 274.1/276.1 [M+H]$^+$ (LC-MS 2).

Step 137.3:
(5-Bromo-6-methoxy-pyridin-3-yl)-acetic acid

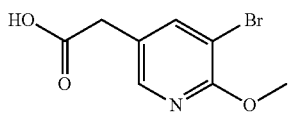

The title compound was prepared in analogy to the procedure described for step 126.3 but using the product from step 131.2. After the pH was adjusted to 3 with 1M HCl, CH$_2$Cl$_2$ was added and the phases were separated. The organic layer was dried (MgSO$_4$), filtered and concentrated to afford the title compound. t$_R$: 0.75 min (LC-MS 2); ESI-MS: 243.9/245.9 [M+H]$^+$ (LC-MS 2).

Example 138

{5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid

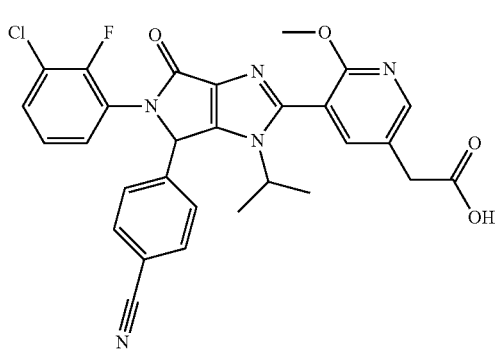 [SMILES: COc1ncc(CC(=O)O)cc1-c1nc2c(n1C(C)C)C(c1ccc(C#N)cc1)N(c1cccc(Cl)c1F)C2=O]

The title compound was prepared in analogy to the procedure described for example 140 but using the product from example 138.1. t$_R$: 0.96 min (LC-MS 2); ESI-MS: 560.4/562.5 [M+H]$^+$ (LC-MS 2).

Step 138.1: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester

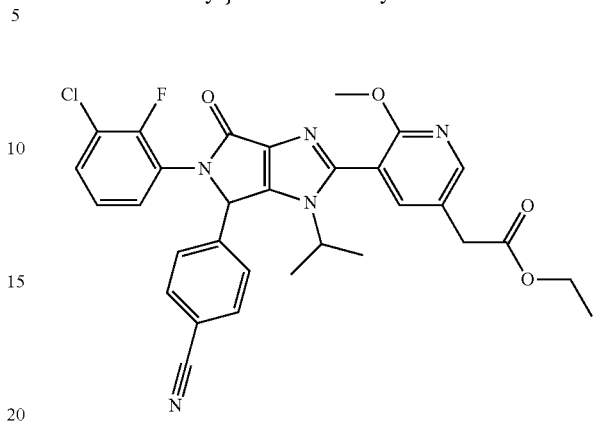

The title compound was prepared in analogy to the procedure described for example 29 but using intermediate AB and the product from step 137.1. The reaction was performed at 70° C. The reaction mixture was poured into brine and extracted with EtOAc. The organic layer was washed with a saturated aqueous NaHCO$_3$ solution, dried (Na$_2$SO$_4$), filtered and concentrated. The residue was purified by flash chromatography (heptane/EtOAc, 80:20→0:100). t$_R$: 1.12 min (LC-MS 2); ESI-MS: 588.4 [M+H]$^+$ (LC-MS 2).

Example 139

4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carboxylic acid amide

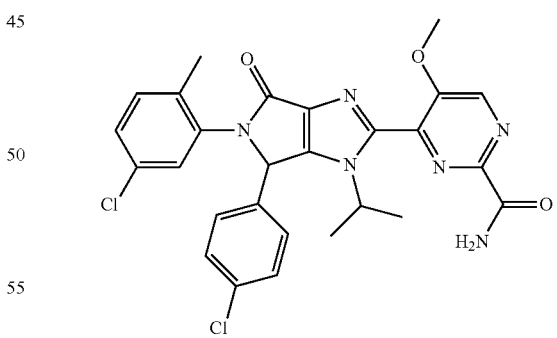

The title compound was prepared in analogy to the procedure described for step 94.1 but using the product from example 170. The residue was purified by preparative HPLC (Waters Sun Fire C18, 30×100 mm, 5 µm; 0.1% TFA-water/acetonitrile; gradient acetonitrile 50-90% in 16 min) to give the title compound. t$_R$: 1.04 min (LC-MS 2); ESI-MS: 551.3/553.3 [M+H]$^+$ (LC-MS 2).

Example 140

{5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid

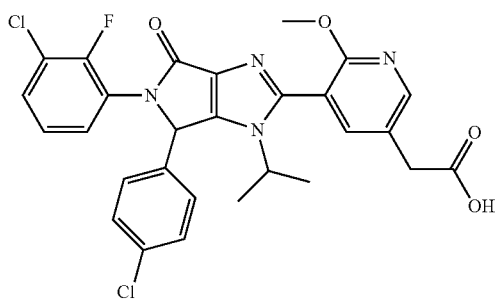 [SMILES: COc1ncc(CC(=O)O)cc1-c1nc2c(n1C(C)C)C(c1ccc(Cl)cc1)N(c1cccc(Cl)c1F)C2=O]

To a solution of the product from step 140.1 (119 mg, 0.2 mmol) in THF/MeOH (0.8 mL, 1:1) was added LiOH (394 µL, 0.8 mmol, 2M) and the mixture was stirred at rt for 30 min. The reaction mixture was poured into a 1M citric acid solution, H$_2$O was added and the mixture was extracted with EtOAc. The organic layer was dried (Na$_2$SO$_4$), filtered and concentrated to afford the title compound. $t_R$: 1.09 min (LC-MS 2); ESI-MS: 569.3/571.3 [M+H]$^+$ (LC-MS 2).

Step 140.1: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid ethyl ester

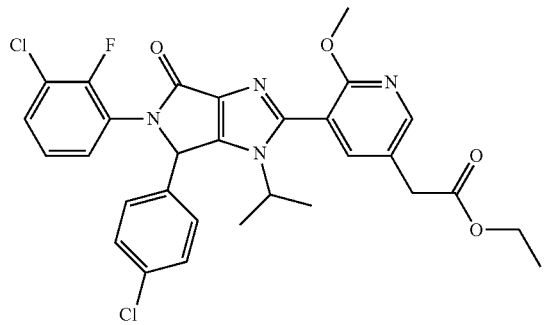 [SMILES: CCOC(=O)Cc1cnc(OC)c(-c2nc3c(n2C(C)C)C(c2ccc(Cl)cc2)N(c2cccc(Cl)c2F)C3=O)c1]

The title compound was prepared in analogy to the procedure described for example 29 but using the product from step 137.1 and intermediate G. The reaction mixture was diluted with a saturated aqueous NaHCO$_3$ solution, and was extracted with EtOAc. The organic layer was washed with brine, dried (Na$_2$SO$_4$), filtered, and concentrated. The residue was purified by flash chromatography (hexane/EtOAc, 4:1). $t_R$: 1.26 min (LC-MS 2); ESI-MS: 597.3/599.3 [M+H]$^+$ (LC-MS 2).

Example 141

{5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid

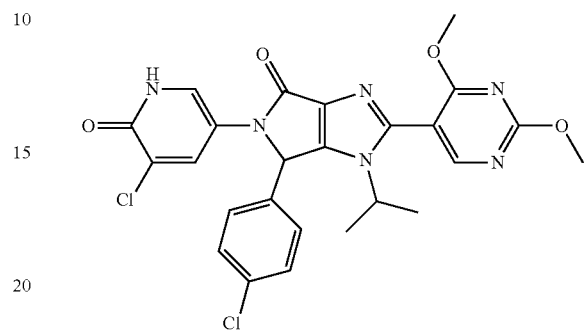

A solution of the product from step 141.1 (115 mg, 0.17 mmol) in TFA (1 mL) was stirred in a microwave oven at 100° C. for 30 min. The reaction mixture was concentrated, diluted with CH$_2$Cl$_2$ and extracted with a saturated aqueous NaHCO$_3$ solution. The organic layer was washed with brine, dried (Na$_2$SO$_4$), filtered and concentrated. The residue was purified by flash chromatography (CH$_2$Cl$_2$/MeOH, 95:5) then triturated in Et$_2$O to afford the title compound. $t_R$: 0.88 min (LC-MS 2); ESI-MS: 541.3/543.3 [M+H]$^+$ (LC-MS 2); R$_f$=0.21 (CH$_2$Cl$_2$/MeOH, 92.5:7.5).

Step 141.1: 5-[5-Chloro-1-(4-methoxy-benzyl)-6-oxo-1,6-dihydro-pyridin-3-yl]-6-(4-chloro-phenyl)-2-(2,4-dimethoxy-pyrimidin-5-yl)-1-isopropyl-5,6-dihydro-1H-pyrrolo[3,4-d]imidazol-4-one

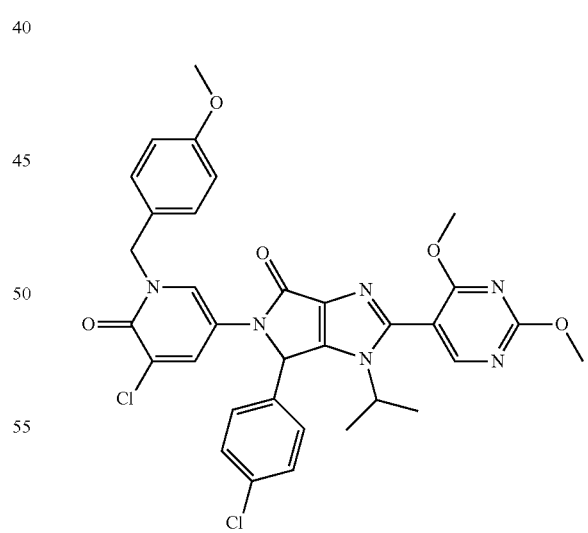

The title compound was prepared in analogy to the procedure described for example 29 but using the product from step 127.2 and 2,4-dimethoxypyrimidin-5-ylboronic acid. After extraction, the residue was purified by flash chromatography (CH$_2$Cl$_2$/MeOH, 95:5). The residue was then purified by preparative HPLC (Column: Sunfire C18, 30×100 mm, 5 µm. Flow: 30 mL/min. Gradient 25-70% B in 20 min; A=0.1%

TFA in water, B=CH₃CN). $t_R$: 1.08 min (LC-MS 2); ESI-MS: 661.5/663.5 [M+H]⁺ (LC-MS 2); $R_f$=0.10 (CH₂Cl₂/MeOH, 92.5:7.5).

Example 142

4-[(S)-2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile

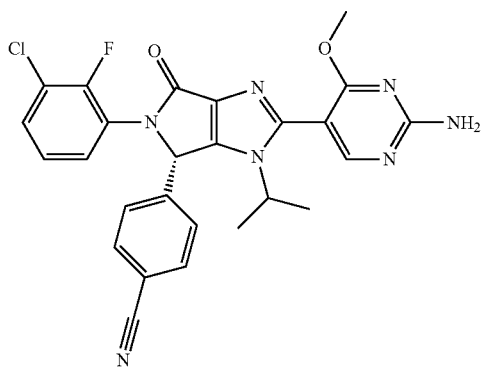 [SMILES: COc1nc(N)ncc1-c1nc2c(n1C(C)C)[C@H](c1ccc(C#N)cc1)N(c1cccc(Cl)c1F)C2=O]

The title compound was obtained after preparative chiral HPLC separation of the racemic product of example 53. $t_R$: 12.90 min (Column: Chiralpak AD-H, Flow 2.0 mL/min. heptane/EtOH 1:1. Detection: UV 210 nm). $t_R$: 0.92 min (LC-MS 2); ESI-MS: 518.4/520.3 [M+H]⁺ (LC-MS 2); ¹H-NMR (DMSO-d₆, 400 MHz) δ ppm 8.10 (s, 1H), 4.83 (d, 2H), 7.52-7.44 (m, 4H), 7.19 (m, 1H), 7.08 (s, 2H), 6.60 (s, 1H), 4.11 (m, 1H), 3.82 (s, 3H), 1.33 (d, 3H), 0.49 (d, 3H).

Example 143

4-[(R)-2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile

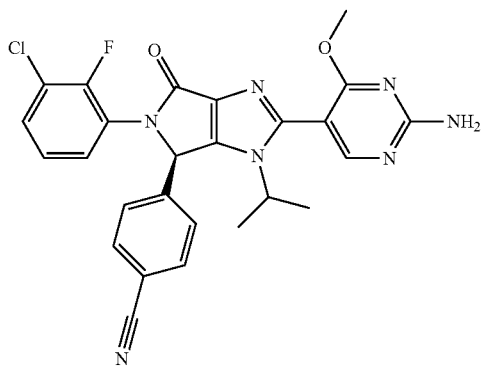 [SMILES: COc1nc(N)ncc1-c1nc2c(n1C(C)C)[C@@H](c1ccc(C#N)cc1)N(c1cccc(Cl)c1F)C2=O]

The title compound was obtained after preparative chiral HPLC separation of the racemic product of example 53. $t_R$: 8.92 min (Column: Chiralpak AD-H, Flow 2.0 mL/min. heptane/EtOH 1:1. Detection: UV 210 nm). $t_R$: 0.92 min (LC-MS 2); ESI-MS: 518.4/520.3 [M+H]⁺ (LC-MS 2); ¹H-NMR (DMSO-d₆, 400 MHz) δ ppm 8.10 (s, 1H), 4.83 (d, 2H), 7.52-7.44 (m, 4H), 7.19 (m, 1H), 7.08 (s, 2H), 6.60 (s, 1H), 4.11 (m, 1H), 3.82 (s, 3H), 1.33 (d, 3H), 0.49 (d, 3H).

Example 144

5-(5-Chloro-2-methyl-phenyl)-6-(4-chloro-phenyl)-1-isopropyl-2-[3-(2-methyl-3H-imidazol-4-yl)-phenyl]-5,6-dihydro-1H-pyrrolo[3,4-d]imidazol-4-one

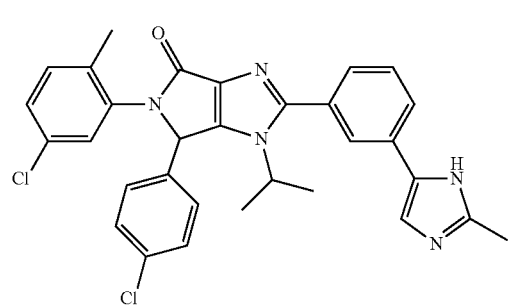 [SMILES: Cc1ncc(-c2cccc(-c3nc4c(n3C(C)C)C(c3ccc(Cl)cc3)N(c3cc(Cl)ccc3C)C4=O)c2)[nH]1]

The title compound was prepared in analogy to the procedure described for example 29 but using the product from step 144.1 and intermediate E. The residue was purified by preparative HPLC (Column: Sunfire C18, 30×100 mm, 5 μm. Flow: 30 mL/min. Gradient 5-100% B in 20 min; A=0.1% TFA in water, B=CH₃CN). The residue was triturated in diisopropylether to afford the title compound. $t_R$: 1.02 min (LC-MS 2); ESI-MS: 556.3/558.3 [M+H]⁺ (LC-MS 2).

Step 144.1: 2-Methyl-5-[3-(4,4,5,5-tetramethyl-[1,3,2]dioxaborolan-2-yl)-phenyl]-1H-imidazole

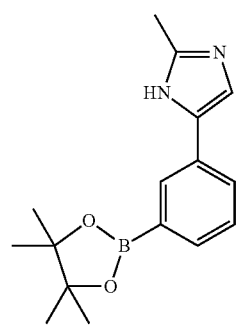 [SMILES: Cc1ncc(-c2cccc(B3OC(C)(C)C(C)(C)O3)c2)[nH]1]

The title compound was prepared in analogy to the procedure described for intermediate S but using the product from step 144.2. The reaction was performed at 115° C. The reaction mixture was dissolved in toluene, filtered over celite and the mother liquor was concentrated to give the title compound (50% purity). $t_R$: 0.76 min (LC-MS 2); ESI-MS: 285.3 [M+H]⁺ (LC-MS 2).

Step 144.2:
5-(3-Bromo-phenyl)-2-methyl-1H-imidazole

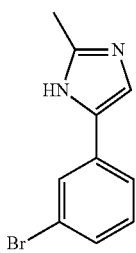

To a solution of the product from step 144.3 (2.3 g, 8.7 mmol) in xylene (45 mL) was added ammonium acetate (3.4 g, 463.6 mmol) and the mixture was stirred at 140° C. for 3 h. The reaction mixture was cooled to rt and concentrated. The residue was diluted with EtOAc and extracted with a saturated aqueous NaHCO$_3$ solution. The organic layer was dried (Na$^2$SO$_4$), filtered and concentrated. The product was purified by flash chromatography (heptanes/EtOAc, 100:0→0:100) to give the title compound. $t_R$: 0.61 min (LC-MS 2); ESI-MS: 234.9/237.0 [M+H]$^+$ (LC-MS 2).

Step 144.3:
N-[2-(3-Bromo-phenyl)-2-oxo-ethyl]-acetamide

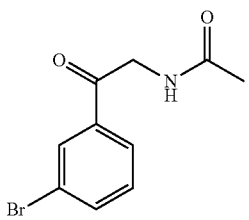

To a solution of the product from step 144.4 (4 g, 13.6 mmol), AcOH (854 µl, 14.9 mmol) and HATU (6.2 g, 16.3 mmol) in DMF (45 mL) was added DIEA (9.5 mL, 54.2 mmol) and the mixture was stirred at rt for 1 h. The reaction mixture was concentrated. The residue was diluted with EtOAc and extracted with H$_2$O and brine. The organic layer was dried (Na$_2$SO$_4$), filtered and concentrated. The product was purified by flash chromatography (heptanes/EtOAc, 30:70→0:100) to give the title compound. $t_R$: 0.73 min (LC-MS 2); ESI-MS: 256.0 [M+H]$^+$ (LC-MS 2).

Step 144.4: 2-Amino-1-(3-bromo-phenyl)-ethanone hydrobromide

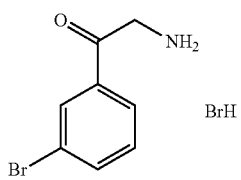 [SMILES: NCC(=O)c1cccc(Br)c1 ; Br]

To a solution of HBr (18.2 mL, 161 mmol) in MeOH (100 mL) was added the product from step 144.5 (22.5 g, 53.7 mmol) and the mixture was stirred at rt over 4 days. The reaction mixture was concentrated and cooled to 0° C. The resulting suspension was filtered and the solid was dried to afford the title compound. $t_R$: 0.49 min (LC-MS 2); ESI-MS: 213.9/216.1 [M+H]$^+$ (LC-MS 2).

Step 144.5: 1-[2-(3-Bromo-phenyl)-2-oxo-ethyl]-3,5,7-triaza-1-azonia-tricyclo[3.3.1.1*3,7]decane hydrobromide

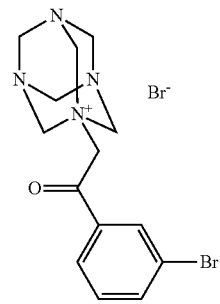 [SMILES: O=C(C[N+]12CN3CN(CN(C3)C1)C2)c1cccc(Br)c1 ; [Br-]]

To a solution of hexamethylenetetramine (8.2 g, 58.4 mmol) in CHCl$_3$ (150 mL) was added 2,3'-dibromoacetophenone (15.2 g, 53 mmol) and the mixture was stirred at rt for 20 h. TNME was added and the resulting solid was filtered, dried in HV to afford the title compound. $t_R$: 0.55 min (LC-MS 2); ESI-MS: 337.1/339.1 [M+H]$^+$ (LC-MS 2).

Example 145

6-(4-Chloro-phenyl)-2-(2,4-dimethoxy-pyrimidin-5-yl)-5-(1,3-dimethyl-2-oxo-hexahydro-pyrimidin-5-yl)-1-isopropyl-5,6-dihydro-1H-pyrrolo[3,4-d]imidazol-4-one

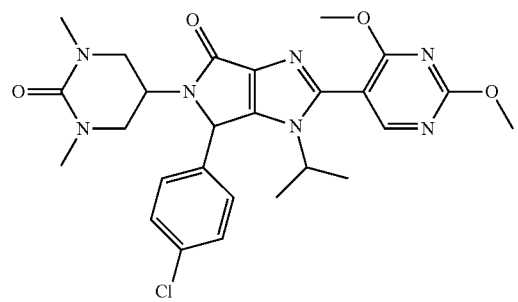 [SMILES: COc1ncc(-c2nc3c(n2C(C)C)C(c2ccc(Cl)cc2)N(C2CN(C)C(=O)N(C)C2)C3=O)c(OC)n1]

The title compound was prepared in analogy to the procedure described for example 29 but using the product from step 128.1 and 2,4-dimethoxypyrimidin-5-ylboronic acid. After extraction, the residue was purified by preparative HPLC. The residue was lyophilized in dioxane to give the title compound. $t_R$: 0.91 min (LC-MS 2); ESI-MS: 540.4/542.3 [M+H]$^+$ (LC-MS 2).

Example 146

{5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid

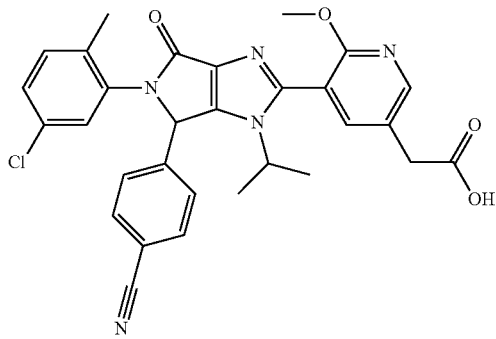 [SMILES: COc1ncc(CC(=O)O)cc1-c1nc2c(n1C(C)C)C(c1ccc(C#N)cc1)N(c1cc(Cl)ccc1C)C2=O]

The title compound was prepared in analogy to the procedure described for example 140 but using the product from example 137. The product was purified by flash chromatography (CH$_2$Cl$_2$/MeOH, 100:0→0:100) to give the title compound. $t_R$: 0.98 min (LC-MS 2); ESI-MS: 556.3/558.3 [M+H]$^+$ (LC-MS 2).

Example 147

2-{5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-N-methyl-acetamide

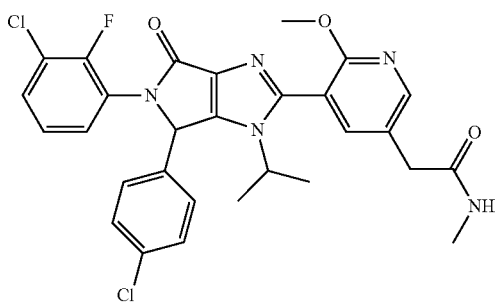 [SMILES: CNC(=O)Cc1cnc(OC)c(-c2nc3c(n2C(C)C)C(c2ccc(Cl)cc2)N(c2cccc(Cl)c2F)C3=O)c1]

To a suspension of the product from step 140 (105 mg, 0.18 mmol), EDC (44 mg, 0.23 mmol) and HOBT (21 mg, 0.14 mmol) in DMF (1.8 mL) was added Et$_3$N (89 µL, 0.64 mmol) and the mixture was stirred at rt 5 min. Methylamine hydrochloride (18 mg, 0.27 mmol) was added and the mixture was stirred at rt 20 h. The reaction mixture was poured into a 1M aqueous NaHCO$_3$ solution and extracted with EtOAc. The organic layer was washed with brine, dried (Na$_2$SO$_4$), filtered and concentrated. The product was purified by flash chromatography (CH$_2$Cl$_2$/MeOH, 96:4→95:5) to give the title compound. $t_R$: 1.07 min (LC-MS 2); ESI-MS: 582.4/584.3 [M+H]$^+$ (LC-MS 2).

Example 148

2-{5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-N-methyl-acetamide

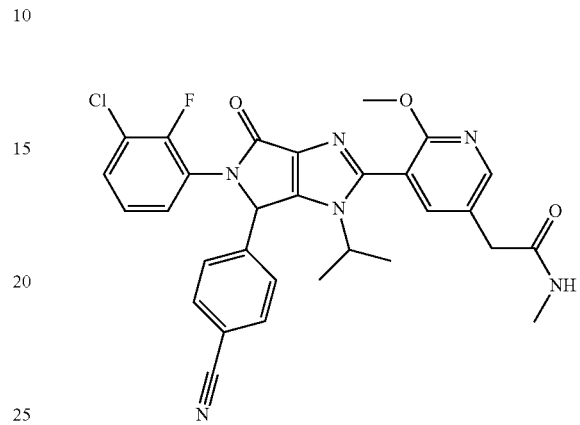

The title compound was prepared in analogy to the procedure described for example 147 but using the product from example 138. $t_R$: 0.94 min (LC-MS 2); ESI-MS: 573.3/575.3 [M+H]$^+$ (LC-MS 2).

Example 149

5-(5-Chloro-2-methyl-phenyl)-6-(4-chloro-phenyl)-2-(2,4-dimethoxy-pyrimidin-5-yl)-1-((S)-2-hydroxy-1-methyl-ethyl)-5,6-dihydro-1H-pyrrolo[3,4-d]imidazol-4-one

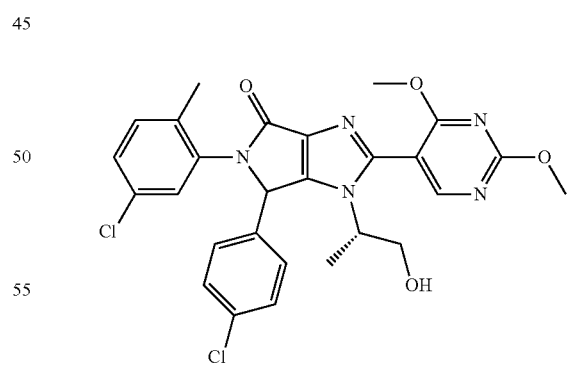

The title compound was prepared in analogy to the procedure described for step 111.2 but using the product from step 149.1. The residue was purified by flash chromatography (CH$_2$Cl$_2$/MeOH, 100:0→95:5). $t_R$: 1.06 min (LC-MS 2); ESI-MS: 554.3/556.4 [M+H]$^+$ (LC-MS 2); $R_f$=0.24 (CH$_2$Cl$_2$/MeOH, 95:5).

Step 149.1: 5-(5-Chloro-2-methyl-phenyl)-6-(4-chloro-phenyl)-2-(2,4-dimethoxy-pyrimidin-5-yl)-1-((S)-1-methyl-2-triisopropylsilanyloxy-ethyl)-5,6-dihydro-1H-pyrrolo[3,4-d]imidazol-4-one

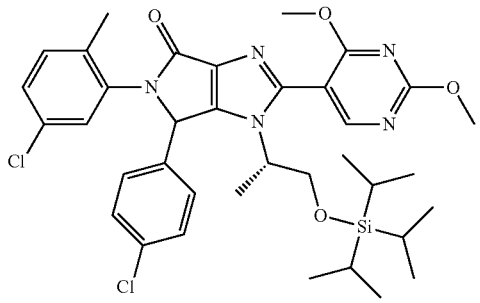 [SMILES: COc1ncc(-c2nc3c(n2[C@@H](C)CO[Si](C(C)C)(C(C)C)C(C)C)C(c2ccc(Cl)cc2)N(c2cc(Cl)ccc2C)C3=O)c(OC)n1]

The title compound was prepared in analogy to the procedure described for example 29 but using the product from step 149.2 and 2,4-dimethoxypyrimidin-5-ylboronic acid. The residue was purified by flash chromatography (heptane/EtOAc, 60:40→0:100). $t_R$: 1.59 min (LC-MS 2); ESI-MS: 710.5/712.5 [M+H]$^+$ (LC-MS 2).

Step 149.2: 2-Bromo-5-(5-chloro-2-methyl-phenyl)-6-(4-chloro-phenyl)-1-((S)-1-methyl-2-triisopropyl-silanyloxy-ethyl)-5,6-dihydro-1H-pyrrolo[3,4-d]imidazol-4-one

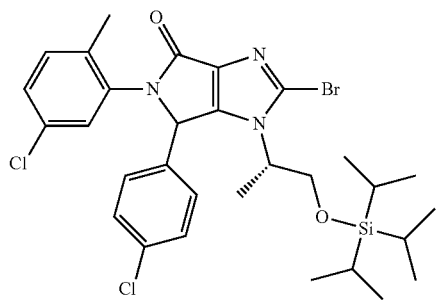 [SMILES: Cc1ccc(Cl)cc1N1C(=O)c2nc(Br)n([C@@H](C)CO[Si](C(C)C)(C(C)C)C(C)C)c2C1c1ccc(Cl)cc1]

The title compound was prepared in analogy to the procedure described for step 93.2 but using the product from step 149.3. The product was purified by flash chromatography (heptane/EtOAc, 2:1). The residue was then triturated in diisopropylether, filtered and concentrated. $t_R$: 1.65 min (LC-MS 2); ESI-MS: 650.3/652.3/654.4 [M+H]$^+$ (LC-MS 2); $R_f$=0.25 (heptane/EtOAc, 2:1).

Step 149.3: 2-Bromo-5-[(5-chloro-2-methyl-phenylamino)-(4-chloro-phenyl)-methyl]-1-((S)-1-methyl-2-triisopropylsilanyloxy-ethyl)-1H-imidazole-4-carboxylic acid

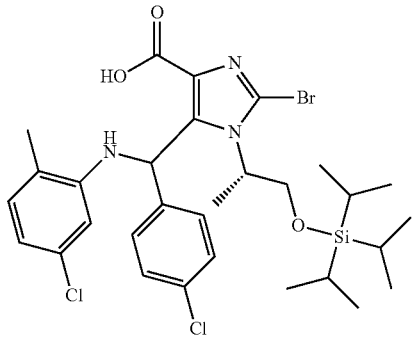 [SMILES: Cc1ccc(Cl)cc1NC(c1ccc(Cl)cc1)c1c(C(=O)O)nc(Br)n1[C@@H](C)CO[Si](C(C)C)(C(C)C)C(C)C]

The title compound was prepared in analogy to the procedure described for step 93.2 but using the product from step 149.4. The product was purified by flash chromatography (CH$_2$Cl$_2$/MeOH, 20:1). $t_R$: 1.66 min (LC-MS 2); ESI-MS: 668.3/670.4/672.4 [M+H]$^+$ (LC-MS 2).

Step 149.4: 2-Bromo-5-[(5-chloro-2-methyl-phenylamino)-(4-chloro-phenyl)-methyl]-1-((S)-1-methyl-2-triisopropylsilanyloxy-ethyl)-1H-imidazole-4-carboxylic acid ethyl ester

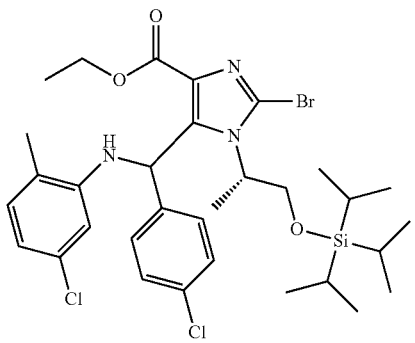 [SMILES: CCOC(=O)c1nc(Br)n([C@@H](C)CO[Si](C(C)C)(C(C)C)C(C)C)c1C(Nc1cc(Cl)ccc1C)c1ccc(Cl)cc1]

The title compound was prepared in analogy to the procedure described for step 93.3 but using the product from step 149.5 and 5-chloro-2-methylaniline. $t_R$: 1.81 min (LC-MS 2); ESI-MS: 696.4/698.4/700.4 [M+H]$^+$ (LC-MS 2); $R_f$=0.33 (heptane/EtOAc, 4:1).

Step 149.5: 2-Bromo-5-[(4-chloro-phenyl)-hydroxymethyl]-1-((S)-1-methyl-2-triisopropylsilanyloxy-ethyl)-1H-imidazole-4-carboxylic acid ethyl ester

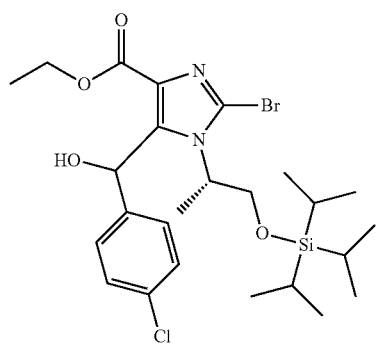 [SMILES: CCOC(=O)c1nc(Br)n([C@@H](C)CO[Si](C(C)C)(C(C)C)C(C)C)c1C(O)c1ccc(Cl)cc1]

The title compound was prepared in analogy to the procedure described for intermediate B but using the product from step 149.6 and 4-chlorobenzaldehyde. The reaction was quenched with a 1M aqueous NH$_4$Cl solution and extracted with EtOAc. The organic layer was dried (Na$_2$SO$_4$), filtered and concentrated. The product was purified by flash chromatography (heptane/EtOAc, 4:1). $t_R$: 1.65 min (LC-MS 2); ESI-MS: 573.3/575.3 [M+H]$^+$ (LC-MS 2); $R_f$=0.18 (heptane/EtOAc, 3:1).

Step 149.6: 2-Bromo-1-((S)-1-methyl-2-triisopropyl-silanyloxy-ethyl)-1H-imidazole-4-carboxylic acid ethyl ester

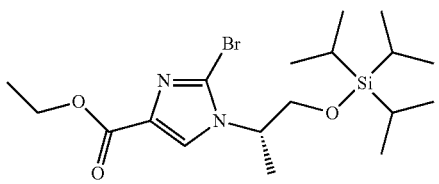 [SMILES: CCOC(=O)c1cn([C@@H](C)CO[Si](C(C)C)(C(C)C)C(C)C)c(Br)n1]

The title compound was prepared in analogy to the procedure described for step 111.7 but using the product from step 149.7. The product was purified by flash chromatography (heptane/EtOAc, 5:1→3:1). $t_R$: 1.49 min (LC-MS 2); ESI-MS: 433.3/435.3 [M+H]$^+$ (LC-MS 2); $R_f$=0.17 (heptane/EtOAc, 3:1).

Step 149.7: 2-Bromo-1-((S)-2-hydroxy-1-methyl-ethyl)-1H-imidazole-4-carboxylic acid ethyl ester

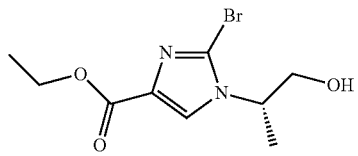

The title compound was prepared in analogy to the procedure described for intermediate A but using the product from step 149.8. The reaction was performed at rt for 4 days. The product was purified by flash chromatography (heptane/EtOAc/MeOH, 1:5:0→0:98:2). The residue was triturated in TBME, then purified by flash chromatography (heptane/EtOAc, 1:5). $t_R$: 0.61 min (LC-MS 2); ESI-MS: 277.1/279.2 [M+H]$^+$ (LC-MS 2); $R_f$=0.27 (CH$_2$Cl$_2$/MeOH, 95:5).

Step 149.8: 1-((S)-2-Hydroxy-1-methyl-ethyl)-1H-imidazole-4-carboxylic acid ethyl ester

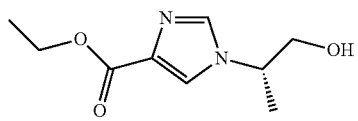

The title compound was prepared in analogy to the procedure described for step 111.9 but using L-alaninol. $t_R$: 0.48 min (LC-MS 2); ESI-MS: 199.1 [M+H]$^+$ (LC-MS 2).

Example 150

{5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester

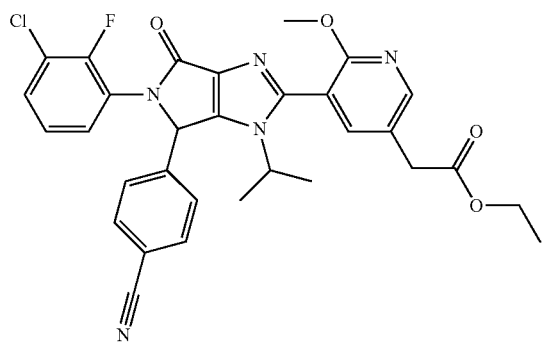 [SMILES: CCOC(=O)Cc1cnc(OC)c(-c2nc3c(n2C(C)C)C(c2ccc(C#N)cc2)N(c2cccc(Cl)c2F)C3=O)c1]

To a solution of intermediate AB (80 mg, 0.17 mmol) and the product from step 137.1 (82 mg, 0.25 mmol) in DME (1.7 mL) was added K$_3$PO$_4$ (71 mg, 0.33 mmol), Pd(OAc)$_2$ (3 mg, 0.01 mmol) and S-Phos (10 mg, 0.02 mmol) and the mixture was stirred at 70° C. for 2 h. The reaction mixture was allowed to cool down to rt, poured into EtOAc and extracted with brine. The organic layer was dried (Na$_2$SO$_4$), filtered and concentrated. The product was purified by flash chromatography (heptane/EtOAc: 80:20→0:100) to afford the title compound. $t_R$: 1.12 min (LC-MS 2); ESI-MS: 588.4/590.3 [M+H]$^+$ (LC-MS 2); $R_f$: 0.21 (CH$_2$Cl$_2$/EtOAc 1:4).

Example 151

2-{5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-N-methyl-acetamide

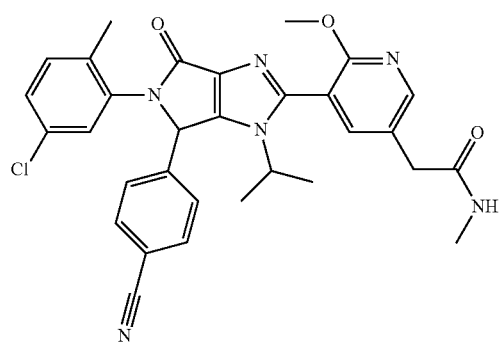 [SMILES: CNC(=O)Cc1cnc(OC)c(-c2nc3c(n2C(C)C)C(c2ccc(C#N)cc2)N(c2cc(Cl)ccc2C)C3=O)c1]

The title compound was prepared in analogy to the procedure described for example 147 but using the product from example 146 and methylamine hydrochloride. $t_R$: 0.97 min (LC-MS 2); ESI-MS: 569.3/571.3 [M+H]$^+$ (LC-MS 2); $R_f$=0.15 (CH$_2$Cl$_2$/MeOH, 20:1).

Example 152

{5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid ethyl ester

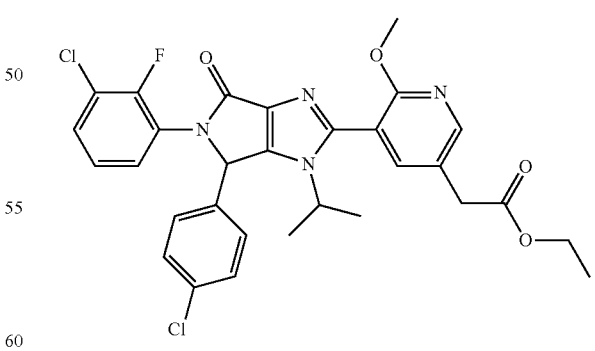

The title compound was prepared in analogy to the procedure described for example 29 but using intermediate G and the product from step 137.1. The reaction was performed at 80° C. The reaction mixture was poured into a saturated aqueous NaHCO$_3$ solution and extracted with EtOAc. The organic layer was washed with brine, dried (Na$_2$SO$_4$), filtered

Example 153

6-(4-Chloro-2-methyl-phenyl)-5-(5-chloro-2-methyl-phenyl)-2-(2,4-dimethoxy-pyrimidin-5-yl)-1-isopropyl-6-methyl-5,6-dihydro-1H-pyrrolo[3,4-d]imidazol-4-one

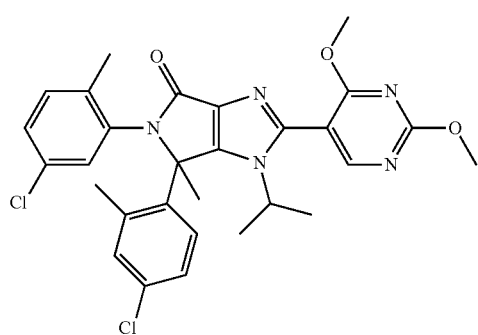 [SMILES: COc1ncc(-c2nc3c(n2C(C)C)C(C)(c2ccc(Cl)cc2C)N(c2cc(Cl)ccc2C)C3=O)c(OC)n1]

To a solution of the product from example 76 (100 mg, 0.18 mmol) in THF (2 mL) at −78° C. was added KHMDS (217 μL, 0.22 mmol, 1M in THF) and the mixture was stirred at −78° C. for 15 min. Methyl iodide (34 μL, 0.54 mmol) was added and the mixture was allowed to warm to rt and the mixture was stirred at rt for 20 h. The reaction mixture was diluted with EtOAc and extracted with a 5% citric acid solution. The organic layer was washed with brine, dried (Na$_2$SO$_4$), filtered and concentrated. The residue was purified by preparative HPLC, then the residue was lyophilized in dioxane. t$_R$: 1.25 min (LC-MS 2); ESI-MS: 566.3/568.2 [M+H]$^+$ (LC-MS 2).

Example 154

2-{3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-phenyl}-N-methyl-acetamide

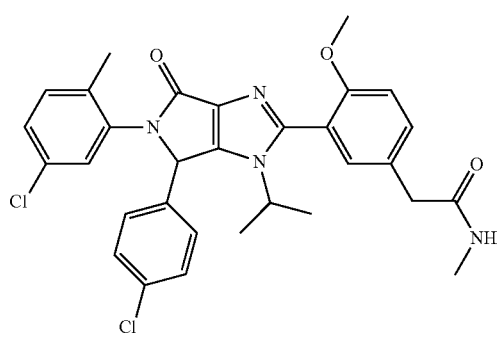 [SMILES: CNC(=O)Cc1ccc(OC)c(-c2nc3c(n2C(C)C)C(c2ccc(Cl)cc2)N(c2cc(Cl)ccc2C)C3=O)c1]

The title compound was prepared in analogy to the procedure described for intermediate F but using the product from step 154.1 and methylamine (2M in THF). The reaction was performed at rt. The reaction mixture was diluted with EtOAc and extracted with H$_2$O. The organic layer was dried (Na$_2$SO$_4$), filtered and concentrated. The residue was purified by preparative HPLC (Waters Sun Fire C18, 30×100 mm, 5 μm; 0.1% TFA-water/acetonitrile; gradient acetonitrile 50-70% in 16 min) to give the title compound. t$_R$: 1.13 min (LC-MS 2); ESI-MS: 577.4/579.4 [M+H]$^+$ (LC-MS 2).

Step 154.1: {3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid

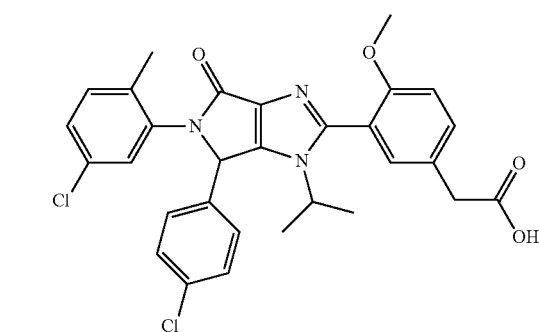 [SMILES: COc1ccc(CC(=O)O)cc1-c1nc2c(n1C(C)C)C(c1ccc(Cl)cc1)N(c1cc(Cl)ccc1C)C2=O]

The title compound was prepared in analogy to the procedure described for step 64.1 but using the product from step 154.2. The reaction was performed at rt. The reaction mixture was diluted with EtOAc and extracted with 5% citric acid. The organic layer was dried (Na$_2$SO$_4$), filtered and concentrated. t$_R$: 1.16 min (LC-MS 2); ESI-MS: 564.4/566.4 [M+H]$^+$ (LC-MS 2).

Step 154.2: {3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid methyl ester

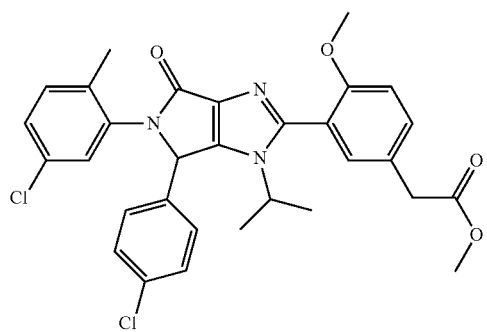 [SMILES: COC(=O)Cc1ccc(OC)c(-c2nc3c(n2C(C)C)C(c2ccc(Cl)cc2)N(c2cc(Cl)ccc2C)C3=O)c1]

The title compound was prepared in analogy to the procedure described for example 1 but using intermediate E and the product from step 154.3. t$_R$: 1.26 min (LC-MS 2); ESI-MS: 578.3/580.3 [M+H]$^+$ (LC-MS 2).

Step 154.3: [4-Methoxy-3-(4,4,5,5-tetramethyl-[1,3,2]dioxaborolan-2-yl)-phenyl]-acetic acid methyl ester

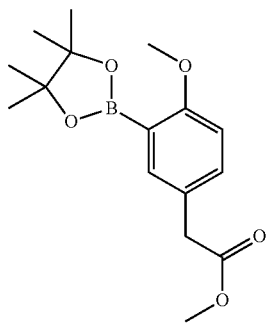 [SMILES: COC(=O)Cc1ccc(OC)c(B2OC(C)(C)C(C)(C)O2)c1]

The title compound was prepared in analogy to the procedure described for intermediate S but using the product from step 154.4. The residue was purified by flash chromatography (hexane/EtOAc). $t_R$: 1.07 min (LC-MS 2); $R_f$: 0.47 (hexane/EtOAc 2:1).

Step 154.3: (3-Bromo-4-methoxy-phenyl)-acetic acid methyl ester

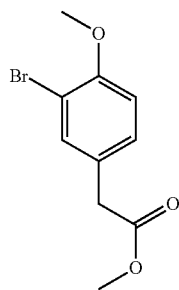

A solution of 3-bromo-4-methoxyphenylacetic acid (7.5 g, 30.6 mmol), MeOH (24 mL) and $H_2SO_4$ (0.8 mL) was stirred at 75° C. for 17 h. The reaction mixture was concentrated. The residue was poured into $H_2O$ and extracted with $CH_2Cl_2$. The organic layer was washed with brine, dried (NaSO$_4$), filtered and concentrated to afford the title compound. $t_R$: 0.99 min (LC-MS 2).

Example 155

2-{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-N,N-dimethyl-acetamide

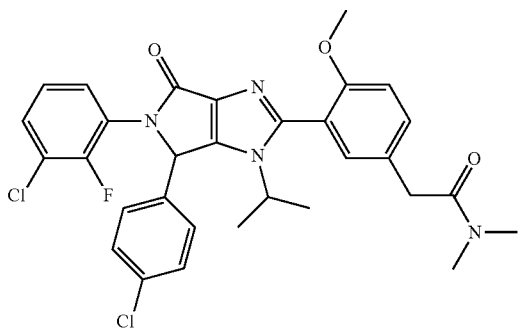 [SMILES: COc1ccc(CC(=O)N(C)C)cc1-c1nc2c(n1C(C)C)C(c1ccc(Cl)cc1)N(c1cccc(Cl)c1F)C2=O]

The title compound was prepared in analogy to the procedure described for intermediate F but using the product from example 162 and dimethylamine (2M in THF). The reaction was performed at rt. The reaction mixture was diluted with EtOAc and extracted with $H_2O$. The organic layer was dried (Na$_2$SO$_4$), filtered and concentrated. The residue was purified by preparative HPLC (Waters Sun Fire C18, 30×100 mm, 5 µm; 0.1% TFA-water/acetonitrile; gradient acetonitrile 50-70% in 16 min) to give the title compound. $t_R$: 1.16 min (LC-MS 2); ESI-MS: 595.4/597.3 [M+H]$^+$ (LC-MS 2).

Example 156

5-(5-Chloro-2-methyl-phenyl)-6-(4-chloro-phenyl)-2-(2,4-dimethoxy-pyrimidin-5-yl)-1-((S)-2-methoxy-1-methyl-ethyl)-5,6-dihydro-1H-pyrrolo[3,4-d]imidazol-4-one

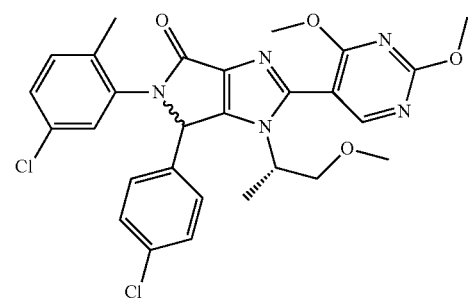 [SMILES: COC[C@H](C)n1c(-c2cnc(OC)nc2OC)nc2c1C(c1ccc(Cl)cc1)N(c1cc(Cl)ccc1C)C2=O]

The title compound was prepared in analogy to the procedure described for step 97.1 but using the product from step 156.1. The residue was purified by flash chromatography (hexane/EtOAc, 100:0→0:100). $t_R$: 1.18 min (LC-MS 2); ESI-MS: 568.5/570.5 [M+H]$^+$ (LC-MS 2).

Step 156.1: 2-Bromo-5-(5-chloro-2-methyl-phenyl)-6-(4-chloro-phenyl)-1-((S)-2-methoxy-1-methyl-ethyl)-5,6-dihydro-1H-pyrrolo[3,4-d]imidazol-4-one

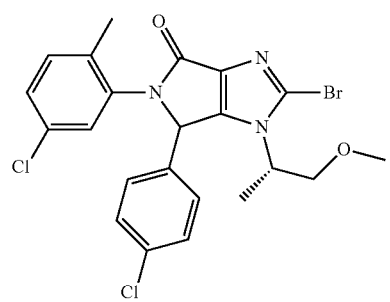 [SMILES: COC[C@H](C)n1c(Br)nc2c1C(c1ccc(Cl)cc1)N(c1cc(Cl)ccc1C)C2=O]

A solution of the product from step 156.2 (850 mg, 1.3 mmol) in DMF (5 mL) was stirred at 100° C. for 1 h. The reaction mixture was cooled to rt, diluted with EtOAc and extracted with a saturated aqueous NaHCO$_3$ solution. The organic layer was washed with brine, dried (Na$_2$SO$_4$), filtered and concentrated. The residue was purified by flash chromatography (hexane/EtOAc, 100:0→60:40) to afford the title compound. $t_R$: 1.19/1.21 min (LC-MS 2); ESI-MS: 508.2/510.2/521.3 [M+H]$^+$ (LC-MS 2).

Step 156.2: 2-Bromo-5-[(5-chloro-2-methyl-phenylamino)-(4-chloro-phenyl)-methyl]-1-((S)-2-methoxy-1-methyl-ethyl)-1H-imidazole-4-carboxylic acid benzotriazol-1-yl ester

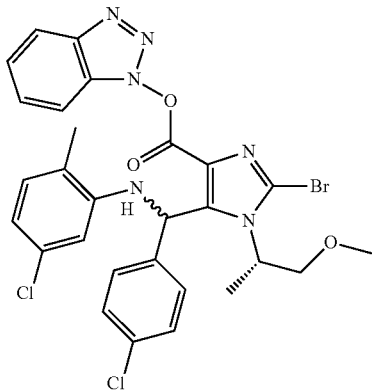

The title compound was prepared in analogy to the procedure described for intermediate E but using the product from step 156.3. The reaction was performed at rt for 1 h. The reaction mixture was diluted with EtOAc and extracted with a saturated aqueous NaHCO$_3$ solution. The organic layer was washed with brine, dried (Na$_2$SO$_4$), filtered and concentrated. The residue was purified by flash chromatography (heptane/EtOAc, 100:0→60:40). $t_R$: 1.45 min (LC-MS 2); ESI-MS: 643.3/645.1/647.2 [M+H]$^+$ (LC-MS 2).

Step 156.3: 2-Bromo-5-[(5-chloro-2-methyl-phenylamino)-(4-chloro-phenyl)-methyl]-1-((S)-2-methoxy-1-methyl-ethyl)-1H-imidazole-4-carboxylic acid

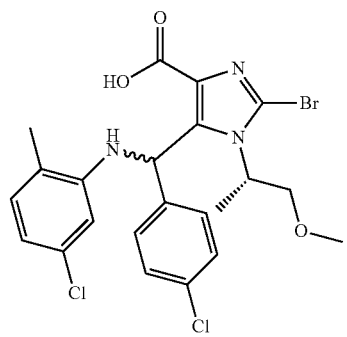 [SMILES: COC[C@H](C)n1c(Br)nc(C(=O)O)c1C(Nc1cc(Cl)ccc1C)c1ccc(Cl)cc1]

The title compound was prepared in analogy to the procedure described for step E1 but using the product from step 156.4. The reaction was performed in EtOH at rt for 20 h. EtOH was removed and at 0° C. was added a citric acid solution, extracted with CH$_2$Cl$_2$, dried (Na$_2$SO$_4$), filtered and concentrated. $t_R$: 1.25 min (LC-MS 2); ESI-MS: 526.1/528.1/530.2 [M+H]$^+$ (LC-MS 2).

Step 156.4: 2-Bromo-5-[(5-chloro-2-methyl-phenylamino)-(4-chloro-phenyl)-methyl]-1-((S)-2-methoxy-1-methyl-ethyl)-1H-imidazole-4-carboxylic acid ethyl ester

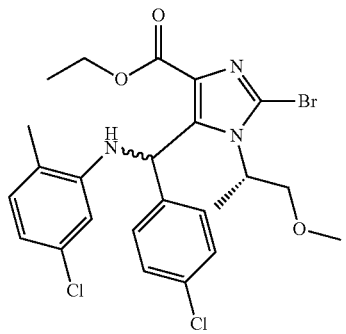 [SMILES: CCOC(=O)c1nc(Br)n([C@@H](C)COC)c1C(Nc1cc(Cl)ccc1C)c1ccc(Cl)cc1]

The title compound was prepared in analogy to the procedure described for step E2 but using the product from step 156.5 and 5-chloro-2-methylaniline. The product was purified by flash chromatography (heptane/EtOAc, 100:0→70:30). $t_R$: 1.44/1.47 min (LC-MS 2); ESI-MS: 554.2/556.3/558.3 [M+H]$^+$ (LC-MS 2).

Step 156.5: 2-Bromo-5-[(S)-(4-chloro-phenyl)-hydroxy-methyl]-1-((S)-2-methoxy-1-methyl-ethyl)-1H-imidazole-4-carboxylic acid ethyl ester

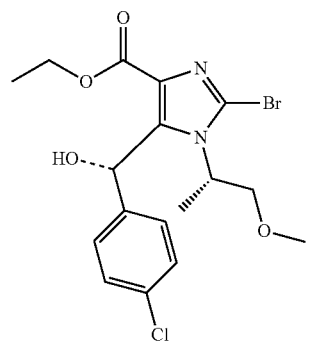 [SMILES: CCOC(=O)c1nc(Br)n([C@@H](C)COC)c1[C@@H](O)c1ccc(Cl)cc1]

The title compound was prepared in analogy to the procedure described for intermediate B but using the product from step 156.6. The reaction was quenched with a 1M aqueous NH$_4$Cl solution and extracted with EtOAc. The organic layer was dried (Na$_2$SO$_4$), filtered and concentrated. The product was purified by flash chromatography (heptane/EtOAc, 100:0→60:40). $t_R$: 1.11 min (LC-MS 2); ESI-MS: 431.2/433.2 [M+H]$^+$ (LC-MS 2).

Step 156.6: 2-Bromo-1-((S)-2-methoxy-1-methyl-ethyl)-1H-imidazole-4-carboxylic acid ethyl ester

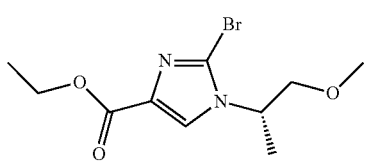 [SMILES: CCOC(=O)c1cn([C@@H](C)COC)c(Br)n1]

The title compound was prepared in analogy to the procedure described for intermediate A but using the product from step 156.7. The product was purified by flash chromatography (hexane/EtOAc, 100:0→1:1). $t_R$: 0.76 min (LC-MS 2); ESI-MS: 291.2/293.2 [M+H]$^+$ (LC-MS 2).

Step 156.7: 1-((S)-2-Methoxy-1-methyl-ethyl)-1H-imidazole-4-carboxylic acid ethyl ester

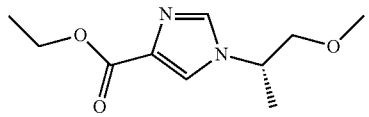

The title compound was prepared in analogy to the procedure described for step 111.9 but using (S)-1-methoxy-2-propylamine. The reaction mixture was concentrated and purified by flash chromatography (hexane/EtOAc, 100:0→0:100). $t_R$: 0.59 min (LC-MS 2); ESI-MS: 213.2 [M+H]$^+$ (LC-MS 2).

Example 157

2-{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-N-methyl-acetamide

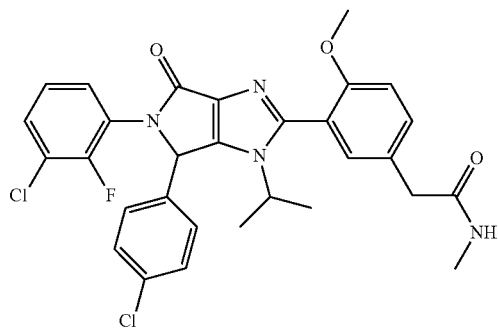 [SMILES: CNC(=O)Cc1ccc(OC)c(-c2nc3c(n2C(C)C)C(c2ccc(Cl)cc2)N(c2cccc(Cl)c2F)C3=O)c1]

The title compound was prepared in analogy to the procedure described for intermediate F but using the product from example 162 and methylamine (2M in THF). The reaction was performed at rt. The reaction mixture was diluted with EtOAc and extracted with H$_2$O. The organic layer was dried (Na$_2$SO$_4$), filtered and concentrated. The residue was purified by preparative HPLC (Waters Sun Fire C18, 30×100 mm, 5 μm; 0.1% TFA-water/acetonitrile; gradient acetonitrile 50-70% in 16 min) to give the title compound. $t_R$: 1.11 min (LC-MS 2); ESI-MS: 581.3/583.3 [M+H]$^+$ (LC-MS 2).

Example 158

5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

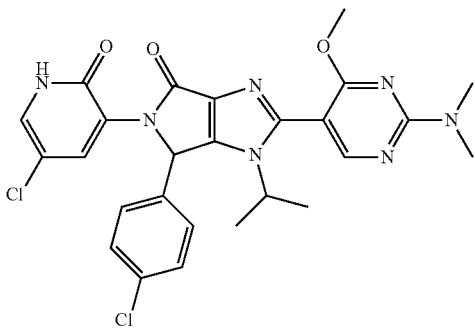 [SMILES: COc1nc(N(C)C)ncc1-c1nc2c(n1C(C)C)C(c1ccc(Cl)cc1)N(c1cc(Cl)c[nH]c1=O)C2=O]

The title compound was prepared in analogy to the procedure described for example 29 but using the product from step 158.1 and intermediate W. The reaction mixture was concentrated and diluted with a saturated aqueous NH$_4$Cl solution and extracted with EtOAc. The organic layer was dried (Na$_2$SO$_4$), filtered and concentrated. The product was purified by flash chromatography (CH$_2$Cl$_2$/MeOH, 99:1→94:6). The residue was purified by preparative chromatography (Waters Sun Fire C18, 30×100 mm, 5 μm; 0.1% TFA-water/acetonitrile; gradient acetonitrile 5-100% in 20 min) to give the title compound. $t_R$: 1.06 min (LC-MS 2); ESI-MS: 554.2/556.2 [M+H]$^+$ (LC-MS 2); R$_f$: 0.42 (CH$_2$Cl$_2$/MeOH 9:1).

Step 158.1: 2-Bromo-5-(5-chloro-2-oxo-1,2-dihydro-pyridin-3-yl)-6-(4-chloro-phenyl)-1-isopropyl-5,6-dihydro-1H-pyrrolo[3,4-d]imidazol-4-one

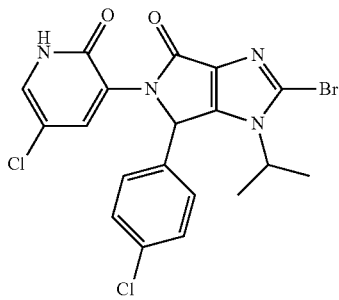 [SMILES: CC(C)n1c(Br)nc2c1C(c1ccc(Cl)cc1)N(c1cc(Cl)c[nH]c1=O)C2=O]

The title compound was prepared in analogy to the procedure described for intermediate E but using the product from step 158.2. The reaction was concentrated and diluted with a saturated aqueous NH$_4$Cl solution and extracted with EtOAc. The organic layer was dried (Na$_2$SO$_4$), filtered and concentrated. The product was purified by flash chromatography (CH$_2$Cl$_2$/MeOH, 99:1→96:4). The residue was purified by preparative chromatography (Waters Sun Fire C18, 30×100 mm, 5 μm; 0.1% TFA-water/acetonitrile; gradient acetonitrile 5-100% in 20 min) to give the title compound. $t_R$: 0.95 min (LC-MS 2); ESI-MS: 481.1/483.1/485.1 [M+H]$^+$ (LC-MS 2); R$_f$: 0.33 (CH$_2$Cl$_2$/MeOH 9:1).

Step 158.2: 2-Bromo-5-[(5-chloro-2-oxo-1,2-dihydro-pyridin-3-ylamino)-(4-chloro-phenyl)-methyl]-1-isopropyl-1H-imidazole-4-carboxylic acid

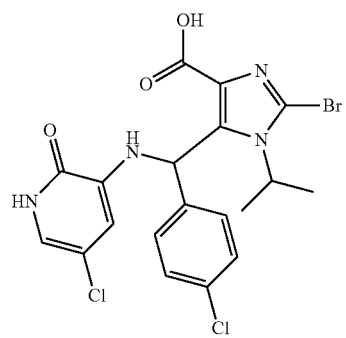 [SMILES: CC(C)n1c(Br)nc(C(=O)O)c1C(Nc1cc(Cl)c[nH]c1=O)c1ccc(Cl)cc1]

The title compound was prepared in analogy to the procedure described for step E1 but using the product from step 158.3. The reaction was concentrated and diluted with a saturated aqueous NH$_4$Cl solution and extracted with CH$_2$Cl$_2$/MeOH 9:1. The organic layer was dried (Na$_2$SO$_4$), filtered and concentrated. The product was used without further purification. $t_R$: 0.97 min (LC-MS 2); ESI-MS: 499.1/501.1/503.1 [M+H]$^+$ (LC-MS 2).

Step 158.3: 2-Bromo-5-[(5-chloro-2-oxo-1,2-dihydro-pyridin-3-ylamino)-(4-chloro-phenyl)-methyl]-1-isopropyl-1H-imidazole-4-carboxylic acid ethyl ester

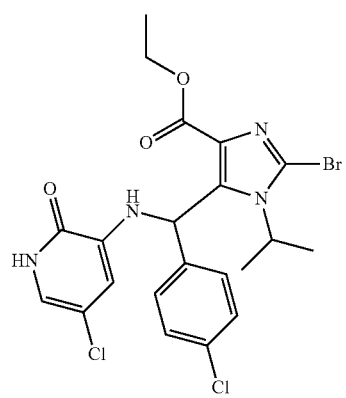 [SMILES: CCOC(=O)c1nc(Br)n(C(C)C)c1C(Nc1cc(Cl)c[nH]c1=O)c1ccc(Cl)cc1]

The title compound was prepared in analogy to the procedure described for step E2 but using intermediate B and 3-amino-5-chloropyridin-2-ol. The reaction mixture was quenched with a saturated aqueous NaHCO$_3$ solution and extracted with EtOAc. The organic layer was washed with a saturated aqueous NaHCO$_3$ solution, dried (Na$_2$SO$_4$), filtered and concentrated. The product was purified by flash chromatography (CH$_2$Cl$_2$/MeOH, 99:1→97:3). $t_R$: 1.15-1.18 min (LC-MS 2); ESI-MS: 527.1/529.1/531.1 [M+H]$^+$ (LC-MS 2); R$_f$: 0.41 (CH$_2$Cl$_2$/MeOH 9:1).

Example 159

2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one

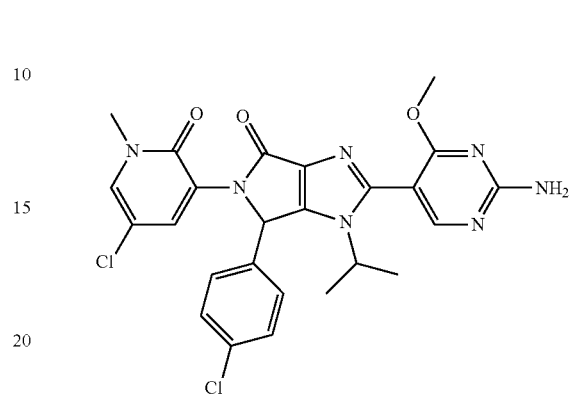

The title compound was prepared in analogy to the procedure described for example 29 but using the product from step 101.1 and intermediate U. The reaction was performed at 110° C. for 30 min. The product was purified by flash chromatography (CH$_2$Cl$_2$/MeOH, 92.7:7.2). The residue was purified by preparative chromatography (Waters Sun Fire C18, 30×100 mm, 5 μm; 0.1% TFA-water/acetonitrile; gradient acetonitrile 20-60% in 20 min) to give the title compound. $t_R$: 0.94 min (LC-MS 2); ESI-MS: 540.2/542.2 [M+H]$^+$ (LC-MS 2); R$_f$: 0.10 (CH$_2$Cl$_2$/MeOH 92.7:7.5); $^1$H-NMR (DMSO-d$_6$, 400 MHz) δ ppm 8.08 (s, 1H), 7.89 (d, 1H), 7.47 (d, 1H), 7.42-7.38 (m, 2H), 7.32-7.25 (m, 2H), 7.06 (s, 2H), 6.68 (s, 1H), 4.10-4.04 (m, 1H), 3.81 (s, 3H), 3.42 (s, 3H), 1.31 (d, 3H), 0.50 (d, 3H).

Example 160

4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

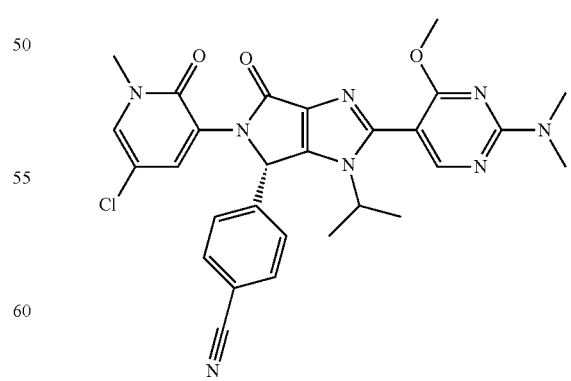

The title compound was obtained after preparative chiral HPLC separation of the racemic product of example 100 (Column: Chiralpak iA, 20×250 mm. Flow 13 mL/min. hex-

Example 161

4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile

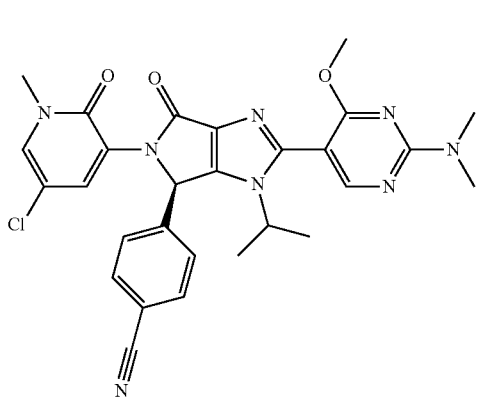 [SMILES: COc1nc(N(C)C)ncc1-c1nc2c(n1C(C)C)[C@@H](c1ccc(C#N)cc1)N(c1cc(Cl)cn(C)c1=O)C2=O]

The title compound was obtained after preparative chiral HPLC separation of the racemic product of example 100 (Column: Chiralpak iA, 20×250 mm. Flow 13 mL/min. hexane/EtOH 50:50). $t_R$: 6.4 min (Column: Chiralpak iA, 4.6× 250 mm. Flow 1 mL/min. hexane/EtOH 50:50).

Example 162

{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid

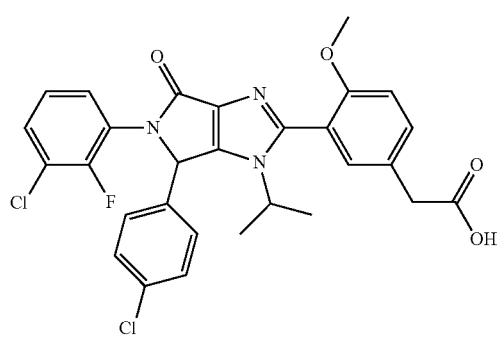 [SMILES: COc1ccc(CC(=O)O)cc1-c1nc2c(n1C(C)C)C(c1ccc(Cl)cc1)N(c1cccc(Cl)c1F)C2=O]

The title compound was prepared in analogy to the procedure described for step 64.1 but using the product from example 165. The reaction was performed at rt. The reaction mixture was diluted with EtOAc and extracted with 5% citric acid. The organic layer was dried (Na$_2$SO$_4$), filtered and concentrated. $t_R$: 1.12 min (LC-MS 2); ESI-MS: 568.2/570.3 [M+H]$^+$ (LC-MS 2).

Example 163

(R)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

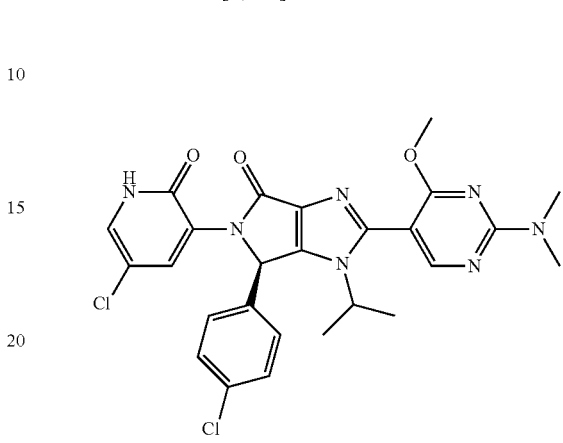

The title compound was obtained after preparative chiral SFC separation of the racemic product of example 158. (Column: Chiralpak AS-H, 30×250 mm. Flow 80 mL/min. scCO$_2$/MeOH 70:30). $t_R$: 5.11 min (Column: Chiralpak AS-H, 4.6× 250 mm. Flow 3 mL/min. scCO$_2$/MeOH 70:30).

Example 164

(S)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

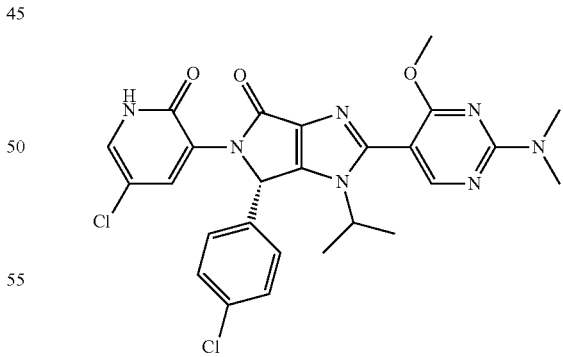

The title compound was obtained after preparative chiral SFC separation of the racemic product of example 158. (Column: Chiralpak AS-H, 30×250 mm. Flow 80 mL/min. scCO$_2$/MeOH 70:30). $t_R$: 1.69 min (Column: Chiralpak AS-H, 4.6× 250 mm. Flow 3 mL/min. scCO$_2$/MeOH 70:30).

Example 165

{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid methyl ester

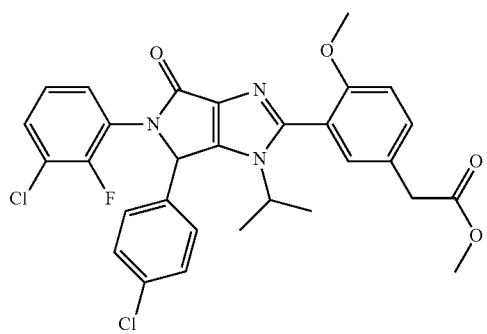 [SMILES: COC(=O)Cc1ccc(OC)c(-c2nc3c(n2C(C)C)C(c2ccc(Cl)cc2)N(c2cccc(Cl)c2F)C3=O)c1]

The title compound was prepared in analogy to the procedure described for example 1 but using intermediate G and the product from step 154.3. $t_R$: 1.21 min (LC-MS 2); ESI-MS: 582.3/584.3 [M+H]$^+$ (LC-MS 2).

Example 166

4-[(R)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile

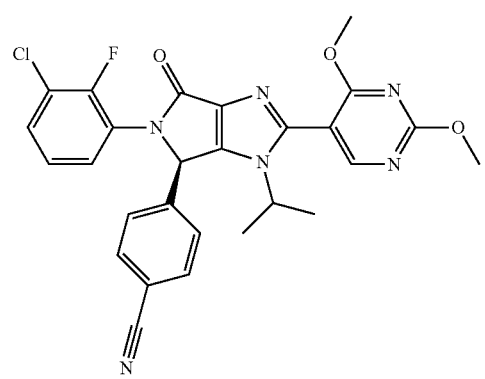 [SMILES: COc1ncc(-c2nc3c(n2C(C)C)[C@@H](c2ccc(C#N)cc2)N(c2cccc(Cl)c2F)C3=O)c(OC)n1]

The title compound was obtained after preparative chiral SFC separation of the racemic product of example 79. (Column: Chiralpak AD-H, 30×250 mm. Flow 100 mL/min. scCO$_2$/EtOH 70:30). $t_R$: 3.50 min (Column: Chiralpak AD-H, 4.6×250 mm. Flow 3 mL/min. scCO$_2$/EtOH 70:30).

Example 167

4-[5-(3-Chloro-4-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile

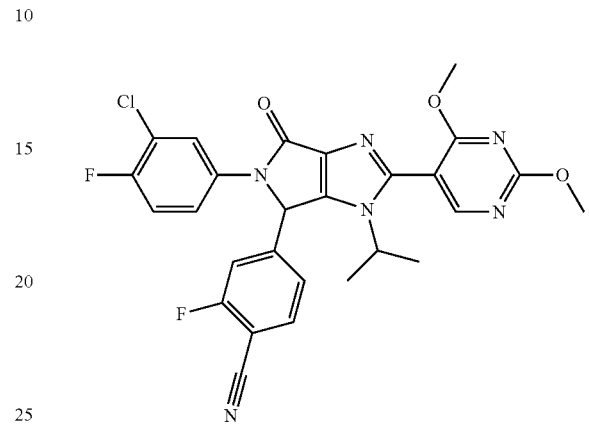

The title compound was prepared in analogy to the procedure described for example 1 but using the product from step 167.1 and 2,4-dimethoxypyrimidin-5-ylboronic acid. After the purification by preparative HPLC, the residue was purified by preparative TLC (EtOAc) to give the title compound. $t_R$: 1.08 min (LC-MS 2); ESI-MS: 551.3 [M+H]$^+$ (LC-MS 2).

Step 167.1: 4-[2-Bromo-5-(3-chloro-4-fluoro-phenyl)-3-isopropyl-6-oxo-3,4,5,6-tetrahydro-pyrrolo[3,4-d]imidazol-4-yl]-2-fluoro-benzonitrile

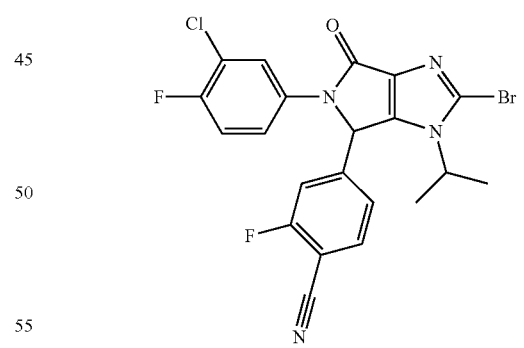

The title compound was prepared in analogy to the procedure described for step 144.3 but using the product from step 167.2. The reaction was performed at 80° C. for 5 h. The product was purified by flash chromatography (heptanes/MeOH 70:30). $t_R$: 1.69 min (Column: Chiralpak AS-H, 4.6×250 mm. Flow 3 mL/min. scCO$_2$/MeOH 70:30). EtOAc, 1:1→0:100) to give the title compound. $t_R$: 1.09 min (LC-MS 2); ESI-MS: 491.1/493.1 [M+H]$^+$ (LC-MS 2).

Step 167.2: 2-Bromo-5-[(3-chloro-4-fluoro-phenylamino)-(4-cyano-3-fluoro-phenyl)-methyl]-1-isopropyl-1H-imidazole-4-carboxylic acid

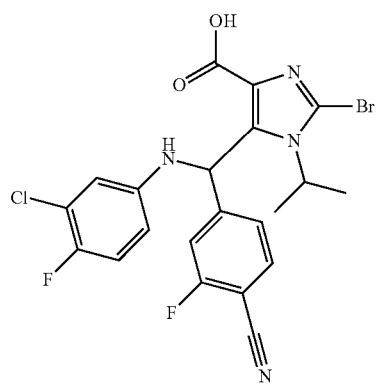 [SMILES: CC(C)n1c(Br)nc(C(=O)O)c1C(Nc1ccc(F)c(Cl)c1)c1ccc(C#N)c(F)c1]

The title compound was prepared in analogy to the procedure described for step E1 but using the product from step 167.3. $t_R$: 1.09 min (LC-MS 2); ESI-MS: 509.0 [M+H]$^+$ (LC-MS 2).

Step 167.3: 2-Bromo-5-[(3-chloro-4-fluoro-phenylamino)-(4-cyano-3-fluoro-phenyl)-methyl]-1-isopropyl-1H-imidazole-4-carboxylic acid ethyl ester

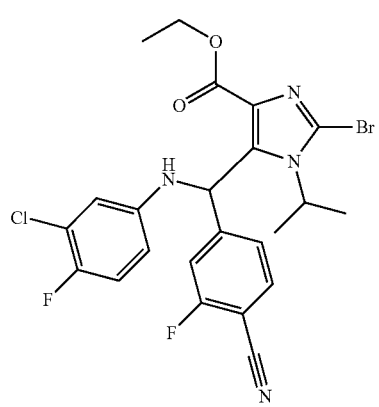 [SMILES: CCOC(=O)c1nc(Br)n(C(C)C)c1C(Nc1ccc(F)c(Cl)c1)c1ccc(C#N)c(F)c1]

The title compound was prepared in analogy to the procedure described for step E2 but using the product from step 167.4 and 3-chloro-4-fluoroaniline. The mixture was extracted with a saturated aqueous NaHCO$_3$ solution. The organic layers were dried (Na$_2$SO$_4$), filtered and concentrated. The product was purified by flash chromatography (hexane/EtOAc, 100:0→60:40). $t_R$: 1.27 min (LC-MS 2); ESI-MS: 537.2/539.2 [M+H]$^+$ (LC-MS 2).

Step 167.4: 2-Bromo-5-[(3-chloro-4-fluoro-phenylamino)-(4-cyano-3-fluoro-phenyl)-methyl]-1-isopropyl-1H-imidazole-4-carboxylic acid ethyl ester

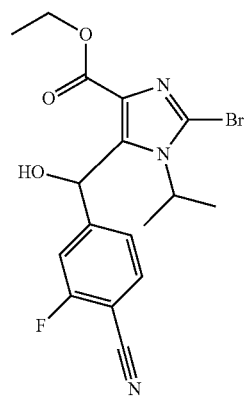 [SMILES: CCOC(=O)c1nc(Br)n(C(C)C)c1C(O)c1ccc(C#N)c(F)c1]

The title compound was prepared in analogy to the procedure described for intermediate B but using intermediate A and 4-cyano-3-fluorobenzaldehyde. The product was purified by flash chromatography (hexane/EtOAc, 100:0→0:100). The residue was then triturated in Et$_2$O to give the title compound as white foam. $t_R$: 1.03 min (LC-MS 2); ESI-MS: 410.1/412.1 [M+H]$^+$ (LC-MS 2).

Example 168

(R)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one

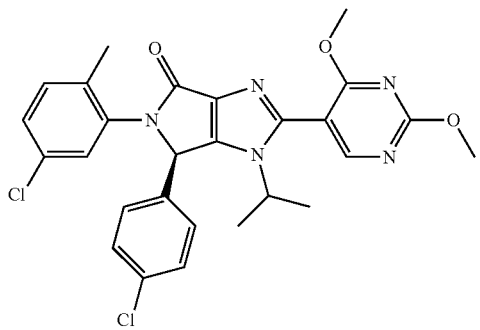 [SMILES: COc1ncc(-c2nc3c(n2C(C)C)[C@@H](c2ccc(Cl)cc2)N(c2cc(Cl)ccc2C)C3=O)c(OC)n1]

The title compound was obtained after preparative chiral SFC separation of the racemic product of example 27. (Column: Chiralpak OD-H, 30×250 mm. Flow 100 mL/min. scCO$_2$/EtOH 65:35). $t_R$: 2.39 min (Column: Chiralpak OD-H, 4.6×250 mm. Flow 3 mL/min. scCO$_2$/EtOH 60:40).

Example 169

(S)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one

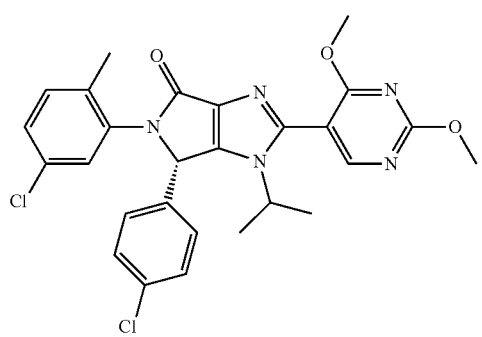 [SMILES: COc1ncc(-c2nc3c(n2C(C)C)[C@H](c2ccc(Cl)cc2)N(c2cc(Cl)ccc2C)C3=O)c(OC)n1]

The title compound was obtained after preparative chiral SFC separation of the racemic product of example 27. (Column: Chiralpak OD-H, 30×250 mm. Flow 100 mL/min. scCO$_2$/EtOH 65:35). t$_R$: 1.77 min (Column: Chiralpak OD-H, 4.6×250 mm. Flow 3 mL/min. scCO$_2$/EtOH 60:40).

Example 170

4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carbonitrile

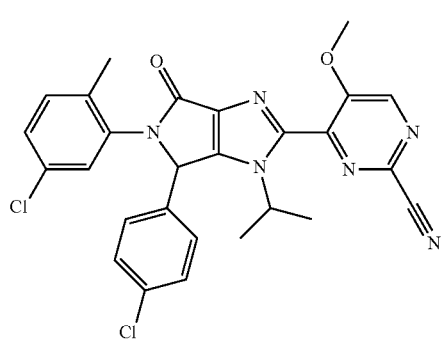 [SMILES: COc1cnc(C#N)nc1-c1nc2c(n1C(C)C)C(c1ccc(Cl)cc1)N(c1cc(Cl)ccc1C)C2=O]

To a solution of the product from step 121.1 (115 mg, 0.2 mmol) in DMF (2 mL) was added Pd(PPh$_3$)$_2$ (73 mg, 0.06 mmol) and Zn(CN)$_2$ (17 mg, 0.15 mmol) and the mixture was stirred at 100° C. for 16 h. The reaction mixture was diluted with EtOAc and extracted with H$_2$O. The organic layer was dried (Na$_2$SO$_4$), filtered and concentrated. The residue was triturated in acetonitrile and MeOH and filtered. The mother liquor was concentrated. The residue was purified by preparative HPLC (Waters Sun Fire C18, 30×100 mm, 5 μm; 0.1% TFA-water/acetonitrile; gradient acetonitrile 50-90% in 16 min) to give the title compound. t$_R$: 1.21 min (LC-MS 2); ESI-MS: 533.2/535.2 [M+H]$^+$ (LC-MS 2).

Example 171

5-(3-Chloro-2-fluoro-phenyl)-6-(4-chloro-phenyl)-2-(2-dimethylamino-5-methoxy-pyrimidin-4-yl)-1-isopropyl-5,6-dihydro-1H-pyrrolo[3,4-d]imidazol-4-one

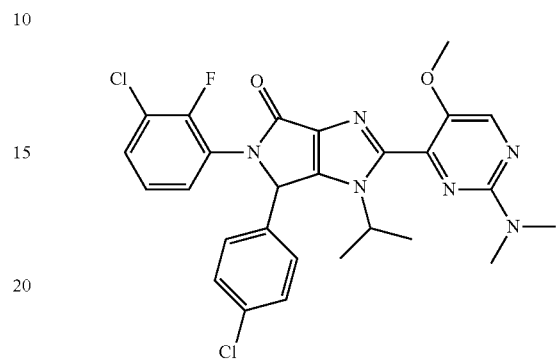

The title compound was prepared in analogy to the procedure described for step W1 but using the product from step 96.1. The reaction was performed at 70° C. for 24 h. The reaction mixture was diluted with EtOAc and extracted with H$_2$O. The organic layer was dried (Na$_2$SO$_4$), filtered and concentrated. The product was purified by SFC chromatography then by preparative HPLC (Waters Sun Fire C18, 30×100 mm, 5 μm; 0.1% TFA-water/acetonitrile; gradient acetonitrile 25-45% in 16 min) to give the title compound. t$_R$: 1.25 min (LC-MS 2); ESI-MS: 555.3/557.3 [M+H]$^+$ (LC-MS 2).

Example 172

5-(5-Chloro-2-methyl-phenyl)-6-(4-chloro-phenyl)-2-(2-dimethylamino-5-methoxy-pyrimidin-4-yl)-1-isopropyl-5,6-dihydro-1H-pyrrolo[3,4-d]imidazol-4-one

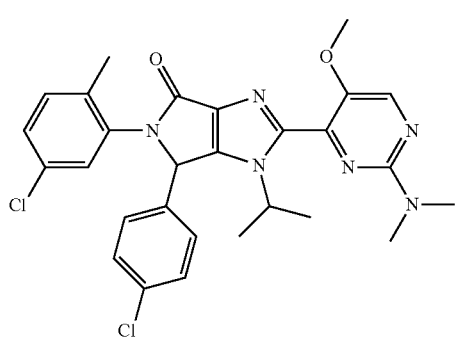 [SMILES: COc1cnc(N(C)C)nc1-c1nc2c(n1C(C)C)C(c1ccc(Cl)cc1)N(c1cc(Cl)ccc1C)C2=O]

The title compound was prepared in analogy to the procedure described for step 171 but using the product from step 121.1. t$_R$: 1.28 min (LC-MS 2); ESI-MS: 551.3/553.3 [M+H]$^+$ (LC-MS 2).

Example 173

3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide

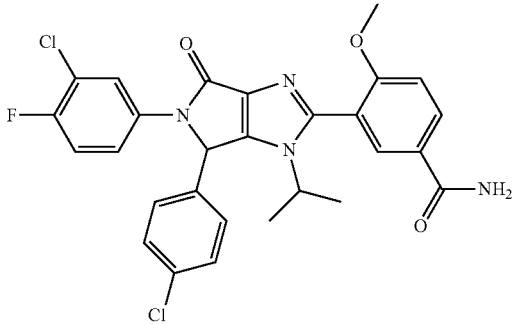 [SMILES: COc1ccc(C(N)=O)cc1-c1nc2c(n1C(C)C)C(c1ccc(Cl)cc1)N(c1ccc(F)c(Cl)c1)C2=O]

The title compound was prepared in analogy to the procedure described for example 1 but using the product from step 173.1 and intermediate Q. The product was purified by SFC chromatography (Column DEAP, 250×30 mm, 5 µm, flow 100 mL/min, grad 23-28% over 6 min) to give the title compound. $t_R$: 1.08 min (LC-MS 2); ESI-MS: 553.3/555.2 [M+H]$^+$ (LC-MS 2).

Step 173.1: 4-Methoxy-3-(4,4,5,5-tetramethyl-[1,3,2]dioxaborolan-2-yl)-benzamide

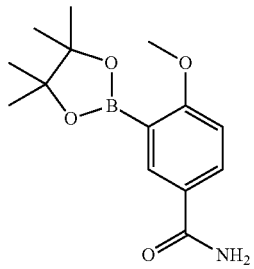 [SMILES: COc1ccc(C(N)=O)cc1B1OC(C)(C)C(C)(C)O1]

The title compound was prepared in analogy to the procedure described for intermediate U but using 3-bromo-4-methoxybenzamide. The reaction was performed at 100° C. for 17 h. ESI-MS: 278.1 [M+H]$^+$ (MS 1).

Example 174

3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide

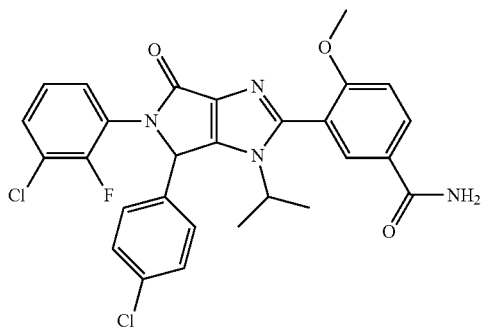 [SMILES: COc1ccc(C(N)=O)cc1-c1nc2c(n1C(C)C)C(c1ccc(Cl)cc1)N(c1cccc(Cl)c1F)C2=O]

The title compound was prepared in analogy to the procedure described for example 1 but using the product from step 173.1 and intermediate G. The reaction was performed at 80° C. for 3 h. After an aqueous workup, the product was purified by SFC chromatography (Column 2-EP, 250×30 mm, 5 µm, flow 100 mL/min, grad 18-23% over 6 min) to give the title compound. $t_R$: 1.06 min (LC-MS 2); ESI-MS: 553.3/555.2 [M+H]$^+$ (LC-MS 2).

Example 175

3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-benzamide

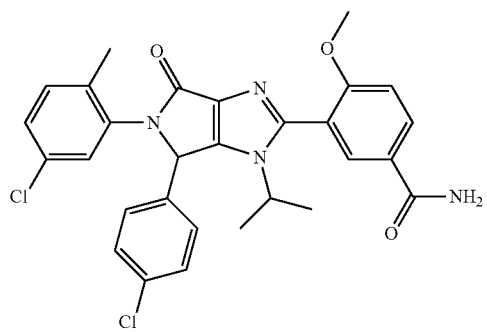 [SMILES: COc1ccc(C(N)=O)cc1-c1nc2c(n1C(C)C)C(c1ccc(Cl)cc1)N(c1cc(Cl)ccc1C)C2=O]

The title compound was prepared in analogy to the procedure described for example 1 but using the product from step 173.1 and intermediate E. The reaction was performed at 80° C. for 3 h. After an aqueous workup, the product was purified by SFC chromatography (Column 2-EP, 250×30 mm, 5 µm, flow 100 mL/min, grad 18-23% over 6 min) to give the title compound. $t_R$: 1.06 min (LC-MS 2); ESI-MS: 553.3/555.2 [M+H]$^+$ (LC-MS 2).

Example 176

3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-benzamide

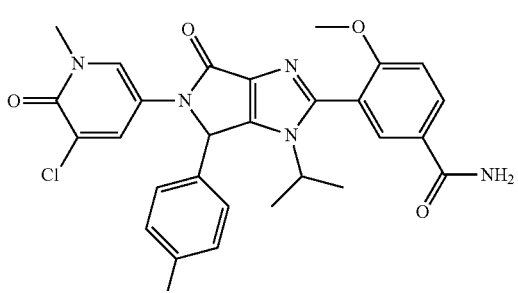

The title compound was prepared in analogy to the procedure described for example 207 but using the product from step 173.1 and intermediate J. The reaction was performed at 110° C. for 10 min under microwave irradiation. The residue was purified by preparative chromatography (Waters Sun Fire C18, 30×100 mm, 5 µm; 0.1% TFA-water/acetonitrile; gra-

Example 177

5-(5-Chloro-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-d]imidazol-4-one

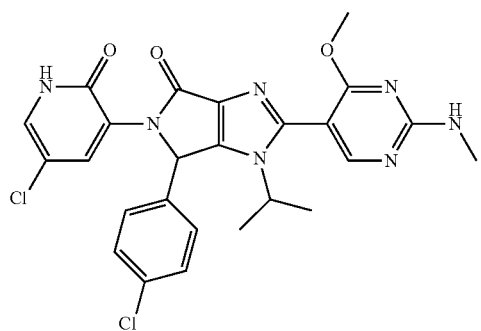

The title compound was prepared in analogy to the procedure described for example 29 but using the product from step 158.1 and intermediate Z. The residue was purified by flash chromatography (CH$_2$Cl$_2$/MeOH, 92.5:7.5), then by preparative HPLC (Column: Sunfire C18, 30×100 mm, 5 μm. Flow: 30 mL/min. Gradient 5-100% B in 20 min; A=0.1% TFA in water, B=CH$_3$CN). t$_R$: 0.92 min (LC-MS 2); ESI-MS: 540.3/542.3 [M+H]$^+$ (LC-MS 2); R$_f$=0.13 (CH$_2$Cl$_2$/MeOH, 92.5:7.5); $^1$H-NMR (DMSO-d$_6$, 400 MHz) δ ppm 12.21 (s, 1H), 8.25-8.03 (m, 1H), 7.60-7.20 (m, 7H), 6.70 (s, 1H), 4.13-4.03 (m, 1H), 3.95-3.72 (m, 3H), 2.84 (s, 3H), 1.31 (d, 3H), 0.50 (d, 3H).

Example 178

5-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-1,3-dimethyl-1H-pyrimidine-2,4-dione

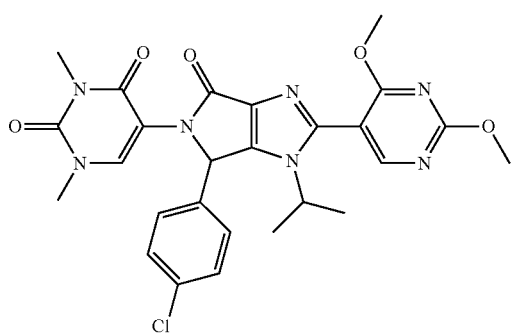 [SMILES: COc1ncc(-c2nc3c(n2C(C)C)C(c2ccc(Cl)cc2)N(c2cn(C)c(=O)n(C)c2=O)C3=O)c(OC)n1]

The title compound was prepared in analogy to the procedure described for example 29 but using the product from step 178.1 and 2,4-dimethoxypyrimidin-5-ylboronic acid. The reaction was performed at 110° C. for 30 min. The product was purified by flash chromatography (CH$_2$Cl$_2$/MeOH, 95:5). The residue was purified by preparative HPLC (Column: Sunfire C18, 30×100 mm, 5 μm. Flow: 30 mL/min. Gradient 30-60% B in 20 min; A=0.1% TFA in water, B=CH$_3$CN) to afford the title compound. t$_R$: 0.93 min (LC-MS 2); ESI-MS: 552.3/554.3 [M+H]$^+$ (LC-MS 2); R$_f$=0.17 (CH$_2$Cl$_2$/MeOH, 95:5); $^1$H-NMR (DMSO-d$_6$, 400 MHz) δ ppm 8.48 (s, 1H), 7.71 (s, 1H), 7.50-7.40 (m, 2H), 7.35-7.20 (m, 2H), 6.10 (s, 1H), 4.15-4.05 (m, 1H), 3.97 (s, 3H), 3.92 (s, 3H), 3.22 (s, 3H), 3.15 (s, 3H), 1.29 (d, 3H), 0.51 (d, 3H).

Step 178.1: 5-[2-Bromo-6-(4-chloro-phenyl)-1-isopropyl-4-oxo-4,6-dihydro-1H-pyrrolo[3,4-d]imidazol-5-yl]-1,3-dimethyl-1H-pyrimidine-2,4-dione

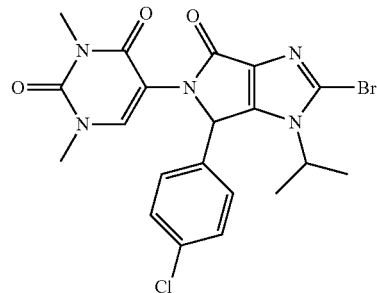 [SMILES: CC(C)n1c(Br)nc2c1C(c1ccc(Cl)cc1)N(c1cn(C)c(=O)n(C)c1=O)C2=O]

The title compound was prepared in analogy to the procedure described for example E but using the product from step 178.2. After extraction, the residue was triturated in EtOAc to afford the title compound. t$_R$: 0.92/0.95 min (LC-MS 2); ESI-MS: 492.2/494.2 [M+H]$^+$ (LC-MS 2).

Step 178.2: 2-Bromo-5-[(4-chloro-phenyl)-(1,3-dimethyl-2,4-dioxo-1,2,3,4-tetrahydro-pyrimidin-5-ylamino)-methyl]-1-isopropyl-1H-imidazole-4-carboxylic acid

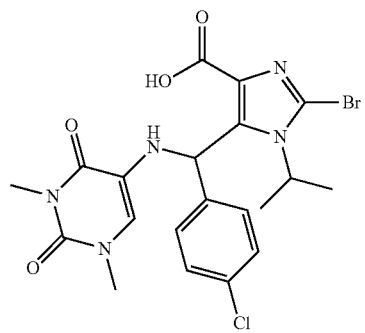 [SMILES: CC(C)n1c(Br)nc(C(=O)O)c1C(Nc1cn(C)c(=O)n(C)c1=O)c1ccc(Cl)cc1]

The title compound was prepared in analogy to the procedure described for step E1 but using the product from step 178.3. After extraction, the residue was triturated in Et$_2$O to afford the title compound. t$_R$: 0.94 min (LC-MS 2); ESI-MS: 510.2/512.2 [M+H]$^+$ (LC-MS 2).

Step 178.3: 2-Bromo-5-[(4-chloro-phenyl)-(1,3-dimethyl-2,4-dioxo-1,2,3,4-tetrahydro-pyrimidin-5-ylamino)-methyl]-1-isopropyl-1H-imidazole-4-carboxylic acid ethyl ester

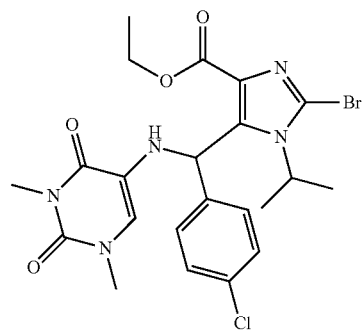 [SMILES: CCOC(=O)c1nc(Br)n(C(C)C)c1C(Nc1cn(C)c(=O)n(C)c1=O)c1ccc(Cl)cc1]

The title compound was prepared in analogy to the procedure described for step E2 but using intermediate B and the product from step 178.4. The reaction mixture was stirred at −10° C. for 18 h. After extraction, the residue was purified by flash chromatography (hexane/EtOAc, 60:40). $t_R$: 1.13 min (LC-MS 2); ESI-MS: 538.2/540.2 [M+H]$^+$ (LC-MS 2), $R_f$=0.22 (hexane/EtOAc, 4:6).

Step 178.4:
5-Amino-1,3-dimethyl-1H-pyrimidine-2,4-dione

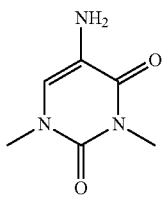

The title compound was prepared in analogy to the procedure described for step 100.4 but using the product from step 178.5. The reaction was performed at rt for 67.5 h. The residue was purified by flash chromatography (CH$_2$Cl$_2$/MeOH/NH$_3$, 99:1:1→97:3:1). $t_R$: 0.31 min (LC-MS 2); ESI-MS: 156.2 [M+H]$^+$ (LC-MS 2); $R_f$=0.47 (CH$_2$Cl$_2$/MeOH, 9:1).

Step 178.5:
1,3-Dimethyl-5-nitro-1H-pyrimidine-2,4-dione

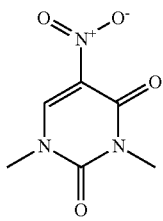

The title compound was prepared in analogy to the procedure described for step 100.5 but using 5-nitrouracil. The reaction was performed at rt for 20 h. The reaction mixture was concentrated and triturated in CH$_2$Cl$_2$. The resulting suspension was filtered and the solid was purified by flash chromatography (CH$_2$Cl$_2$/MeOH, 94:6). $t_R$: 0.41 min (LC-MS 2); ESI-MS: 186.1 [M+H]$^+$ (LC-MS 2); $R_f$=0.55 (CH$_2$Cl$_2$/MeOH, 9:1).

Example 179

5-[6-(4-Chloro-phenyl)-2-(2-dimethylamino-4-methoxy-pyrimidin-5-yl)-1-isopropyl-4-oxo-4,6-dihydro-1H-pyrrolo[3,4-d]imidazol-5-yl]-1,3-dimethyl-1H-pyrimidine-2,4-dione

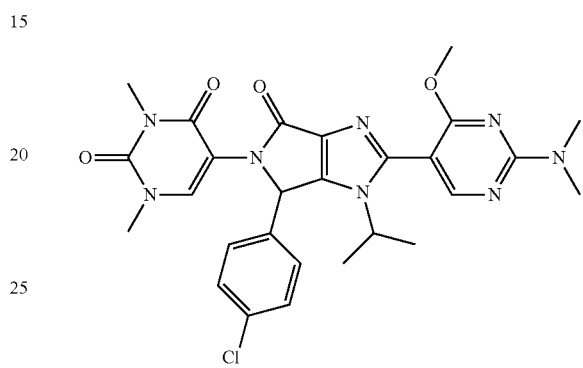

The title compound was prepared in analogy to the procedure described for example 29 but using the product from step 178.1 and intermediate W. The reaction was performed at 110° C. for 30 min. The product was purified by flash chromatography (CH$_2$Cl$_2$/MeOH, 95:5). The residue was purified by preparative HPLC (Column: Sunfire C18, 30×100 mm, 5 μm. Flow: 30 mL/min. Gradient 30-70% B in 20 min; A=0.1% TFA in water, B=CH$_3$CN) to afford the title compound. $t_R$: 1.01 min (LC-MS 2); ESI-MS: 565.4/567.3 [M+H]$^+$ (LC-MS 2); $R_f$=0.19 (CH$_2$Cl$_2$/MeOH, 95:5).

Example 180

5-[2-(2-Amino-4-methoxy-pyrimidin-5-yl)-6-(4-chloro-phenyl)-1-isopropyl-4-oxo-4,6-dihydro-1H-pyrrolo[3,4-d]imidazol-5-yl]-1,3-dimethyl-1H-pyrimidine-2,4-dione

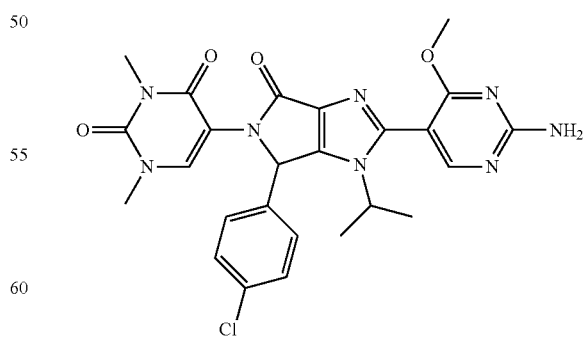

The title compound was prepared in analogy to the procedure described for example 29 but using the product from step 178.1 and intermediate U. The reaction was performed at 110° C. for 30 min. The product was purified by flash chromatography (CH₂Cl₂/MeOH, 92.5:7.5). The residue was purified by preparative HPLC (Column: Sunfire C18, 30×100 mm, 5 μm. Flow: 30 mL/min.

Gradient 5-100% B in 20 min; A=0.1% TFA in water, B=CH₃CN), then the residue was triturated in Et₂O to afford the title compound. t_R: 0.81 min (LC-MS 2); ESI-MS: 537.3/538.3 [M+H]⁺ (LC-MS 2); R_f=0.28 (CH₂Cl₂/MeOH, 92.5:7.5).

Example 181

5-(5-Chloro-2-methyl-phenyl)-6-(4-chloro-phenyl)-1-cyclopropyl-2-(2,4-dimethoxy-pyrimidin-5-yl)-5,6-dihydro-1H-pyrrolo[3,4-d]imidazol-4-one

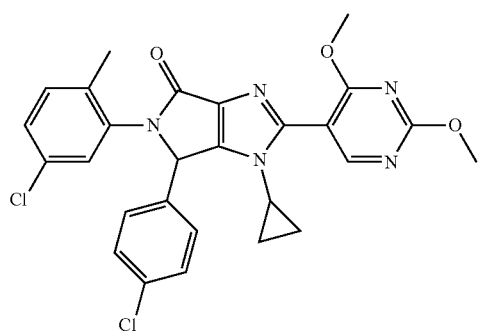 [SMILES: COc1ncc(-c2nc3c(n2C2CC2)C(c2ccc(Cl)cc2)N(c2cc(Cl)ccc2C)C3=O)c(OC)n1]

The title compound was prepared in analogy to the procedure described for step 97.1 but using the product from step 181.1. The residue was purified by flash chromatography (hexane/EtOAc, 100:0→20:80). t_R: 1.19 min (LC-MS 2); ESI-MS: 536.4/538.2 [M+H]⁺ (LC-MS 2); ¹H-NMR (DMSO-d₆, 400 MHz) δ ppm 8.52 (s, 1H), 7.41-7.21 (m, 6H), 6.36 (s, 1H), 4.04 (s, 3H), 4.01 (s, 3H), 2.05 (s, 3H), 1.28 (m, 3H), 0.59 (m, 3H).

Step 181.1: 2-Bromo-5-(5-chloro-2-methyl-phenyl)-6-(4-chloro-phenyl)-1-cyclopropyl-5,6-dihydro-1H-pyrrolo[3,4-d]imidazol-4-one

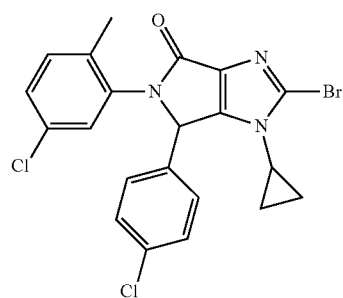 [SMILES: Cc1ccc(Cl)cc1N1C(=O)c2nc(Br)n(C3CC3)c2C1c1ccc(Cl)cc1]

The title compound was prepared in analogy to the procedure described for intermediate E but using the product from step 181.2. The reaction mixture was diluted with EtOAc and extracted with a saturated aqueous NaHCO₃ solution. The organic layer was washed with brine, dried (Na₂SO₄), filtered and concentrated. The residue was purified by flash chromatography (heptane/EtOAc, 100:0→1:1). t_R: 1.23 min (LC-MS 2); ESI-MS: 576.2/478.1/480.1 [M+H]⁺ (LC-MS 2).

Step 181.2: 2-Bromo-5-[(5-chloro-2-methyl-phenylamino)-(4-chloro-phenyl)-methyl]-1-cyclopropyl-1H-imidazole-4-carboxylic acid

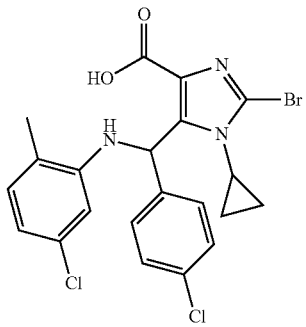 [SMILES: Cc1ccc(Cl)cc1NC(c1ccc(Cl)cc1)c1c(C(=O)O)nc(Br)n1C1CC1]

The title compound was prepared in analogy to the procedure described for step 156.3 but using the product from step 181.3. t_R: 1.27 in (LC-MS 2); ESI-MS: 494.2/496.2/498.2 [M+H]⁺ (LC-MS 2).

Step 181.3: 2-Bromo-5-[(5-chloro-2-methyl-phenylamino)-(4-chloro-phenyl)-methyl]-1-cyclopropyl-1H-imidazole-4-carboxylic acid ethyl ester

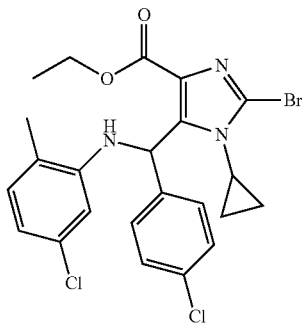 [SMILES: CCOC(=O)c1nc(Br)n(C2CC2)c1C(Nc1cc(Cl)ccc1C)c1ccc(Cl)cc1]

The title compound was prepared in analogy to the procedure described for step E2 but using the product from step AN2 and 5-chloro-1-methylaniline. The reaction was extracted with a saturated aqueous NaHCO₃ solution, washed with brine, dried (Na₂SO₄), filtered and concentrated. The residue was purified by flash chromatography (heptane/EtOAc, 100:0→1:1). t_R: 1.48 min (LC-MS 2); ESI-MS: 522.1/524.1/526.0 [M+H]⁺ (LC-MS 2).

Example 182

4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-3-methyl-benzonitrile

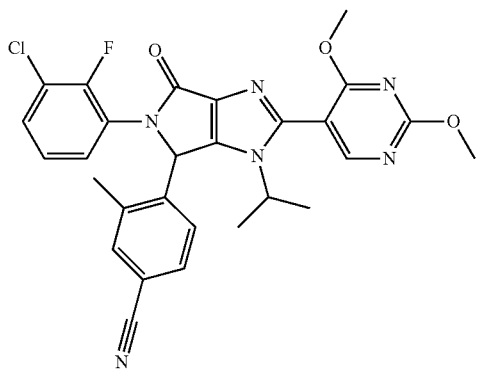 [SMILES: COc1ncc(-c2nc3c(n2C(C)C)C(c2ccc(C#N)cc2C)N(c2cccc(Cl)c2F)C3=O)c(OC)n1]

The title compound was prepared in analogy to the procedure described for example 1 but using the product from step 182.1 and 2,4-dimethoxypyrimidin-5-ylboronic acid. The reaction mixture was diluted with EtOAc and extracted with a saturated aqueous NaHCO₃ solution. The organic layer was washed with brine, dried (Na₂SO₄), filtered and concentrated. The product was purified by preparative HPLC (Waters Sun Fire C18, 30×100 mm, 5 µm; 0.1% TFA-water/acetonitrile; gradient acetonitrile 50-75% in 25 min). The residue was purified by preparative TLC (CH₂Cl₂/MeOH, 9:1). The residue was lyophilized in dioxane. The residue was triturated in Diisopropylether to afford the title compound. $t_R$: 1.07 min (LC-MS 2); ESI-MS: 547.3/549.3 [M+H]⁺ (LC-MS 2); $R_f$=0.52 (CH₂Cl₂/MeOH, 9:1).

Step 182.1: 4-[2-Bromo-5-(3-chloro-2-fluoro-phenyl)-3-isopropyl-6-oxo-3,4,5,6-tetrahydro-pyrrolo[3,4-d]imidazol-4-yl]-3-methyl-benzonitrile

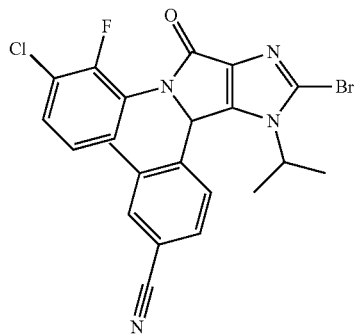 [SMILES: Cc1cc(C#N)ccc1C1c2c(nc(Br)n2C(C)C)C(=O)N1c1cccc(Cl)c1F]

The title compound was prepared in analogy to the procedure described for step 144.3 but using the product from step 182.2. The reaction was performed at 80° C. for 3 h. The residue was diluted with EtOAc and extracted with a saturated aqueous NaHCO₃ solution/H₂O. The organic layer was washed with brine, dried (Na₂SO₄), filtered and concentrated. The product was purified by flash chromatography (heptanes/EtOAc, 1:1→10:90). The residue was lyophilized in dioxane to afford the title compound. $t_R$: 1.11 min (LC-MS 2); ESI-MS: 487.1/489.1 [M+H]⁺ (LC-MS 2); $R_f$=0.22 (hexane/EtOAc, 1:2).

Step 182.2: 2-Bromo-5-[(3-chloro-2-fluoro-phenylamino)-(4-cyano-2-methyl-phenyl)-methy]-1-isopropyl-1H-imidazole-4-carboxylic acid

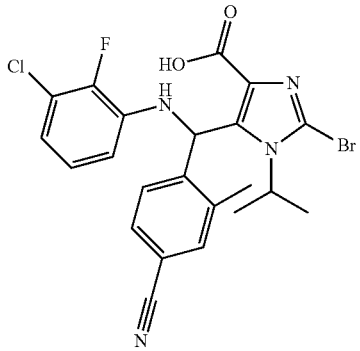 [SMILES: Cc1cc(C#N)ccc1C(Nc1cccc(Cl)c1F)c1c(C(=O)O)nc(Br)n1C(C)C]

The title compound was prepared in analogy to the procedure described for step E1 but using the product from step 182.3. $t_R$: 1.13 min (LC-MS 2); ESI-MS: 505.0/507.2/509.0 [M+H]⁺ (LC-MS 2).

Step 182.3: 2-Bromo-5-[(3-chloro-2-fluoro-phenylamino)-(4-cyano-2-methyl-phenyl)-methyl]-1-isopropyl-1H-imidazole-4-carboxylic acid ethyl ester

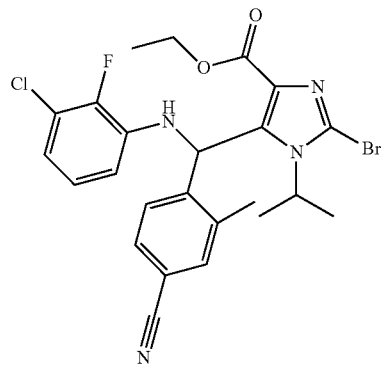 [SMILES: CCOC(=O)c1nc(Br)n(C(C)C)c1C(Nc1cccc(Cl)c1F)c1ccc(C#N)cc1C]

The title compound was prepared in analogy to the procedure described for step E2 but using the product from step 182.4. The resulting mixture was extracted with a saturated aqueous NaHCO₃ solution. The organic layers were washed with brine, dried (MgSO₄), filtered and concentrated. The crude product was purified by flash chromatography (heptane/EtOAc, 95:5→80:20). $t_R$: 1.30 min (LC-MS 2); ESI-MS: 533.1/535.2 [M+H]⁺ (LC-MS 2), $R_f$=0.42 (hexane/EtOAc, 1:1).

Step 182.4: 2-Bromo-5-[(4-cyano-2-methyl-phenyl)-hydroxy-methyl]-1-isopropyl-1H-imidazole-4-carboxylic acid ethyl ester

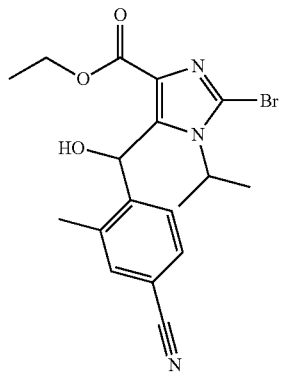 [SMILES: CCOC(=O)c1nc(Br)n(C(C)C)c1C(O)c1ccc(C#N)cc1C]

The title compound was obtained in analogy to the procedure described for intermediate B using the product from step 182.5. The resulting solid was purified by flash chromatography (heptane/EtOAc, 80:20→60:40). $t_R$: 1.01 min (LC-MS 2); ESI-MS: 406.1/408.0 [M+H]⁺ (LC-MS 2).

Step 182.5: 4-Formyl-3-methyl-benzonitrile

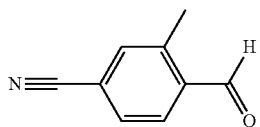

To a solution of 4-bromo-3-methylbenzonitrile (20 g, 102 mmol) in THF (500 mL) at −100° C. was slowly added a solution of n-BuLi 1.6M in hexanes (70 mL, 112 mmol). DMF (11 mL, 143 mmol) was then added and the mixture was allowed to warm to −50° C. over 30 min. The reaction mixture was quenched with brine. The reaction mixture was diluted with EtOAc and extracted with brine. The organic layer was dried ($Na_2SO_4$), filtered and concentrated. The residue was purified by flash chromatography (hexane/EtOAc, 80:20) the residue was triturated in $Et_2O$/hexane 90:10 to afford the title compound. $t_R$: 0.86 min (LC-MS 2); $R_f$=0.40 (hexane/EtOAc, 8:2).

Example 183

4-[5-(3-Chloro-2-fluoro-phenyl)-3-isopropyl-2-(2-methoxy-phenyl)-6-oxo-3,4,5,6-tetrahydro-pyrrolo[3,4-d]imidazol-4-yl]-3-methyl-benzonitrile

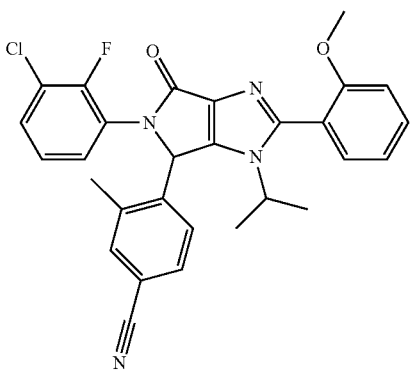 [SMILES: COc1ccccc1-c1nc2c(n1C(C)C)C(c1ccc(C#N)cc1C)N(c1cccc(Cl)c1F)C2=O]

The title compound was prepared in analogy to the procedure described for example 1 but using the product from step 182.1 and 2-methoxyphenylboronic acid. The reaction mixture was diluted with EtOAc and extracted with a saturated aqueous $NaHCO_3$ solution. The organic layer was washed with brine, dried ($Na_2SO_4$), filtered and concentrated. The product was purified by preparative HPLC (Waters Sun Fire C18, 30×100 mm, 5 μm; 0.1% TFA-water/acetonitrile; gradient acetonitrile 50-75% in 25 min). $t_R$: 1.13 min (LC-MS 2); ESI-MS: 515.3/516.4 $[M+H]^+$ (LC-MS 2).

Example 184

5-(3-Chloro-2-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

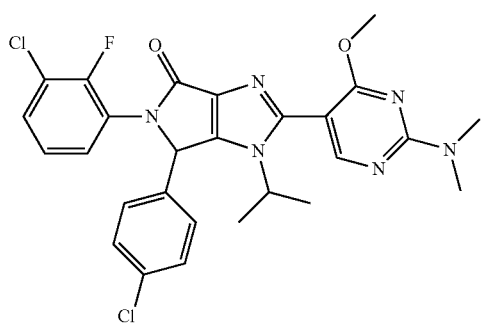 [SMILES: COc1nc(N(C)C)ncc1-c1nc2c(n1C(C)C)C(c1ccc(Cl)cc1)N(c1cccc(Cl)c1F)C2=O]

The title compound was prepared in analogy to the procedure described for example 29 but using intermediates G and W. The product was purified by preparative HPLC (Waters Sun Fire C18, 30×100 mm, 5 μm; 0.1% TFA-water/acetonitrile; gradient acetonitrile 50-70% in 16 min) to provide the title compound. $t_R$: 1.26 min (LC-MS 2); ESI-MS: 555.3/557.1 $[M+H]^+$ (LC-MS 2).

Example 185

5-(3-Chloro-4-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

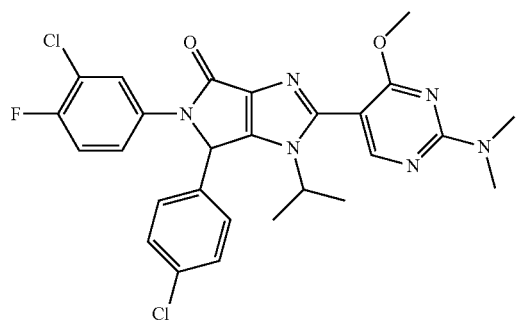 [SMILES: COc1nc(N(C)C)ncc1-c1nc2c(n1C(C)C)C(c1ccc(Cl)cc1)N(c1ccc(F)c(Cl)c1)C2=O]

The title compound was prepared in analogy to the procedure described for example 29 but using intermediates Q and W. The product was purified by preparative HPLC (Waters Sun Fire C18, 30×100 mm, 5 μm; 0.1% TFA-water/acetonitrile; gradient acetonitrile 50-70% in 16 min) to provide the title compound. $t_R$: 1.25 min (LC-MS 2); ESI-MS: 555.3/557.1 $[M+H]^+$ (LC-MS 2).

Example 186

3-[5-(5-Chloro-2-methyl-phenyl)-6-(4-cyano-2-methyl-phenyl)-1-isopropyl-4-oxo-1,4,5,6-tetrahydro-pyrrolo[3,4-d]imidazol-2-yl]-4-methoxy-N,N-dimethyl-benzamide

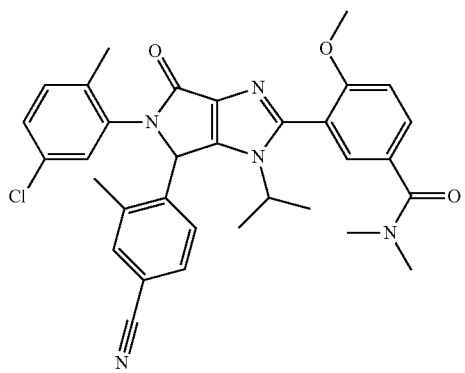 [SMILES: COc1ccc(C(=O)N(C)C)cc1-c1nc2c(n1C(C)C)C(c1ccc(C#N)cc1C)N(c1cc(Cl)ccc1C)C2=O]

The title compound was prepared in analogy to the procedure described for example 1 but using the product from step 186.1 and intermediate M. The mixture was diluted in EtOAc and extracted with a saturated aqueous $NaHCO_3$ solution. The organic layers were washed with brine, dried ($Na_2SO_4$), filtered and concentrated. The residue was purified by preparative HPLC (Waters Sun Fire C18, 30×100 mm, 5 μm; 0.1% TFA-water/acetonitrile; gradient acetonitrile 50-75% in 25 min) to provide the title compound. $t_R$: 1.05 min (LC-MS 2); ESI-MS: 582.2/584.2 $[M+H]^+$ (LC-MS 2).

Step 186.1: 4-[2-Bromo-5-(5-chloro-2-methyl-phenyl)-3-isopropyl-6-oxo-3,4,5,6-tetrahydro-pyrrolo[3,4-d]imidazol-4-yl]-3-methyl-benzonitrile

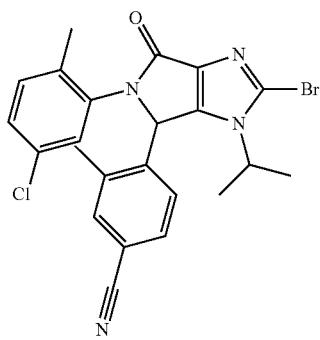 [SMILES: Cc1cc(C#N)ccc1C1c2c(nc(Br)n2C(C)C)C(=O)N1c1cc(Cl)ccc1C]

The title compound was prepared in analogy to the procedure described for step 182.1 but using the product from step 186.2. The product was purified by flash chromatography (heptanes/EtOAc, 7:3→3:7) to afford the title compound. $t_R$: 1.10 min (LC-MS 2); ESI-MS: 483.1/485.0 [M+H]$^+$ (LC-MS 2); $R_f$=0.69 (EtOAc).

Step 186.2: 2-Bromo-5-[(5-chloro-2-methyl-phenylamino)-(4-cyano-2-methyl-phenyl)-methyl]-1-isopropyl-1H-imidazole-4-carboxylic acid

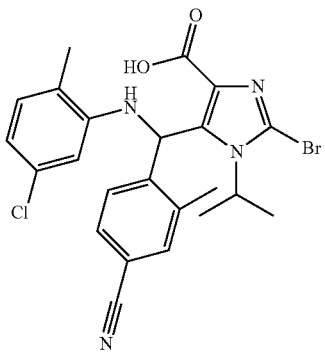 [SMILES: Cc1ccc(Cl)cc1NC(c1ccc(C#N)cc1C)c1c(C(=O)O)nc(Br)n1C(C)C]

The title compound was prepared in analogy to the procedure described for step E1 but using the product from step 186.3. $t_R$: 1.16 min (LC-MS 2); ESI-MS: 501.2/503.3 [M+H]$^+$ (LC-MS 2).

Step 186.3: 2-Bromo-5-[(5-chloro-2-methyl-phenylamino)-(4-cyano-2-methyl-phenyl)-methyl]-1-isopropyl-1H-imidazole-4-carboxylic acid ethyl ester

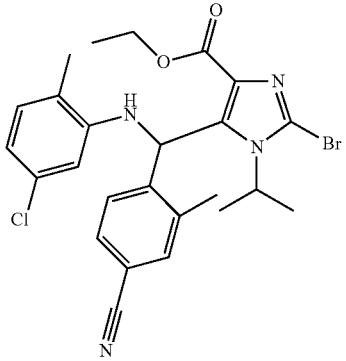 [SMILES: CCOC(=O)c1nc(Br)n(C(C)C)c1C(Nc1cc(Cl)ccc1C)c1ccc(C#N)cc1C]

The title compound was prepared in analogy to the procedure described for step E2 but using the product from step 182.4. The reaction mixture was stirred at rt for 4 days. The mixture was extracted with a saturated aqueous NaHCO$_3$ solution. The organic layers were dried (Na$_2$SO$_4$), filtered and concentrated. The residue was purified by flash chromatography (hexane/EtOAc, 95:5→80:20) to afford the title compound. $t_R$: 1.33 min (LC-MS 2); ESI-MS: 529.2/531.1 [M+H]$^+$ (LC-MS 2).

Example 187

4-[5-(5-Chloro-2-methyl-phenyl)-2-(1-ethyl-5-methoxy-2-oxo-1,2-dihydro-pyridin-4-yl)-3-isopropyl-6-oxo-3,4,5,6-tetrahydro-pyrrolo[3,4-d]imidazol-4-yl]-benzonitrile

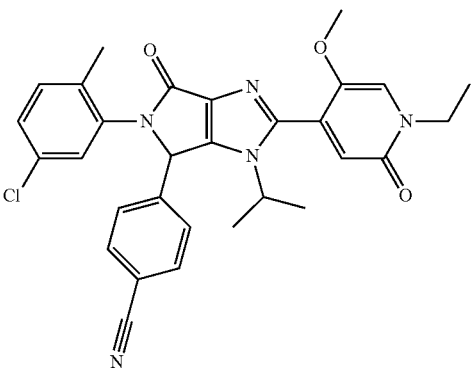 [SMILES: CCn1cc(OC)c(-c2nc3c(n2C(C)C)C(c2ccc(C#N)cc2)N(c2cc(Cl)ccc2C)C3=O)cc1=O]

The title compound was prepared in analogy to the procedure described for example 29 but using intermediate H and the product from step 187.1. The reaction was performed at 110° C. for 1 h. The reaction mixture was dissolved in EtOAc and extracted with a saturated aqueous NaHCO$_3$ solution. The organic layer was washed with brine, dried (Na$_2$SO$_4$), filtered and concentrated. The residue was purified by preparative HPLC (Waters Sun Fire C18, 30×100 mm, 5 μm; 0.1% TFA-water/acetonitrile; gradient acetonitrile 5-100% in 20 min) to give the title compound. $t_R$: 0.99 min (LC-MS 2); ESI-MS: 542.2/544.3 [M+H]$^+$ (LC-MS 2), $R_f$=0.23 (CH$_2$Cl$_2$/MeOH, 9:1); $^1$H-NMR (DMSO-d$_6$, 400 MHz) ppm 7.88-7.74 (m, 3H), 7.58-7.41 (m, 3H), 7.28-7.03 (m, 2H), 6.69 (s, 1H), 6.52 (s, 1H), 4.19-4.05 (m, 1H), 4.00-3.86 (m, 2H), 3.64 (s, 3H), 1.97-1.83 (m, 3H), 1.36-1.21 (m, 6H), 0.60-0.40 (m, 3H).

Step 187.1: (1-ethyl-5-methoxy-2-oxo-1,2-dihydro-pyridin-4-yl)boronic acid

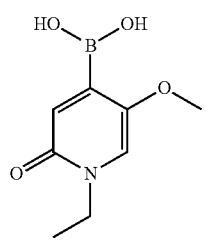

The title compound was prepared in analogy to the procedure described for intermediate S but using the product from step 187.2. The reaction was performed at 80° C. for 2 h. The reaction mixture was filtered over celite and concentrated. The residue was purified by flash chromatography (CH$_2$Cl$_2$/MeOH, 90:10) to afford the title compound. t$_R$: 0.40 min (LC-MS 2); ESI-MS: 198.1 [M+H]$^+$ (LC-MS 2).

Step 187.2:
1-Ethyl-4-iodo-5-methoxy-1H-pyridin-2-one

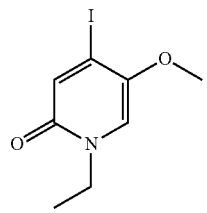

The title compound was prepared in analogy to the procedure described for step 100.5 but using the product from step 187.3 and ethyl iodide. The reaction was stirred at rt for 30 min. The reaction mixture was quenched by addition of a saturated aqueous NaHCO$_3$ solution, and extracted with EtOAc. The organic layer was dried (Na$_2$SO$_4$), filtered, and concentrated. The residue was purified by flash chromatography (CH$_2$Cl$_2$/MeOH, 99:1→97:3) to afford the title compound. t$_R$: 0.69 min (LC-MS 2); ESI-MS: 280.0 [M+H]$^+$ (LC-MS 2); R$_f$=0.60 (CH$_2$Cl$_2$/MeOH, 9:1).

Step 187.3: 4-Iodo-5-methoxy-1H-pyridin-2-one

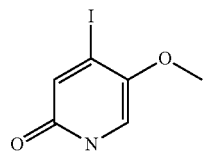

A solution of the product from step 187.4 (440 mg, 1.2 mmol) and TFA (457 µL, 5.9 mmol) in CH$_2$Cl$_2$ (5 mL) was stirred at rt for 10 min. The reaction mixture was quenched with a saturated aqueous NaHCO$_3$ solution. The resulting suspension was filtered and the solid dried to afford the title compound. t$_R$: 0.55 min (LC-MS 2); ESI-MS: 252.0 [M+H]$^+$ (LC-MS 2).

Step 187.4:
4-Iodo-5-methoxy-2-(4-methoxy-benzyloxy)-pyridine

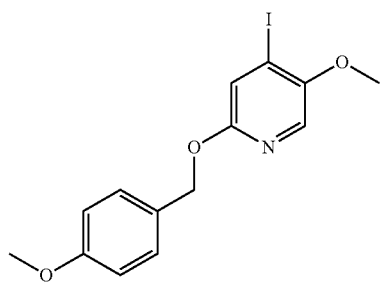

To a solution of 4-methoxybenzyl alcohol (342 mg, 2.1 mmol) in DMF (5 mL) at 0° C. was added portionwise NaH (108 mg, 2.5 mmol) and the mixture was stirred for 30 min. The product from step 187.5 (545 mg, 2.1 mmol) was added dropwise and the mixture was stirred at 80° C. for 5 min. The reaction mixture was quenched by addition of a saturated aqueous NaHCO$_3$ solution, and extracted with EtOAc. The organic layer was dried (Na$_2$SO$_4$), filtered, and concentrated. The residue was purified by flash chromatography (heptane/EtOAc, 98:2→95:5) to afford the title compound. t$_R$: 1.28 min (LC-MS 2); ESI-MS: 372.1 [M+H]$^+$ (LC-MS 2); R$_f$=0.28 (heptane/EtOAc, 9:1).

Step 187.5: 2-Fluoro-4-iodo-5-methoxy-pyridine

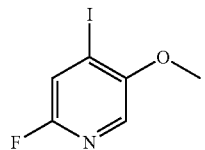

A solution of the product from step 187.6 (730 mg, 3.0 mmol), K$_2$CO$_3$ (1.3 g, 9.2 mmol) and methyl iodide (573 µL, 9.2 mmol) in DMF (3 mL) was stirred at 60° C. for 1 h. The reaction mixture was quenched with a saturated aqueous NaHCO$_3$ solution and extracted with EtOAc. The organic layer was dried (Na$_2$SO$_4$), filtered and concentrated. The product was purified by flash chromatography (hexane/EtOAc, 97.5:2.5→95:5t) to provide the title compound. t$_R$: 0.94 min (LC-MS 2); R$_f$=0.32 (heptane/EtOAc, 9:1).

Step 187.6: 6-Fluoro-4-iodo-pyridin-3-ol

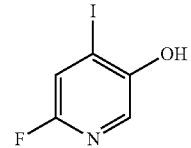

A solution of the product from step 187.7 (886 mg, 3.1 mmol) and HCl 6M (3.1 mL, 18.8 mmol) in THF (5 mL) was stirred at 60° C. for 1 h. The reaction mixture was quenched with a saturated aqueous NaHCO$_3$ solution and extracted with EtOAc. The organic layer was dried (Na$_2$SO$_4$), filtered and concentrated. The product was used without further purification. t$_R$: 0.75 min (LC-MS 2); ESI-MS: 240.1 [M+H]$^+$ (LC-MS 2).

Step 187.7:
2-Fluoro-4-iodo-5-methoxymethoxy-pyridine

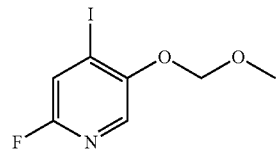

To a solution of the product from step 187.8 (1 g, 6.4 mmol) in THF (20 mL) at −78° C. was added dropwise t-Buli 1.7M in hexanes (7.5 mL, 12.7 mmol) and the mixture was stirred for 30 min. Then iodine (4.2 g, 9.5 mmol) in THF (10 mL) was added. The mixture was allowed to warm up and stirred at rt for 1 h. The reaction mixture was quenched with H$_2$O and extracted with EtOAc. The organic layer was washed with brine, dried (Na$_2$SO$_4$), filtered and concentrated. The residue was purified by flash chromatography (heptane/EtOAc, 100:0→95:5) to afford the title compound. $t_R$: 0.97 min (LC-MS 2); ESI-MS: 284.0 [M+H]$^+$ (LC-MS 2); R$_f$=0.31 (heptane/EtOAc, 9:1).

Step 187.8: 2-Fluoro-5-methoxymethoxy-pyridine

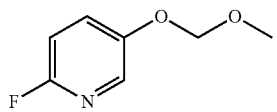

To a solution of 5-fluoro-2-hydroxypyridine (4.9 g, 43.2 mmol) in DMF (50 mL) at 0° C. was added portionwise NaH (2.3 g, 52.2 mmol) and the mixture was stirred at 0° C. for 10 min. Chloromethyl methyl ether (3.6 mL, 47.5 mmol) was added dropwise and the mixture was stirred at rt for 30 min. The reaction mixture was quenched by addition of water, and extracted with EtOAc. The organic layer was washed with brine, dried (Na$_2$SO$_4$), filtered, and concentrated. The residue was purified by flash chromatography (heptane/EtOAc, 97.5:2.5→92.5:7.5) to afford the title compound. $t_R$: 0.71 min (LC-MS 2); ESI-MS: 158.1 [M+H]$^+$ (LC-MS 2); R$_f$=0.33 (heptane/EtOAc, 9:1).

Example 188

4-[5-(5-Chloro-2-methyl-phenyl)-2-(2,4-dimethoxy-pyrimidin-5-yl)-3-isopropyl-6-oxo-3,4,5,6-tetrahydro-pyrrolo[3,4-d]imidazol-4-yl]-3-methyl-benzonitrile

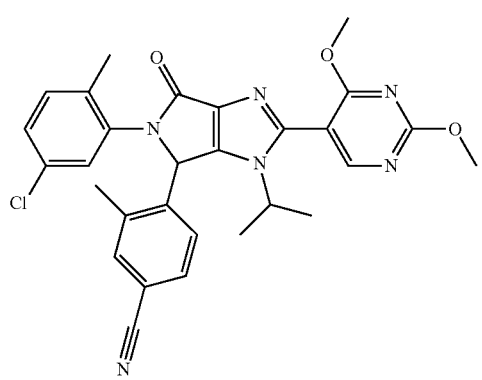 [SMILES: COc1ncc(-c2nc3c(n2C(C)C)C(c2ccc(C#N)cc2C)N(c2cc(Cl)ccc2C)C3=O)c(OC)n1]

The title compound was prepared in analogy to the procedure described for example 1 but using the product from step 186.1 and 2,4-dimethoxypyrimidin-5-ylboronic acid. The reaction mixture was diluted in EtOAc and extracted with a saturated aqueous NaHCO$_3$ solution. The organic layer was washed with brine, dried (Na$_2$SO$_4$), filtered and concentrated. The product was purified by preparative TLC (EtOAc), then by preparative TLC (CH$_2$Cl$_2$/MeOH, 9:1). The residue was purified by preparative HPLC (Waters Sun Fire C18, 30×100 mm, 5 µm; 0.1% TFA-water/acetonitrile; gradient acetonitrile 50-75% in 13 min) to give the title compound. $t_R$: 1.09 min (LC-MS 2); ESI-MS: 543.4/545.2 [M+H]$^+$ (LC-MS 2), R$_f$: 0.24 (EtOAc).

Example 189

3-[(R)-5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide

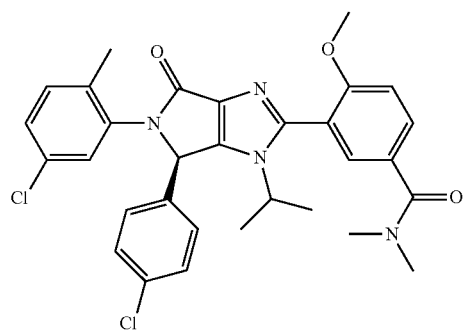 [SMILES: COc1ccc(C(=O)N(C)C)cc1-c1nc2c(n1C(C)C)[C@@H](c1ccc(Cl)cc1)N(c1cc(Cl)ccc1C)C2=O]

The title compound was obtained after preparative chiral HPLC separation of the racemic product of example 23. (Column: AD-H, 20×200 mm. Flow 7 mL/min. n-heptane/EtOH 50:50). $t_R$: 9.1 min (Column: AD-H, 4.6×250 mm. Flow 1 mL/min. n-heptane/EtOH 50:50).

Example 190

3-[(S)-5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide

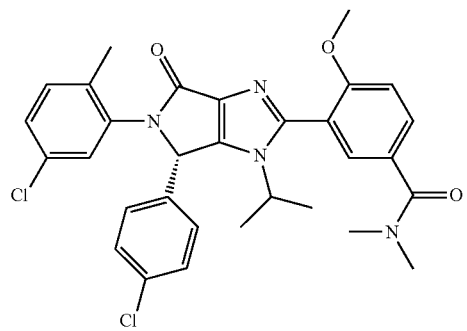 [SMILES: COc1ccc(C(=O)N(C)C)cc1-c1nc2c(n1C(C)C)[C@H](c1ccc(Cl)cc1)N(c1cc(Cl)ccc1C)C2=O]

The title compound was obtained after preparative chiral HPLC separation of the racemic product of example 23. (Column: AD-H, 20×200 mm. Flow 7 mL/min. n-heptane/EtOH 50:50). $t_R$: 4.3 min (Column: AD-H, 4.6×250 mm. Flow 1 mL/min. n-heptane/EtOH 50:50).

Example 191

4-[5-(5-Chloro-2-methyl-phenyl)-3-isopropyl-2-(2-methoxy-phenyl)-6-oxo-3,4,5,6-tetrahydro-pyrrolo[3,4-d]imidazol-4-yl]-3-methyl-benzonitrile

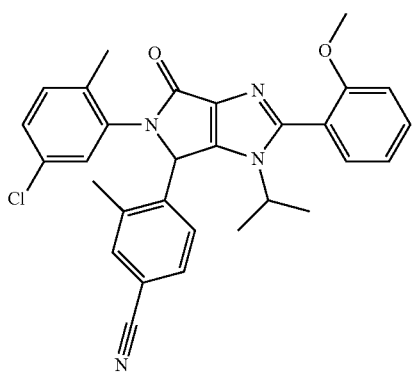 [SMILES: COc1ccccc1-c1nc2c(n1C(C)C)C(c1ccc(C#N)cc1C)N(c1cc(Cl)ccc1C)C2=O]

The title compound was prepared in analogy to the procedure described for example 1 but using the product from step 186.1 and 2-methoxyphenylboronic acid. The reaction mixture was diluted in EtOAc and extracted with a saturated aqueous NaHCO$_3$ solution. The organic layer was washed with brine, dried (Na$_2$SO$_4$), filtered and concentrated. The residue was purified by preparative HPLC (Waters Sun Fire C18, 30×100 mm, 5 µm; 0.1% TFA-water/acetonitrile; gradient acetonitrile 40-85%) to give the title compound. $t_R$: 1.13/1.16 min (LC-MS 2); ESI-MS: 511.3/513.4 [M+H]$^+$ (LC-MS 2), R$_f$: 0.57 (EtOAc).

Example 192

2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one

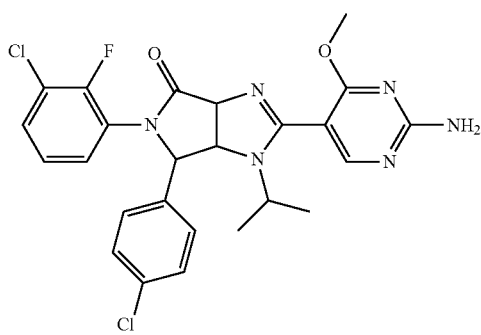 [SMILES: COc1nc(N)ncc1C1=NC2C(=O)N(c3cccc(Cl)c3F)C(c3ccc(Cl)cc3)C2N1C(C)C]

The title compound was prepared in analogy to the procedure described for example 29 but using intermediates G and U. The reaction was performed at 110° C. The residue was purified by preparative HPLC (Waters Sun Fire C18, 30×100 mm, 5 µm; 0.1% TFA-water/acetonitrile; gradient acetonitrile 25-45% in 16 min) to give the title compound. $t_R$: 1.07 min (LC-MS 2); ESI-MS: 527.2/529.2 [M+H]$^+$ (LC-MS 2).

Example 193

2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one

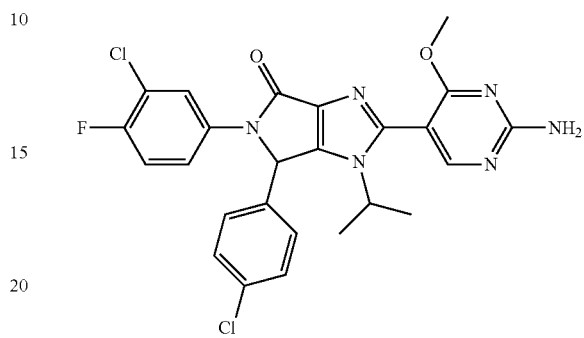

The title compound was prepared in analogy to the procedure described for example 29 but using intermediates Q and U. The reaction was performed at 110° C. The residue was purified by preparative HPLC (Waters Sun Fire C18, 30×100 mm, 5 µm; 0.1% TFA-water/acetonitrile; gradient acetonitrile 25-45% in 16 min) to give the title compound. $t_R$: 1.10 min (LC-MS 2); ESI-MS: 527.2/529.3 [M+H]$^+$ (LC-MS 2).

Example 194

3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-benzonitrile

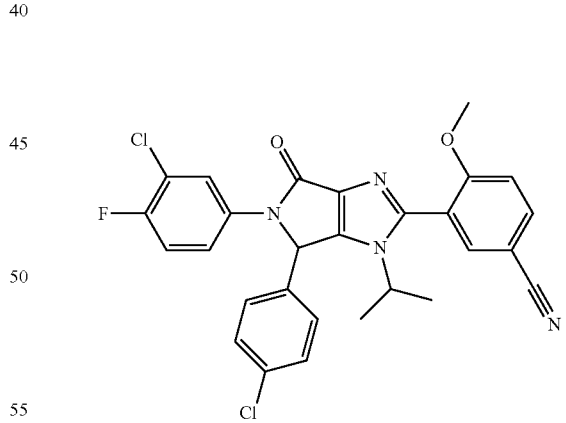

The title compound was prepared in analogy to the procedure described for example 29 but using intermediate Q and 5-cyano-2-methoxyphenylboronic acid. The reaction was performed at 110° C. The residue was purified by SFC chromatography (Column 2-EP, 250×30 mm, 5 µm, flow 100 mL/min, grad 20-25% over 6 min) to give the title compound. $t_R$: 1.24 min (LC-MS 2); ESI-MS: 535.2/537.2 [M+H]$^+$ (LC-MS 2).

Example 195

5-(3-Chloro-4-fluoro-phenyl)-6-(4-chloro-phenyl)-1-isopropyl-2-[2-methoxy-5-(morpholine-4-carbonyl)-phenyl]-5,6-dihydro-1H-pyrrolo[3,4-d]imidazol-4-one

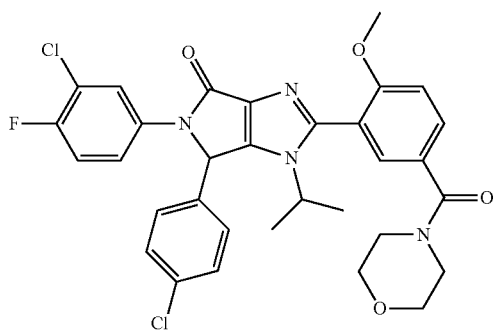 [SMILES: COc1ccc(C(=O)N2CCOCC2)cc1-c1nc2c(n1C(C)C)C(c1ccc(Cl)cc1)N(c1ccc(F)c(Cl)c1)C2=O]

The title compound was prepared in analogy to the procedure described for example 29 but using intermediates Q and O. The reaction was performed at 110° C. The residue was purified by SFC chromatography (Column 2-EP, 250×30 mm, 5 µm, flow 100 mL/min, grad 17-22% over 6 min). The residue was purified by preparative HPLC (Column: Sunfire C18, 30×100 mm, 5 µm. Flow: 30 mL/min. Gradient 50-70% B in 16 min; A=0.1% TFA in water, B=CH$_3$CN). t$_R$: 1.13 min (LC-MS 2); ESI-MS: 623.3/625.3 [M+H]$^+$ (LC-MS 2).

Example 196

5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one

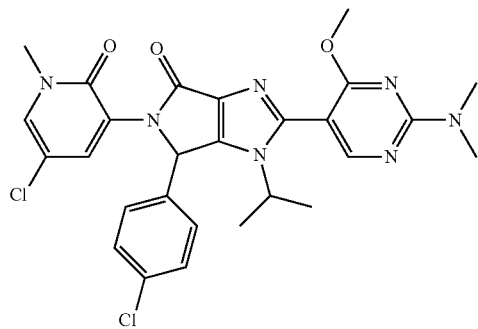

The title compound was prepared in analogy to the procedure described for example 29 but using intermediate W and the product from step 101.1. The reaction was performed at 110° C. The residue was purified by flash chromatography (CH$_2$Cl$_2$/MeOH, 95:5). The residue was purified by preparative HPLC (Column: Sunfire C18, 30×100 mm, 5 µm. Flow: 30 mL/min. Gradient 30-70% B in 20 min; A=0.1% TFA in water, B=CH$_3$CN). The residue was purified by SFC chromatography (Column 2-EP, 250×30 mm, 5 µm, flow 100 mL/min, grad 13-18% over 11 min). t$_R$: 1.13 min (LC-MS 2); ESI-MS: 568.3/570.3 [M+H]$^+$ (LC-MS 2); R$_f$=0.15 (CH$_2$Cl$_2$/MeOH, 95:5); $^1$H-NMR (DMSO-d$_6$, 400 MHz) δ ppm 8.19 (s, 1H), 7.89 (d, 1H), 7.47 (d, 1H), 7.45-7.35 (m, 2H), 7.30-7.20 (m, 2H), 6.68 (s, 1H), 4.13-4.03 (m, 1H), 3.87 (s, 3H), 3.42 (s, 3H), 3.16 (s, 6H), 1.31 (d, 3H), 0.50 (d, 3H).

Example 197

3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide

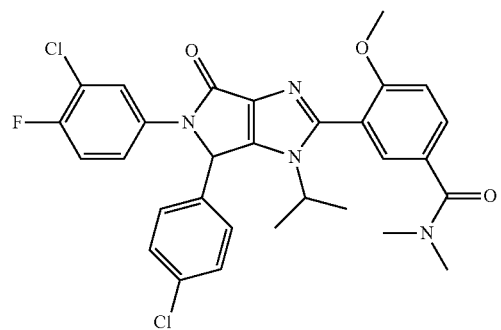 [SMILES: COc1ccc(C(=O)N(C)C)cc1-c1nc2c(n1C(C)C)C(c1ccc(Cl)cc1)N(c1ccc(F)c(Cl)c1)C2=O]

The title compound was prepared in analogy to the procedure described for example 29 but using intermediates Q and M. The reaction was performed at 110° C. The residue was purified by preparative HPLC (Column: Sunfire C18, 30×100 mm, 5 µm. Flow: 30 mL/min. Gradient 30-70% B in 16 min; A=0.1% TFA in water, B=CH$_3$CN). t$_R$: 1.14 min (LC-MS 3); ESI-MS: 581.3/583.3 [M+H]$^+$ (LC-MS 3).

Example 198

5-(3-Chloro-4-fluoro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one

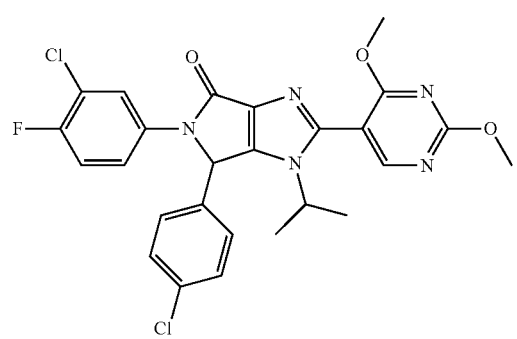 [SMILES: COc1ncc(-c2nc3c(n2C(C)C)C(c2ccc(Cl)cc2)N(c2ccc(F)c(Cl)c2)C3=O)c(OC)n1]

The title compound was prepared in analogy to the procedure described for example 29 but using intermediate Q and 2,4-dimethoxypyrimidin-5-ylboronic acid. The reaction was performed at 110° C. The residue was purified by SFC chromatography (Column Diol, 250×30 mm, 5 µm, flow 100 mL/min, grad 22% over 7 min). $t_R$: 1.22 min (LC-MS 2); ESI-MS: 542.2/544.2 [M+H]$^+$ (LC-MS 2).

Example 199

4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile

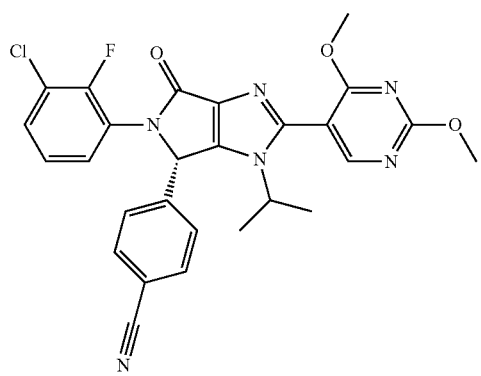

The title compound was obtained after preparative chiral SFC separation of the racemic product of example 79 (Column: Chiralpak AD-H, 30×250 mm, Flow 100 mL/min, scCO$_2$/EtOH 70:30). $t_R$: 4.73 min (Column: Chiralpak AD-H, 4.6×250 mm, Flow 3 mL/min, scCO$_2$/EtOH 70:30).

Example 200

3-[5-(5-Chloro-1-methyl-2-oxo-1,2-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide

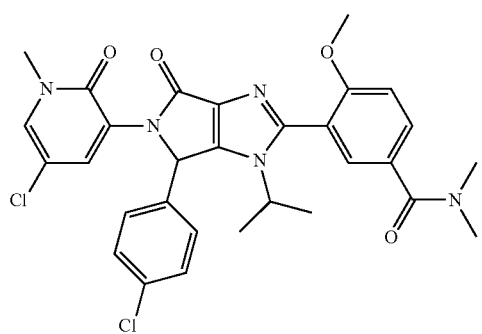 [SMILES: COc1ccc(C(=O)N(C)C)cc1-c1nc2c(n1C(C)C)C(c1ccc(Cl)cc1)N(c1cc(Cl)cn(C)c1=O)C2=O]

The title compound was prepared in analogy to the procedure described for example 29 but using the product from step 101.1 and intermediate M. The reaction mixture was diluted in EtOAc/water and extracted twice with EtOAc. The combined organic extracts were washed with water and brine and then dried (Na$_2$SO$_4$) and concentrated. The product was purified by flash chromatography (CH$_2$Cl$_2$/MeOH, 92.5:7.5). The residue was purified by preparative chromatography (Waters Sun Fire C18, 30×100 mm, 5 µm; 0.1% TFA-water/acetonitrile; gradient acetonitrile 5-100% in 20 min) to give the title compound. $t_R$: 0.99 min (LC-MS 2); ESI-MS: 594.3/596.3 [M+H]$^+$ (LC-MS 2); R$_f$: 0.15 (CH$_2$Cl$_2$/MeOH 92.5:7.5).

Example 201

5-(5-Chloro-1-methyl-2-oxo-1,2-dihydro-pyridin-3-yl)-6-(4-chloro-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one

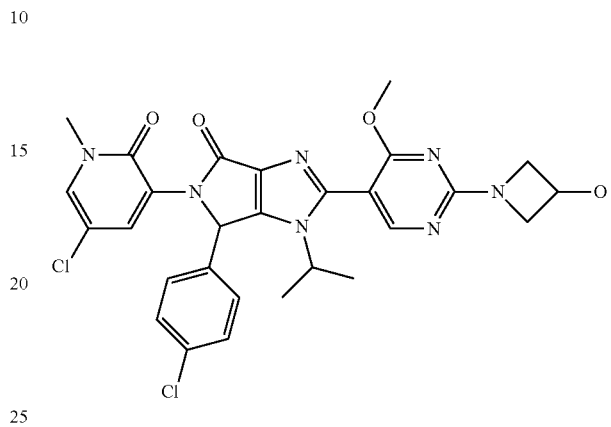

The title compound was prepared in analogy to the procedure described for example 29 but using the product from step 101.1 and intermediate AE. The reaction mixture was diluted in EtOAc/water and extracted twice with EtOAc. The combined organic extracts were washed with water and brine and then dried (Na$_2$SO$_4$) and concentrated. The product was purified by flash chromatography (CH$_2$Cl$_2$/MeOH, 92.5:7.5). The residue was purified by preparative chromatography (Waters Sun Fire C18, 30×100 mm, 5 µm; 0.1% TFA-water/acetonitrile; gradient acetonitrile 20-60% in 20 min) to give the title compound. $t_R$: 0.96 min (LC-MS 2); ESI-MS: 596.3/598.3 [M+H]$^+$ (LC-MS 2); R$_f$: 0.14 (CH$_2$Cl$_2$/MeOH 92.5:7.5).

Example 202

5-(5-Chloro-1-methyl-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-d]imidazol-4-one

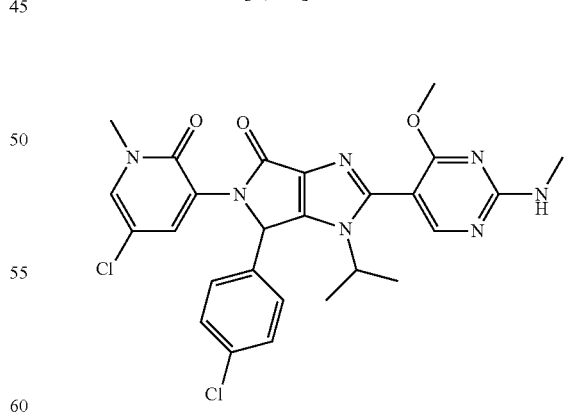

The title compound was prepared in analogy to the procedure described for example 29 but using the product from step 101.1 and intermediate Z. The reaction mixture was diluted in EtOAc/water and extracted twice with EtOAc. The combined organic extracts were washed with water and brine and then dried (Na$_2$SO$_4$) and concentrated. The product was purified by flash chromatography (CH$_2$Cl$_2$/MeOH, 92.5:7.5). The residue was purified by preparative chromatography (Waters Sun Fire C18, 30×100 mm, 5 μm; 0.1% TFA-water/acetonitrile; gradient acetonitrile 30-60% in 20 min) to give the title compound. t$_R$: 1.02 min (LC-MS 2); ESI-MS: 554.2/556.2 [M+H]$^+$ (LC-MS 2); R$_f$: 0.15 (CH$_2$Cl$_2$/MeOH 92.5:7.5).

Example 203

(S)-2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one

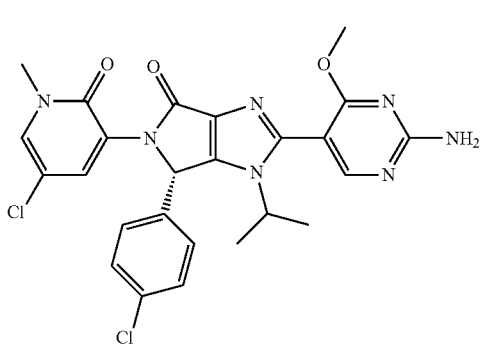 [SMILES: COc1nc(N)ncc1-c1nc2c(n1C(C)C)[C@H](c1ccc(Cl)cc1)N(c1cc(Cl)cn(C)c1=O)C2=O]

The title compound was obtained after preparative chiral SFC separation of the racemic product of example 159. (Column: Chiralpak IA, 30×250 mm. Flow 140 g/min. scCO2/(MeOH/DCM, 9:1+0.1% IPAm), 60:40). t$_R$: 4.3 min (Column: Chiralpak IA, 4.6×250 mm. Flow 3 mL/min. scCO2/(MeOH/DCM, 9:1+1% IPAm), 65:35).

Example 204

(R)-2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one

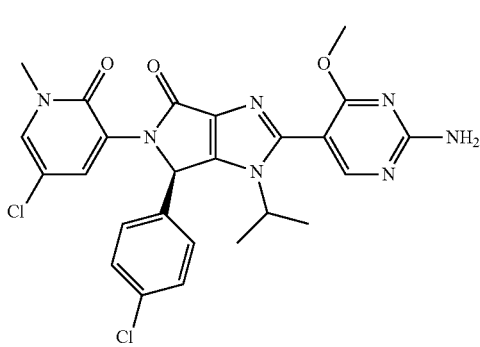 [SMILES: COc1nc(N)ncc1-c1nc2c(n1C(C)C)[C@@H](c1ccc(Cl)cc1)N(c1cc(Cl)cn(C)c1=O)C2=O]

The title compound was obtained after preparative chiral SFC separation of the racemic product of example 159. (Column: Chiralpak IA, 30×250 mm. Flow 140 g/min. scCO2/(MeOH/DCM, 9:1+0.1% IPAm), 60:40). t$_R$: 3.1 min (Column: Chiralpak IA, 4.6×250 mm. Flow 3 mL/min. scCO2/(MeOH/DCM, 9:1+1% IPAm), 65:35).

Example 205

(S)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one

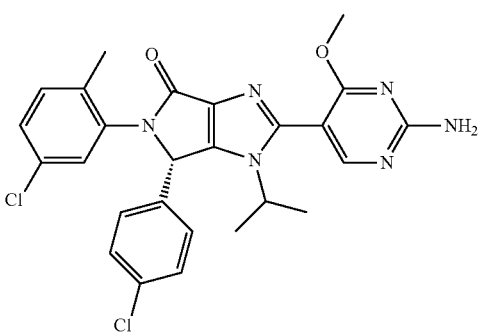 [SMILES: COc1nc(N)ncc1-c1nc2c(n1C(C)C)[C@H](c1ccc(Cl)cc1)N(c1cc(Cl)ccc1C)C2=O]

The title compound was obtained after preparative chiral SFC separation of the racemic product of example 37. (Column: Chiralpak IA, 30×250 mm. Flow 140 g/min. scCO2/MeOH, 72:28). t$_R$: 4.35 min (Column: Chiralpak IA, 4.6×250 mm. Flow 3 mL/min. scCO2/MeOH, 70:30).

Example 206

(R)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one

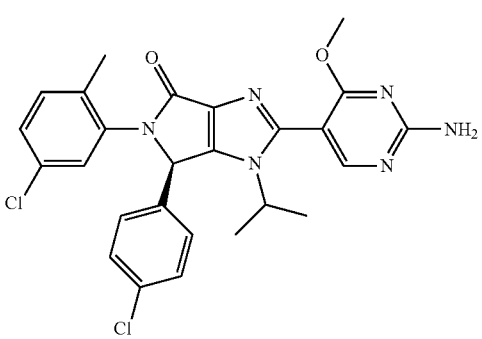 [SMILES: COc1nc(N)ncc1-c1nc2c(n1C(C)C)[C@@H](c1ccc(Cl)cc1)N(c1cc(Cl)ccc1C)C2=O]

The title compound was obtained after preparative chiral SFC separation of the racemic product of example 37. (Column: Chiralpak IA, 30×250 mm. Flow 140 g/min. scCO2/MeOH, 72:28). t$_R$: 3.22 min (Column: Chiralpak IA, 4.6×250 mm. Flow 3 mL/min. scCO2/MeOH, 70:30).

Example 207

3-[6-(4-Chloro-phenyl)-5-(5-chloro-pyridin-3-yl)-1-isopropyl-4-oxo-1,4,5,6-tetrahydro-pyrrolo[3,4-d]imidazol-2-yl]-4-methoxy-N,N-dimethyl-benzamide

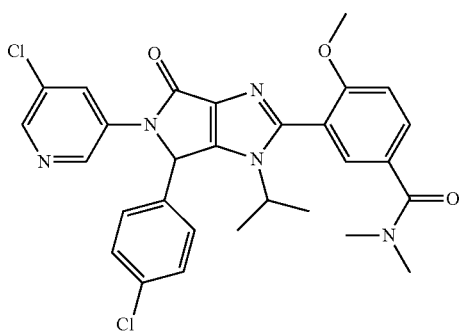 [SMILES: COc1ccc(C(=O)N(C)C)cc1-c1nc2c(n1C(C)C)C(c1ccc(Cl)cc1)N(c1cncc(Cl)c1)C2=O]

To a solution of intermediate AF (75 mg, 0.16 mmol) in DME/Water/EtOH (1 mL, 286 µL, 143 µL) were added intermediate M (72 mg, 0.32 mmol) and $Na_2CO_3$ (52 mg, 0.49 mmol). The mixture was degassed 5 min and then $Pd(PPh_3)_2Cl_2$ (12 mg, 0.02 mmol) was added. The reaction mixture was stirred under microwave irradiation at 120° C. for 20 min. EtOAc and water were added and the phases were separated. The organic phase was dried ($Na_2SO_4$), filtered and concentrated. The residue was purified by preparative chromatography (Waters Sun Fire C18, 30×100 mm, 5 µm; 0.1% TFA-water/acetonitrile; gradient acetonitrile 35-100% in 20 min) to give the title compound. $t_R$: 1.05 min (LC-MS 2); ESI-MS: 564.2/566.2 [M+H]$^+$ (LC-MS 2).

Example 208

5-(3-Chloro-2-fluoro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one

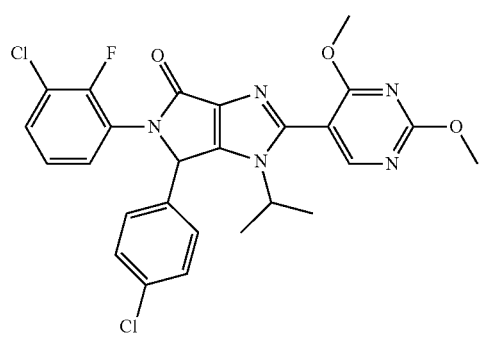 [SMILES: COc1ncc(-c2nc3c(n2C(C)C)C(c2ccc(Cl)cc2)N(c2cccc(Cl)c2F)C3=O)c(OC)n1]

The title compound was prepared in analogy to the procedure described for example 1 but using the intermediate G and 2,4-dimethoxypyrimidine-5-boronic acid. The reaction mixture was diluted in EtOAc/water and extracted twice with EtOAc. The combined organic extracts were combined, dried ($Na_2SO_4$) and concentrated. The residue was purified by preparative chromatography (Waters Sun Fire C18, 30×100 mm, 5 µm; 0.1% TFA-water/acetonitrile; gradient acetonitrile 30-70% in 16 min) to give the title compound. $t_R$: 1.17 min (LC-MS 2); ESI-MS: 542.2/544.2 [M+H]$^+$ (LC-MS 2).

Example 209

3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-N-isopropyl-4-methoxy-benzamide

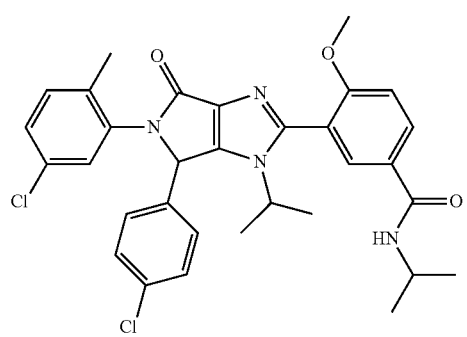 [SMILES: COc1ccc(C(=O)NC(C)C)cc1-c1nc2c(n1C(C)C)C(c1ccc(Cl)cc1)N(c1cc(Cl)ccc1C)C2=O]

The title compound was prepared in analogy to the procedure described for example 1 but using the product from step 209.1 and the intermediate M. The reaction mixture was diluted in EtOAc/water and extracted twice with EtOAc. The combined organic extracts were combined, dried ($Na_2SO_4$) and concentrated. The residue was purified by preparative chiral SFC separation of the racemic product of example 37. (Column: Diol, 30×250 mm. Flow 100 mL/min. scCO2/MeOH, gradient MeOH 23-28% in 6 min). to give the title compound. $t_R$: 1.20 min (LC-MS 2); ESI-MS: 591.1/593.1 [M+H]$^+$ (LC-MS 2).

Step 209.1: (R)-2-Bromo-5-(5-chloro-2-methyl-phenyl)-6-(4-chloro-phenyl)-1-isopropyl-5,6-dihydro-1H-pyrrolo[3,4-d]imidazol-4-one

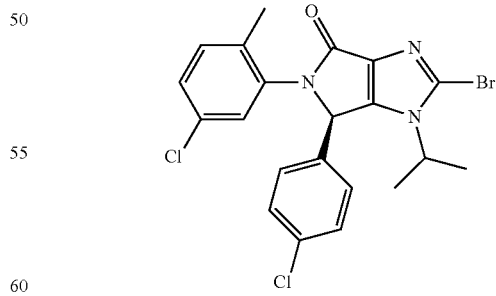

The title compound was obtained after preparative chiral SFC separation of the racemic intermediate E. (Column: Chiralcel OD-H, 30×250 mm. Flow 140 g/min. scCO2/MeOH, 70:30). $t_R$: 5.1 min (Column: Chiralcel OD-H, 4.6× 250 mm. Flow 3 mL/min. scCO2/MeOH, 70:30).

Example 210

5-(3-Chloro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one

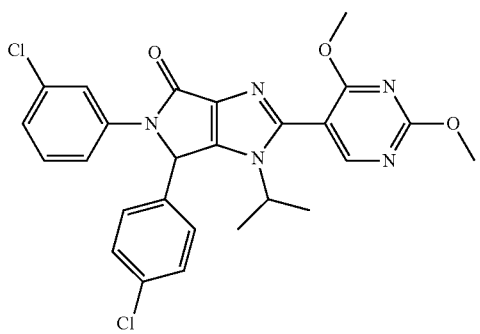 [SMILES: COc1ncc(-c2nc3c(n2C(C)C)C(c2ccc(Cl)cc2)N(c2cccc(Cl)c2)C3=O)c(OC)n1]

The title compound was prepared in analogy to the procedure described for example 207 but using the intermediate AG and 2,4-dimethoxypyrimidine-5-boronic acid The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 µm; 0.1% TFA-water/acetonitrile; gradient acetonitrile 35-100% in 20 min) to give the title compound. $t_R$: 1.21 min (LC-MS 2); ESI-MS: 524.2/526.1 [M+H]$^+$ (LC-MS 2).

Example 211

3-[5-(3-Chloro-phenyl)-6-(4-chloro-phenyl)-1-isopropyl-4-oxo-1,4,5,6-tetrahydro-pyrrolo[3,4-d]imidazol-2-yl]-4-methoxy-benzonitrile

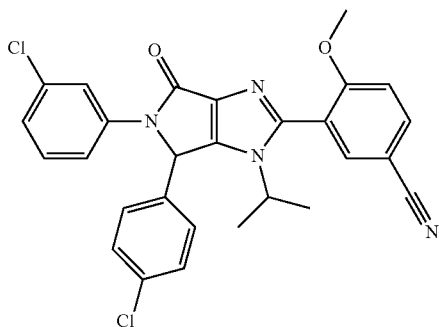 [SMILES: COc1ccc(C#N)cc1-c1nc2c(n1C(C)C)C(c1ccc(Cl)cc1)N(c1cccc(Cl)c1)C2=O]

The title compound was prepared in analogy to the procedure described for example 207 but using the intermediate AG and 5-cyano-2-methoxyphenylboronic acid The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 µm; 0.1% TFA-water/acetonitrile; gradient acetonitrile 35-100% in 20 min) to give the title compound. $t_R$: 1.24 min (LC-MS 2); ESI-MS: 517.2/519.2 [M+H]$^+$ (LC-MS 2).

Example 212

4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzoic acid

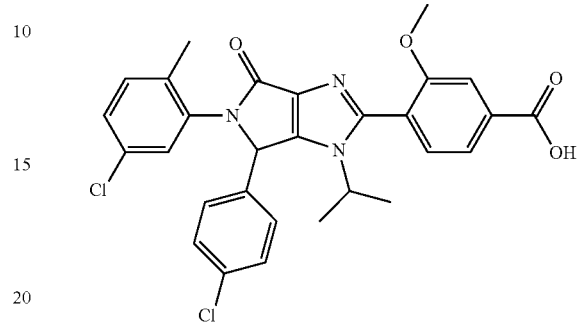

The title compound was prepared in analogy to the procedure described for example 1 but using the intermediate E and 4-carboxy-2-methoxyphenylboronic acid. The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 µm; 0.1% TFA-water/acetonitrile; gradient acetonitrile 50-100% in 16 min) to give the title compound. $t_R$: 1.14 min (LC-MS 2); ESI-MS: 550.2/552.2 [M+H]$^+$ (LC-MS 2).

Example 213

6-(4-Chloro-2-methyl-phenyl)-5-(3-chloro-phenyl)-1-isopropyl-2-[2-methoxy-5-(morpholine-4-carbonyl)-phenyl]-5,6-dihydro-1H-pyrrolo[3,4-d]imidazol-4-one

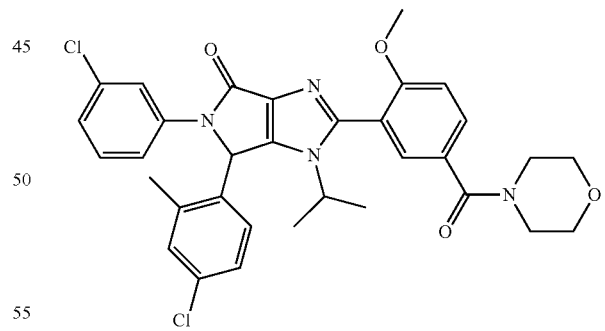

The title compound was prepared in analogy to the procedure described for example 207 but using intermediate O and the product from step 214.1. The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 µm; 0.1% TFA-water/acetonitrile; gradient acetonitrile 35-100% in 20 min) to give the title compound. $t_R$: 1.21 min (LC-MS 2); ESI-MS: 619.3/621.4 [M+H]$^+$ (LC-MS 2).

Example 214

6-(4-Chloro-2-methyl-phenyl)-5-(3-chloro-phenyl)-2-(2,4-dimethoxy-pyrimidin-5-yl)-1-isopropyl-5,6-dihydro-1H-pyrrolo[3,4-d]imidazol-4-one

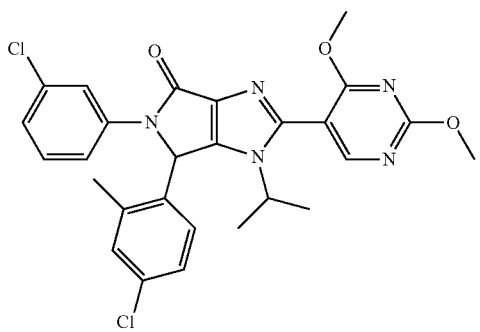 [SMILES: COc1ncc(-c2nc3c(n2C(C)C)C(c2ccc(Cl)cc2C)N(c2cccc(Cl)c2)C3=O)c(OC)n1]

The title compound was prepared in analogy to the procedure described for example 207 but using the product from step 214.1 and 2,4-dimethoxypyrimidine-5-boronic acid The reaction mixture was diluted in EtOAc/water and extracted twice with EtOAc. The combined organic extracts were combined, dried ($Na_2SO_4$) and concentrated. The residue was purified by preparative chromatography (Waters Sun Fire C18, 30×100 mm, 5 μm; 0.1% TFA-water/acetonitrile; gradient acetonitrile 35-100% in 20 min) to give the title compound. $t_R$: 1.29 min (LC-MS 2); ESI-MS: 538.2/540.2 $[M+H]^+$ (LC-MS 2).

Step 214.1: 2-Bromo-6-(4-chloro-2-methyl-phenyl)-5-(3-chloro-phenyl)-1-isopropyl-5,6-dihydro-1H-pyrrolo[3,4-d]imidazol-4-one

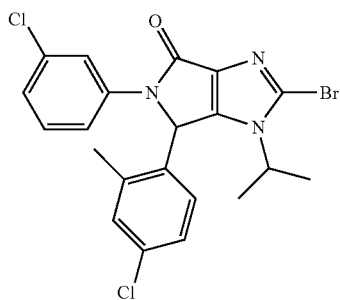 [SMILES: Cc1cc(Cl)ccc1C1c2c(nc(Br)n2C(C)C)C(=O)N1c1cccc(Cl)c1]

The title compound was prepared in analogy to the procedure described for example 64 but using the product from step 214.2. The reaction was quenched with saturated $NaHCO_3$ then extracted twice with EtOAc. The combined organic extracts were combined, dried ($Na_2SO_4$) and concentrated. The product was purified by flash chromatography (heptane/EtOAc, 9:1) to give the title compound. $t_R$: 1.28 min (LC-MS 2); ESI-MS: 478.2/480.1/482.1 $[M+H]^+$ (LC-MS 2).

Step 214.2: 2-Bromo-5-[(4-chloro-2-methyl-phenyl)-(3-chloro-phenylamino)-methyl]-1-isopropyl-1H-imidazole-4-carboxylic acid

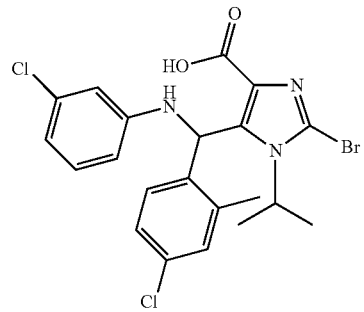 [SMILES: Cc1cc(Cl)ccc1C(Nc1cccc(Cl)c1)c1c(C(=O)O)nc(Br)n1C(C)C]

The title compound was prepared in analogy to the procedure described for step E1 but using the product from step 214.3. The reaction mixture was diluted in EtOAc/water and extracted twice with EtOAc. The combined organic extracts were combined, dried ($Na_2SO_4$) and concentrated to give the title compound. $t_R$: 1.28 min (LC-MS 2); ESI-MS: 496.1/498.1/500.2 $[M+H]^+$ (LC-MS 2).

Step 214.3: 2-Bromo-5-[(4-chloro-2-methyl-phenyl)-(3-chloro-phenylamino)-methyl]-1-isopropyl-1H-imidazole-4-carboxylic acid ethyl ester

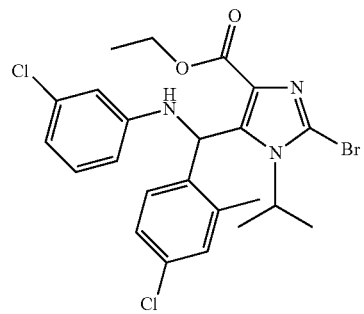 [SMILES: CCOC(=O)c1nc(Br)n(C(C)C)c1C(Nc1cccc(Cl)c1)c1ccc(Cl)cc1C]

The title compound was prepared in analogy to the procedure described for step E2 with the intermediate C and the 3-chloroaniline. The reaction mixture was diluted in DCM/water and the phases were separated. The organic phase was dried ($Na_2SO_4$) and concentrated. The product was purified by flash chromatography (heptane/EtOAc, 9:1) to give the title compound. $t_R$: 1.47 min (LC-MS 2); ESI-MS: 524.0/526.0/528.2 $[M+H]^+$ (LC-MS 2).

Example 215

3-[6-(4-Chloro-2-methyl-phenyl)-5-(3-chloro-phenyl)-1-isopropyl-4-oxo-1,4,5,6-tetrahydro-pyrrolo[3,4-d]imidazol-2-yl]-4-methoxy-benzonitrile

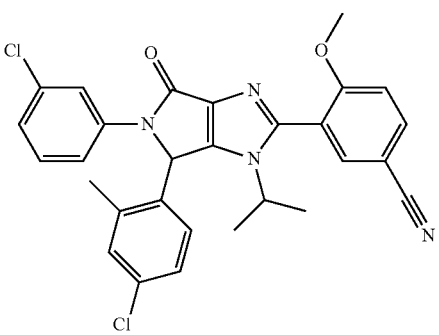 [SMILES: COc1ccc(C#N)cc1-c1nc2c(n1C(C)C)C(c1ccc(Cl)cc1C)N(c1cccc(Cl)c1)C2=O]

The title compound was prepared in analogy to the procedure described for example 207 but using the product from step 214.1 and 5-cyano-2-methoxyphenylboronic acid The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 µm; 0.1% TFA-water/acetonitrile; gradient acetonitrile 35-100% in 20 min) to give the title compound. t$_R$: 1.29 min (LC-MS 2); ESI-MS: 531.3/533.2 [M+H]$^+$ (LC-MS 2).

Example 216

4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzonitrile

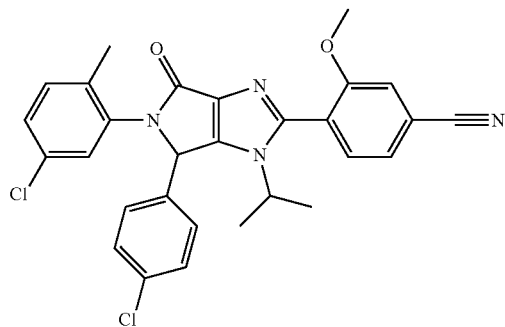 [SMILES: COc1cc(C#N)ccc1-c1nc2c(n1C(C)C)C(c1ccc(Cl)cc1)N(c1cc(Cl)ccc1C)C2=O]

The title compound was prepared in analogy to the procedure described for example 1 but using intermediates E and S. The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 µm; 0.1% TFA-water/acetonitrile; gradient acetonitrile 50-100% in 16 min) to give the title compound. t$_R$: 1.23 min (LC-MS 2); ESI-MS: 531.2/533.3 [M+H]$^+$ (LC-MS 2).

Example 217

3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-4-methoxy-benzamide

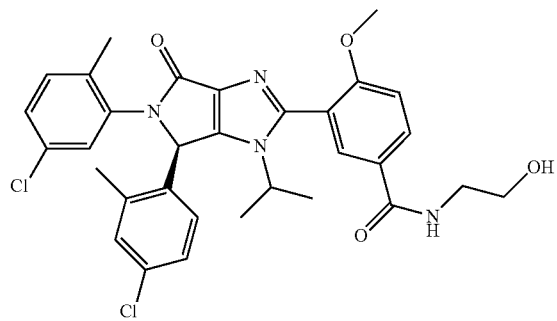 [SMILES: COc1ccc(C(=O)NCCO)cc1-c1nc2c(n1C(C)C)[C@@H](c1ccc(Cl)cc1C)N(c1cc(Cl)ccc1C)C2=O]

The title compound was obtained after preparative chiral chromatography separation of the racemic example 11. (Column: Chiralcel OD, 30×250 mm, heptane/EtOH, 85:15+0.1% DEA). t$_R$: 1.10/1.12 min (LC-MS 2); ESI-MS: 607.3/609.3 [M+H]$^+$ (LC-MS 2).

Example 218

3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-4-methoxy-benzamide

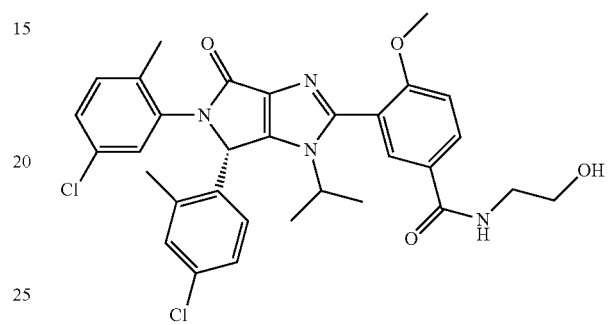

The title compound was obtained after preparative chiral chromatography separation of the racemic example 11. (Column: Chiralcel OD, 30×250 mm, heptane/EtOH, 85:15+0.1% DEA). t$_R$: 1.10/1.12 min (LC-MS 2); ESI-MS: 607.3/609.3 [M+H]$^+$ (LC-MS 2).

Example 219

4-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-3-methoxy-benzamide

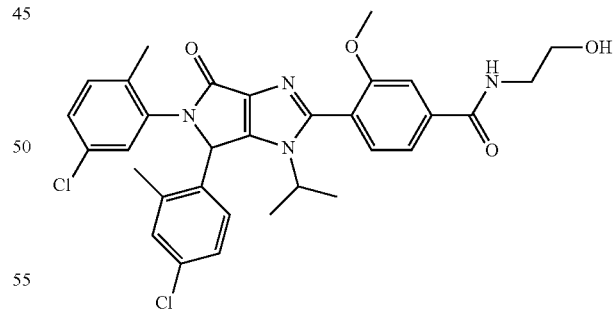

The title compound was prepared in analogy to the procedure described for example 1 but using intermediate F and the product from step 219.1. The reaction mixture was diluted in EtOAc/water and extracted twice with EtOAc. The combined organic extracts were combined, dried (Na$_2$SO$_4$) and concentrated. The residue was purified by SFC (Column: DEAP, 30×250 mm. Flow 100 mL/min. scCO2/MeOH, gradient of MeOH 20-25% in 6 min) t$_R$: 1.09/1.12 min (LC-MS 2); ESI-MS: 607.4/609.2 [M+H]$^+$ (LC-MS 2).

Step 219.1: (4((2-hydroxyethyl)carbamoyl)-2-methoxyphenyl)boronic acid

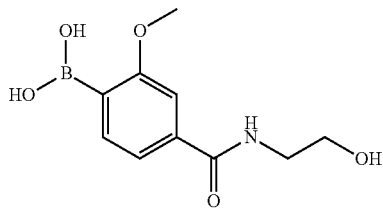 [SMILES: COc1cc(C(=O)NCCO)ccc1B(O)O]

The title compound was prepared in analogy to the procedure described for Intermediate K from 4-carboxy-2-methoxyphenyl boronic acid and ethanolamine. The solvent was removed and then water and EtOAc were added. The phases were separated and the aqueous one was extracted twice with EtOAc. The organics extracts were combined and dried (Na$_2$SO$_4$), and concentrated. The residue was triturated in acetonitrile to give the title compound. $t_R$: 0.42 min (LC-MS 2); ESI-MS: 240.1 [M+H]$^+$ (LC-MS 2).

Example 220

4-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-3-methoxy-benzamide

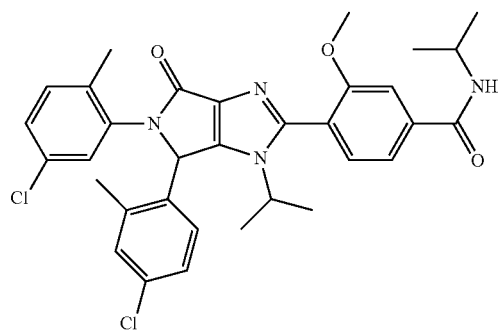 [SMILES: COc1cc(C(=O)NC(C)C)ccc1-c1nc2c(n1C(C)C)C(c1ccc(Cl)cc1C)N(c1cc(Cl)ccc1C)C2=O]

The title compound was prepared in analogy to the procedure described for example 1 but using intermediate F and product from step 220.1. The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 μm; 0.1% TFA-water/acetonitrile; gradient acetonitrile 50-100% in 16 min). The residue was purified by SFC (Column: DEAP, 30×250 mm. Flow 100 mL/min. scCO$_2$/MeOH, gradient of MeOH: 15 to 20% in 6 min). to give the title compound. $t_R$: 1.25 min (LC-MS 2); ESI-MS: 605.4/607.3 [M+H]$^+$ (LC-MS 2).

Step 220.1: (4-(isopropylcarbamoyl)-2-methoxyphenyl)boronic acid

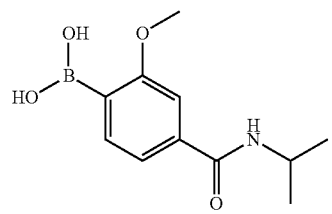 [SMILES: COc1cc(C(=O)NC(C)C)ccc1B(O)O]

The title compound was prepared in analogy to the procedure described for Intermediate K from 4-carboxy-2-methoxyphenyl boronic acid and isopropylamine. The solvent was removed and then water and EtOAc were added. The phases were separated and the aqueous one was extracted twice with EtOAc. The organic extracts were combined and dried (Na$_2$SO$_4$), and concentrated. The residue was triturated in acetonitrile to give the title compound. $t_R$: 0.63 min (LC-MS 2); ESI-MS: 238.5 [M+H]$^+$ (LC-MS 2).

Example 221

5-(5-Chloro-2-methyl-phenyl)-6-(4-chloro-2-methyl-phenyl)-2-(2-ethyl-phenyl)-1-isopropyl-5,6-dihydro-1H-pyrrolo[3,4-d]imidazol-4-one

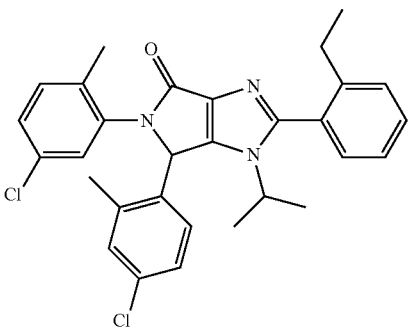 [SMILES: CCc1ccccc1-c1nc2c(n1C(C)C)C(c1ccc(Cl)cc1C)N(c1cc(Cl)ccc1C)C2=O]

The title compound was prepared in analogy to the procedure described for example 1 but using intermediate F and 2-ethylphenylboronic acid. The reaction mixture was diluted in EtOAc/water and extracted twice with EtOAc. The combined organic extracts were combined, dried (Na$_2$SO$_4$) and concentrated. The product was purified by flash chromatography (hexane/EtOAc, 95:5→1:1). The residue was purified by SFC (Column: NH2 Reprosil 70, 30×250 mm. Flow 100 mL/min. scCO2/MeOH, gradient of MeOH 15-20% in 6 min). to give the title compound. $t_R$: 1.42/1.47 min (LC-MS 2); ESI-MS: 518.2/520.2 [M+H]$^+$ (LC-MS 2).

Example 222

3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-N,N-dimethyl-benzamide

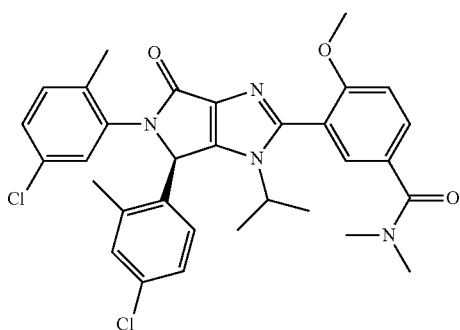 [SMILES: COc1ccc(C(=O)N(C)C)cc1-c1nc2c(n1C(C)C)[C@@H](c1ccc(Cl)cc1C)N(c1cc(Cl)ccc1C)C2=O]

The title compound was obtained after preparative chiral chromatography separation of the racemic example 9. (Column: Chiralcel OD, 30×250 mm, heptane/EtOH, 65:35). $t_R$: 1.17/1.21 min (LC-MS 2); ESI-MS: 591.3/593.3 [M+H]$^+$ (LC-MS 2).

Example 223

3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-N,N-dimethyl-benzamide

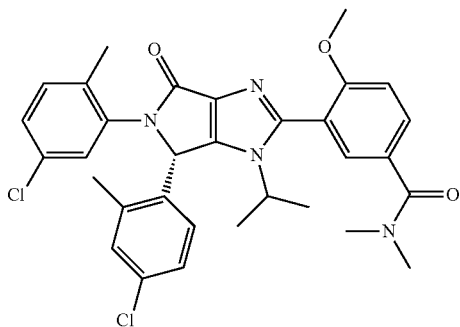 [SMILES: COc1ccc(C(=O)N(C)C)cc1-c1nc2c(n1C(C)C)[C@H](c1ccc(Cl)cc1C)N(c1cc(Cl)ccc1C)C2=O]

The title compound was obtained after preparative chiral chromatography separation of the racemic example 9. (Column: Chiralcel OD, 30×250 mm, heptane/EtOH, 65:35). $t_R$: 1.17/1.21 min (LC-MS 2); ESI-MS: 591.3/593.3 [M+H]$^+$ (LC-MS 2).

Example 224

6-(4-Chloro-2-methyl-phenyl)-5-(4-chloro-pyridin-2-yl)-2-(5-hydroxymethyl-2-methoxy-phenyl)-1-isopropyl-5,6-dihydro-1H-pyrrolo[3,4-d]imidazol-4-one

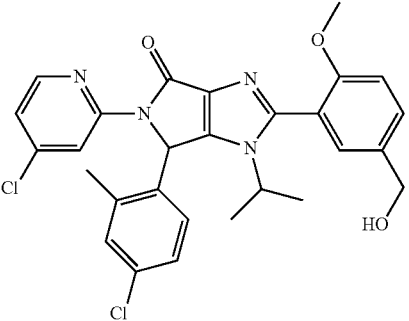 [SMILES: COc1ccc(CO)cc1-c1nc2c(n1C(C)C)C(c1ccc(Cl)cc1C)N(c1cc(Cl)ccn1)C2=O]

The title compound was prepared in analogy to the procedure described for example 1 but using intermediate I and product from step 224.1. The reaction mixture was diluted in EtOAc/water and extracted twice with EtOAc. The combined organic extracts were combined, dried (Na$_2$SO$_4$) and concentrated. The residue was purified by preparative chromatography (Waters Sun Fire C18, 30×100 mm, 5 μm; 0.1% TFA-water/acetonitrile; gradient acetonitrile 50-90% in 16 min). The residue was purified by SFC (Column: 2-EP, 30×250 mm. Flow 100 mL/min. scCO2/MeOH, gradient of MeOH: 20 to 25% in 6 min). to give the title compound. $t_R$: 1.25 min (LC-MS 2); ESI-MS: 537.2/539.2 [M+H]$^+$ (LC-MS 2).

Step 224.1: (4-(isopropylcarbamoyl)-2-methoxyphenyl)boronic acid

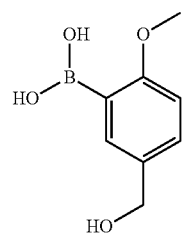

The title compound was prepared in analogy to the procedure described for example 18 from 5-formyl-2-methoxyphenylboronic acid. The reaction mixture was poured in Ice-water and was extracted twice with EtOAc. The organic extracts were combined, dried (Na2SO4) and concentrated to give the title compound. $t_R$: 0.49 min (LC-MS2); ESI-MS: 364.6 [M+H]$^+$ (LC-MS 2).

Example 225

3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-4-methoxy-benzamide

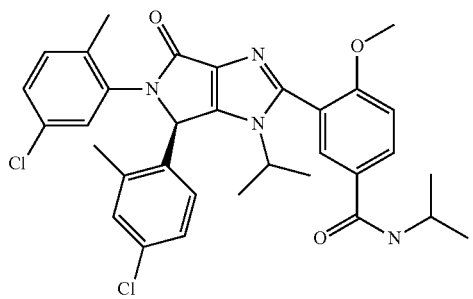 [SMILES: COc1ccc(C(=O)NC(C)C)cc1-c1nc2c(n1C(C)C)[C@@H](c1ccc(Cl)cc1C)N(c1cc(Cl)ccc1C)C2=O]

The title compound was obtained after preparative chiral SFC separation of the racemic example 12. (Column: Chiralcel OD-H, 30×250 mm. Flow 80 mL/min. scCO2/EtOH/2-propylamine, 75:25:0.25). $t_R$: 8.06 min (Column: Chiralpak IA, 4.6×250 mm. Flow 3 mL/min. scCO2/EtOH/2-propylamine, 80:20:0.2). ESI-MS: 605.3.3/607.2 [M+H]$^+$ (LC-MS 2).

Example 226

3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-4-methoxy-benzamide

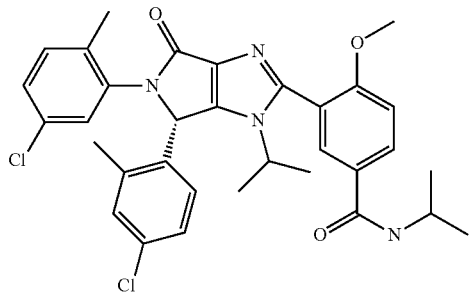 [SMILES: COc1ccc(C(=O)NC(C)C)cc1-c1nc2c(n1C(C)C)[C@H](c1ccc(Cl)cc1C)N(c1cc(Cl)ccc1C)C2=O]

The title compound was obtained after preparative chiral SFC separation of the racemic example 12. (Column: Chiralcel OD-H, 30×250 mm. Flow 80 mL/min. scCO2/EtOH/2-propylamine, 75:25:0.25). $t_R$: 4.67 min (Column: Chiralpak IA, 4.6×250 mm. Flow 3 mL/min. scCO2/EtOH/2-propylamine, 80:20:0.2). ESI-MS: 605.3.3/607.2 [M+H]$^+$ (LC-MS 2).

Example 227

6-(4-Chloro-2-methyl-phenyl)-5-(5-chloro-2-methyl-pyridin-3-yl)-1-isopropyl-2-(2-methoxy-phenyl)-5,6-dihydro-1H-pyrrolo[3,4-d]imidazol-4-one

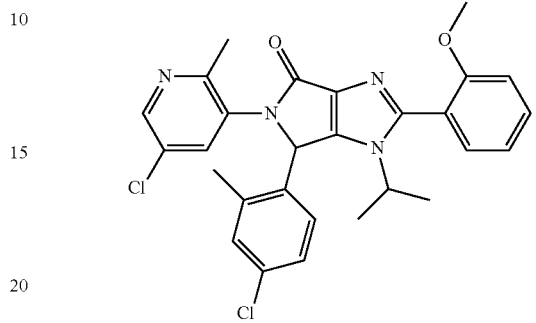

To a solution of the product from step 227.1 (100 mg, 0.18 mmol) and HATU (106 mg, 0.28 mmol) in DMF (1.5 mL) was added DIPEA (66 µL, 0.38 mmol) and the mixture was stirred under microwave irradiation at 105° C. for 30 min. The crude was purified by preparative HPLC (Waters Sun Fire C18, 30×100 mm, 5 µm; 0.1% TFA-water/acetonitrile; gradient acetonitrile 5-100% in 20 min) to give the title compound. $t_R$: 1.25 min (LC-MS 2); ESI-MS: 521.2/523.2 [M+H]$^+$ (LC-MS 2).

Step 227.1: 5-[(4-Chloro-2-methyl-phenyl)-(5-chloro-2-methyl-pyridin-3-ylamino)-methyl]-1-isopropyl-2-(2-methoxy-phenyl)-1H-imidazole-4-carboxylic acid

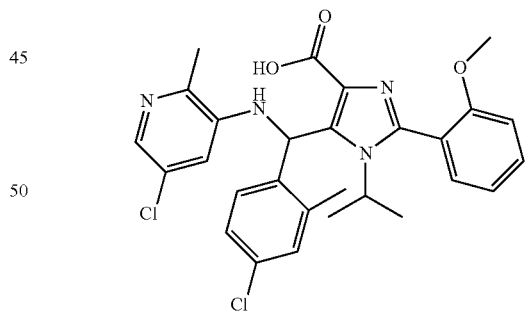

To a solution of the product from step 227.2 (220 mg, 0.39 mmol) in dioxane/H$_2$O (3.7 mL, 4:1) was added LiOH.H$_2$O (25 mg, 0.60 mmol) and the mixture was stirred at 60° C. for 4 h. The reaction mixture was poured into a 10% citric acid solution and stirred for 10 min. The mixture was extracted with EtOAc. The organic layer was dried (Na$_2$SO$_4$), filtered and concentrated. The product was purified by flash chromatography (heptane/EtOAc). $t_R$: 1.16 min (LC-MS2); ESI-MS: 539.2/541.2 [M+H]$^+$ (LC-MS 2).

Step 227.2: 5-[(4-Chloro-2-methyl-phenyl)-(5-chloro-2-methyl-pyridin-3-ylamino)-methyl]-1-isopropyl-2-(2-methoxy-phenyl)-1H-imidazole-4-carboxylic acid ethyl ester

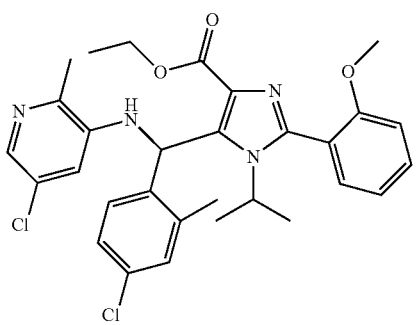 [SMILES: CCOC(=O)c1nc(-c2ccccc2OC)n(C(C)C)c1C(Nc1cc(Cl)cnc1C)c1ccc(Cl)cc1C]

To a solution of the product from step 227.6 (300 mg, 0.576 mmol) in $CH_2Cl_2$ (5 ml) was added the product from step 227.3 (200 mg, 1.403 mmol) and the mixture was stirred at 40° C. for 20 h. The reaction mixture was diluted in EtOAc and extracted with citric acid (10%). The organic phase was washed with brine, dried (Na2SO4), filtered and concentrated. The product was purified by flash chromatography (heptane/EtOAc). $t_R$: 1.40 min (LC-MS 2); ESI-MS: 567.2/569.2 $[M+H]^+$ (LC-MS 2).

Step 227.3: 5-Chloro-2-methyl-pyridin-3-ylamine

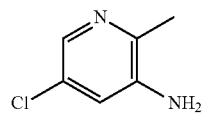

The title compound was prepared in analogy to the procedure described for example 100.4 using the product from step 227.4. The reaction was performed in EtOH at rt, for 20 h. After extraction, the product was used without purification. $t_R$: 0.42 min (LC-MS2); ESI-MS: 143.0/145.0 $[M+H]^+$ (LC-MS 2).

Step 227.4: 5-Chloro-2-methyl-3-nitro-pyridine

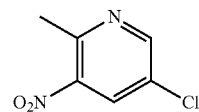

To a suspension of the product from step 227.5 (9.9 g, 23.4 mmol) in $H_2O$ (25 mL) was added concentrated HCl (25 mL, 304 mmol) and the mixture was stirred at 100° C. for 20 h. The reaction mixture was allowed to cool to RT and extracted with $Et_2O$. The organic layer was washed with brine, dried ($Na_2SO_4$), filtered and concentrated. The product was used without further purification for the next step. $t_R$: 0.80 min (LC-MS 2).

Step 227.5: 2-(5-Chloro-3-nitro-pyridin-2-yl)-malonic acid diethyl ester

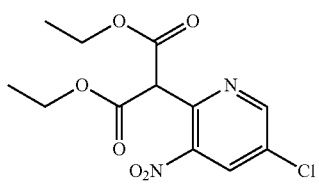

To a solution of NaH (2 g, 50 mmol) in DMF (30 mL) was added diethylmalonate (7.9 mL, 52 mmol) and the mixture was stirred at rt for 10 min. A solution of 2,5-dichloro-3-nitropyridine (5 g, 25.9 mmol) in DMF (10 mL) was added and the mixture was stirred at 40° C. for 2 h. The reaction mixture was concentrated. The residue was dissolved in $H_2O$ and pH was adjusted to 7 with 2M HCl. The aqueous solution was extracted with $Et_2O$. The organic layer was washed with $H_2O$, dried ($Na_2SO_4$), filtered and concentrated. The product was purified by flash chromatography (heptane/EtOAc). $t_R$: 1.07 min (LC-MS 2); ESI-MS: 317.2/319.1 $[M+H]^+$ (LC-MS 2).

Step 227.6: 5-[(4-Chloro-2-methyl-phenyl)-methanesulfonyloxy-methyl]-1-isopropyl-2-(2-methoxy-phenyl)-1H-imidazole-4-carboxylic acid ethyl ester

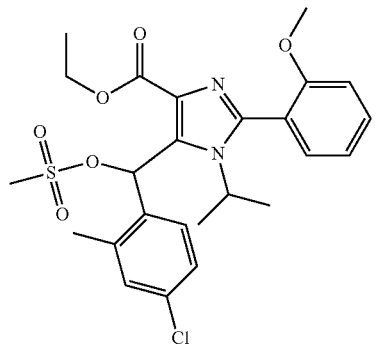 [SMILES: CCOC(=O)c1nc(-c2ccccc2OC)n(C(C)C)c1C(OS(C)(=O)=O)c1ccc(Cl)cc1C]

To a solution of intermediate D (3.3 g, 7.6 mmol) and $Et_3N$ (2.6 mL, 18.7 mmol) in $CH_2Cl_2$ at 0° C. was added MsCl (1.2 mL, 15.4 mmol) and the mixture was stirred at rt for 1 h. The reaction mixture was poured into cold water and extracted with $CH_2Cl_2$. The organic layer was dried ($Na_2SO_4$), filtered and concentrated. The product was used without further purification. $t_R$: 1.44 min (LC-MS 2); ESI-MS: 457 (reaction with MeOH) $[M+H]^+$ (LC-MS 2).

Example 228

N-{3-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-benzyl}-2-hydroxy-acetamide

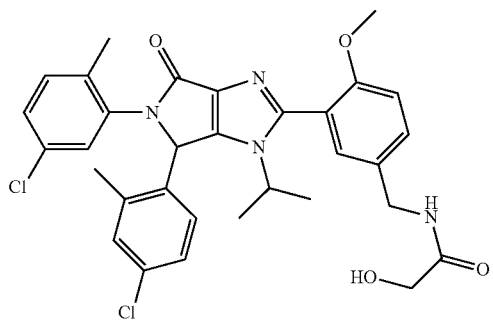 [SMILES: COc1ccc(CNC(=O)CO)cc1-c1nc2c(n1C(C)C)C(c1ccc(Cl)cc1C)N(c1cc(Cl)ccc1C)C2=O]

The product from step 228.1 (106 mg, 0.16 mmol) was dissolved in MeOH (2.7 mL) with K2CO3 (56 mg, 0.41 mmol). The reaction mixture was stirred at RT for 3 h. It was diluted in EtOAc/water and extracted twice with EtOAc. The organic extracts were combined, dried (Na$_2$SO$_4$) and concentrated. The residue was triturated in EtOAc to give the title compound. $t_R$: 1.15 min (LC-MS 2); ESI-MS: 607.3/609.2 [M+H]$^+$ (LC-MS 2).

Step 228.1: Acetic acid {3-[6-(4-chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-benzylcarbamoyl}-methyl ester

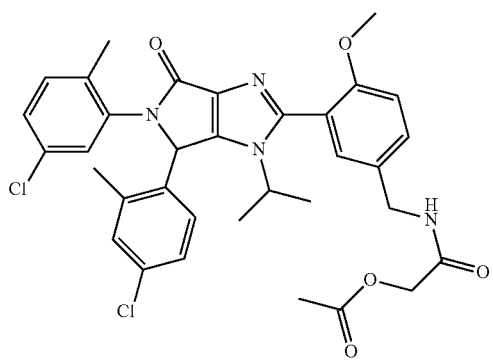 [SMILES: COc1ccc(CNC(=O)COC(C)=O)cc1-c1nc2c(n1C(C)C)C(c1ccc(Cl)cc1C)N(c1cc(Cl)ccc1C)C2=O]

The product from example 16 (90 mg, 0.16 mmol) was dissolved in THF (1.6 mL) with TEA (27 µL, 0.20 mmol) and then acetoxyacetyl chloride (19 µL, 0.18 mmol) was added. The reaction mixture was stirred at RT for 30 min. It was then concentrated to give the title compound. $t_R$: 1.24 min (LC-MS 2); ESI-MS: 649.3/651.2 [M+H]$^+$ (LC-MS 2).

Example 229

5-[5-Chloro-1-(2-hydroxy-ethyl)-6-oxo-1,6-dihydro-pyridin-3-yl]-6-(4-chloro-2-methyl-phenyl)-1-isopropyl-2-(2-methoxy-phenyl)-5,6-dihydro-1H-pyrrolo[3,4-d]imidazol-4-one

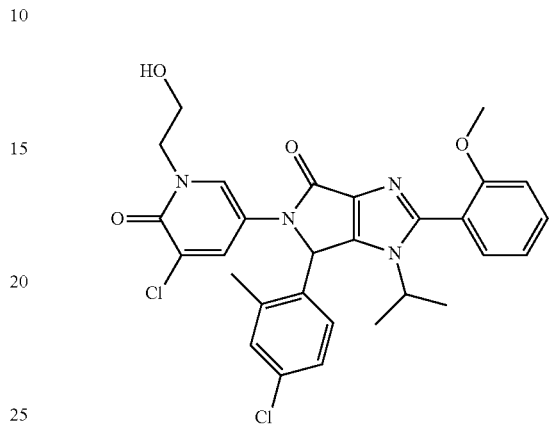

The title compound was prepared in analogy to the procedure described for example 227 using the product from step 229.1. The reaction was performed at 110° C. for 45 min. $t_R$: 1.04 min (LC-MS 2); ESI-MS: 567.2/569.2 [M+H]$^+$ (LC-MS 2).

Step 229.1: 5-[[5-Chloro-1-(2-hydroxy-ethyl)-6-oxo-1,6-dihydro-pyridin-3-ylamino]-(4-chloro-2-methyl-phenyl)-methyl]-1-isopropyl-2-(2-methoxy-phenyl)-1H-imidazole-4-carboxylic acid

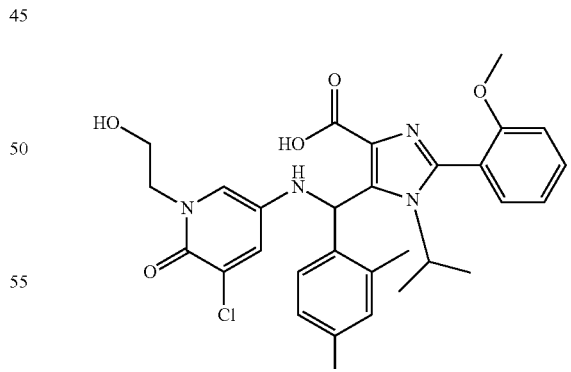

The title compound was prepared in analogy to the procedure described for step 227.1 using the product from step 229.2. $t_R$: 0.93 min (LC-MS 2); ESI-MS: 585.2/587.2 [M+H]$^+$ (LC-MS 2).

Step 229.2: 5-[[5-Chloro-1-(2-hydroxy-ethyl)-6-oxo-1,6-dihydro-pyridin-3-ylamino]-(4-chloro-2-methyl-phenyl)-methyl]-1-isopropyl-2-(2-methoxy-phenyl)-1H-imidazole-4-carboxylic acid ethyl ester

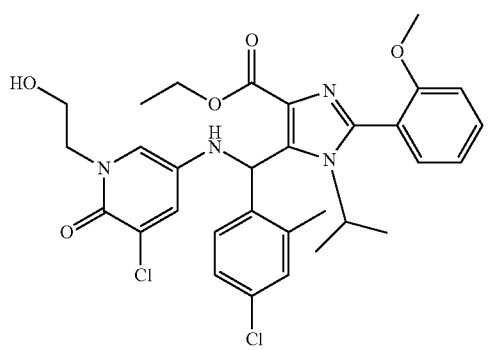 [SMILES: CCOC(=O)c1nc(-c2ccccc2OC)n(C(C)C)c1C(Nc1cc(Cl)c(=O)n(CCO)c1)c1ccc(Cl)cc1C]

The title compound was prepared in analogy to the procedure described for step 227.2 using the products from steps 227.6 and 229.3. $t_R$: 1.18 min (LC-MS 2); ESI-MS: 613.2/615.2 [M+H]$^+$ (LC-MS 2).

Step 229.3: 5-Amino-3-chloro-1-(2-hydroxy-ethyl)-1H-pyridin-2-one

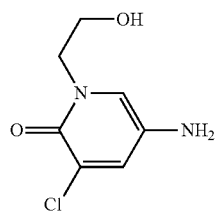 [SMILES: Nc1cc(Cl)c(=O)n(CCO)c1]

A mixture of the compound prepared in step 229.4 (3.4 g, 18.1 mmol), iron powder (3 g, 54.3 mmol), EtOH (68 mL), and a saturated aqueous solution of NH$_4$Cl (17 mL) was stirred for 1 h at reflux. The reaction mixture was allowed to cool to rt, filtered through a pad of celite, and concentrated. The residue was purified by flash chromatography (CH$_2$Cl$_2$/MeOH, 99:1) to provide the title compound. ESI-MS: 189 [M+H]$^+$ (LC-MS 2); R$_f$=0.17 (CH$_2$Cl$_2$/MeOH, 99:1).

Step 229.4: 3-Chloro-1-(2-hydroxy-ethyl)-5-nitro-1H-pyridin-2-one

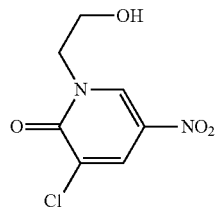 [SMILES: O=c1c(Cl)cc([N+](=O)[O-])cn1CCO]

2-Bromo-ethanol (17.2 g, 138 mmol) was added dropwise to a cold (0° C.) mixture of the compound prepared in step 229.5 (12 g, 69 mmol) and K$_2$CO$_3$ (19 g, 138 mmol) in DMF (60 mL). The reaction mixture was allowed to warm to rt, stirred for 48 h, cooled to 0° C., quenched by slow addition of ice cooled water, and stirred for 2 h. The resulting precipitate was collected by vacuum filtration to afford 11 g of the title compound. ESI-MS: 217 [M–H]$^-$ (LC-MS 2); R$_f$=0.27 (CH$_2$Cl$_2$/MeOH, 95:5).

Step 229.5: 3-Chloro-5-nitro-pyridin-2-ol

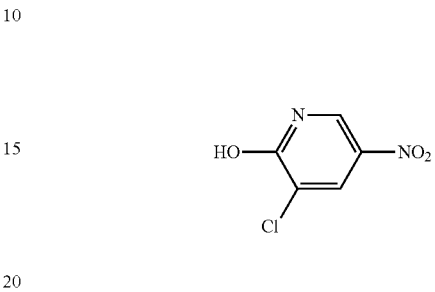

To a warm (50° C.) solution of 2-hydroxy-5-nitro-pyridine (17 g, 121 mmol) in concentrated HCl (80 mL) was added dropwise NaClO$_3$ (4.5 g, 42.5 mmol) in water (70 mL), keeping the internal temperature below 60° C. The reaction mixture was stirred for 15 min and then cooled to 0° C. The resulting precipitate was collected by vacuum filtration and dried to provide 19.7 g of the title compound. ESI-MS: 173 [M–H]$^-$ (LC-MS 2); R$_f$=0.55 (hexane/EtOAc, 1:1).

Example 230

5-[5-Chloro-1-(2-methoxy-ethyl)-6-oxo-1,6-dihydro-pyridin-3-yl]-6-(4-chloro-2-methyl-phenyl)-1-isopropyl-2-(2-methoxy-phenyl)-5,6-dihydro-1H-pyrrolo[3,4-d]imidazol-4-one

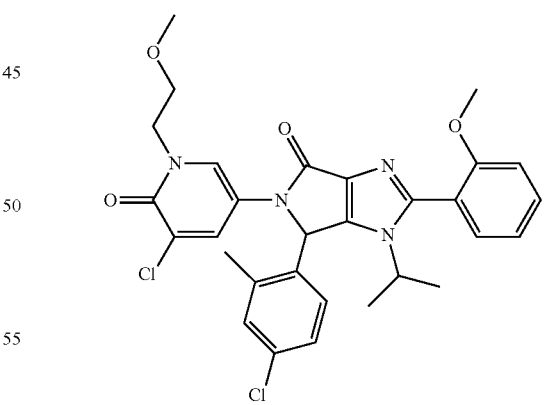

The title compound was prepared in analogy to the procedure described for example 227 using the product from step 230.1. The crude was purified by preparative HPLC (Waters Sun Fire C18, 30×100 mm, 5 μm; 0.1% TFA-water/acetonitrile; gradient acetonitrile 5-100% in 20 min) to give the title compound. $t_R$: 1.14 min (LC-MS 2); ESI-MS: 581.2/583.2 [M+H]$^+$ (LC-MS 2).

Step 230.1: 5-[[5-Chloro-1-(2-methoxy-ethyl)-6-oxo-1,6-dihydro-pyridin-3-ylamino]-(4-chloro-2-methyl-phenyl)-methyl]-1-isopropyl-2-(2-methoxy-phenyl)-1H-imidazole-4-carboxylic acid

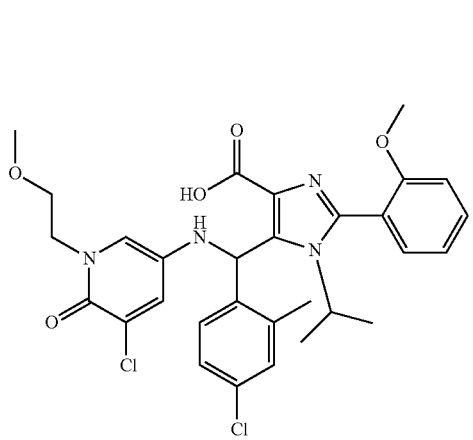 [SMILES: COCCn1cc(NC(c2ccc(Cl)cc2C)c2c(C(=O)O)nc(-c3ccccc3OC)n2C(C)C)cc(Cl)c1=O]

The title compound was prepared in analogy to the procedure described for step 227.1 using the product from step 230.2. The reaction mixture was dissolved in CH$_2$Cl$_2$ and dimethylamine hydrochloride (1 eq) and a drop of MeOH were added. The mixture was stirred at rt 1 h, then concentrated. The residue was suspended in CH$_2$Cl$_2$ and filtered. The mother liquor was concentrated. The crude was purified by preparative HPLC (Waters Sun Fire C18, 30×100 mm, 5 μm; 0.1% TFA-water/acetonitrile; gradient acetonitrile 5-100% in 20 min) to give the title compound. t$_R$: 1.00 min (LC-MS 2); ESI-MS: 599.3/601.2 [M+H]$^+$ (LC-MS 2).

Step 230.2: 5-[[5-Chloro-1-(2-methoxy-ethyl)-6-oxo-1,6-dihydro-pyridin-3-ylamino]-(4-chloro-2-methyl-phenyl)-methyl]-1-isopropyl-2-(2-methoxy-phenyl)-1H-imidazole-4-carboxylic acid ethyl ester

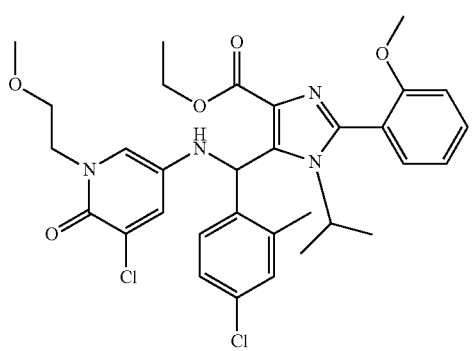 [SMILES: CCOC(=O)c1nc(-c2ccccc2OC)n(C(C)C)c1C(Nc1cc(Cl)c(=O)n(CCOC)c1)c1ccc(Cl)cc1C]

The title compound was prepared in analogy to the procedure described for step 227.2 using the products from steps 227.6 and 230.3. The product was purified by flash chromatography (heptane/EtOAc, 1:1→0:100). t$_R$: 1.28 min (LC-MS 2); ESI-MS: 627.3/629.2 [M+H]$^+$ (LC-MS 2).

Step 230.3: 5-Amino-3-chloro-1-(2-methoxy-ethyl)-1H-pyridin-2-one

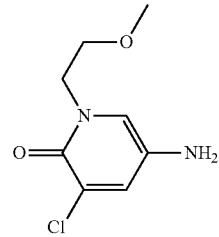

The title compound was prepared in analogy to the procedure described in step 229.4 but using the compound prepared in step 230.4. The crude material was purified by flash chromatography (CH$_2$Cl$_2$/MeOH, 95:5) to provide the title compound. ESI-MS: 203 [M+H]$^+$ (LC-MS 2); R$_f$=0.28 (CH$_2$Cl$_2$/MeOH, 99.75:0.25).

Step 230.4: 3-Chloro-1-(2-methoxy-ethyl)-5-nitro-1H-pyridin-2-one

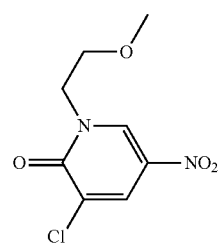

The title compound was prepared in analogy to the procedure described in step 229.5 but using 1-bromo-2-methoxy-ethane. The reaction mixture was allowed to warm to rt, stirred for 4 h, heated to 70° C., stirred for 4 h, and quenched by addition of ice cooled water. The resulting precipitate was collected by vacuum filtration to afford the title compound. ESI-MS: 233 [M–H]$^-$ (LC-MS 2); R$_f$=0.33 (CH$_2$Cl$_2$/MeOH, 95:5).

Example 231

5-(5-Chloro-1-methyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-d]imidazol-4-one

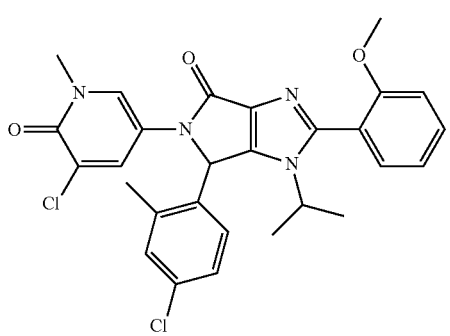 [SMILES: COc1ccccc1-c1nc2c(n1C(C)C)C(c1ccc(Cl)cc1C)N(c1cc(Cl)c(=O)n(C)c1)C2=O]

The title compound was prepared in analogy to the procedure described for example 227 using the product from step 231.1. The reaction was performed at 110° C. for 45 min. The crude was purified by preparative HPLC (Waters Sun Fire C18, 30×100 mm, 5 µm; 0.1% TFA-water/acetonitrile; gradient acetonitrile 5-100% in 20 min) to give the title compound. $t_R$: 1.10 min (LC-MS 2); ESI-MS: 537.2/539.1 [M+H]$^+$ (LC-MS 2).

Step 231.1: 5-[(5-Chloro-1-methyl-6-oxo-1,6-dihydro-pyridin-3-ylamino)-(4-chloro-2-methyl-phenyl)-methyl]-1-isopropyl-2-(2-methoxy-phenyl)-1H-imidazole-4-carboxylic acid

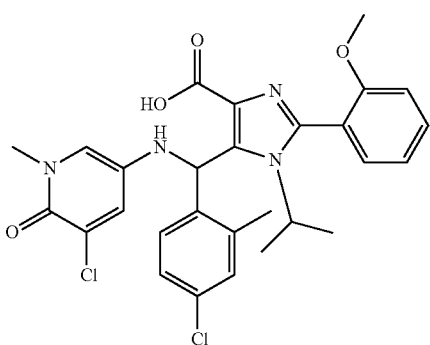 [SMILES: COc1ccccc1-c1nc(C(=O)O)c(C(Nc2cc(Cl)c(=O)n(C)c2)c2ccc(Cl)cc2C)n1C(C)C]

The title compound was prepared in analogy to the procedure described for step 230.1 using the product from step 231.2. $t_R$: 0.97 min (LC-MS 2); ESI-MS: 555.2/557.2 [M+H]$^+$ (LC-MS 2).

Step 231.2: 5-[(5-Chloro-1-methyl-6-oxo-1,6-dihydro-pyridin-3-ylamino)-(4-chloro-2-methyl-phenyl)-methyl]-1-isopropyl-2-(2-methoxy-phenyl)-1H-imidazole-4-carboxylic acid ethyl ester

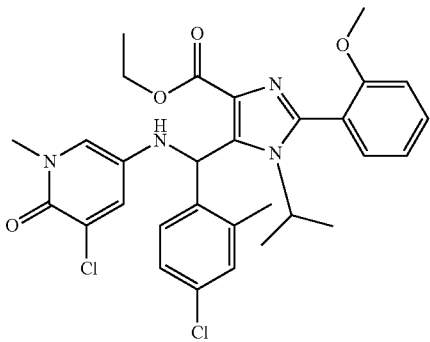 [SMILES: CCOC(=O)c1nc(-c2ccccc2OC)n(C(C)C)c1C(Nc1cc(Cl)c(=O)n(C)c1)c1ccc(Cl)cc1C]

The title compound was prepared in analogy to the procedure described for step 227.2 using the products from steps 227.6 and J3. The product was purified by flash chromatography (heptane/EtOAc, 1:1→0:100). $t_R$: 1.26 min (LC-MS 2); ESI-MS: 583.2/585.2 [M+H]$^+$ (LC-MS 2).

Example 232

5-(5-Chloro-1-ethyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-d]imidazol-4-one

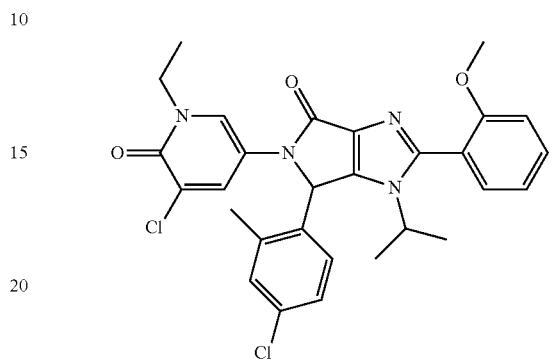

The title compound was prepared in analogy to the procedure described for example 227 using the product from step 232.1. The reaction was performed under microwave irradiation at 100° C. for 5.5 h and at 110° C. for 4 h. The reaction mixture was poured into a 10% citric acid solution and stirred for 10 min. The mixture was extracted with CH$_2$Cl$_2$. The organic layer was dried (Na$_2$SO$_4$), filtered and concentrated. The crude was purified by preparative HPLC (Waters Sun Fire C18, 30×100 mm, 5 µm; 0.1% TFA-water/acetonitrile; gradient acetonitrile 5-100% in 20 min) to give the title compound. $t_R$: 1.12 min (LC-MS 2); ESI-MS: 551.2/553.2 [M+H]$^+$ (LC-MS 2).

Step 232.1: 5-[(5-Chloro-1-ethyl-6-oxo-1,6-dihydro-pyridin-3-ylamino)-(4-chloro-2-methyl-phenyl)-methyl]-1-isopropyl-2-(2-methoxy-phenyl)-1H-imidazole-4-carboxylic acid anion

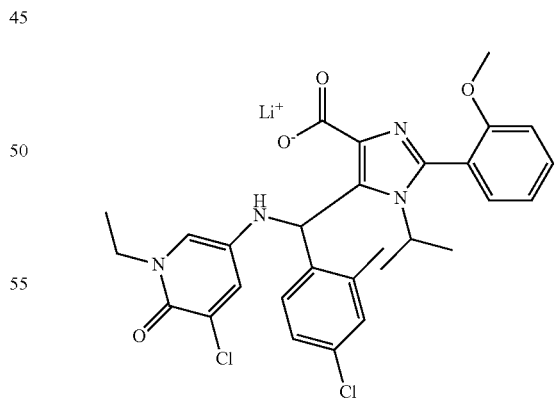

The title compound was prepared in analogy to the procedure described for step 227.1 using the product from step 232.2. After completion, the reaction mixture was concentrated. The resulting lithium salt was used without further purification. $t_R$: 1.04 min (LC-MS 2); ESI-MS: 569.2/571.2 [M+H]$^+$ (LC-MS 2).

Step 232.2: 5-[(5-Chloro-1-ethyl-6-oxo-1,6-dihydro-pyridin-3-ylamino)-(4-chloro-2-methyl-phenyl)-methyl]-1-isopropyl-2-(2-methoxy-phenyl)-1H-imidazole-4-carboxylic acid ethyl ester

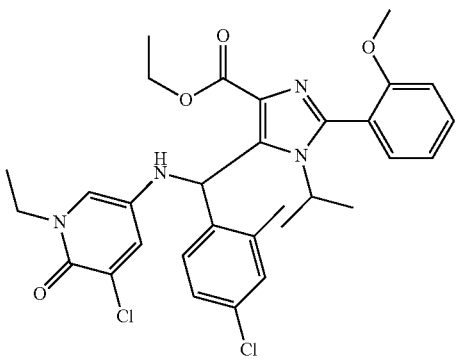 [SMILES: CCOC(=O)c1nc(-c2ccccc2OC)n(C(C)C)c1C(Nc1cc(Cl)c(=O)n(CC)c1)c1ccc(Cl)cc1C]

The title compound was prepared in analogy to the procedure described for step 227.2 using the products from steps 227.6 and 232.3. The product was purified by flash chromatography (heptane/EtOAc, 7:3→0:100). $t_R$: 1.30 min (LC-MS 2); ESI-MS: 597.3/599.3 [M+H]$^+$ (LC-MS 2).

Step 232.3:
5-Amino-3-chloro-1-ethyl-1H-pyridin-2-one

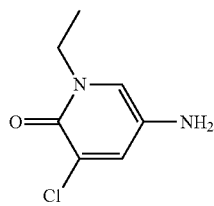

The title compound was prepared in analogy to the procedure described in step 229.4 but using the compound prepared in step 232.4. The crude material was purified by flash chromatography (CH$_2$Cl$_2$/MeOH, 95:5) to provide the title compound. $t_R$: 2.39 min (HPLC 3); R$_f$=0.14 (CH$_2$Cl$_2$/MeOH, 9:1).

Step 232.4:
3-Chloro-1-ethyl-5-nitro-1H-pyridin-2-one

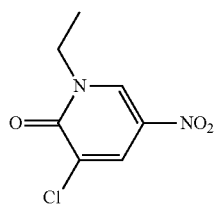

The title compound was prepared in analogy to the procedure described in step 229.5 but using ethyl iodide. The crude material was purified by flash chromatography (hexane/EtOAc, 92:8) to afford the title compound. $t_R$: 3.49 min (HPLC 2); ESI-MS: 203 [M+H]$^+$ (LC-MS 2); R$_f$=0.49 (hexane/EtOAc, 1:1).

Example 233

2-(2-Amino-pyridin-4-yl)-5-(3-chloro-2-fluoro-phenyl)-6-(4-chloro-phenyl)-1-isopropyl-5,6-dihydro-1H-pyrrolo[3,4-d]imidazol-4-one

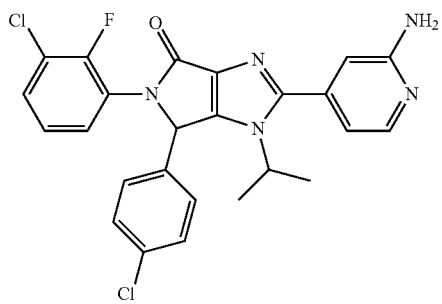 [SMILES: CC(C)n1c(-c2ccnc(N)c2)nc2c1C(c1ccc(Cl)cc1)N(c1cccc(Cl)c1F)C2=O]

The title compound was prepared in analogy to the procedure described for example 1 but using intermediate G and 4-(4,4,5,5-tetramethyl-1,3,2-dioxaborolan-2-yl)pyridine-2-amine. After workup, the residue was triturated in Et$_2$O and hexane to give the title compound. $t_R$: 0.96 min (LC-MS 2); ESI-MS: 496.2/498.2 [M+H]$^+$ (LC-MS 2).

Example 234

5-(3-Chloro-2-fluoro-phenyl)-6-(4-chloro-phenyl)-2-[5-(1-hydroxy-2-methyl-propyl)-2-methoxy-phenyl]-1-isopropyl-5,6-dihydro-1H-pyrrolo[3,4-d]imidazol-4-one

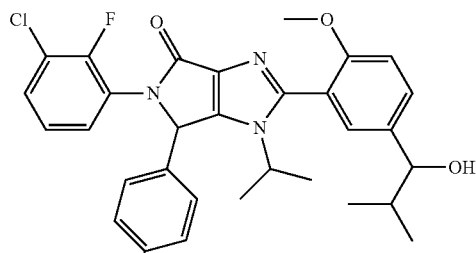

To a solution of the product from step 234.1 (90 mg, 0.17 mmol) in THF (3 mL) at 0° C. was added isopropylmagnesium bromide 1M (1.1 mL, 1.1 mmol) and the mixture was stirred at 0° C. for 1.5 h. The reaction mixture was quenched with H$_2$O and extracted with EtOAc. The organic layer was washed with brine, dried (Na$_2$SO$_4$), filtered and concentrated. The crude was purified by flash chromatography (heptane/EtOAc, 100:0→20:80) to afford the title compound. $t_R$: 1.26 min (LC-MS 2); ESI-MS: 582.3/584.3 [M+H]$^+$ (LC-MS 2).

Step 234.1: 3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-benzaldehyde

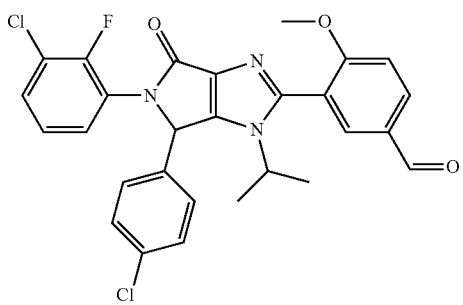 [SMILES: COc1ccc(C=O)cc1-c1nc2c(n1C(C)C)C(c1ccc(Cl)cc1)N(c1cccc(Cl)c1F)C2=O]

The title compound was prepared in analogy to the procedure described for example 1 using intermediate G and 5-formyl-2-methoxyphenylboronic acid. The crude was purified by flash chromatography (CH$_2$Cl$_2$/MeOH, 100:0→90:10) then was purified by MPLC (Column: xBridge C18, 30×100 mm, Flow: 30 mL/min. 5-60% B in 4 min; A=0.1% TFA in water, B=0.1% TFA in CH$_3$CN) to afford the title compound. t$_R$: 1.17 min (LC-MS 2); ESI-MS: 538.3/540.3 [M+H]$^+$ (LC-MS 2).

Example 235

5-(3-Chloro-2-fluoro-phenyl)-6-(4-chloro-phenyl)-2-[5-(1-hydroxy-ethyl)-2-methoxy-phenyl]-1-isopropyl-5,6-dihydro-1H-pyrrolo[3,4-d]imidazol-4-one

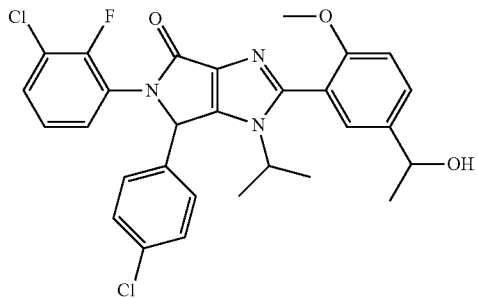 [SMILES: COc1ccc(C(C)O)cc1-c1nc2c(n1C(C)C)C(c1ccc(Cl)cc1)N(c1cccc(Cl)c1F)C2=O]

The title compound was prepared in analogy to the procedure described for example 234 using methylmagnesium bromide. After extraction, the residue was purified by MPLC (Column: xBridge C18, 30×100 mm, Flow: 30 mL/min. 5-60% B in 4 min to 100% B in 3 min; A=0.1% TFA in water, B=0.1% TFA in CH$_3$CN) to afford the title compound. t$_R$: 1.16 min (LC-MS 2); ESI-MS: 554.3/556.3 [M+H]$^+$ (LC-MS 2).

Example 236

5-(3-Chloro-2-fluoro-phenyl)-6-(4-chloro-phenyl)-1-isopropyl-2-(4-methoxy-pyridin-3-yl)-5,6-dihydro-1H-pyrrolo[3,4-d]imidazol-4-one

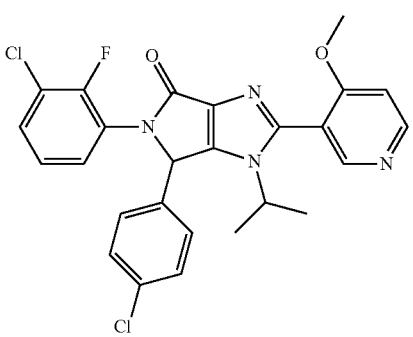 [SMILES: COc1ccncc1-c1nc2c(n1C(C)C)C(c1ccc(Cl)cc1)N(c1cccc(Cl)c1F)C2=O]

The title compound was prepared in analogy to the procedure described for example 1 using intermediate G and 2-methoxy-5-pyridineboronic acid. The product was purified by preparative HPLC (Waters Sun Fire C18, 30×100 mm, 5 μm; 0.1% TFA-water/acetonitrile; gradient acetonitrile 40-80% in 16 min) to give the title compound. t$_R$: 1.20 min (LC-MS 2); ESI-MS: 511.3 [M+H]$^+$ (LC-MS 2).

Example 237

5-(5-(3-chloro-2-fluorophenyl)-6-(4-chlorophenyl)-1-isopropyl-4-oxo-1,4,5,6-tetrahydropyrrolo[3,4-d]imidazol-2-yl)-6-methoxy-N,N-dimethylpyridazine-3-carboxamide

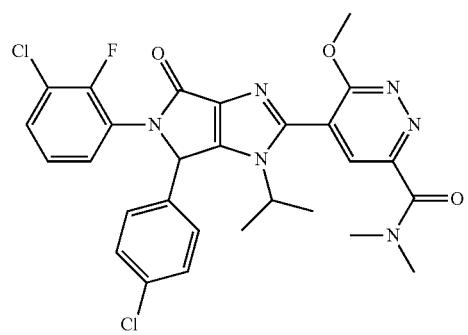 [SMILES: COc1nnc(C(=O)N(C)C)cc1-c1nc2c(n1C(C)C)C(c1ccc(Cl)cc1)N(c1cccc(Cl)c1F)C2=O]

The title compound was prepared in analogy to the procedure described for example 1 using intermediate G and the product from step 237.1. The reaction was performed at 90° C. After extraction, the product was purified by preparative MPLC (Waters Sun Fire C18, 30×100 mm, 5 pm; 0.1% TFA-water/acetonitrile; gradient acetonitrile 40-80% in 16 min) to give the title compound. t$_R$: 1.10 min (LC-MS 2); ESI-MS: 583.1/585.1 [M+H]$^+$ (LC-MS 2).

Step 237.1: (6-(dimethylcarbamoyl)-3-methoxypyridazin-4-yl)zinc

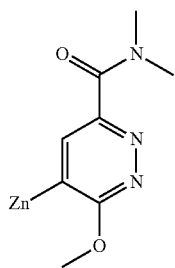

The title compound was prepared in analogy to the procedure described for step 96.2 using the product from step 237.2.

Step 237.2: 6-methoxy-N,N-dimethylpyridazine-3-carboxamide

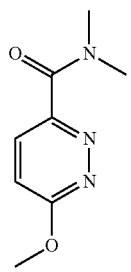

To a solution of 6-methoxypyridazine-3-carboxalic acid (1.56 g, 10.12 mmol) in THF (21 mL) at 5° C. was added 1-chloro-N,N,2-trimethyl-1-propenylamine (1.87 mL, 14.17 mmol) and the mixture was stirred at rt for 1 h. dimethyl amine 2M in THF (20.2 mL, 40.5 mmol) was added and the mixture was stirred at rt for 2 h. The reaction mixture was diluted with EtOAc and extracted with H$_2$O. The organic layers were dried (Na$_2$SO$_4$), filtered and concentrated to afford the title compound. t$_R$: 0.46 min (LC-MS 2); ESI-MS: 182.1 [M+H]$^+$ (LC-MS 2).

Example 238

2-(4-(5-(5-chloro-1-methyl-2-oxo-1,2-dihydropyridin-3-yl)-6-(4-chloro-2-methylphenyl)-1-isopropyl-4-oxo-1,4,5,6-tetrahydropyrrolo[3,4-d]imidazol-2-yl)-5-methoxypyridin-2-yl)acetonitrile

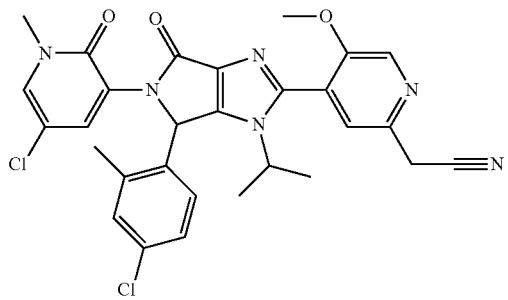 [SMILES: COc1cnc(CC#N)cc1-c1nc2c(n1C(C)C)C(c1ccc(Cl)cc1C)N(c1cc(Cl)cn(C)c1=O)C2=O]

The title compound was obtained in analogy to the procedure described for example 29 but using the products from steps 238.1 and 238.4. The reaction mixture was diluted in EtOAc and extracted with a saturated NaHCO$_3$ solution. The organic layer was washed with brine, dried (Na$_2$SO$_4$), filtered and concentrated. The product was purified by flash chromatography (CH$_2$Cl$_2$/MeOH, 100:0→40:60). t$_R$: 1.00 min (LC-MS 2); ESI-MS: 577.1/579.1 [M+H]$^+$ (LC-MS 2).

Step 238.1: 2-bromo-5-(5-chloro-1-methyl-2-oxo-1,2-dihydropyridin-3-yl)-6-(4-chloro-2-methylphenyl)-1-isopropyl-5,6-dihydropyrrolo[3,4-d]imidazol-4(1H)-one

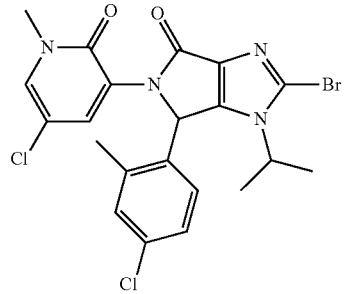 [SMILES: Cc1cc(Cl)ccc1C1c2c(nc(Br)n2C(C)C)C(=O)N1c1cc(Cl)cn(C)c1=O]

The title compound was obtained in analogy to the procedure described for step 91.1 but using the product from step 238.2. The reaction mixture was extracted with a saturated NaHCO$_3$ solution. The organic layer was washed with brine, dried (Na$_2$SO$_4$), filtered and concentrated. The product was used without further purification. t$_R$: 1.06 min (LC-MS 2); ESI-MS: 509.0/511.0/513.0 [M+H]$^+$ (LC-MS 2).

Step 238.2: 2-Bromo-5-[(5-chloro-1-methyl-2-oxo-1,2-dihydro-pyridin-3-ylamino)-(4-chloro-2-methylphenyl)-methyl]-1-isopropyl-1H-imidazole-4-carboxylic acid

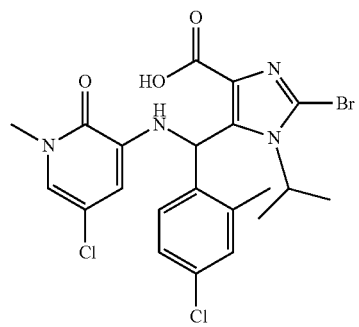 [SMILES: Cc1cc(Cl)ccc1C(Nc1cc(Cl)cn(C)c1=O)c1c(C(=O)O)nc(Br)n1C(C)C]

The title compound was obtained in analogy to the procedure described for step 227.1 but using the product from step 238.3. The reaction was performed at rt. t$_R$: 1.06 min (LC-MS 2); ESI-MS: 527.0/529.0 [M+H]$^+$ (LC-MS 2).

Step 238.3: 2-Bromo-5-[(5-chloro-1-methyl-2-oxo-1,2-dihydro-pyridin-3-ylamino)-(4-chloro-2-methylphenyl)-methyl]-1-isopropyl-1H-imidazole-4-carboxylic acid ethyl ester

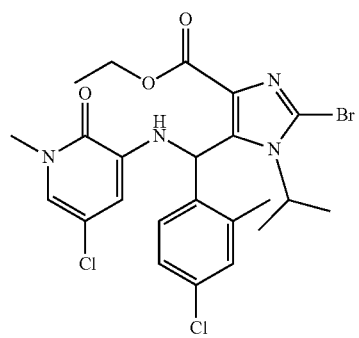 [SMILES: CCOC(=O)c1nc(Br)n(C(C)C)c1C(Nc1cc(Cl)cn(C)c1=O)c1ccc(Cl)cc1C]

The title compound was obtained in analogy to the procedure described for step E2 but using the product from step 100.4 and intermediate C. The reaction mixture was extracted with H₂O. The organic layers were washed with a saturated NaHCO₃ solution, dried (Na₂SO₄), filtered and concentrated. The residue was purified by flash chromatography (heptane/EtOAc, 1:1→0:100). $t_R$: 1.26 min (LC-MS 2); ESI-MS: 555.0/557.0/559.0 [M+H]⁺ (LC-MS 2).

Step 238.4: 2-(5-methoxy-4-(4,4,5,5-tetramethyl-1,3,2-dioxaborolan-2-yl)pyridin-2-yl)acetonitrile

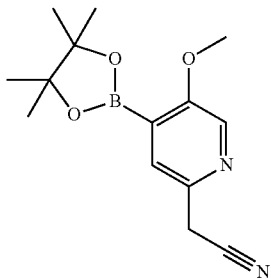 [SMILES: COc1cnc(CC#N)cc1B1OC(C)(C)C(C)(C)O1]

The title compound was obtained in analogy to the procedure described for intermediate S using 2-(4-chloro-5-methoxypyridin-2-yl)acetonitrile. The reaction was performed at 90° C. The reaction mixture was diluted with toluene and filtered over Hyflo to afford the title compound.

Example 239

4-(5-(3-chloro-2-fluorophenyl)-2-(2-(cyanomethyl)-5-methoxypyridin-4-yl)-3-isopropyl-6-oxo-3,4,5,6-tetrahydropyrrolo[3,4-d]imidazol-4-yl)-3-methylbenzonitrile

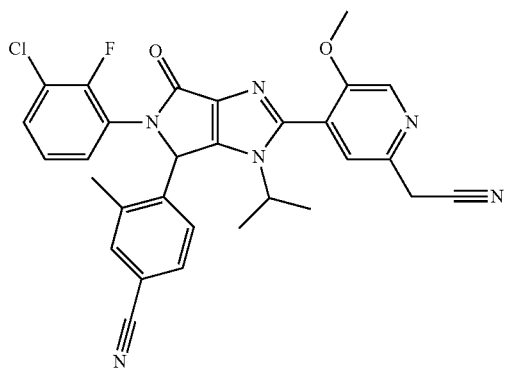 [SMILES: COc1cnc(CC#N)cc1-c1nc2c(n1C(C)C)C(c1ccc(C#N)cc1C)N(c1cccc(Cl)c1F)C2=O]

The title compound was obtained in analogy to the procedure described for step 97.1 but using the products from steps 239.1 and 238.4. The residue was purified by flash chromatography (heptane/CH₂Cl₂/MeOH, 90:9.5:0.5→15:81:4).

The residue was purified by preparative HPLC (Waters Sun Fire C18, 30×100 mm, 5 μm; 0.1% TFA-water/acetonitrile; gradient acetonitrile 5-100% in 20 min). The residue was purified by flash chromatography (CH₂Cl₂/MeOH, 100:0→90:10) to give the title compound. $t_R$: 1.01 min (LC-MS 2); ESI-MS: 555.2/557.1 [M+H]⁺ (LC-MS 2).

Step 239.1: 4-(2-bromo-5-(3-chloro-2-fluorophenyl)-3-isopropyl-6-oxo-3,4,5,6-tetrahydropyrrolo[3,4-d]imidazol-4-yl)-3-methylbenzonitrile

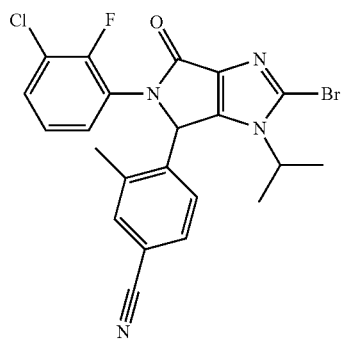 [SMILES: Cc1cc(C#N)ccc1C1c2c(nc(Br)n2C(C)C)C(=O)N1c1cccc(Cl)c1F]

The title compound was obtained in analogy to the procedure described for step 93.2 but using the product from step 239.2. After completion, the reaction mixture was extracted with a saturated NaHCO₃ solution. The organic layers were washed with water then brine, dried (Na₂SO₄), filtered and concentrated. The residue was triturated in hexane to afford the title compound. $t_R$: 1.06 min (LC-MS 2); ESI-MS: 487.0/489.0 [M+H]⁺ (LC-MS 2).

Step 239.2: 2-bromo-5-((3-chloro-2-fluorophenylamino)(4-cyano-2-methylphenyl)methyl)-1-isopropyl-1H-imidazole-4-carboxylic acid

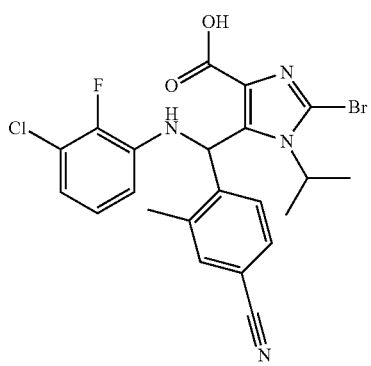 [SMILES: Cc1cc(C#N)ccc1C(Nc1cccc(Cl)c1F)c1c(C(=O)O)nc(Br)n1C(C)C]

The title compound was obtained in analogy to the procedure described for step 93.2 but using the product from step 239.3. $t_R$: 1.13 min (LC-MS 2); ESI-MS: 505.0/507.0 [M+H]⁺ (LC-MS 2).

Step 239.3: ethyl 2-bromo-5-((3-chloro-2-fluorophenylamino)(4-cyano-2-methylphenyl)methyl)-1-isopropyl-1H-imidazole-4-carboxylate

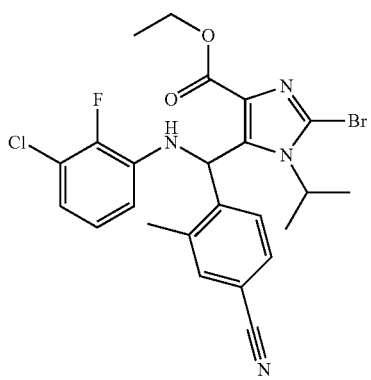 [SMILES: CCOC(=O)c1nc(Br)n(C(C)C)c1C(Nc1cccc(Cl)c1F)c1ccc(C#N)cc1C]

The title compound was obtained in analogy to the procedure described for step E2 but using the product from step 182.4 and 3-chloro-2-fluoroaniline. After extraction, the residue was purified by flash chromatography (heptane/EtOAc, 90:10→0:100). $t_R$: 1.30 min (LC-MS 2); ESI-MS: 533.0/535.1 [M+H]$^+$ (LC-MS 2).

Example 240

4-(5-(3-chloro-4-fluorophenyl)-2-(2-(cyanomethyl)-5-methoxypyridin-4-yl)-3-isopropyl-6-oxo-3,4,5,6-tetrahydropyrrolo[3,4-d]imidazol-4-yl)benzonitrile

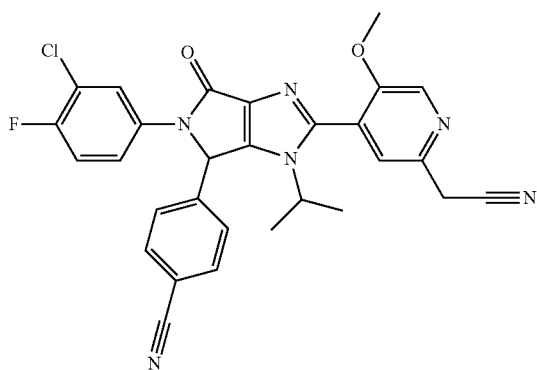 [SMILES: COc1cnc(CC#N)cc1-c1nc2c(n1C(C)C)C(c1ccc(C#N)cc1)N(c1ccc(F)c(Cl)c1)C2=O]

The title compound was obtained in analogy to the procedure described for step 97.1 but using the product from steps 238.4 and intermediate AC. The residue was purified by flash chromatography (heptane/CH$_2$Cl$_2$/MeOH, 90:9.5:0.5→15:81:4). The residue was purified by preparative HPLC (Waters Sunfire C18, 30×100 mm, 5 μm; 0.1% TFA-water/acetonitrile; gradient acetonitrile 5-100% in 20 min). $t_R$: 1.00 min (LC-MS 2); ESI-MS: 541.1/543.2 [M+H]$^+$ (LC-MS 2)

Example 241

{4-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile

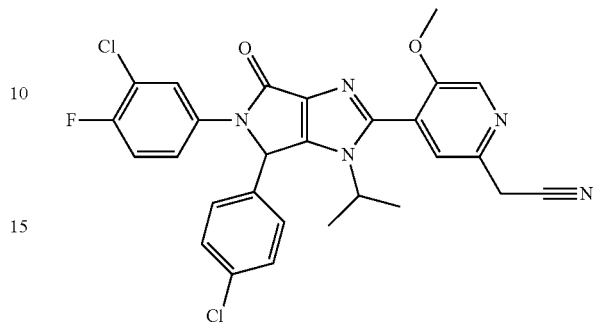

The title compound was obtained in analogy to the procedure described for step 97.1 but using the products from steps 241.1 and 238.4. The reaction was performed at 80° C. After extraction, the residue was purified by flash chromatography (heptane/CH$_2$Cl$_2$/MeOH, 90:9.5:0.5→15:81:4). The residue was purified by preparative HPLC (Waters Sunfire C18, 30×100 mm, 5 μm; 0.1% TFA-water/acetonitrile; gradient acetonitrile 5-100% in 20 min). $t_R$: 1.14 min (LC-MS 2); ESI-MS: 550.2/552.1 [M+H]$^+$ (LC-MS 2); R$_f$=0.21 (CH$_2$Cl$_2$/MeOH, 20:1).

Step 241.1: 2-Bromo-5-(3-chloro-4-fluoro-phenyl)-6-(4-chloro-phenyl)-1-isopropyl-5,6-dihydro-1H-pyrrolo[3,4-d]imidazol-4-one

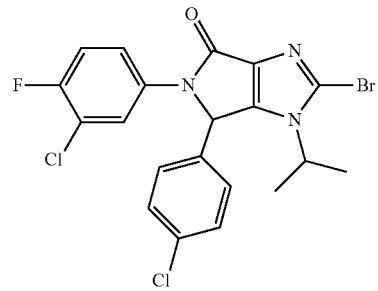 [SMILES: CC(C)n1c(Br)nc2c1C(c1ccc(Cl)cc1)N(c1ccc(F)c(Cl)c1)C2=O]

The title compound was obtained in analogy to the procedure described for example AK but using the product from step 241.2. The residue was purified by flash chromatography (heptane/EtOAc, 2:1). $t_R$: 1.21 min (LC-MS 2); ESI-MS: 482.1/484.1/486.1 [M+H]$^+$ (LC-MS 2)

Step 241.2: 2-Bromo-N-(3-chloro-4-fluorophenyl)-5-((4-chlorophenyl)(hydroxy)methyl)-1-isopropyl-1H-imidazole-4-carboxamide

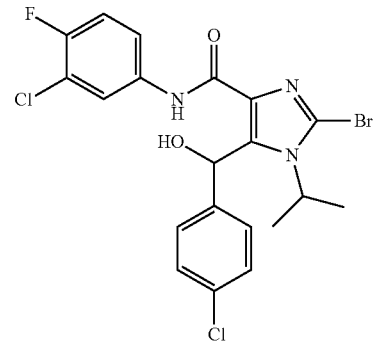 [SMILES: CC(C)n1c(Br)nc(C(=O)Nc2ccc(F)c(Cl)c2)c1C(O)c1ccc(Cl)cc1]

The title compound was obtained in analogy to the procedure described for step AK1 but using intermediate B and 3-chloro-4-fluoroaniline. After completion, the reaction mixture was diluted in EtOAc and extracted with a 1M citric acid solution. The organic layers were washed with a saturated NaHCO₃ and brine, dried (Na₂SO₄), filtered and concentrated. The residue was purified by flash chromatography (CH₂Cl₂). $t_R$: 1.43 min (LC-MS 2); ESI-MS: 500.0 [M+H]⁺ (LC-MS 2)

Example 242

4-[5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-3-methyl-benzonitrile

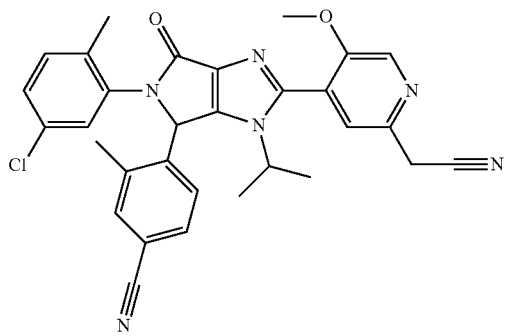 [SMILES: COc1cnc(CC#N)cc1-c1nc2c(n1C(C)C)C(c1ccc(C#N)cc1C)N(c1cc(Cl)ccc1C)C2=O]

The title compound was obtained in analogy to the procedure described for step 97.1 but using the products from steps 186.1 and 238.4. The reaction was performed at 80° C. After extraction, the residue was purified by flash chromatography (CH₂Cl₂/MeOH, 100:0→97:3). The residue was triturated in CH₂Cl₂/TBME to afford the title compound. $t_R$: 1.05 min (LC-MS 2); ESI-MS: 551.2/553.1 [M+H]⁺ (LC-MS 2).

Example 243

6-(4-Chloro-phenyl)-5-(2,6-dimethyl-pyrimidin-4-yl)-1-isopropyl-2-(5-methoxy-1-methyl-2-oxo-1,2-dihydro-pyridin-4-yl)-5,6-dihydro-1H-pyrrolo[3,4-d]imidazol-4-one

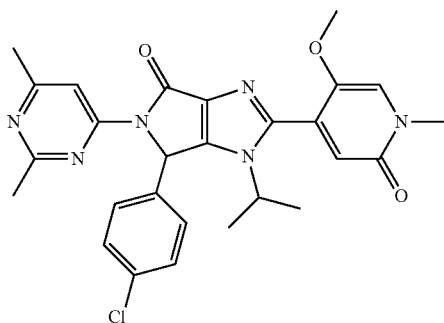 [SMILES: COc1cn(C)c(=O)cc1-c1nc2c(n1C(C)C)C(c1ccc(Cl)cc1)N(c1cc(C)nc(C)n1)C2=O]

The title compound was prepared in analogy to the procedure described for example 1 but using the products from steps 262.1 and 105.1. After extraction, the product was purified by preparative HPLC (Waters Sun Fire C18, 30×100 mm, 5 µm; 0.1% TFA-water/acetonitrile; gradient acetonitrile 20-40% in 16 min). The residue was then purified by SFC chromatography (Column DEAP, 250×30 mm, 5 µm, flow 100 mL/min, grad 10-15% over 6 min) to give the title compound. $t_R$: 0.89 min (LC-MS 2); ESI-MS: 519.2/521.2 [M+H]⁺ (LC-MS 2).

Example 244

5-(3-Chloro-2-fluoro-phenyl)-6-(4-chloro-phenyl)-1-isopropyl-2-(3-methoxy-1-methyl-6-oxo-1,6-dihydro-pyridazin-4-yl)-5,6-dihydro-1H-pyrrolo[3,4-d]imidazol-4-one

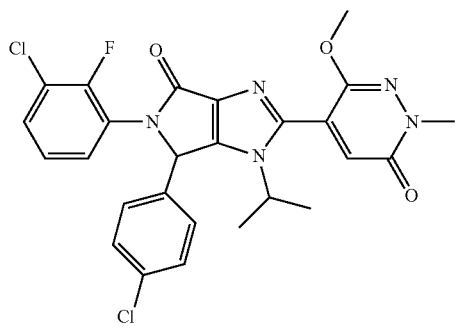 [SMILES: COc1nn(C)c(=O)cc1-c1nc2c(n1C(C)C)C(c1ccc(Cl)cc1)N(c1cccc(Cl)c1F)C2=O]

The title compound was obtained in analogy to the procedure described for example 1 but using intermediate G and the product from step 244.1. The reaction was performed at 90° C. for 1.5 h. After a purification by preparative HPLC, the residue was purified by SFC chromatography (Column: Reprosil 70 NH₂, 250×30 mm, 5 µm, flow 100 mL/min, grad 5-50%) to afford the title compound. $t_R$: 1.14 min (LC-MS 2); ESI-MS: 542.1/544.1 [M+H]⁺ (LC-MS 2).

Step 244.1: (3-methoxy-1-methyl-6-oxo-1,6-dihydropyridazin-4-yl)zinc

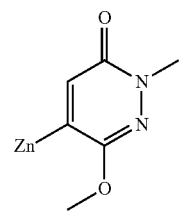

The title compound was prepared in analogy to the procedure described for step 96.2 using the product from step 244.2.

Step 244.2:
6-Methoxy-2-methyl-2H-pyridazin-3-one

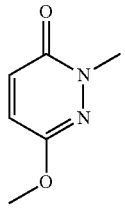

The title compound was obtained in analogy to the procedure described for step 105.2 but using 3-chloro-6-methoxy-pyridazine. The reaction was performed at 50° C. for 2 h. 1M NaOH solution was added and the mixture was stirred at rt for 20 h. The reaction mixture was diluted with $CH_2Cl_2$ and extracted with $H_2O$. The organic layer was dried ($Na_2SO_4$), filtered and concentrated to give the title compound. $t_R$: 0.48 min (LC-MS 2); ESI-MS: 141.1 $[M+H]^+$ (LC-MS 2).

Example 245

5-(5-Chloro-2-methyl-phenyl)-6-(5-chloro-pyridin-2-yl)-2-(2-dimethylamino-4-methoxy-pyrimidin-5-yl)-1-isopropyl-5,6-dihydro-1H-pyrrolo[3,4-d]imidazol-4-one

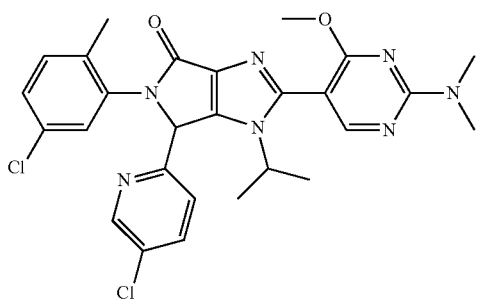 [SMILES: COc1nc(N(C)C)ncc1-c1nc2c(n1C(C)C)C(c1ccc(Cl)cn1)N(c1cc(Cl)ccc1C)C2=O]

The title compound was prepared in analogy to the procedure described for example 29 but using the product from step 245.1 and intermediate W. After extraction, the crude was purified by preparative HPLC. The residue was triturated in diisopropyl ether to afford the title compound. $t_R$: 1.19 min (LC-MS 2); ESI-MS: 552.3 $[M+H]^+$ (LC-MS 2).

Step 245.1: 2-Bromo-5-(5-chloro-2-methyl-phenyl)-6-(5-chloro-pyridin-2-yl)-1-isopropyl-5,6-dihydro-1H-pyrrolo[3,4-d]imidazol-4-one

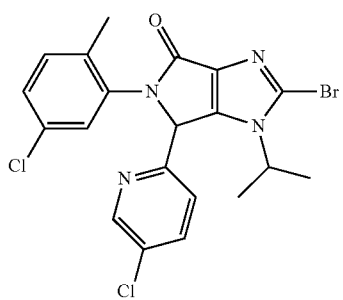 [SMILES: Cc1ccc(Cl)cc1N1C(=O)c2nc(Br)n(C(C)C)c2C1c1ccc(Cl)cn1]

To a solution of the product from step 245.2 (440 mg, 638 mmol) in EtOH (15 mL) was added $Mo(CO)_6$ (253 mg, 958 mmol) and the mixture was stirred at 80° C. for 5 h. The mixture was concentrated then purified by flash chromatography (heptane/EtOAc, 100:0→0:100) to afford the title compound. $t_R$: 1.13 min (LC-MS 2); ESI-MS: 479.0/481.1/483.1 $[M+H]^+$ (LC-MS 2).

Step 245.2: 2-Bromo-5-(5-chloro-2-methyl-phenyl)-6-(5-chloro-1-oxy-pyridin-2-yl)-1-isopropyl-5,6-dihydro-1H-pyrrolo[3,4-d]imidazol-4-one

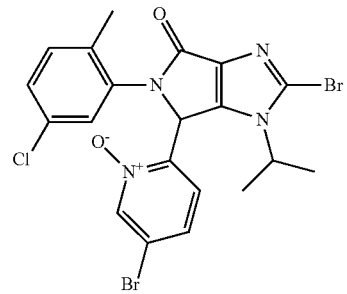 [SMILES: Cc1ccc(Cl)cc1N1C(=O)c2nc(Br)n(C(C)C)c2C1c1ccc(Br)c[n+]1[O-]]

The title compound was prepared in analogy to the procedure described for step 91.1 but using the product from step 245.3. After completion, the reaction mixture was quenched with MeOH and concentrated. The residue was purified by flash chromatography (heptane/EtOAc, 100:0→0:100) to afford the title compound. $t_R$: 0.96 min (LC-MS 2); ESI-MS: 494.9/497.0/499.0 $[M+H]^+$ (LC-MS 2).

Step 245.3: 2-Bromo-5-[(5-chloro-2-methyl-phenylamino)-(5-chloro-1-oxy-pyridin-2-yl)-methyl]-1-isopropyl-1H-imidazole-4-carboxylic acid

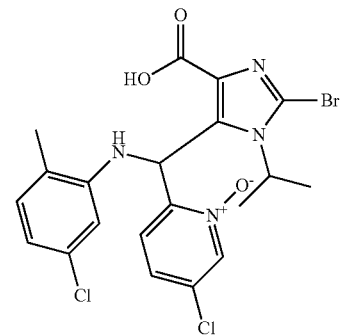 [SMILES: Cc1ccc(Cl)cc1NC(c1c(C(=O)O)nc(Br)n1C(C)C)c1ccc(Cl)c[n+]1[O-]]

The title compound was prepared in analogy to the procedure described for step E1 but using the product from step 245.4. After pH was adjusted at 5, the mixture was concentrated and the resulting suspension was filtered. The resulting solid was dried to afford the title compound. $t_R$: 1.04 min (LC-MS 2); ESI-MS: 513.0/515.0/517.2 $[M+H]^+$ (LC-MS 2).

Step 245.4: 2-Bromo-5-[(5-chloro-2-methyl-phenylamino)-(5-chloro-1-oxy-pyridin-2-yl)-methyl]-1-isopropyl-1H-imidazole-4-carboxylic acid ethyl ester

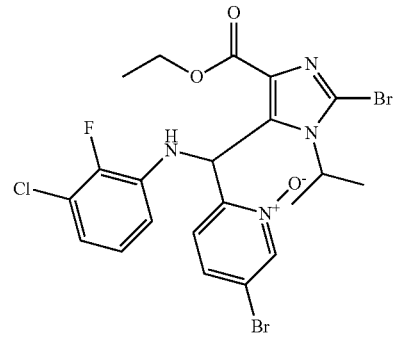 [SMILES: CCOC(=O)c1nc(Br)n(C(C)C)c1C(Nc1cccc(Cl)c1F)c1ccc(Br)c[n+]1[O-]]

The title compound was prepared in analogy to the procedure described for step E2 but using the product from step 245.5 and 5-chloro-2-methylaniline. The reaction mixture was extracted with a saturated aqueous NaHCO$_3$ solution. The organic layer was dried (Na$_2$SO$_4$), filtered and concentrated. The product was purified by flash chromatography (heptane/EtOAc, 100:0→0:100) to provide the title compound. t$_R$: 1.24 min (LC-MS 2); ESI-MS: 541.0/543.1/545.0 [M+H]$^+$ (LC-MS 2).

Step 245.5: 2-Bromo-5-[(5-chloro-1-oxy-pyridin-2-yl)-hydroxy-methyl]-1-isopropyl-1H-imidazole-4-carboxylic acid ethyl ester

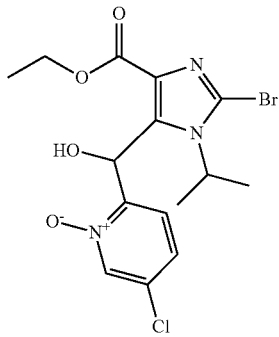 [SMILES: CCOC(=O)c1nc(Br)n(C(C)C)c1C(O)c1ccc(Cl)c[n+]1[O-]]

To a solution of the product from step 245.6 (12.7 g, 31.5 mmol) in CHCl$_3$ at 0° C. was added m-CPBA (17.7 g, 103 mmol) and the mixture was stirred at rt for 5 h. The reaction mixture was diluted with CH$_2$Cl$_2$ and extraction with a saturated Na$_2$CO$_3$ solution. The organic layer was dried (Na$_2$SO$_4$), filtered and concentrated. The product was used without further purification for the next step. t$_R$: 0.78 min (LC-MS 2); ESI-MS: 418.0/420.0 [M+H]$^+$ (LC-MS 2).

Step 245.6: 2-Bromo-5-[(5-chloro-pyridin-2-yl)-hydroxy-methyl]-1-isopropyl-1H-imidazole-4-carboxylic acid ethyl ester

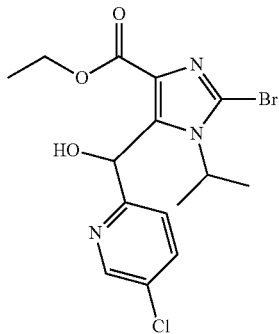 [SMILES: CCOC(=O)c1nc(Br)n(C(C)C)c1C(O)c1ccc(Cl)cn1]

The title compound was obtained in analogy to the procedure described for intermediate B but using 5-chloro-2-formylpyridine. After completion, the reaction mixture was diluted with EtOAc and extracted with a saturated NaHCO$_3$ solution. The organic layer was dried (Na$_2$SO$_4$), filtered and concentrated. The residue was purified by flas chromatography (heptane/EtOAc, 100:0→0:100) to give the title compound. t$_R$: 1.00 min (LC-MS 2); ESI-MS: 402.0/404.0 [M+H]$^+$ (LC-MS 2).

Example 246

4-[5-(3-Chloro-2-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-2-fluoro-benzonitrile

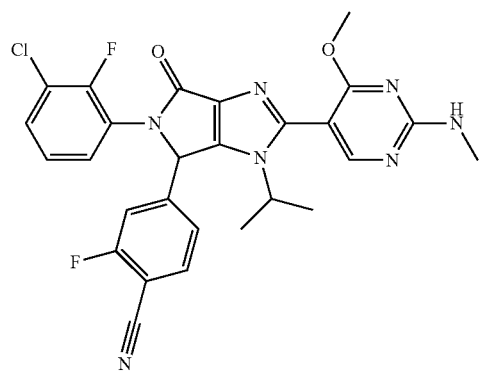 [SMILES: CNc1ncc(-c2nc3c(n2C(C)C)C(c2ccc(C#N)c(F)c2)N(c2cccc(Cl)c2F)C3=O)c(OC)n1]

The title compound was obtained in analogy to the procedure described for step 91.1 but using the product from step 246.1 and intermediate Z. The reaction was performed at 100° C. The residue was purified by preparative HPLC (Waters Sun Fire C18, 30×100 mm, 5 µm; 0.1% TFA-water/acetonitrile; gradient acetonitrile 15-65% in 20 min) and then by preparative TLC (EtOAc/MeOH, 85:15) to afford the title compound. t$_R$: 1.03 (LC-MS 2); ESI-MS: 550.1/552.1 [M+H]$^+$ (LC-MS 2); R$_f$=0.32 (EtOAc/MeOH, 85:15).

Step 246.1: 4-[2-Bromo-5-(3-chloro-2-fluoro-phenyl)-3-isopropyl-6-oxo-3,4,5,6-tetrahydro-pyrrolo[3,4-d]imidazol-4-yl]-2-fluoro-benzonitrile

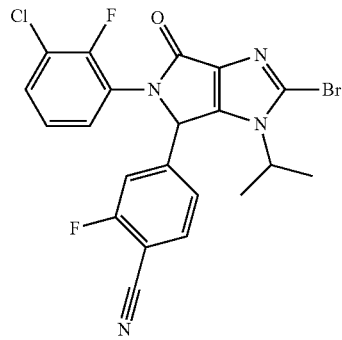 [SMILES: CC(C)n1c(Br)nc2c1C(c1ccc(C#N)c(F)c1)N(c1cccc(Cl)c1F)C2=O]

The title compound was obtained in analogy to the procedure described for step 93.1 but using the product from step 246.2. After extraction, the residue was triturated in MeOH and filtered to afford the title compound. The rest of the mother liquor was purified by preparative HPLC (Waters Sun Fire C18, 30×100 mm, 5 µm; 0.1% TFA-water/acetonitrile;

gradient acetonitrile 30-80% in 20 min to afford the title compound. $t_R$: 1.07 (LC-MS 2); ESI-MS: 491.1/493.1 [M+H]$^+$ (LC-MS 2).

Step 246.2: 2-Bromo-5-[(3-chloro-2-fluoro-phenylamino)-(4-cyano-3-fluoro-phenyl)-methyl]-1-isopropyl-1H-imidazole-4-carboxylic acid

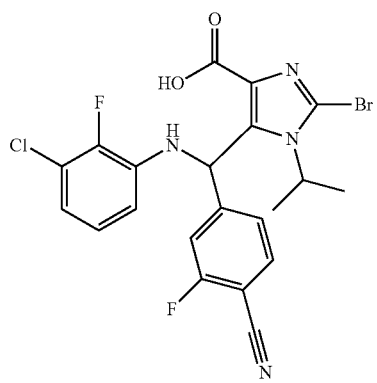 [SMILES: CC(C)n1c(Br)nc(C(=O)O)c1C(Nc1cccc(Cl)c1F)c1ccc(C#N)c(F)c1]

The title compound was obtained in analogy to the procedure described for step E1 but using the product from step 246.3. $t_R$: 1.13 min (LC-MS 2); ESI-MS: 509.3/511.1/513.2 [M+H]$^+$ (LC-MS 2).

Step 246.3: 2-Bromo-5-[(3-chloro-2-fluoro-phenylamino)-(4-cyano-3-fluoro-phenyl)-methyl]-1-isopropyl-1H-imidazole-4-carboxylic acid ethyl ester

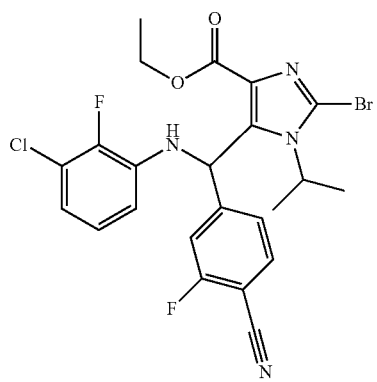 [SMILES: CCOC(=O)c1nc(Br)n(C(C)C)c1C(Nc1cccc(Cl)c1F)c1ccc(C#N)c(F)c1]

The title compound was prepared in analogy to the procedure described for step E2 but using the product from step 167.4 and 3-chloro-2-fluoroaniline. The mixture was extracted with a saturated aqueous NaHCO$_3$ solution. The organic layers were dried (Na$_2$SO$_4$), filtered and concentrated. The product was purified by flash chromatography (hexane/EtOAc, 100:0→0:100). $t_R$: 1.31 min (LC-MS 2); ESI-MS: 537.2/539.2/541.2 [M+H]$^+$ (LC-MS 2).

Example 247

4-[5-(3-Chloro-2-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile

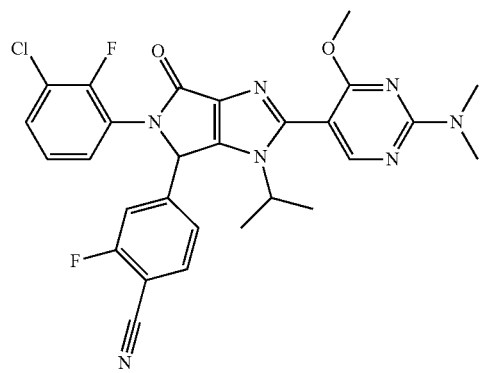

The title compound was obtained in analogy to the procedure described for step 91.1 but using the product from step 246.1 and intermediate W. The reaction was performed at 100° C. After extraction, the residue was purified by preparative HPLC (Waters Sun Fire C18, 30×100 mm, 5 pm; 0.1% TFA-water/acetonitrile; gradient acetonitrile 38-60% in 20 min) and then triturated in diisopropylether to afford the title compound. $t_R$: 1.13 (LC-MS 2); ESI-MS: 564.1 [M+H]$^+$ (LC-MS 2).

Example 248

4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile

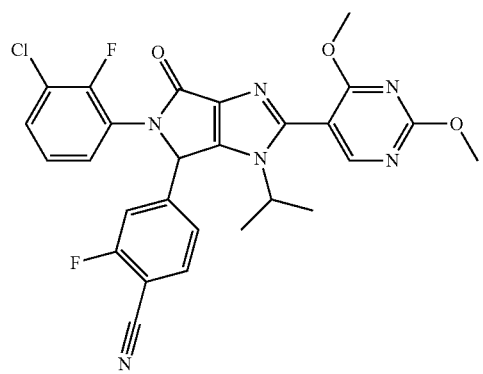 [SMILES: COc1ncc(-c2nc3c(n2C(C)C)C(c2ccc(C#N)c(F)c2)N(c2cccc(Cl)c2F)C3=O)c(OC)n1]

The title compound was obtained in analogy to the procedure described for step 91.1 but using the product from step 246.1 and 2,4-dimethoxypyrimidin-5-ylboronic acid. The reaction was performed at 100° C. After extraction, the residue was purified by preparative HPLC (Waters Sun Fire C18, 30×100 mm, 5 μm; 0.1% TFA-water/acetonitrile; gradient acetonitrile 40-65% in 20 min) and then purified by preparative TLC (EtOAc/EtOH, 85:15) to afford the title compound.

$t_R$: 1.06 (LC-MS 2); ESI-MS: 551.1/553.1 [M+H]$^+$ (LC-MS 2); $R_f$=0.41 (EtOAc/EtOH, 85:15).

Example 249

4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carboxylic acid dimethylamide

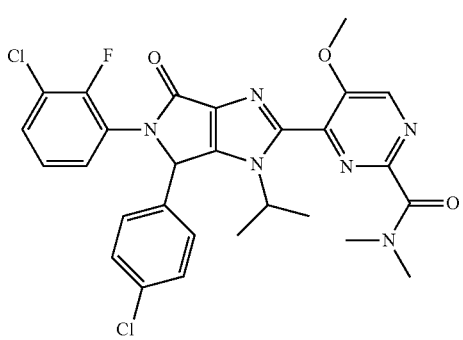 [SMILES: COc1cnc(C(=O)N(C)C)nc1-c1nc2c(n1C(C)C)C(c1ccc(Cl)cc1)N(c1cccc(Cl)c1F)C2=O]

The title compound was obtained in analogy to the procedure described for step 96.1 but using intermediate G and the product from step and the product from step 249.1. The reaction was performed at 90° C. After extraction, the residue was purified by preparative HPLC (Waters Sun Fire C18, 30×100 mm, 5 μm; 0.1% TFA-water/acetonitrile; gradient acetonitrile 40-60% in 16 min) to afford the title compound. $t_R$: 1.06 (LC-MS 2); ESI-MS: 583.1/585.1 [M+H]$^+$ (LC-MS 2).

Step 249.1: (2-(dimethylcarbamoyl)-5-methoxypyrimidin-4-yl)zinc

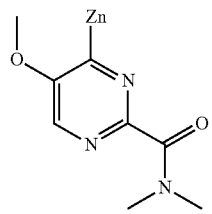

The title compound was obtained in analogy to the procedure described for step 96.2 but using the product from step 249.2. The reaction was stirred at rt for 16 h.

Step 249.2: 5-Methoxy-pyrimidine-2-carboxylic acid dimethylamide

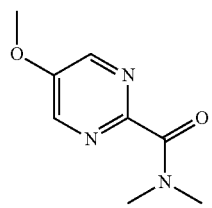

The title compound was obtained in analogy to the procedure described for step 237.2 but using 5-methoxy-2-pyrimidine carboxylic acid. After completion, the reaction mixture was diluted with EtOAc and extracted with H$_2$O, NaCl was added to the aqueous layer and extracted with EtOAc. The organic layers were dried (Na$_2$SO$_4$), filtered and concentrated to afford the title compound. $t_R$: 0.44 min (LC-MS 2); ESI-MS: 182.1 [M+H]$^+$ (LC-MS 2).

Example 250

{4-[(S)-5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile

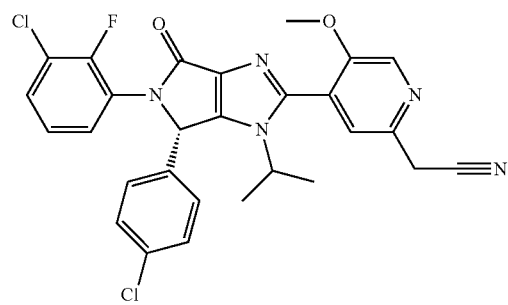 [SMILES: COc1cnc(CC#N)cc1-c1nc2c(n1C(C)C)[C@H](c1ccc(Cl)cc1)N(c1cccc(Cl)c1F)C2=O]

The title compound was obtained after preparative chiral SFC separation (Column: Chiralpak AD-H, 30×250 mm, Flow 140 g/min, CO$_2$/EtOH 75:25, Detection: UV 210 nm, cycle time 12 min) of the racemic product of example 136. $t_R$: 4.25 min (Column: Chiralpak AD-H, 4.6×250 mm, Flow 3 mL/min. CO$_2$/EtOH 7:3, Detection: UV 210 nm). $t_R$: 1.12 min (LC-MS 2); ESI-MS: 550.1/552.1 [M+H]$^+$ (LC-MS 2); $^1$H-NMR (DMSO-d$_6$, 400 MHz) ppm 8.57 (s, 1H), 7.51 (s, 1H), 7.49-7.20 (m, 7H), 6.58 (s, 1H), 4.22 (s, 2H), 4.14-4.06 (m, 1H), 3.93 (s, 3H), 1.34 (d, 3H), 0.50 (d, 3H).

Example 251

{4-[(R)-5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile

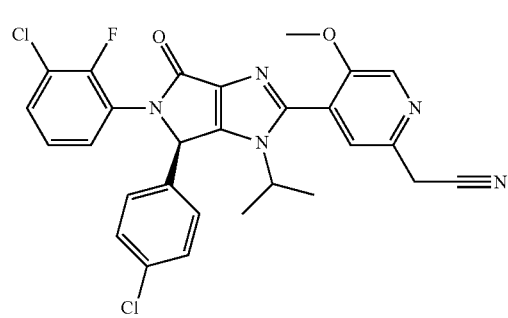 [SMILES: COc1cnc(CC#N)cc1-c1nc2c(n1C(C)C)[C@@H](c1ccc(Cl)cc1)N(c1cccc(Cl)c1F)C2=O]

The title compound was obtained after preparative chiral SFC separation (Column: Chiralpak AD-H, 30×250 mm, Flow 140 g/min, CO$_2$/EtOH 75:25, Detection: UV 210 nm, cycle time 12 min) of the racemic product of example 136. $t_R$:

5.27 min (Column: Chiralpak AD-H, 4.6×250 mm, Flow 3 mL/min. CO$_2$/EtOH 7:3, Detection: UV 210 nm). $t_R$: 1.12 min (LC-MS 2); ESI-MS: 550.1/552.1 [M+H]$^+$ (LC-MS 2); $^1$H-NMR (DMSO-d$_6$, 400 MHz) ppm 8.57 (s, 1H), 7.51 (s, 1H), 7.49-7.20 (m, 7H), 6.58 (s, 1H), 4.22 (s, 2H), 4.14-4.06 (m, 1H), 3.93 (s, 3H), 1.34 (d, 3H), 0.50 (d, 3H).

Example 252

4-[(S)-5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile

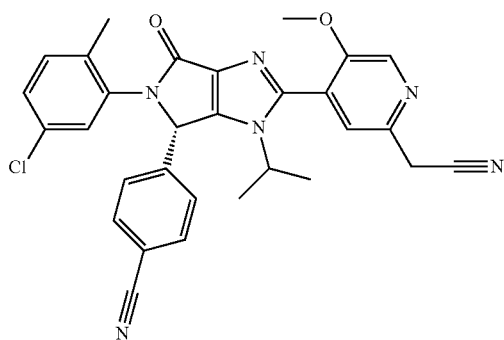 [SMILES: COc1cnc(CC#N)cc1-c1nc2c(n1C(C)C)[C@H](c1ccc(C#N)cc1)N(c1cc(Cl)ccc1C)C2=O]

The title compound was obtained after preparative chiral HPLC separation (Column: IA 20 μm, 30×500 mm, Flow 60 mL/min, heptane/EtOH/MeOH 66:17:17, Detection: UV 210 nm) of the racemic product of example 135. $t_R$: 13.01 min (Column: Chiralpak AS-H, 4.6×250 mm, Flow 1 mL/min. heptane/EtOH/MeOH 70:15:15, Detection: UV 220 nm). $t_R$: 1.01 min (LC-MS 2). ESI-MS: 537.2/538.2 [M+H]$^+$ (LC-MS 2); $^1$H-NMR (DMSO-d$_6$, 400 MHz) δ ppm 8.58 (s, 1H), 7.88-7.76 (m, 3H), 7.57-7.49 (m, 3H), 7.21-7.12 (m, 2H), 6.74 (s, 1H), 4.22 (s, 2H), 4.14-4.06 (m, 1H), 3.94 (s, 3H), 1.93 (s, 3H), 1.33 (d, 3H), 0.55-0.43 (m, 3H).

Example 253

4-[(R)-5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile

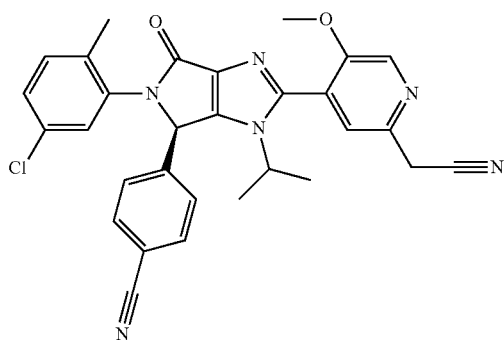 [SMILES: COc1cnc(CC#N)cc1-c1nc2c(n1C(C)C)[C@@H](c1ccc(C#N)cc1)N(c1cc(Cl)ccc1C)C2=O]

The title compound was obtained after preparative chiral HPLC separation (Column: IA 20 μm, 30×500 mm, Flow 60 mL/min, heptane/EtOH/MeOH 66:17:17, Detection: UV 210 nm) of the racemic product of example 135. $t_R$: 25.19 min (Column: Chiralpak AS-H, 4.6×250 mm, Flow 1 mL/min. heptane/EtOH/MeOH 70:15:15, Detection: UV 220 nm). $t_R$: 1.01 min (LC-MS 2). ESI-MS: 537.2/538.2 [M+H]$^+$ (LC-MS 2); $^1$H-NMR (DMSO-d$_6$, 400 MHz) δ ppm 8.58 (s, 1H), 7.88-7.76 (m, 3H), 7.57-7.49 (m, 3H), 7.21-7.12 (m, 2H), 6.74 (s, 1H), 4.22 (s, 2H), 4.14-4.06 (m, 1H), 3.94 (s, 3H), 1.93 (s, 3H), 1.33 (d, 3H), 0.55-0.43 (m, 3H).

Example 254

4-[(S)-5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile

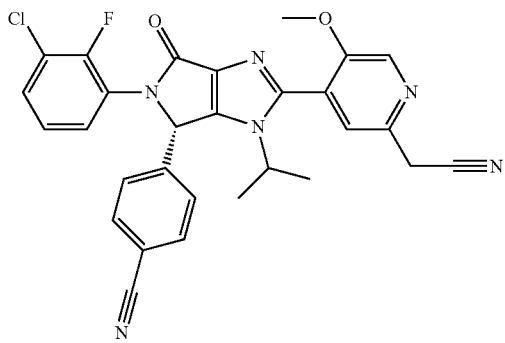 [SMILES: COc1cnc(CC#N)cc1-c1nc2c(n1C(C)C)[C@H](c1ccc(C#N)cc1)N(c1cccc(Cl)c1F)C2=O]

The title compound was obtained after preparative chiral HPLC separation (Column: Chiralpak AS-H 5 μm, 20×250 mm, Flow 15 mL/min, heptane/EtOH/MeOH 80:10:10, Detection: UV 210/254 nm) of the racemic product of example 134. $t_R$: 17.82 min (Column: Chiralpak AS-H, 4.6×250 mm, Flow 1 mL/min. heptane/EtOH/MeOH 80:10:10, Detection: UV 210 nm). $t_R$: 0.98 min (LC-MS 2); ESI-MS: 541.1/543.2 [M+H]$^+$ (LC-MS 2); $^1$H-NMR (DMSO-d$_6$, 400 MHz) δ ppm 8.35 (s, 1H), 7.93 (s, 1H), 7.50-7.40 (m, 4H), 7.37-7.31 (m, 2H), 7.21 (t, 1H), 6.58 (s, 1H), 4.10 (s, 2H), 4.08 (s, 1H), 3.89 (s, 3H), 1.35 (d, 3H), 0.52 (d, 3H).

Example 255

4-[(R)-5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile

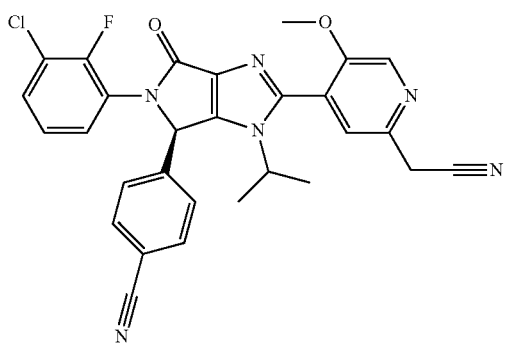 [SMILES: COc1cnc(CC#N)cc1-c1nc2c(n1C(C)C)[C@@H](c1ccc(C#N)cc1)N(c1cccc(Cl)c1F)C2=O]

The title compound was obtained after preparative chiral HPLC separation (Column: Chiralpak AS-H 5 μm, 20×250 mm, Flow 15 mL/min, heptane/EtOH/MeOH 80:10:10, Detection: UV 210/254 nm) of the racemic product of example 134. $t_R$: 23.77 min (Column: Chiralpak AS-H, 4.6× 250 mm, Flow 1 mL/min. heptane/EtOH/MeOH 80:10:10, Detection: UV 210 nm). $t_R$: 0.98 min (LC-MS 2); ESI-MS: 541.1/543.2 [M+H]$^+$ (LC-MS 2); $^1$H-NMR (DMSO-d$_6$, 400 MHz) δ ppm 8.35 (s, 1H), 7.93 (s, 1H), 7.50-7.40 (m, 4H), 7.37-7.31 (m, 2H), 7.21 (t, 1H), 6.58 (s, 1H), 4.10 (s, 2H), 4.08 (s, 1H), 3.89 (s, 3H), 1.35 (d, 3H), 0.52 (d, 3H).

Example 256

4-[5-(3-Chloro-2-fluoro-phenyl)-2-(2,4-dimethoxy-pyrimidin-5-yl)-3-((R)-2-methoxy-1-methyl-ethyl)-6-oxo-3,4,5,6-tetrahydro-pyrrolo[3,4-d]imidazol-4-yl]-benzonitrile

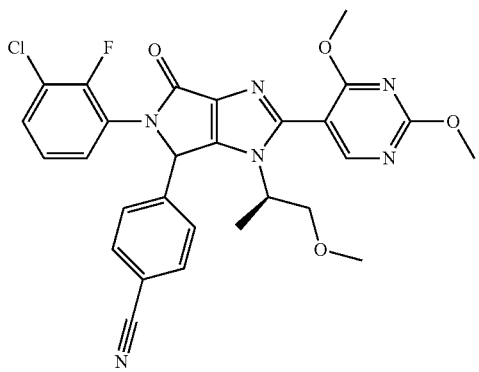 [SMILES: COC[C@@H](C)n1c(-c2cnc(OC)nc2OC)nc2c1C(c1ccc(C#N)cc1)N(c1cccc(Cl)c1F)C2=O]

The title compound was prepared in analogy to the procedure described for step 97.1 but using the product from step 256.1. After extraction, the product was purified by flash chromatography (heptane/EtOAc, 1:1→0:100). $t_R$: 1.00/1.02 min (LC-MS 2); ESI-MS: 563.2/565.1 [M+H]$^+$ (LC-MS 2); R$_f$=0.07 (heptane/EtOAc, 1:4).

Step 256.1: 4-[2-Bromo-5-(3-chloro-2-fluoro-phenyl)-3-((R)-2-methoxy-1-methyl-ethyl)-6-oxo-3,4,5,6-tetrahydro-pyrrolo[3,4-d]imidazol-4-yl]-benzonitrile

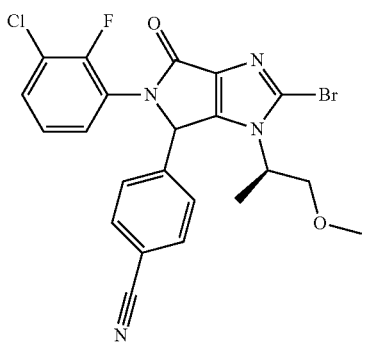 [SMILES: COC[C@@H](C)n1c(Br)nc2c1C(c1ccc(C#N)cc1)N(c1cccc(Cl)c1F)C2=O]

The title compound was prepared in analogy to the procedure described for step 93.1 but using the product from step 256.2. After extraction, the product was purified by flash chromatography (heptane/EtOAc, 80:20→0:100). $t_R$: 1.00/1.03 min (LC-MS 2); ESI-MS: 503.0/505.0 [M+H]$^+$ (LC-MS 2); R$_f$=0.14 (heptane/EtOAc, 1:2).

Step 256.2: 2-Bromo-5-[(3-chloro-2-fluoro-phenylamino)-(4-cyano-phenyl)-methyl]-1-((R)-2-methoxy-1-methyl-ethyl)-1H-imidazole-4-carboxylic acid

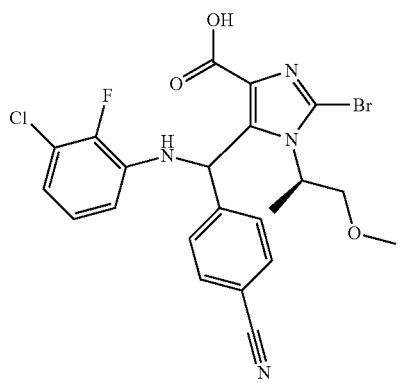 [SMILES: COC[C@@H](C)n1c(Br)nc(C(=O)O)c1C(Nc1cccc(Cl)c1F)c1ccc(C#N)cc1]

The title compound was prepared in analogy to the procedure described for step 93.2 but using the product from step 256.3. The product was used without purification after the extraction. $t_R$: 1.08 min (LC-MS 2); ESI-MS: 519.0/521.0 [M+H]$^+$ (LC-MS 2).

Step 256.3: 2-Bromo-5-[(3-chloro-2-fluoro-phenylamino)-(4-cyano-phenyl)-methyl]-1-((R)-2-methoxy-1-methyl-ethyl)-1H-imidazole-4-carboxylic acid ethyl ester

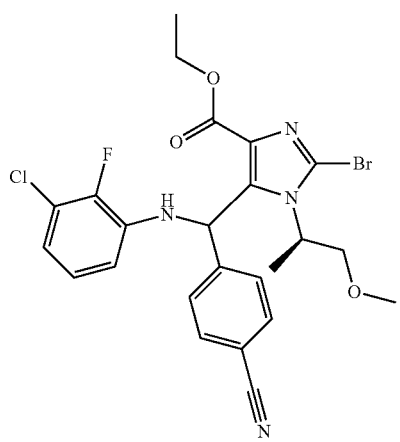 [SMILES: CCOC(=O)c1nc(Br)n([C@H](C)COC)c1C(Nc1cccc(Cl)c1F)c1ccc(C#N)cc1]

The title compound was prepared in analogy to the procedure described for step E2 but using the product from step 256.4 and 3-chloro-2-fluoroaniline. After completion, the reaction mixture was extracted with H$_2$O and washed with a saturated NaHCO$_3$ solution. The organic was dried (Na$_2$SO$_4$), filtered and concentrated. The residue was purified by flash chromatography (heptane/EtOAc, 80:20→52:48). $t_R$: 1.27 min (LC-MS 2); ESI-MS: 549.1/551.0 [M+H]$^+$ (LC-MS 2); R$_f$=0.31 (heptane/EtOAc, 1:1).

Step 256.4: 2-Bromo-5-[(4-cyano-phenyl)-hydroxy-methyl]-1-((R)-2-methoxy-1-methyl-ethyl)-1H-imidazole-4-carboxylic acid ethyl ester

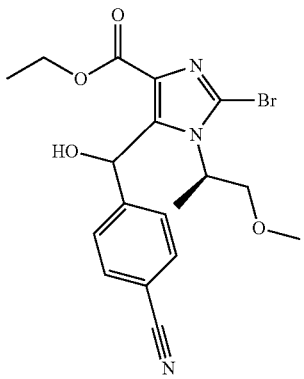 [SMILES: CCOC(=O)c1nc(Br)n([C@H](C)COC)c1C(O)c1ccc(C#N)cc1]

The title compound was prepared in analogy to the procedure described for step 111.6 but using the product from step 256.5. After extraction, the product was purified by flash chromatography (heptane/EtOAc, 80:20→20:80). $t_R$: 0.92 min (LC-MS 2); ESI-MS: 422.0/424.0 [M+H]$^+$ (LC-MS 2); $R_f$=0.33 (heptane/EtOAc, 1:2).

Step 256.5: 2-Bromo-1-((R)-2-methoxy-1-methyl-ethyl)-1H-imidazole-4-carboxylic acid ethyl ester

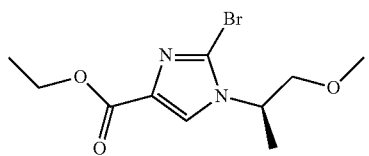 [SMILES: CCOC(=O)c1cn([C@H](C)COC)c(Br)n1]

The title compound was prepared in analogy to the procedure described for intermediate A but using the product from step 256.6. The reaction was performed at rt for 6 days. The product was purified by flash chromatography (heptane/EtOAc, 100:0→40:60). $t_R$: 0.76 min (LC-MS 2); ESI-MS: 291.0/293.0 [M+H]$^+$ (LC-MS 2); $R_f$=0.0.41 (CH$_2$Cl$_2$/MeOH, 20:1).

Step 256.6: 1-((R)-2-Methoxy-1-methyl-ethyl)-1H-imidazole-4-carboxylic acid ethyl ester

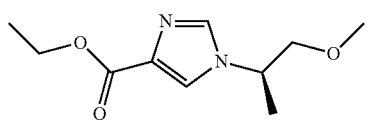

The title compound was obtained in analogy to the procedure described for step 100.5 but using the product from step 111.9. After extraction, the residue was purified by flash chromatography (heptane/CH$_2$Cl$_2$/MeOH, 100:0:0→85:14:1) to afford the title compound. $t_R$: 0.60 (LC-MS 2); ESI-MS: 213.1 [M+H]$^+$ (LC-MS 2).

Example 257

4-[5-(5-chloro-2-methyl-phenyl)-2-(2,4-dimethoxy-pyrimidin-5-yl)-3-((R)-2-methoxy-1-methyl-ethyl)-6-oxo-3,4,5,6-tetrahydro-pyrrolo[3,4-d]imidazol-4-yl]-benzonitrile

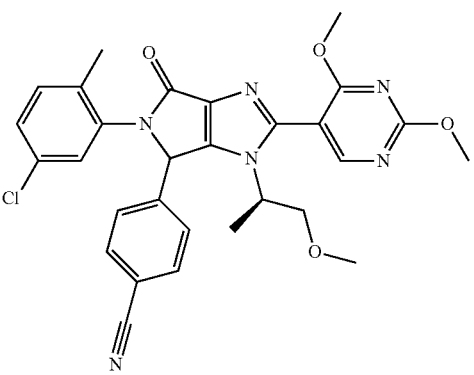 [SMILES: COC[C@@H](C)n1c(-c2cnc(OC)nc2OC)nc2c1C(c1ccc(C#N)cc1)N(c1cc(Cl)ccc1C)C2=O]

The title compound was prepared in analogy to the procedure described for step 97.1 but using the product from step 257.1 and 2,4-dimethoxypyrimidin-5-ylboronic acid. After extraction, the product was purified by flash chromatography (heptane/EtOAc, 1:1→0:100). $t_R$: 1.02/1.04 min (LC-MS 2); ESI-MS: 559.1/561.2 [M+H]$^+$ (LC-MS 2); $R_f$=0.09 (heptane/EtOAc, 1:4).

Step 257.1: 4-[2-Bromo-5-(5-chloro-2-methyl-phenyl)-3-((R)-2-methoxy-1-methyl-ethyl)-6-oxo-3,4,5,6-tetrahydro-pyrrolo[3,4-d]imidazol-4-yl]-benzonitrile

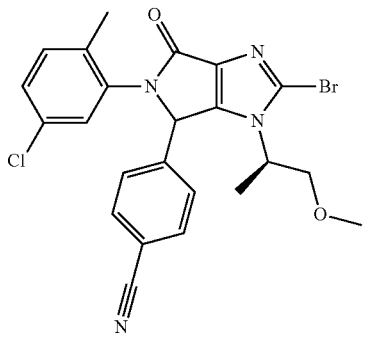 [SMILES: COC[C@@H](C)n1c(Br)nc2c1C(c1ccc(C#N)cc1)N(c1cc(Cl)ccc1C)C2=O]

The title compound was prepared in analogy to the procedure described for step 93.1 but using the product from step 257.2. After extraction, the product was purified by flash chromatography (heptane/EtOAc, 80:20→0:100). $t_R$: 1.03/1.04 min (LC-MS 2); ESI-MS: 499.0/501.0 [M+H]$^+$ (LC-MS 2); $R_f$=0.18 (heptane/EtOAc, 1:2).

Step 257.2: 2-Bromo-5-[(5-chloro-2-methyl-phenylamino)-(4-cyano-phenyl)-methyl]-1-((R)-2-methoxy-1-methyl-ethyl)-1H-imidazole-4-carboxylic acid

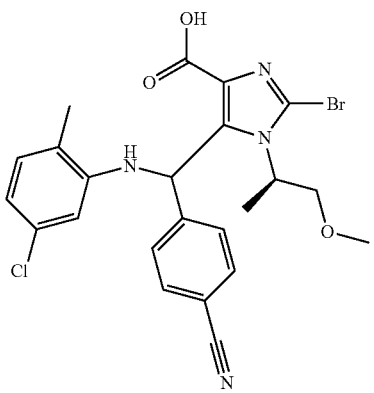 [SMILES: COC[C@@H](C)n1c(Br)nc(C(=O)O)c1C(Nc1cc(Cl)ccc1C)c1ccc(C#N)cc1]

The title compound was prepared in analogy to the procedure described for step 93.2 but using the product from step 257.3. The product was used without purification after the extraction. $t_R$: 1.12 min (LC-MS 2); ESI-MS: 517.0/519.0 [M+H]$^+$ (LC-MS 2).

Step 257.3: 2-Bromo-5-[(5-chloro-2-methyl-phenylamino)-(4-cyano-phenyl)-methyl]-1-((R)-2-methoxy-1-methyl-ethyl)-1H-imidazole-4-carboxylic acid ethyl ester

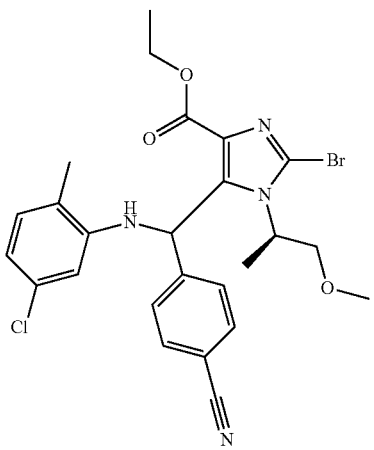 [SMILES: CCOC(=O)c1nc(Br)n([C@H](C)COC)c1C(Nc1cc(Cl)ccc1C)c1ccc(C#N)cc1]

The title compound was prepared in analogy to the procedure described for step E2 but using the product from step 256.4 and 5-chloro-2-methylaniline. After completion, the reaction mixture was extracted with H$_2$O and washed with a saturated NaHCO$_3$ solution. The organic was dried (Na$_2$SO$_4$), filtered and concentrated. The residue was purified by flash chromatography (heptane/EtOAc, 80:20→1:1). $t_R$: 1.30/1.32 min (LC-MS 2); ESI-MS: 545.1/547.1 [M+H]$^+$ (LC-MS 2); R$_f$=0.30 (heptane/EtOAc, 1:1).

Example 258

5-(3-Chloro-2-fluoro-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one

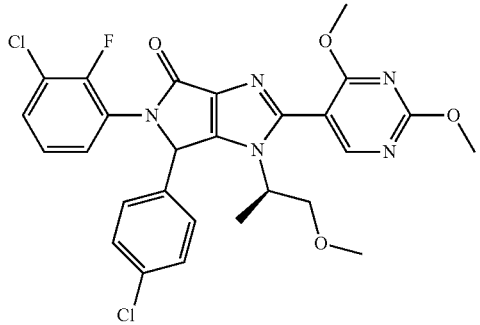 [SMILES: COC[C@@H](C)n1c(-c2cnc(OC)nc2OC)nc2c1C(c1ccc(Cl)cc1)N(c1cccc(Cl)c1F)C2=O]

The title compound was prepared in analogy to the procedure described for step 97.1 but using the product from step 258.1. After extraction, the product was purified by flash chromatography (heptane/EtOAc, 1:1→5:95). $t_R$: 1.14/1.16 min (LC-MS 2); ESI-MS: 572.1/574.1 [M+H]$^+$ (LC-MS 2); R$_f$=0.09 (heptane/EtOAc, 1:4).

Step 258.1: 2-Bromo-5-(3-chloro-2-fluoro-phenyl)-6-(4-chloro-phenyl)-1-((R)-2-methoxy-1-methyl-ethyl)-5,6-dihydro-1H-pyrrolo[3,4-d]imidazol-4-one

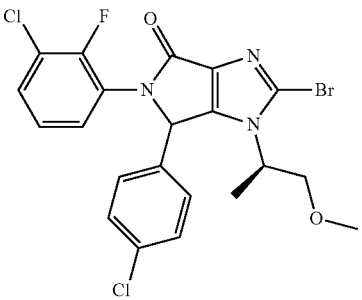 [SMILES: COC[C@@H](C)n1c(Br)nc2c1C(c1ccc(Cl)cc1)N(c1cccc(Cl)c1F)C2=O]

The title compound was prepared in analogy to the procedure described for step 93.1 but using the product from step 258.2. After extraction, the product was purified by flash chromatography (heptane/EtOAc, 80:20→25:75). $t_R$: 1.15/1.17 min (LC-MS 2); ESI-MS: 512.0/514.0/516.0 [M+H]$^+$ (LC-MS 2); R$_f$=0.09 (heptane/EtOAc, 1:1).

Step 258.2: 2-Bromo-5-[(3-chloro-2-fluoro-phenylamino)-(4-chloro-phenyl)-methyl]-1-((R)-2-methoxy-1-methyl-ethyl)-1H-imidazole-4-carboxylic acid

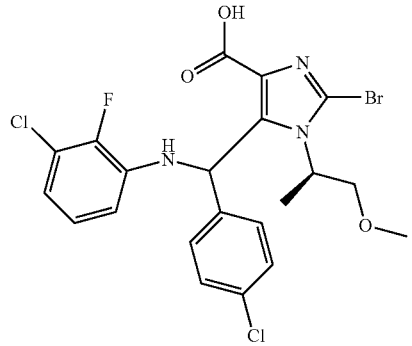 [SMILES: COC[C@@H](C)n1c(Br)nc(C(=O)O)c1C(Nc1cccc(Cl)c1F)c1ccc(Cl)cc1]

The title compound was prepared in analogy to the procedure described for step 93.2 but using the product from step 258.3. The product was used without purification after the extraction. $t_R$: 1.21 min (LC-MS 2); ESI-MS: 530.1/531.9/534.0 [M+H]$^+$ (LC-MS 2).

Step 258.3: 2-Bromo-5-[(3-chloro-2-fluoro-phenylamino)-(4-chloro-phenyl)-methyl]-1-((R)-2-methoxy-1-methyl-ethyl)-1H-imidazole-4-carboxylic acid ethyl ester

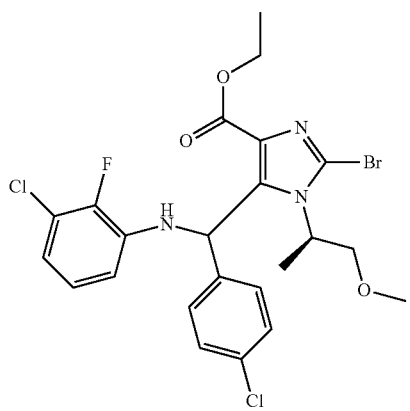 [SMILES: CCOC(=O)c1nc(Br)n([C@H](C)COC)c1C(Nc1cccc(Cl)c1F)c1ccc(Cl)cc1]

The title compound was prepared in analogy to the procedure described for step E2 but using the product from step 258.4 and 3-chloro-2-fluoroaniline. After completion, the reaction mixture was extracted with a saturated NaHCO$_3$ solution and washed with H$_2$O. The organic was dried (Na$_2$SO$_4$), filtered and concentrated. The residue was purified by flash chromatography (heptane/EtOAc, 90:10→0:100). $t_R$: 1.40/1.46 min (LC-MS 2); ESI-MS: 558.0/560.0/562.0 [M+H]$^+$ (LC-MS 2); R$_f$=0.37 (heptane/EtOAc, 1:1).

Step 258.4: 2-Bromo-5-[(4-chloro-phenyl)-hydroxymethyl]-1-((R)-2-methoxy-1-methyl-ethyl)-1H-imidazole-4-carboxylic acid ethyl ester

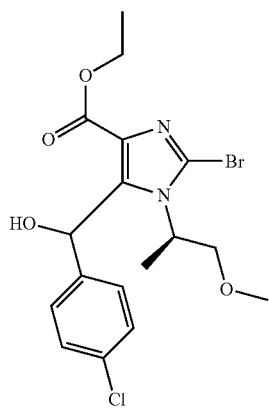 [SMILES: CCOC(=O)c1nc(Br)n([C@H](C)COC)c1C(O)c1ccc(Cl)cc1]

The title compound was obtained in analogy to the procedure described for intermediate B but using 4-chlorobenzaldehyde and the product from step 256.5. After completion, the reaction mixture was quenched with a 1M NH$_4$Cl solution and extracted with EtOAc. The organic layer was dried (Na$_2$SO$_4$), filtered and concentrated. The residue was purified by flas chromatography (heptane/EtOAc, 80:20→20:80) to give the title compound. $t_R$: 1.08 min (LC-MS 2); ESI-MS: 431.1/433.0 [M+H]$^+$ (LC-MS 2).

Example 259

5-(3-Chloro-4-fluoro-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one

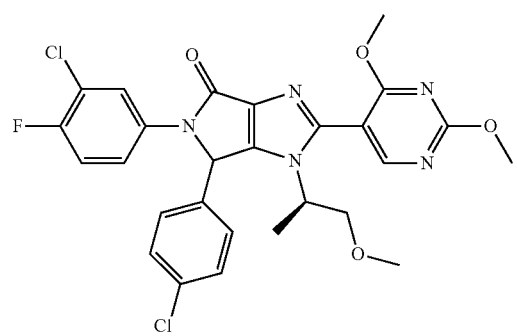 [SMILES: COC[C@@H](C)n1c(-c2cnc(OC)nc2OC)nc2c1C(c1ccc(Cl)cc1)N(c1ccc(F)c(Cl)c1)C2=O]

The title compound was prepared in analogy to the procedure described for step 97.1 but using the product from step 259.1. After extraction, the product was purified by flash chromatography (heptane/EtOAc, 1:1→0:100). $t_R$: 1.16/1.18 min (LC-MS 2); ESI-MS: 572.1/574.1 [M+H]$^+$ (LC-MS 2); R$_f$=0.10 (heptane/EtOAc, 1:4).

Step 259.1: 2-Bromo-5-(3-chloro-4-fluoro-phenyl)-6-(4-chloro-phenyl)-1-((R)-2-methoxy-1-methyl-ethyl)-5,6-dihydro-1H-pyrrolo[3,4-d]imidazol-4-one

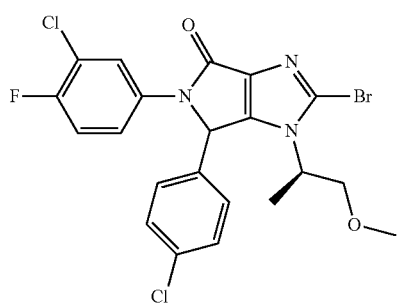 [SMILES: COC[C@@H](C)n1c(Br)nc2c1C(c1ccc(Cl)cc1)N(c1ccc(F)c(Cl)c1)C2=O]

The title compound was prepared in analogy to the procedure described for step 93.1 but using the product from step 259.2. After extraction, the product was purified by flash chromatography (heptane/EtOAc, 80:20→25:75). $t_R$: 1.17/1.20 min (LC-MS 2); ESI-MS: 511.9/514.0/516.0 [M+H]$^+$ (LC-MS 2); R$_f$=0.11 (heptane/EtOAc, 1:1).

Step 259.2: 2-Bromo-5-[(3-chloro-4-fluoro-phenylamino)-(4-chloro-phenyl)-methyl]-1-((R)-2-methoxy-1-methyl-ethyl)-1H-imidazole-4-carboxylic acid

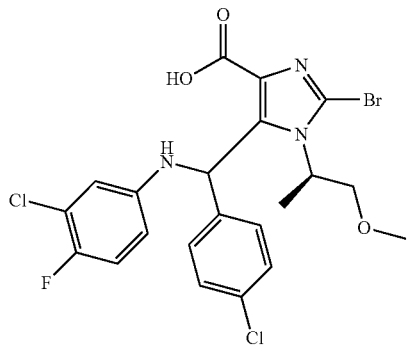 [SMILES: COC[C@@H](C)n1c(Br)nc(C(=O)O)c1C(Nc1ccc(F)c(Cl)c1)c1ccc(Cl)cc1]

The title compound was prepared in analogy to the procedure described for step 93.2 but using the product from step 259.3. The product was used without purification after the extraction. $t_R$: 1.18 min (LC-MS 2); ESI-MS: 530.0/532.0/534.0 [M+H]$^+$ (LC-MS 2).

Step 259.3: 2-Bromo-5-[(3-chloro-4-fluoro-phenylamino)-(4-chloro-phenyl)-methyl]-1-((R)-2-methoxy-1-methyl-ethyl)-1H-imidazole-4-carboxylic acid ethyl ester

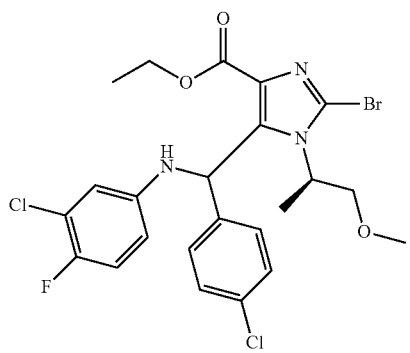 [SMILES: CCOC(=O)c1nc(Br)n([C@H](C)COC)c1C(Nc1ccc(F)c(Cl)c1)c1ccc(Cl)cc1]

The title compound was prepared in analogy to the procedure described for step E2 but using the product from step 258.4 and 3-chloro-4-fluoroaniline. After completion, the reaction mixture was extracted with a saturated NaHCO$_3$ solution and washed with H$_2$O. The organic was dried (Na$_2$SO$_4$), filtered and concentrated. The residue was purified by flash chromatography (heptane/EtOAc, 90:10→0:100). $t_R$: 1.37/1.41 min (LC-MS 2); ESI-MS: 558.0/560.0/562.0 [M+H]$^+$ (LC-MS 2); R$_f$=0.37 (heptane/EtOAc, 1:1).

Example 260

6-(4-Chloro-phenyl)-2-(2,4-dimethoxy-pyrimidin-5-yl)-5-(4-fluoro-3-methyl-phenyl)-1-isopropyl-5,6-dihydro-1H-pyrrolo[3,4-d]imidazol-4-one

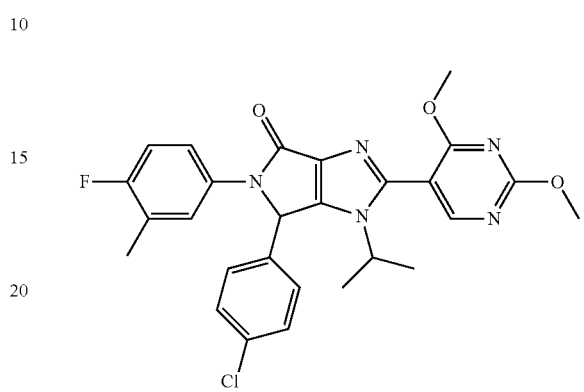

The title compound was prepared in analogy to the procedure described for example 1 but using the product from step 260.1 and 2,4-dimethoxypyrimidin-5-ylboronic acid. After extraction, the product was purified by preparative HPLC (Waters Sun Fire C18, 30×100 mm, 5 µm; 0.1% TFA-water/acetonitrile; gradient acetonitrile 40-60% in 16 min). $t_R$: 1.16 min (LC-MS 2); ESI-MS: 522.2/524.2 [M+H]$^+$ (LC-MS 2).

Step 260.1: 2-Bromo-6-(4-chloro-phenyl)-5-(4-fluoro-3-methyl-phenyl)-1-isopropyl-5,6-dihydro-1H-pyrrolo[3,4-d]imidazol-4-one

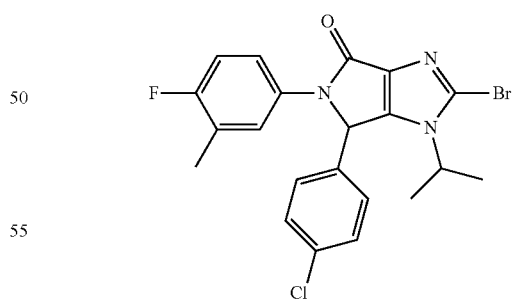

The title compound was prepared in analogy to the procedure described for step 91.1 but using the product from step 260.2. The extraction was performed in CH$_2$Cl$_2$. The product was triturated in Et$_2$O to afford the title compound. $t_R$: 1.18 min (LC-MS 2); ESI-MS: 462.1/464.1 [M+H]$^+$ (LC-MS 2).

Step 260.2: 2-Bromo-5-[(4-chloro-phenyl)-(4-fluoro-3-methyl-phenylamino)-methyl]-1-isopropyl-1H-imidazole-4-carboxylic acid

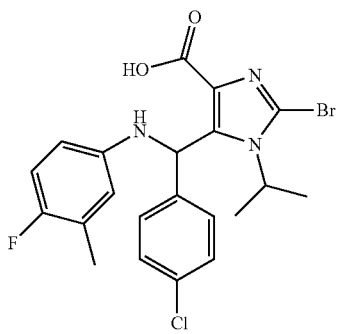 [SMILES: Cc1cc(NC(c2ccc(Cl)cc2)c2c(C(=O)O)nc(Br)n2C(C)C)ccc1F]

The title compound was prepared in analogy to the procedure described for step E1 but using the product from step 260.3. $t_R$: 1.19 min (LC-MS 2); ESI-MS: 480.0/482.0 [M+H]$^+$ (LC-MS 2).

Step 260.3: 2-Bromo-5-[(4-chloro-phenyl)-(4-fluoro-3-methyl-phenylamino)-methyl]-1-isopropyl-1H-imidazole-4-carboxylic acid ethyl ester

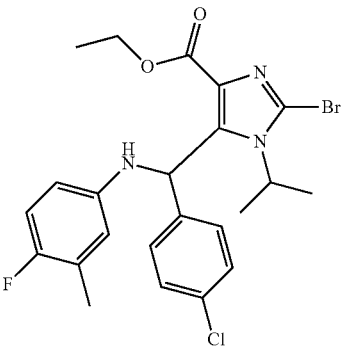 [SMILES: CCOC(=O)c1nc(Br)n(C(C)C)c1C(Nc1ccc(F)c(C)c1)c1ccc(Cl)cc1]

The title compound was prepared in analogy to the procedure described for step E2 but using intermediate B and 4-fluoro-3-methylaniline. After completion, the reaction mixture was extracted with HCl and washed with a saturated NaHCO$_3$ solution. The organic was dried (Na$_2$SO$_4$), filtered and concentrated. The product was used without further purification. $t_R$: 1.37 min (LC-MS 2); ESI-MS: 508.1/510.1 [M+H]$^+$ (LC-MS 2).

Example 261

6-(4-Chloro-phenyl)-2-(2,4-dimethoxy-pyrimidin-5-yl)-1-isopropyl-5-(2-methoxy-5-methyl-phenyl)-5,6-dihydro-1H-pyrrolo[3,4-d]imidazol-4-one

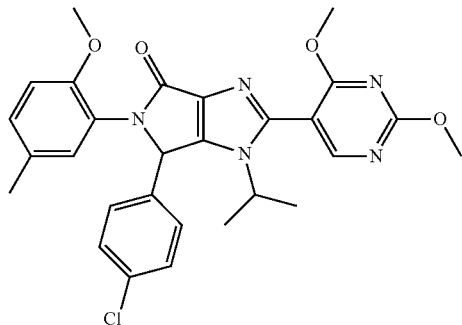 [SMILES: COc1ncc(-c2nc3c(n2C(C)C)C(c2ccc(Cl)cc2)N(c2cc(C)ccc2OC)C3=O)c(OC)n1]

The title compound was prepared in analogy to the procedure described for example 1 but using the product from step 261.1 and 2,4-dimethoxypyrimidin-5-ylboronic acid. After extraction, the product was purified by preparative HPLC (Waters Sun Fire C18, 30×100 mm, 5 μm; 0.1% TFA-water/acetonitrile; gradient acetonitrile 40-60% in 16 min). $t_R$: 1.14 min (LC-MS 2); ESI-MS: 534.2/536.2 [M+H]$^+$ (LC-MS 2).

Step 261.1: 2-Bromo-6-(4-chloro-phenyl)-1-isopropyl-5-(2-methoxy-5-methyl-phenyl)-5,6-dihydro-1H-pyrrolo[3,4-d]imidazol-4-one

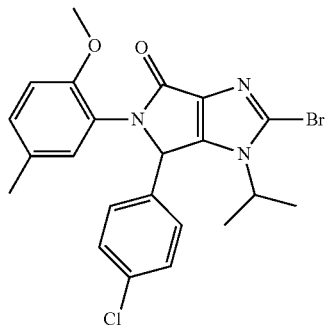 [SMILES: COc1ccc(C)cc1N1C(=O)c2nc(Br)n(C(C)C)c2C1c1ccc(Cl)cc1]

The title compound was prepared in analogy to the procedure described for step 91.1 but using the product from step 261.2. The extraction was performed in CH$_2$Cl$_2$. The product was triturated in Et$_2$O to afford the title compound. $t_R$: 1.16 min (LC-MS 2); ESI-MS: 474.0/476.0 [M+H]$^+$ (LC-MS 2).

Step 261.2: 2-Bromo-5-[(4-chloro-phenyl)-(2-methoxy-5-methyl-phenylamino)-methyl]-1-isopropyl-1H-imidazole-4-carboxylic acid

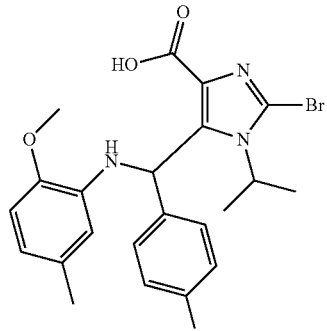

The title compound was prepared in analogy to the procedure described for step E1 but using the product from step 261.3. $t_R$: 1.21 min (LC-MS 2); ESI-MS: 492.0/494.1 [M+H]$^+$ (LC-MS 2).

Step 261.3: 2-Bromo-5-[(4-chloro-phenyl)-(2-methoxy-5-methyl-phenylamino)-methyl]-1-isopropyl-1H-imidazole-4-carboxylic acid ethyl ester

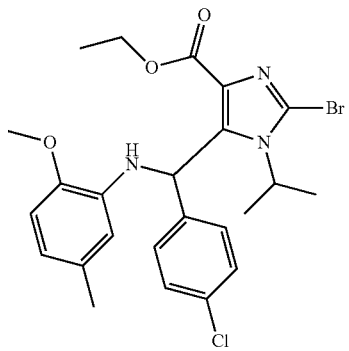 [SMILES: CCOC(=O)c1nc(Br)n(C(C)C)c1C(Nc1cc(C)ccc1OC)c1ccc(Cl)cc1]

The title compound was prepared in analogy to the procedure described for step E2 but using intermediate B and 2-methoxy-5-methylaniline. After completion, the reaction mixture was extracted with HCl and washed with a saturated NaHCO$_3$ solution. The organic was dried (Na$_2$SO$_4$), filtered and concentrated. The product was used without further purification. $t_R$: 1.40 min (LC-MS 2); ESI-MS: 520.1/522.1 [M+H]$^+$ (LC-MS 2).

Example 262

6-(4-Chloro-phenyl)-2-(2,4-dimethoxy-pyrimidin-5-yl)-5-(2,6-dimethyl-pyrimidin-4-yl)-1-isopropyl-5,6-dihydro-1H-pyrrolo[3,4-d]imidazol-4-one

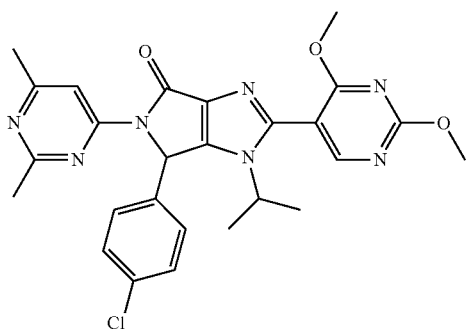 [SMILES: COc1ncc(-c2nc3c(n2C(C)C)C(c2ccc(Cl)cc2)N(c2cc(C)nc(C)n2)C3=O)c(OC)n1]

The title compound was prepared in analogy to the procedure described for example 1 but using the product from step 262.1 and 2,4-dimethoxypyrimidin-5-ylboronic acid. After extraction, the product was purified by preparative HPLC (Waters Sun Fire C18, 30×100 mm, 5 µm; 0.1% TFA-water/acetonitrile; gradient acetonitrile 20-40% in 16 min). $t_R$: 1.07 min (LC-MS 2); ESI-MS: 520.2/522.2 [M+H]$^+$ (LC-MS 2).

Step 262.1: 2-Bromo-6-(4-chloro-phenyl)-5-(2,6-dimethyl-pyrimidin-4-yl)-1-isopropyl-5,6-dihydro-1H-pyrrolo[3,4-d]imidazol-4-one

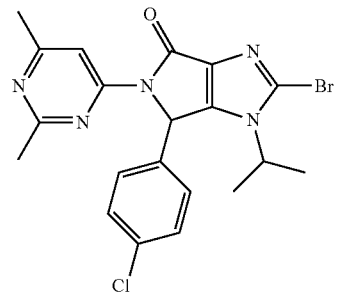 [SMILES: Cc1cc(N2C(=O)c3nc(Br)n(C(C)C)c3C2c2ccc(Cl)cc2)nc(C)n1]

The title compound was prepared in analogy to the procedure described for step 91.1 but using the product from step 262.2. The extraction was performed in CH$_2$Cl$_2$. The product was triturated in Et$_2$O to afford the title compound. $t_R$: 1.10 min (LC-MS 2); ESI-MS: 460.0/462.0/464.1 [M+H]$^+$ (LC-MS 2).

Step 262.2: 2-Bromo-5-[(4-chloro-phenyl)-(2,6-dimethyl-pyrimidin-4-ylamino)-methyl]-1-isopropyl-1H-imidazole-4-carboxylic acid

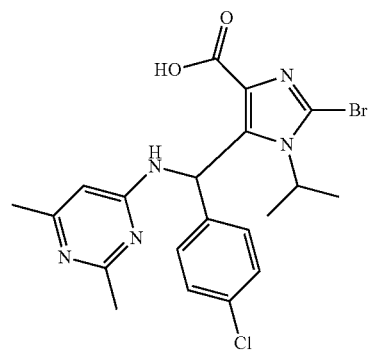 [SMILES: Cc1cc(NC(c2ccc(Cl)cc2)c2c(C(=O)O)nc(Br)n2C(C)C)nc(C)n1]

The title compound was prepared in analogy to the procedure described for step E1 but using the product from step 262.3. After the acidic workup, the product was in the aqueous layer. A saturated NaHCO$_3$ solution was added to the aqueous layer and extracted with EtOAc. The organic layer was dried (Na$_2$SO$_4$), filtered and concentrated to afford the title compound. $t_R$: 0.76 min (LC-MS 2); ESI-MS: 478.1/480.1 [M+H]$^+$ (LC-MS 2).

Step 262.3: 2-Bromo-5-[(4-chloro-phenyl)-(2,6-dimethyl-pyrimidin-4-ylamino)-methyl]-1-isopropyl-1H-imidazole-4-carboxylic acid ethyl ester

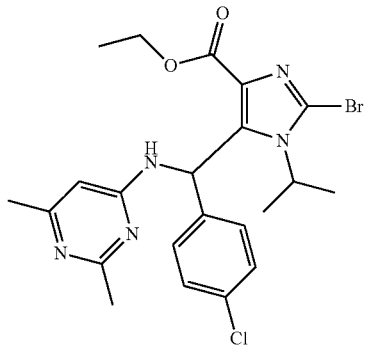 [SMILES: CCOC(=O)c1nc(Br)n(C(C)C)c1C(Nc1cc(C)nc(C)n1)c1ccc(Cl)cc1]

The title compound was prepared in analogy to the procedure described for step E2 but using intermediate B and 4-amino-2,6-dimethylpyrimidine. After completion, the reaction mixture was extracted with 1M HCl and washed with a saturated NaHCO₃ solution. The organic was dried (Na₂SO₄), filtered and concentrated. The product was used without further purification. $t_R$: 0.82 min (LC-MS 2); ESI-MS: 506.0/508.1 [M+H]⁺ (LC-MS 2).

Example 263

(S)-2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one

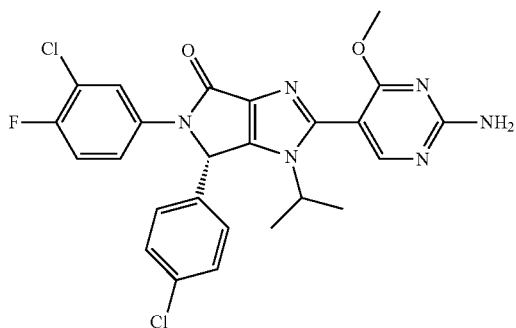

The title compound was obtained after preparative chiral SFC separation of the racemic product of example 193 (Column: IC 20 μm, 50×106 mm, Flow 50 mL/min, heptane/EtOH/MeOH, 60:20:20, UV Detection 210 nm). $t_R$: 7.15 min (Column: Chiralpak IC, 20 μm, 4.6×250 mm. Flow: 2 mL/min. heptane/EtOH/MeOH, 75:15:15, UV Detection 220 nm).

Example 264

(R)-2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one

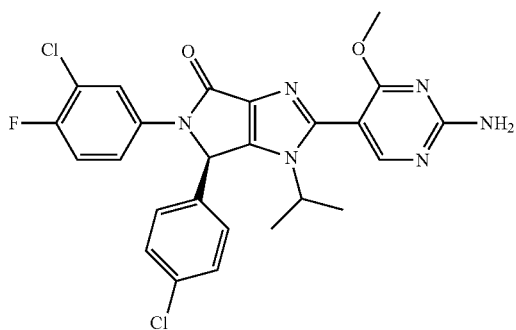 [SMILES: COc1nc(N)ncc1-c1nc2c(n1C(C)C)[C@@H](c1ccc(Cl)cc1)N(c1ccc(F)c(Cl)c1)C2=O]

The title compound was obtained after preparative chiral SFC separation of the racemic product of example 193 (Column: IC 20 μm, 50×106 mm, Flow 50 mL/min, heptane/EtOH/MeOH, 60:20:20, UV Detection 210 nm). $t_R$: 18.22 min (Column: Chiralpak IC, 20 μm, 4.6×250 mm. Flow: 2 mL/min. heptane/EtOH/MeOH, 75:15:15, UV Detection 220 nm).

Example 265

(S)-2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one

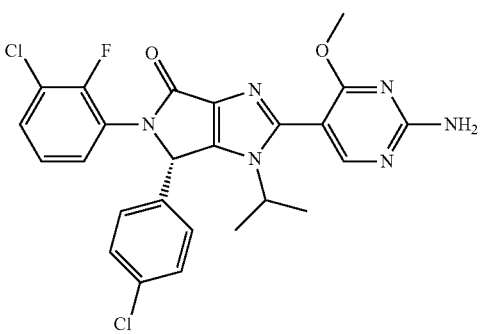

The title compound was obtained after preparative chiral SFC separation of the racemic product of example 192 (Column: IC 20 μm, 50×106 mm, Flow 30 mL/min, heptane/EtOH/MeOH, 50:25:25, UV Detection 210 nm). $t_R$: 5.67 min (Column: Chiralpak IC, 20 μm, 4.6×250 mm. Flow: 2 mL/min. heptane/EtOH/MeOH, 50:25:25, UV Detection 220 nm).

Example 266

(R)-2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one

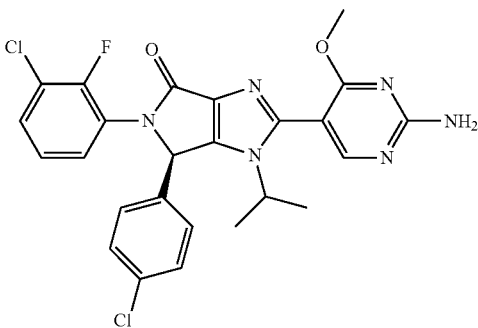 [SMILES: COc1nc(N)ncc1-c1nc2c(n1C(C)C)[C@@H](c1ccc(Cl)cc1)N(c1cccc(Cl)c1F)C2=O]

The title compound was obtained after preparative chiral SFC separation of the racemic product of example 192 (Column: IC 20 μm, 50×106 mm, Flow 30 mL/min, heptane/EtOH/MeOH, 50:25:25, UV Detection 210 nm). $t_R$: 15.35 min (Column: Chiralpak IC, 20 μm, 4.6×250 mm. Flow: 2 mL/min. heptane/EtOH/MeOH, 50:25:25, UV Detection 220 nm).

Example 267

6-(4-Chloro-phenyl)-5-(4-fluoro-3-methyl-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one

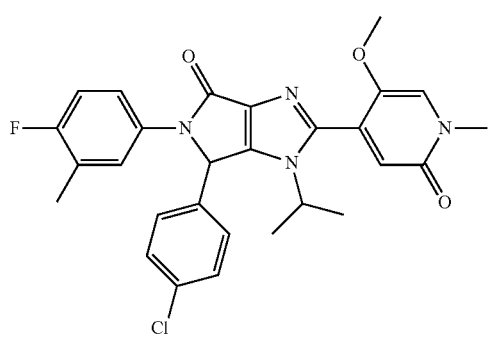 [SMILES: COc1cn(C)c(=O)cc1-c1nc2c(n1C(C)C)C(c1ccc(Cl)cc1)N(c1ccc(F)c(C)c1)C2=O]

The title compound was prepared in analogy to the procedure described for example 1 but using the products from steps 260.1 and 105.1. After extraction, the product was purified by preparative HPLC (Waters Sun Fire C18, 30×100 mm, 5 μm; 0.1% TFA-water/acetonitrile; gradient acetonitrile 40-60% in 16 min). $t_R$: 1.03 min (LC-MS 2); ESI-MS: 521.2/523.2 [M+H]$^+$ (LC-MS 2).

Example 268

6-(4-Chloro-phenyl)-1-isopropyl-2-(5-methoxy-1-methyl-2-oxo-1,2-dihydro-pyridin-4-yl)-5-(2-methoxy-5-methyl-phenyl)-5,6-dihydro-1H-pyrrolo[3,4-d]imidazol-4-one

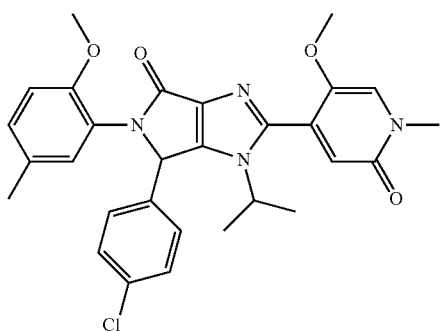 [SMILES: COc1cn(C)c(=O)cc1-c1nc2c(n1C(C)C)C(c1ccc(Cl)cc1)N(c1cc(C)ccc1OC)C2=O]

The title compound was prepared in analogy to the procedure described for example 1 but using the products from steps 261.1 and 105.1. After extraction, the product was purified by preparative HPLC (Waters Sun Fire C18, 30×100 mm, 5 μm; 0.1% TFA-water/acetonitrile; gradient acetonitrile 40-60% in 16 min). The residue was dissolved in MeOH and filtered over a Stratosphere SPE cartridge (PL-Thiol MP SPE) to remove the palladium. $t_R$: 1.01 min (LC-MS 2); ESI-MS: 533.2/535.2 [M+H]$^+$ (LC-MS 2).

Example 269

5-(5-Chloro-1-methyl-6-oxo-1,6-dihydro-pyridin-3-yl)-6-(4-chloro-phenyl)-1-isopropyl-2-(2-methoxy-pyrimidin-5-yl)-5,6-dihydro-1H-pyrrolo[3,4-d]imidazol-4-one

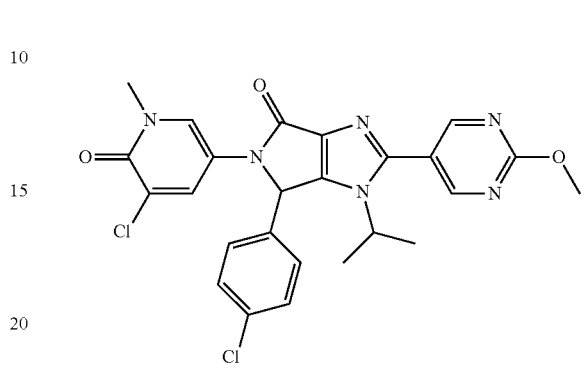

The title compound was prepared in analogy to the procedure described for example 1 using the product from Intermediate J and (2-methoxy-pyrimidin-5-yl)boronic acid as starting materials. The reaction was performed in presence of PdCl$_2$(dppf) (15 mol %) as catalyst. $t_R$: 0.90 min (LC-MS 4); ESI-MS: 527.0 [M+H]$^+$ (LC-MS 4). 1H-NMR (DMSO-d6, 400 MHz) δ ppm 8.85 (s, 2H), 7.93 (d, J=6.60 Hz, 2H), 7.51-7.43 (m, 2H), 7.39 (d, J=7.09 Hz, 2H), 6.51 (s, 1H), 4.42 (quin, J=6.66 Hz, 1H), 4.01 (s, 3H), 3.45 (s, 3H), 1.40 (d, J=6.72 Hz, 3H), 0.67 (d, J=6.72 Hz, 3H).

Example 270

5-(5-Chloro-1-methyl-6-oxo-1,6-dihydro-pyridin-3-yl)-6-(4-chloro-2-methyl-phenyl)-1-isopropyl-2-(2-methoxy-pyridine-3-yl)-5,6-dihydro-1H-pyrrolo[3,4-d]imidazol-4-one

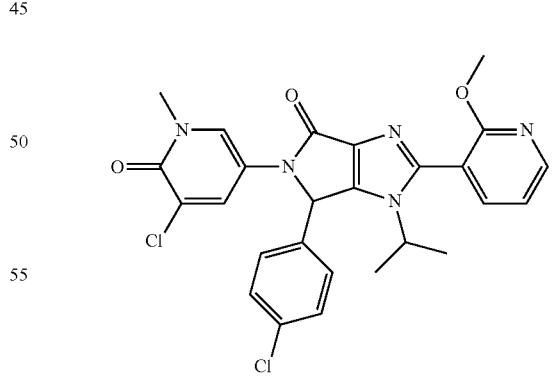

The title compound was prepared in analogy to the procedure described for example 1 using the product from intermediate J and (2-methoxy-pyridine-3-yl)boronic acid as starting materials. The reaction was performed in presence of PdCl$_2$(PPh$_3$)$_2$ (20 mol %) as catalyst. $t_R$: 0.98 min (LC-MS 4); ESI-MS: 526.3 [M+H]$^+$ (LC-MS 4).

Example 271

6-(4-Chloro-2-phenyl)-5-(1,5-dimethyl-6-oxo-1,6-dihydro-pyridin-3-yl)-1-isopropyl-2-(2-methoxy-pyrimidin-5-yl)-5,6-dihydro-1H-pyrrolo[3,4-d]imidazol-4-one

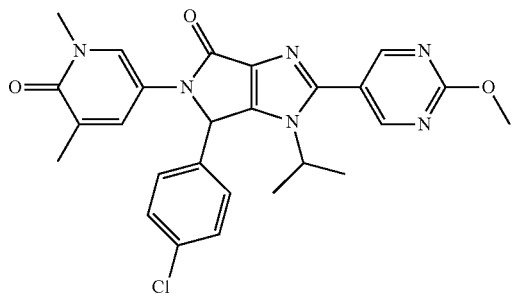 [SMILES: COc1ncc(-c2nc3c(n2C(C)C)C(c2ccc(Cl)cc2)N(c2cc(C)c(=O)n(C)c2)C3=O)cn1]

The title compound was prepared in analogy to the procedure described for example 1 using the product from step 271.1 and (2-methoxy-pyrimidin-5-yl)boronic acid as starting materials. The reaction was performed in presence of PdCl$_2$(dppf) (15 mol %) as catalyst. t$_R$: 0.87 min (LC-MS 4); ESI-MS: 505.3 [M+H]$^+$ (LC-MS 4).

Step 271.1: 2-Bromo-6-(4-chloro-phenyl)-5-(1,5-dimethyl-6-oxo-1,6-dihydro-pyridin-3-yl)-1-isopropyl-5,6-dihydro-1H-pyrrolo[3,4-d]imidazol-4-one

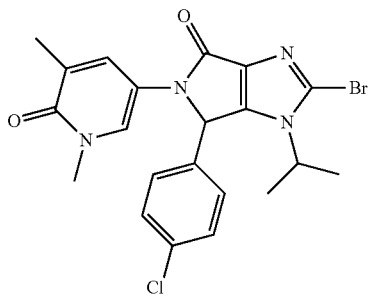 [SMILES: Cc1cc(N2C(=O)c3nc(Br)n(C(C)C)c3C2c2ccc(Cl)cc2)cn(C)c1=O]

The title compound was prepared in analogy to the procedure described for intermediate F using the product from step 271.2 as starting material. t$_R$: 0.92 min (LC-MS 4); ESI-MS: 477.2 [M+H]$^+$ (LC-MS 4); 1H-NMR (CDCl3, 400 MHz) δ ppm 7.35 (d, J=8.59 Hz, 2H), 7.06 (d, J=8.59 Hz, 2H), 7.03 (d, J=2.34 Hz, 1H), 6.69 (dd, J=2.73 Hz, 1H), 5.50 (s, 1H), 4.58 (quin, J=6.83 Hz, 1H), 3.40 (s, 3H); 2.05 (s, 3H), 1.45 (d, J=7.03 Hz, 3H), 0.82 (d, J=7.03 Hz, 3H).

Step 271.2: 2-Bromo-5-[(-4-chloro-phenyl)-(1,5-dimethyl-6-oxo-1,6-dihydro-pyridin-3-ylamino)-methyl]-1-isopropyl-1H-imidazole-4-carboxylic acid

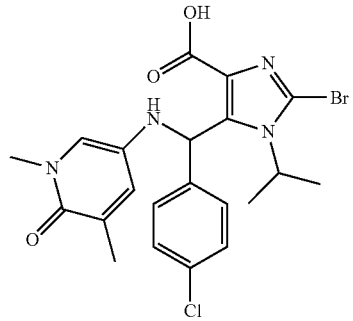 [SMILES: Cc1cc(NC(c2ccc(Cl)cc2)c2c(C(=O)O)nc(Br)n2C(C)C)cn(C)c1=O]

The title compound was prepared in analogy to the procedure described for step E1 using the product from step 271.3. t$_R$: 0.91 min (LC-MS 4); ESI-MS: 495.2 [M+H]$^+$ (LC-MS 4).

Step 271.3: 2-Bromo-5-[(4-chloro-phenyl)-(1,5-dimethyl-6-oxo-1,6-dihydro-pyridin-3-ylamino)-methyl]-1-isopropyl-1H-imidazole-4-carboxylic acid ethyl ester

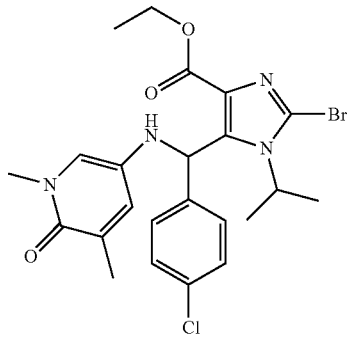 [SMILES: CCOC(=O)c1nc(Br)n(C(C)C)c1C(Nc1cc(C)c(=O)n(C)c1)c1ccc(Cl)cc1]

The title compound was prepared in analogy to the procedure described for step E2 using 2-bromo-5-[(4-chlorophenyl)-hydroxy-methyl]-1-cyclobutyl-1H-imidazole-4-carboxylic acid ethyl ester (product of step AK2) and the product from step 271.4 as starting materials. t$_R$: 1.09 min (LC-MS 4); ESI-MS: 523.2 [M+H]$^+$ (LC-MS 4).

Step 271.4: 5-Amino-1,3-dimethyl-1H-pyridin-2-one

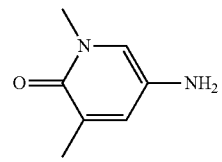

The compound prepared in step 271.5 (15.6 g, 93 mmol), was dissolved in THF/MeOH (1:1, 400 mL) and hydrogenated over Pd—C (10% BASF 4505 D/R; 2.0 g, 18 mmol) at rt for 4.5 h. The catalyst was removed by 2 consecutive filtrations over celite and a pad of silica gel. The filtrate was concentrated and dried to give the title compound as a brown solid. t$_R$: 0.23 min (LC-MS 4); ESI-MS: 139.1 [M+H]$^+$ (LC-MS 4). $^1$H-NMR (DMSO-d6, 400 MHz) δ ppm 6.94 (s, 1H), 6.70 (s, 1H), 4.14 (bs, 2H), 3.29 (s, 3H), 1.92 (s, 3H).

Step 271.5: 1,3-Dimethyl-5-nitro-1H-pyridin-2-one

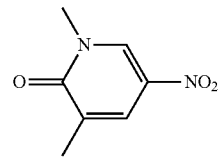

Methyl iodide (9.1 mL, 146 mmol) was added to a cold (0° C.) mixture of 3-chloro-2-hydroxy-5-nitropyrindine (15 g, 97 mmol) and K$_2$CO$_3$ (26.9 g, 195 mmol) in DMF (100 mL). The reaction mixture was allowed to warm to rt, stirred for 12 h, quenched by addition of water, and extracted with EtOAc. The organic phase was washed with brine, dried (Na$_2$SO$_4$), filtered, concentrated and dried to afford the title compound as a white solid. t$_R$: 0.58 min (LC-MS 4); 1H-NMR (DMSO-d6, 400 MHz) δ ppm 9.05 (d, J=3.1 Hz, 1H), 8.09-7.98 (m, 1H), 3.45 (s, 3H), 2.05 (s, 3H).

Example 272

6-(4-Chloro-phenyl)-5-(1,5-dimethyl-6-oxo-1,6-dihydro-pyridin-3-yl)-1-isopropyl-2-(2-methoxy-pyridin-3-yl)-5,6-dihydro-1H-pyrrolo[3,4-d]imidazol-4-one

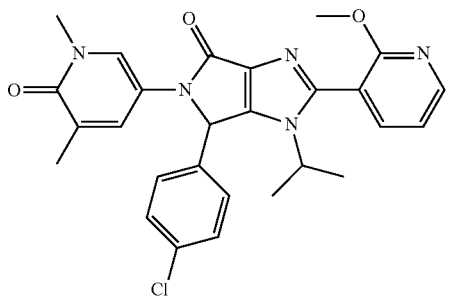 [SMILES: COc1ncccc1-c1nc2c(n1C(C)C)C(c1ccc(Cl)cc1)N(c1cc(C)c(=O)n(C)c1)C2=O]

The title compound was prepared in analogy to the procedure described for example 1 using the product from step 271.1 and (2-methoxy-pyridine-3-yl)boronic acid as starting materials. The reaction was performed in presence of PdCl$_2$(dppf) (15 mol %) as catalyst. t$_R$: 0.95 min (LC-MS 4); ESI-MS: 504.3 [M+H]$^+$ (LC-MS 4).

Example 273

6-(4-Chloro-2-phenyl)-2-(2,4-dimethoxy-pyrimidin-5-yl)-5-(1,5-dimethyl-6-oxo-1,6-dihydro-pyridin-3-yl)-1-isopropyl-5,6-dihydro-1H-pyrrolo[3,4-d]imidazol-4-one

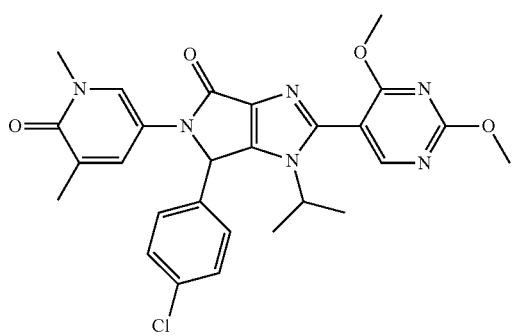 [SMILES: COc1ncc(-c2nc3c(n2C(C)C)C(c2ccc(Cl)cc2)N(c2cc(C)c(=O)n(C)c2)C3=O)c(OC)n1]

The title compound was prepared in analogy to the procedure described for example 1 using the product from step 271.1 and (2,4-dimethoxy-pyrimidin-5-yl)boronic acid as starting materials. t$_R$: 0.92 min (LC-MS 4); ESI-MS: 535.3 [M+H]$^+$ (LC-MS 4).

Example 274

6-(4-Chloro-2-phenyl)-1-cyclobutyl-2-(2,4-dimethoxy-pyrimidin-5-yl)-5-(1,5-dimethyl-6-oxo-1,6-dihydro-pyridin-3-yl)-5,6-dihydro-1H-pyrrolo[3,4-d]imidazol-4-one

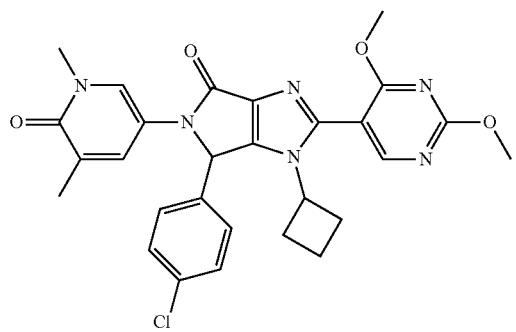 [SMILES: COc1ncc(-c2nc3c(n2C2CCC2)C(c2ccc(Cl)cc2)N(c2cc(C)c(=O)n(C)c2)C3=O)c(OC)n1]

The title compound was prepared in analogy to the procedure described for example 1 using the product from step 274.1 and (2,4-dimethoxy-pyrimidin-5-yl)boronic acid as starting materials. t$_R$: 0.96 min (LC-MS 4); ESI-MS: 547.3 [M+H]$^+$ (LC-MS 4).

Step 274.1: 2-Bromo-6-(4-chloro-phenyl)-5-(1,5-dimethyl-6-oxo-1,6-dihydro-pyridin-3-yl)-1-cyclobutyl-5,6-dihydro-1H-pyrrolo[3,4-d]imidazol-4-one

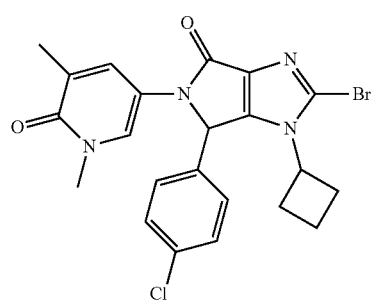 [SMILES: Cc1cc(N2C(=O)c3nc(Br)n(C4CCC4)c3C2c2ccc(Cl)cc2)cn(C)c1=O]

The title compound was prepared in analogy to the procedure described for intermediate F using the product from step 274.2 as starting material. t$_R$: 0.96 min (LC-MS 4); ESI-MS: 489.2 [M+H]$^+$ (LC-MS 4).

Step 274.2: 2-Bromo-5-[(-4-chloro-phenyl)-(1,5-dimethyl-6-oxo-1,6-dihydro-pyridin-3-ylamino)-methyl]-1-cyclobutyl-1H-imidazole-4-carboxylic acid

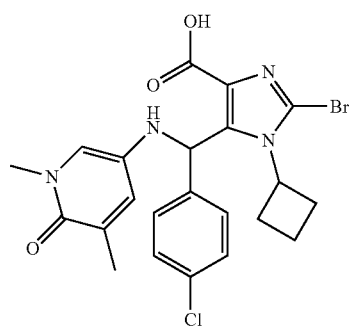 [SMILES: Cc1cc(NC(c2ccc(Cl)cc2)c2c(C(=O)O)nc(Br)n2C2CCC2)cn(C)c1=O]

The title compound was prepared in analogy to the procedure described for step E1 using the product from step 274.3. t$_R$: 0.94 min (LC-MS 4); ESI-MS: 507.0 [M+H]$^+$ (LC-MS 4).

Step 274.3: 2-Bromo-5-[(4-chloro-phenyl)-(1,5-dimethyl-6-oxo-1,6-dihydro-pyridin-3-ylamino)-methyl]-1-cyclobutyl-1H-imidazole-4-carboxylic acid ethyl ester

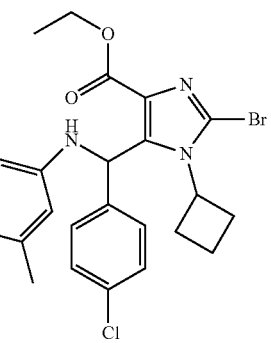

The title compound was prepared in analogy to the procedure described for step E2 using 2-bromo-5-[(4-chlorophenyl)-hydroxy-methyl]-1-cyclobutyl-1H-imidazole-4-carboxylic acid ethyl ester (product from step AK2) and the product from step 271.4 as starting materials. $t_R$: 1.13 min (LC-MS 4); ESI-MS: 535.3 [M+H]$^+$ (LC-MS 4).

The following examples have been synthesized according to described procedures herein or known literature methods using the appropriate starting materials and methods known to the skilled person in the art:

| example 275: 5-(5-Chloro-2-methyl-phenyl)-6-(5-chloro-pyridin-2-yl)-2-(2-dimethylamino-4-methoxy-pyrimidin-5-yl)-1-isopropyl-5,6-dihydro-1H-pyrrolo[3,4-d]imidazol-4-one | 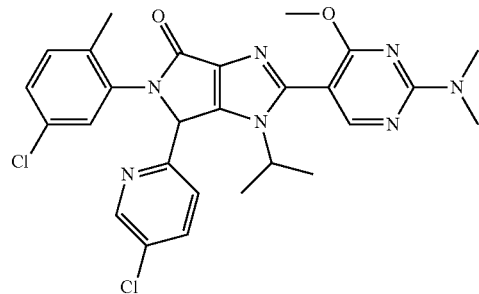 [SMILES: COc1nc(N(C)C)ncc1-c1nc2c(n1C(C)C)C(c1ccc(Cl)cn1)N(c1cc(Cl)ccc1C)C2=O] | $t_R$: 1.19 min (LC-MS 4); ESI-MS: 552.3 [M + H]$^+$ (LC-MS 4) |
|---|---|---|
| example 276: 5-(5-Chloro-2-methyl-phenyl)-6-(5-chloro-pyridin-2-yl)-2-(2,4-dimethoxy-pyrimidin-5-yl)-1-isopropyl-5,6-dihydro-1H-pyrrolo[3,4-d]imidazol-4-one | 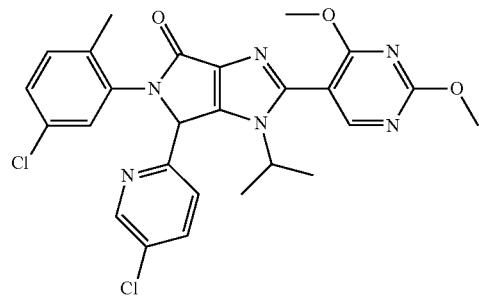 [SMILES: COc1ncc(-c2nc3c(n2C(C)C)C(c2ccc(Cl)cn2)N(c2cc(Cl)ccc2C)C3=O)c(OC)n1] | $t_R$: 1.11 min (LC-MS 4); ESI-MS: 539.2 [M + H]$^+$ (LC-MS 4); 1H-NMR (600 MHz, DMSO-d6) d ppm 8.60 (br, 1H), 8.50 (br, 1H), 7.95 (br, 1H), 7.80 (br, 1H), 7.56-7.45 (m, 1H), 7.25-7.12 (m, 2H), 6.75-6.64 (m, 1H), 4.6-4.2 (m, 1H), 4.10-4.05 (2s, 6H), 2.00 (s, 3H), 0.75-0.50 (m, 6H) |
| example 277: 4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile | 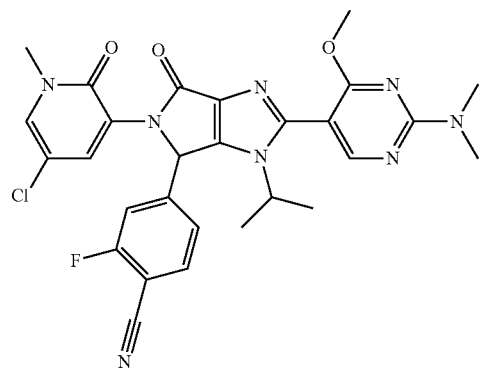 [SMILES: COc1nc(N(C)C)ncc1-c1nc2c(n1C(C)C)C(c1ccc(C#N)c(F)c1)N(c1cc(Cl)cn(C)c1=O)C2=O] | $t_R$: 0.99 min (LC-MS 4); ESI-MS: 577.2 [M + H]$^+$ (LC-MS 4); 1H-NMR (400 MHz, DMSO-d6) δ ppm 0.55 (d, J = 6.65 Hz, 3H) 1.34 (d, J = 6.78 Hz, 3H) 3.19 (s, 6H) 3.44 (s, 3H) 3.89 (s, 3H) 4.04-4.19 (m, 1H) 6.77 (s, 1H) 7.40-7.47 (m, 1H) 7.61 (d, J = 2.89 Hz, 2H) 7.95 (m, J = 2.80 Hz, 2H) 8.22 (s, 1H) |

| | | |
|---|---|---|
| example 278:<br>4-[5-(5-Chloro-1-methyl-2-oxo-1,2-dihydro-pyridin-3-yl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile | 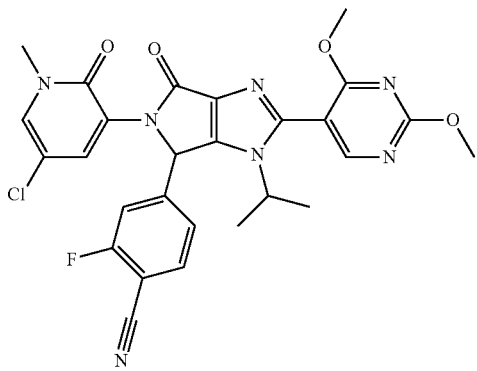 [SMILES: COc1ncc(-c2nc3c(n2C(C)C)C(c2ccc(C#N)c(F)c2)N(c2cc(Cl)cn(C)c2=O)C3=O)c(OC)n1] | $t_R$: 0.90 min (LC-MS 4); ESI-MS: 564.2 [M + H]$^+$ (LC-MS 4); 1H-NMR (400 MHz, DMSO-d6) δ ppm 0.55 (d, J = 6.78 Hz, 3H) 1.34 (d, J = 6.78 Hz, 3H) 3.45 (s, 3H) 3.94 (s, 3H) 3.99 (s, 3H) 4.09-4.20 (m, 1H) 6.79 (s, 1H) 7.38-7.49 (m, 1H) 7.62 (s, 2H) 7.96 (s, 2H) 8.50 (s, 1H) |
| example 279:<br>(S)-5-(5-Chloro-1-methyl-2-oxo-1,2-dihydro-pyridin-3-yl)-6-(4-chloro-phenyl)-2-(2,4-dihydroxy-pyrimidin-5-yl)-1-isopropyl-5,6-dihydro-1H-pyrrolo[3,4-d]imidazol-4-one | 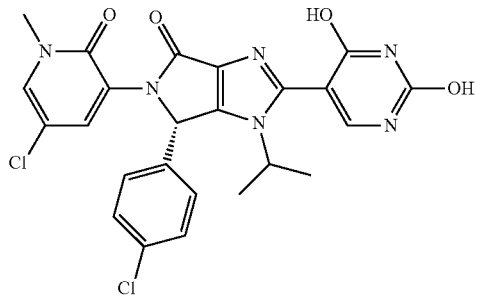 [SMILES: CC(C)n1c(-c2cnc(O)nc2O)nc2c1[C@H](c1ccc(Cl)cc1)N(c1cc(Cl)cn(C)c1=O)C2=O] | $t_R$: 0.80 min (LC-MS 4); ESI-MS: 527.3 [M + H]$^+$ (LC-MS 4) |
| example 280:<br>(R)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one | 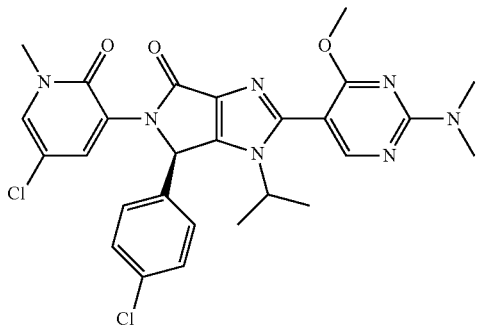 [SMILES: COc1nc(N(C)C)ncc1-c1nc2c(n1C(C)C)[C@@H](c1ccc(Cl)cc1)N(c1cc(Cl)cn(C)c1=O)C2=O] | chiral separation of example 196:<br>$t_R$: 1.10 min (LC-MS 4); ESI-MS: 568.3 [M + H]$^+$ (LC-MS 4) |
| example 281:<br>(S)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one | 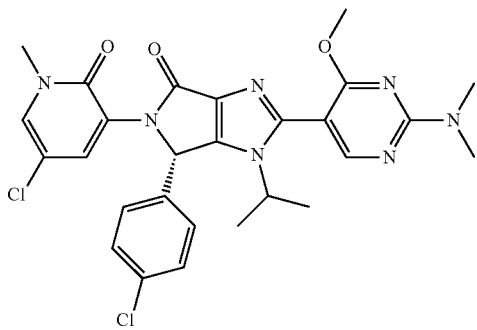 | chiral separation of example 196:<br>$t_R$: 1.10 min (LC-MS 4); ESI-MS: 568.3 [M + H]$^+$ (LC-MS 4) |

| example 282:<br>(S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 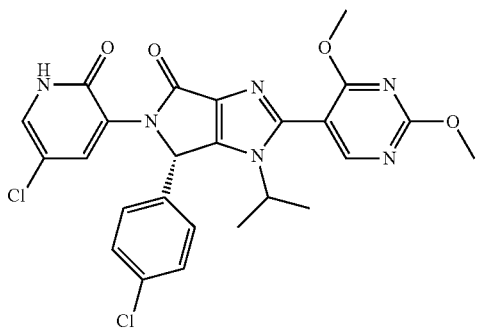 [SMILES: COc1ncc(-c2nc3c(n2C(C)C)[C@H](c2ccc(Cl)cc2)N(c2cc(Cl)c[nH]c2=O)C3=O)c(OC)n1] | chiral separation of example 122:<br>$t_R$: 0.94 min (LC-MS 4);<br>ESI-MS: 541.2 [M + H]$^+$<br>(LC-MS 4) |
| example 283:<br>(R)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 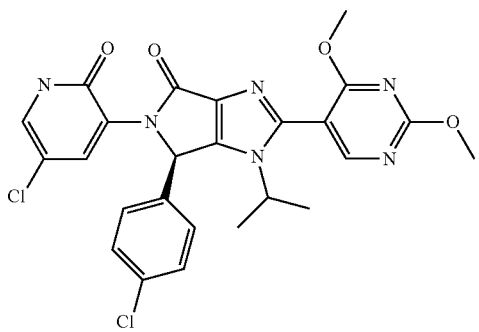 [SMILES: COc1ncc(-c2nc3c(n2C(C)C)[C@@H](c2ccc(Cl)cc2)N(c2cc(Cl)c[nH]c2=O)C3=O)c(OC)n1] | chiral separation from example 122:<br>$t_R$: 0.94 min (LC-MS 4);<br>ESI-MS: 541.2 [M + H]$^+$<br>(LC-MS 4) |
| example 284:<br>6-(4-Chloro-3-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one | 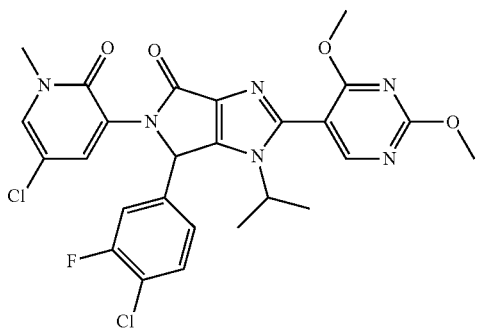 [SMILES: COc1ncc(-c2nc3c(n2C(C)C)C(c2ccc(Cl)c(F)c2)N(c2cc(Cl)cn(C)c2=O)C3=O)c(OC)n1] | $t_R$: 1.02 min (LC-MS 4);<br>ESI-MS: 573.2 [M + H]$^+$<br>(LC-MS 4) |
| example 285:<br>6-(4-Chloro-3-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one | 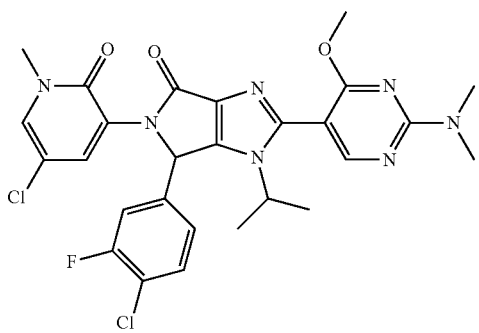 [SMILES: COc1nc(N(C)C)ncc1-c1nc2c(n1C(C)C)C(c1ccc(Cl)c(F)c1)N(c1cc(Cl)cn(C)c1=O)C2=O] | $t_R$: 1.12 min (LC-MS 4);<br>ESI-MS: 586.1 [M + H]$^+$<br>(LC-MS 4) |

| example | structure | notes |
|---|---|---|
| example 286:<br>5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-d]imidazol-4-one | 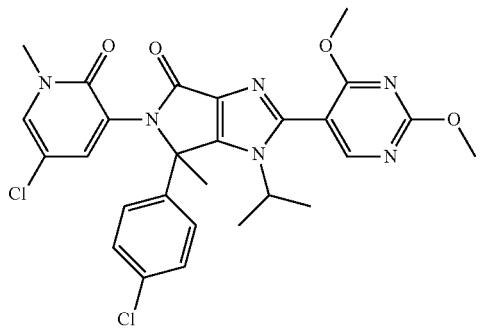 [SMILES: COc1ncc(-c2nc3c(n2C(C)C)C(C)(c2ccc(Cl)cc2)N(c2cc(Cl)cn(C)c2=O)C3=O)c(OC)n1] | Example 103 was in dissolved in THF (2 mL) and immersed in a dry ice bath. Then, 1.2 eq. KHMDS (1M in THF, Aldrich) was added and the reaction mixture was stirred for 15 min at −78° C. 3 eq. MeI (Aldrich) were added at −78° C. The dry ice bath was removed and the reaction mixture was allowed to warm up to room temperature.<br>$t_R$: 1.00 min (LC-MS 4);<br>ESI-MS: 569.2 [M + H]$^+$ (LC-MS 4) |
| example 287:<br>6-(4-Chloro-3-fluoro-phenyl)-5-(5-chloro-1-methyl-6-oxo-1,6-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one | 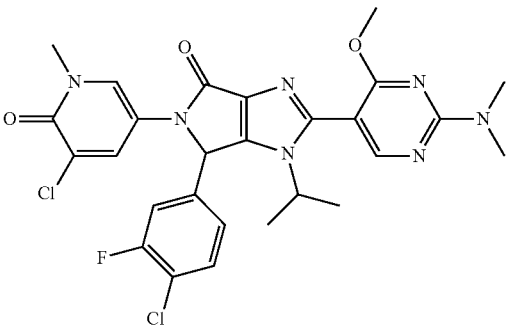 | $t_R$: 1.06 min (LC-MS 4);<br>ESI-MS: 586.1/588.2 [M + H]$^+$ (LC-MS 4); 1H-NMR (400 MHz, DMSO-d6) δ ppm 0.57 (d, J = 6.53 Hz, 3H) 1.35 (d, J = 6.65 Hz, 3H) 3.19 (s, 6H) 3.46 (s, 3H) 3.89 (s, 3H) 4.03-4.19 (m, 1H) 6.44 (s, 1H) 7.22-7.35 (m, 1H) 7.40-7.53 (m, 1H) 7.58-7.69 (m, 1H) 7.85-8.01 (m, 2H) 8.21 (s, 1H) |
| example 288:<br>4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile | 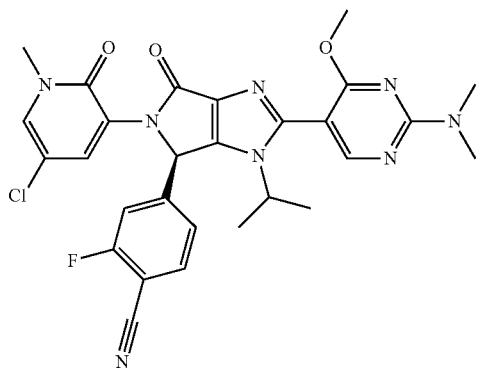 [SMILES: COc1nc(N(C)C)ncc1-c1nc2c(n1C(C)C)[C@@H](c1ccc(C#N)c(F)c1)N(c1cc(Cl)cn(C)c1=O)C2=O] | chiral separation of example 277:<br>$t_R$: 0.99 min (LC-MS 4);<br>ESI-MS: 577.2 [M + H]$^+$ (LC-MS 4); 1H-NMR (400 MHz, DMSO-d6) δ ppm 0.48-0.60 (m, 3H) 1.29-1.38 (m, 3H) 3.19 (s, 6H) 3.44 (s, 3H) 3.89 (s, 3H) 4.05-4.16 (m, 1H) 6.73-6.80 (m, 1H) 7.38-7.48 (m, 1H) 7.55-7.64 (m, 2H) 7.90-7.99 (m, 2H) 8.22 (s, 1H) |
| example 289:<br>4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile | 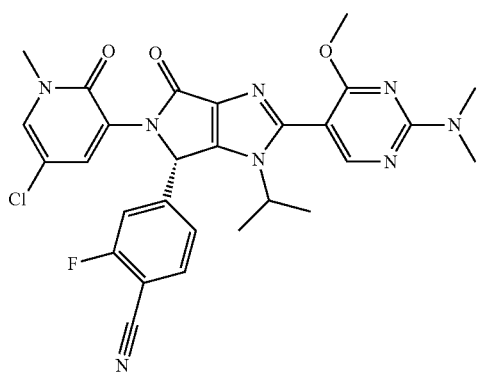 [SMILES: COc1nc(N(C)C)ncc1-c1nc2c(n1C(C)C)[C@H](c1ccc(C#N)c(F)c1)N(c1cc(Cl)cn(C)c1=O)C2=O] | chiral separation of example 277:<br>$t_R$: 0.99 min (LC-MS 4);<br>ESI-MS: 577.1 [M + H]$^+$ (LC-MS 4); 1H-NMR (400 MHz, DMSO-d6) δ ppm 0.48-0.60 (m, 3H) 1.29-1.38 (m, 3H) 3.19 (s, 6H) 3.44 (s, 3H) 3.89 (s, 3H) 4.05-4.16 (m, 1H) 6.73-6.80 (m, 1H) 7.38-7.48 (m, 1H) 7.55-7.64 (m, 2H) 7.90-7.99 (m, 2H) 8.22 (s, 1H) |

| example | structure | data |
|---|---|---|
| example 290:<br>6-(4-Chloro-3-fluoro-phenyl)-5-(5-chloro-1-methyl-6-oxo-1,6-dihydro-pyridin-3-yl)-2-(2,4-dimethoxy-pyrimidin-5-yl)-1-isopropyl-5,6-dihydro-1H-pyrrolo[3,4-d]imidazol-4-one | 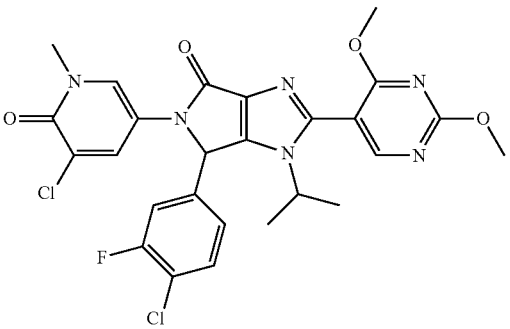 [SMILES: COc1ncc(-c2nc3c(n2C(C)C)C(c2ccc(Cl)c(F)c2)N(c2cc(Cl)c(=O)n(C)c2)C3=O)c(OC)n1] | $t_R$: 0.96 min (LC-MS 4); ESI-MS: 573.1 [M + H]$^+$ (LC-MS 4); 1H-NMR (400 MHz, DMSO-d6) δ ppm 0.57 (d, J = 6.78 Hz, 3H) 1.36 (d, J = 6.78 Hz, 3H) 3.46 (s, 3H) 3.95 (s, 3H) 3.99 (s, 3H) 4.08-4.21 (m, 1H) 6.47 (s, 1H) 7.24-7.34 (m, 1H) 7.41-7.53 (m, 1H) 7.60-7.70 (m, 1H) 7.87-7.92 (m, 1H) 7.93-7.99 (m, 1H) 8.49 (s, 1H) |
| example 291:<br>6-(4-Chloro-phenyl)-2-(2,4-dimethoxy-pyrimidin-5-yl)-5-(1,4-dimethyl-6-oxo-1,6-dihydro-pyridin-2-yl)-1-isopropyl-5,6-dihydro 1H-pyrrolo[3,4-d]imidazol-4-one | 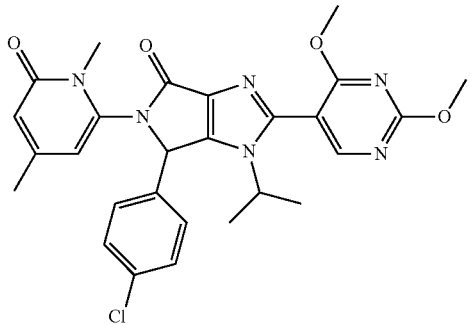 [SMILES: COc1ncc(-c2nc3c(n2C(C)C)C(c2ccc(Cl)cc2)N(c2cc(C)cc(=O)n2C)C3=O)c(OC)n1] | $t_R$: 0.95 min (LC-MS 4); ESI-MS: 535.1 [M + H]$^+$ (LC-MS 4) |
| example 292:<br>6-(4-Chloro-phenyl)-2-(2,4-dimethoxy-pyrimidin-5-yl)-5-(1,5-dimethyl-2-oxo-1,2-dihydro-pyridin-3-yl)-1-isopropyl-5,6-dihydro-1H-pyrrolo[3,4-d]imidazol-4-one | 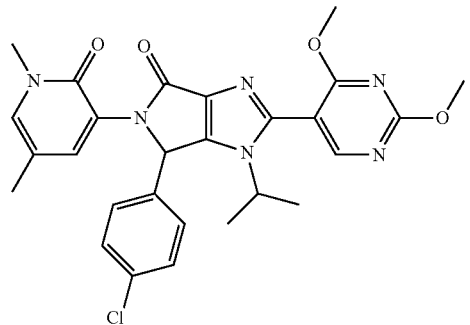 [SMILES: COc1ncc(-c2nc3c(n2C(C)C)C(c2ccc(Cl)cc2)N(c2cc(C)cn(C)c2=O)C3=O)c(OC)n1] | $t_R$: 0.97 min (LC-MS 4); ESI-MS: 535.2 [M + H]$^+$ (LC-MS 4); 1H-NMR (600 MHz, DMSO-d6) δ ppm 8.50 (s, 1H), 7.45-7.42 (m, 3H), 7.30 (d, 2H), 7.22 (s, 1H), 6.68 (s, 1H), 4.11 (m, 1H), 4.00-3.92 (m, 6H), 3.41 (s, 3H), 1.95 (s, 3H), 1.36-0.49 (m, 6H) |
| example 293:<br>6-(4-Chloro-phenyl)-2-(2-dimethylamino-4-methoxy-pyrimidin-5-yl)-5-(1,5-dimethyl-2-oxo-1,2-dihydro-pyridin-3-yl)-1-isopropyl-5,6-dihydro-1H-pyrrolo[3,4-d]imidazol-4-one | 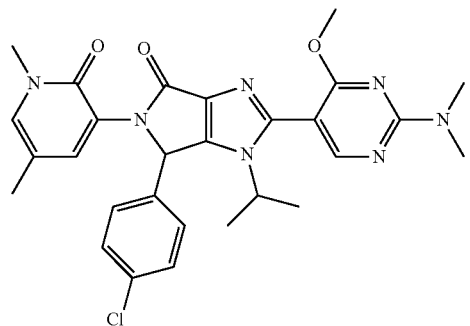 [SMILES: COc1nc(N(C)C)ncc1-c1nc2c(n1C(C)C)C(c1ccc(Cl)cc1)N(c1cc(C)cn(C)c1=O)C2=O] | $t_R$: 1.06 min (LC-MS 4); ESI-MS: 548.2 [M + H]$^+$ (LC-MS 4) |

-continued

| | | |
|---|---|---|
| example 294:<br>5-(5-Chloro-1-difluoromethyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 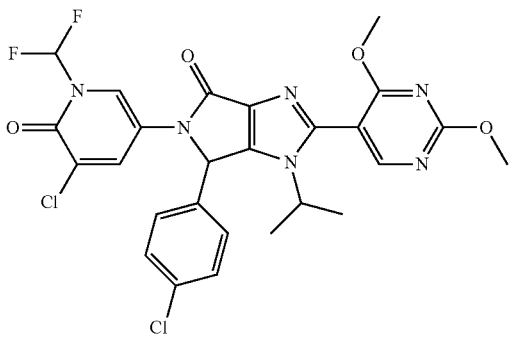 [SMILES: COc1ncc(-c2nc3c(n2C(C)C)C(c2ccc(Cl)cc2)N(c2cc(Cl)c(=O)n(C(F)F)c2)C3=O)c(OC)n1] | $t_R$: 1.07 min (LC-MS 4);<br>ESI-MS: 591.1/593.2<br>[M + H]$^+$ (LC-MS 4) |
| example 295:<br>5-(5-Chloro-1-methyl-d3-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 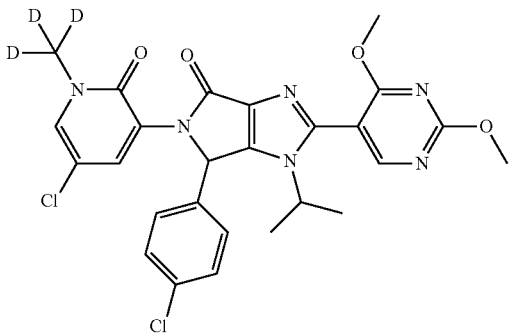 [SMILES: [2H]C([2H])([2H])n1cc(Cl)cc(N2C(=O)c3nc(-c4cnc(OC)nc4OC)n(C(C)C)c3C2c2ccc(Cl)cc2)c1=O] | $t_R$: 1.03 min (LC-MS 4);<br>ESI-MS: 558.2/560.2<br>[M + H]$^+$ (LC-MS 4) |
| example 296:<br>5-(5-Chloro-1-ethyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 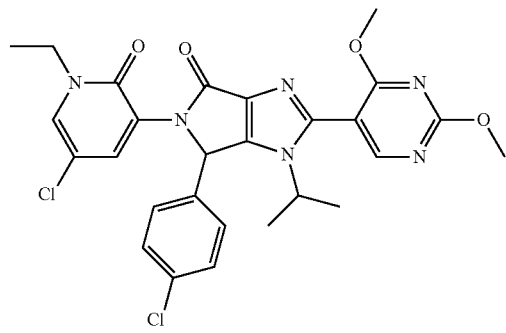 [SMILES: CCn1cc(Cl)cc(N2C(=O)c3nc(-c4cnc(OC)nc4OC)n(C(C)C)c3C2c2ccc(Cl)cc2)c1=O] | $t_R$: 1.09 min (LC-MS 4);<br>ESI-MS: 569.2/571.2<br>[M + H]$^+$ (LC-MS 4) |
| example 297:<br>5-(5-Chloro-1-methyl-2-oxo-1,2-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-d]imidazol-4-one | 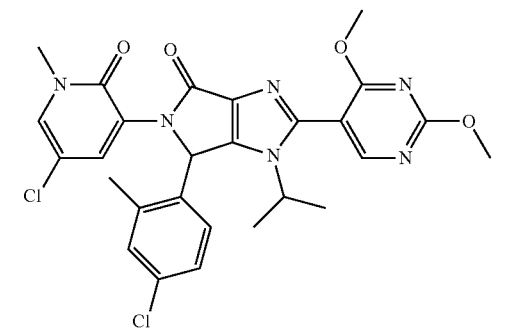 [SMILES: COc1ncc(-c2nc3c(n2C(C)C)C(c2ccc(Cl)cc2C)N(c2cc(Cl)cn(C)c2=O)C3=O)c(OC)n1] | $t_R$: 1.08 min (LC-MS 4);<br>ESI-MS: 569.2/571.3<br>[M + H]$^+$ (LC-MS 4) | example 298:
5-(5-Chloro-1-methyl-2-oxo-1,2-dihydro-pyridin-3-yl)-6-(4-chloro-phenyl)-1-isopropyl-2-(4-methoxy-2-oxo-1,2-dihydro-pyrimidin-5-yl)-5,6-dihydro-1H-pyrrolo[3,4-d]imidazol-4-one

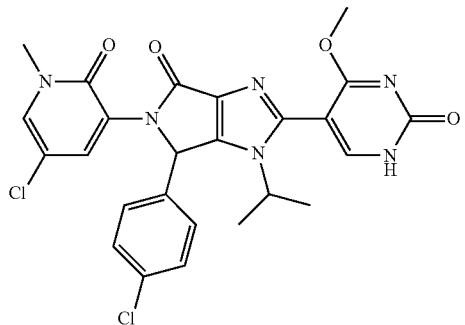 [SMILES: COc1nc(=O)[nH]cc1-c1nc2c(n1C(C)C)C(c1ccc(Cl)cc1)N(c1cc(Cl)cn(C)c1=O)C2=O]

$t_R$: 0.84 min (LC-MS 4); ESI-MS: 541.4.2/543.2 [M + H]$^+$ (LC-MS 4); 1H-NMR (400 MHz, DMSO-d6) δ ppm 11.87 (s, NH, 1H), 8.05 (s, 1H), 7.94 (d, 1H), 7.51 (d, 1H), 7.42-7.30 (m, 4H), 6.69 (s, 1H), 4,19 (m, 1H), 3.82 (s, 3H), 3.44 (s, 3H), 1.34/0.53 (2d, 6H)

example 299:
6-(4-Chloro-phenyl)-5-(2,6-dimethyl-pyrimidin-4-yl)-1-isopropyl-2-(5-methoxy-1-methyl-2-oxo-1,2-dihydro-pyridin-4-yl)-5,6-dihydro-1H-pyrrolo[3,4-d]imidazol-4-one

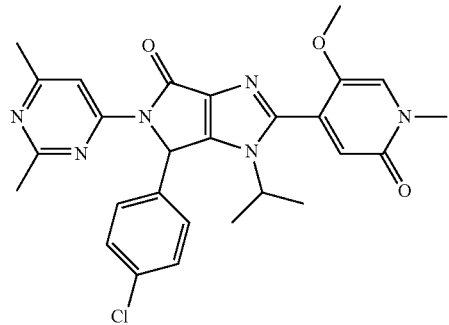 [SMILES: COc1cn(C)c(=O)cc1-c1nc2c(n1C(C)C)C(c1ccc(Cl)cc1)N(c1cc(C)nc(C)n1)C2=O]

$t_R$: 0.89 min (LC-MS 2); ESI-MS: 519.2 [M + H]$^+$ (LC-MS 2)

example 300:
6-(4-Chloro-phenyl)-2-(2,4-dimethoxy-pyrimidin-5-yl)-1-isopropyl-5-(3-methoxy-6-methyl-pyridazin-4-yl)-5,6-dihydro-1H-pyrrolo[3,4-d]imidazol-4-one

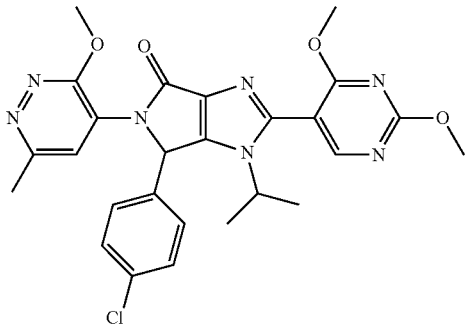 [SMILES: COc1ncc(-c2nc3c(n2C(C)C)C(c2ccc(Cl)cc2)N(c2cc(C)nnc2OC)C3=O)c(OC)n1]

$t_R$: 0.94 min (LC-MS 2); ESI-MS: 536.3/538.1 [M + H]$^+$ (LC-MS 2)

example 301:
5-(5-Chloro-2-methoxy-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one

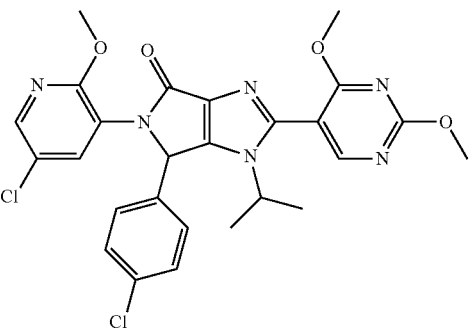 [SMILES: COc1ncc(-c2nc3c(n2C(C)C)C(c2ccc(Cl)cc2)N(c2cc(Cl)cnc2OC)C3=O)c(OC)n1]

$t_R$: 1.15 min (LC-MS 2); ESI-MS: 555.1/557.2 [M + H]$^+$ (LC-MS 2)

-continued

| | | |
|---|---|---|
| example 302:<br>6-(4-Chloro-phenyl)-2-(2-dimethylamino-4-methoxy-pyrimidin-5-yl)-1-isopropyl-5-(3-methoxy-6-methyl-pyridazin-4-yl)-5,6-dihydro-1H-pyrrolo[3,4-d]imidazol-4-one | 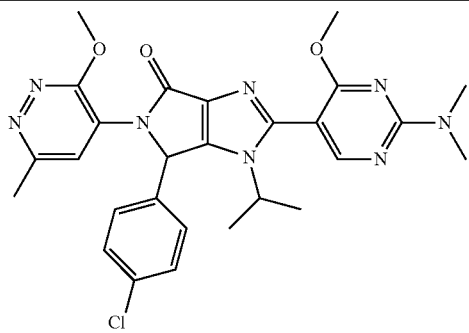 | $t_R$: 1.06 min (LC-MS 2);<br>ESI-MS: 549.2 [M + H]$^+$<br>(LC-MS 2) |
| example 303:<br>6-(4-Chloro-2-fluoro-phenyl)-5-(3-chloro-2-fluoro-phenyl)-2-(2-dimethylamino-4-methoxy-pyrimidin-5-yl)-1-isopropyl-5,6-dihydro-1H-pyrrolo[3,4-d]imidazol-4-one | 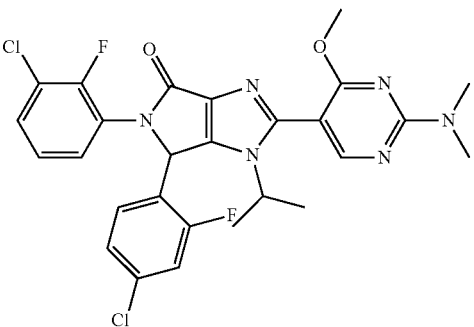 [SMILES: COc1nc(N(C)C)ncc1-c1nc2c(n1C(C)C)C(c1ccc(Cl)cc1F)N(c1cccc(Cl)c1F)C2=O] | $t_R$: 1.27 min (LC-MS 2);<br>ESI-MS: 573.3/575.2<br>[M + H]$^+$ (LC-MS 2) |
| example 304:<br>6-(4-Chloro-2-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one | 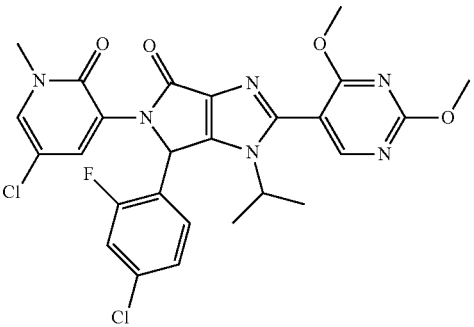 [SMILES: COc1ncc(-c2nc3c(n2C(C)C)C(c2ccc(Cl)cc2F)N(c2cc(Cl)cn(C)c2=O)C3=O)c(OC)n1] | $t_R$: 1.02 min (LC-MS 2);<br>ESI-MS: 573.1/575.1<br>[M + H]$^+$ (LC-MS 2) |
| example 305:<br>6-(4-Chloro-2-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one | 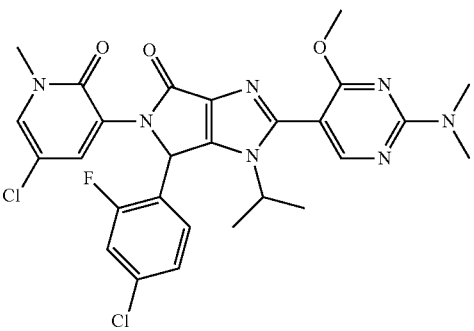 [SMILES: COc1nc(N(C)C)ncc1-c1nc2c(n1C(C)C)C(c1ccc(Cl)cc1F)N(c1cc(Cl)cn(C)c1=O)C2=O] | $t_R$: 1.12 min (LC-MS 2);<br>ESI-MS: 586.1/588.1<br>[M + H]$^+$ (LC-MS 2) |
| example 306:<br>6-(4-Chloro-phenyl)-2-(2-dimethylamino-4-methoxy-pyrimidin-5-yl)-5-(4-fluoro-2,5-dimethyl-2H-pyrazol-3-yl)-1-isopropyl-5,6-dihydro-1H-pyrrolo[3,4-d]imidazol-4-one | 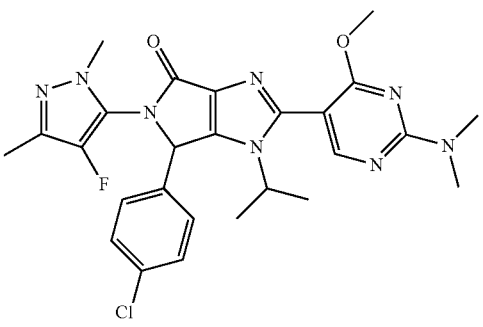 | $t_R$: 1.14 min (LC-MS 2);<br>ESI-MS: 539.3 [M + H]$^+$<br>(LC-MS 2) |

-continued

| | | |
|---|---|---|
| example 307:<br>(S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 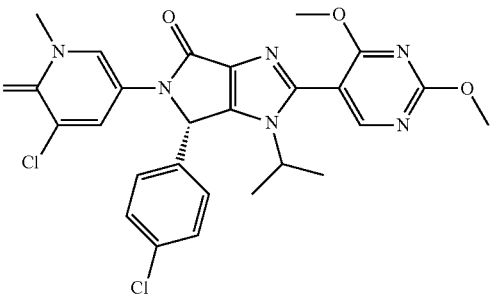 | $t_R$: 0.95 min (LC-MS 2);<br>ESI-MS: 555.2/557.2<br>[M + H]$^+$ (LC-MS 2); $t_R$:<br>2.32 min (Column:<br>Chiralcel OD H 4.6 × 250<br>mm. Flow 3.0 mL/min.<br>scCO$_2$/MeOH 65:35.<br>Detection: UV 210 nM),<br>>99% ee |
| example 308:<br>(R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one | 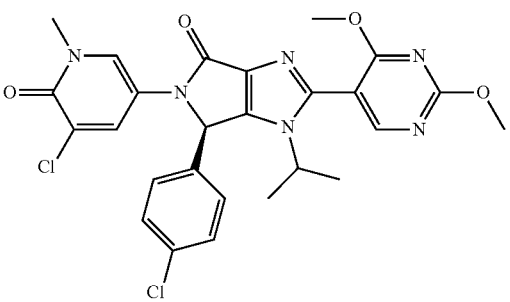 [SMILES: COc1ncc(-c2nc3c(n2C(C)C)[C@@H](c2ccc(Cl)cc2)N(c2cc(Cl)c(=O)n(C)c2)C3=O)c(OC)n1] | $t_R$: 0.95 min (LC-MS 2);<br>ESI-MS: 555.1/557.1<br>[M + H]$^+$ (LC-MS 2); $t_R$:<br>5.13 min (Column:<br>Chiralcel OD H 4.6 × 250<br>mm. Flow 3.0 mL/min.<br>scCO$_2$/MeOH 65:35.<br>Detection: UV 210 nM),<br>>99% ee |
| example 309:<br>6-(4-Chloro-phenyl)-5-(5-cyclopropyl-4-fluoro-2-methyl-2H-pyrazol-3-yl)-2-(2,4-dimethoxy-pyrimidin-5-yl)-1-isopropyl-5,6-dihydro-1H-pyrrolo[3,4-d]imidazol-4-one | 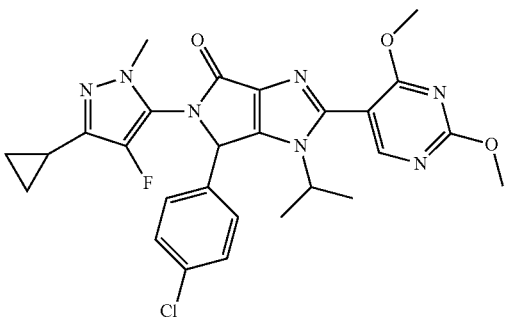 [SMILES: COc1ncc(-c2nc3c(n2C(C)C)C(c2ccc(Cl)cc2)N(c2c(F)c(C4CC4)nn2C)C3=O)c(OC)n1] | $t_R$: 1.13 min (LC-MS 4);<br>ESI-MS: 552.2 [M + H]$^+$<br>(LC-MS 4) |
| example 310:<br>6-(4-Chloro-phenyl)-5-(5-cyclopropyl-4-fluoro-2-methyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-d]imidazol-4-one | 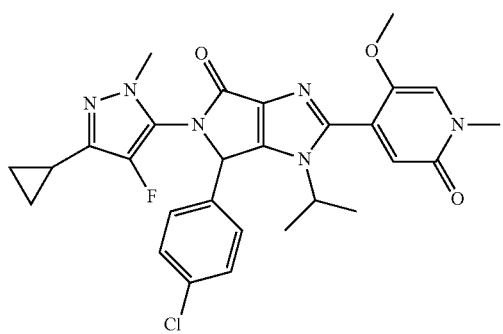 [SMILES: COc1cn(C)c(=O)cc1-c1nc2c(n1C(C)C)C(c1ccc(Cl)cc1)N(c1c(F)c(C3CC3)nn1C)C2=O] | $t_R$: 0.98 min (LC-MS 4);<br>ESI-MS: 551.2 [M + H]$^+$<br>(LC-MS 4) |
| example 311:<br>4-{5-(3-Chloro-2-fluoro-phenyl)-2-[2-(1,1-dioxo-1-thiomorpholin-4-yl)-4-methoxy-pyrimidin-5-yl]-3-isopropyl-6-oxo-3,4,5,6-tetrahydro-pyrrolo[3,4-d]imidazol-4-yl}-benzonitrile | 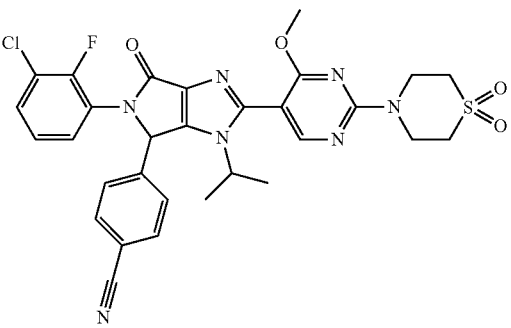 [SMILES: COc1nc(N2CCS(=O)(=O)CC2)ncc1-c1nc2c(n1C(C)C)C(c1ccc(C#N)cc1)N(c1cccc(Cl)c1F)C2=O] | $t_R$: 1.00 min (LC-MS 4);<br>ESI-MS: 636.2, 638.2<br>[M + H]$^+$ (LC-MS 4) |

-continued

| | | |
|---|---|---|
| example 312: 4-{5-(3-Chloro-2-fluoro-phenyl)-2-[2-((S)-3-hydroxy-piperidin-1-yl)-4-methoxy-pyrimidin-5-yl]-3-isopropyl-6-oxo-3,4,5,6-tetrahydro-pyrrolo[3,4-d]imidazol-4-yl}-benzonitrile | 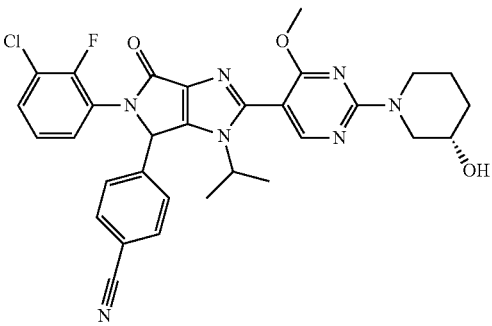 [SMILES: COc1nc(N2CCC[C@H](O)C2)ncc1-c1nc2c(n1C(C)C)C(c1ccc(C#N)cc1)N(c1cccc(Cl)c1F)C2=O] | $t_R$: 1.02 min (LC-MS 4); ESI-MS: 602.2, 604.3 [M + H]$^+$ (LC-MS 4) |
| example 313: 2-(2-amino-4-methoxypyrimidin-5-yl)-5-(3-chloro-4-fluorophenyl)-6-(4-chlorophenyl)-1-((R)-1-methoxypropan-2-yl)-5,6-dihydropyrrolo[3,4-d]imidazol-4(1H)-one | 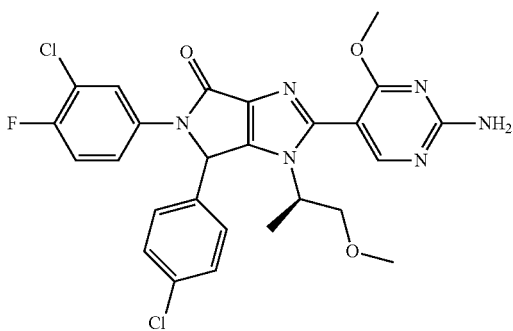 [SMILES: COC[C@@H](C)n1c(-c2cnc(N)nc2OC)nc2c1C(c1ccc(Cl)cc1)N(c1ccc(F)c(Cl)c1)C2=O] | $t_R$: 1.06/1.08 min (LC-MS 2); ESI-MS: 557.1/559.1 [M + H]$^+$ (LC-MS 2); Rf = 0.19 (EtOAc-MeOH, 20:1). |
| example 314: 2-(2-amino-4-methoxypyrimidin-5-yl)-5-(5-chloro-2-methylphenyl)-6-(4-chlorophenyl)-1-((R)-1-methoxypropan-2-yl)-5,6-dihydropyrrolo[3,4-d]imidazol-4(1H)-one | 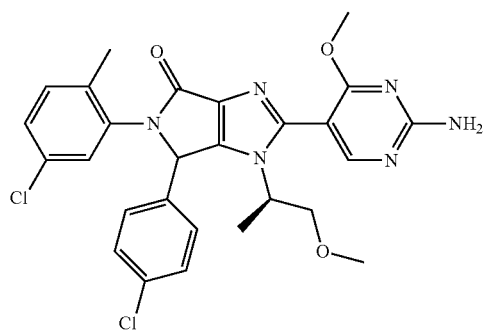 [SMILES: COC[C@@H](C)n1c(-c2cnc(N)nc2OC)nc2c1C(c1ccc(Cl)cc1)N(c1cc(Cl)ccc1C)C2=O] | $t_R$: 1.07/1.09 min (LC-MS 2); ESI-MS: 553.1/555.1 [M + H]$^+$ (LC-MS 2); Rf = 0.09 (EtOAc-MeOH, 98:2). |
| example 315: (R)-5-(3-chloro-2-fluorophenyl)-6-(4-chlorophenyl)-2-(2,4-dimethoxypyrimidin-5-yl)-1-((R)-1-hydroxypropan-2-yl)-5,6-dihydropyrrolo[3,4-d]imidazol-4(1H)-one | 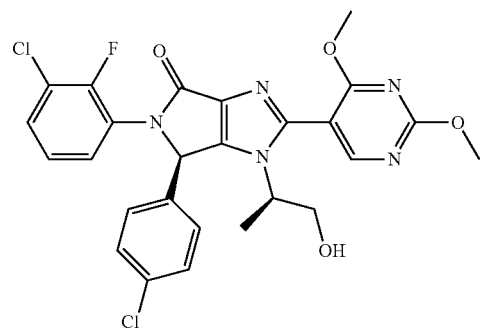 [SMILES: COc1ncc(-c2nc3c(n2[C@H](C)CO)[C@@H](c2ccc(Cl)cc2)N(c2cccc(Cl)c2F)C3=O)c(OC)n1] | $t_R$: 1.01 min (LC-MS 2); ESI-MS: 558.1/560.0 [M + H]$^+$ (LC-MS 2) |

| | | |
|---|---|---|
| example 316:<br>(S)-5-(3-chloro-2-fluorophenyl)-6-(4-chlorophenyl)-2-(2,4-dimethoxypyrimidin-5-yl)-1-((R)-1-hydroxypropan-2-yl)-5,6-dihydropyrrolo[3,4-d]imidazol-4(1H)-one | 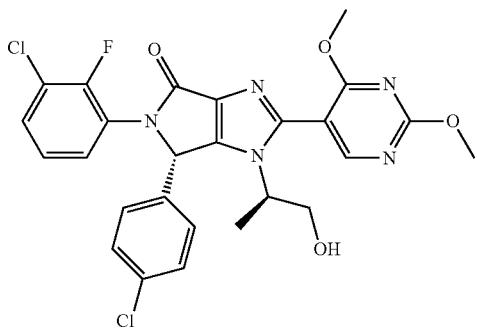 [SMILES: COc1ncc(-c2nc3c(n2[C@H](C)CO)[C@H](c2ccc(Cl)cc2)N(c2cccc(Cl)c2F)C3=O)c(OC)n1] | $t_R$: 1.04 min (LC-MS 2); ESI-MS: 558.1/560.0 [M + H]⁺ (LC-MS 2) |
| example 317:<br>(S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one | 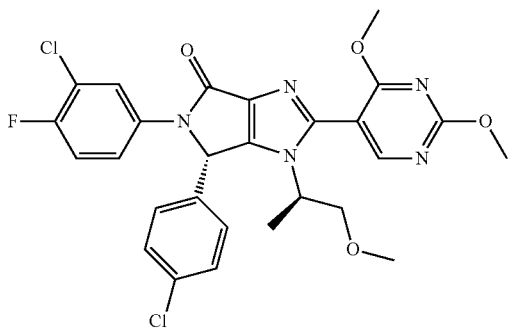 [SMILES: COC[C@@H](C)n1c(-c2cnc(OC)nc2OC)nc2c1[C@H](c1ccc(Cl)cc1)N(c1ccc(F)c(Cl)c1)C2=O] | $t_R$: 1.19 min (LC-MS 2); ESI-MS: 572.0/574.0 [M + H]⁺ (LC-MS 2); Rf = 0.10 (heptane - EtOAc, 1:4); 1H-NMR (DMSO-d6, 600 MHz) δ ppm 8.43 (s, 1H), 7.84 (d, 1H), 7.54 (m, 1H), 7.42-7.32 (m, 5H), 6.64 (s, 1H), 4.16 (m, 1H), 3.97 (s, 3H), 3.91 (s, 3H), 3.62 (m, 1H), 3.41 (m, 1H), 3.22 (s, 3H), 0.52 (d, 3H). |
| example 318:<br>(R)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one | 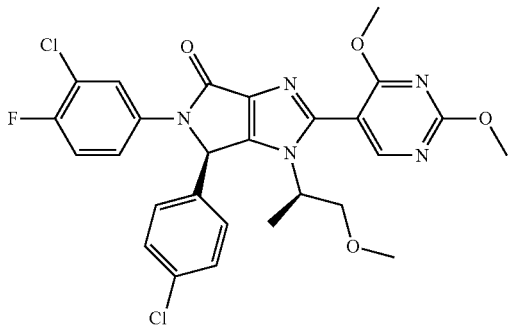 [SMILES: COC[C@@H](C)n1c(-c2cnc(OC)nc2OC)nc2c1[C@@H](c1ccc(Cl)cc1)N(c1ccc(F)c(Cl)c1)C2=O] | $t_R$: 1.17 min (LC-MS 2); ESI-MS: 572.0/574.0 [M + H]⁺ (LC-MS 2); Rf = 0.10 (heptane - EtOAc, 1:4). |
| example 319:<br>5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one | 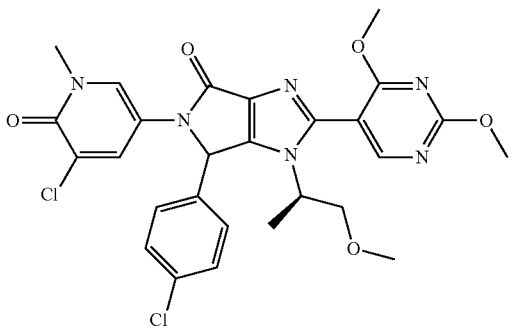 [SMILES: COC[C@@H](C)n1c(-c2cnc(OC)nc2OC)nc2c1C(c1ccc(Cl)cc1)N(c1cc(Cl)c(=O)n(C)c1)C2=O] | $t_R$: 0.91/0.93 min (LC-MS 2); ESI-MS: 585.0/587.0 [M + H]⁺ (LC-MS 2); Rf = 0.07/0.10 (DCM - MeOH, 20:1). |

| | | |
|---|---|---|
| example 320:<br>5-(5-chloro-1-methyl-2-oxo-1,2-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one | 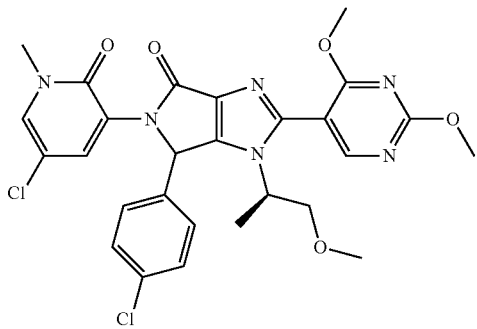 [SMILES: COC[C@@H](C)n1c(-c2cnc(OC)nc2OC)nc2c1C(c1ccc(Cl)cc1)N(c1cc(Cl)cn(C)c1=O)C2=O] | $t_R$: 0.99/1.01 min (LC-MS 2); ESI-MS: 585.0/587.0 [M + H]$^+$ (LC-MS 2); Rf = 0.07/0.10 (DCM-MeOH, 20:1). |
| example 321:<br>5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one | 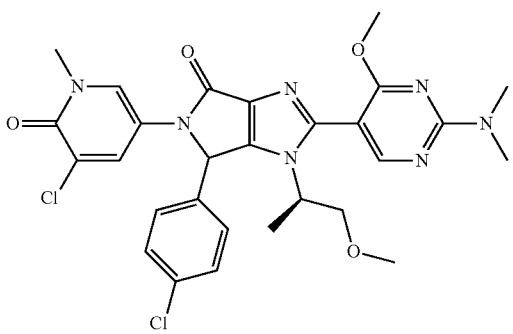 | $t_R$: 0.99/1.02 min (LC-MS 2); ESI-MS: 598.1/600.1 [M + H]$^+$ (LC-MS 2); Rf = 0.18/0.23 (EtOAc-MeOH, 10:1). |
| example 322:<br>(S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one | 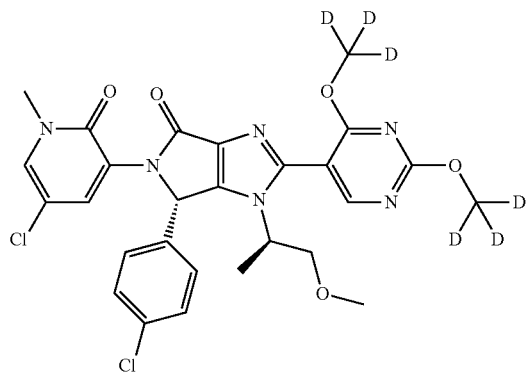 | $t_R$: 1.01 min (LC-MS 2); ESI-MS: 561.2/563.2 [M + H]$^+$ (LC-MS 2); 1H-NMR (DMSO-d6, 600 MHz) δ ppm 8.49 (s, 1H), 7.91 (s, 1H), 7.50 (s, 1H), 7.42 (m, 2H), 7.33 (m, 2H), 6.72 (s, 1H), 4.12 (m, 1H), 3.44 (s, 3H), 1.34 (d, 3H), 0.52 (d, 3H). |
| example 323:<br>(S)-5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one | 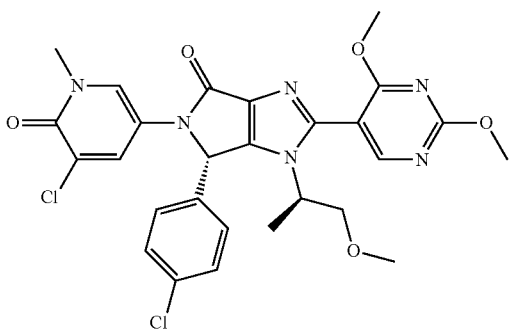 [SMILES: COC[C@@H](C)n1c(-c2cnc(OC)nc2OC)nc2c1[C@H](c1ccc(Cl)cc1)N(c1cc(Cl)c(=O)n(C)c1)C2=O] | $t_R$: 0.94 min (LC-MS 2); ESI-MS: 585.1/587.1 [M + H]$^+$ (LC-MS 2); 1H-NMR (DMSO-d6, 600 MHz) δ ppm 8.44 (s, 1H), 7.89 (s, 1H), 7.87 (s, 1H), 7.44 (d, 2H), 7.35 (bs, 2H), 6.30 (s, 1H), 4.17 (m, 1H), 3.98 (s, 3H), 3.92 (s, 3H), 3.53 (m, 1H), 3.45 (s, 3H), 3.40 (m, 1H), 3.22 (s, 3H), 0.55 (d, 3H) |

-continued

| | | |
|---|---|---|
| example 324:<br>(R)-5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one | 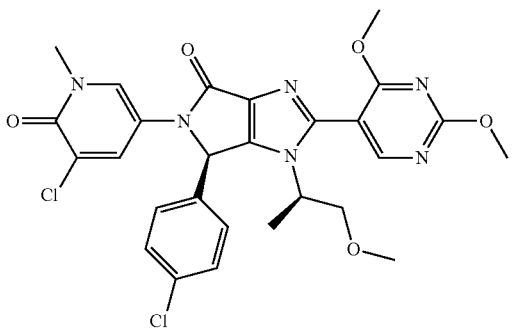 [SMILES: COC[C@@H](C)n1c(-c2cnc(OC)nc2OC)nc2c1[C@@H](c1ccc(Cl)cc1)N(c1cc(Cl)c(=O)n(C)c1)C2=O] | $t_R$: 0.91 min (LC-MS 2);<br>ESI-MS: 585.1/587.1<br>[M + H]$^+$ (LC-MS 2) |
| example 325:<br>(S)-5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one | 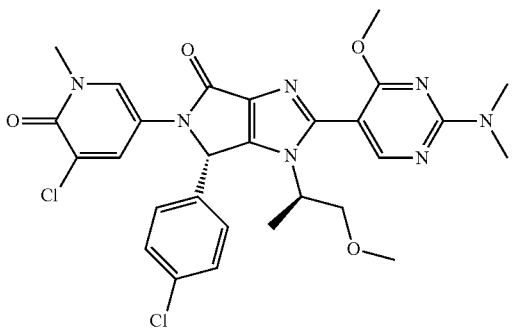 [SMILES: COC[C@@H](C)n1c(-c2cnc(N(C)C)nc2OC)nc2c1[C@H](c1ccc(Cl)cc1)N(c1cc(Cl)c(=O)n(C)c1)C2=O] | $t_R$: 1.03 min (LC-MS 2);<br>ESI-MS: 598.0/600.0<br>[M + H]$^+$ (LC-MS 2); 1H-NMR (DMSO-d6, 600 MHz) δ ppm 8.17 (s, 1H), 7.87 (m, 2H), 7.43 (m, 2H), 7.34 (bs, 2H), 6.28 (s, 1H), 4.13 (m, 1H), 3.87 (s, 3H), 3.54 (m, 1H), 3.45 (s, 3H), 3.41 (m, 1H), 3.22 (s, 3H), 3.18 (6H, s), 0.55 (d, 3H) |
| example 326:<br>(R)-5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one | 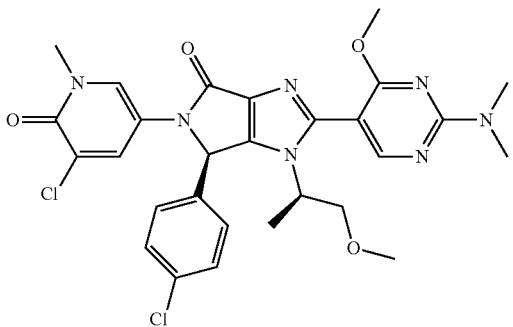 [SMILES: COC[C@@H](C)n1c(-c2cnc(N(C)C)nc2OC)nc2c1[C@@H](c1ccc(Cl)cc1)N(c1cc(Cl)c(=O)n(C)c1)C2=O] | $t_R$: 0.91 min (LC-MS 2);<br>ESI-MS: 598.0/600.0<br>[M + H]$^+$ (LC-MS 2) |

Selected compounds have been crystallized and further characterized. The experimental procedures and the instrument and method description are outlined below:

Instrument Name: X-Ray Diffractometer

Model: D8 Advance

Manufacturer: Bruker AXS GMBH

Wavelength: 1.5406 A (Cu)

Generator setting: 30 Kv; 40 mA

Monochromator

Detector: PSD-Lynx Eye

Experiment Method:

2-Theta start: 2.0 degree

2-Theta end: 40.0 degree

Integration stepsize: 0.0157 degree

Scan Time: 13.02 min

Temperature: room temperature

The following methods A to G below disclose methods to obtain certain crystalline forms of Example compounds described herein.

A. 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile (Example 79) crystalline Form A

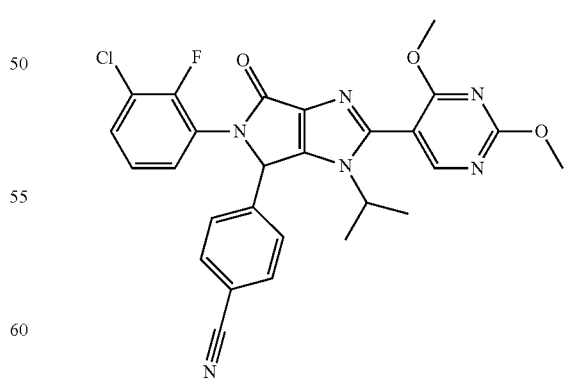

The compound of Example 79 was triturated in diisopropylether and stirred overnight at rt. The suspension was filtered, and the colorless solid was dried under high vacuum overnight at rt to give crystalline material Form A.

| Angle 2-Theta ° | d value Angstrom | Intensity |
|---|---|---|
| 6.54 | 13.50 | Medium |
| 10.00 | 8.83 | Low |
| 10.88 | 8.13 | Low |
| 14.29 | 6.19 | Medium |
| 15.72 | 5.63 | Medium |
| 16.78 | 5.28 | High |
| 17.82 | 4.97 | Medium |
| 19.41 | 4.57 | High |
| 20.10 | 4.41 | Medium |
| 20.67 | 4.29 | Medium |
| 23.65 | 3.76 | High |
| 25.82 | 3.44 | High |

B. 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile (Example 199) crystalline Form A

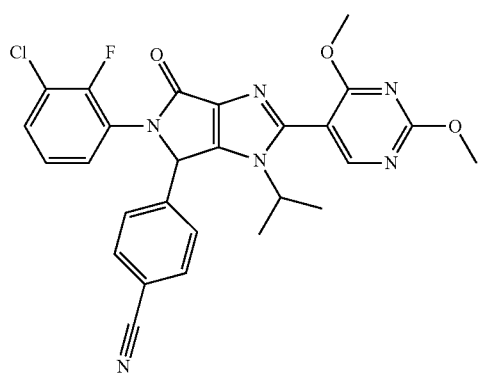 [SMILES: COc1ncc(-c2nc3c(n2C(C)C)C(c2ccc(C#N)cc2)N(c2cccc(Cl)c2F)C3=O)c(OC)n1]

The compound of Example 199 (2.20 g) was dissolved in 25 ml ethyl acetate under stirring. Colorless solid was formed again and the suspension was stirred for one additional hour. Under stirring 25 ml diisopropyl ether were added and the mixture was stirred for 5 minutes. The suspension was filtered and the residue was washed with diisopropyl ether (two times 10 ml). The colorless solid was dried at the high vacuum pump over night at 50° C. to obtain 2.03 g colorless crystals Form A.

| Angle 2-Theta ° | d value Angstrom | Intensity |
|---|---|---|
| 6.25 | 14.13 | Medium |
| 9.44 | 9.36 | Low |
| 10.34 | 8.55 | Medium |
| 14.02 | 6.31 | Low |
| 14.83 | 5.97 | Medium |
| 15.33 | 5.77 | Medium |
| 15.84 | 5.59 | Medium |
| 16.96 | 5.22 | High |
| 19.16 | 4.63 | Medium |
| 19.50 | 4.55 | Medium |
| 20.94 | 4.24 | Medium |
| 22.32 | 3.98 | Medium |
| 25.05 | 3.55 | Medium |
| 25.74 | 3.46 | Medium |
| 27.33 | 3.26 | Low |

C. (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Example 102) crystalline Form A (ethanol solvate)

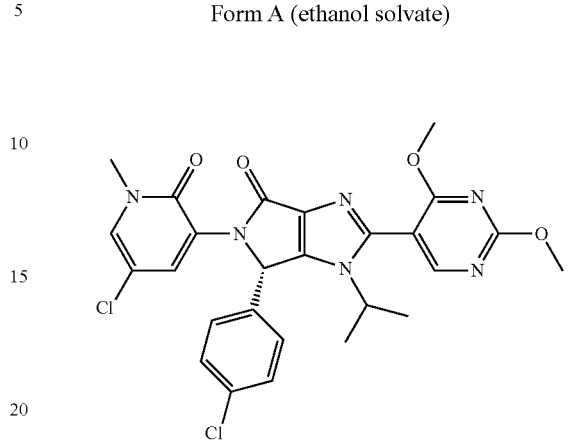

The compound of Example 102 (2.02 g, ee 99.8%) was taken up in ethanol and the mixture was heated to reflux under stirring to get a clear solution (total amount ethanol used: 48 ml). The clear yellowish solution was allowed to cool down to ambient temperature under stirring overnight. The precipitate was filtered off and dried under high vacuum to obtain 1.78 g colorless solid Form A ethanol solvate. The solid contains 7.5% ethanol (1 equivalent), seen by 1H-NMR.

| Angle 2-Theta ° | d value Angstrom | Intensity |
|---|---|---|
| 9.44 | 9.36 | Low |
| 9.89 | 8.94 | High |
| 10.69 | 8.27 | Low |
| 12.33 | 7.17 | Medium |
| 14.61 | 6.06 | Medium |
| 16.21 | 5.46 | Medium |
| 16.66 | 5.32 | Medium |
| 17.50 | 5.07 | Medium |
| 17.78 | 4.98 | Medium |
| 19.83 | 4.47 | Medium |
| 20.56 | 4.32 | Medium |
| 22.35 | 3.97 | Medium |
| 22.98 | 3.87 | Medium |
| 25.81 | 3.44897 | Medium |

D. (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Example 102) crystalline Form B (succinic acid co-crystal)

The compound of Example 102 (100 mg) was dissolved in 2 ml ethyl acetate and warmed to 55° C. 25.5 mg (1.2 equivalent) succinic acid was added to the solution and the mixture was cooled down to 5° C. and warmed back to 55° C. for 4 times in one day. The formed precipitate was filtered off and dried at 40° C. under vacuum for 4 hours to yield the product as colorless powder Form B succinic acid form (stoichiometry by NMR 1.04 succinic acid to I free form).

| Angle 2-Theta ° | d value Angstrom | Intensity |
|---|---|---|
| 9.037 | 9.78 | High |
| 11.64 | 7.60 | Low |
| 14.55 | 6.08 | Low |
| 15.14 | 5.85 | Low |
| 15.60 | 5.68 | Low |
| 16.55 | 5.35 | Low |
| 17.27 | 5.13 | High |
| 19.52 | 4.54 | Medium |
| 19.87 | 4.46 | Low |
| 20.85 | 4.26 | Medium |
| 21.14 | 4.20 | Medium |
| 23.42 | 3.80 | Medium |
| 23.67 | 3.76 | Medium |
| 24.54 | 3.62 | Medium |
| 26.95 | 3.31 | Medium |

E. (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one (Example 102) crystalline Form C (hydrate)

The compound of Example 102 (10 mg) was dissolved in 0.1 ml IPA (isopropyl alcohol) under shaking or heating at 50° C. White solid was formed after sonication for 5 seconds and the suspension was stirred for 2 days at room temperature. The solid was separated by centrifugation and dried at 40° C. in vacuum for 2 days to obtain IPA solvate. Said IPA solvate (8 mg) was suspended in 0.2 ml MeOH:H$_2$O (1:9, v/v) under stirring for 2 days at room temperature. The resulting solid was separated by centrifugation and dried in air for 2 hours to yield the Form C hydrate as white powder.

Alternatively, ethanol solvate from Method C above was dissolved in methanol, and clear solution obtained after 10 min with continuous stirring at room temperature. Water was added and precipitation observed after 10 min at room temperature, then further water was added while stirring for up to 24 hours. The resulting solid was separated by centrifugation., then dried at room temperature to yield the Form C hydrate.

| Angle 2-Theta ° | d value Angstrom | Intensity |
|---|---|---|
| 8.14 | 10.86 | Low |
| 10.09 | 8.76 | Medium |
| 11.92 | 7.42 | Low |
| 14.52 | 6.10 | Medium |
| 14.88 | 5.95 | Medium |
| 16.93 | 5.23 | Medium |
| 17.56 | 5.05 | Medium |
| 17.98 | 4.93 | Low |
| 19.18 | 4.62 | Medium |
| 20.46 | 4.34 | High |
| 20.87 | 4.25 | Medium |
| 21.86 | 4.06 | Medium |
| 25.00 | 3.56 | High |
| 25.68 | 3.47 | Medium |
| 25.95 | 3.43 | Low |
| 28.57 | 3.12 | Medium |
| 32.17 | 2.78 | Medium |

F. 4-[(S)-5-(5-Chloro-1-methyl-2-oxo-1,2-dihydropyridin-3-yl)-2-(2-dimethylamino-4-methoxy-pyrimidin-5-yl)-3-isopropyl-6-oxo-3,4,5,6-tetrahydropyrrolo[3,4-d]imidazol-4-yl]-benzonitrile (Example 160) crystalline Form A

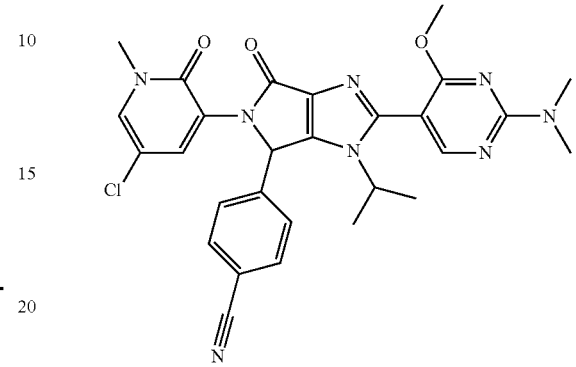

The compound of Example 160 (473 mg) was triturated in diethylether and stirred. After 1 hour, the solid was filtered off and dried to afford crystalline colorless material Form A.

| Angle 2-Theta ° | d value Angstrom | Intensity |
|---|---|---|
| 7.57 | 11.67 | Medium |
| 9.11 | 9.70 | Medium |
| 10.25 | 8.62 | High |
| 11.16 | 7.92 | High |
| 12.18 | 7.26 | Medium |
| 14.47 | 6.12 | Medium |
| 17.38 | 5.10 | High |
| 18.37 | 4.83 | High |
| 19.03 | 4.66 | Medium |
| 20.78 | 4.27 | High |
| 21.94 | 4.05 | Medium |
| 23.53 | 3.78 | Medium |
| 24.09 | 3.69 | Medium |

G. (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one (Example 317) crystalline Form A

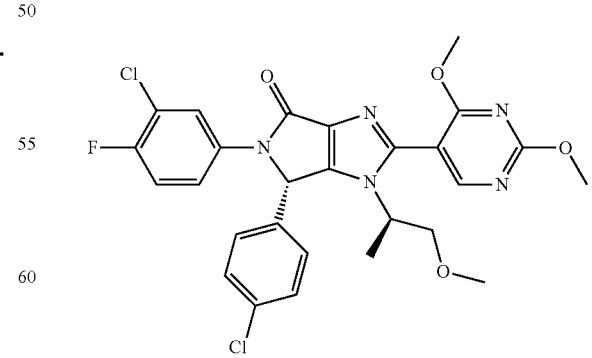

The compound of Example 317 (486 mg, 0.849 mmol) was triturated for 2 hrs in 24 ml of a mixture of water/ethanol (95/5), then sonicated and afterwards stirred at rt for 4 days.

The solid was filtered off, washed with water and dried under high vacuum at 50° C. for 24 hrs to yield 416 mg of colorless solid Form A.

| Angle 2-Theta ° | d value Angstrom | Intensity |
|---|---|---|
| 6.76 | 13.07 | Low |
| 8.48 | 10.42 | Low |
| 9.98 | 8.85 | Medium |
| 12.56 | 7.04 | Medium |
| 14.58 | 6.07 | High |
| 14.95 | 5.92 | Medium |
| 15.55 | 5.70 | Medium |
| 16.62 | 5.33 | Low |
| 17.08 | 5.19 | High |
| 17.44 | 5.08 | High |
| 19.72 | 4.50 | Medium |
| 23.83 | 3.73 | Medium |
| 25.78 | 3.45 | Medium |
| 26.26 | 3.39 | Medium |

Figure 1:
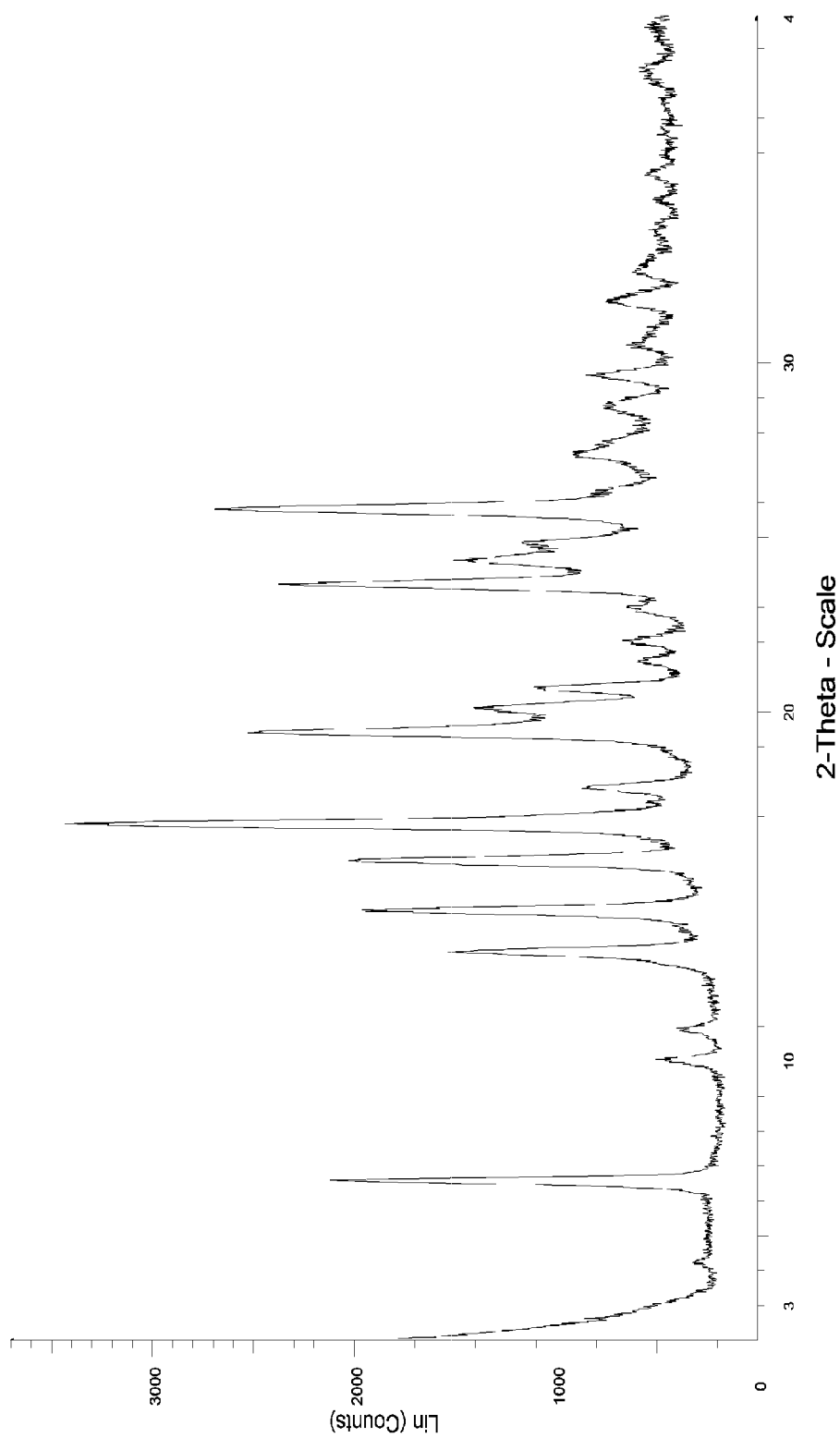
FIG. 1 discloses the X-ray powder diffraction data for the solid form obtained from Example 79 using method A herein.
Figure 2:
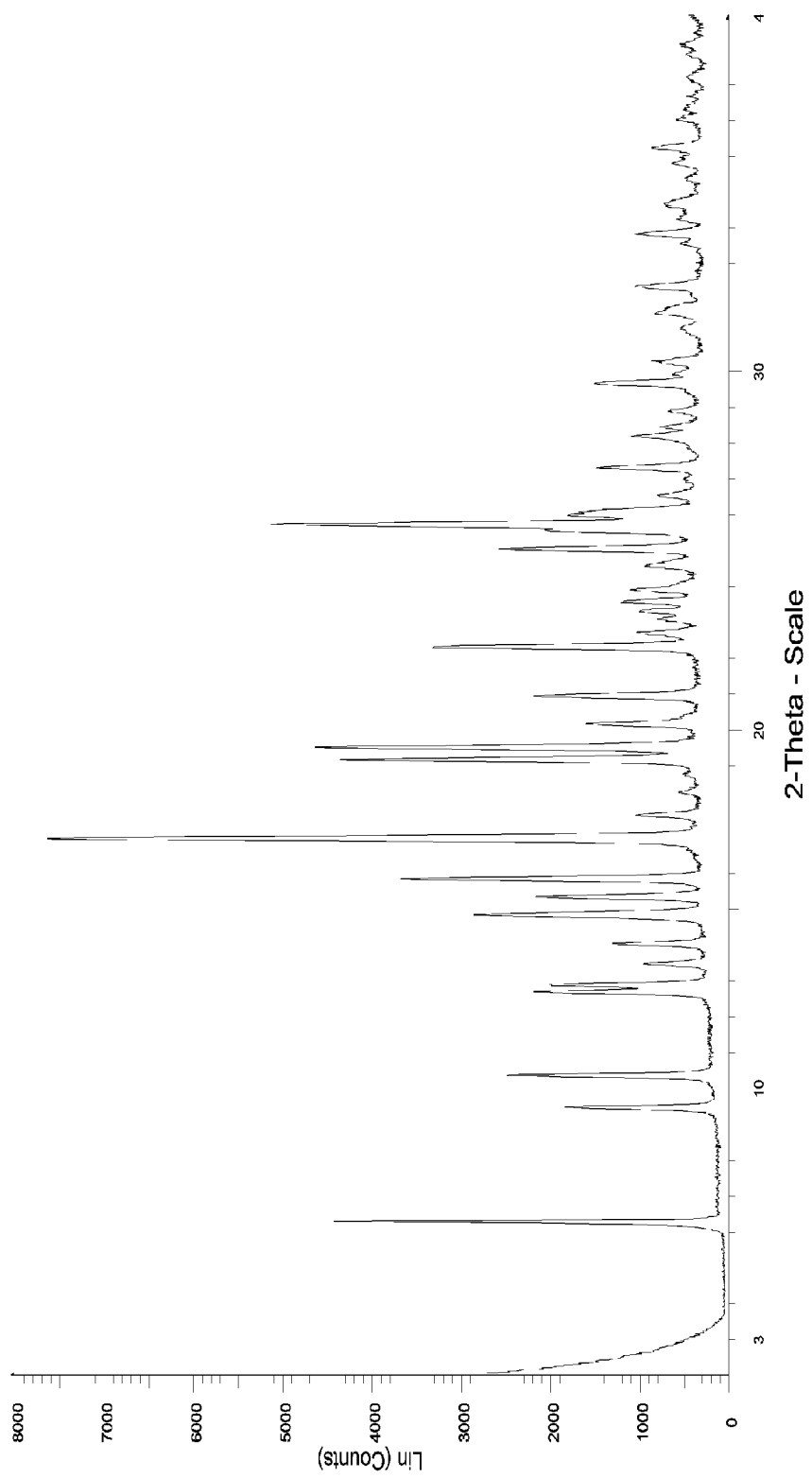
FIG. 2 discloses the X-ray powder diffraction data for the solid form obtained from Example 199 using method B herein.
Figure 3:
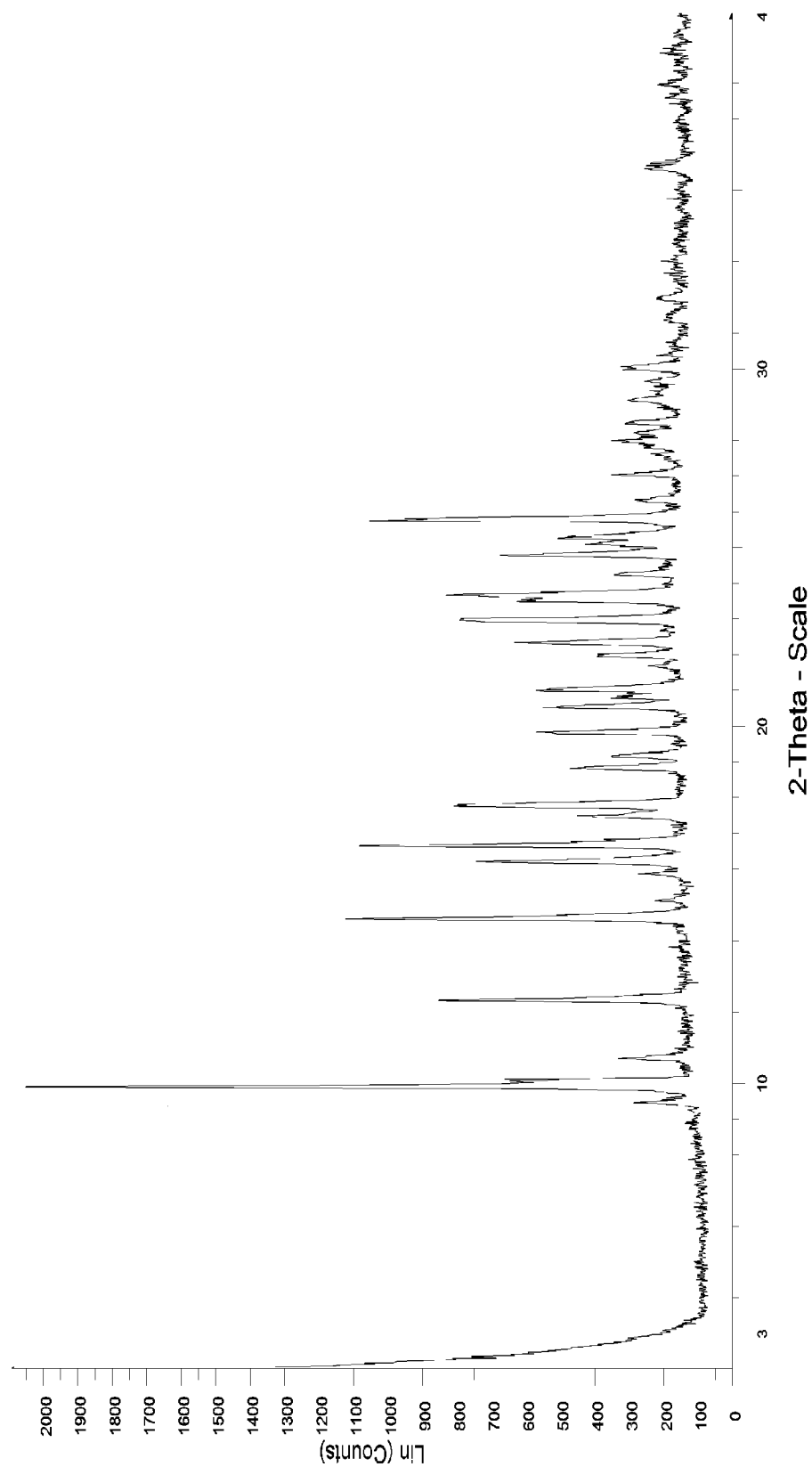
FIG. 3 discloses the X-ray powder diffraction data for the solid form obtained from Example 102 using method C herein.
Figure 4:
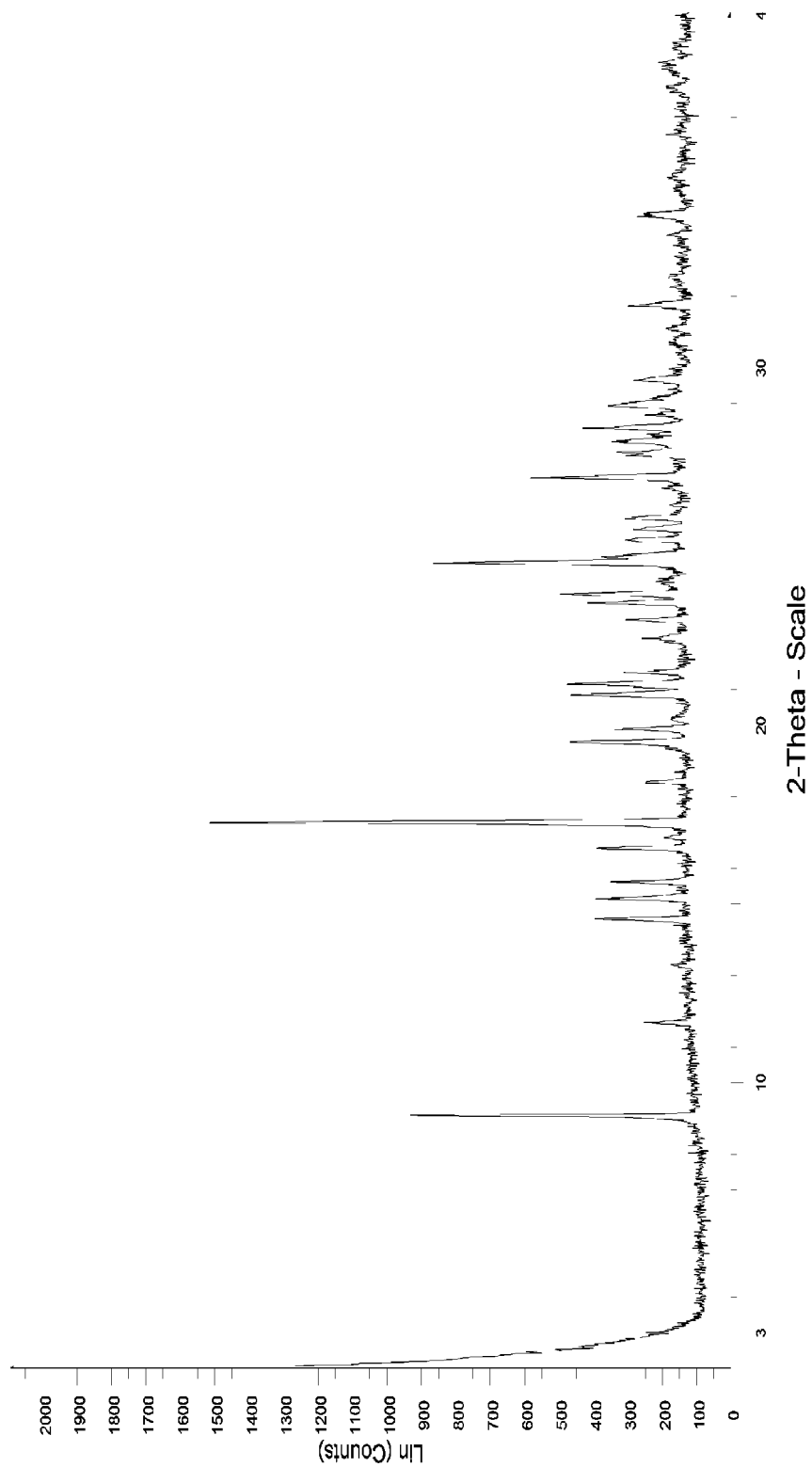
FIG. 4 discloses the X-ray powder diffraction data for the solid form obtained from Example 102 using method D herein.
Figure 5:
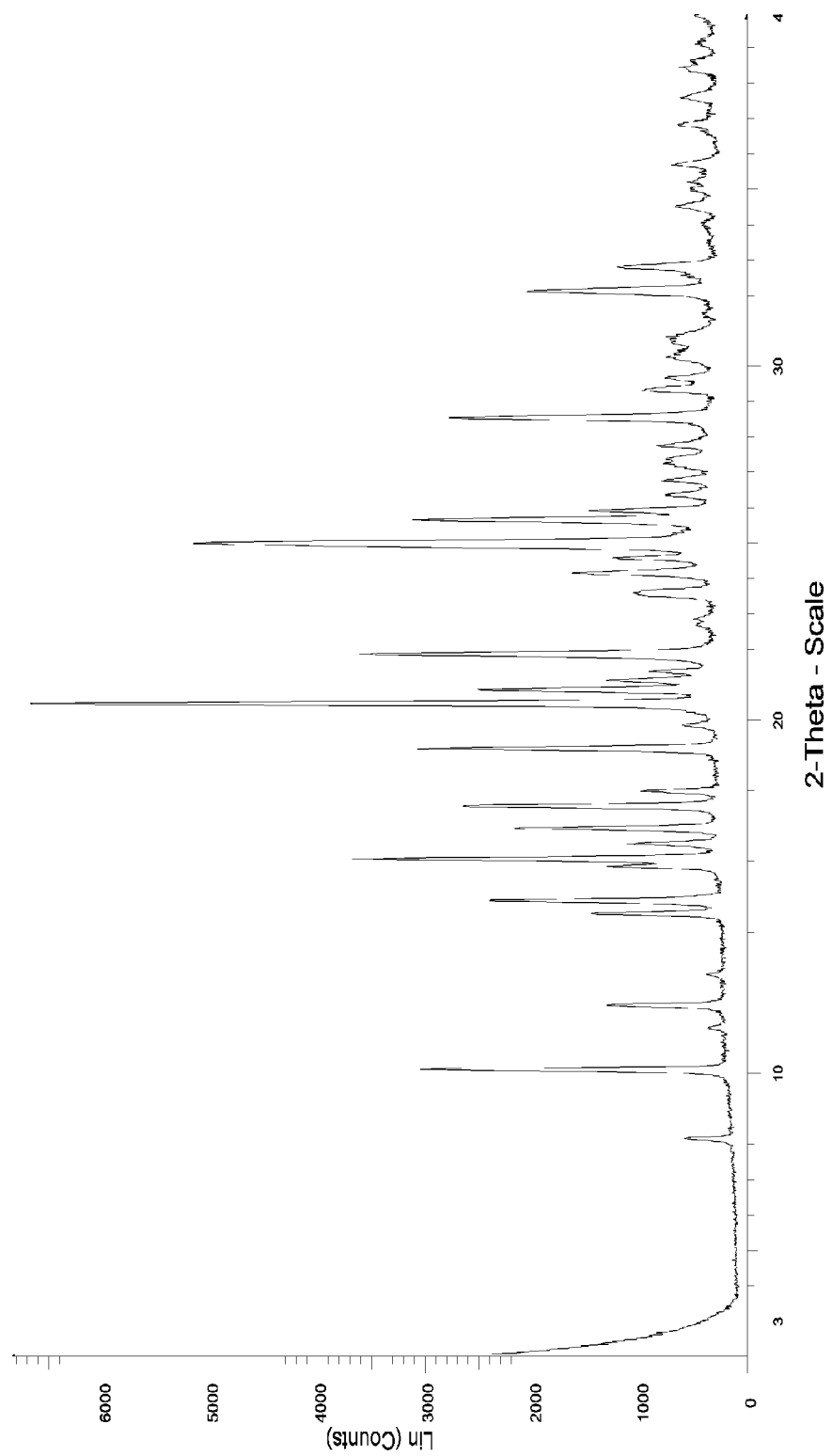
FIG. 5 discloses the X-ray powder diffraction data for the solid form obtained from Example 102 using method E herein.
Figure 6:
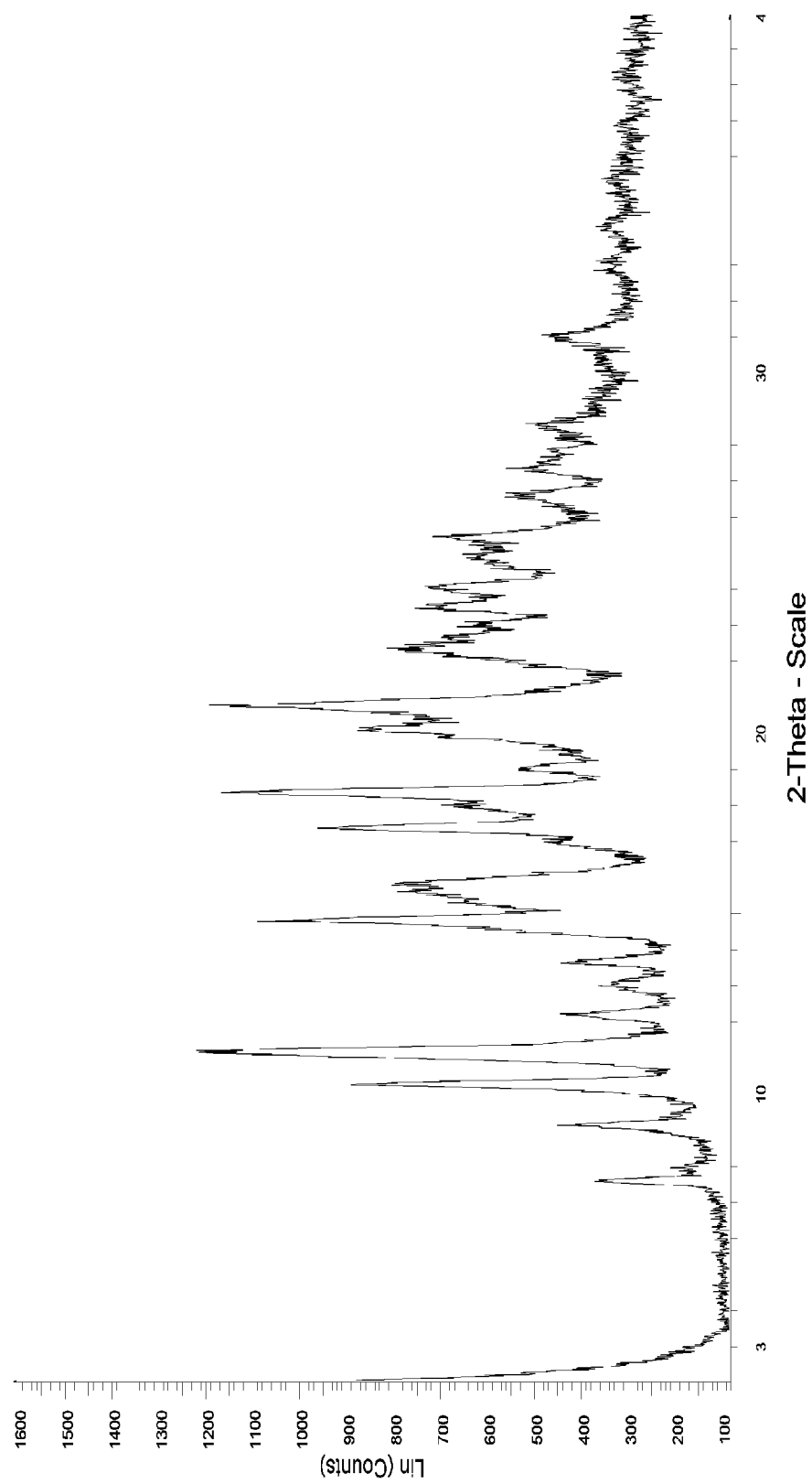
FIG. 6 discloses the X-ray powder diffraction data for the solid form obtained from Example 160 using method F herein.
Figure 7:
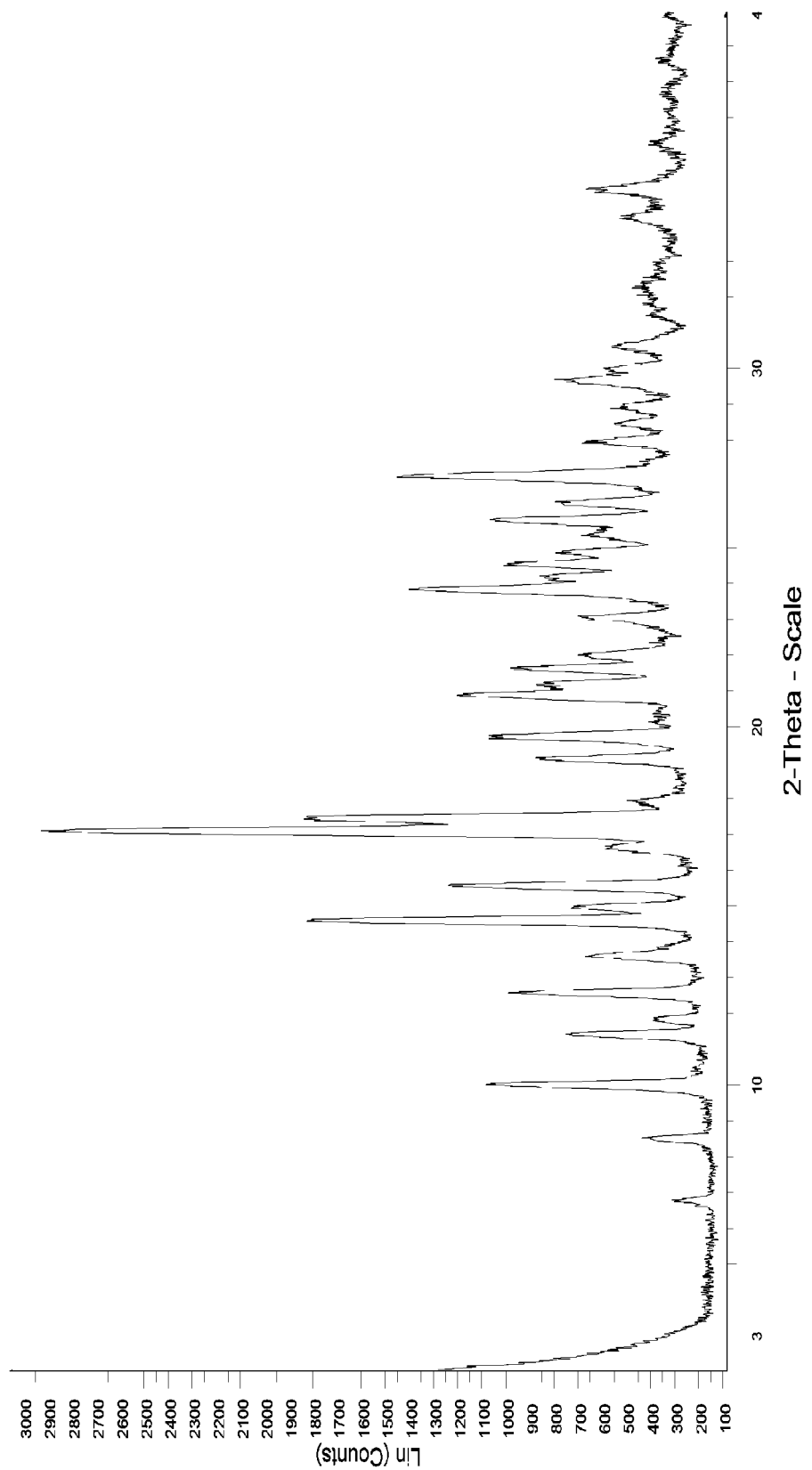
FIG. 7 discloses the X-ray powder diffraction data for the solid form obtained from Example 317 using method G herein.

Described below are a number of embodiments (EX) of the first aspect of the invention.

EX1 In one embodiment of the invention there is provided a crystalline form of any of:
4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile
4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile
(S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one
4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile
(S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one EX2 A crystalline form according to EX1, consisting essentially of said form, as described herein.

EX3 A crystalline form according to EX1, wherein said form as described herein, is in substantially pure form.

EX4 The crystalline form A of 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile, according to any one of EX1 to EX3, characterized by a x-ray powder diffraction pattern comprising 4 or more 2 theta values selected from the group consisting of 6.54±0.2, 14.29±0.2, 15.72±0.2, 16.78±0.2, 17.82±0.2, 19.41±0.2, 20.10±0.2°, 20.67±0.2, 23.65±0.2 and 25.82±0.2, at a temperature of about 22° C., in particular 16.78±0.2, 19.41±0.2, 23.65±0.2 and 25.82±0.2.

EX5 The crystalline form A of 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile according to any one of EX1 to EX3, characterized by a x-ray powder diffraction pattern comprising 4 or more 2 theta values selected from the group consisting of 6.25±0.2, 10.34±0.2, 14.83±0.2, 15.33±0.2, 15.84±0.2, 19.16±0.2, 19.50±0.2°,20.94±0.2, 22.32±0.2, 25.05±0.2 and 25.74±0.2, at a temperature of about 22° C.

EX6 The crystalline form A of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one according to any one of EX1 to EX3, characterized by a x-ray powder diffraction pattern comprising 4 or more 2 theta values selected from the group consisting of 9.89±0.2, 12.33±0.2, 14.61±0.2, 16.21±0.2, 16.66±0.2, 17.50±0.2, 17.78±0.2, 19.83±0.2, 20.56±0.2, 22.35±0.2, 22.98±0.2° at a temperature of about 22° C.

EX7 The crystalline form B of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one according to any one of EX1 to EX3, characterized by a x-ray powder diffraction pattern comprising 4 or more 2 theta values selected from the group consisting of 9.04±0.2, 17.27±0.2, 19.52±0.2, 20.85±0.2, 21.14±0.2, 23.42±0.2, 23.67±0.2, 24.54±0.2, 26.95±0.2° at a temperature of about 22° C.

EX8 The crystalline form C of (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one according to any one of EX1 to EX3, characterized by a x-ray powder diffraction pattern comprising 4 or more 2 theta values selected from the group consisting of 10.09±0.2, 14.52±0.2, 14.88±0.2, 16.93±0.2, 17.56±0.2, 19.18±0.2, 20.46±0.2, 20.87±0.2, 21.86±0.2, 25.00±0.2 25.68±0.2, 28.57±0.2, 32.17±0.2° at a temperature of about 22° C.

EX9 The crystalline form A of 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile according to any one of EX1 to EX3, characterized by a x-ray powder diffraction pattern comprising 4 or more 2 theta values selected from the group consisting of 7.57±0.2, 9.11±0.2, 10.25±0.2, 11.16±0.2, 12.18±0.2, 14.47±0.2, 17.38±0.2, 18.37±0.2, 19.03±0.2, 20.78±0.2, 21.94±0.2, 23.53±0.2 and 24.09±0.2° at a temperature of about 22° C.

EX10 The crystalline form A of (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one according to any one of EX1 to EX3, characterized by a x-ray powder diffraction pattern comprising 4 or more 2 theta values selected from the group consisting of 9.98±0.2, 12.56±0.2, 14.58±0.2, 14.95±0.2, 15.55±0.2, 17.08±0.2, 17.44±0.2, 19.72±0.2, 23.83±0.2, 25.78±0.2, 26.26±0.2° at a temperature of about 22° C., in particular 14.58±0.2, 17.08±0.2 and 17.44±0.2.

In another aspect of the invention, there is provided any compound, salt or solid form thereof, as defined herein.

Biological Data:

Time Resolved Fluorescence Energy Transfer (TR-FRET) Assay

The inhibition of p53-MDM2 and p53-MDM4 interactions is measured by time resolved fluorescence energy transfer (TR-FRET). Fluorescence energy transfer (or Foerster resonance energy transfer) describes an energy transfer between donor and acceptor fluorescent molecules. For this assay, human MDM2 protein (amino acids 2-188) and human MDM4 protein (amino acids 2-185), tagged with a C-terminal biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 620 nm. The ratiometric FRET assay readout is calculated from the raw data of the two distinct fluorescence signals measured in time resolved mode (fluorescence 665 nm/fluorescence 620 nm×1000).

The test is performed in white 384-well plates (Greiner Bio-One, reference 781207) in a total volume of 60 µL by adding 1 µL of compounds tested at different concentrations diluted in 100% DMSO (1.7% final DMSO concentration) in reaction buffer (PBS, 125 mM NaCl, 0.001% Novexin (consists of carbohydrate polymers), designed to increase the solubility and stability of proteins; Expedeon Ltd., Cambridgeshire, United Kingdom), 0.01% Gelatin, 0.01% 0.2%, Pluronic F-127 (block copolymer from ethylenoxide and propyleneoxide), 1 mM DTT). After addition of 0.1 nM MDM2-biotinylated or 2.5 nM MDM4-biotinylated (internal preparations, both MDM2 and MDM4 are biotinylated at the C-terminal of the peptide construct), and 0.1 nM (p53-MDM2 assay) or 0.625 nM (p53-MDM4 assay) Europium labeled streptavidin (Perkin Elmer), respectively, the solution is pre-incubated for 15 minutes at room temperature, then 10 nM Cy5-p53 peptide (internal preparation, the Cy5 dye is directly bound to the N-terminal part of p53 peptide construct) is added before an incubation at room temperature for 15 minutes prior to reading the plate. For measurement of samples, a Victor II microplate reader (Perkin Elmer) is used with the following settings in the p53-MDM4 assay: Excitation 340 nm, Emission Donor 620 nm and Emission Acceptor 665 nm. Tecan genios Pro is used as a microplate reader for the fluorescence measurements in the p53-MDM2 assay. $IC_{50}$ values are calculated by curve fitting using XLfit. If not specified, reagents are purchased from Sigma-Aldrich Chemie GmBH, Buchs, Switzerland.

| Example | $IC_{50}$ P53-MDM2 (nM) | $IC_{50}$ P53-MDM4 (µM) |
| --- | --- | --- |
| 1 | 0.17 | 0.468 |
| 2 | 0.17 | 0.411 |
| 3 | 0.65 | 0.703 |
| 4 | 0.14 | 0.175 |
| 5 | 0.25 | 0.534 |
| 6 | n.d. | 7.09 |
| 7 | 0.17 | 0.530 |
| 8 | 2.27 | n.d. |
| 9 | 0.07 | 0.229 |
| 10 | 0.20 | 0.179 |
| 11 | 0.15 | 0.120 |
| 12 | 0.15 | 0.217 |
| 13 | 0.18 | n.d. |
| 14 | 0.18 | n.d. |
| 15 | 0.22 | 0.79 |
| 16 | 0.09 | n.d. |
| 17 | 0.07 | n.d. |
| 18 | 0.14 | 0.34 |
| 19 | 0.15 | n.d. |
| 20 | 0.17 | 0.76 |
| 21 | 0.12 | n.d. |
| 22 | 0.13 | n.d. |
| 23 | 0.13 | n.d. |
| 24 | 0.20 | n.d. |
| 25 | 0.16 | n.d. |
| 26 | 0.23 | n.d. |
| 27 | 0.137 | n.d. |
| 28 | 0.62 | n.d. |
| 29 | 0.22 | n.d. |
| 30 | 0.37 | n.d. |
| 31 | 0.19 | n.d. |
| 32 | 0.19 | n.d. |
| 33 | 0.47 | n.d. |
| 34 | 0.65 | n.d. |
| 35 | 0.16 | n.d. |
| 36 | 0.13 | n.d. |
| 37 | 0.27 | n.d. |
| 38 | 0.19 | n.d. |
| 39 | 0.17 | n.d. |
| 40 | 0.74 | n.d. |
| 41 | 0.15 | n.d. |
| 42 | 0.11 | n.d. |
| 43 | 0.27 | 3.38 |
| 44 | 0.60 | 7.8 |
| 45 | 2.95 | 31.5 |
| 46 | 0.16 | n.d. |
| 47 | 0.40 | n.d. |
| 48 | 0.34 | n.d. |
| 49 | 0.42 | n.d. |
| 50 | 0.39 | n.d. |
| 51 | 0.16 | n.d. |
| 52 | 0.17 | n.d. |
| 53 | 1.03 | n.d. |
| 54 | 0.31 | n.d. |
| 55 | 0.19 | n.d. |
| 56 | 1.21 | n.d. |
| 57 | 0.28 | n.d. |
| 58 | 0.20 | n.d. |
| 59 | 0.20 | n.d. |
| 60 | 0.18 | n.d. |
| 61 | 0.13 | n.d. |
| 62 | 0.21 | n.d. |
| 63 | 0.17 | n.d. |
| 64 | 0.41 | 0.71 |
| 65 | 3.58 | n.d. |
| 66 | 0.23 | n.d. |
| 67 | 1.15 | n.d. |
| 68 | 0.71 | n.d. |
| 69 | 0.18 | 0.49 |
| 70 | 0.14 | n.d. |
| 71 | n.d. | 11.42 |
| 72 | 1.02 | n.d. |
| 73 | 0.42 | n.d. |
| 74 | 0.34 | n.d. |
| 75 | 0.07 | n.d. |
| 76 | 14.7 | n.d. |
| 77 | 0.19 | n.d. |
| 78 | 2.07 | n.d. |
| 79 | 0.36 | n.d. |
| 80 | 0.27 | n.d. |
| 81 | 0.35 | n.d. |
| 82 | 0.4 | n.d. |

| Example | IC$_{50}$ P53-MDM2 (nM) | P53-MDM4 (μM) |
|---|---|---|
| 83 | 1.47 | n.d. |
| 84 | 1.54 | n.d. |
| 85 | 11.8 | n.d. |
| 86 | 4.6 | n.d. |
| 87 | 31.7 | n.d. |
| 88 | 3.6 | n.d. |
| 89 | 0.04 | n.d. |
| 90 | 1.10 | n.d. |
| 91 | 0.45 | n.d. |
| 92 | 1.64 | n.d. |
| 93 | 0.36 | n.d. |
| 94 | 0.32 | n.d. |
| 95 | 1.31 | n.d. |
| 96 | 0.62 | n.d. |
| 97 | n.d. | n.d. |
| 98 | 15.1 | n.d. |
| 99 | 11.8 | n.d. |
| 100 | 0.64 | n.d. |
| 101 | 0.34 | n.d. |
| 102 | 0.23 | n.d. |
| 103 | 299.7 | n.d. |
| 104 | 5.61 | n.d. |
| 105 | 0.31 | n.d. |
| 106 | 0.28 | n.d. |
| 107 | 0.32 | n.d. |
| 108 | 1.10 | n.d. |
| 109 | 0.35 | n.d. |
| 110 | 0.23 | n.d. |
| 111 | 0.25 | n.d. |
| 112 | 0.56 | n.d. |
| 113 | 0.11 | n.d. |
| 114 | 0.70 | n.d. |
| 115 | 0.62 | n.d. |
| 116 | 2.3 | n.d. |
| 117 | 0.09 | n.d. |
| 118 | 4.29 | n.d. |
| 119 | 4.97 | n.d. |
| 120 | 0.57 | n.d. |
| 121 | 0.26 | n.d. |
| 122 | 0.25 | n.d. |
| 123 | 3.44 | n.d. |
| 124 | 2.33 | n.d. |
| 125 | 4.99 | n.d. |
| 126 | 0.24 | n.d. |
| 127 | 0.14 | n.d. |
| 128 | 3.79 | n.d. |
| 129 | 0.41 | n.d. |
| 130 | 0.18 | n.d. |
| 131 | 1.65 | n.d. |
| 132 | 1.93 | n.d. |
| 133 | 0.65 | n.d. |
| 134 | 0.69 | n.d. |
| 135 | 0.27 | n.d. |
| 136 | 0.20 | n.d. |
| 137 | 1.62 | n.d. |
| 138 | 4.74 | n.d. |
| 139 | 0.66 | n.d. |
| 140 | 1.32 | n.d. |
| 141 | 0.20 | n.d. |
| 142 | 0.36 | n.d. |
| 143 | 105.6 | n.d. |
| 144 | 1.70 | n.d. |
| 145 | 2.80 | n.d. |
| 146 | 2.4 | n.d. |
| 147 | 0.66 | n.d. |
| 148 | 1.83 | n.d. |
| 149 | 1.74 | n.d. |
| 150 | 2.18 | n.d. |
| 151 | 1.95 | n.d. |
| 152 | 1.01 | n.d. |
| 153 | 0.38 | n.d. |
| 154 | 0.17 | n.d. |
| 155 | 0.17 | n.d. |
| 156 | 1.27 | n.d. |
| 157 | 0.27 | n.d. |
| 158 | 0.14 | n.d. |
| 159 | 1.35 | n.d. |
| 160 | 0.33 | n.d. |
| 161 | 153.2 | n.d. |
| 162 | 0.32 | n.d. |
| 163 | 39.6 | n.d. |
| 164 | 0.10 | n.d. |
| 165 | 0.32 | n.d. |
| 166 | 214.3 | n.d. |
| 167 | 0.44 | n.d. |
| 168 | 15.8 | n.d. |
| 169 | 0.11 | n.d. |
| 170 | 0.16 | n.d. |
| 171 | 0.52 | n.d. |
| 172 | 0.29 | n.d. |
| 173 | 0.08 | n.d. |
| 174 | 0.11 | n.d. |
| 175 | 0.10 | n.d. |
| 176 | 0.68 | n.d. |
| 177 | 0.19 | n.d. |
| 178 | 43.4 | n.d. |
| 179 | 6.83 | n.d. |
| 180 | 102.7 | n.d. |
| 181 | 1.32 | n.d. |
| 182 | 0.18 | n.d. |
| 183 | 0.38 | n.d. |
| 184 | 0.31 | n.d. |
| 185 | 0.36 | n.d. |
| 186 | 0.27 | n.d. |
| 187 | 0.57 | n.d. |
| 188 | 0.33 | n.d. |
| 189 | 70.5 | n.d. |
| 190 | 0.13 | n.d. |
| 191 | 0.27 | n.d. |
| 192 | 0.42 | n.d. |
| 193 | 0.49 | n.d. |
| 194 | 0.17 | n.d. |
| 195 | 0.15 | n.d. |
| 196 | 0.16 | n.d. |
| 197 | 0.11 | n.d. |
| 198 | 0.20 | n.d. |
| 199 | 0.16 | n.d. |
| 200 | 0.29 | n.d. |
| 201 | 0.26 | n.d. |
| 202 | 0.19 | n.d. |
| 203 | 0.68 | n.d. |
| 204 | 68.6 | n.d. |
| 205 | 0.11 | n.d. |
| 206 | 82.5 | n.d. |
| 207 | 1.05 | n.d. |
| 208 | 0.15 | n.d. |
| 209 | 0.09 | n.d. |
| 210 | 0.63 | n.d. |
| 211 | 0.39 | n.d. |
| 212 | n.d | n.d. |
| 213 | 0.54 | n.d. |
| 214 | 0.50 | n.d. |
| 215 | 0.43 | n.d. |
| 216 | 0.29 | n.d. |
| 217 | 13.4 | n.d. |
| 218 | 0.05 | n.d. |
| 219 | 0.25 | n.d. |
| 220 | 0.24 | n.d. |
| 221 | 0.24 | n.d. |
| 222 | 36.8 | n.d. |
| 223 | 0.09 | n.d. |
| 224 | 5.81 | n.d. |
| 225 | 5.39 | n.d. |
| 226 | 0.08 | n.d. |
| 227 | 0.37 | n.d. |
| 228 | 0.08 | n.d. |
| 229 | 0.77 | n.d. |
| 230 | 0.56 | n.d. |
| 231 | 0.77 | n.d. |
| 232 | 0.97 | n.d. |

| Example | IC$_{50}$ P53-MDM2 (nM) | IC$_{50}$ P53-MDM4 (µM) |
|---|---|---|
| 233 | 6.60 | n.d. |
| 234 | 0.29 | n.d. |
| 235 | 0.21 | n.d. |
| 236 | n.d | n.d. |
| 237 | 2.22 | n.d. |
| 238 | 1.09 | n.d. |
| 239 | 0.54 | n.d. |
| 240 | 1.2 | n.d. |
| 241 | 0.41 | n.d. |
| 242 | 0.27 | n.d. |
| 243 | 142.6 | n.d. |
| 244 | 21.5 | n.d. |
| 245 | 0.12 | n.d. |
| 246 | 0.15 | n.d. |
| 247 | 0.08 | n.d. |
| 248 | n.d | n.d. |
| 249 | n.d | n.d. |
| 250 | 0.13 | n.d. |
| 251 | 4.4 | n.d. |
| 252 | 0.20 | n.d. |
| 253 | 57.7 | n.d. |
| 254 | 0.27 | n.d. |
| 255 | 60.4 | n.d. |
| 256 | 0.28 | n.d. |
| 257 | 0.17 | n.d. |
| 258 | 0.15 | n.d. |
| 259 | 0.15 | n.d. |
| 260 | 0.85 | n.d. |
| 261 | 0.63 | n.d. |
| 262 | 92.7 | n.d. |
| 263 | 0.2 | n.d. |
| 264 | 284.2 | n.d. |
| 265 | 0.18 | n.d. |
| 266 | 505.7 | n.d. |
| 267 | 1.18 | n.d. |
| 268 | 1.16 | n.d. |
| 269 | n.d. | n.d. |
| 270 | n.d. | n.d. |
| 271 | n.d. | n.d. |
| 272 | n.d. | n.d. |
| 273 | n.d. | n.d. |
| 274 | n.d. | n.d. |
| 275 | 0.122 | n.d. |
| 276 | 2.813 | n.d. |
| 277 | 0.35 | n.d. |
| 278 | 0.99 | n.d. |
| 279 | 17.244 | n.d. |
| 280 | 417.076 | n.d. |
| 281 | 0.081 | n.d. |
| 282 | 0.1015 | n.d. |
| 283 | 76.542 | n.d. |
| 284 | 0.525 | n.d. |
| 285 | 0.19 | n.d. |
| 286 | 0.71 | n.d. |
| 287 | 0.117 | n.d. |
| 288 | 51.102 | n.d. |
| 289 | 0.152 | n.d. |
| 290 | 0.252 | n.d. |
| 291 | 2.406 | n.d. |
| 292 | 1.16 | n.d. |
| 293 | 0.253 | n.d. |
| 294 | 0.396 | n.d. |
| 295 | 0.318 | n.d. |
| 296 | 0.32 | n.d. |
| 297 | 0.417 | n.d. |
| 298 | 10.194 | n.d. |
| 299 | 142.5 | n.d. |
| 300 | 5.926 | n.d. |
| 301 | 0.243 | n.d. |
| 302 | 1.268 | n.d. |
| 303 | 0.352 | n.d. |
| 304 | 1.065 | n.d. |
| 305 | 0.313 | n.d. |
| 306 | 0.204 | n.d. |
| 307 | 0.124 | n.d. |
| 308 | 125.333 | n.d. |
| 309 | 1.77 | n.d. |
| 310 | 3.224 | n.d. |
| 311 | 0.631 | n.d. |
| 312 | 0.319 | n.d. |
| 313 | 0.371 | n.d. |
| 314 | 0.213 | n.d. |
| 315 | 40.946 | n.d. |
| 316 | 0.107 | n.d. |
| 317 | 0.089 | 0.95 |
| 318 | 43.728 | n.d. |
| 319 | 0.414 | n.d. |
| 320 | 0.81 | n.d. |
| 321 | 0.144 | n.d. |
| 322 | 0.161 | n.d. |
| 323 | 0.135 | n.d. |
| 324 | 21.715 | n.d. |
| 325 | 0.059 | n.d. |
| 326 | 6.133 | n.d. | n.d. = not determined

There are also assays that could be used to demonstrate the effect of the compounds of this invention in a cellular context.

Cellular Proliferation Assay in SJSA-1 and SAOS-2 Cells Based on YO-PRO®-1 Iodide Staining The effect of PPI (protein-protein interaction) inhibitors on cell growth of p53 wild-type or mutant cells is assessed in a proliferation assay based on YO-PRO®-1 iodide staining (J Immunol Methods. 1995; 185(2):249-58). The principal of this assay is the use of the DNA-intercalating dye YO-PRO®-1 iodide which upon binding to DNA emits a strong fluorescence signal. In addition, the dye is membrane-impermeant and thus, apoptotic cells can be distinguished from the viable cell population during the same assay. In the absence of cell permeabilization, the dye is only entering into cells that are beginning to undergo apoptosis. After treatment of the cells with a lysis buffer, the total cell number can be estimated.

To test PPI inhibitors on cell growth, SJSA-1 cells (p53 wild-type cells) and SAOS-2 cells (p53 null cells) are plated out into 96-well micro-titer plates and treated with decreasing concentrations of the compounds. After a 72 hour incubation period, 2.5 µM YO-PRO®-1 iodide is directly added to the cells and a first read-out is performed using a standard fluorescence plate reader (filter setting 485/530 nm) revealing the relative number of apoptotic cells. Subsequently, cells are permeabilized by directly adding lysis buffer containing the detergent NP40, EDTA and EGTA to obtain final concentrations of 0.01% and 5 mM, respectively. After complete permeabilization, the total cell number is quantified during a second read using the fluorescence plate reader with the same settings.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

In vivo Experiments

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, $3 \times 10^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated. As an alternative to cell line SJSA-1, other cell lines may also be used in the same manner, for example,

- the HCT116 colon carcinoma cell line (ATCC No. CCL-247);
- the LNCaP clone FGC prostate carcinoma cell line (ATCC No. CRL-1740);
- the RKO colon carcinoma cell line (ATCC No. CRL-2577);
- the HT1080 fibrosarcoma cell line (ATCC No. CCL-121);
- the A375 malignant melanoma cell line (ATCC No. CRL-1619),
- the NCI-H460 large cell lung carcinoma cell line (ATCC No. HTB-177);
- the JEG-3 choriocarcinoma (ATCC No. HTB-36)
- the ZR-75-1 breast ductal carcinoma (ATCC No. CRL-1500)

What is claimed is:

1. A compound of formula (I) or a pharmaceutically acceptable salt thereof,

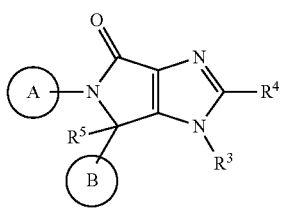

wherein

A is selected from:

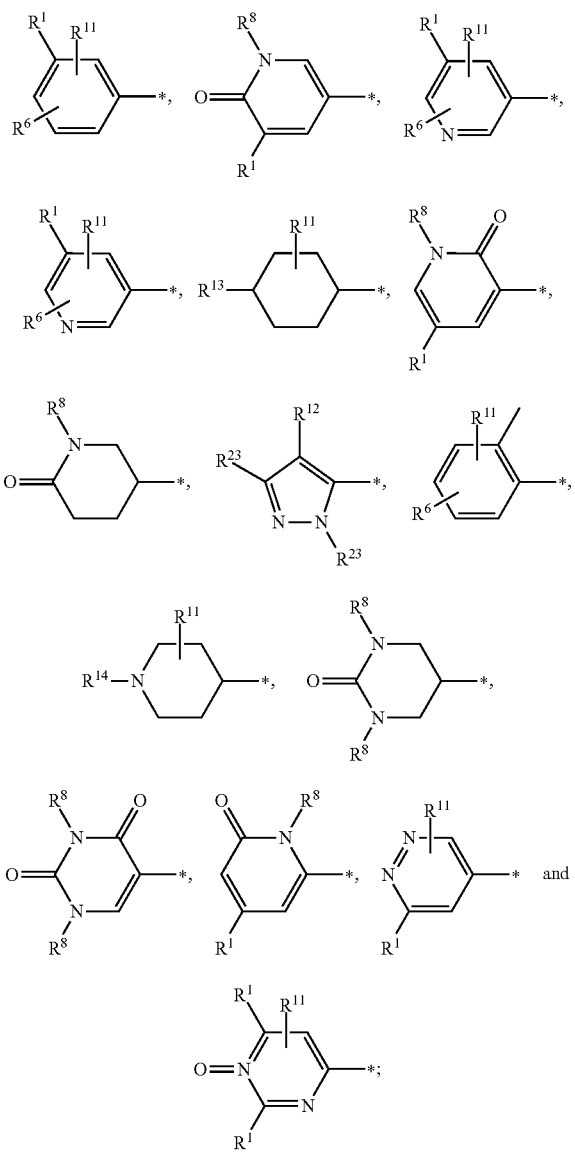

B is selected from:

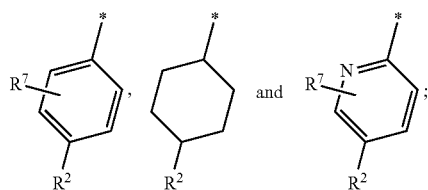

each $R^1$ is independently selected from halo and methyl;

$R^2$ is selected from chloro, fluoro, trifluoromethyl, methyl and cyano;

$R^3$ is selected from isopropyl, cyclopropyl, isobutyl, cyclobutyl and cyclopentyl, or $R^3$ is:

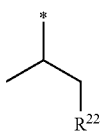

wherein R²² is selected from OH, OCH₃, NH₂, NHMe, NMe₂, NHCOMe and NHCOH;

R⁴ is selected from:

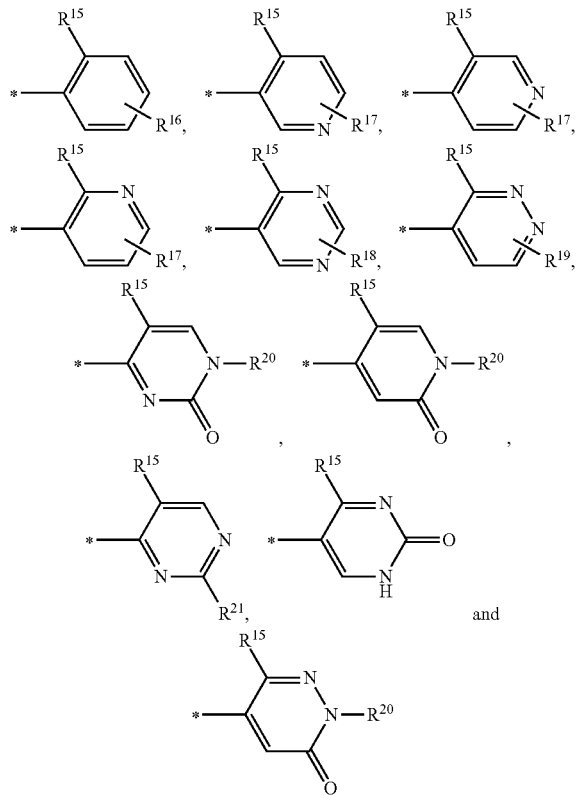

wherein
R¹⁵ is independently selected from OCH₃, CH₂CH₃, OH, OCF₃ and H;

R¹⁶ is selected from H, —O—(C₁-C₄)alkyl, halo, OCF₃, CN, —C(O)NR⁹R¹⁰, —C(O)-morpholin-4-yl, hydroxy-azetidin-1-yl-carbonyl, —CH₂NR⁹R¹⁰, —CH₂NR⁹—C(O)R¹⁰, CH₂CN, methyl-imidazolyl-, —CH₂C(O)NR⁹R¹⁰, —CH₂C(O)OH, —C(O)OH, —CH₂C(O)O—(C₁-C₄)alkyl, —N(R⁹)—C(O)—(C₁-C₄)alkyl, —NR⁹R¹⁰ and (C₁-C₄)alkyl optionally substituted by 1 or 2 OH;

R¹⁷ is selected from H, O(C₁-C₄)alkyl, —CH₂C(O)NR⁹R¹⁰, —CH₂C(O)O—(C₁-C₄)alkyl, —CH₂C(O)OH, —NR⁹R¹⁰, —C(O)NR⁹R¹⁰, —CH₂NR⁹R¹⁰, —C(O)OCH₃ and —CH₂CN;

R¹⁸ is selected from H, O(C₁-C₄)alkyl, OH, CH₂NR⁹R¹⁰, —NR⁹R¹⁰ and azetidin-1-yl, said azetidin-1-yl being substituted with OH or both CH₃ and OH, R¹⁹ is selected from H, O(C₁-C₄)alkyl, (C₁-C₄)alkyl, —NR⁹R¹⁰, —N(R⁹)—C(O)—(C₁-C₄)alkyl and —C(O)NR⁹R¹⁰;

R²⁰ is selected from H, CH₃ and —CH₂CH₃;

R²¹ is selected from —NR⁹R¹⁰, —CH₂NR⁹R¹⁰, C(O)NR⁹R¹⁰ and CN;

R⁵ is selected from:
H,
heterocyclyl¹-C(O)—(CH₂)ₙ—,
(C₁-C₄)alkyl-, said (C₁-C₄)alkyl- being optionally substituted with 1 or 2 substituents independently selected from —OH or =O,
heterocyclyl¹-(C₁-C₄)alkyl-, wherein said alkyl of heterocyclyl¹--(C₁-C₄)alkyl- is optionally substituted by 1 or 2 OH, and said heterocyclyl¹ can be optionally substituted by methyl or ethyl,
(C₁-C₄)alkyl-O—C(O)—(CH₂)ₘ—, and
cyano;

R⁶ is selected from:
H,
(C₁-C₄)alkyl-, optionally substituted with (C₁-C₄) alkoxy,
(C₁-C₄)alkoxy, optionally substituted with (C₁-C₄) alkoxy,
(C₁-C₄)alkoxy(C₁-C₄)alkoxy(C₁-C₄)alkyl-,
halo,
R⁹(R¹⁰)N—C(O)—(CH₂)ₘ—,
cyano,
R⁹(R¹⁰)N—(CH₂)ₘ—,
R⁹(R¹⁰)N—(CH₂)ₙ—O—(CH₂)ₘ—,
(C₁-C₄)alkyl-C(O)—(R¹⁰)N—(CH₂)ₘ—,
—O—(CH₂)ₚ-heteroaryl²;

R⁷ is selected from:
H,
halo, and
(C₁-C₄)alkyl-, optionally substituted with (C₁-C₄) alkoxy;

each R⁸ is independently selected from H, methyl, ethyl, hydroxyethyl and methoxyethyl, wherein said methyl or ethyl is optionally substituted with 1, 2 or 3 fluoro substituents;

each R⁹ is independently selected from H, methyl or ethyl;

each R¹⁰ is independently selected from H and (C₁-C₄) alkyl wherein said (C₁-C₄) alkyl is optionally substituted by 1 or 2 substituents independently selected from methoxy, ethoxy, hydroxy and halo;

or R⁹ and R¹⁰, together with the N atom to which they are attached, can join to form a saturated 5 or 6 membered heterocyclic ring further comprising ring carbon atoms and optionally one ring heteroatom independently selected from N, O and S, and wherein when the ring contains a S atom, said S is optionally substituted with one or two oxo substituents;

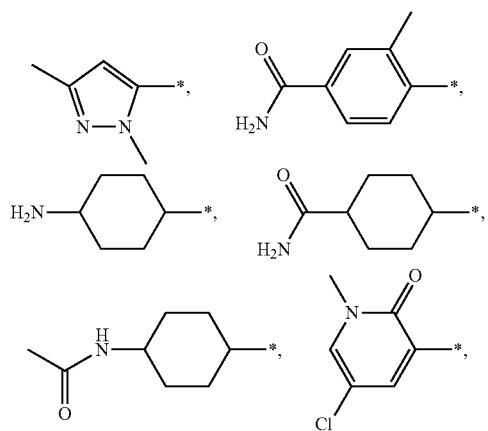

-continued

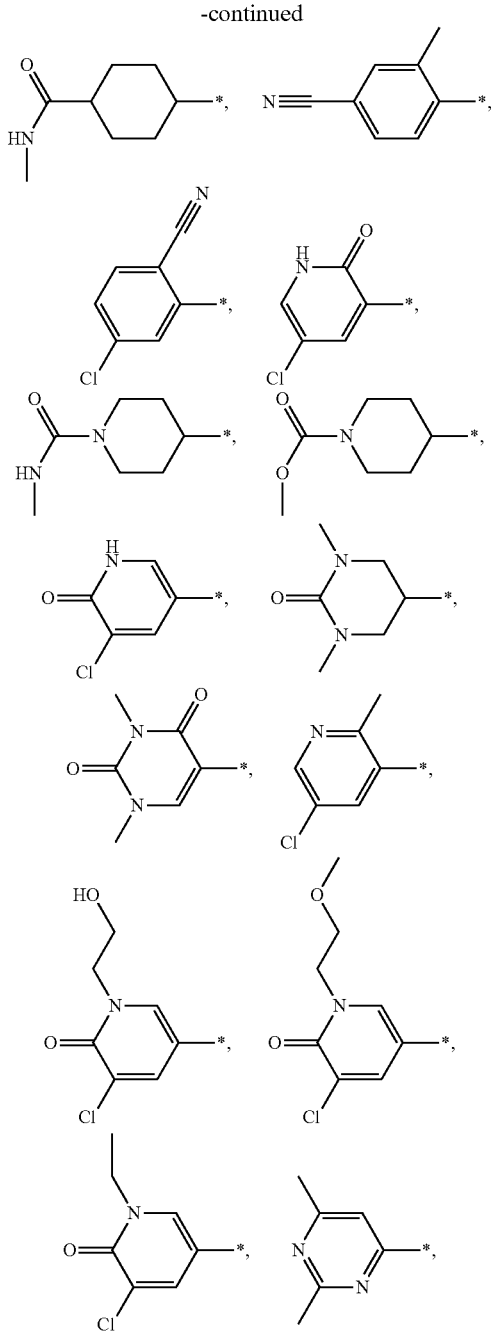

R[11] is H, (C$_1$-C$_4$)alkyl, (C$_1$-C$_4$) alkoxy or halo;
R[12] is H or halo;
R[13] is selected from NH$_2$, —C(O)OH, —NH(C(O)—CH$_3$) and —C(O)—NH(CH$_3$);
R[14] is selected from —C(O)— NR[9](R[10]), (C$_1$-C$_4$)alkyl, —C(O)(C$_1$-C$_4$)alkyl, —C(O)O(C$_1$-C$_4$)alkyl;
each R[23] is independently selected from H, halo, cyclopropyl and (C$_1$-C$_4$)alkyl;
n is 1, 2 or 3;
p is 0, 1, 2 or 3;
heterocyclyl[1] is a 3, 4, 5 or 6 membered fully saturated or partially unsaturated monocyclic group comprising ring carbon atoms and 1 or 2 ring heteroatoms independently selected from N, O and S;
heteroaryl[2] is a 5 or 6 membered fully unsaturated monocyclic group comprising ring carbon atoms and 1, 2, 3 or 4 ring heteroatoms independently selected from N, O and S, wherein the total number of ring S atoms does not exceed 1, and the total number of ring O atoms does not exceed 1;

and m is 0, 1 or 2;

* indicates the point of attachment to the remainder of the molecule.

2. The compound or a pharmaceutically acceptable salt thereof according to claim 1, wherein A is selected from:

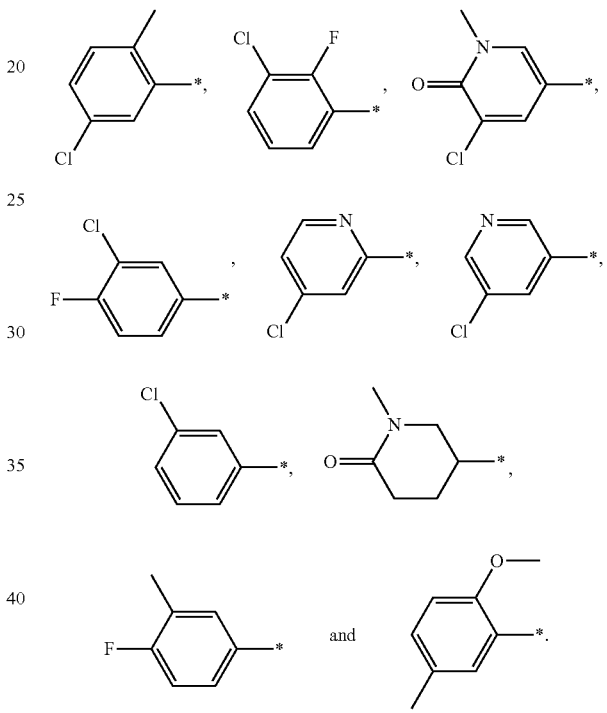

3. A compound or a pharmaceutically acceptable salt thereof according to claim 1, wherein A is selected from:

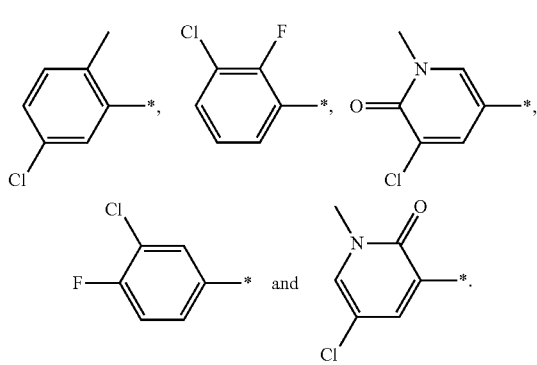

4. The compound or a pharmaceutically acceptable salt thereof according to claim 1, wherein B is selected from:

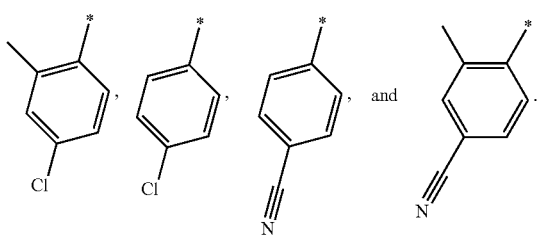

5. The compound or a pharmaceutically acceptable salt thereof according to claim 1, wherein each $R^1$ is independently selected from chloro, fluoro and methyl.

6. The compound or a pharmaceutically acceptable salt thereof according to claim 1, wherein $R^2$ is selected from chloro and cyano.

7. The compound or a pharmaceutically acceptable salt thereof according to claim 1, wherein $R^3$ is selected from isopropyl, cyclobutyl, cyclopropyl, 2-methoxy-1-methyl-ethyl and 2-hydroxy-1-methyl-ethyl.

8. The compound or a pharmaceutically acceptable salt thereof according to claim 1, wherein $R^4$ is selected from

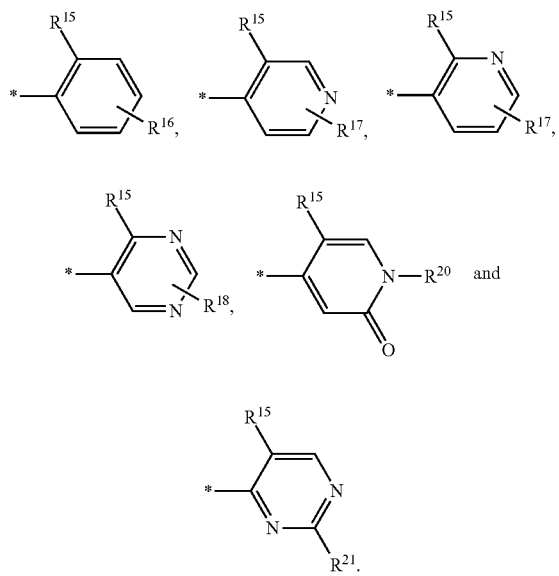

9. The compound or a pharmaceutically acceptable salt thereof according to claim 1, wherein $R^4$ is selected from:

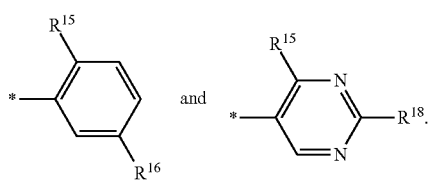

10. The compound or a pharmaceutically acceptable salt thereof according to claim 1, wherein $R^4$ is selected from

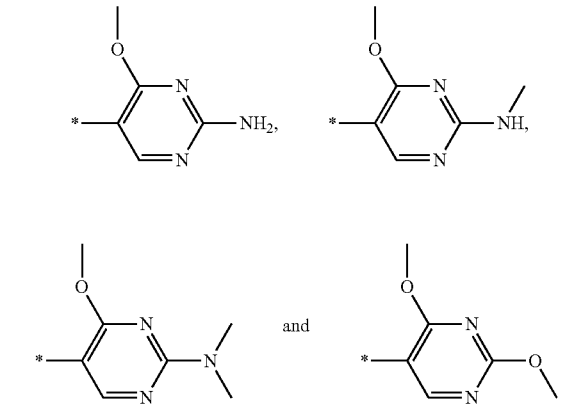

11. The compound or a pharmaceutically acceptable salt thereof according to claim 1, wherein $R^5$ is selected from:

H, $(C_1-C_4)$alkyl-, said $(C_1-C_4)$alkyl- being optionally substituted with 1 or 2 substituents independently selected from —OH or =O, $(C_1-C_4)$alkyl-O—C(O)—$(CH_2)_m$—, and cyano.

12. The compound or a pharmaceutically acceptable salt thereof according to claim 1, wherein $R^5$ is H.

13. The compound or a pharmaceutically acceptable salt thereof according to claim 1, wherein $R^6$ is selected from:

H, methyl, methoxy fluoro chloro cyano and

—C(O)NH$_2$.

14. The compound or a pharmaceutically acceptable salt thereof according to claim 1, wherein $R^7$ is selected from H and $(C_1-C_4)$alkyl.

15. The compound or a pharmaceutically acceptable salt thereof according to claim 1, wherein the compound of formula (I) has the stereochemistry shown in formula (IA):

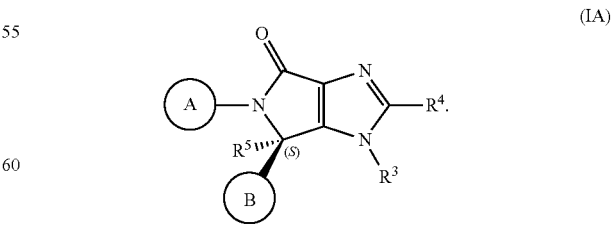

16. The compound or a pharmaceutically acceptable salt thereof according to claim 1, wherein the compound of formula (I) has the stereochemistry shown in formula (IB):

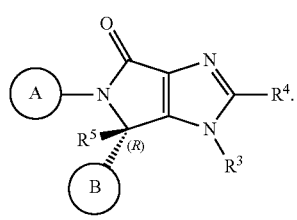

(IB)

17. The compound of formula (I) according to claim 1 or a Pharmaceutically acceptable salt thereof, selected from:

1: 5-(5-Chloro-2-methyl-phenyl)-6-(4-chloro-2-methyl-phenyl)-2-(5-fluoro-2-methoxy-phenyl)-1-isopropyl-4-oxo-5,6,-dihydro-1H-pyrrolo[3,4-d]imidazol-4-one;
2: 5-(5-Chloro-2-methyl-phenyl)-6-(4-chloro-2-methyl-phenyl)-2-(6-fluoro-2-methoxy-phenyl)-1-isopropyl-4-oxo-5,6,-dihydro-1H-pyrrolo[3,4-d]imidazol-4-one;
3: 5-(5-Chloro-2-methyl-phenyl)-6-(4-chloro-2-methyl-phenyl)-1-isopropyl-2-(2-trifluoromethoxy-phenyl)-5,6,-dihydro-1H-pyrrolo[3,4-d]imidazol-4-one;
4: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidaol-2-yl]-4-methoxy-benzonitrile;
5: 5-(5-Chloro-2-methyl-phenyl)-6-(4-chloro-2-methyl-phenyl)-1-isopropyl-2-(2-methoxy-phenyl)-5,6,-dihydro-1H-pyrrolo[3,4-d]imidazol-4-one;
6: 5-(5-Chloro-2-methyl-phenyl)-6-(4-chloro-2-methyl-phenyl)-2-(4-methoxy-pyridin-3-yl)-1-isopropyl-5,6,-dihydro-1H-pyrrolo[3,4-d]imidazol-4-one;
7: 5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one;
8: 5-(5-Chloro-2-methyl-phenyl)-6-(4-chloro-2-methyl-phenyl)-2-(2-methoxy-pyridin-3-yl)-1-isopropyl-5,6,-dihydro-1H-pyrrolo[3,4-d]imidazol-4-one;
9: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N,N-dimethyl benzamide;
10: 5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N-methyl benzamide;
11: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-N-(2-hydroxyethyl)-4-methoxy-benzamide;
12: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-N-isopropyl-4-methoxy-benzamide;
13: 5-(5-Chloro-2-methyl-phenyl)-6-(4-chloro-2-methyl-phenyl)-1-isopropyl-2-[2-methoxy-5-(morpholine-4-carbonyl)-phenyl]-5,6-dihydro-1H-pyrrolo[3,4-d]imidazol-4-one;
14: 5-(5-Chloro-2-methyl-phenyl)-6-(4-chloro-2-methyl-phenyl)-2-[5-(3-hydroxy-azetidine-1-carbonyl)-2-methoxy-phenyl]1-isopropyl-5,6-dihydro-1H-pyrrolo[3,4-d]imidazol-4-one;
15: 5-(5-Chloro-2-methyl-phenyl)-6-(4-chloro-2-methyl-phenyl)-1-isopropyl-2-(3-methoxy-pyridin-4-yl)-5,6,-dihydro-1H-pyrrolo[3,4-d]imidazol-4-one;
16: 2-(5-Amino methyl-2-methoxy-phenyl-5-(5-chloro-2-methyl-phenyl)-6-(4-chloro-2-methyl-phenyl)-1-isopropyl-5,6-dihydro-1H-pyrrolo[3,4-d]imidazole-4-one;
17: N-{3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-benzyl}-acetamide;
18: 5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one;
19: 5-(5-Chloro-2-methyl-phenyl)-6-(4-chloro-phenyl)-2-(5-hydroxymethyl-2-methoxy-phenyl)-1-isopropyl-5,6-dihydro-1H-pyrrolo[3,4-d]imidazole-4-one;
20: 5-(3-Chloro-2-fluoro-phenyl)-6-(4-chloro-phenyl)-2-(5-hydroxymethyl-2-methoxy-phenyl)-1-isopropyl-5,6-dihydro-1H-pyrrolo[3,4-d]imidazole-4-one;
21: 5-(5-Chloro-2-methyl-phenyl)-6-(4-chloro-2-methyl-phenyl)-2-(4-hydroxymethyl-2-methoxy-phenyl)-1-isopropyl-5,6-dihydro-1H-pyrrolo[3,4-d]imidazole-4-one;
22: 5-(5-Chloro-2-methyl-phenyl)-6-(4-chloro-2-methyl-phenyl)-2-(4-hydroxymethyl-2-methoxy-phenyl)-1-isopropyl-5,6-dihydro-1H-pyrrolo[3,4-d]imidazole-4-one;
23: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl benzamide;
24: 3-[5-(5-Chloro-2-methyl-phenyl)-6-(4-chloro-phenyl)-1-isopropyl-4-oxo-1,4,5,6-tetrahydro-pyrrolo[3,4-d]imidaol-2-yl]-4-methoxy-benzonitrile;
25: 5-(5-Chloro-2-methyl-phenyl)-6-(4-chloro-phenyl)-1-isopropyl-2-[2-methoxy-5-(morpholine-4-carbonyl)-phenyl]-5,6-dihydro-1H-pyrrolo[3,4-d]imidazol-4-one;
26: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzonitrile;
27: 5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazole-4-one;
28: 5-(5-Chloro-2-methyl-phenyl)-6-(4-chloro-phenyl)-2-(3,6-pyridazin-4-yl)-1-isopropyl-5,6-dihydro-1H-pyrrolo[3,4-d]imidazole-4-one;
29: 5-(5-Chloro-2-methyl-phenyl)-6-(4-chloro-2-methyl-phenyl)-2-(2,6-dimethoxy-pyridin-3-yl)-1-isopropyl-5,6-dihydro-1H-pyrrolo[3,4-d]imidazol-4-one;
30: 5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-d]imidazol-4-one;
31: 5-(5-Chloro-2-methyl-phenyl)-6-(4-chloro-phenyl)-1-isopropyl-2-(4-methoxy-2-methylamino-pyrimidin-5-yl)-5,6-dihydro-1H-pyrrolo[3,4-d]imidazol-4-one;
32: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one;
33: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one;
34: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-ethyl-benzonitrile;
35: 5-(5-Chloro-2-methyl-phenyl)-6-(4-chloro-2-methyl-phenyl)-2-(2-dimethylamino-4-methoxy-pyrimidin-5-yl)-1-isopropyl-5,6-dihydro-1H-pyrrolo[3,4-d]imidazol-4-one;
36: 5-(5-Chloro-2-methyl-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

37: 2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one;

38: 5-(5-Chloro-2-methyl-phenyl)-6-(4-chloro-phenyl)-2-{2-[(2-hydroxy-ethyl)-methyl-amino]-4-methoxy-pyrimidin-5-yl}-1-isopropyl-5,6-dihydro-1H-pyrrolo[3,4-d]imidazol-4-one;

39: 5-(5-Chloro-2-methyl-phenyl)-6-(4-chloro-phenyl)-2-[2-(2-hydroxy-ethyl amino)-4-methoxy-pyrimidin-5-yl]-1-isopropyl-5,6-dihydro-1H-pyrrolo[3,4-d]imidazol-4-one;

40: 4-[2-(2-Amino-4-methoxy-pyrimidin-5-yl)-5-(5-chloro-2-methyl-phenyl)-3-isopropyl-6-oxo-3,4,5,6-tetrahydro-pyrrolo[3,4-d]imidazol-4-yl]-benzonitrile;

41: 4-[5-(5-Chloro-2-methyl-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile;

42: 4-[5-(5-Chloro-2-methyl-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

43: 4-[5-(5-Chloro-1-methyl-6-oxo-1,6-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

44: 4-[5-(5-Chloro-1-methyl-6-oxo-1,6-dihydro-pyridin-3-yl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile;

45: 4-[2-(2-Amino-4-methoxy-pyrimidin-5-yl)-5-(5-chloro-1-methyl-6-oxo-1,6-dihydro-pyridin-3-yl)-3-isopropyl-6-oxo-3,4,5,6-tetrahydro-pyrrolo[3,4-d]imidazol-4-yl]-benzonitrile;

46: 5-(5-Chloro-2-methyl-phenyl)-6-(4-chloro-2-methyl-phenyl)-1-isopropyl-2-(4-methoxy-2-methylamino-pyrimidin-5-yl)-5,6-dihydro-1H-pyrrolo[3,4-d]imidazol-4-one;

47: 5-(5-Chloro-2-methyl-phenyl)-6-(4-chloro-2-methyl-phenyl)-2-(2-ethyl-6-methoxy-pyridin-3-yl)-1-isopropyl-5,6-dihydro-1H-pyrrolo[3,4-d]imidazol-4-one;

48: 2-(2-Amino-4-methoxy-pyrimidin-5-yl)-5-(5-chloro-2-methyl-phenyl)-6-(4-chloro-2-methyl-phenyl)-1-isopropyl-5,6-dihydro-1H-pyrrolo[3,4-d]imidazol-4-one;

49: 3-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-ethyl-benzonitrile;

50: 5-(5-Chloro-2-methyl-phenyl)-6-(4-chloro-phenyl)-1-isopropyl-2-(4-methoxy-pyrimidin-5-yl)-5,6-dihydro-1H-pyrrolo[3,4-d]imidazol-4-one;

51: 5-(5-Chloro-2-methyl-phenyl)-6-(4-chloro-2-methyl-phenyl)-2-{2-[(2-hydroxy-ethyl)-methyl-amino]-4-methoxy-pyrimidin-5-yl}-1-isopropyl-5,6-dihydro-1H-pyrrolo[3,4-d]imidazol-4-one;

52: 5-(5-Chloro-2-methyl-phenyl)-6-(4-chloro-2-methyl-phenyl)-2-[2-(2-hydroxy-ethyl amino)-4-methoxy-pyrimidin-5-yl]-1-isopropyl-5,6-dihydro-1H-pyrrolo[3,4-d]imidazol-4-one;

53: 4-[2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile;

54: 4-[5-(3-Chloro-2-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile;

55: 4-[5-(3-Chloro-2-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

56: 4-[2-(2-Amino-4-methoxy-pyrimidin-5-yl)-5-(3-chloro-4-fluoro-phenyl)-3-isopropyl-6-oxo-3,4,5,6-tetrahydro-pyrrolo[3,4-d]imidazol-4-yl]-benzonitrile;

57: 4-[5-(3-Chloro-4-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-benzonitrile;

58: 4-[5-(3-Chloro-4-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

59: 5-(5-Chloro-2-methyl-phenyl)-6-(4-chloro-phenyl)-2-[2-(3-hydroxy-3-methyl-azetidin-1-yl)-4-methoxy-pyrimidin-5-yl]-1-isopropyl-5,6-dihydro-1H-pyrrolo[3,4-d]imidazol-4-one 60: 5-(5-Chloro-2-methyl-phenyl)-6-(4-chloro-2-methyl-phenyl)-2-[2-(3-hydroxy-3-methyl-azetidin-1-yl)-4-methoxy-pyrimidin-5-yl]-1-isopropyl-5,6-dihydro-1H-pyrrolo[3,4-d]imidazol-4-one;

61: 5-(5-Chloro-2-methyl-phenyl)-6-(4-chloro-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one;

62: 5-(5-Chloro-2-methyl-phenyl)-6-(4-chloro-2-methyl-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one;

63: 2-(4-Amino methyl-2-methoxy-phenyl-5-(5-chloro-2-methyl-phenyl)-6-(4-chloro-phenyl)-1-isopropyl-5,6-dihydro-1H-pyrrolo[3,4-d]imidazole-4-one;

64: 5-(3-Chloro-2-fluoro-phenyl)-6-(4-chloro-2-methyl-phenyl)-1-isopropyl-2-(2-methoxy-phenyl)-5,6-dihydro-1H-pyrrolo[3,4-d]imidazole-4-one;

65: 5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

66: 5-(5-Chloro-1-methyl-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

67: 2-(2-Amino-4-methoxy-pyrimidin-5-yl)-5-(5-chloro-1-methyl-6-oxo-1,6-dihydro-pyridin-3-yl)-6-(4-chloro-phenyl)-1-isopropyl-5,6-dihydro-1H-pyrrolo[3,4-d]imidazol-4-one;

68: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide;

69: 5-(3-Chloro-2-fluoro-phenyl)-6-(4-chloro-phenyl)-1-isopropyl-2-[2-methoxy-5-(morpholine-4-carbonyl)phenyl]-5,6-dihydro-1H-pyrrolo[3,4-d]imidazole-4-one;

70: 3-[5-(3-Chloro-2-fluoro-phenyl)-6-(4-chloro-phenyl)-1-isopropyl-4-oxo-1,4,5,6-tetrahydropyrrolo[3,4-d]imidazol-2-yl]-4-methoxy-N,N-dimethyl benzamide;

71: 6-(4-Chloro-2-methyl-phenyl)-5-(4-chloro-pyrimidin-2-yl)-1-isopropyl-2-(2-methoxy-phenyl)-5,6,-dihydro-1H-pyrrolo[3,4-d]imidazol-4-one;

72: 6-(4-Chloro-phenyl)-5-(5-chloro-pyridin-3-yl)-2-(2,4-dimethoxy-pyrimidin-5-yl)-1-isopropyl-5,6-dihydro-1H-pyrrolo[3,4-d]imidazole-4-one;

73: 3-[5-(3-Chloro-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl benzamide;

74: 4-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-4-methoxy-N,N-dimethyl benzamide;

75: (S)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one;

76: (R)-5-(5-Chloro-2-methyl-phenyl)-6-(4-chloro-2-methyl-phenyl)-2-(2,4-dimethoxy-pyrimidin-5-yl)-1-isopropyl-5,6,-dihydro-1H-pyrrolo[3,4-d]imidazol-4-one;

77: 4-[5-(5-Chloro-2-methyl-phenyl)-3-isopropyl-2-(2-methoxy-phenyl)-6-oxo-3,4,5,6-tetrahydro-pyrrolo[3,4-d]imidazol-4-yl]-benzonitrile;

78: 4-[5-(5-Chloro-2-methyl-phenyl)-2-(2-hydroxy-phenyl)-3-isopropyl-6-oxo-3,4,5,6-tetrahydro-pyrrolo[3,4-d]imidazol-4-yl]-benzonitrile;

79: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

80: 4-[5-(3-Chloro-4-fluoro-phenyl)-3-isopropyl-2-(2-methoxy-phenyl)-6-oxo-3,4,5,6-tetrahydro-pyrrolo[3,4-d]imidazol-4-yl]-benzonitrile;

81: 3-[5-(3-Chloro-4-fluoro-phenyl)-6-(4-cyano-phenyl)-1-isopropyl-4-oxo-1,4,5,6-tetrahydro-pyrrolo[3,4-d]imidazol-2-yl]-4-methoxy-N,N-dimethyl-benzamide;

82: 4-[5-(3-Chloro-4-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

83: 6-(4-Chloro-phenyl)-1-isopropyl-2-(2-methoxy-phenyl)-5-(1-methyl-6-oxo-piperidin-3-yl)-5,6-dihydro-1H-pyrrolo[3,4-d]imidazol-4-one;

84: 6-(4-Chloro-phenyl)-2-(2,4-dimethoxy-pyrimidin-5-yl)-1-isopropyl-5-(1-methyl-6-oxo-piperidin-3-yl)-5,6-dihydro-1H-pyrrolo[3,4-d]imidazol-4-one;

85: 5-(3-Chloro-4-fluoro-phenyl)-6-(4-chloro-phenyl)-1-cyclobutyl-2-(2,4-dimethoxy-pyrimidin-5-yl)-5,6-dihydro-1H-pyrrolo[3,4-d]imidazol-4-one;

86: 5-(5-Chloro-2-methyl-phenyl)-6-(4-chloro-phenyl)-1-cyclobutyl-2-(2,4-dimethoxy-pyrimidin-5-yl)-5,6-dihydro-1H-pyrrolo[3,4-d]imidazol-4-one;

87: 4-[5-(3-Chloro-4-fluoro-phenyl)-3-cyclobutyl-2-(2,4-dimethoxy-pyrimidin-5-yl)-6-oxo-3,4,5,6-tetrahydro-pyrrolo[3,4-d]imidazol-4-yl]-benzonitrile;

88: 5-(3-Chloro-4-fluoro-phenyl)-6-(4-chloro-phenyl)-1-cyclopropyl-2-(2,4-dimethoxy pyrimidin-5-yl)-5,6-dihydro-1H-pyrrolo[3,4-d]imidazol-4-one;

89: (S)-5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one;

90: (R)-5-(5-Chloro-2-methyl-phenyl)-6-(4-chloro-2-methyl-phenyl)-2-(5-hydroxymethyl-2-methoxy-phenyl)-1-isopropyl-5,6-dihydro-1H-pyrrolo[3,4-d]imidazole-4-one;

91: 6-(4-Chloro-phenyl)-2-(2-dimethylamino-4-methoxy-pyrimidin-5-yl)-5-(2,5-dimethyl-2H-pyrazol-3-yl)-1-isopropyl-5,6-dihydro-1H-pyrrolo[3,4-d]imidazol-4-one;

92: 6-(4-Chloro-phenyl)-2-(2,4-dimethoxy-pyrimidin-5-yl)-5-(2,5-dimethyl-2H-pyrazol-3-yl)-1-isopropyl-5,6-dihydro-1H-pyrrolo[3,4-d]imidazol-4-one;

93: {4-[5-(3-Chloro-2-fluoro-phenyl)-6-(4-chloro-2-methyl-phenyl)-1-isopropyl-4-oxo-1,4,5,6-tetrahydro-pyrrolo[3,4-d]imidazol-2-yl]-5-methoxy-pyridin-2-yl}-acetonitrile;

94: 4-[6-(4-Chloro-phenyl)-2-(2-dimethylamino-4-methoxy-pyrimidin-5-yl)-1-isopropyl-4-oxo-4,6-dihydro-1H-pyrrolo[3,4-d]imidazol-5-yl]-3-methyl-benzamide;

95: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-3-methyl-benzamide;

96: 5-(3-Chloro-2-fluoro-phenyl)-6-(4-chloro-phenyl)-1-isopropyl-2-(5-methoxy-2-oxo-1,2-dihydro-pyrimidin-4-yl)-5,6-dihydro-1H-pyrrolo[3,4-d]imidazol-4-one;

97: 5-(4-Amino-cyclohexyl)-6-(4-chloro-phenyl)-2-(2,4-dimethoxy-pyrimidin-5-yl)-1-isopropyl-5,6-dihydro-1H-pyrrolo[3,4-d]imidazol-4-one;

98: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid;

99: N-{4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexyl}-acetamide;

100: 4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

101: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

102: (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

103: (R)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

104: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-cyclohexanecarboxylic acid methylamide;

105: 5-(3-Chloro-4-fluoro-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one;

106: {4-[5-(5-Chloro-2-methyl-phenyl)-6-(4-chloro-2-methyl-phenyl)-1-isopropyl-4-oxo-1,4,5,6-tetrahydro-pyrrolo[3,4-d]imidazol-2-yl]-5-methoxy-pyridin-2-yl}-acetonitrile;

107: {4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile;

108: {4-[5-(5-Chloro-1-methyl-2-oxo-1,2-dihydro-pyridin-3-yl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile;

109: 5-(3-Chloro-2-fluoro-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one;

110: 5-(5-Chloro-2-methyl-phenyl)-6-(4-chloro-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one;

111: 5-(5-Chloro-2-methyl-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one;

112: 5-(3-Chloro-4-fluoro-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one;

113: 5-(5-Chloro-2-methyl-phenyl)-6-(4-chloro-phenyl)-2-(2-dimethylamino-4-methoxy-pyrimidin-5-yl)-1-((R)-2-hydroxy-1-methyl-ethyl)-5,6-dihydro-1H-pyrrolo[3,4-d]imidazol-4-one;

114: 5-(3-Chloro-2-fluoro-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one;

115: 5-(5-Chloro-2-methyl-phenyl)-2-(2,4-dimethoxy-pyrimidin-5-yl)-1-isopropyl-6-(4-methyl-cyclohexyl)-5,6-dihydro-1H-pyrrolo[3,4-d]imidazol-4-one;

116: 4-(4-Chloro-2-methyl-phenyl)-5-(5-chloro-2-methyl-phenyl)-2-(2,4-dimethoxy-pyrimidin-5-yl)-3-isopropyl-6-oxo-3,4,5,6-tetrahydro-pyrrolo[3,4-d]imidazole-4-carboxylic acid ethyl ester;

117: 5-(5-Chloro-2-methyl-phenyl)-6-(4-chloro-phenyl)-2-(2,4-dimethoxy-pyrimidin-5-yl)-1-((R)-2-hydroxy-1-methyl-ethyl)-5,6-dihydro-1H-pyrrolo[3,4-d]imidazol-4-one;

118: 4-[2-(2-Amino-4-methoxy-pyrimidin-5-yl)-6-(4-chloro-phenyl)-1-isopropyl-4-oxo-4,6-dihydro-1H-pyrrolo[3,4-d]imidazol-5-yl]-3-methyl-benzonitrile;

119: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-3-methyl-benzonitrile;

120: 4-Chloro-2-[6-(4-chloro-phenyl)-2-(2,4-dimethoxy-pyrimidin-5-yl)-1-isopropyl-4-oxo-4,6-dihydro-1H-pyrrolo[3,4-d]imidazol-5-yl]-benzonitrile;

121: 5-(5-Chloro-2-methyl-phenyl)-6-(4-chloro-phenyl)-2-{2-[(2-hydroxy-ethyl)-methyl-amino]-5-methoxy-pyrimidin-4-yl}-1-isopropyl-5,6-dihydro-1H-pyrrolo[3,4-d]imidazol-4-one;

122: 5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

123: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid methylamide;

124: 4-[5-(5-Chloro-1-methyl-2-oxo-1,2-dihydro-pyridin-3-yl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

125: 4-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-piperidine-1-carboxylic acid methyl ester;

126: 2-{4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-N-methyl-acetamide;

127: 5-(5-Chloro-6-oxo-1,6-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

128: 2-(2-Amino-4-methoxy-pyrimidin-5-yl)-6-(4-chloro-phenyl)-5-(1,3-dimethyl-2-oxo-hexahydro-pyrimidin-5-yl)-1-isopropyl-5,6-dihydro-1H-pyrrolo[3,4-d]imidazol-4-one;

129: 6-(4-Chloro-phenyl)-2-(2-dimethylamino-4-methoxy-pyrimidin-5-yl)-5-(1,3-dimethyl-2-oxo-hexahydro-pyrimidin-5-yl)-1-isopropyl-5,6-dihydro-1H-pyrrolo[3,4-d]imidazol-4-one;

130: 4-[5-(3-Chloro-2-fluoro-phenyl)-2-(5-cyanomethyl-2-methoxy-phenyl)-3-isopropyl-6-oxo-3,4,5,6-tetrahydro-pyrrolo[3,4-d]imidazol-4-yl]-benzonitrile;

131: 4-[5-(5-Chloro-2-methyl-phenyl)-2-(5-cyanomethyl-2-methoxy-pyridin-3-yl)-3-isopropyl-6-oxo-3,4,5,6-tetrahydro-pyrrolo[3,4-d]imidazol-4-yl]-benzonitrile;

132: 4-[5-(3-Chloro-2-fluoro-phenyl)-2-(5-cyanomethyl-2-methoxy-pyridin-3-yl)-3-isopropyl-6-oxo-3,4,5,6-tetrahydro-pyrrolo[3,4-d]imidazol-4-yl]-benzonitrile;

133: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetonitrile;

134: 4-[5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile;

135: 4-[5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile;

136: {4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile;

137: {5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester;

138: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid;

139: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carboxylic acid amide;

140: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid;

141: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid;

142: 4-[(S)-2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile;

143: 4-[(R)-2-(2-Amino-4-methoxy-pyrimidin-5-yl)-5-(3-chloro-2-fluoro-phenyl)-3-isopropyl-6-oxo-3,4,5,6-tetrahydro-pyrrolo[3,4-d]imidazol-4-yl]-benzonitrile;

144: 5-(5-Chloro-2-methyl-phenyl)-6-(4-chloro-phenyl)-1-isopropyl-2-[3-(2-methyl-3H-imidazol-4-yl)-phenyl]-5,6-dihydro-1H-pyrrolo[3,4-d]imidazol-4-one;

145: 6-(4-Chloro-phenyl)-2-(2,4-dimethoxy-pyrimidin-5-yl)-5-(1,3-dimethyl-2-oxo-hexahydro-pyrimidin-5-yl)-1-isopropyl-5,6-dihydro-1H-pyrrolo[3,4-d]imidazol-4-one;

146: {5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid;

147: 2-{5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-N-methyl-acetamide;

148: 2-{5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-N-methyl-acetamide;

149: 5-(5-Chloro-2-methyl-phenyl)-6-(4-chloro-phenyl)-2-(2,4-dimethoxy-pyrimidin-5-yl)-1-((S)-2-hydroxy-1-methyl-ethyl)-5,6-dihydro-1H-pyrrolo[3,4-d]imidazol-4-one;

150: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid ethyl ester;

151: 2-{5-[5-(5-Chloro-2-methyl-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-N-methyl-acetamide;

152: {5-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-6-methoxy-pyridin-3-yl}-acetic acid ethyl ester;

153: 6-(4-Chloro-2-methyl-phenyl)-5-(5-chloro-2-methyl-phenyl)-2-(2,4-dimethoxy-pyrimidin-5-yl)-1-isopropyl-6-methyl-5,6-dihydro-1H-pyrrolo[3,4-d]imidazol-4-one;

154: 2-{3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-phenyl}-N-methyl-acetamide;

155: 2-{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-N,N-dimethyl-acetamide;

156: 5-(5-Chloro-2-methyl-phenyl)-6-(4-chloro-phenyl)-2-(2,4-dimethoxy-pyrimidin-5-yl)-1-((S)-2-methoxy-1-methyl-ethyl)-5,6-dihydro-1H-pyrrolo[3,4-d]imidazol-4-one;

157: 2-{3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-N-methyl-acetamide;

158: 5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

159: 2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one;

160: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

161: 4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-benzonitrile;

162: {3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid;

163: (R)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

164: (S)-5-(5-Chloro-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

165: {3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-phenyl}-acetic acid methyl ester;

166: 4-[(R)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

167: 4-[5-(3-Chloro-4-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile;

168: (R)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one;

169: (S)-5-(5-Chloro-2-methyl-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one;

170: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carbonitrile;

171: 5-(3-Chloro-2-fluoro-phenyl)-6-(4-chloro-phenyl)-2-(2-dimethylamino-5-methoxy-pyrimidin-4-yl)-1-isopropyl-5,6-dihydro-1H-pyrrolo[3,4-d]imidazol-4-one;

172: 5-(5-Chloro-2-methyl-phenyl)-6-(4-chloro-phenyl)-2-(2-dimethylamino-5-methoxy-pyrimidin-4-yl)-1-isopropyl-5,6-dihydro-1H-pyrrolo[3,4-d]imidazol-4-one;

173: 3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide;

174: 3-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-4-methoxy-benzamide;

175: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-benzamide;

176: 3-[5-(5-Chloro-1-methyl-6-oxo-1,6-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-benzamide;

177: 5-(5-Chloro-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-d]imidazol-4-one;

178: 5-[6-(4-Chloro-phenyl)-2-(2,4-dimethoxy-pyrimidin-5-yl)-1-isopropyl-4-oxo-4,6-dihydro-1H-pyrrolo[3,4-d]imidazol-5-yl]-1,3-dimethyl-1H-pyrimidine-2,4-dione;

179: 5-[6-(4-Chloro-phenyl)-2-(2-dimethylamino-4-methoxy-pyrimidin-5-yl)-1-isopropyl-4-oxo-4,6-dihydro-1H-pyrrolo[3,4-d]imidazol-5-yl]-1,3-dimethyl-1H-pyrimidine-2,4-dione;

180: 5-[2-(2-Amino-4-methoxy-pyrimidin-5-yl)-6-(4-chloro-phenyl)-1-isopropyl-4-oxo-4,6-dihydro-1H-pyrrolo[3,4-d]imidazol-5-yl]-1,3-dimethyl-1H-pyrimidine-2,4-dione;

181: 5-(5-Chloro-2-methyl-phenyl)-6-(4-chloro-phenyl)-1-cyclopropyl-2-(2,4-dimethoxy-pyrimidin-5-yl)-5,6-dihydro-1H-pyrrolo[3,4-d]imidazol-4-one;

182: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-3-methyl-benzonitrile;

183: 4-[5-(3-Chloro-2-fluoro-phenyl)-3-isopropyl-2-(2-methoxy-phenyl)-6-oxo-3,4,5,6-tetrahydro-pyrrolo[3,4-d]imidazol-4-yl]-3-methyl-benzonitrile;
184: 5-(3-Chloro-2-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;
185: 5-(3-Chloro-4-fluoro-phenyl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;
186: 3-[5-(5-Chloro-2-methyl-phenyl)-6-(4-cyano-2-methyl-phenyl)-1-isopropyl-4-oxo-1,4,5,6-tetrahydro-pyrrolo[3,4-d]imidazol-2-yl]-4-methoxy-N,N-dimethyl-benzamide;
187: 4-[5-(5-Chloro-2-methyl-phenyl)-2-(1-ethyl-5-methoxy-2-oxo-1,2-dihydro-pyridin-4-yl)-3-isopropyl-6-oxo-3,4,5,6-tetrahydro-pyrrolo[3,4-d]imidazol-4-yl]-benzonitrile;
188: 4-[5-(5-Chloro-2-methyl-phenyl)-2-(2,4-dimethoxy-pyrimidin-5-yl)-3-isopropyl-6-oxo-3,4,5,6-tetrahydro-pyrrolo[3,4-d]imidazol-4-yl]-3-methyl-benzonitrile;
189: 3-[(R)-5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide;
190: 3-[(S)-5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide;
191: 4-[5-(5-Chloro-2-methyl-phenyl)-3-isopropyl-2-(2-methoxy-phenyl)-6-oxo-3,4,5,6-tetrahydro-pyrrolo[3,4-d]imidazol-4-yl]-3-methyl-benzonitrile;
192: 2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one;
193: 2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one;
194: 3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-benzonitrile;
195: 5-(3-Chloro-4-fluoro-phenyl)-6-(4-chloro-phenyl)-1-isopropyl-2-[2-methoxy-5-(morpholine-4-carbonyl)-phenyl]-5,6-dihydro-1H-pyrrolo[3,4-d]imidazol-4-one;
196: 5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;
197: 3-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide;
198: 5-(3-Chloro-4-fluoro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one;
199: 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;
200: 3-[5-(5-Chloro-1-methyl-2-oxo-1,2-dihydro-pyridin-3-yl)-6-(4-chloro-phenyl)-1-isopropyl-4-oxo-1,4,5,6-tetrahydro-pyrrolo[3,4-d]imidazol-2-yl]-4-methoxy-N,N-dimethyl-benzamide;
201: 5-(5-Chloro-1-methyl-2-oxo-1,2-dihydro-pyridin-3-yl)-6-(4-chloro-phenyl)-2-[2-(3-hydroxy-azetidin-1-yl)-4-methoxy-pyrimidin-5-yl]-1-isopropyl-5,6-dihydro-1H-pyrrolo[3,4-d]imidazol-4-one;
202: 5-(5-Chloro-1-methyl-2-oxo-1,2-dihydro-pyridin-3-yl)-6-(4-chloro-phenyl)-1-isopropyl-2-(4-methoxy-2-methylamino-pyrimidin-5-yl)-5,6-dihydro-1H-pyrrolo[3,4-d]imidazol-4-one;
203: (S)-2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one;
204: (R)-2-(2-Amino-4-methoxy-pyrimidin-5-yl)-5-(5-chloro-1-methyl-2-oxo-1,2-dihydro-pyridin-3-yl)-6-(4-chloro-phenyl)-1-isopropyl-5,6-dihydro-1H-pyrrolo[3,4-d]imidazol-4-one;
205: (S)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one;
206: (R)-2-(2-Amino-4-methoxy-pyrimidin-5-yl)-5-(5-chloro-2-methyl-phenyl)-6-(4-chloro-phenyl)-1-isopropyl-5,6-dihydro-1H-pyrrolo[3,4-d]imidazol-4-one;
207: 3-[6-(4-Chloro-phenyl)-5-(5-chloro-pyridin-3-yl)-1-isopropyl-4-oxo-1,4,5,6-tetrahydro-pyrrolo[3,4-d]imidazol-2-yl]-4-methoxy-N,N-dimethyl-benzamide;
208: 5-(3-Chloro-2-fluoro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one;
209: 3-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-N-isopropyl-4-methoxy-benzamide;
210: 5-(3-Chloro-phenyl)-6-(4-chloro-phenyl)-2-(2,4-dimethoxy-pyrimidin-5-yl)-1-isopropyl-5,6-dihydro-1H-pyrrolo[3,4-d]imidazol-4-one;
211: 3-[5-(3-Chloro-phenyl)-6-(4-chloro-phenyl)-1-isopropyl-4-oxo-1,4,5,6-tetrahydro-pyrrolo[3,4-d]imidazol-2-yl]-4-methoxy-benzonitrile;
212: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzoic acid;
213: 6-(4-Chloro-2-methyl-phenyl)-5-(3-chloro-phenyl)-1-isopropyl-2-[2-methoxy-5-(morpholine-4-carbonyl)-phenyl]-5,6-dihydro-1H-pyrrolo[3,4-d]imidazol-4-one;
214: 6-(4-Chloro-2-methyl-phenyl)-5-(3-chloro-phenyl)-2-(2,4-dimethoxy-pyrimidin-5-yl)-1-isopropyl-5,6-dihydro-1H-pyrrolo[3,4-d]imidazol-4-one;
215: 3-[6-(4-Chloro-2-methyl-phenyl)-5-(3-chloro-phenyl)-1-isopropyl-4-oxo-1,4,5,6-tetrahydro-pyrrolo[3,4-d]imidazol-2-yl]-4-methoxy-benzonitrile;
216: 4-[5-(5-Chloro-2-methyl-phenyl)-6-(4-chloro-phenyl)-1-isopropyl-4-oxo-1,4,5,6-tetrahydro-pyrrolo[3,4-d]imidazol-2-yl]-3-methoxy-benzonitrile;
217: 3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-4-methoxy-benzamide;
218: 3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-4-methoxy-benzamide;
219: 4-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-(2-hydroxy-ethyl)-3-methoxy-benzamide;
220: 4-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-3-methoxy-benzamide;

221: 5-(5-Chloro-2-methyl-phenyl)-6-(4-chloro-2-methyl-phenyl)-2-(2-ethyl-phenyl)-1-isopropyl-5,6-dihydro-1H-pyrrolo[3,4-d]imidazol-4-one;
222: 3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-N,N-dimethyl-benzamide;
223: 3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-N,N-dimethyl-benzamide;
224: 6-(4-Chloro-2-methyl-phenyl)-5-(4-chloro-pyridin-2-yl)-2-(5-hydroxymethyl-2-methoxy-phenyl)-1-isopropyl-5,6-dihydro-1H-pyrrolo[3,4-d]imidazol-4-one;
225: 3-[(R)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-4-methoxy-benzamide;
226: 3-[(S)-6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-N-isopropyl-4-methoxy-benzamide;
227: 6-(4-Chloro-2-methyl-phenyl)-5-(5-chloro-2-methyl-pyridin-3-yl)-1-isopropyl-2-(2-methoxy-phenyl)-5,6-dihydro-1H-pyrrolo[3,4-d]imidazol-4-one;
228: N-{3-[6-(4-Chloro-2-methyl-phenyl)-5-(5-chloro-2-methyl-phenyl)-1-isopropyl-4-oxo-1,4,5,6-tetrahydro-pyrrolo[3,4-d]imidazol-2-yl]-4-methoxy-benzyl}-2-hydroxy-acetamide;
229: 5-[5-Chloro-1-(2-hydroxy-ethyl)-6-oxo-1,6-dihydro-pyridin-3-yl]-6-(4-chloro-2-methyl-phenyl)-1-isopropyl-2-(2-methoxy-phenyl)-5,6-dihydro-1H-pyrrolo[3,4-d]imidazol-4-one;
230: 5-[5-Chloro-1-(2-methoxy-ethyl)-6-oxo-1,6-dihydro-pyridin-3-yl]-6-(4-chloro-2-methyl-phenyl)-1-isopropyl-2-(2-methoxy-phenyl)-5,6-dihydro-1H-pyrrolo[3,4-d]imidazol-4-one;
231: 5-(5-Chloro-1-methyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-d]imidazol-4-one;
232: 5-(5-Chloro-1-ethyl-6-oxo-1,6-dihydro-pyridin-3-yl)-6-(4-chloro-2-methyl-phenyl)-1-isopropyl-2-(2-methoxy-phenyl)-5,6-dihydro-1H-pyrrolo[3,4-d]imidazol-4-one;
233: 2-(2-Amino-pyridin-4-yl)-5-(3-chloro-2-fluoro-phenyl)-6-(4-chloro-phenyl)-1-isopropyl-5,6-dihydro-1H-pyrrolo[3,4-d]imidazol-4-one;
234: 5-(3-Chloro-2-fluoro-phenyl)-6-(4-chloro-phenyl)-2-[5-(1-hydroxy-2-methyl-propyl)-2-methoxy-phenyl]-1-isopropyl-5,6-dihydro-1H-pyrrolo[3,4-d]imidazol-4-one;
235: 5-(3-Chloro-2-fluoro-phenyl)-6-(4-chloro-phenyl)-2-[5-(1-hydroxy-ethyl)-2-methoxy-phenyl]-1-isopropyl-5,6-dihydro-1H-pyrrolo[3,4-d]imidazol-4-one;
236: 5-(3-Chloro-2-fluoro-phenyl)-6-(4-chloro-phenyl)-1-isopropyl-2-(4-methoxy-pyridin-3-yl)-5,6-dihydro-1H-pyrrolo[3,4-d]imidazol-4-one;
237: 5-(5-(3-chloro-2-fluorophenyl)-6-(4-chlorophenyl)-1-isopropyl-4-oxo-1,4,5,6-tetrahydropyrrolo[3,4-d]imidazol-2-yl)-6-methoxy-N,N-dimethylpyridazine-3-carboxamide;
238: 2-(4-(5-(5-chloro-1-methyl-2-oxo-1,2-dihydropyridin-3-yl)-6-(4-chloro-2-methylphenyl)-1-isopropyl-4-oxo-1,4,5,6-tetrahydropyrrolo[3,4-d]imidazol-2-yl)-5-methoxypyridin-2-yl)acetonitrile;
239: 4-(5-(3-chloro-2-fluorophenyl)-2-(2-(cyanomethyl)-5-methoxypyridin-4-yl)-3-isopropyl-6-oxo-3,4,5,6-tetrahydropyrrolo[3,4-d]imidazol-4-yl)-3-methylbenzonitrile;
240: 4-(5-(3-chloro-4-fluorophenyl)-2-(2-(cyanomethyl)-5-methoxypyridin-4-yl)-3-isopropyl-6-oxo-3,4,5,6-tetrahydropyrrolo[3,4-d]imidazol-4-yl)benzonitrile;
241: {4-[5-(3-Chloro-4-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile;
242: 4-[5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-3-methyl-benzonitrile;
243: 6-(4-Chloro-phenyl)-5-(2,6-dimethyl-pyrimidin-4-yl)-1-isopropyl-2-(5-methoxy-1-methyl-2-oxo-1,2-dihydro-pyridin-4-yl)-5,6-dihydro-1H-pyrrolo[3,4-d]imidazol-4-one;
244: 5-(3-Chloro-2-fluoro-phenyl)-6-(4-chloro-phenyl)-1-isopropyl-2-(3-methoxy-1-methyl-6-oxo-1,6-dihydro-pyridazin-4-yl)-5,6-dihydro-1H-pyrrolo[3,4-d]imidazol-4-one;
245: 5-(5-Chloro-2-methyl-phenyl)-6-(5-chloro-pyridin-2-yl)-2-(2-dimethylamino-4-methoxy-pyrimidin-5-yl)-1-isopropyl-5,6-dihydro-1H-pyrrolo[3,4-d]imidazol-4-one;
246: 4-[5-(3-Chloro-2-fluoro-phenyl)-3-isopropyl-2-(4-methoxy-2-methylamino-pyrimidin-5-yl)-6-oxo-3,4,5,6-tetrahydro-pyrrolo[3,4-d]imidazol-4-yl]-2-fluoro-benzonitrile;
247: 4-[5-(3-Chloro-2-fluoro-phenyl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile;
248: 4-[5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile;
249: 4-[5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyrimidine-2-carboxylic acid dimethylamide;
250: {4-[(S)-5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile;
251: {4-[(R)-5-(3-Chloro-2-fluoro-phenyl)-6-(4-chloro-phenyl)-1-isopropyl-4-oxo-1,4,5,6-tetrahydro-pyrrolo[3,4-d]imidazol-2-yl]-5-methoxy-pyridin-2-yl}-acetonitrile;
252: 4-[(S)-5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile;
253: 4-[(R)-5-(5-Chloro-2-methyl-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile;
254: 4-[(S)-5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile;
255: 4-[(R)-5-(3-Chloro-2-fluoro-phenyl)-2-(2-cyanomethyl-5-methoxy-pyridin-4-yl)-3-isopropyl-6-oxo-3,4,5,6-tetrahydro-pyrrolo[3,4-d]imidazol-4-yl]-benzonitrile;

256: 4-[5-(3-Chloro-2-fluoro-phenyl)-2-(2,4-dimethoxy-pyrimidin-5-yl)-3-((R)-2-methoxy-1-methyl-ethyl)-6-oxo-3,4,5,6-tetrahydro-pyrrolo[3,4-d]imidazol-4-yl]-benzonitrile;

257: 4-[5-(5-chloro-2-methyl-phenyl)-2-(2,4-dimethoxy-pyrimidin-5-yl)-3-((R)-2-methoxy-1-methyl-ethyl)-6-oxo-3,4,5,6-tetrahydro-pyrrolo[3,4-d]imidazol-4-yl]-benzonitrile;

258: 5-(3-Chloro-2-fluoro-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one;

259: 5-(3-Chloro-4-fluoro-phenyl)-6-(4-chloro-phenyl)-2-(2,4-dimethoxy-pyrimidin-5-yl)-1-((R)-2-methoxy-1-methyl-ethyl)-5,6-dihydro-1H-pyrrolo[3,4-d]imidazol-4-one;

260: 6-(4-Chloro-phenyl)-2-(2,4-dimethoxy-pyrimidin-5-yl)-5-(4-fluoro-3-methyl-phenyl)-1-isopropyl-5,6-dihydro-1H-pyrrolo[3,4-d]imidazol-4-one;

261: 6-(4-Chloro-phenyl)-2-(2,4-dimethoxy-pyrimidin-5-yl)-1-isopropyl-5-(2-methoxy-5-methyl-phenyl)-5,6-dihydro-1H-pyrrolo[3,4-d]imidazol-4-one;

262: 6-(4-Chloro-phenyl)-2-(2,4-dimethoxy-pyrimidin-5-yl)-5-(2,6-dimethyl-pyrimidin-4-yl)-1-isopropyl-5,6-dihydro-1H-pyrrolo[3,4-d]imidazol-4-one;

263: (S)-2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one;

264: (R)-2-(2-Amino-4-methoxy-pyrimidin-5-yl)-5-(3-chloro-4-fluoro-phenyl)-6-(4-chloro-phenyl)-1-isopropyl-5,6-dihydro-1H-pyrrolo[3,4-d]imidazol-4-one;

265: (S)-2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one;

266: (R)-2-(2-Amino-4-methoxy-pyrimidin-5-yl)-5-(3-chloro-2-fluoro-phenyl)-6-(4-chloro-phenyl)-1-isopropyl-5,6-dihydro-1H-pyrrolo[3,4-d]imidazol-4-one;

267: 6-(4-Chloro-phenyl)-5-(4-fluoro-3-methyl-phenyl)-1-isopropyl-2-(5-methoxy-1-methyl-2-oxo-1,2-dihydro-pyridin-4-yl)-5,6-dihydro-1H-pyrrolo[3,4-d]imidazol-4-one;

268: 6-(4-Chloro-phenyl)-1-isopropyl-2-(5-methoxy-1-methyl-2-oxo-1,2-dihydro-pyridin-4-yl)-5-(2-methoxy-5-methyl-phenyl)-5,6-dihydro-1H-pyrrolo[3,4-d]imidazol-4-one;

269: 5-(5-Chloro-1-methyl-6-oxo-1,6-dihydro-pyridin-3-yl)-6-(4-chloro-phenyl)-1-isopropyl-2-(2-methoxy-pyrimidin-5-yl)-5,6-dihydro-1H-pyrrolo[3,4-d]imidazol-4-one;

270: 5-(5-Chloro-1-methyl-6-oxo-1,6-dihydro-pyridin-3-yl)-6-(4-chloro-2-methyl-phenyl)-1-isopropyl-2-(2-methoxy-pyridine-3-yl)-5,6-dihydro-1H-pyrrolo[3,4-d]imidazol-4-one;

271: 6-(4-Chloro-2-phenyl)-5-(1,5-dimethyl-6-oxo-1,6-dihydro-pyridin-3-yl)-1-isopropyl-2-(2-methoxy-pyrimidin-5-yl)-5,6-dihydro-1H-pyrrolo[3,4-d]imidazol-4-one;

272: 6-(4-Chloro-phenyl)-5-(1,5-dimethyl-6-oxo-1,6-dihydro-pyridin-3-yl)-1-isopropyl-2-(2-methoxy-pyridin-3-yl)-5,6-dihydro-1H-pyrrolo[3,4-d]imidazol-4-one;

273: 6-(4-Chloro-2-phenyl)-2-(2,4-dimethoxy-pyrimidin-5-yl)-5-(1,5-dimethyl-6-oxo-1,6-dihydro-pyridin-3-yl)-1-isopropyl-5,6-dihydro-1H-pyrrolo[3,4-d]imidazol-4-one;

274: 6-(4-Chloro-2-phenyl)-1-cyclobutyl-2-(2,4-dimethoxy-pyrimidin-5-yl)-5-(1,5-dimethyl-6-oxo-1,6-dihydro-pyridin-3-yl)-5,6-dihydro-1H-pyrrolo[3,4-d]imidazol-4-one;

275: 5-(5-Chloro-2-methyl-phenyl)-6-(5-chloro-pyridin-2-yl)-2-(2-dimethylamino-4-methoxy-pyrimidin-5-yl)-1-isopropyl-5,6-dihydro-1H-pyrrolo[3,4-d]imidazol-4-one;

276: 5-(5-Chloro-2-methyl-phenyl)-6-(5-chloro-pyridin-2-yl)-2-(2,4-dimethoxy-pyrimidin-5-yl)-1-isopropyl-5,6-dihydro-1H-pyrrolo[3,4-d]imidazol-4-one;

277: 4-[5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluorobenzonitrile;

278: 4-[5-(5-Chloro-1-methyl-2-oxo-1,2-dihydro-pyridin-3-yl)-2-(2,4-dimethoxy-pyrimidin-5-yl)-3-isopropyl-6-oxo-3,4,5,6-tetrahydro-pyrrolo[3,4-d]imidazol-4-yl]-2-fluoro-benzonitrile;

279: (S)-5-(5-Chloro-1-methyl-2-oxo-1,2-dihydro-pyridin-3-yl)-6-(4-chloro-phenyl)-2-(2,4-dihydroxy-pyrimidin-5-yl)-1-isopropyl-5,6-dihydro-1H-pyrrolo[3,4-d]imidazol-4-one;

280: (R)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrrolo[3,4-d]imidazol-4-one;

281: (S)-5-(5-Chloro-1-methyl-2-oxo-1,2-dihydro-pyridin-3-yl)-6-(4-chloro-phenyl)-2-(2-dimethylamino-4-methoxy-pyrimidin-5-yl)-1-isopropyl-5,6-dihydro-1H-pyrolo[3,4-d]imidazol-4-one;

282: (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

283: (R)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

284: 6-(4-Chloro-3-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one;

285: 6-(4-Chloro-3-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one;

286: 5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-6-methyl-5,6-dihydro-1H-pyrrolo[3,4-d]imidazol-4-one;

287: 6-(4-Chloro-3-fluoro-phenyl)-5-(5-chloro-1-methyl-6-oxo-1,6-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one;

288: 4-[(R)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile;

289: 4-[(S)-5-(5-Chloro-1-methyl-2-oxo-1,2-dihydro-pyridin-3-yl)-2-(2-dimethylamino-4-methoxy-pyrimidin-5-yl)-3-isopropyl-6-oxo-3,4,5,6-tetrahydro-pyrrolo[3,4-d]imidazol-4-yl]-2-fluoro-benzonitrile;

290: 6-(4-Chloro-3-fluoro-phenyl)-5-(5-chloro-1-methyl-6-oxo-1,6-dihydro-pyridin-3-yl)-2-(2,4-dimethoxy-pyrimidin-5-yl)-1-isopropyl-5,6-dihydro-1H-pyrrolo[3,4-d]imidazol-4-one;

291: 6-(4-Chloro-phenyl)-2-(2,4-dimethoxy-pyrimidin-5-yl)-5-(1,4-dimethyl-6-oxo-1,6-dihydro-pyridin-2-yl)-1-isopropyl-5,6-dihydro-1H-pyrrolo[3,4-d]imidazol-4-one;

292: 6-(4-Chloro-phenyl)-2-(2,4-dimethoxy-pyrimidin-5-yl)-5-(1,5-dimethyl-2-oxo-1,2-dihydro-pyridin-3-yl)-1-isopropyl-5,6-dihydro-1H-pyrrolo[3,4-d]imidazol-4-one;

293: 6-(4-Chloro-phenyl)-2-(2-dimethylamino-4-methoxy-pyrimidin-5-yl)-5-(1,5-dimethyl-2-oxo-1,2-dihydro-pyridin-3-yl)-1-isopropyl-5,6-dihydro-1H-pyrrolo[3,4-d]imidazol-4-one;

294: 5-(5-Chloro-1-difluoromethyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

295: 5-(5-Chloro-1-methyl-d3-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

296: 5-(5-Chloro-1-ethyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

297: 5-(5-Chloro-1-methyl-2-oxo-1,2-dihydro-pyridin-3-yl)-6-(4-chloro-2-methyl-phenyl)-2-(2,4-dimethoxy-pyrimidin-5-yl)-1-isopropyl-5,6-dihydro-1H-pyrrolo[3,4-d]imidazol-4-one;

298: 5-(5-Chloro-1-methyl-2-oxo-1,2-dihydro-pyridin-3-yl)-6-(4-chloro-phenyl)-1-isopropyl-2-(4-methoxy-2-oxo-1,2-dihydro-pyrimidin-5-yl)-5,6-dihydro-1H-pyrrolo[3,4-d]imidazol-4-one;

299: 6-(4-Chloro-phenyl)-5-(2,6-dimethyl-pyrimidin-4-yl)-1-isopropyl-2-(5-methoxy-1-methyl-2-oxo-1,2-dihydro-pyridin-4-yl)-5,6-dihydro-1H-pyrrolo[3,4-d]imidazol-4-one;

300: 6-(4-Chloro-phenyl)-2-(2,4-dimethoxy-pyrimidin-5-yl)-1-isopropyl-5-(3-methoxy-6-methyl-pyridazin-4-yl)-5,6-dihydro-1H-pyrrolo[3,4-d]imidazol-4-one;

301: 5-(5-Chloro-2-methoxy-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

302: 6-(4-Chloro-phenyl)-2-(2-dimethylamino-4-methoxy-pyrimidin-5-yl)-1-isopropyl-5-(3-methoxy-6-methyl-pyridazin-4-yl)-5,6-dihydro-1H-pyrrolo[3,4-d]imidazol-4-one;

303: 6-(4-Chloro-2-fluoro-phenyl)-5-(3-chloro-2-fluoro-phenyl)-2-(2-dimethylamino-4-methoxy-pyrimidin-5-yl)-1-isopropyl-5,6-dihydro-1H-pyrrolo[3,4-d]imidazol-4-one;

304: 6-(4-Chloro-2-fluoro-phenyl)-5-(5-chloro-1-methyl-2-oxo-1,2-dihydro-pyridin-3-yl)-2-(2,4-dimethoxy-pyrimidin-5-yl)-1-isopropyl-5,6-dihydro-1H-pyrrolo[3,4-d]imidazol-4-one;

305: 6-(4-Chloro-2-fluoro-phenyl)-5-(5-chloro-1-methyl-2-oxo-1,2-dihydro-pyridin-3-yl)-2-(2-dimethylamino-4-methoxy-pyrimidin-5-yl)-1-isopropyl-5,6-dihydro-1H-pyrrolo[3,4-d]imidazol-4-one;

306: 6-(4-Chloro-phenyl)-2-(2-dimethylamino-4-methoxy-pyrimidin-5-yl)-5-(4-fluoro-2,5-dimethyl-2H-pyrazol-3-yl)-1-isopropyl-5,6-dihydro-1H-pyrrolo[3,4-d]imidazol-4-one;

307: (S)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

308: (R)-5-(5-Chloro-1-methyl-6-oxo-1,6-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

309: 6-(4-Chloro-phenyl)-5-(5-cyclopropyl-4-fluoro-2-methyl-2H-pyrazol-3-yl)-2-(2,4-dimethoxy-pyrimidin-5-yl)-1-isopropyl-5,6-dihydro-1H-pyrrolo[3,4-d]imidazol-4-one;

310: 6-(4-Chloro-phenyl)-5-(5-cyclopropyl-4-fluoro-2-methyl-2H-pyrazol-3-yl)-1-isopropyl-2-(5-methoxy-1-methyl-2-oxo-1,2-dihydro-pyridin-4-yl)-5,6-dihydro-1H-pyrrolo[3,4-d]imidazol-4-one;

311: 4-{5-(3-Chloro-2-fluoro-phenyl)-2-[2-(1,1-dioxo-1-thiomorpholin-4-yl)-4-methoxy-pyrimidin-5-yl]-3-isopropyl-6-oxo-3,4,5,6-tetrahydro-pyrrolo[3,4-d]imidazol-4-yl}-benzonitrile;

312: 4-{5-(3-Chloro-2-fluoro-phenyl)-2-[2-((S)-3-hydroxy-piperidin-1-yl)-4-methoxy-pyrimidin-5-yl]-3-isopropyl-6-oxo-3,4,5,6-tetrahydro-pyrrolo[3,4-d]imidazol-4-yl}-benzonitrile;

313: 2-(2-amino-4-methoxypyrimidin-5-yl)-5-(3-chloro-4-fluorophenyl)-6-(4-chlorophenyl)-1-((R)-1-methoxypropan-2-yl)-5,6-dihydropyrrolo[3,4-d]imidazol-4(1H)-one;

314: 2-(2-amino-4-methoxypyrimidin-5-yl)-5-(5-chloro-2-methylphenyl)-6-(4-chlorophenyl)-1-((R)-1-methoxypropan-2-yl)-5,6-dihydropyrrolo[3,4-d]imidazol-4(1H)-one;

315: (R)-5-(3-chloro-2-fluorophenyl)-6-(4-chlorophenyl)-2-(2,4-dimethoxypyrimidin-5-yl)-1-((R)-1-hydroxypropan-2-yl)-5,6-dihydropyrrolo[3,4-d]imidazol-4(1H)-one;

316: (S)-5-(3-chloro-2-fluorophenyl)-6-(4-chlorophenyl)-2-(2,4-dimethoxypyrimidin-5-yl)-1-((R)-1-hydroxypropan-2-yl)-5,6-dihydropyrrolo[3,4-d]imidazol-4(1H)-one;

317: (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

318: (R)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

319: 5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

320: 5-(5-chloro-1-methyl-2-oxo-1,2-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

321: 5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one;

322: (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one;

323: (S)-5-(5-chloro-1-methyl-6-oxo-1,6-dihydropyridin-3-yl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;

324: (R)-5-(5-chloro-1-methyl-6-oxo-1,6-dihydropyridin-3-yl)-6-(4-chlorophenyl)-2-(2,4-dimethoxypyrimidin- 5-yl)-1-((R)-1-methoxypropan-2-yl)-5,6-dihydropyr-rolo[3,4-d]imidazol-4(1H)-one;

325: (S)-5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one; and 326: (R)-5-(5-chloro-1-methyl-6-oxo-1,6-dihydropyridin-3-yl)-6-(4-chlorophenyl)-2-(2-(dimethylamino)-4-methoxypyrimidin-5-yl)-1-((R)-1-methoxypropan-2-yl)-5,6-dihydropyrrolo[3,4-d]imidazol-4(1H)-one.

18. A compound of formula (I) according to claim 1 or a pharmaceutically acceptable salt thereof, selected from:

102: (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

199: 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile;

282: (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one;

317: (S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one; and 322: (S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one.

19. A pharmaceutical composition comprising a compound of formula (I) or a pharmaceutically acceptable salt therof according to claim 1, and one or more pharmaceutically acceptable carriers.

20. A method of modulating murine double minute 2 and/or murine double minute 4 activity in a subject, comprising the step of administering to a subject a therapeutically effective amount of a compound of formula (I) or a pharmaceutically acceptable salt thereof according to claim 1.

21. A compound (S)-5-(5-Chloro-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof.

22. A compound (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, or a pharmaceutically acceptable salt thereof.

23. A compound 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile, or a pharmaceutically acceptable salt thereof.

24. A compound (S)-5-(3-Chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one, or a pharmaceutically acceptable salt thereof.

25. A compound (S)-5-(5-Chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one, or a pharmaceutically acceptable salt thereof.

* * * * *

UNITED STATES PATENT AND TRADEMARK OFFICE
CERTIFICATE OF CORRECTION

PATENT NO. : 8,815,926 B2
APPLICATION NO. : 13/748790
DATED : August 26, 2014
INVENTOR(S) : Pascal Furet et al.

It is certified that error appears in the above-identified patent and that said Letters Patent is hereby corrected as shown below:

In the claims

In column 386, the formula spanning from lines 13-17, that appears as " 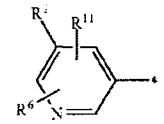 ", should appear as 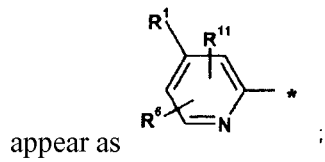 ;

the formula spanning from lines 42-48, that appears as " 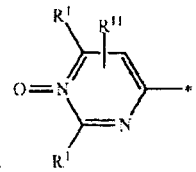 ", should appear as 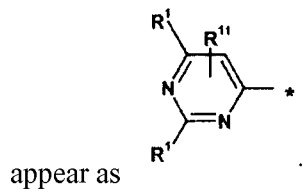 .

Signed and Sealed this
Ninth Day of August, 2016

Michelle K. Lee
*Director of the United States Patent and Trademark Office*

In column 388, the formulae spanning from lines 50-66, that appears as:
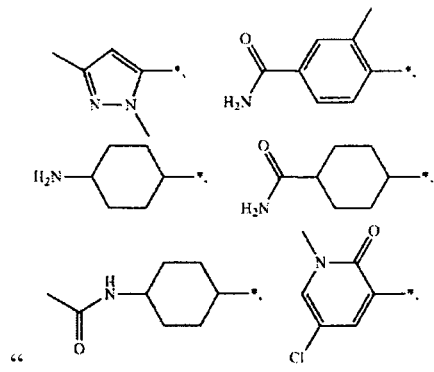
" ", should be deleted.
In column 389, the formulae spanning from lines 1-50, that appears as:
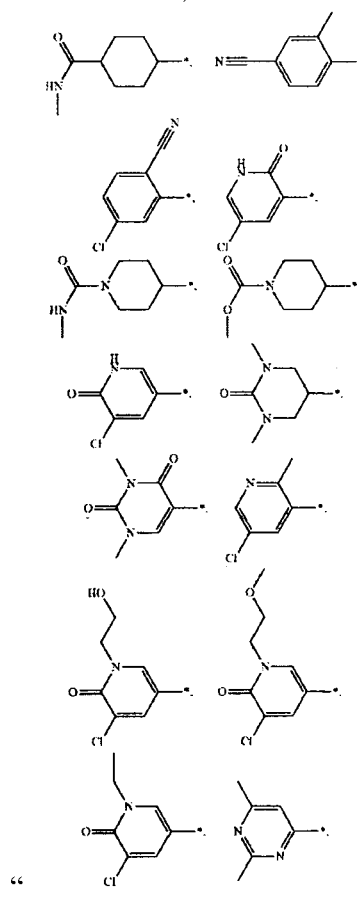
" ", should be deleted.
In column 390, the formulae spanning from lines 39-44, that appears as "  "

should appear as follows:

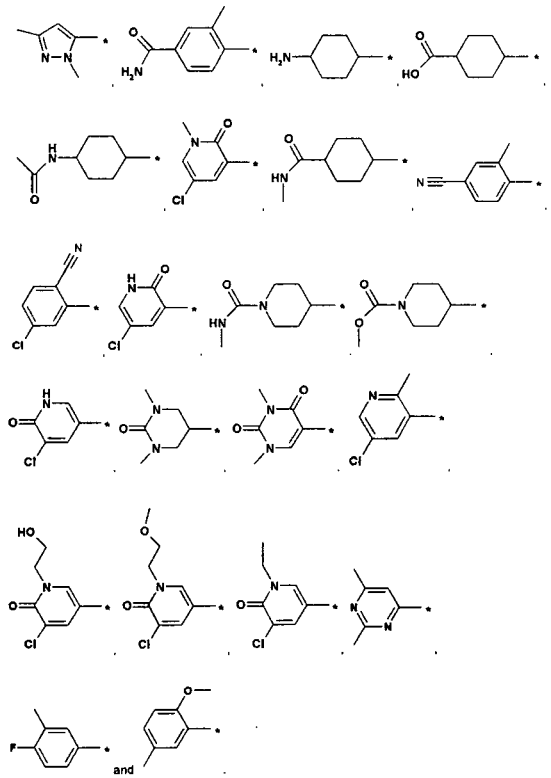

In column 394, delete the text spanning from lines 55-57, that appears as:

"33: 5-(5-Chloro-2-methyl-phenyl)-6-(4-chloro-phenyl)-2-(2,6-dimethoxy-pyridin-3-yl)-1-isopropyl-5,6-dihydro-1H-pyrrolo[3,4-d]imidazol-4-one;".

In column 400, delete the text spanning from lines 48-50, that appears as:

"141: {5-[5-(3-Chloro-2-fluoro-phenyl)-6-(4-cyano-phenyl)-1-isopropyl-4-oxo-1,4,5,6-tetrahydro-pyrrolo[3,4-d]imidazol-2-yl]-6-methoxy-pyridin-3-yl}-acetic acid;".